US005646042A

United States Patent [19]
Stinchcomb et al.

[11] Patent Number: 5,646,042
[45] Date of Patent: Jul. 8, 1997

[54] C-MYB TARGETED RIBOZYMES

[75] Inventors: Dan T. Stinchcomb; Kenneth Draper; James McSwiggen; Thale Jarvis, all of Boulder, Colo.

[73] Assignee: Ribozyme Pharmaceuticals, Inc., Boulder, Colo.

[21] Appl. No.: 373,124

[22] Filed: Jan. 13, 1995

Related U.S. Application Data

[63] Continuation-in-part of Ser. No. 987,132, Dec. 7, 1992, abandoned, and a continuation-in-part of Ser. No. 192,943, Feb. 7, 1994, which is a continuation of Ser. No. 936,422, Aug. 26, 1992, abandoned, and a continuation of Ser. No. 245,466, May 18, 1994, abandoned.

[51] Int. Cl.$^6$ .............................. C12N 5/22; C12N 5/16; C12N 9/22; C12Q 1/68
[52] U.S. Cl. ........................... 435/366; 435/6; 435/513; 435/172.3; 435/302.1; 435/353; 435/325; 536/23.1; 536/23.2; 536/24.5; 514/44
[58] Field of Search .................... 435/6, 91.31, 172.1, 435/172.3, 320.1, 240.2, 240.1; 536/23.1, 23.2, 24.5; 514/44

[56] References Cited

U.S. PATENT DOCUMENTS

| | | | |
|---|---|---|---|
| 4,987,071 | 1/1991 | Cech | 435/91.31 |
| 5,168,053 | 12/1992 | Altman | 514/44 |
| 5,213,580 | 5/1993 | Slepian et al. | 623/1 |
| 5,328,470 | 7/1994 | Nabel et al. | 604/101 |

FOREIGN PATENT DOCUMENTS

| | | |
|---|---|---|
| 2106819 | 9/1993 | Canada. |
| 0519463 | 12/1991 | European Pat. Off.. |
| 9103162 | 3/1991 | WIPO. |
| 9115580 | 10/1991 | WIPO. |
| 9118625 | 12/1991 | WIPO. |
| 9118624 | 12/1991 | WIPO. |
| 9118913 | 12/1991 | WIPO. |
| 9200080 | 1/1992 | WIPO. |
| 9207065 | 4/1992 | WIPO. |
| 9220348 | 11/1992 | WIPO. |
| 9302654 | 2/1993 | WIPO. |
| 9308845 | 5/1993 | WIPO. |
| 9309789 | 5/1993 | WIPO. |
| 9315187 | 8/1993 | WIPO. |
| 9323569 | 11/1993 | WIPO. |
| 9402595 | 2/1994 | WIPO. |

OTHER PUBLICATIONS

Akhtar and Juliano, "Cellular Uptake and Intracellular Fate of AntiSense Oligonucleotides," *Trends Cell Biol.* 2:139–144 (1992).

Alitalo et al., "Aberrant Expression of An Amplified c–myb oncogene in two cell lines from a colon carcinoma," *Proc. Natl. Acad. Sci. USA* 81:4534–4538 (1984).

Anfossi et al., "An oligomer complementary to c–myb–encoded mRNA inhibits proliferation of human myeloid leukemia cell lines," *Proc. Natl. Acad. Sci. USA* 86:3379–3383 (1989).

Austin et al., "Intimal Proliferation of Smooth Muscle Cells as an Explanation for Recurrent Coronary Artery Stenosis After Percutaneous Transluminal Coronary Angioplasty," *J. Am. Coll. Cardiol.* 6:369–375 (1985).

Banskota et al., "Insulin, Insulin–Like Growth Factor I and Platelet–Derived Growth Factor Interact Additively in the Induction of the Protooncogene c–myc and Cellular Proliferation in Cultured Bovine Aortic Smooth Muscle Cells," *Molec.Endocrinol.,* 3:1183–1190 (1989).

Barinaga, "Gene Therapy for Clogged Arteries Passes Test in Pigs," *Science* 265:738 (1994).

Belknap et al., "Transcriptional Regulation in Vascular Cells; Genetically Modified Animals," *J. Cell. Biochem.* S18A:277 (1994).

Bennett et al., "Cationic Lipids Enhance Cellular Uptake and Acitivity of Phosphorothioate Antisense Oligonucleotides," *Mol. Pharmacology* 41:1023–1033 (1992).

Biotech Abstracts Act. #91–00050 EP 388758 (Sep. 26, 1990).

Biro et al., "Inhibitory Effects of Antisense Oligodeoxynucleotides targeting c–myc mRNA on smooth muscle cell proliferation and migration," *Proc. Natl. Acad. Sci. USA,* 90:654–658 (1993).

Blam et al., "Addition of Growth Hormone Secretion Signal to Basic Fibroblast Growth Factors Results in Cell Transformation and Secretion of Aberrant Forms of the Protein," *Oncogene* 3:129–136 (1988).

Brown et al., "Expression of the c–myb Proto–oncogene in Bovine Vascular Smooth Muscle Cells," *J. Biol. Chem.* 267:4625–4630 (1992).

Bywater et al., "Expression of Recombinant Platelet–Derived Growth Factor A–Chain and B–Chaim Homodimers in Rat Cells and Human Fibroblastic Reveals Differences in Protein Processing and Autocrine Effects," *Mol. Cell Biol.* 8:2753–2762 (1988).

Calabretta et al., "Normal and Leukemic Hematopoietic Cells Manifest Differential Sensitivity to Inhibitory Effects of c–myb Antisense Oligodeoxynucleotides: An in vitro study relevant to bone marrow purging," *Proc. Natl. Acad. Sci. USA,* 88:2351–2355 (1991).

Califf et al., "Restenosis: The Clinical Issues," in *Textbook of Interventional Cardiology,* E.J. Topol, ed., W. B. Saunders, Philadelphia, pp. 363–394 (1990).

Cameron and Jennings, "Specific Gene Suppression by Engineered Ribozymes in Monkey Cells." *Proc. Natl. Acad. Sci. USA* 86:9139 (1989).

Carter, "Adeno–Associated Virus Vectors," *Curr Opi. Biotech.* 3:533–539 (1992).

Castanatto et al., "Antisense Catalytic RNAs as Therapeutic Agents," *Adv. in Pharmacol.* 25:289–317 (1984).

(List continued on next page.)

Primary Examiner—John L. Leguyader
Attorney, Agent, or Firm—Lyon & Lyon

[57] ABSTRACT

Enzymatic nucleic acid molecules which cleave c–myb RNA or other RNAs associated with restenosis or cancer.

220 Claims, 19 Drawing Sheets

OTHER PUBLICATIONS

Chen, "Multitarget-Ribozyme Directed to Cleave at up to Nine Highly Conserved HIV-1 env RNA Regions Inhibits HIV-1 Replication-Potential Effectiveness Against Most Presently Sequenced HIV-1 Isolates," *Nucleic Acids Res.* 20:4581–4589 (1992).

Chomcyzynski and Sacchi, "Single Step Method of RNA Isolation by Acid Guanidinum Thiocyanate-Phenol-Chloroform Extraction," *Analytical Biochem.* 162:156–159 (1987).

Chowrira and Burke, "Extensive Phosphorothioate Substitution Yields Highly Active and Nuclease-Resistant Hairpin Ribozymes," *Nucleic Acids Res.* 20:2835–2840 (1992).

Chowrira et al., "In Vitro and in Vivo Comparison of Hammerhead, Hairpin, and Hepatitis Delta Virus Self-Processing Ribozyme Cassettes," *J. Biol. Chem.* 269:25856–25864 (1994).

Chuat and Galibert, "Can Ribozymes be Used to Regulate Procaryote Gene Expression?" *Biochem. and Biophys. Res. Comm.* 162:1025 (1989).

Cleary et al., "Cloning and Structural Analysis of cDNAs For bcl-2 And A Hybrid bci-2/Immunoglobulin Transcript Resulting From the t(14;18) Translocation," *Cell* 47:199–28 (1986).

Clowes et al., "Kinetics of Cellular Proliferation After Arterial Injury," *Lab Invest.* 49:327–333 (1983).

Collins and Olive, "Reaction Conditions and Kinetics of Self-Cleavage of a Ribozyme Derived From Neurospora VS RNA," *Biochemistry* 32:2795–2799 (1993).

Cotten et al., "High-Efficiency Receptor-Mediated Delivery of Small and Large (48 Kilobase Gene Constructs Using the Endosome-Disruption Activity of Defective or Chemically Inactivated Adenovirus Particles," *Proc. Natl. Acad. Sci. USA* 89:6094–6098 (1992).

Cotten et al., "Transferrin-Polycation-Mediated Introduction of DNA into Human Leukemic Cells: Stimulation by Agents that Affect the Survival of Transfected DNA or Modulate Transferrin Receptor Levels" (Abstract), *Proc. Natl. Acad. Sci. USA* 87:4033–4037 (1990).

Cotten et al., "Chicken Adenovirus (CELO Virus) Particles Augment Receptor-Mediated DNA Delivery to Mammalian Cells and Yield Exceptional Levels of Stable Transformants," *J. Virol.* 67:3777–3785 (1993).

Cristiano et al., "Hepatic Gene Therapy: Adenovirus Enhancement of Receptor-Mediated Gene Delivery and Expression in Primary Hepatocytes," *Proc. Natl. Acad. Sci. USA* 90:2122–2126 (1993).

Curiel et al., "Adenovirus Enhancement of Transferrin-Polylysine-Mediated Gene Delivery," *Proc. Nat. Acad. Sci. USA*, 88:8850–8854 (1994).

Dropulic et al., "Functional Characterization of a U5 Ribozyme: Intracellular Suppression of Human Immunodeficiency Virus Type I Expresion," *J Virol.* 66:1432–1441 (1992).

Ege et al., "Enhancement of DNA-Mediated Gene Transfer by Inhibitors of Autophagic-Lysosomal Function," *Exp. Cell Res.* 155:9–16 (1984).

Elroy-Stein and Moss, "Cytoplasmic Expression System Based on Constitutive Synthesis of Bacteriophage T7 RNA Polymerase in Mammalian Cells," *Proc. Natl. Acad. Sci. USA* 87:6743–7 1990).

Ferguson et al., "Compensation for Treating Wounds to Inhibit Scar Tissue—Contains Agent Esp. Antibody, Which Selectively Neutralises Fibrotic Growth Factors," WPI Acc# 92-3659974/44.

Ferns et al., "Inhibition of Neointimal Smooth Muscle Accumulation After Angioplasty by an Antibody to PDGF," *Science* 253:1129–1132 (1991).

Gao and Huang, "Cytoplasmic Expression of a Reporter Gene by Co-Delivery of T7 RNA Polymerase and T7 Promoter Sequence with Cationic Liposomes," *Nucleic Acids Res.* 21:2867–72 (1993).

Garratt et al., "Differential Histopathology of Primary Atherosclerotic and Restenotic Lesions in Coronary Arteries and Saphenous Vein Bypass Grafts: Analysis of Tissue Obtained From 73 Patients by Directional Atherectomy," *J. Am. Coll. Cardio.* 17:442–428 (1991).

Goldberg et al., "Vascular Smooth Muscle Cell Kinetics: A New Assay for Studying patterns of Cellular Proliferation in vivo," *Science* 205:920–922 (1979).

Griffin and Baylin, "Expression of the c-myb Oncogene in Human Small Cell Lung Carcinoma," *Cancer Res.* 45:272–275 (1985).

Grotendorst et al., "Attachment of Smooth Muscle Cells to Collagen and Their Migration Toward Platelet-Derived Growth Factor," *Proc. Natl. Acad. Sci. USA* 78:3669–3672 (982).

Guerrier-Takada et al., "The RNA Moiety of Ribonuclease P Is the Catalytic Subunit of the Enzyme," *Cell* 35:849 (1983).

Hajjar et al., "Tumor Necrosis Factor-Mediated Release of Platelet-Derived Growth Factor From Cultured Endothelial Cells," *J. Exp. Med.* 166:235–245 (1987).

Hampel and Tritz, "RNA Catalytic Properties of the Minimum (−)sTRSV Sequence," *Biochemistry* 28:4929–4933 (1989).

Hampel et al., "'Hairpin' Catalytic RNA Model: Evidence for Helices and Sequence Requirement for Substrate RNA," *Nucleic Acids Research* 18:299–304 (1990).

Harris et al., "Receptor-Mediated Gene Transfer to Airway Epithelial Cells in Primary Culture," *Am. J. Respir. Cell Mol. Biol.,* 9:441–447 (1993).

Haseloff and Gerlach, "Simple RNA Enzymes with New and Highly Specific Endoribonuclease Activities," *Nature* 334:585–591 (1988).

Herschlag, "Implications of Ribozyme Kinetics for Targeting the Cleavage of Specific RNA Molecules in vivo: More Isn't Always Better," *Proc. Natl. Acad. Sci. USA* 88:6921–5 (1991).

Hertel et al., "Numbering System for the Hammerhead," *Nucleic Acids Res.,* 20:3252 (1992).

Higashiyama et al, "A Heparin-Binding Growth Factor Secreted by Macrophage-Like Cells That is Related to EFG," *Science* 251:936–939 (1991).

Jaeger et al., "Improved Predictions of Secondary Structures for RNA," *Proc. Natl. Acad. Sci. USA* 86:7706–7710 (1989).

Jeffries and Symons, "A Catalytic 13-mer Ribozyme," *Nucleic Acids Research* 17:1371 (1989).

Kashani-Sabet et al., "Reversal of the Malignant Phenotype by an Anti-ras Ribozyme," *Antisense Research & Development* 2:3–15 (1992).

Kaye et al., "Structure and Expression of the Human L-myc Gene Reveal a Complex Pattern Of Alternative mRNA Processing," *Mol. Cell. Biol.* 8:186–195 (1988).

Kindy and Sonenshein, "Regulation of Oncogene Expression in Cultured Aortic Smooth Muscle Cells," *J. Biol. Chem.* 261:12865–12868 (1986).

Klagsbrun and Edelman, "Biological and Biochemical Properties of Fibroblast Growth Factors," *Arteriosclerosis* 9:269–278 (1989).

Koizumi et al., "Ribozymes Designed to Inhibit Transformation of NIH3T3 Cells by the Activated c–Ha–ras Gene," *Gene* 117:179 (1992).

Komuro et al., "Endothelin stimulates c–fos and c–myc expression and proliferation of vascular smooth muscle cells," *FEBS Letters* 238:249–252 (1988).

Kunapuli et al, "Molecular Cloning of Human Angiotensinogen cDNA and Evidence for the Presence of Its mRNA in Rat Heart—DNA Sequence," *Circ. Res.* 60:786–790 (1987).

Lieber et al., "Stable High–Level Gene Expression in Mammalian Cells by T7 Phage $NA Polymerase," *Methods Enzymol.* 217:47–66 (1993).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lindner and Reidy, "Proliferation of Smooth Muscle Cells After Vascular Injury is Inhibited by an Antibody Against Basic Fibroblast Growth Factor," *Proc. Natl. Acad. Sci. USA* 88:3739–3743 (1991).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Majello et al., "Human c–myb Protooncogene: Nucleotide Sequence of cDNA and Organization of the Genomic Locus" *Proc. Natl. Acad. Sci. USA,* 83:9636–9640 (1986).

Mamone et al., "Design of Hammerhead Ribozymes Targeted to Sequences in HIV, HSV and the RAT ANF Gene," Abstract of Keystone, CO (May 27, 1992).

McGrath et al., "Structure and Organization of the Human Ki–ras Protooncogene And a Related Processed Pseudogene," 304:501–506 (1983).

Melani et al., "Inhibition of Proliferation by c–myb Antisense Oligodeoxynucleotide in Colon Adenocarcinoma Cell Lines that Express c–myb, "*Cancer Res.* 51:2897–2901 (1991).

Milligan and Uhlenbeck, "Synthesis of Small RNAs Using T7 RNA Polymerase," *Methods Enzymol.* 180:51–62 (1989).

Minvielle et al., "A Novel Calcitonin Carboxyl–Terminal Peptide Produced in Medullary Thyroid Carcinoma by Alternative RNA Processing of the Calcitonin–Calcitonin Gene–Related Peptide Gene," *J. Biol. Chem.* 266:24627–24631 (1991).

Nabel et al., "Site–Specific Gene Expression in Vivo by Direct Gene Transfer Into the Arterial Wall," *Science* 249:1285–1288 (1990).

Nabel et al., "Recombinant Platelet–Derived Growth Factor B Gene Expression in Porcine Arteries Induces Intimal Hyperplasia In Vivo," *J. Clin. Invest.* 91:1822–1829 (1993).

Ohno et al., "Gene Therapy for Vascular Smooth Muscle Cell Proliferation After Arterial Injury," *Science* 265:781–784 (1994).

Ohkawa et al., *Nucleic Acids Symp. Ser.* 27:15–6 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Ortigao et al., "Antisense Effects of Oligodeoxynucleotides with Inverted Terminal Internucleotidic Linkages: A Minimal Modification Protecting Against Nucleolytic Degradation," *Antisense Research and Development* 2:129–146 (1992).

Pavco et al., "Regulation of Self–Splicing Reactions by Antisense RNA," Abstract of Keystone, CO (May 27, 1992).

Perreault et al., "Mixed Deoxyribo— and Ribo–Oligonucleotides with Catalytic Activity," *Nature* 344:565–568 (1990).

Perrotta and Been, "Cleavage of Oligoribonucleotides by a Ribozyme Derived from the Hepatitis δ Virus RNA Sequence," *Biochemistry* 31:16 (1992).

Pieken et al., "Kinetic Characterization of Ribonuclease–Resistant 2'–Modified Hammerhead Ribozymes," *Science* 253:314–317 (1991).

Popoma et al., "Clinical Trials of Restenosis After Coronary Angioplasty," *Circulation* 84:1426–1436 (1991).

Raines et al., "Interleukin–1 Mitogenic Activity for Fibroblasts and Smooth Muscle Cells Is Due to PDGF–AA," *Science* 243:393–396 (1989).

Raschella et al., "Inhibition of Proliferation by c–myb Antisense RNA and Oligodeoxynucleotides in Transformed Neuroectodermal Cell Lines," *Cancer Res.* 52:4221–4226 (1992).

Ratajczak et al., "In Vivo Treatment of Human Leukemia in a scid Mouse Model With c–myb Antisense Oligodeoxynucleotides," *Proc. Natl. Acad. Sci. USA* 89:11823–11827 (1992).

Riessen et al., "Arterial Gene Transfer Using Pure DNa Applied Directly to a Hydrogel–Coated Angioplasty Balloon," *Human Gene Therapy* 4:749–758 (1993).

Ross et al., "A Platelet–Dependent Serum Factor That Stimulates the Proliferation of Arterial Smooth Muscle Cells In Vitro," *Proc. Natl. Acad. Sci. USA* 71:1207–1210 (1974).

Rossi et al., *J. Cell Biochem.* Suppl 14A:D428 (1990).

Rossi et al, "Ribozymes as Anti–HIV–1 Therapeutic Agents: Principles, Applications, and Problems," *Aids Research and Human Retroviruses* 8:183 (1992).

Ruben et al., "Isolation of a rel–related human cDNA that potentially encodes the 65–kD subunit of NF, kappba B," *Science* 251:5000 (1991).

Ruben et al., "Isolation of a rel–related human cDNA that potentially encodes the 65–kD subunit of NF, kappba B," *Science* 254:5028 (1991).

Saville and Collins, "RNA–Mediated Ligation of Self––Cleavage Products of a Neurospora Mitochondrial Plasmid Transcript," *Proc. Natl. Acad. Sci. USA* 88:8826–8830 (1991).

Saville and Collins, "A Site–Specific Self–Cleavage Reaction Performed by a Novel RNA In Neurospora Mitochondria," *Cell* 61:685–696 (1990).

Sarver et al., "Ribozymes as Potential Anti–HIV–1 Therapeutic Agents," *Science* 247:1222–1225 (1990).

Sarver et al., "Catalytic RNAs (Ribozymes): A New Frontier in Biomedical Applications," *AIDS Res. Revs.* 2:259 (1992).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Semba, "A v-erbB-Related Protooncogene, C-erB-2, Is Distinct From the c-erbB-1/Epidermal Growth Factor-Receptor Gene and Is Amplified in A Human Salivary Gland Adenocarcinoma," *Proc. Natl. Acad. Sci. USA* 82:6497-6501 (1985).

Seth et al., "Mechanism of Enhancement of DNA Expression Consequent to Cointernalization of a Replication-Deficient Adenovirus and Unmodified Plasmid dDNA," *J. Virol.,* 68:933-940 (1994).

Sessa et al., "Molecular Cloning and Expression of a cDNA Encoding Endothelial Cell Nitric Oxide Synthase," *J. Biol. Chem.* 267:15274-15276 (1992).

Shi et al., "Downregulation of c-myc Expression by Antisense Oligonucleotides Inhibits Proliferation of Human Smooth Muscle Cell," *Circulation* 88:1190-1195 (1993).

Simons et al., "Antisence c-myb Oligonucleotides Inhibit Intimal Arterial Smooth Muscle Cell Accumulation in vivo," *Nature* 359:67-70 (1992).

Simons et al., "Relation Between Activated Smooth Muscle Cells in Coronary-Artery Lesions and Restenosis After Atherectomy," *New Engl. J. Med.* 328:608-613 (1993).

Sioud and Drulica, "Prevention of Human Immunodeficiency Virus Type 1 Integrase Expression in *Escherichia coli* by a Ribozyme," *Proc. Natl. Acad. Sci. USA* 88:7303 (1991).

Sjolund et al., "Arterial Smooth Muscle Cells Express Platelet-Derived Growth Factor (PDGF) A Chain mRNA, Secrete a PDGF-Like Mitogen, and Bind Exogenous PDGF in a Phenotype— and Growth State-Dependent Manner," *J. Cell. Biol.* 106:403-413 (1988).

Slamon et al., "Studies of the Human c-myb Gene and Its Products In Human Acute Leukemias," *Science* 233:3467-351 (1986).

Slamon et al., "Expression of Cellular Oncogenes in Human Malignancies," *Science* 224:256-262 (1984).

Steele et al., "Balloon Angioplasty—Natural History of the Pathophysiological Response to Injury in a Pig Model," *Circ. Res.* 57:105-112 (1985).

Taira et al., "Construction of a novel RNA-transcript-trimming plasmid which can be used both in vitro in place of run-off and (G)-free transcriptions and in vivo as multi-sequences transcription vectors," *Nucleic Acids Research* 19:5125-30 (1991).

Ten Dijke et al., "Recombinant Transforming Growth Factor Type Beta-3 Biological Activities and Receptor-Binding Properties in Isolated Bone Cells," *Mol. Cell Biol.* 10:4473-4479 (1990).

Tessler et al, "Basic Fibroblast Growth Factor Accumulates in the Nuclei of Vairous BFGF-Producing Cell Types," *J. Cell. Physiol.* 145:310-317 (1990).

Thiele et al., "Regulation of c-myb Expression in Human Neuroblastoma Cells During Retinoci Acid-Induced Differentiation," *Mol. Cell. Biol.* 8:1677-1683 (1988).

Thompson et al., "Molecular Quantification of Residual Disease in Chronic Myelogenous Leukemia After Bone Marrow Transplantation," *Blood* 79:1692-1635 (1992).

Torelli et al., "Expression of c-myb Protoncogene and Other Cell Cycle-Related Genes in Normal and Neoplastic Human Colonic Mucosa," *Cancer Res.* 47:5266-5269 (1987).

Torrence et al., "Targeting RNA for degradation with a (2'-5') oligoadenylate-antisense chimera," *Proc. Natl. Acad. Sci. USA* 90:1300-1304 (1993).

Uhlenbeck, "A Small Catalytic Oligoribonucleotide," *Nature* 327:596-600 (1987).

Usman et al., "Chemical modification of hammerhead ribozymes: activity and nuclease resistance," *Nucleic Acids Symposium Series* 31:163-164 (1994).

Usman and Cedergren, "Exploiting the chemical synthesis of RNA," *Trends in Biochem. Sci.* 17:334-339 (1992).

Usman et al., "Automated Chemical Synthesis of Long Oligoribonucleotides Using 2'-O-Silylated Ribonucleoside 3'-O-Phosphoramidtes on a Controlled-Pore Glass Support: Synthesis of a 43-Nucleotide Sequence Similar to the 3'-Half Molecule of an *Escherichia coli* Formylmethoionine tRNA," *J. Am. Chem. Soc.* 109:7845-7854 (1987).

Ventura et al., "Activation of HIV-Specific Ribozyme Activity by Self-Cleavage," *Nucleic Acids Res.* 21:3249-55 (1993).

Weerasinghe et al., "Resistance to Human Immunodeficiency Virus Type 1 (HIV-1) Infection in Human CD4$^+$ Lymphocyte-Derived Cell Lines Conferred by Using Retroviral Vectors Expressing an HIV-1 RNA-Specific Ribozyme," *Journal of Virology* 65:5531-4 (1994).

Wagner et al., "Gene inhibition using antisense oligodeoxynucleotides," *Nature* 372:333-335 (1994).

Weiser et al., "The Growth-Related Transcription Factor OCT-1 is Expressed as a Function of Vascular Smooth Muscle Cell Modulation," *J. Cell. Biochem.* S18A:282 (1994).

Westin et al., "Alternative Splicing of the Human c-myb Gene," *Oncogene* 5:1117-1124 (1990).

Willard et al., Willard et al., "Recombinant Adenovirus in an Efficient Vector for In Vivo Gene Transfer and can be Preferentially Directed at Vascular Endothelium or Smooth Muscle Cells,"*Circulation—Abstracts from the 6th Scientific Sessions,* New Orleans Convention Center, New Orleans, Louisiana, Nov. 16-19, 1992.

Woolf et al., "Specificity of Antisense Oligonucleotides in vivo," *Proc. Natl. Acad. Sci. USA* 89:7305-7309 (1992).

Yu et al., "A Hairpin Ribozyme Inhibits Expression of Diverse Strains of Human Immunodeficiency Virus Type 1," *Proc. Natl. Acad. Sci. U S A* 90:6340-6344 (1993).

Zabner et al., "Adenovirus-Mediated Gene Transfer Transiently Corrects the Chloride Transport Defect in Nasal Epithelia of Patients with Cystic Fibrosis," *Cell* 75:207-216 (1993).

Zenke et al., "Receptor-mediated Endocytosis of Transferrin-Polycation Conjugates: An Efficient Way to Introduce DNA into Hematopoietic Cells" (Abstract), *Proc. Natl. Acad. Sci. USA* 87:3655-3659 (1990).

Zhou et al., "Synthesis of Function mRNA in Mammalian ells by Bacteriophage T3 RNA Polymerase," *Mol. Cell. Biol.* 10:4529-4537 (1990).

TARGET RNA
+DNA OLIGO
+RNAse H

2'-O-Methyl Ribozyme

2'-O-Methyl P=S Ribozyme

2'-C-Allyl iT Ribozyme

2'-C-Allyl P=S Ribozyme

FIG. 13a.

5'---GGAGAAUUGGAAAAC---3'
3'  ccucuuA  ccuuuug 5'
         a         c
          a       U G
           g     G   A
            c c     U
             g   c
              g a
             a   G
            a
           a

10 P=S 5' and 3' Ribozyme

Uppercase = ribonucleotides
Lower case = 2'-O-methylnucleotides
U = 2'-C-Allyl
s = phosphorothioate linkages 5'---GGAGAAUUGGAAAAC---3'
3'  ccucuuA  ccuuuug 5'
         a         c
          a       U G
           g     G   A
            c c     U
             g   c
              g a
             a   G
            a
           a

5 P=S 3' Ribozyme

Uppercase = ribonucleotides
Lower case = 2'-O-methylnucleotides
U = 2'-C-Allyl
s = phosphorothioate linkages 5'---GGAGAAUUGGAAAAC---3'
3'iT  ccucuuA  ccuuuug 5'
         a         c
          a       U G
           g     G   A
            c c     U
             g   c
              g a
             a   G
            a
           a

5 P=S Loop Ribozyme

Uppercase = ribonucleotides
Lower case = 2'-O-methylnucleotides
U = 2'-C-Allyl
s = phosphorothioate linkages
iT = 3'-3' Inverted T 5'---GGAGAAUUGGAAAAC---3'
3'iT  ccucuuA  ccuuuug 5'
         a         c
          a       U G
           g     G   A
            c c     U
             g   c
              g a
             a   G
            a
           a

5 P=S 5' Ribozyme

Uppercase = ribonucleotides
Lower case = 2'-O-methylnucleotides
U = 2'-C-Allyl
s = phosphorothioate linkages
iT = 3'-3' Inverted T

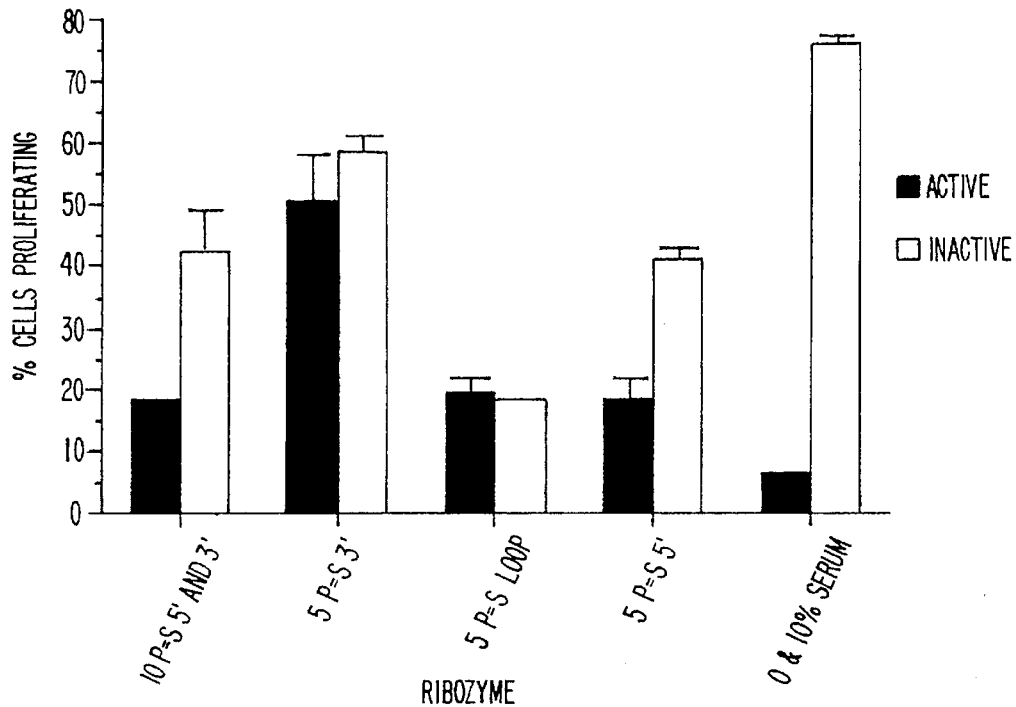
FIG. 13b.
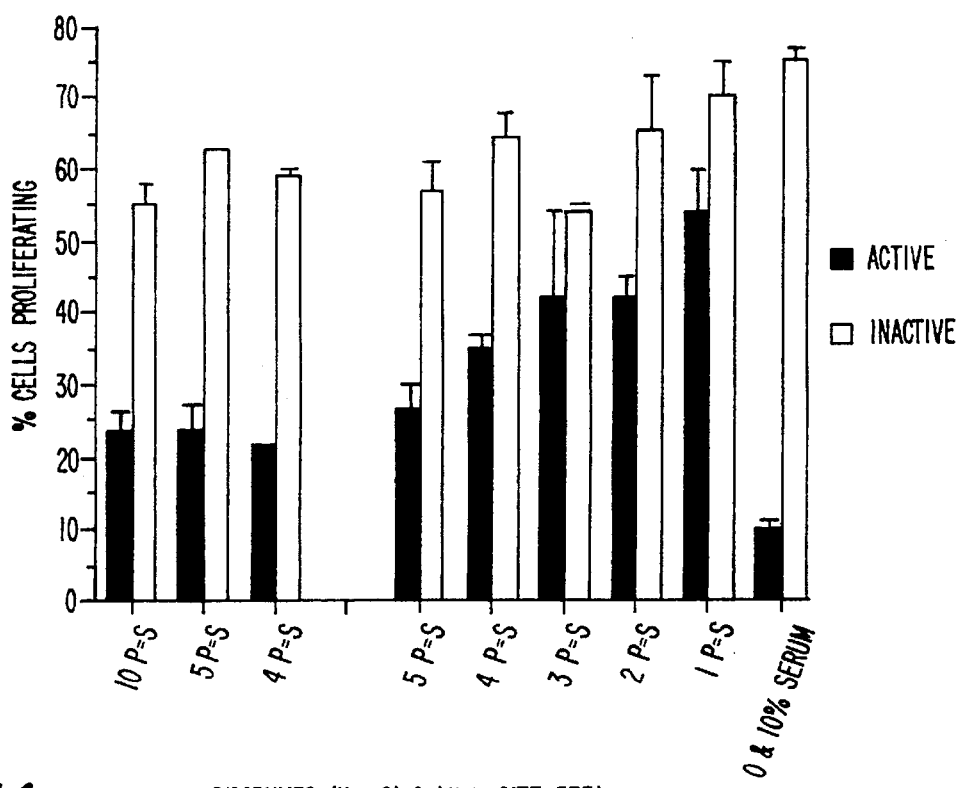
FIG. 14. RIBOZYMES (U₄-2'-C-Allyl; SITE 575)

Uppercase = ribonucleotides

Lower case = 2′-O-methylnucleotides

H = 3′-3′ abasic deoxyribose

U = 2′C-allyl s = phosphorothioate linkages

SEQUENCE LISTING ( 1 ) GENERAL INFORMATION:

( i i i ) NUMBER OF SEQUENCES: 2627

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGCGGCAGCG CCCUGCCGAC GCCGGGG 27

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCGCGGCUCU CGGC  14

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCAUGGCCC GAA  13

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CGGCACAGCA UAUAUAGCAG UGACGAGGA  29

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GACUUUGAGA UGUGUGACCA UGACUAUGAU GGG  33

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CUGGAAAGCG UC  12

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GGAAGAGGAU GAAAAACUGA AGAAG  25

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GAAGAACUGG UGGAACAGAA UGGAAC 26

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CUGGAAAGUU AUUGCCAA 18

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCCGAAUCGA ACAGAUGUGC AG 22

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GAAAGUACUA AACCCUGAG 19

( 2 ) INFORMATION FOR SEQ ID NO:12:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CUUGGACCAA AGAAGAAGAU CAGAGAGUGA UA 32

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ACAGAAAUAC GGUCCGAAAC GUUGGUCUG 29

( 2 ) INFORMATION FOR SEQ ID NO:14:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

UUAUUGCCAA GCACUUAAAG GGGAGAAUUG GAA 33

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GAAUCCAGAA GUUAAGAA                                      18

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GGAAGACAGA AUUAUUUACC AGGCACA                        27

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CAAGAGACUG GGGAACAGAU                                  20

( 2 ) INFORMATION FOR SEQ ID NO:18:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AAAUCGCAAA GCUA                                                  14

( 2 ) INFORMATION FOR SEQ ID NO:19:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGACGAACUG AUAAUGCUAU CAAGAACC                      28

( 2 ) INFORMATION FOR SEQ ID NO:20:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

ACUGGAAUUC UACAAUGCGU CGGAAGGUCG AACA              34

( 2 ) INFORMATION FOR SEQ ID NO:21:

( i ) SEQUENCE CHARACTERISTICS:
: ( A ) LENGTH: 19 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:21:

CAGCCAGCAG UGGCCACAA 19

( 2 ) INFORMATION FOR SEQ ID NO:22:

: ( i ) SEQUENCE CHARACTERISTICS:
: ( A ) LENGTH: 33 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:22:

CAUUUGAUGG GUUUUGCUCA GGCUCCGCCU ACA 33

( 2 ) INFORMATION FOR SEQ ID NO:23:

: ( i ) SEQUENCE CHARACTERISTICS:
: ( A ) LENGTH: 27 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:23:

GCUCAACUCC CUGCCACUGG CCAGCCC 27

( 2 ) INFORMATION FOR SEQ ID NO:24:

: ( i ) SEQUENCE CHARACTERISTICS:
: ( A ) LENGTH: 25 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:24:

AACAACGACU AUUCCUAUUA CCACA 25

( 2 ) INFORMATION FOR SEQ ID NO:25:

: ( i ) SEQUENCE CHARACTERISTICS:
: ( A ) LENGTH: 30 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:25:

CAAAAUGUCU CCAGUCAUGU UCCAUACCCU 30

( 2 ) INFORMATION FOR SEQ ID NO:26:

: ( i ) SEQUENCE CHARACTERISTICS:
: ( A ) LENGTH: 34 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:26:

AAAUAUAGUC AAUGUCCCUC AGCCAGCUGC CGCA 34

( 2 ) INFORMATION FOR SEQ ID NO:27:

: ( i ) SEQUENCE CHARACTERISTICS:

( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:27:

AGAGACACUA UAAUGAUGAA GACCCUGAGA AGGA    34

( 2 ) INFORMATION FOR SEQ ID NO:28:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:28:

AAAGCGAAUA AAGGAAUUAG AAUUG    25

( 2 ) INFORMATION FOR SEQ ID NO:29:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:29:

CUCCUAAUGU CAACCGA    17

( 2 ) INFORMATION FOR SEQ ID NO:30:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:30:

AGCUAAAAGG ACAGCAGGUG CUACCAACAC AGAA    34

( 2 ) INFORMATION FOR SEQ ID NO:31:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:31:

CCCGGGUGGC ACAGCACCAC CAUUGCCGAC CACA    34

( 2 ) INFORMATION FOR SEQ ID NO:32:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:32:

AACACCACUC CACUCCAUCU CUGCCAGCGG AUCC    34

( 2 ) INFORMATION FOR SEQ ID NO:33:

( i ) SEQUENCE CHARACTERISTICS:
( A ) LENGTH: 12 base pairs
( B ) TYPE: nucleic acid ( C ) STRANDEDNESS: single
( D ) TOPOLOGY: linear ( x i ) SEQUENCE DESCRIPTION: SEQ ID NO:33:

UACCUGAAGA AA 12

( 2 ) INFORMATION FOR SEQ ID NO:34:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:34:

AUGAUCGUCC ACCAGGGCAC CAUU 24

( 2 ) INFORMATION FOR SEQ ID NO:35:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:35:

CAGAAACACU CCAAUUUA 18

( 2 ) INFORMATION FOR SEQ ID NO:36:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( x i ) SEQUENCE DESCRIPTION: SEQ ID NO:36:

AAACUCAGAC U 11

( 2 ) INFORMATION FOR SEQ ID NO:37:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( x i ) SEQUENCE DESCRIPTION: SEQ ID NO:37:

AUGCCUUCUU UAAC 14

( 2 ) INFORMATION FOR SEQ ID NO:38:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( x i ) SEQUENCE DESCRIPTION: SEQ ID NO:38:

UUACAACACC A 11

( 2 ) INFORMATION FOR SEQ ID NO:39:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:39:

ACUCAAAAGG AAAAUACUGU UUUUAGAACC C     31

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CAGCUAUCAA AAGGUCAAUC UUAGAAAGCU     30

( 2 ) INFORMATION FOR SEQ ID NO:41:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

CUCCAAGAAC UCCUACACCA UUCAA     25

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

ACAUGCACUU GCAGCUCAAG AA     22

( 2 ) INFORMATION FOR SEQ ID NO:43:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

UACGGUCCCC UGAAGAUGCU ACCUCAGA     28

( 2 ) INFORMATION FOR SEQ ID NO:44:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

CACCCUCUCA UCUAGUAGAA GAUCUGCAGG A     31

( 2 ) INFORMATION FOR SEQ ID NO:45:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

UCAAACAGGA AUCUGAUGAA UCUGGA 26

(2) INFORMATION FOR SEQ ID NO:46:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:46:

AAGAAAAUGG A 11

(2) INFORMATION FOR SEQ ID NO:47:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:47:

CUUACUGAAG AAAAUCAAAC AAGA 24

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:48:

AAUCUCCAAC UGAUAAAUCA G 21

(2) INFORMATION FOR SEQ ID NO:49:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:49:

GCUCACACCA CUGGGA 16

(2) INFORMATION FOR SEQ ID NO:50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:50:

CCUCGCCUGU GCGAGAUGCA CCGAAUAUUC 30

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:51:

GGCACCAGCA UCAGAAGAUG AAGAC 25

( 2 ) INFORMATION FOR SEQ ID NO:52:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

CAUUUACAGU ACC　　　　　　　　　　　　　　　　　　　　　　　　　13

( 2 ) INFORMATION FOR SEQ ID NO:53:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CCCUGGCGAG CCCCUUGCA　　　　　　　　　　　　　　　　　　　　19

( 2 ) INFORMATION FOR SEQ ID NO:54:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GCCUUGUAGC AGUACCUGGG A　　　　　　　　　　　　　　　　　　21

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

GUCAAGCUCG UAAAUACGUG AA　　　　　　　　　　　　　　　　　　22

( 2 ) INFORMATION FOR SEQ ID NO:56:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GAACAGUUCA A　　　　　　　　　　　　　　　　　　　　　　　　11

( 2 ) INFORMATION FOR SEQ ID NO:57:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

AUGAAACUUU UCAU　　　　　　　　　　　　　　　　　　　　　　14

( 2 ) INFORMATION FOR SEQ ID NO:58:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

AAAAUAAAUA ACAGUC　　　　　　　　　　　　　　　　　　　　　　　　　16

( 2 ) INFORMATION FOR SEQ ID NO:59:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

UGAAUUGUAG CC　　　　　　　　　　　　　　　　　　　　　　　　　　12

( 2 ) INFORMATION FOR SEQ ID NO:60:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

UUAAUAUCUU AAU　　　　　　　　　　　　　　　　　　　　　　　　　13

( 2 ) INFORMATION FOR SEQ ID NO:61:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

AUUUAUCUGG UAUUUUAAAG GAUCCAACAG AUC　　　　　　　　　　　　　33

( 2 ) INFORMATION FOR SEQ ID NO:62:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

CCAGUAUUUC A　　　　　　　　　　　　　　　　　　　　　　　　　　11

( 2 ) INFORMATION FOR SEQ ID NO:63:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CUCGAUCACU AAACAUAUG　　　　　　　　　　　　　　　　　　　　　　19

( 2 ) INFORMATION FOR SEQ ID NO:64:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:64:

CAUAUAUUUU UAAAAAUC                                                            18

( 2 ) INFORMATION FOR SEQ ID NO:65:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

UGCUAUGGUC UUAGCCU                                                             17

( 2 ) INFORMATION FOR SEQ ID NO:66:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

AGUAUCAGAG G                                                                     11

( 2 ) INFORMATION FOR SEQ ID NO:67:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

UAGGUAAUUG ACUAU                                                                 15

( 2 ) INFORMATION FOR SEQ ID NO:68:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

UAUUUCAGAC UUUUUAAUUU UAUAUAUAUA UACA                         34

( 2 ) INFORMATION FOR SEQ ID NO:69:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

CAAUACAUUU GAAACUUGU UUGGGAGACU CUGC                            34

( 2 ) INFORMATION FOR SEQ ID NO:70:

( i ) SEQUENCE CHARACTERISTICS:
        ( A ) LENGTH: 25 base pairs

-continued ( B ) TYPE: nucleic acid
        ( C ) STRANDEDNESS: single
        ( D ) TOPOLOGY: linear ( x i ) SEQUENCE DESCRIPTION: SEQ ID NO:70:

GUGGUUUUUU UGUUAUUGUU GGUUU    25

( 2 ) INFORMATION FOR SEQ ID NO:71:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

UUCUUUUUUG GGAGAU    16

( 2 ) INFORMATION FOR SEQ ID NO:72:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

CUAUGUUUUG UUUUG    15

( 2 ) INFORMATION FOR SEQ ID NO:73:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

AGCCUGACUG UUUUAUA    17

( 2 ) INFORMATION FOR SEQ ID NO:74:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

UCGAUUUGAU C    11

( 2 ) INFORMATION FOR SEQ ID NO:75:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

UGGAUCCUGU GUU    13

( 2 ) INFORMATION FOR SEQ ID NO:76:

( i ) SEQUENCE CHARACTERISTICS:
        ( A ) LENGTH: 25 base pairs
        ( B ) TYPE: nucleic acid
        ( C ) STRANDEDNESS: single ( D ) TOPOLOGY: linear ( x i ) SEQUENCE DESCRIPTION: SEQ ID NO:76:

UUGAUAGCCA GUCACUGCCU UAAGA                                                    25

( 2 ) INFORMATION FOR SEQ ID NO:77:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:77:

ACAUUUGAUG CAAGAUGGCC AGCACU                                                   26

( 2 ) INFORMATION FOR SEQ ID NO:78:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:78:

CGGUGUACUU ACUGCC                                                              16

( 2 ) INFORMATION FOR SEQ ID NO:79:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:79:

CGUCACUUGG GGAAA                                                               15

( 2 ) INFORMATION FOR SEQ ID NO:80:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:80:

GUCUGUUAUU GCCAA                                                               15

( 2 ) INFORMATION FOR SEQ ID NO:81:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:81:

CUGUUAUUGC CAAGC                                                               15

( 2 ) INFORMATION FOR SEQ ID NO:82:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:82:

GGAGAAUUGG AAAAC                                                                    15

( 2 ) INFORMATION FOR SEQ ID NO:83:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

AAAACCUCCU GGACA                                                                    15

( 2 ) INFORMATION FOR SEQ ID NO:84:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

UAAUGCUAUC AAGAA                                                                    15

( 2 ) INFORMATION FOR SEQ ID NO:85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

CAAGCUUCCA GAAGA                                                                    15

( 2 ) INFORMATION FOR SEQ ID NO:86:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

UUCCUAUUAC CACAU                                                                    15

( 2 ) INFORMATION FOR SEQ ID NO:87:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

UGUCCCUCAG CCAGC                                                                    15

( 2 ) INFORMATION FOR SEQ ID NO:88:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

AGCGAAUAAA GGAAU                                                                15

(2) INFORMATION FOR SEQ ID NO:89:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:89:

UUAGAAUUUG CAGAA                                                                15

(2) INFORMATION FOR SEQ ID NO:90:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:90:

CAGCUAUCAA AAGGU                                                                15

(2) INFORMATION FOR SEQ ID NO:91:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:91:

ACACCAUUCA AACAU                                                                15

(2) INFORMATION FOR SEQ ID NO:92:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:92:

CACCAUUCAA ACAUG                                                                15

(2) INFORMATION FOR SEQ ID NO:93:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:93:

AUACGGUCCC CUGAA                                                                15

(2) INFORMATION FOR SEQ ID NO:94:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:94:

CUGGAAUUGU UGCUG                                                                15

( 2 ) INFORMATION FOR SEQ ID NO:95:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

GAAUUGUUGC UGAGU        15

( 2 ) INFORMATION FOR SEQ ID NO:96:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

AUAUUCUUAC AAGCU        15

( 2 ) INFORMATION FOR SEQ ID NO:97:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

UCCGUUUUAA UGGCA        15

( 2 ) INFORMATION FOR SEQ ID NO:98:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

ACAAUGUUCU CAAAG        15

( 2 ) INFORMATION FOR SEQ ID NO:99:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

ACGGUCCCU GAAG        14

( 2 ) INFORMATION FOR SEQ ID NO:100:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

ACAGUUGAGA GCAG        14

( 2 ) INFORMATION FOR SEQ ID NO:101:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:101:

UUUCCCCUG AUGAGGCCGA AAGGCCGAAA GUGACG    36

( 2 ) INFORMATION FOR SEQ ID NO:102:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:102:

UUGGCAACUG AUGAGGCCGA AAGGCCGAAA ACAGAC    36

( 2 ) INFORMATION FOR SEQ ID NO:103:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:103:

GCUUGGCCUG AUGAGGCCGA AAGGCCGAAA UAACAG    36

( 2 ) INFORMATION FOR SEQ ID NO:104:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:104:

GCUUUCCUG AUGAGGCCGA AAGGCCGAAA UUCUCC    36

( 2 ) INFORMATION FOR SEQ ID NO:105:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:105:

UGUCCAGCUG AUGAGGCCGA AAGGCCGAAA GGUUUU    36

( 2 ) INFORMATION FOR SEQ ID NO:106:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:106:

UUCUUGACUG AUGAGGCCGA AAGGCCGAAA GCAUUA    36

( 2 ) INFORMATION FOR SEQ ID NO:107:

( i ) SEQUENCE CHARACTERISTICS:

( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

UCUUCUGCUG AUGAGGCGA AAGGCCGAAA AGCUCG                                  36

( 2 ) INFORMATION FOR SEQ ID NO:108:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

AUGUGGUCUG AUGAGGCCGA AAGGCCGAAA UAGGAA                                  36

( 2 ) INFORMATION FOR SEQ ID NO:109:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

GCCGGCUCUG AUGAGCGCGA AAGCGCGAAA GGGACG                                  36

( 2 ) INFORMATION FOR SEQ ID NO:110:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

GCUCCUUCUG AUGAGGCCGA AAGGCCGAAA UUCGCU                                  36

( 2 ) INFORMATION FOR SEQ ID NO:111:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:111:

UUCUGCACUG AUGAGGCCGA AAGGCCGAAA UUCUAA                                  36

( 2 ) INFORMATION FOR SEQ ID NO:112:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:112:

ACCUUUUCUG AUGAGGCCGA AAGGCCGAAA UAGCUG                                  36

( 2 ) INFORMATION FOR SEQ ID NO:113:

( i ) SEQUENCE CHARACTERISTICS:
        ( A ) LENGTH: 36 base pairs
        ( B ) TYPE: nucleic acid ( C ) STRANDEDNESS: single
( D ) TOPOLOGY: linear ( x i ) SEQUENCE DESCRIPTION: SEQ ID NO:113:

AUGUUUGCUG AUGAGGCCGA AAGGCCGAAA UGGUGU     36

( 2 ) INFORMATION FOR SEQ ID NO:114:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:114:

CAUGUUUCUG AUGAGGCCGA AAGGCCGAAA AUGGUG     36

( 2 ) INFORMATION FOR SEQ ID NO:115:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:115:

UUCAGGGCUG AUGAGGCCGA AAGGCCGAAA CCGUAU     36

( 2 ) INFORMATION FOR SEQ ID NO:116:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

CAGCAACCUG AUGAGGCCGA AAGGCCGAAA UUCCAG     36

( 2 ) INFORMATION FOR SEQ ID NO:117:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

ACUCAGCCUG AUGAGGCCGA AAGGCCGAAA CAAUUC     36

( 2 ) INFORMATION FOR SEQ ID NO:118:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:118:

AGCUUGUCUG AUGAGGCCGA AAGGCCGAAA GAAUAU     36

( 2 ) INFORMATION FOR SEQ ID NO:119:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (xi) SEQUENCE DESCRIPTION: SEQ ID NO:119:

UGUCAUUCUG AUGAGGCCGA AAGGCCGAAA AACAGA          36

(2) INFORMATION FOR SEQ ID NO:120:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:120:

CUUUGAGCUG AUGAGGCCGA AAGGCCGAAA CAUUGU          36

(2) INFORMATION FOR SEQ ID NO:121:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:121:

UCAGGGAGAA GUAUACCAGA GAAACACACG CG          32

(2) INFORMATION FOR SEQ ID NO:122:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:122:

GCUCUCAGAA GUUGACCAGA GAAACACACG CG          32

(2) INFORMATION FOR SEQ ID NO:123:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:123:

CUUUCCCUGA UGAGGCCGAA AGGCCGAAAU UCUC          34

(2) INFORMATION FOR SEQ ID NO:124:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:124:

UGCUUUCCCU GAUGAGGCCG AAAGGCCGAA AUUCUCCC          38

(2) INFORMATION FOR SEQ ID NO:125:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:125:

```
CUGCUUUCCC  UGAUGAGGCC  GAAAGGCCGA  AAUUCUCCCU                                40
```

( 2 ) INFORMATION FOR SEQ ID NO:126:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:126:

```
ACUGCUUUCC  CUGAUGAGGC  CGAAAGGCCG  AAAUUCUCCC  UU                            42
```

( 2 ) INFORMATION FOR SEQ ID NO:127:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

```
ACACUGCUUU  CCCUGAUGAG  GCCGAAAGGC  CGAAAUUCUC  CCUUUU                        46
```

( 2 ) INFORMATION FOR SEQ ID NO:128:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

```
AGUGCUUGGC  AACUGAUGAG  GCCGAAAGGC  CGAAAACAGA  CCAACG                        46
```

( 2 ) INFORMATION FOR SEQ ID NO:129:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

```
GAUUGACCUU  UUCUGAUGAG  GCCGAAAGGC  CGAAAUAGCU  GGAGUU                        46
```

( 2 ) INFORMATION FOR SEQ ID NO:130:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

```
GCGCAGCCGG  GGAGGG                                                            16
```

( 2 ) INFORMATION FOR SEQ ID NO:131:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

```
CGGCAGCCCG  GUCGGU                                                            16
```

( 2 ) INFORMATION FOR SEQ ID NO:132:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

CCGCCGCCCG CCGCGC 16

( 2 ) INFORMATION FOR SEQ ID NO:133:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

AUACGGUCCG AAACGU 16

( 2 ) INFORMATION FOR SEQ ID NO:134:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

CUACUGCCUG GACGAA 16

( 2 ) INFORMATION FOR SEQ ID NO:135:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

CAGCUGCCGC AGCCAU 16

( 2 ) INFORMATION FOR SEQ ID NO:136:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

UUGCCGACCA CACCAG 16

( 2 ) INFORMATION FOR SEQ ID NO:137:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

AUACUGUUUU UAGAAC 16

( 2 ) INFORMATION FOR SEQ ID NO:138:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

AUACGGUCCC CUGAAG         16

( 2 ) INFORMATION FOR SEQ ID NO:139:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

GGACAGUCUG AAUACC         16

( 2 ) INFORMATION FOR SEQ ID NO:140:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

CAACUGUUCA CGCAGA         16

( 2 ) INFORMATION FOR SEQ ID NO:141:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

ACGCAGACCU CGCCUG         16

( 2 ) INFORMATION FOR SEQ ID NO:142:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

UUGCAGCCUU GUAGCA         16

( 2 ) INFORMATION FOR SEQ ID NO:143:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

CAACAGUUGA GAGCAG         16

( 2 ) INFORMATION FOR SEQ ID NO:144:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (xi) SEQUENCE DESCRIPTION: SEQ ID NO:144:

UAACAGUCUU ACCUAA                                                                      16

(2) INFORMATION FOR SEQ ID NO:145:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:145:

UGACUGUUUU AUAAUU                                                                      16

(2) INFORMATION FOR SEQ ID NO:146:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:146:

GAACUGUUGC AUGGAU                                                                      16

(2) INFORMATION FOR SEQ ID NO:147:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:147:

UCACUGCCUU AAGAAC                                                                      16

(2) INFORMATION FOR SEQ ID NO:148:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:148:

UUACUGCCUU GUAGCA                                                                      16

(2) INFORMATION FOR SEQ ID NO:149:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:149:

CCCUCCCCAG AAGCGCACCA GAGAAACACA CGUUGUGGUA CAUUACCUGG UA                               52

(2) INFORMATION FOR SEQ ID NO:150:

(i) SEQUENCE CHARACTERISTICS:
        (A) LENGTH: 52 base pairs (B) TYPE: nucleic acid
(C) STRANDEDNESS: single
(D) TOPOLOGY: linear (xi) SEQUENCE DESCRIPTION: SEQ ID NO:150:

ACCGACCGAG AAGCCGACCA GAGAAACACA CGUUGUGGUA CAUUACCUGG UA    52

(2) INFORMATION FOR SEQ ID NO:151:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:151:

GCGCGGCGAG AAGCGGACCA GAGAAACACA CGUUGUGGUA CAUUACCUGG UA    52

(2) INFORMATION FOR SEQ ID NO:152:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:152:

ACGUUUCGAG AAGUAUACCA GAGAAACACA CGUUGUGGUA CAUUACCUGG UA    52

(2) INFORMATION FOR SEQ ID NO:153:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:153:

UUCGUCCAAG AAGUAGACCA GAGAAACACA CGUUGUGGUA CAUUACCUGG UA    52

(2) INFORMATION FOR SEQ ID NO:154:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:154:

AUGGCUGCAG AAGCUGACCA GAGAAACACA CGUUGUGGUA CAUUACCUGG UA    52

(2) INFORMATION FOR SEQ ID NO:155:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:155:

CUGGUGUGAG AAGCAAACCA GAGAAACACA CGUUGUGGUA CAUUACCUGG UA    52

(2) INFORMATION FOR SEQ ID NO:156:

(i) SEQUENCE CHARACTERISTICS:
(A) LENGTH: 52 base pairs
(B) TYPE: nucleic acid
(C) STRANDEDNESS: single (D) TOPOLOGY: linear (xi) SEQUENCE DESCRIPTION: SEQ ID NO:156:

GUUCUAAAAG AAGUAUACCA GAGAAACACA CGUUGUGGUA CAUUACCUGG UA 52

(2) INFORMATION FOR SEQ ID NO:157:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:157:

CUUCAGGGAG AAGUAUACCA GAGAAACACA CGUUGUGGUA CAUUACCUGG UA 52

(2) INFORMATION FOR SEQ ID NO:158:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:158:

GGUAUUCAAG AAGUCCACCA GAGAAACACA CGUUGUGGUA CAUUACCUGG UA 52

(2) INFORMATION FOR SEQ ID NO:159:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:159:

UCUGCGUGAG AAGUUGACCA GAGAAACACA CGUUGUGGUA CAUUACCUGG UA 52

(2) INFORMATION FOR SEQ ID NO:160:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:160:

CAGGCGAGAG AAGCGUACCA GAGAAACACA CGUUGUGGUA CAUUACCUGG UA 52

(2) INFORMATION FOR SEQ ID NO:161:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:161:

UGCUACAAAG AAGCAAACCA GAGAAACACA CGUUGUGGUA CAUUACCUGG UA 52

(2) INFORMATION FOR SEQ ID NO:162:

(i) SEQUENCE CHARACTERISTICS:
        (A) LENGTH: 52 base pairs
        (B) TYPE: nucleic acid
        (C) STRANDEDNESS: single
        (D) TOPOLOGY: linear ( x i ) SEQUENCE DESCRIPTION: SEQ ID NO:162:

CUGCUCUCAG AAGUUGACCA GAGAAACACA CGUUGUGGUA CAUUACCUGG UA     52

( 2 ) INFORMATION FOR SEQ ID NO:163:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:163:

UUAGGUAAAG AAGUUAACCA GAGAAACACA CGUUGUGGUA CAUUACCUGG UA     52

( 2 ) INFORMATION FOR SEQ ID NO:164:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:164:

AAUUAUAAAG AAGUCAACCA GAGAAACACA CGUUGUGGUA CAUUACCUGG UA     52

( 2 ) INFORMATION FOR SEQ ID NO:165:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:165:

AUCCAUGCAG AAGUUCACCA GAGAAACACA CGUUGUGGUA CAUUACCUGG UA     52

( 2 ) INFORMATION FOR SEQ ID NO:166:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:166:

GUUCUUAAAG AAGUGAACCA GAGAAACACA CGUUGUGGUA CAUUACCUGG UA     52

( 2 ) INFORMATION FOR SEQ ID NO:167:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:167:

UGCUACAAAG AAGUAAACCA GAGAAACACA CGUUGUGGUA CAUUACCUGG UA     52

( 2 ) INFORMATION FOR SEQ ID NO:168:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:168:

```
CGCGUGGUAC AUUACCUGGU A                                                                21
```

( 2 ) INFORMATION FOR SEQ ID NO:169:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:169:

```
CGCGUGGUAC AUUACCUGGU A                                                                21
```

( 2 ) INFORMATION FOR SEQ ID NO:170:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:170:

```
AACCUGUUUC CUCCUCC                                                                     17
```

( 2 ) INFORMATION FOR SEQ ID NO:171:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:171:

```
GGAGGAGGCU GAUGAGGCCG AAAGGCCGAA AACAGGUU                                              38
```

( 2 ) INFORMATION FOR SEQ ID NO:172:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:172:

```
ACCUGUUUCC UCCUCCU                                                                     17
```

( 2 ) INFORMATION FOR SEQ ID NO:173:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:173:

```
AGGAGGAGCU GAUGAGGCCG AAAGGCCGAA AACAGGU                                               38
```

( 2 ) INFORMATION FOR SEQ ID NO:174:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

```
UGUUUCCUCC UCCUCCU                                                                     17
```

( 2 ) INFORMATION FOR SEQ ID NO:175:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

AGGAGGAGCU GAUGAGGCCG AAAGGCCGAA AGGAAACA        38

( 2 ) INFORMATION FOR SEQ ID NO:176:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

UUCCUCCUCC UCCUUCU        17

( 2 ) INFORMATION FOR SEQ ID NO:177:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:177:

AGAAGGAGCU GAUGAGGCCG AAAGGCCGAA AGGAGGAA        38

( 2 ) INFORMATION FOR SEQ ID NO:178:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:178:

CUCCUCCUCC UUCUCCU        17

( 2 ) INFORMATION FOR SEQ ID NO:179:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:179:

AGGAGAAGCU GAUGAGGCCG AAAGGCCGAA AGGAGGAG        38

( 2 ) INFORMATION FOR SEQ ID NO:180:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:180:

CUCCUCCUUC UCCUCCU        17

( 2 ) INFORMATION FOR SEQ ID NO:181:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:181:

AGGAGGAGCU GAUGAGGCCG AAAGGCCGAA AGGAGGAG                38

( 2 ) INFORMATION FOR SEQ ID NO:182:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:182:

UCCUCCUUCU CCUCCUC                                       17

( 2 ) INFORMATION FOR SEQ ID NO:183:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:183:

GAGGAGGACU GAUGAGGCCG AAAGGCCGAA AAGGAGGA                38

( 2 ) INFORMATION FOR SEQ ID NO:184:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:184:

CUCCUUCUCC UCCUCCU                                       17

( 2 ) INFORMATION FOR SEQ ID NO:185:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:185:

AGGAGGAGCU GAUGAGGCCG AAAGGCCGAA AGAAGGAG                38

( 2 ) INFORMATION FOR SEQ ID NO:186:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:186:

CUUCUCCUCC UCCUCCG                                       17

( 2 ) INFORMATION FOR SEQ ID NO:187:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:187:

CGGAGGAGCU GAUGAGGCCG AAAGGCCGAA AGGAGAAG 38

(2) INFORMATION FOR SEQ ID NO:188:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:188:

CUCCUCCUCC UCCGUGA 17

(2) INFORMATION FOR SEQ ID NO:189:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:189:

UCACGGAGCU GAUGAGGCCG AAAGGCCGAA AGGAGGAG 38

(2) INFORMATION FOR SEQ ID NO:190:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:190:

CUCCUCCUCC GUGACCU 17

(2) INFORMATION FOR SEQ ID NO:191:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:191:

AGGUCACGCU GAUGAGGCCG AAAGGCCGAA AGGAGGAG 38

(2) INFORMATION FOR SEQ ID NO:192:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:192:

CGUGACCUCC UCCUCCU 17

(2) INFORMATION FOR SEQ ID NO:193:

(i) SEQUENCE CHARACTERISTICS:
(A) LENGTH: 38 base pairs
(B) TYPE: nucleic acid ( C ) STRANDEDNESS: single
        ( D ) TOPOLOGY: linear ( x i ) SEQUENCE DESCRIPTION: SEQ ID NO:193:

AGGAGGAGCU GAUGAGGCCG AAAGGCCGAA AGGUCACG                                    3 8

( 2 ) INFORMATION FOR SEQ ID NO:194:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:194:

GACCUCCUCC UCCUCUU                                                           1 7

( 2 ) INFORMATION FOR SEQ ID NO:195:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:195:

AAGAGGAGCU GAUGAGGCCG AAAGGCCGAA AGGAGGUC                                    3 8

( 2 ) INFORMATION FOR SEQ ID NO:196:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:196:

CUCCUCCUCC UCUUUCU                                                           1 7

( 2 ) INFORMATION FOR SEQ ID NO:197:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:197:

AGAAAGAGCU GAUGAGGCCG AAAGGCCGAA AGGAGGAG                                    3 8

( 2 ) INFORMATION FOR SEQ ID NO:198:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:198:

CUCCUCCUCU UUCUCCU                                                           1 7

( 2 ) INFORMATION FOR SEQ ID NO:199:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:199:

AGGAGAAACU GAUGAGGCCG AAAGGCCGAA AGGAGGAG 38

( 2 ) INFORMATION FOR SEQ ID NO:200:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:200:

CCUCCUCUUU CUCCUGA 17

( 2 ) INFORMATION FOR SEQ ID NO:201:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:201:

UCAGGAGACU GAUGAGGCCG AAAGGCCGAA AGAGGAGG 38

( 2 ) INFORMATION FOR SEQ ID NO:202:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

CUCCUCUUUC UCCUGAG 17

( 2 ) INFORMATION FOR SEQ ID NO:203:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

CUCAGGAGCU GAUGAGGCCG AAAGGCCGAA AAGAGGAG 38

( 2 ) INFORMATION FOR SEQ ID NO:204:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

UCCUCUUUCU CCUGAGA 17

( 2 ) INFORMATION FOR SEQ ID NO:205:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

```
    UCUCAGGACU  GAUGAGGCCG  AAAGGCCGAA  AAAGAGGA                              38
```

( 2 ) INFORMATION FOR SEQ ID NO:206:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:206:

```
    CUCUUUCUCC  UGAGAAA                                                       17
```

( 2 ) INFORMATION FOR SEQ ID NO:207:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:207:

```
    UUUCUCAGCU  GAUGAGGCCG  AAAGGCCGAA  AGAAAGAG                              38
```

( 2 ) INFORMATION FOR SEQ ID NO:208:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:208:

```
    GAGAAACUUC  GCCCCAG                                                       17
```

( 2 ) INFORMATION FOR SEQ ID NO:209:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:209:

```
    CUGGGGCGCU  GAUGAGGCCG  AAAGGCCGAA  AGUUCUC                               38
```

( 2 ) INFORMATION FOR SEQ ID NO:210:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:210:

```
    AGAAACUUCG  CCCCAGC                                                       17
```

( 2 ) INFORMATION FOR SEQ ID NO:211:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:211:

```
    GCUGGGGCCU  GAUGAGGCCG  AAAGGCCGAA  AAGUUUCU                              38
```

( 2 ) INFORMATION FOR SEQ ID NO:212:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:212:

CCGCGGCUCU CGCGGAG 17

( 2 ) INFORMATION FOR SEQ ID NO:213:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:213:

CUCCGCGACU GAUGAGGCCG AAAGGCCGAA AGCCGCGG 38

( 2 ) INFORMATION FOR SEQ ID NO:214:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:214:

GCGGCUCUCG CGGAGCC 17

( 2 ) INFORMATION FOR SEQ ID NO:215:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:215:

GGCUCCGCCU GAUGAGGCCG AAAGGCCGAA AGAGCCGC 38

( 2 ) INFORMATION FOR SEQ ID NO:216:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:216:

CACAGCAUAU AUAGCAG 17

( 2 ) INFORMATION FOR SEQ ID NO:217:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:217:

CUGCUAUACU GAUGAGGCCG AAAGGCCGAA AUGCUGUG 38

( 2 ) INFORMATION FOR SEQ ID NO:218:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:218:

CAGCAUAUAU AGCAGUG                          17

( 2 ) INFORMATION FOR SEQ ID NO:219:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:219:

CACUGCUACU GAUGAGGCCG AAAGGCCGAA AUAUGCUG        38

( 2 ) INFORMATION FOR SEQ ID NO:220:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:220:

GCAUAUAUAG CAGUGAC                          17

( 2 ) INFORMATION FOR SEQ ID NO:221:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

GUCACUGCCU GAUGAGGCCG AAAGGCCGAA AUAUAUGC        38

( 2 ) INFORMATION FOR SEQ ID NO:222:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:222:

UGAGGACUUU GAGAUGU                          17

( 2 ) INFORMATION FOR SEQ ID NO:223:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:223:

ACAUCUCACU GAUGAGGCCG AAAGGCCGAA AGUCCUCA        38

( 2 ) INFORMATION FOR SEQ ID NO:224:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:224:

GAGGACUUUG AGAUGUG      17

( 2 ) INFORMATION FOR SEQ ID NO:225:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:225:

CACAUCUCCU GAUGAGGCCG AAAGGCCGAA AAGUCCUC      38

( 2 ) INFORMATION FOR SEQ ID NO:226:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:226:

CCAUGACUAU GAUGGGC      17

( 2 ) INFORMATION FOR SEQ ID NO:227:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:227:

GCCCAUCACU GAUGAGGCCG AAAGGCCGAA AGUCAUGG      38

( 2 ) INFORMATION FOR SEQ ID NO:228:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:228:

GGGCUGCUUC CCAAGUC      17

( 2 ) INFORMATION FOR SEQ ID NO:229:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:229:

GACUUGGGCU GAUGAGGCCG AAAGGCCGAA AGCAGCCC      38

( 2 ) INFORMATION FOR SEQ ID NO:230:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:230:

GGCUGCUUCC CAAGUCU                                                              17

(2) INFORMATION FOR SEQ ID NO:231:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:231:

AGACUUGGCU GAUGAGGCCG AAAGGCCGAA AAGCAGCC                                       38

(2) INFORMATION FOR SEQ ID NO:232:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:232:

GCGUCACUUG GGGAAAA                                                              17

(2) INFORMATION FOR SEQ ID NO:233:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:233:

UUUUCCCCU GAUGAGGCCG AAAGGCCGAA AGUGACGC                                        38

(2) INFORMATION FOR SEQ ID NO:234:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:234:

GGAAAGUUAU UGCCAAU                                                              17

(2) INFORMATION FOR SEQ ID NO:235:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:235:

AUUGGCAACU GAUGAGGCCG AAAGGCCGAA AACUUUCC                                       38

(2) INFORMATION FOR SEQ ID NO:236:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO:236:

AAAGUUAUUG CCAAUUA  17

(2) INFORMATION FOR SEQ ID NO:237:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:237:

UAAUUGGCCU GAUGAGGCCG AAAGGCCGAA AUAACUUU  38

(2) INFORMATION FOR SEQ ID NO:238:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:238:

UUGCCAAUUA UCUCCCG  17

(2) INFORMATION FOR SEQ ID NO:239:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:239:

CGGGAGAUCU GAUGAGGCCG AAAGGCCGAA AUUGGCAA  38

(2) INFORMATION FOR SEQ ID NO:240:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:240:

UGCCAAUUAU CUCCCGA  17

(2) INFORMATION FOR SEQ ID NO:241:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:241:

UCGGGAGACU GAUGAGGCCG AAAGGCCGAA AAUUGGCA  38

(2) INFORMATION FOR SEQ ID NO:242:

(i) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:242:

CCAAUUAUCU CCCGAAU 17

( 2 ) INFORMATION FOR SEQ ID NO:243:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:243:

AUUCGGGACU GAUGAGGCCG AAAGGCCGAA AUAAUUGG 38

( 2 ) INFORMATION FOR SEQ ID NO:244:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:244:

AAUUAUCUCC CGAAUCG 17

( 2 ) INFORMATION FOR SEQ ID NO:245:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:245:

CGAUUCGGCU GAUGAGGCCG AAAGGCCGAA AGAUAAUU 38

( 2 ) INFORMATION FOR SEQ ID NO:246:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:246:

UCCCGAAUCG AACAGAU 17

( 2 ) INFORMATION FOR SEQ ID NO:247:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:247:

AUCUGUUCCU GAUGAGGCCG AAAGGCCGAA AUUCGGGA 38

( 2 ) INFORMATION FOR SEQ ID NO:248:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:248:

```
AAAGUACUAA ACCCUGA                                                                      17
```

( 2 ) INFORMATION FOR SEQ ID NO:249:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:249:

```
UCAGGGUUCU GAUGAGGCCG AAAGGCCGAA AGUACUUU                                                38
```

( 2 ) INFORMATION FOR SEQ ID NO:250:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:250:

```
CCUGAGCUCA UCAAGGG                                                                      17
```

( 2 ) INFORMATION FOR SEQ ID NO:251:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:251:

```
CCCUUGAUCU GAUGAGGCCG AAAGGCCGAA AGCUCAGG                                                38
```

( 2 ) INFORMATION FOR SEQ ID NO:252:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:252:

```
GAGCUCAUCA AGGGUCC                                                                      17
```

( 2 ) INFORMATION FOR SEQ ID NO:253:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:253:

```
GGACCCUUCU GAUGAGGCCG AAAGGCCGAA AUGAGCUC                                                38
```

( 2 ) INFORMATION FOR SEQ ID NO:254:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:254:

```
AGGGUCCUUG GACCAAA                                                                      17
```

( 2 ) INFORMATION FOR SEQ ID NO:255:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:255:

UUUGGUCCCU GAUGAGGCCG AAAGGCCGAA AGGACCCU                    38

( 2 ) INFORMATION FOR SEQ ID NO:256:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:256:

AAGAAGAUCA GAGAGUG                                          17

( 2 ) INFORMATION FOR SEQ ID NO:257:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:257:

CACUCUCUCU GAUGAGGCCG AAAGGCCGAA AUCUUCUU                    38

( 2 ) INFORMATION FOR SEQ ID NO:258:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:258:

AGAGUGAUAG AGCUUGU                                          17

( 2 ) INFORMATION FOR SEQ ID NO:259:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:259:

ACAAGCUCCU GAUGAGGCCG AAAGGCCGAA AUCACUCU                    38

( 2 ) INFORMATION FOR SEQ ID NO:260:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:260:

AUAGAGCUUG UACAGAA                                          17

( 2 ) INFORMATION FOR SEQ ID NO:261:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:261:

UUCUGUACCU GAUGAGGCCG AAAGGCGAA AGCUCUAU    38

( 2 ) INFORMATION FOR SEQ ID NO:262:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:262:

ACAGAAAUAC GGUCCGA    17

( 2 ) INFORMATION FOR SEQ ID NO:263:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:263:

UCGGACCGCU GAUGAGGCCG AAAGGCCGAA AUUUCUGU    38

( 2 ) INFORMATION FOR SEQ ID NO:264:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:264:

GGUCUGUUAU UGCCAAG    17

( 2 ) INFORMATION FOR SEQ ID NO:265:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:265:

CUUGGCAACU GAUGAGGCCG AAAGGCCGAA AACAGACC    38

( 2 ) INFORMATION FOR SEQ ID NO:266:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:266:

UCUGUUAUUG CCAAGCA    17

( 2 ) INFORMATION FOR SEQ ID NO:267:

( i ) SEQUENCE CHARACTERISTICS:

( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:267:

UGCUUGGCCU GAUGAGGCCG AAAGGCCGAA AUAACAGA        38

( 2 ) INFORMATION FOR SEQ ID NO:268:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:268:

CAAGCACUUA AAGGGGA        17

( 2 ) INFORMATION FOR SEQ ID NO:269:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:269:

UCCCCUUUCU GAUGAGGCCG AAAGGCCGAA AGUGCUUG        38

( 2 ) INFORMATION FOR SEQ ID NO:270:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:270:

AAGCACUUAA AGGGGAG        17

( 2 ) INFORMATION FOR SEQ ID NO:271:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:271:

CUCCCUUCU GAUGAGGCCG AAAGGCCGAA AAGUGCUU        38

( 2 ) INFORMATION FOR SEQ ID NO:272:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:272:

GGGAGAAUUG GAAAACA        17

( 2 ) INFORMATION FOR SEQ ID NO:273:

( i ) SEQUENCE CHARACTERISTICS:
( A ) LENGTH: 38 base pairs
( B ) TYPE: nucleic acid ( C ) STRANDEDNESS: single
( D ) TOPOLOGY: linear ( x i ) SEQUENCE DESCRIPTION: SEQ ID NO:273:

UGUUUCCCU GAUGAGGCCG AAAGGCCGAA AUUCUCCC 38

( 2 ) INFORMATION FOR SEQ ID NO:274:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:274:

GGUGGCAUAA CCACUUG 17

( 2 ) INFORMATION FOR SEQ ID NO:275:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:275:

CAAGUGGUCU GAUGAGGCCG AAAGGCCGAA AUGCCACC 38

( 2 ) INFORMATION FOR SEQ ID NO:276:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:276:

UAACCACUUG AAUCCAG 17

( 2 ) INFORMATION FOR SEQ ID NO:277:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:277:

CUGGAUUCCU GAUGAGGCCG AAAGGCCGAA AGUGGUUA 38

( 2 ) INFORMATION FOR SEQ ID NO:278:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:278:

ACUUGAAUCC AGAAGUU 17

( 2 ) INFORMATION FOR SEQ ID NO:279:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:279:

AACUUCUGCU GAUGAGGCCG AAAGGCCGAA AUUCAAGU              38

( 2 ) INFORMATION FOR SEQ ID NO:280:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:280:

CAGAAGUUAA GAAAACC              17

( 2 ) INFORMATION FOR SEQ ID NO:281:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:281:

GGUUUUCUCU GAUGAGGCCG AAAGGCCGAA AACUUCUG              38

( 2 ) INFORMATION FOR SEQ ID NO:282:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:282:

GAAAACCUCC UGGACAG              17

( 2 ) INFORMATION FOR SEQ ID NO:283:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:283:

CUGUCCAGCU GAUGAGGCCG AAAGGCCGAA AGGUUUUC              38

( 2 ) INFORMATION FOR SEQ ID NO:284:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:284:

GACAGAAUUA UUUACCA              17

( 2 ) INFORMATION FOR SEQ ID NO:285:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:285:

```
UGGUAAAUCU GAUGAGGCCG AAAGGCCGAA AUUCUGUC                                    38
```

( 2 ) INFORMATION FOR SEQ ID NO:286:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:286:

```
ACAGAAUUAU UUACCAG                                                           17
```

( 2 ) INFORMATION FOR SEQ ID NO:287:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:287:

```
CUGGUAAACU GAUGAGGCCG AAAGGCCGAA AAUUCUGU                                    38
```

( 2 ) INFORMATION FOR SEQ ID NO:288:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:288:

```
AGAAUUAUUU ACCAGGC                                                           17
```

( 2 ) INFORMATION FOR SEQ ID NO:289:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:289:

```
GCCUGGUACU GAUGAGGCCG AAAGGCCGAA AUAAUUCU                                    38
```

( 2 ) INFORMATION FOR SEQ ID NO:290:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:290:

```
GAAUUAUUUA CCAGGCA                                                           17
```

( 2 ) INFORMATION FOR SEQ ID NO:291:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:291:

```
UGCCUGGUCU GAUGAGGCCG AAAGGCCGAA AAUAAUUC                                    38
```

( 2 ) INFORMATION FOR SEQ ID NO:292:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:292:

AAUUAUUUAC CAGGCAC                                                          17

( 2 ) INFORMATION FOR SEQ ID NO:293:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:293:

GUGCCUGGCU GAUGAGGCCG AAAGGCCGAA AAAUAAUU                                   38

( 2 ) INFORMATION FOR SEQ ID NO:294:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:294:

GCAGAAAUCG CAAAGCU                                                          17

( 2 ) INFORMATION FOR SEQ ID NO:295:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:295:

AGCUUUGCCU GAUGAGGCCG AAAGGCCGAA AUUUCUGC                                   38

( 2 ) INFORMATION FOR SEQ ID NO:296:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:296:

GCAAAGCUAC UGCCUGG                                                          17

( 2 ) INFORMATION FOR SEQ ID NO:297:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:297:

CCAGGCAGCU GAUGAGGCCG AAAGGCCGAA AGCUUUGC                                   38

( 2 ) INFORMATION FOR SEQ ID NO:298:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:298:

GAACUGAUAA UGCUAUC                                                            17

( 2 ) INFORMATION FOR SEQ ID NO:299:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:299:

GAUAGCAUCU GAUGAGGCCG AAAGGCCGAA AUCAGUUC               38

( 2 ) INFORMATION FOR SEQ ID NO:300:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:300:

AUAAUGCUAU CAAGAAC                                                           17

( 2 ) INFORMATION FOR SEQ ID NO:301:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:301:

GUUCUUGACU GAUGAGGCCG AAAGGCCGAA AGCAUUAU               38

( 2 ) INFORMATION FOR SEQ ID NO:302:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:302:

AAUGCUAUCA AGAACCA                                                           17

( 2 ) INFORMATION FOR SEQ ID NO:303:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:303:

UGGUUCUUCU GAUGAGGCCG AAAGGCCGAA AUAGCAUU               38

( 2 ) INFORMATION FOR SEQ ID NO:304:

( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:304:

ACUGGAAUUC UACAAUG 17

( 2 ) INFORMATION FOR SEQ ID NO:305:

: ( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:305:

CAUUGUAGCU GAUGAGGCCG AAAGGCCGAA AUUCCAGU 38

( 2 ) INFORMATION FOR SEQ ID NO:306:

: ( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:306:

CUGGAAUUCU ACAAUGC 17

( 2 ) INFORMATION FOR SEQ ID NO:307:

: ( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:307:

GCAUUGUACU GAUGAGGCCG AAAGGCCGAA AAUUCCAG 38

( 2 ) INFORMATION FOR SEQ ID NO:308:

: ( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:308:

GGAAUUCUAC AAUGCGU 17

( 2 ) INFORMATION FOR SEQ ID NO:309:

: ( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:309:

ACGCAUUGCU GAUGAGGCCG AAAGGCCGAA AGAAUUCC 38

( 2 ) INFORMATION FOR SEQ ID NO:310:

: ( i ) SEQUENCE CHARACTERISTICS:
: ( A ) LENGTH: 17 base pairs ( B ) TYPE: nucleic acid
( C ) STRANDEDNESS: single
( D ) TOPOLOGY: linear ( x i ) SEQUENCE DESCRIPTION: SEQ ID NO:310:

GGAAGGUUAU CUGCAGG 17

( 2 ) INFORMATION FOR SEQ ID NO:311:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:311:

CCUGCAGACU GAUGAGGCCG AAAGGCCGAA AACCUUCC 38

( 2 ) INFORMATION FOR SEQ ID NO:312:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:312:

AAGGUUAUCU GCAGGAG 17

( 2 ) INFORMATION FOR SEQ ID NO:313:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:313:

CUCCUGCACU GAUGAGGCCG AAAGGCCGAA AUAACCUU 38

( 2 ) INFORMATION FOR SEQ ID NO:314:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:314:

AGGAGUCUUC AAAAGCC 17

( 2 ) INFORMATION FOR SEQ ID NO:315:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:315:

GGCUUUUGCU GAUGAGGCCG AAAGGCCGAA AGACUCCU 38

( 2 ) INFORMATION FOR SEQ ID NO:316:

( i ) SEQUENCE CHARACTERISTICS:
( A ) LENGTH: 17 base pairs
( B ) TYPE: nucleic acid
( C ) STRANDEDNESS: single ( D ) TOPOLOGY: linear ( x i ) SEQUENCE DESCRIPTION: SEQ ID NO:316:

GGAGUCUUCA AAAGCCA                                                                                                  17

( 2 ) INFORMATION FOR SEQ ID NO:317:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:317:

UGGCUUUUCU GAUGAGGCCG AAAGGCCGAA AAGACUCC                                                                            38

( 2 ) INFORMATION FOR SEQ ID NO:318:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:318:

CACAAGCUUC CAGAAGA                                                                                                  17

( 2 ) INFORMATION FOR SEQ ID NO:319:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:319:

UCUUCUGGCU GAUGAGGCCG AAAGGCCGAA AGCUUGUG                                                                            38

( 2 ) INFORMATION FOR SEQ ID NO:320:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:320:

ACAAGCUUCC AGAAGAA                                                                                                  17

( 2 ) INFORMATION FOR SEQ ID NO:321:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:321:

UUCUUCUGCU GAUGAGGCCG AAAGGCCGAA AAGCUUGU                                                                            38

( 2 ) INFORMATION FOR SEQ ID NO:322:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:322:

ACAGUCAUUU GAUGGGU 17

( 2 ) INFORMATION FOR SEQ ID NO:323:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:323:

ACCCAUCACU GAUGAGGCCG AAAGGCCGAA AUGACUGU 38

( 2 ) INFORMATION FOR SEQ ID NO:324:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:324:

CAGUCAUUUG AUGGGUU 17

( 2 ) INFORMATION FOR SEQ ID NO:325:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:325:

AACCCAUCCU GAUGAGGCCG AAAGGCCGAA AAUGACUG 38

( 2 ) INFORMATION FOR SEQ ID NO:326:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:326:

GAUGGGUUUU GCUCAGG 17

( 2 ) INFORMATION FOR SEQ ID NO:327:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:327:

CCUGAGCACU GAUGAGGCCG AAAGGCCGAA AACCCAUC 38

( 2 ) INFORMATION FOR SEQ ID NO:328:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:328:

AUGGGUUUUG CUCAGGC                                                                                    17

( 2 ) INFORMATION FOR SEQ ID NO:329:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:329:

GCCUGAGCCU GAUGAGGCCG AAAGGCCGAA AAACCCAU                                                              38

( 2 ) INFORMATION FOR SEQ ID NO:330:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:330:

GUUUUGCUCA GGCUCCG                                                                                    17

( 2 ) INFORMATION FOR SEQ ID NO:331:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:331:

CGGAGCCUCU GAUGAGGCCG AAAGGCCGAA AGCAAAAC                                                              38

( 2 ) INFORMATION FOR SEQ ID NO:332:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:332:

CUCAGGCUCC GCCUACA                                                                                    17

( 2 ) INFORMATION FOR SEQ ID NO:333:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:333:

UGUAGGCGCU GAUGAGGCCG AAAGGCCGAA AGCCUGAG                                                              38

( 2 ) INFORMATION FOR SEQ ID NO:334:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:334:

CUCCGCCUAC AGCUCAA                                                                                    17

( 2 ) INFORMATION FOR SEQ ID NO:335:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:335:

UUGAGCUGCU GAUGAGGCCG AAAGGCCGAA AGGCGGAG      38

( 2 ) INFORMATION FOR SEQ ID NO:336:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:336:

CUACAGCUCA ACUCCCU      17

( 2 ) INFORMATION FOR SEQ ID NO:337:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:337:

AGGGAGUUCU GAUGAGGCCG AAAGGCCGAA AGCUGUAG      38

( 2 ) INFORMATION FOR SEQ ID NO:338:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:338:

GCUCAACUCC CUGCCAC      17

( 2 ) INFORMATION FOR SEQ ID NO:339:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:339:

GUGGCAGGCU GAUGAGGCCG AAAGGCCGAA AGUUGAGC      38

( 2 ) INFORMATION FOR SEQ ID NO:340:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:340:

CCACUGUUAA CAACGAC      17

( 2 ) INFORMATION FOR SEQ ID NO:341:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:341:

GUCGUUGUCU GAUGAGGCCG AAAGGCCGAA AACAGUGG 38

( 2 ) INFORMATION FOR SEQ ID NO:342:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:342:

CAACGACUAU UCCUAUU 17

( 2 ) INFORMATION FOR SEQ ID NO:343:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:343:

AAUAGGAACU GAUGAGGCCG AAAGGCCGAA AGUCGUUG 38

( 2 ) INFORMATION FOR SEQ ID NO:344:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:344:

ACGACUAUUC CUAUUAC 17

( 2 ) INFORMATION FOR SEQ ID NO:345:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:345:

GUAAUAGGCU GAUGAGGCCG AAAGGCCGAA AUAGUCGU 38

( 2 ) INFORMATION FOR SEQ ID NO:346:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:346:

CGACUAUUCC UAUUACC 17

( 2 ) INFORMATION FOR SEQ ID NO:347:

( i ) SEQUENCE CHARACTERISTICS:

(A) LENGTH: 38 base pairs
              (B) TYPE: nucleic acid
              (C) STRANDEDNESS: single
              (D) TOPOLOGY: linear (xi) SEQUENCE DESCRIPTION: SEQ ID NO:347:

GGUAAUAGCU GAUGAGGCCG AAAGGCCGAA AAUAGUCG    38

(2) INFORMATION FOR SEQ ID NO:348:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (xi) SEQUENCE DESCRIPTION: SEQ ID NO:348:

CUAUUCCUAU UACCACA    17

(2) INFORMATION FOR SEQ ID NO:349:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (xi) SEQUENCE DESCRIPTION: SEQ ID NO:349:

UGUGGUAACU GAUGAGGCCG AAAGGCCGAA AGGAAUAG    38

(2) INFORMATION FOR SEQ ID NO:350:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (xi) SEQUENCE DESCRIPTION: SEQ ID NO:350:

AUUCCUAUUA CCACAUU    17

(2) INFORMATION FOR SEQ ID NO:351:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (xi) SEQUENCE DESCRIPTION: SEQ ID NO:351:

AAUGUGGUCU GAUGAGGCCG AAAGGCCGAA AUAGGAAU    38

(2) INFORMATION FOR SEQ ID NO:352:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (xi) SEQUENCE DESCRIPTION: SEQ ID NO:352:

UUCCUAUUAC CACAUUU    17

(2) INFORMATION FOR SEQ ID NO:353:

(i) SEQUENCE CHARACTERISTICS:
              (A) LENGTH: 38 base pairs
              (B) TYPE: nucleic acid (C) STRANDEDNESS: single
(D) TOPOLOGY: linear (xi) SEQUENCE DESCRIPTION: SEQ ID NO:353:

AAAUGUGGCU GAUGAGGCCG AAAGGCCGAA AAUAGGAA  38

(2) INFORMATION FOR SEQ ID NO:354:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:354:

UACCACAUUU CUGAAGC  17

(2) INFORMATION FOR SEQ ID NO:355:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:355:

GCUUCAGACU GAUGAGGCCG AAAGGCCGAA AUGUGGUA  38

(2) INFORMATION FOR SEQ ID NO:356:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:356:

ACCACAUUUC UGAAGCA  17

(2) INFORMATION FOR SEQ ID NO:357:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:357:

UGCUUCAGCU GAUGAGGCCG AAAGGCCGAA AAUGUGGU  38

(2) INFORMATION FOR SEQ ID NO:358:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:358:

CCACAUUUCU GAAGCAC  17

(2) INFORMATION FOR SEQ ID NO:359:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:359:

GUGCUUCACU GAUGAGGCCG AAAGGCCGAA AAAUGUGG 38

( 2 ) INFORMATION FOR SEQ ID NO:360:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:360:

AAAUGUCUCC AGUCAUG 17

( 2 ) INFORMATION FOR SEQ ID NO:361:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:361:

CAUGACUGCU GAUGAGGCCG AAAGGCCGAA AGACAUUU 38

( 2 ) INFORMATION FOR SEQ ID NO:362:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:362:

GUCAUGUUCC AUACCCU 17

( 2 ) INFORMATION FOR SEQ ID NO:363:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:363:

AGGGUAUGCU GAUGAGGCCG AAAGGCCGAA AACAUGAC 38

( 2 ) INFORMATION FOR SEQ ID NO:364:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:364:

UGUUCCAUAC CCUGUAG 17

( 2 ) INFORMATION FOR SEQ ID NO:365:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:365:

```
     CUACAGGGCU GAUGAGGCCG AAAGGCCGAA AUGGAACA                              38
```

( 2 ) INFORMATION FOR SEQ ID NO:366:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:366:

```
     GUAGCGUUAC AUGUAAA                                                    17
```

( 2 ) INFORMATION FOR SEQ ID NO:367:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:367:

```
     UUUACAUGCU GAUGAGGCCG AAAGGCCGAA AACGCUAC                             38
```

( 2 ) INFORMATION FOR SEQ ID NO:368:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:368:

```
     UUACAUGUAA AUAUAGU                                                    17
```

( 2 ) INFORMATION FOR SEQ ID NO:369:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:369:

```
     ACUAUAUUCU GAUGAGGCCG AAAGGCCGAA ACAUGUAA                             38
```

( 2 ) INFORMATION FOR SEQ ID NO:370:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:370:

```
     AUGUAAAUAU AGUCAAU                                                    17
```

( 2 ) INFORMATION FOR SEQ ID NO:371:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:371:

```
     AUUGACUACU GAUGAGGCCG AAAGGCCGAA AUUUACAU                             38
```

( 2 ) INFORMATION FOR SEQ ID NO:372:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:372:

GUAAAUAUAG UCAAUGU       17

( 2 ) INFORMATION FOR SEQ ID NO:373:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:373:

ACAUUGACCU GAUGAGGCCG AAAGGCCGAA AUAUUUAC       38

( 2 ) INFORMATION FOR SEQ ID NO:374:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:374:

AUGUCCCUCA GCCAGCU       17

( 2 ) INFORMATION FOR SEQ ID NO:375:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:375:

AGCUGGCUCU GAUGAGGCCG AAAGGCCGAA AGGGACAU       38

( 2 ) INFORMATION FOR SEQ ID NO:376:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:376:

GCAGCCAUUC AGAGACA       17

( 2 ) INFORMATION FOR SEQ ID NO:377:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:377:

UGUCUCUGCU GAUGAGGCCG AAAGGCCGAA AUGGCUGC       38

( 2 ) INFORMATION FOR SEQ ID NO:378:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:378:

CAGCCAUUCA GAGACAC             17

( 2 ) INFORMATION FOR SEQ ID NO:379:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:379:

GUGUCUCUCU GAUGAGGCCG AAAGGCCGAA AAUGGCUG         38

( 2 ) INFORMATION FOR SEQ ID NO:380:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:380:

GAGACACUAU AAUGAUG             17

( 2 ) INFORMATION FOR SEQ ID NO:381:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:381:

CAUCAUUACU GAUGAGGCCG AAAGGCCGAA AGUGUCUC         38

( 2 ) INFORMATION FOR SEQ ID NO:382:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:382:

GACACUAUAA UGAUGAA             17

( 2 ) INFORMATION FOR SEQ ID NO:383:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:383:

UUCAUCAUCU GAUGAGGCCG AAAGGCCGAA AUAGUGUC         38

( 2 ) INFORMATION FOR SEQ ID NO:384:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:384:

AAGCGAAUAA AGGAAUU                                    17

( 2 ) INFORMATION FOR SEQ ID NO:385:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:385:

AAUUCCUUCU GAUGAGGCCG AAAGGCCGAA AUUCGCUU            38

( 2 ) INFORMATION FOR SEQ ID NO:386:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:386:

AAAGGAAUUA GAAUUGC                                    17

( 2 ) INFORMATION FOR SEQ ID NO:387:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:387:

GCAAUUCUCU GAUGAGGCCG AAAGGCCGAA AUUCCUUU            38

( 2 ) INFORMATION FOR SEQ ID NO:388:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:388:

AAGGAAUUAG AAUUGCU                                    17

( 2 ) INFORMATION FOR SEQ ID NO:389:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:389:

AGCAAUUCCU GAUGAGGCCG AAAGGCCGAA AAUUCCUU            38

( 2 ) INFORMATION FOR SEQ ID NO:390:

( i ) SEQUENCE CHARACTERISTICS:
        ( A ) LENGTH: 17 base pairs ( B ) TYPE: nucleic acid
        ( C ) STRANDEDNESS: single
        ( D ) TOPOLOGY: linear ( x i ) SEQUENCE DESCRIPTION: SEQ ID NO:390:

AUUAGAAUUG CUCCUAA 17

( 2 ) INFORMATION FOR SEQ ID NO:391:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:391:

UUAGGAGCCU GAUGAGGCCG AAAGGCCGAA AUUCUAAU 38

( 2 ) INFORMATION FOR SEQ ID NO:392:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:392:

GAAUUGCUCC UAAUGUC 17

( 2 ) INFORMATION FOR SEQ ID NO:393:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:393:

GACAUUAGCU GAUGAGGCCG AAAGGCCGAA AGCAAUUC 38

( 2 ) INFORMATION FOR SEQ ID NO:394:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:394:

UUGCUCCUAA UGUCAAC 17

( 2 ) INFORMATION FOR SEQ ID NO:395:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:395:

GUUGACAUCU GAUGAGGCCG AAAGGCCGAA AGGAGCAA 38

( 2 ) INFORMATION FOR SEQ ID NO:396:

( i ) SEQUENCE CHARACTERISTICS:
        ( A ) LENGTH: 17 base pairs
        ( B ) TYPE: nucleic acid
        ( C ) STRANDEDNESS: single ( D ) TOPOLOGY: linear ( x i ) SEQUENCE DESCRIPTION: SEQ ID NO: 396:

AAUGAGCUAA AAGGACA                              17

( 2 ) INFORMATION FOR SEQ ID NO:397:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:397:

UGUCCUUUCU GAUGAGGCCG AAAGGCCGAA AGCUCAUU                              38

( 2 ) INFORMATION FOR SEQ ID NO:398:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:398:

AUGCAGCUAC CCCGGGU                              17

( 2 ) INFORMATION FOR SEQ ID NO:399:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:399:

ACCCGGGGCU GAUGAGGCCG AAAGGCCGAA AGCUGCAU                              38

( 2 ) INFORMATION FOR SEQ ID NO:400:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:400:

ACCACCAUUG CCGACCA                              17

( 2 ) INFORMATION FOR SEQ ID NO:401:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:401:

UGGUCGGCCU GAUGAGGCCG AAAGGCCGAA AUGGUGGU                              38

( 2 ) INFORMATION FOR SEQ ID NO:402:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (xi) SEQUENCE DESCRIPTION: SEQ ID NO:402:

CCAGACCUCA UGGAGAC                                                        17

(2) INFORMATION FOR SEQ ID NO:403:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:403:

GUCUCCAUCU GAUGAGGCCG AAAGGCCGAA AGGUCUGG                                 38

(2) INFORMATION FOR SEQ ID NO:404:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:404:

CACCUGUUUC CUGUUUG                                                        17

(2) INFORMATION FOR SEQ ID NO:405:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:405:

CAAACAGGCU GAUGAGGCCG AAAGGCCGAA AACAGGUG                                 38

(2) INFORMATION FOR SEQ ID NO:406:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:406:

ACCUGUUUCC UGUUUGG                                                        17

(2) INFORMATION FOR SEQ ID NO:407:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:407:

CCAAACAGCU GAUGAGGCCG AAAGGCCGAA AAACAGGU                                 38

(2) INFORMATION FOR SEQ ID NO:408:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:408:

UUCCUGUUUG GGAGAAC                    17

( 2 ) INFORMATION FOR SEQ ID NO:409:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:409:

GUUCUCCCCU GAUGAGGCCG AAAGGCCGAA AACAGGAA                    38

( 2 ) INFORMATION FOR SEQ ID NO:410:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:410:

ACACCACUCC ACUCCAU                    17

( 2 ) INFORMATION FOR SEQ ID NO:411:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:411:

AUGGAGUGCU GAUGAGGCCG AAAGGCCGAA AGUGGUGU                    38

( 2 ) INFORMATION FOR SEQ ID NO:412:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:412:

ACUCCACUCC AUCUCUG                    17

( 2 ) INFORMATION FOR SEQ ID NO:413:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:413:

CAGAGAUGCU GAUGAGGCCG AAAGGCCGAA AGUGGAGU                    38

( 2 ) INFORMATION FOR SEQ ID NO:414:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:414:

CACUCCAUCU CUGCCAG                    17

( 2 ) INFORMATION FOR SEQ ID NO:415:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:415:

CUGGCAGACU GAUGAGGCCG AAAGGCCGAA AUGGAGUG      38

( 2 ) INFORMATION FOR SEQ ID NO:416:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:416:

CUCCAUCUCU GCCAGCG      17

( 2 ) INFORMATION FOR SEQ ID NO:417:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:417:

CGCUGGCACU GAUGAGGCCG AAAGGCCGAA AGAUGGAG      38

( 2 ) INFORMATION FOR SEQ ID NO:418:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:418:

CAGCGGAUCC UGGCUCC      17

( 2 ) INFORMATION FOR SEQ ID NO:419:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:419:

GGAGCCAGCU GAUGAGGCCG AAAGGCCGAA AUCCGCUG      38

( 2 ) INFORMATION FOR SEQ ID NO:420:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:420:

UCCUGGCUCC CUACCUG      17

( 2 ) INFORMATION FOR SEQ ID NO:421:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:421:

CAGGUAGGCU GAUGAGGCCG AAAGGCCGAA AGCCAGGA 38

( 2 ) INFORMATION FOR SEQ ID NO:422:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:422:

GGCUCCCUAC CUGAAGA 17

( 2 ) INFORMATION FOR SEQ ID NO:423:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:423:

UCUUCAGGCU GAUGAGGCCG AAAGGCCGAA AGGGAGCC 38

( 2 ) INFORMATION FOR SEQ ID NO:424:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:424:

AAGCGCCUCG CCAGCAA 17

( 2 ) INFORMATION FOR SEQ ID NO:425:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:425:

UUGCUGGCCU GAUGAGGCCG AAAGGCCGAA AGGCGCUU 38

( 2 ) INFORMATION FOR SEQ ID NO:426:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:426:

UGCAUGAUCG UCCACCA 17

( 2 ) INFORMATION FOR SEQ ID NO:427:

( i ) SEQUENCE CHARACTERISTICS:

(A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:427:

UGGUGGACCU GAUGAGGCCG AAAGGCCGAA AUCAUGCA 38

(2) INFORMATION FOR SEQ ID NO:428:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:428:

GGCACCAUUC UGGAUAA 17

(2) INFORMATION FOR SEQ ID NO:429:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:429:

UUAUCCAGCU GAUGAGGCCG AAAGGCCGAA AUGGUGCC 38

(2) INFORMATION FOR SEQ ID NO:430:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:430:

GCACCAUUCU GGAUAAU 17

(2) INFORMATION FOR SEQ ID NO:431:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:431:

AUUAUCCACU GAUGAGGCCG AAAGGCCGAA AAUGGUGC 38

(2) INFORMATION FOR SEQ ID NO:432:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:432:

UUCUGGAUAA UGUUAAG 17

(2) INFORMATION FOR SEQ ID NO:433:

(i) SEQUENCE CHARACTERISTICS:
        (A) LENGTH: 38 base pairs
        (B) TYPE: nucleic acid ( C ) STRANDEDNESS: single
( D ) TOPOLOGY: linear ( x i ) SEQUENCE DESCRIPTION: SEQ ID NO:433:

CUUAACAUCU GAUGAGGCCG AAAGGCCGAA AUCCAGAA 38

( 2 ) INFORMATION FOR SEQ ID NO:434:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:434:

AUAAUGUUAA GAACCUC 17

( 2 ) INFORMATION FOR SEQ ID NO:435:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:435:

GAGGUUCUCU GAUGAGGCCG AAAGGCCGAA AACAUUAU 38

( 2 ) INFORMATION FOR SEQ ID NO:436:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:436:

AAGAACCUCU UAGAAUU 17

( 2 ) INFORMATION FOR SEQ ID NO:437:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:437:

AAUUCUAACU GAUGAGGCCG AAAGGCCGAA AGGUUCUU 38

( 2 ) INFORMATION FOR SEQ ID NO:438:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:438:

GAACCUCUUA GAAUUUG 17

( 2 ) INFORMATION FOR SEQ ID NO:439:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:439:

CAAAUUCUCU GAUGAGGCCG AAAGGCCGAA AGAGGUUC 38

( 2 ) INFORMATION FOR SEQ ID NO:440:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:440:

AACCUCUUAG AAUUUGC 17

( 2 ) INFORMATION FOR SEQ ID NO:441:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:441:

GCAAAUUCCU GAUGAGGCCG AAAGGCCGAA AAGAGGUU 38

( 2 ) INFORMATION FOR SEQ ID NO:442:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:442:

CUUAGAAUUU GCAGAAA 17

( 2 ) INFORMATION FOR SEQ ID NO:443:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:443:

UUUCUGCACU GAUGAGGCCG AAAGGCCGAA AUUCUAAG 38

( 2 ) INFORMATION FOR SEQ ID NO:444:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:444:

UUAGAAUUUG CAGAAAC 17

( 2 ) INFORMATION FOR SEQ ID NO:445:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:445:

GUUUCUGCCU GAUGAGGCCG AAAGGCCGAA AAUUCUAA          38

( 2 ) INFORMATION FOR SEQ ID NO:446:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:446:

GAAACACUCC AAUUUAU          17

( 2 ) INFORMATION FOR SEQ ID NO:447:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:447:

AUAAAUUGCU GAUGAGGCCG AAAGGCCGAA AGUGUUUC          38

( 2 ) INFORMATION FOR SEQ ID NO:448:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:448:

ACUCCAAUUU AUAGAUU          17

( 2 ) INFORMATION FOR SEQ ID NO:449:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:449:

AAUCUAUACU GAUGAGGCCG AAAGGCCGAA AUUGGAGU          38

( 2 ) INFORMATION FOR SEQ ID NO:450:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:450:

CUCCAAUUUA UAGAUUC          17

( 2 ) INFORMATION FOR SEQ ID NO:451:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:451:

GAAUCUAUCU GAUGAGGCCG AAAGGCCGAA AAUUGGAG          38

( 2 ) INFORMATION FOR SEQ ID NO:452:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:452:

UCCAAUUUAU AGAUUCU				17

( 2 ) INFORMATION FOR SEQ ID NO:453:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:453:

AGAAUCUACU GAUGAGGCCG AAAGGCCGAA AAAUUGGA				38

( 2 ) INFORMATION FOR SEQ ID NO:454:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:454:

CAAUUUAUAG AUUCUUU				17

( 2 ) INFORMATION FOR SEQ ID NO:455:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:455:

AAAGAAUCCU GAUGAGGCCG AAAGGCCGAA AUAAAUUG				38

( 2 ) INFORMATION FOR SEQ ID NO:456:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:456:

UUAUAGAUUC UUUCUUA				17

( 2 ) INFORMATION FOR SEQ ID NO:457:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:457:

UAAGAAAGCU GAUGAGGCCG AAAGGCCGAA AUCUAUAA				38

( 2 ) INFORMATION FOR SEQ ID NO:458:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:458:

UAUAGAUUCU UUCUUAA     17

( 2 ) INFORMATION FOR SEQ ID NO:459:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:459:

UUAAGAAACU GAUGAGGCCG AAAGGCCGAA AAUCUAUA     38

( 2 ) INFORMATION FOR SEQ ID NO:460:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:460:

UAGAUUCUUU CUUAAAC     17

( 2 ) INFORMATION FOR SEQ ID NO:461:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:461:

GUUUAAGACU GAUGAGGCCG AAAGGCCGAA AGAAUCUA     38

( 2 ) INFORMATION FOR SEQ ID NO:462:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:462:

AGAUUCUUUC UUAAACA     17

( 2 ) INFORMATION FOR SEQ ID NO:463:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:463:

UGUUUAAGCU GAUGAGGCCG AAAGGCCGAA AAGAAUCU     38

( 2 ) INFORMATION FOR SEQ ID NO:464:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:464:

GAUUCUUUCU UAAACAC                                                           17

( 2 ) INFORMATION FOR SEQ ID NO:465:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:465:

GUGUUUAACU GAUGAGGCCG AAAGGCCGAA AAAGAAUC                                    38

( 2 ) INFORMATION FOR SEQ ID NO:466:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:466:

UUCUUUCUUA AACACUU                                                           17

( 2 ) INFORMATION FOR SEQ ID NO:467:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:467:

AAGUGUUUCU GAUGAGGCCG AAAGGCCGAA AGAAAGAA                                    38

( 2 ) INFORMATION FOR SEQ ID NO:468:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:468:

UCUUUCUUAA ACACUUC                                                           17

( 2 ) INFORMATION FOR SEQ ID NO:469:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:469:

GAAGUGUUCU GAUGAGGCCG AAAGGCCGAA AAGAAAGA                                    38

( 2 ) INFORMATION FOR SEQ ID NO:470:

( i ) SEQUENCE CHARACTERISTICS:
      ( A ) LENGTH: 17 base pairs ( B ) TYPE: nucleic acid
        ( C ) STRANDEDNESS: single
        ( D ) TOPOLOGY: linear ( x i ) SEQUENCE DESCRIPTION: SEQ ID NO:470:

UAAACACUUC CAGUAAC 17

( 2 ) INFORMATION FOR SEQ ID NO:471:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:471:

GUUACUGGCU GAUGAGGCCG AAAGGCCGAA AGUGUUUA 38

( 2 ) INFORMATION FOR SEQ ID NO:472:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:472:

AAACACUUCC AGUAACC 17

( 2 ) INFORMATION FOR SEQ ID NO:473:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:473:

GGUUACUGCU GAUGAGGCCG AAAGGCCGAA AAGUGUUU 38

( 2 ) INFORMATION FOR SEQ ID NO:474:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:474:

UGAAAACUCA GACUUGG 17

( 2 ) INFORMATION FOR SEQ ID NO:475:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:475:

CCAAGUCUCU GAUGAGGCCG AAAGGCCGAA AGUUUCA 38

( 2 ) INFORMATION FOR SEQ ID NO:476:

( i ) SEQUENCE CHARACTERISTICS:
        ( A ) LENGTH: 17 base pairs
        ( B ) TYPE: nucleic acid
        ( C ) STRANDEDNESS: single ( D ) TOPOLOGY: linear ( x i ) SEQUENCE DESCRIPTION: SEQ ID NO:476:

CUCAGACUUG GAAAUGC                                            17

( 2 ) INFORMATION FOR SEQ ID NO:477:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:477:

GCAUUCCCU GAUGAGGCCG AAAGGCCGAA AGUCUGAG                       38

( 2 ) INFORMATION FOR SEQ ID NO:478:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:478:

AAAUGCCUUC UUUAACU                                            17

( 2 ) INFORMATION FOR SEQ ID NO:479:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:479:

AGUUAAAGCU GAUGAGGCCG AAAGGCCGAA AGGCAUUU                      38

( 2 ) INFORMATION FOR SEQ ID NO:480:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:480:

AAUGCCUUCU UUAACUU                                            17

( 2 ) INFORMATION FOR SEQ ID NO:481:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:481:

AAGUUAAACU GAUGAGGCCG AAAGGCCGAA AAGGCAUU                      38

( 2 ) INFORMATION FOR SEQ ID NO:482:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:482:

UGCCUUCUUU AACUUCC                                                17

( 2 ) INFORMATION FOR SEQ ID NO:483:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:483:

GGAAGUUACU GAUGAGGCCG AAAGGCCGAA AGAAGGCA                          38

( 2 ) INFORMATION FOR SEQ ID NO:484:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:484:

GCCUUCUUUA ACUUCCA                                                17

( 2 ) INFORMATION FOR SEQ ID NO:485:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:485:

UGGAAGUUCU GAUGAGGCCG AAAGGCCGAA AAGAAGGC                          38

( 2 ) INFORMATION FOR SEQ ID NO:486:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:486:

CCUUCUUUAA CUUCCAC                                                17

( 2 ) INFORMATION FOR SEQ ID NO:487:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:487:

GUGGAAGUCU GAUGAGGCCG AAAGGCCGAA AAAGAAGG                          38

( 2 ) INFORMATION FOR SEQ ID NO:488:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:488:

CUUUACUUC CACCCCC                                                                      17

( 2 ) INFORMATION FOR SEQ ID NO:489:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:489:

GGGGGUGGCU GAUGAGGCCG AAAGGCCGAA AGUUAAAG                                               38

( 2 ) INFORMATION FOR SEQ ID NO:490:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:490:

UUUAACUUCC ACCCCC                                                                      17

( 2 ) INFORMATION FOR SEQ ID NO:491:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:491:

GGGGGUGCU GAUGAGGCCG AAAGGCCGAA AAGUUAAA                                                38

( 2 ) INFORMATION FOR SEQ ID NO:492:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:492:

ACCCCCCUCA UUGGUCA                                                                     17

( 2 ) INFORMATION FOR SEQ ID NO:493:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:493:

UGACCAAUCU GAUGAGGCCG AAAGGCCGAA AGGGGGGU                                               38

( 2 ) INFORMATION FOR SEQ ID NO:494:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:494:

CCCCUCAUUG GUCACAA                                                                     17

( 2 ) INFORMATION FOR SEQ ID NO:495:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:495:

UUGUGACCCU GAUGAGGCCG AAAGGCCGAA AUGAGGGG                    38

( 2 ) INFORMATION FOR SEQ ID NO:496:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:496:

UCACAAAUUG ACUGUUA                                           17

( 2 ) INFORMATION FOR SEQ ID NO:497:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:497:

UAACAGUCCU GAUGAGGCCG AAAGGCCGAA AUUUGUGA                    38

( 2 ) INFORMATION FOR SEQ ID NO:498:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:498:

UGACUGUUAC AACACCA                                           17

( 2 ) INFORMATION FOR SEQ ID NO:499:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:499:

UGGUGUUGCU GAUGAGGCCG AAAGGCCGAA AACAGUCA                    38

( 2 ) INFORMATION FOR SEQ ID NO:500:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:500:

AACACCAUUU CAUAGAG                                           17

( 2 ) INFORMATION FOR SEQ ID NO:501:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:501:

CUCUAUGACU GAUGAGGCCG AAAGGCCGAA AUGGUGUU    38

( 2 ) INFORMATION FOR SEQ ID NO:502:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:502:

ACACCAUUUC AUAGAGA    17

( 2 ) INFORMATION FOR SEQ ID NO:503:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:503:

UCUCUAUGCU GAUGAGGCCG AAAGGCCGAA AAUGGUGU    38

( 2 ) INFORMATION FOR SEQ ID NO:504:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:504:

CACCAUUUCA UAGAGAC    17

( 2 ) INFORMATION FOR SEQ ID NO:505:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:505:

GUCUCUAUCU GAUGAGGCCG AAAGGCCGAA AAAUGGUG    38

( 2 ) INFORMATION FOR SEQ ID NO:506:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:506:

CAUUUCAUAG AGACCAG    17

( 2 ) INFORMATION FOR SEQ ID NO:507:

( i ) SEQUENCE CHARACTERISTICS:

( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:507:

CUGGUCUCCU GAUGAGGCCG AAAGGCCGAA AUGAAAUG    38

( 2 ) INFORMATION FOR SEQ ID NO:508:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:508:

UGAAAACUCA AAAGGAA    17

( 2 ) INFORMATION FOR SEQ ID NO:509:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:509:

UUCCUUUUCU GAUGAGGCCG AAAGGCCGAA AGUUUUCA    38

( 2 ) INFORMATION FOR SEQ ID NO:510:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:510:

AGGAAAAUAC UGUUUUU    17

( 2 ) INFORMATION FOR SEQ ID NO:511:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:511:

AAAAACAGCU GAUGAGGCCG AAAGGCCGAA AUUUCCU    38

( 2 ) INFORMATION FOR SEQ ID NO:512:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:512:

AUACUGUUUU UAGAACC    17

( 2 ) INFORMATION FOR SEQ ID NO:513:

( i ) SEQUENCE CHARACTERISTICS:
        ( A ) LENGTH: 38 base pairs
        ( B ) TYPE: nucleic acid ( C ) STRANDEDNESS: single
( D ) TOPOLOGY: linear ( x i ) SEQUENCE DESCRIPTION: SEQ ID NO:513:

GGUUCUAACU GAUGAGGCCG AAAGGCCGAA AACAGUAU 38

( 2 ) INFORMATION FOR SEQ ID NO:514:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:514:

UACUGUUUUU AGAACCC 17

( 2 ) INFORMATION FOR SEQ ID NO:515:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:515:

GGGUUCUACU GAUGAGGCCG AAAGGCCGAA AAACAGUA 38

( 2 ) INFORMATION FOR SEQ ID NO:516:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:516:

ACUGUUUUUA GAACCCC 17

( 2 ) INFORMATION FOR SEQ ID NO:517:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:517:
GGGGUUCUCU GAUGAGGCCG AAAGGCCGAA AAAACAGU ( 2 ) INFORMATION FOR SEQ ID NO:518:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:518:

CUGUUUUUAG AACCCCA 17

( 2 ) INFORMATION FOR SEQ ID NO:519:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:519:

UGGGGUUCCU GAUGAGGCCG AAAGGCCGAA AAAAACAG 38

( 2 ) INFORMATION FOR SEQ ID NO:520:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:520:

CCCCAGCUAU CAAAAGG 17

( 2 ) INFORMATION FOR SEQ ID NO:521:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:521:

CCUUUUGACU GAUGAGGCCG AAAGGCCGAA AGCUGGGG 38

( 2 ) INFORMATION FOR SEQ ID NO:522:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:522:

CCAGCUAUCA AAAGGUC 17

( 2 ) INFORMATION FOR SEQ ID NO:523:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:523:

GACCUUUUCU GAUGAGGCCG AAAGGCCGAA AUAGCUGG 38

( 2 ) INFORMATION FOR SEQ ID NO:524:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:524:

AGGUCAAUCU UAGAAAG 17

( 2 ) INFORMATION FOR SEQ ID NO:525:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:525:

CUUUCUAACU GAUGAGGCCG AAAGGCCGAA AUUGACCU 38

( 2 ) INFORMATION FOR SEQ ID NO:526:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:526:

GUCAAUCUUA GAAAGCU               17

( 2 ) INFORMATION FOR SEQ ID NO:527:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:527:

AGCUUUCUCU GAUGAGGCCG AAAGGCCGAA AGAUUGAC     38

( 2 ) INFORMATION FOR SEQ ID NO:528:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:528:

UCAAUCUUAG AAAGCUC ( 2 ) INFORMATION FOR SEQ ID NO:529:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:529:

GAGCUUUCCU GAUGAGGCCG AAAGGCCGAA AAGAUUGA     38

( 2 ) INFORMATION FOR SEQ ID NO:530:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:530:

AGAAAGCUCU CCAAGAA               17

( 2 ) INFORMATION FOR SEQ ID NO:531:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:531:

UUCUUGGACU GAUGAGGCCG AAAGGCCGAA AGCUUUCU     38

( 2 ) INFORMATION FOR SEQ ID NO:532:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:532:

AAAGCUCUCC AAGAACU                               17

( 2 ) INFORMATION FOR SEQ ID NO:533:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:533:

AGUUCUUGCU GAUGAGGCCG AAAGGCCGAA AGAGCUUU        38

( 2 ) INFORMATION FOR SEQ ID NO:534:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:534:

CAAGAACUCC UACACCA                               17

( 2 ) INFORMATION FOR SEQ ID NO:535:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:535:

UGGUGUAGCU GAUGAGGCCG AAAGGCCGAA AGUUCUUG        38

( 2 ) INFORMATION FOR SEQ ID NO:536:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:536:

GAACUCCUAC ACCAUUC                               17

( 2 ) INFORMATION FOR SEQ ID NO:537:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:537:

GAAUGGUGCU GAUGAGGCCG AAAGGCCGAA AGGAGUUC        38

( 2 ) INFORMATION FOR SEQ ID NO:538:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:538:

UACACCAUUC AAACAUG 17

(2) INFORMATION FOR SEQ ID NO:539:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:539:

CAUGUUUGCU GAUGAGGCCG AAAGGCCGAA AUGGUGUA (2) INFORMATION FOR SEQ ID NO:540:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:540:

ACACCAUUCA AACAUGC 17

(2) INFORMATION FOR SEQ ID NO:541:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:541:

GCAUGUUUCU GAUGAGGCCG AAAGGCCGAA AAUGGUGU 38

(2) INFORMATION FOR SEQ ID NO:542:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:542:

CAUGCACUUG CAGCUCA 17

(2) INFORMATION FOR SEQ ID NO:543:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:543:

UGAGCUGCCU GAUGAGGCCG AAAGGCCGAA AGUGCAUG 38

(2) INFORMATION FOR SEQ ID NO:544:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO:544:

UUGCAGCUCA AGAAAUU 17

(2) INFORMATION FOR SEQ ID NO:545:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:545:

AAUUUCUUCU GAUGAGGCCG AAAGGCCGAA AGCUGCAA 38

(2) INFORMATION FOR SEQ ID NO:546:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:546:

CAAGAAAUUA AAUACGG 17

(2) INFORMATION FOR SEQ ID NO:547:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:547:

CCGUAUUUCU GAUGAGGCCG AAAGGCCGAA AUUUCUUG 38

(2) INFORMATION FOR SEQ ID NO:548:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:548:

AAGAAAUUAA AUACGGU 17

(2) INFORMATION FOR SEQ ID NO:549:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:549:

ACCGUAUUCU GAUGAGGCCG AAAGGCCGAA AAUUUCUU 38

(2) INFORMATION FOR SEQ ID NO:550:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:550:

AAUUAAAUAC GGUCCCC ( 2 ) INFORMATION FOR SEQ ID NO:551:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:551:

GGGGACCGCU GAUGAGGCCG AAAGGCCGAA AUUUAAUU 38

( 2 ) INFORMATION FOR SEQ ID NO:552:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:552:

AAGAUGCUAC CUCAGAC 17

( 2 ) INFORMATION FOR SEQ ID NO:553:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:553:

GUCUGAGGCU GAUGAGGCCG AAAGGCCGAA AGCAUCUU 38

( 2 ) INFORMATION FOR SEQ ID NO:554:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:554:

UGCUACCUCA GACACCC 17

( 2 ) INFORMATION FOR SEQ ID NO:555:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:555:

GGGUGUCUCU GAUGAGGCCG AAAGGCCGAA AGGUAGCA 38

( 2 ) INFORMATION FOR SEQ ID NO:556:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:556:

GACACCCUCU CAUCUAG 17

( 2 ) INFORMATION FOR SEQ ID NO:557:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:557:

CUAGAUGACU GAUGAGGCCG AAAGGCCGAA AGGGUGUC      38

( 2 ) INFORMATION FOR SEQ ID NO:558:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:558:

CACCCUCUCA UCUAGUA      17

( 2 ) INFORMATION FOR SEQ ID NO:559:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:559:

UACUAGAUCU GAUGAGGCCG AAAGGCCGAA AGAGGGUG      38

( 2 ) INFORMATION FOR SEQ ID NO:560:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:560:

CCUCUCAUCU AGUAGAA      17

( 2 ) INFORMATION FOR SEQ ID NO:561:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:561:

UUCUACUACU GAUGAGGCCG AAAGGCCGAA AUGAGAGG ( 2 ) INFORMATION FOR SEQ ID NO:562:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:562:

UCUCAUCUAG UAGAAGA      17

( 2 ) INFORMATION FOR SEQ ID NO:563:

( i ) SEQUENCE CHARACTERISTICS:
        ( A ) LENGTH: 38 base pairs
        ( B ) TYPE: nucleic acid ( C ) STRANDEDNESS: single
         ( D ) TOPOLOGY: linear ( x i ) SEQUENCE DESCRIPTION: SEQ ID NO:563:

UCUUCUACCU GAUGAGGCCG AAAGGCCGAA AGAUGAGA    38

( 2 ) INFORMATION FOR SEQ ID NO:564:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:564:

UAGAAGAUCU GCAGGAU    17

( 2 ) INFORMATION FOR SEQ ID NO:565:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:565:

AUCCUGCACU GAUGAGGCCG AAAGGCCGAA AUCUUCUA    38

( 2 ) INFORMATION FOR SEQ ID NO:566:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:566:

GAUGUGAUCA AACAGGA    17

( 2 ) INFORMATION FOR SEQ ID NO:567:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:567:

UCCUGUUUCU GAUGAGGCCG AAAGGCCGAA AUCACAUC    38

( 2 ) INFORMATION FOR SEQ ID NO:568:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:568:

ACAGGAAUCU GAUGAAU    17

( 2 ) INFORMATION FOR SEQ ID NO:569:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:569:

AUUCAUCACU GAUGAGGCCG AAAGGCCGAA AUUCCUGU    38

( 2 ) INFORMATION FOR SEQ ID NO:570:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:570:

UGAUGAAUCU GGAAUUG    17

( 2 ) INFORMATION FOR SEQ ID NO:571:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:571:

CAAUUCCACU GAUGAGGCCG AAAGGCCGAA AUUCAUCA    38

( 2 ) INFORMATION FOR SEQ ID NO:572:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:572:

UCUGGAAUUG UUGCUGA ( 2 ) INFORMATION FOR SEQ ID NO:573:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:573:

UCAGCAACCU GAUGAGGCCG AAAGGCCGAA AUUCCAGA    38

( 2 ) INFORMATION FOR SEQ ID NO:574:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:574:

GCUGAGUUUC AAGAAAA    17

( 2 ) INFORMATION FOR SEQ ID NO:575:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:575:

UUUUCUUGCU GAUGAGGCCG AAAGGCCGAA AACUCAGC    38

( 2 ) INFORMATION FOR SEQ ID NO:576:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:576:

CUGAGUUUCA AGAAAAU         17

( 2 ) INFORMATION FOR SEQ ID NO:577:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:577:

AUUUCUUCU GAUGAGGCCG AAAGGCCGAA AAACUCAG         38

( 2 ) INFORMATION FOR SEQ ID NO:578:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:578:

ACCACCCUUA CUGAAGA         17

( 2 ) INFORMATION FOR SEQ ID NO:579:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:579:

UCUUCAGUCU GAUGAGGCCG AAAGGCCGAA AGGGUGGU         38

( 2 ) INFORMATION FOR SEQ ID NO:580:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:580:

CCACCCUUAC UGAAGAA         17

( 2 ) INFORMATION FOR SEQ ID NO:581:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:581:

UUCUUCAGCU GAUGAGGCCG AAAGGCCGAA AAGGGUGG         38

( 2 ) INFORMATION FOR SEQ ID NO:582:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:582:

AAGAAAAUCA AACAAGA    17

( 2 ) INFORMATION FOR SEQ ID NO:583:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:583:

UCUUGUUUCU GAUGAGGCCG AAAGGCCGAA AUUUUCUU ( 2 ) INFORMATION FOR SEQ ID NO:584:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:584:

GGUGGAAUCU CCAACUG    17

( 2 ) INFORMATION FOR SEQ ID NO:585:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:585:

CAGUUGGACU GAUGAGGCCG AAAGGCCGAA AUUCCACC    38

( 2 ) INFORMATION FOR SEQ ID NO:586:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:586:

UGGAAUCUCC AACUGAU    17

( 2 ) INFORMATION FOR SEQ ID NO:587:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:587:

AUCAGUUGCU GAUGAGGCCG AAAGGCCGAA AGAUUCCA    38

( 2 ) INFORMATION FOR SEQ ID NO:588:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:588:

CAACUGAUAA AUCAGGA                                              17

(2) INFORMATION FOR SEQ ID NO:589:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:589:

UCCUGAUUCU GAUGAGGCCG AAAGGCCGAA AUCAGUUG                        38

(2) INFORMATION FOR SEQ ID NO:590:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:590:

UGAUAAAUCA GGAAACU                                              17

(2) INFORMATION FOR SEQ ID NO:591:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:591:

AGUUUCCUCU GAUGAGGCCG AAAGGCCGAA AUUUAUCA                        38

(2) INFORMATION FOR SEQ ID NO:592:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:592:

AGGAAACUUC UUCUGCU                                              17

(2) INFORMATION FOR SEQ ID NO:593:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:593:

AGCAGAAGCU GAUGAGGCCG AAAGGCCGAA AGUUUCCU                        38

(2) INFORMATION FOR SEQ ID NO:594:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO:594:

GGAAACUUCU UCUGCUC (2) INFORMATION FOR SEQ ID NO:595:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:595:

GAGCAGAACU GAUGAGGCCG AAAGGCCGAA AAGUUUCC 38

(2) INFORMATION FOR SEQ ID NO:596:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:596:

AAACUUCUUC UGCUCAC 17

(2) INFORMATION FOR SEQ ID NO:597:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:597:

GUGAGCAGCU GAUGAGGCCG AAAGGCCGAA AGAAGUUU 38

(2) INFORMATION FOR SEQ ID NO:598:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:598:

AACUUCUUCU GCUCACA 17

(2) INFORMATION FOR SEQ ID NO:599:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:599:

UGUGAGCACU GAUGAGGCCG AAAGGCCGAA AAGAAGUU 38

(2) INFORMATION FOR SEQ ID NO:600:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:600:

CUUCUGCUCA CACCACU 17

(2) INFORMATION FOR SEQ ID NO:601:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (xi) SEQUENCE DESCRIPTION: SEQ ID NO:601:

AGUGGUGUCU GAUGAGGCCG AAAGGCCGAA AGCAGAAG 38

(2) INFORMATION FOR SEQ ID NO:602:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:602:

GUCUGAAUAC CCAACUG 17

(2) INFORMATION FOR SEQ ID NO:603:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (xi) SEQUENCE DESCRIPTION: SEQ ID NO:603:

CAGUUGGGCU GAUGAGGCCG AAAGGCCGAA AUUCAGAC 38

(2) INFORMATION FOR SEQ ID NO:604:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:604:

CAACUGUUCA CGCAGAC 17

(2) INFORMATION FOR SEQ ID NO:605:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (xi) SEQUENCE DESCRIPTION: SEQ ID NO:605:

GUCUGCGUCU GAUGAGGCCG AAAGGCCGAA AACAGUUG (2) INFORMATION FOR SEQ ID NO:606:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:606:

GCAGACCUCG CCUGUGG 17

(2) INFORMATION FOR SEQ ID NO:607:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:607:

CCACAGGCCU GAUGAGGCCG AAAGGCCGAA AGGUCUGC          38

( 2 ) INFORMATION FOR SEQ ID NO:608:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:608:

CACCGAAUAU UCUUACA          17

( 2 ) INFORMATION FOR SEQ ID NO:609:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:609:

UGUAAGAACU GAUGAGGCCG AAAGGCCGAA AUUCGGUG          38

( 2 ) INFORMATION FOR SEQ ID NO:610:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:610:

CCGAAUAUUC UUACAAG          17

( 2 ) INFORMATION FOR SEQ ID NO:611:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:611:

CUUGUAAGCU GAUGAGGCCG AAAGGCCGAA AUAUUCGG          38

( 2 ) INFORMATION FOR SEQ ID NO:612:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:612:

CGAAUAUUCU UACAAGC          17

( 2 ) INFORMATION FOR SEQ ID NO:613:

( i ) SEQUENCE CHARACTERISTICS:

-continued ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:613:

GCUUGUAACU GAUGAGGCCG AAAGGCCGAA AAUAUUCG                38

( 2 ) INFORMATION FOR SEQ ID NO:614:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:614:

AAUAUUCUUA CAAGCUC                                       17

( 2 ) INFORMATION FOR SEQ ID NO:615:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:615:

GAGCUUGUCU GAUGAGGCCG AAAGGCCGAA AGAAUAUU                38

( 2 ) INFORMATION FOR SEQ ID NO:616:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:616:
                AUAUUCUUAC AAGCUCC ( 2 ) INFORMATION FOR SEQ ID NO:617:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:617:

GGAGCUUGCU GAUGAGGCCG AAAGGCCGAA AAGAAUAU                38

( 2 ) INFORMATION FOR SEQ ID NO:618:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:618:

UACAAGCUCC GUUUUAA                                       17

( 2 ) INFORMATION FOR SEQ ID NO:619:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:619:

UUAAAACGCU GAUGAGGCCG AAAGGCCGAA AGCUUGUA                     38

( 2 ) INFORMATION FOR SEQ ID NO:620:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:620:

GCUCCGUUUU AAUGGCA                                            17

( 2 ) INFORMATION FOR SEQ ID NO:621:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:621:

UGCCAUUACU GAUGAGGCCG AAAGGCCGAA AACGGAGC                     38

( 2 ) INFORMATION FOR SEQ ID NO:622:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:622:

CUCCGUUUUA AUGGCAC                                            17

( 2 ) INFORMATION FOR SEQ ID NO:623:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:623:

GUGCCAUUCU GAUGAGGCCG AAAGGCCGAA AAACGGAG                     38

( 2 ) INFORMATION FOR SEQ ID NO:624:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:624:

UCCGUUUUAA UGGCACC                                            17

( 2 ) INFORMATION FOR SEQ ID NO:625:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:625:

```
GGUGCCAUCU GAUGAGGCCG AAAGGCCGAA AAAACGGA                                   38
```

( 2 ) INFORMATION FOR SEQ ID NO:626:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:626:

```
ACCAGCAUCA GAAGAUG                                                          17
```

( 2 ) INFORMATION FOR SEQ ID NO:627:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:627:

```
CAUCUUCUCU GAUGAGGCCG AAAGGCCGAA AUGCUGGU
```

( 2 ) INFORMATION FOR SEQ ID NO:628:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:628:

```
ACAAUGUUCU CAAAGCA                                                          17
```

( 2 ) INFORMATION FOR SEQ ID NO:629:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:629:

```
UGCUUUGACU GAUGAGGCCG AAAGGCCGAA AACAUUGU                                   38
```

( 2 ) INFORMATION FOR SEQ ID NO:630:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:630:

```
AAUGUUCUCA AAGCAUU                                                          17
```

( 2 ) INFORMATION FOR SEQ ID NO:631:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:631:

```
AAUGCUUUCU GAUGAGGCCG AAAGGCCGAA AGAACAUU                                   38
```

( 2 ) INFORMATION FOR SEQ ID NO:632:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:632:

CAAAGCAUUU ACAGUAC                           17

( 2 ) INFORMATION FOR SEQ ID NO:633:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:633:

GUACUGUACU GAUGAGGCCG AAAGGCCGAA AUGCUUUG         38

( 2 ) INFORMATION FOR SEQ ID NO:634:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:634:

AAAGCAUUUA CAGUACC                           17

( 2 ) INFORMATION FOR SEQ ID NO:635:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:635:

GGUACUGUCU GAUGAGGCCG AAAGGCCGAA AAUGCUUU         38

( 2 ) INFORMATION FOR SEQ ID NO:636:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:636:

AAGCAUUUAC AGUACCU                           17

( 2 ) INFORMATION FOR SEQ ID NO:637:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:637:

AGGUACUGCU GAUGAGGCCG AAAGGCCGAA AAAUGCUU         38

( 2 ) INFORMATION FOR SEQ ID NO:638:

( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:638:

CAGUACCUAA AAACAGG ( 2 ) INFORMATION FOR SEQ ID NO:639:

( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:639:

CCUGUUUUCU GAUGAGGCCG AAAGGCCGAA AGGUACUG    38

( 2 ) INFORMATION FOR SEQ ID NO:640:

( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:640:

GAGCCCCUUG CAGCCUU    17

( 2 ) INFORMATION FOR SEQ ID NO:641:

( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:641:

AAGGCUGCCU GAUGAGGCCG AAAGGCCGAA AGGGGCUC    38

( 2 ) INFORMATION FOR SEQ ID NO:642:

( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:642:

UGCAGCCUUG UAGCAGU    17

( 2 ) INFORMATION FOR SEQ ID NO:643:

( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:643:

ACUGCUACCU GAUGAGGCCG AAAGGCCGAA AGGCUGCA    38

( 2 ) INFORMATION FOR SEQ ID NO:644:

( i ) SEQUENCE CHARACTERISTICS:
: ( A ) LENGTH: 17 base pairs
: ( B ) TYPE: nucleic acid
: ( C ) STRANDEDNESS: single ( D ) TOPOLOGY: linear ( x i ) SEQUENCE DESCRIPTION: SEQ ID NO:644:

ACCUGCAUCC UGUGGAA 17

( 2 ) INFORMATION FOR SEQ ID NO:645:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:645:

UUCCACAGCU GAUGAGGCCG AAAGGCCGAA AUGCAGGU 38

( 2 ) INFORMATION FOR SEQ ID NO:646:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:646:

GAUGACAUCU UCCAGUC 17

( 2 ) INFORMATION FOR SEQ ID NO:647:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:647:

GACUGGAACU GAUGAGGCCG AAAGGCCGAA AUGUCAUC 38

( 2 ) INFORMATION FOR SEQ ID NO:648:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:648:

UGACAUCUUC CAGUCAA 17

( 2 ) INFORMATION FOR SEQ ID NO:649:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:649:

UUGACUGGCU GAUGAGGCCG AAAGGCCGAA AGAUGUCA ( 2 ) INFORMATION FOR SEQ ID NO:650:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:650:

GACAUCUUCC AGUCAAG    17

(2) INFORMATION FOR SEQ ID NO:651:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:651:

CUUGACUGCU GAUGAGGCCG AAAGGCCGAA AAGAUGUC    38

(2) INFORMATION FOR SEQ ID NO:652:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:652:

CUUCCAGUCA AGCUCGU    17

(2) INFORMATION FOR SEQ ID NO:653:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:653:

ACGAGCUUCU GAUGAGGCCG AAAGGCCGAA ACUGGAAG    38

(2) INFORMATION FOR SEQ ID NO:654:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:654:

GUCAAGCUCG UAAAUAC    17

(2) INFORMATION FOR SEQ ID NO:655:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:655:

GUAUUUACCU GAUGAGGCCG AAAGGCCGAA AGCUUGAC    38

(2) INFORMATION FOR SEQ ID NO:656:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:656:

UCGUAAAUAC GUGAAUG    17

( 2 ) INFORMATION FOR SEQ ID NO:657:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:657:

CAUUCACGCU GAUGAGGCCG AAAGGCCGAA AUUUACGA        38

( 2 ) INFORMATION FOR SEQ ID NO:658:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:658:

GAAUGCAUUC UCAGCCC        17

( 2 ) INFORMATION FOR SEQ ID NO:659:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:659:

GGGCUGAGCU GAUGAGGCCG AAAGGCCGAA AUGCAUUC        38

( 2 ) INFORMATION FOR SEQ ID NO:660:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:660:

AAUGCAUUCU CAGCCCG ( 2 ) INFORMATION FOR SEQ ID NO:661:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:661:

CGGGCUGACU GAUGAGGCCG AAAGGCCGAA AAUGCAUU        38

( 2 ) INFORMATION FOR SEQ ID NO:662:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:662:

UGCAUUCUCA GCCCGGA        17

( 2 ) INFORMATION FOR SEQ ID NO:663:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:663:

UCCGGGCUCU GAUGAGGCCG AAAGGCCGAA AGAAUGCA 38

(2) INFORMATION FOR SEQ ID NO:664:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:664:

UGAGACAUUU CCAGAAA 17

(2) INFORMATION FOR SEQ ID NO:665:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:665:

UUUCUGGACU GAUGAGGCCG AAAGGCCGAA AUGUCUCA 38

(2) INFORMATION FOR SEQ ID NO:666:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:666:

GAGACAUUUC CAGAAAA 17

(2) INFORMATION FOR SEQ ID NO:667:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:667:

UUUUCUGGCU GAUGAGGCCG AAAGGCCGAA AAUGUCUC 38

(2) INFORMATION FOR SEQ ID NO:668:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:668:

AGACAUUUCC AGAAAAG 17

(2) INFORMATION FOR SEQ ID NO:669:

(i) SEQUENCE CHARACTERISTICS:
(A) LENGTH: 38 base pairs
(B) TYPE: nucleic acid ( C ) STRANDEDNESS: single
        ( D ) TOPOLOGY: linear ( x i ) SEQUENCE DESCRIPTION: SEQ ID NO:669:

CUUUCUGCU GAUGAGGCCG AAAGGCCGAA AAAUGUCU 38

( 2 ) INFORMATION FOR SEQ ID NO:670:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:670:

AAAAGCAUUA UGGUUUU 17

( 2 ) INFORMATION FOR SEQ ID NO:671:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:671:

AAAACCAUCU GAUGAGGCCG AAAGGCCGAA AUGCUUUU ( 2 ) INFORMATION FOR SEQ ID NO:672:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:672:

AAAGCAUUAU GGUUUUC 17

( 2 ) INFORMATION FOR SEQ ID NO:673:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:673:

GAAAACCACU GAUGAGGCCG AAAGGCCGAA AAUGCUUU 38

( 2 ) INFORMATION FOR SEQ ID NO:674:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:674:

UUAUGGUUUU CAGAACA 17

( 2 ) INFORMATION FOR SEQ ID NO:675:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:675:

UGUUCUGACU GAUGAGGCCG AAAGGCCGAA AACCAUAA 38

(2) INFORMATION FOR SEQ ID NO:676:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:676:

UAUGGUUUUC AGAACAC 17

(2) INFORMATION FOR SEQ ID NO:677:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:677:

GUGUUCUGCU GAUGAGGCCG AAAGGCCGAA AAACCAUA 38

(2) INFORMATION FOR SEQ ID NO:678:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:678:

AUGGUUUUCA GAACACU 17

(2) INFORMATION FOR SEQ ID NO:679:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:679:

AGUGUUCUCU GAUGAGGCCG AAAGGCCGAA AAAACCAU 38

(2) INFORMATION FOR SEQ ID NO:680:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:680:

AGAACACUUC AAGUUGA 17

(2) INFORMATION FOR SEQ ID NO:681:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:681:

UCAACUUGCU GAUGAGGCCG AAAGGCCGAA AGUGUUCU 38

( 2 ) INFORMATION FOR SEQ ID NO:682:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:682:

GAACACUUCA AGUUGAC ( 2 ) INFORMATION FOR SEQ ID NO:683:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:683:

GUCAACUUCU GAUGAGGCCG AAAGGCCGAA AAGUGUUC 38

( 2 ) INFORMATION FOR SEQ ID NO:684:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:684:

CUUCAAGUUG ACUUGGG 17

( 2 ) INFORMATION FOR SEQ ID NO:685:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:685:

CCCAAGUCCU GAUGAGGCCG AAAGGCCGAA ACUUGAAG 38

( 2 ) INFORMATION FOR SEQ ID NO:686:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:686:

AGUUGACUUG GGAUAUA 17

( 2 ) INFORMATION FOR SEQ ID NO:687:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:687:

UAUAUCCCCU GAUGAGGCCG AAAGGCCGAA AGUCAACU 38

( 2 ) INFORMATION FOR SEQ ID NO:688:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:688:

CUUGGGAUAU AUCAUUC 17

( 2 ) INFORMATION FOR SEQ ID NO:689:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:689:

GAAUGAUACU GAUGAGGCCG AAAGGCCGAA AUCCCAAG 38

( 2 ) INFORMATION FOR SEQ ID NO:690:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:690:

UGGGAUAUAU CAUUCCU 17

( 2 ) INFORMATION FOR SEQ ID NO:691:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:691:

AGGAAUGACU GAUGAGGCCG AAAGGCCGAA AUAUCCCA 38

( 2 ) INFORMATION FOR SEQ ID NO:692:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:692:

GGAUAUAUCA UUCCUCA 17

( 2 ) INFORMATION FOR SEQ ID NO:693:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:693:

UGAGGAAUCU GAUGAGGCCG AAAGGCCGAA AUAUAUCC ( 2 ) INFORMATION FOR SEQ ID NO:694:

( i ) SEQUENCE CHARACTERISTICS:
   ( A ) LENGTH: 17 base pairs
   ( B ) TYPE: nucleic acid
   ( C ) STRANDEDNESS: single ( D ) TOPOLOGY: linear ( x i ) SEQUENCE DESCRIPTION: SEQ ID NO:694:

UAUAUCAUUC CUCAACA                                                                                      17

( 2 ) INFORMATION FOR SEQ ID NO:695:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:695:

UGUUGAGGCU GAUGAGGCCG AAAGGCCGAA AUGAUAUA                                                                38

( 2 ) INFORMATION FOR SEQ ID NO:696:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:696:

AUAUCAUUCC UCAACAU                                                                                      17

( 2 ) INFORMATION FOR SEQ ID NO:697:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:697:

AUGUUGAGCU GAUGAGGCCG AAAGGCCGAA AAUGAUAU                                                                38

( 2 ) INFORMATION FOR SEQ ID NO:698:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:698:

UCAUUCCUCA ACAUGAA                                                                                      17

( 2 ) INFORMATION FOR SEQ ID NO:699:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:699:

UUCAUGUUCU GAUGAGGCCG AAAGGCCGAA AGGAAUGA                                                                38

( 2 ) INFORMATION FOR SEQ ID NO:700:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:700:

AUGAAACUUU UCAUGAA 17

( 2 ) INFORMATION FOR SEQ ID NO:701:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:701:

UUCAUGAACU GAUGAGGCCG AAAGGCCGAA AGUUCAU 38

( 2 ) INFORMATION FOR SEQ ID NO:702:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:702:

UGAAACUUUU CAUGAAU 17

( 2 ) INFORMATION FOR SEQ ID NO:703:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:703:

AUUCAUGACU GAUGAGGCCG AAAGGCCGAA AAGUUCA 38

( 2 ) INFORMATION FOR SEQ ID NO:704:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:704:

GAAACUUUUC AUGAAUG ( 2 ) INFORMATION FOR SEQ ID NO:705:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:705:

CAUUCAUGCU GAUGAGGCCG AAAGGCCGAA AAAGUUUC 38

( 2 ) INFORMATION FOR SEQ ID NO:706:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:706:

AAACUUUUCA UGAAUGG 17

( 2 ) INFORMATION FOR SEQ ID NO:707:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:707:

CCAUUCAUCU GAUGAGGCCG AAAGGCCGAA AAAAGUUU                    38

( 2 ) INFORMATION FOR SEQ ID NO:708:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:708:

AAGAACCUAU UUUUGUU                                           17

( 2 ) INFORMATION FOR SEQ ID NO:709:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:709:

AACAAAAACU GAUGAGGCCG AAAGGCCGAA AGGUUCUU                    38

( 2 ) INFORMATION FOR SEQ ID NO:710:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:710:

GAACCUAUUU UUGUUGU                                           17

( 2 ) INFORMATION FOR SEQ ID NO:711:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:711:

ACAACAAACU GAUGAGGCCG AAAGGCCGAA AUAGGUUC                    38

( 2 ) INFORMATION FOR SEQ ID NO:712:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:712:

AACCUAUUUU UGUUGUG                                           17

( 2 ) INFORMATION FOR SEQ ID NO:713:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:713:

CACAACAACU GAUGAGGCCG AAAGGCCGAA AAUAGGUU 38

( 2 ) INFORMATION FOR SEQ ID NO:714:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:714:

ACCUAUUUUU GUUGUGG 17

( 2 ) INFORMATION FOR SEQ ID NO:715:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:715:
CCACAACACU GAUGAGGCCG AAAGGCCGAA AAAUAGGU ( 2 ) INFORMATION FOR SEQ ID NO:716:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:716:

CCUAUUUUUG UUGUGGU 17

( 2 ) INFORMATION FOR SEQ ID NO:717:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:717:

ACCACAACCU GAUGAGGCCG AAAGGCCGAA AAAAUAGG 38

( 2 ) INFORMATION FOR SEQ ID NO:718:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:718:

AAGUGCAUUU AGUUGAA 17

( 2 ) INFORMATION FOR SEQ ID NO:719:

( i ) SEQUENCE CHARACTERISTICS:
    ( A ) LENGTH: 38 base pairs
    ( B ) TYPE: nucleic acid (C) STRANDEDNESS: single
(D) TOPOLOGY: linear (x i) SEQUENCE DESCRIPTION: SEQ ID NO:719:

UUCAACUACU GAUGAGGCCG AAAGGCCGAA AUGCACUU                         38

(2) INFORMATION FOR SEQ ID NO:720:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (x i) SEQUENCE DESCRIPTION: SEQ ID NO:720:

AGUGCAUUUA GUUGAAU                                                17

(2) INFORMATION FOR SEQ ID NO:721:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (x i) SEQUENCE DESCRIPTION: SEQ ID NO:721:

AUUCAACUCU GAUGAGGCCG AAAGGCCGAA AAUGCACU                         38

(2) INFORMATION FOR SEQ ID NO:722:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (x i) SEQUENCE DESCRIPTION: SEQ ID NO:722:

GUGCAUUUAG UUGAAUG                                                17

(2) INFORMATION FOR SEQ ID NO:723:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (x i) SEQUENCE DESCRIPTION: SEQ ID NO:723:

CAUUCAACCU GAUGAGGCCG AAAGGCCGAA AAAUGCAC                         38

(2) INFORMATION FOR SEQ ID NO:724:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (x i) SEQUENCE DESCRIPTION: SEQ ID NO:724:

UGAAGUCUUC UUGGAUU                                                17

(2) INFORMATION FOR SEQ ID NO:725:

(i) SEQUENCE CHARACTERISTICS:
       (A) LENGTH: 38 base pairs
       (B) TYPE: nucleic acid
       (C) STRANDEDNESS: single
       (D) TOPOLOGY: linear ( x i ) SEQUENCE DESCRIPTION: SEQ ID NO:725:

AAUCCAAGCU GAUGAGGCCG AAAGGCCGAA AGACUUCA 38

( 2 ) INFORMATION FOR SEQ ID NO:726:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:726:

GAAGUCUUCU UGGAUUU ( 2 ) INFORMATION FOR SEQ ID NO:727:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:727:

AAAUCCAACU GAUGAGGCCG AAAGGCCGAA AAGACUUC 38

( 2 ) INFORMATION FOR SEQ ID NO:728:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:728:

AGUCUUCUUG GAUUUCA 17

( 2 ) INFORMATION FOR SEQ ID NO:729:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:729:

UGAAUCCCU GAUGAGGCCG AAAGGCCGAA AGAAGACU 38

( 2 ) INFORMATION FOR SEQ ID NO:730:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:730:

UCUUGGAUUU CACCCAA 17

( 2 ) INFORMATION FOR SEQ ID NO:731:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:731:

UUGGGUGACU GAUGAGGCCG AAAGGCCGAA AUCCAAGA 38

( 2 ) INFORMATION FOR SEQ ID NO:732:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:732:

CUUGGAUUUC ACCCAAC                            17

( 2 ) INFORMATION FOR SEQ ID NO:733:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:733:

GUUGGGUGCU GAUGAGGCCG AAAGGCCGAA AAUCCAAG        38

( 2 ) INFORMATION FOR SEQ ID NO:734:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:734:

UUGGAUUUCA CCCAACU                            17

( 2 ) INFORMATION FOR SEQ ID NO:735:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:735:

AGUUGGGUCU GAUGAGGCCG AAAGGCCGAA AAAUCCAA        38

( 2 ) INFORMATION FOR SEQ ID NO:736:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:736:

ACCCAACUAA AAGGAUU                            17

( 2 ) INFORMATION FOR SEQ ID NO:737:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:737:

AAUCCUUUCU GAUGAGGCCG AAAGGCCGAA AGUUGGGU ( 2 ) INFORMATION FOR SEQ ID NO:738:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:738:

AAAAGGAUUU UUAAAAA                   17

( 2 ) INFORMATION FOR SEQ ID NO:739:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:739:

UUUUUAAACU GAUGAGGCCG AAAGGCCGAA AUCCUUUU      38

( 2 ) INFORMATION FOR SEQ ID NO:740:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:740:

AAAGGAUUUU UAAAAAU                   17

( 2 ) INFORMATION FOR SEQ ID NO:741:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:741:

AUUUUUAACU GAUGAGGCCG AAAGGCCGAA AAUCCUUU      38

( 2 ) INFORMATION FOR SEQ ID NO:742:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:742:

AAGGAUUUUU AAAAAUA                   17

( 2 ) INFORMATION FOR SEQ ID NO:743:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:743:

UAUUUUUACU GAUGAGGCCG AAAGGCCGAA AAAUCCUU      38

( 2 ) INFORMATION FOR SEQ ID NO:744:

( i ) SEQUENCE CHARACTERISTICS:
  ( A ) LENGTH: 17 base pairs (B) TYPE: nucleic acid
(C) STRANDEDNESS: single
(D) TOPOLOGY: linear (x i) SEQUENCE DESCRIPTION: SEQ ID NO:744:

AGGAUUUUUA AAAAUAA                                                              17

(2) INFORMATION FOR SEQ ID NO:745:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:745:

UUAUUUUUCU GAUGAGGCCG AAAGGCCGAA AAAAUCCU                                        38

(2) INFORMATION FOR SEQ ID NO:746:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO:746:

GGAUUUUUAA AAAUAAA                                                              17

(2) INFORMATION FOR SEQ ID NO:747:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:747:

UUUAUUUUCU GAUGAGGCCG AAAGGCCGAA AAAAAUCC                                        38

(2) INFORMATION FOR SEQ ID NO:748:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO:748:
                    UUAAAAAUAA AUAACAG (2) INFORMATION FOR SEQ ID NO:749:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:749:

CUGUUAUUCU GAUGAGGCCG AAAGGCCGAA AUUUUUAA                                        38

(2) INFORMATION FOR SEQ ID NO:750:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:750:

AAAUAAAUAA CAGUCUU                                                17

( 2 ) INFORMATION FOR SEQ ID NO:751:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:751:

AAGACUGUCU GAUGAGGCCG AAAGGCCGAA AUUUAUUU                          38

( 2 ) INFORMATION FOR SEQ ID NO:752:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:752:

AACAGUCUUA CCUAAAU                                                17

( 2 ) INFORMATION FOR SEQ ID NO:753:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:753:

AUUUAGGUCU GAUGAGGCCG AAAGGCCGAA AGACUGUU                          38

( 2 ) INFORMATION FOR SEQ ID NO:754:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:754:

ACAGUCUUAC CUAAAUU                                                17

( 2 ) INFORMATION FOR SEQ ID NO:755:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:755:

AAUUUAGGCU GAUGAGGCCG AAAGGCCGAA AAGACUGU                          38

( 2 ) INFORMATION FOR SEQ ID NO:756:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:756:

UCUUACCUAA AUUAUUA  17

( 2 ) INFORMATION FOR SEQ ID NO:757:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:757:

UAAUAAUUCU GAUGAGGCCG AAAGGCCGAA AGGUAAGA  38

( 2 ) INFORMATION FOR SEQ ID NO:758:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:758:

ACCUAAAUUA UUAGGUA  17

( 2 ) INFORMATION FOR SEQ ID NO:759:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:759:

UACCUAAUCU GAUGAGGCCG AAAGGCCGAA AUUUAGGU ( 2 ) INFORMATION FOR SEQ ID NO:760:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:760:

CCUAAAUUAU UAGGUAA  17

( 2 ) INFORMATION FOR SEQ ID NO:761:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:761:

UUACCUAACU GAUGAGGCCG AAAGGCCGAA AAUUUAGG  38

( 2 ) INFORMATION FOR SEQ ID NO:762:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:762:

UAAAUUAUUA GGUAAUG  17

( 2 ) INFORMATION FOR SEQ ID NO:763:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:763:

CAUUACCUCU GAUGAGGCCG AAAGGCCGAA AUAAUUUA                38

( 2 ) INFORMATION FOR SEQ ID NO:764:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:764:

AAAUUAUUAG GUAAUGA                                       17

( 2 ) INFORMATION FOR SEQ ID NO:765:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:765:

UCAUUACCCU GAUGAGGCCG AAAGGCCGAA AAUAAUUU                38

( 2 ) INFORMATION FOR SEQ ID NO:766:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:766:

UAAUGAAUUG UAGCCAG                                       17

( 2 ) INFORMATION FOR SEQ ID NO:767:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:767:

CUGGCUACCU GAUGAGGCCG AAAGGCCGAA AUUCAUUA                38

( 2 ) INFORMATION FOR SEQ ID NO:768:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:768:

CAGUUGUUAA UAUCUUA                                       17

( 2 ) INFORMATION FOR SEQ ID NO:769:

( i ) SEQUENCE CHARACTERISTICS:

( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:769:

UAAGAUAUCU GAUGAGGCCG AAAGGCCGAA AACAACUG    38

( 2 ) INFORMATION FOR SEQ ID NO:770:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:770:
UUGUUAAUAU CUUAAUG ( 2 ) INFORMATION FOR SEQ ID NO:771:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:771:

CAUUAAGACU GAUGAGGCCG AAAGGCCGAA AUUAACAA    38

( 2 ) INFORMATION FOR SEQ ID NO:772:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:772:

GUUAAUAUCU UAAUGCA    17

( 2 ) INFORMATION FOR SEQ ID NO:773:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:773:

UGCAUUAACU GAUGAGGCCG AAAGGCCGAA AUAUUAAC    38

( 2 ) INFORMATION FOR SEQ ID NO:774:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:774:

UAAUAUCUUA AUGCAGA    17

( 2 ) INFORMATION FOR SEQ ID NO:775:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:775:

UCUGCAUUCU GAUGAGGCCG AAAGGCCGAA AGAUAUUA 38

( 2 ) INFORMATION FOR SEQ ID NO:776:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:776:

AAUAUCUUAA UGCAGAU 17

( 2 ) INFORMATION FOR SEQ ID NO:777:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:777:

AUCUGCAUCU GAUGAGGCCG AAAGGCCGAA AAGAUAUU 38

( 2 ) INFORMATION FOR SEQ ID NO:778:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:778:

AUGCAGAUUU UUUUAAA 17

( 2 ) INFORMATION FOR SEQ ID NO:779:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:779:

UUUAAAAACU GAUGAGGCCG AAAGGCCGAA AUCUGCAU 38

( 2 ) INFORMATION FOR SEQ ID NO:780:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:780:

UGCAGAUUUU UUUAAAA 17

( 2 ) INFORMATION FOR SEQ ID NO:781:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:781:

UUUUAAAACU GAUGAGGCCG AAAGGCCGAA AAUCUGCA ( 2 ) INFORMATION FOR SEQ ID NO:782:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:782:

GCAGAUUUUU UUAAAAA                                                                    17

( 2 ) INFORMATION FOR SEQ ID NO:783:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:783:

UUUUUAAACU GAUGAGGCCG AAAGGCCGAA AAAUCUGC                                              38

( 2 ) INFORMATION FOR SEQ ID NO:784:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:784:

CAGAUUUUUU UAAAAAA                                                                    17

( 2 ) INFORMATION FOR SEQ ID NO:785:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:785:

UUUUUUAACU GAUGAGGCCG AAAGGCCGAA AAAAUCUG                                              38

( 2 ) INFORMATION FOR SEQ ID NO:786:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:786:

AGAUUUUUUU AAAAAAA                                                                    17

( 2 ) INFORMATION FOR SEQ ID NO:787:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:787:

UUUUUUUACU GAUGAGGCCG AAAGGCCGAA AAAAAUCU                                              38

( 2 ) INFORMATION FOR SEQ ID NO:788:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:788:

GAUUUUUUUA AAAAAAA                                      17

( 2 ) INFORMATION FOR SEQ ID NO:789:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:789:

UUUUUUUUCU GAUGAGGCCG AAAGGCCGAA AAAAAAUC          38

( 2 ) INFORMATION FOR SEQ ID NO:790:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:790:

AUUUUUUUAA AAAAAAC                                      17

( 2 ) INFORMATION FOR SEQ ID NO:791:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:791:

GUUUUUUUCU GAUGAGGCCG AAAGGCCGAA AAAAAAAU          38

( 2 ) INFORMATION FOR SEQ ID NO:792:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:792:

AAAAACAUAA AAUGAUU ( 2 ) INFORMATION FOR SEQ ID NO:793:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:793:

AAUCAUUUCU GAUGAGGCCG AAAGGCCGAA AUGUUUUU          38

( 2 ) INFORMATION FOR SEQ ID NO:794:

( i ) SEQUENCE CHARACTERISTICS:
        ( A ) LENGTH: 17 base pairs (B) TYPE: nucleic acid
            (C) STRANDEDNESS: single
            (D) TOPOLOGY: linear (xi) SEQUENCE DESCRIPTION: SEQ ID NO:794:

AAAAUGAUUU AUCUGUA                                                              17

(2) INFORMATION FOR SEQ ID NO:795:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:795:

UACAGAUACU GAUGAGGCCG AAAGGCCGAA AUCAUUUU                                        38

(2) INFORMATION FOR SEQ ID NO:796:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:796:

AAAUGAUUUA UCUGUAU                                                              17

(2) INFORMATION FOR SEQ ID NO:797:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:797:

AUACAGAUCU GAUGAGGCCG AAAGGCCGAA AAUCAUUU                                        38

(2) INFORMATION FOR SEQ ID NO:798:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:798:

AAUGAUUUAU CUGUAUU                                                              17

(2) INFORMATION FOR SEQ ID NO:799:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:799:

AAUACAGACU GAUGAGGCCG AAAGGCCGAA AAAUCAUU                                        38

(2) INFORMATION FOR SEQ ID NO:800:

(i) SEQUENCE CHARACTERISTICS:
            (A) LENGTH: 17 base pairs
            (B) TYPE: nucleic acid
            (C) STRANDEDNESS: single ( D ) TOPOLOGY: linear ( x i ) SEQUENCE DESCRIPTION: SEQ ID NO:800:

UGAUUUAUCU GUAUUUU                                                                  17

( 2 ) INFORMATION FOR SEQ ID NO:801:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:801:

AAAAUACACU GAUGAGGCCG AAAGGCCGAA AUAAAUCA                                            38

( 2 ) INFORMATION FOR SEQ ID NO:802:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:802:

AUCUGUAUUU UAAAGGA                                                                  17

( 2 ) INFORMATION FOR SEQ ID NO:803:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:803:

UCCUUUAACU GAUGAGGCCG AAAGGCCGAA AUACAGAU ( 2 ) INFORMATION FOR SEQ ID NO:804:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:804:

UCUGUAUUU AAAGGAU                                                                   17

( 2 ) INFORMATION FOR SEQ ID NO:805:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:805:

AUCCUUUACU GAUGAGGCCG AAAGGCCGAA AAUACAGA                                            38

( 2 ) INFORMATION FOR SEQ ID NO:806:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:806:

CUGUAUUUUA AAGGAUC                                                              17

(2) INFORMATION FOR SEQ ID NO:807:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:807:

GAUCCUUUCU GAUGAGGCCG AAAGGCCGAA AAAUACAG                                        38

(2) INFORMATION FOR SEQ ID NO:808:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:808:

UGUAUUUUAA AGGAUCC                                                               17

(2) INFORMATION FOR SEQ ID NO:809:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:809:

GGAUCCUUCU GAUGAGGCCG AAAGGCCGAA AAAAUACA                                        38

(2) INFORMATION FOR SEQ ID NO:810:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:810:

UAAAGGAUCC AACAGAU                                                               17

(2) INFORMATION FOR SEQ ID NO:811:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:811:

AUCUGUUGCU GAUGAGGCCG AAAGGCCGAA AUCCUUUA                                        38

(2) INFORMATION FOR SEQ ID NO:812:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:812:

CAACAGAUCA GUAUUUU                                                               17

( 2 ) INFORMATION FOR SEQ ID NO:813:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:813:

AAAAUACUCU GAUGAGGCCG AAAGGCCGAA AUCUGUUG    38

( 2 ) INFORMATION FOR SEQ ID NO:814:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:814:
        AUCAGUAUUU UUUCCUG ( 2 ) INFORMATION FOR SEQ ID NO:815:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:815:

CAGGAAAACU GAUGAGGCCG AAAGGCCGAA AUACUGAU    38

( 2 ) INFORMATION FOR SEQ ID NO:816:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:816:

UCAGUAUUUU UUCCUGU    17

( 2 ) INFORMATION FOR SEQ ID NO:817:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:817:

ACAGGAAACU GAUGAGGCCG AAAGGCCGAA AAUACUGA    38

( 2 ) INFORMATION FOR SEQ ID NO:818:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:818:

CAGUAUUUUU UCCUGUG    17

( 2 ) INFORMATION FOR SEQ ID NO:819:

( i ) SEQUENCE CHARACTERISTICS:

( A ) LENGTH: 38 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:819:

CACAGGAACU GAUGAGGCCG AAAGGCCGAA AAAUACUG                                    38

( 2 ) INFORMATION FOR SEQ ID NO:820:

( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:820:

AGUAUUUUUU CCUGUGA                                                           17

( 2 ) INFORMATION FOR SEQ ID NO:821:

( i ) SEQUENCE CHARACTERISTICS:
              ( A ) LENGTH: 38 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:821:

UCACAGGACU GAUGAGGCCG AAAGGCCGAA AAAAUACU                                    38

( 2 ) INFORMATION FOR SEQ ID NO:822:

( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:822:

GUAUUUUUUC CUGUGAU                                                           17

( 2 ) INFORMATION FOR SEQ ID NO:823:

( i ) SEQUENCE CHARACTERISTICS:
              ( A ) LENGTH: 38 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:823:

AUCACAGGCU GAUGAGGCCG AAAGGCCGAA AAAAAUAC                                    38

( 2 ) INFORMATION FOR SEQ ID NO:824:

( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:824:

UAUUUUUUCC UGUGAUG                                                           17

( 2 ) INFORMATION FOR SEQ ID NO:825:

( i ) SEQUENCE CHARACTERISTICS:
              ( A ) LENGTH: 38 base pairs
              ( B ) TYPE: nucleic acid (C) STRANDEDNESS: single
            (D) TOPOLOGY: linear (xi) SEQUENCE DESCRIPTION: SEQ ID NO:825:

CAUCACAGCU GAUGAGGCCG AAAGGCCGAA AAAAAAUA (2) INFORMATION FOR SEQ ID NO:826:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:826:

GAUGGGUUUU UUGAAAU                                                          17

(2) INFORMATION FOR SEQ ID NO:827:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:827:

AUUUCAAACU GAUGAGGCCG AAAGGCCGAA AACCCAUC                                   38

(2) INFORMATION FOR SEQ ID NO:828:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:828:

AUGGGUUUUU UGAAAUU                                                          17

(2) INFORMATION FOR SEQ ID NO:829:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:829:

AAUUUCAACU GAUGAGGCCG AAAGGCCGAA AAACCCAU                                   38

(2) INFORMATION FOR SEQ ID NO:830:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:830:

UGGGUUUUUU GAAAUUU                                                          17

(2) INFORMATION FOR SEQ ID NO:831:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:831:

AAAUUUCACU GAUGAGGCCG AAAGGCCGAA AAAACCCA 38

( 2 ) INFORMATION FOR SEQ ID NO:832:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:832:

GGGUUUUUUG AAAUUUG 17

( 2 ) INFORMATION FOR SEQ ID NO:833:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:833:

CAAAUUUCCU GAUGAGGCCG AAAGGCCGAA AAAAACCC 38

( 2 ) INFORMATION FOR SEQ ID NO:834:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:834:

UUUGAAAUUU GACACAU 17

( 2 ) INFORMATION FOR SEQ ID NO:835:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:835:

AUGUGUCACU GAUGAGGCCG AAAGGCCGAA AUUUCAAA 38

( 2 ) INFORMATION FOR SEQ ID NO:836:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:836:
        UUGAAAUUUG ACACAUU ( 2 ) INFORMATION FOR SEQ ID NO:837:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:837:

AAUGUGUCCU GAUGAGGCCG AAAGGCCGAA AAUUUCAA 38

( 2 ) INFORMATION FOR SEQ ID NO:838:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:838:

UGACACAUUA AAAGGUA 17

( 2 ) INFORMATION FOR SEQ ID NO:839:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:839:

UACCUUUUCU GAUGAGGCCG AAAGGCCGAA AUGUGUCA 38

( 2 ) INFORMATION FOR SEQ ID NO:840:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:840:

GACACAUUAA AAGGUAC 17

( 2 ) INFORMATION FOR SEQ ID NO:841:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:841:

GUACCUUUCU GAUGAGGCCG AAAGGCCGAA AAUGUGUC 38

( 2 ) INFORMATION FOR SEQ ID NO:842:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:842:

AAGGUACUCC AGUAUUU 17

( 2 ) INFORMATION FOR SEQ ID NO:843:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:843:

AAAUACUGCU GAUGAGGCCG AAAGGCCGAA AGUACCUU 38

( 2 ) INFORMATION FOR SEQ ID NO:844:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:844:

UCCAGUAUUU CACUUUU 17

( 2 ) INFORMATION FOR SEQ ID NO:845:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:845:

AAAAGUGACU GAUGAGGCCG AAAGGCCGAA AUACUGGA 38

( 2 ) INFORMATION FOR SEQ ID NO:846:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:846:

CCAGUAUUUC ACUUUUC 17

( 2 ) INFORMATION FOR SEQ ID NO:847:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:847:
GAAAAGUGCU GAUGAGGCCG AAAGGCCGAA AAUACUGG ( 2 ) INFORMATION FOR SEQ ID NO:848:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:848:

CAGUAUUUCA CUUUUCU 17

( 2 ) INFORMATION FOR SEQ ID NO:849:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:849:

AGAAAAGUCU GAUGAGGCCG AAAGGCCGAA AAAUACUG 38

( 2 ) INFORMATION FOR SEQ ID NO:850:

( i ) SEQUENCE CHARACTERISTICS:
    ( A ) LENGTH: 17 base pairs
    ( B ) TYPE: nucleic acid
    ( C ) STRANDEDNESS: single ( D ) TOPOLOGY: linear ( x i ) SEQUENCE DESCRIPTION: SEQ ID NO:850:

AUUUCACUUU UCUCGAU                                            17

( 2 ) INFORMATION FOR SEQ ID NO:851:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:851:

AUCGAGAACU GAUGAGGCCG AAAGGCCGAA AGUGAAAU                      38

( 2 ) INFORMATION FOR SEQ ID NO:852:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:852:

UUUCACUUUU CUCGAUC                                            17

( 2 ) INFORMATION FOR SEQ ID NO:853:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:853:

GAUCGAGACU GAUGAGGCCG AAAGGCCGAA AAGUGAAA                      38

( 2 ) INFORMATION FOR SEQ ID NO:854:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:854:

UUCACUUUUC UCGAUCA                                            17

( 2 ) INFORMATION FOR SEQ ID NO:855:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:855:

UGAUCGAGCU GAUGAGGCCG AAAGGCCGAA AAAGUGAA                      38

( 2 ) INFORMATION FOR SEQ ID NO:856:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:856:

UCACUUUUCU CGAUCAC 17

( 2 ) INFORMATION FOR SEQ ID NO:857:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:857:

GUGAUCGACU GAUGAGGCCG AAAGGCCGAA AAAAGUGA 38

( 2 ) INFORMATION FOR SEQ ID NO:858:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:858:

ACUUUUCUCG AUCACUA ( 2 ) INFORMATION FOR SEQ ID NO:859:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:859:

UAGUGAUCCU GAUGAGGCCG AAAGGCCGAA AGAAAAGU 38

( 2 ) INFORMATION FOR SEQ ID NO:860:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:860:

UUCUCGAUCA CUAAACA 17

( 2 ) INFORMATION FOR SEQ ID NO:861:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:861:

UGUUUAGUCU GAUGAGGCCG AAAGGCCGAA AUCGAGAA 38

( 2 ) INFORMATION FOR SEQ ID NO:862:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:862:

CGAUCACUAA ACAUAUG 17

( 2 ) INFORMATION FOR SEQ ID NO:863:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:863:

CAUAUGUUCU GAUGAGGCCG AAAGGCCGAA AGUGAUCG    38

( 2 ) INFORMATION FOR SEQ ID NO:864:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:864:

CUAAACAUAU GCAUAUA    17

( 2 ) INFORMATION FOR SEQ ID NO:865:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:865:

UAUAUGCACU GAUGAGGCCG AAAGGCCGAA AUGUUUAG    38

( 2 ) INFORMATION FOR SEQ ID NO:866:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:866:

AUAUGCAUAU AUUUUUA    17

( 2 ) INFORMATION FOR SEQ ID NO:867:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:867:

UAAAAAUACU GAUGAGGCCG AAAGGCCGAA AUGCAUAU    38

( 2 ) INFORMATION FOR SEQ ID NO:868:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:868:

AUGCAUAUAU UUUUAAA    17

( 2 ) INFORMATION FOR SEQ ID NO:869:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:869:

UUUAAAAACU GAUGAGGCCG AAAGGCCGAA AUAUGCAU ( 2 ) INFORMATION FOR SEQ ID NO:870:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:870:

GCAUAUAUUU UUAAAAA     17

( 2 ) INFORMATION FOR SEQ ID NO:871:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:871:

UUUUUAAACU GAUGAGGCCG AAAGGCCGAA AUAUAUGC     38

( 2 ) INFORMATION FOR SEQ ID NO:872:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:872:

CAUAUAUUUU UAAAAAU     17

( 2 ) INFORMATION FOR SEQ ID NO:873:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:873:

AUUUUUAACU GAUGAGGCCG AAAGGCCGAA AAUAUAUG     38

( 2 ) INFORMATION FOR SEQ ID NO:874:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:874:

AUAUAUUUUU AAAAAUC     17

( 2 ) INFORMATION FOR SEQ ID NO:875:

( i ) SEQUENCE CHARACTERISTICS:
    ( A ) LENGTH: 38 base pairs
    ( B ) TYPE: nucleic acid (C) STRANDEDNESS: single
(D) TOPOLOGY: linear (xi) SEQUENCE DESCRIPTION: SEQ ID NO:875:

GAUUUUUACU GAUGAGGCCG AAAGGCCGAA AAAUAUAU  38

(2) INFORMATION FOR SEQ ID NO:876:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (xi) SEQUENCE DESCRIPTION: SEQ ID NO:876:

UAUAUUUUUA AAAAUCA  17

(2) INFORMATION FOR SEQ ID NO:877:

(i) SEQUENCE CHARACTERISTICS:
 (A) LENGTH: 38 base pairs
 (B) TYPE: nucleic acid
 (C) STRANDEDNESS: single
 (D) TOPOLOGY: linear (xi) SEQUENCE DESCRIPTION: SEQ ID NO:877:

UGAUUUUUCU GAUGAGGCCG AAAGGCCGAA AAAAUAUA  38

(2) INFORMATION FOR SEQ ID NO:878:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (xi) SEQUENCE DESCRIPTION: SEQ ID NO:878:

AUAUUUUUAA AAAUCAG  17

(2) INFORMATION FOR SEQ ID NO:879:

(i) SEQUENCE CHARACTERISTICS:
 (A) LENGTH: 38 base pairs
 (B) TYPE: nucleic acid
 (C) STRANDEDNESS: single
 (D) TOPOLOGY: linear (xi) SEQUENCE DESCRIPTION: SEQ ID NO:879:

CUGAUUUUCU GAUGAGGCCG AAAGGCCGAA AAAAAUAU  38

(2) INFORMATION FOR SEQ ID NO:880:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (xi) SEQUENCE DESCRIPTION: SEQ ID NO:880:
          UUAAAAAUCA GUAAAAG (2) INFORMATION FOR SEQ ID NO:881:

(i) SEQUENCE CHARACTERISTICS:
 (A) LENGTH: 38 base pairs
 (B) TYPE: nucleic acid
 (C) STRANDEDNESS: single
 (D) TOPOLOGY: linear (xi) SEQUENCE DESCRIPTION: SEQ ID NO:881:

```
CUUUUACUCU GAUGAGGCCG AAAGGCCGAA AUUUUUAA                    38
```

( 2 ) INFORMATION FOR SEQ ID NO:882:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:882:

```
AAAAGCAUUA CUCUAAG                                           17
```

( 2 ) INFORMATION FOR SEQ ID NO:883:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:883:

```
CUUAGAGUCU GAUGAGGCCG AAAGGCCGAA AUGCUUUU                    38
```

( 2 ) INFORMATION FOR SEQ ID NO:884:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:884:

```
AAAGCAUUAC UCUAAGU                                           17
```

( 2 ) INFORMATION FOR SEQ ID NO:885:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:885:

```
ACUUAGAGCU GAUGAGGCCG AAAGGCCGAA AAUGCUUU                    38
```

( 2 ) INFORMATION FOR SEQ ID NO:886:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:886:

```
GCAUUACUCU AAGUGUA                                           17
```

( 2 ) INFORMATION FOR SEQ ID NO:887:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:887:

```
UACACUUACU GAUGAGGCCG AAAGGCCGAA AGUAAUGC                    38
```

( 2 ) INFORMATION FOR SEQ ID NO:888:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:888:

AUUACUCUAA GUGUAGA                17

( 2 ) INFORMATION FOR SEQ ID NO:889:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:889:

UCUACACUCU GAUGAGGCCG AAAGGCCGAA AGAGUAAU        38

( 2 ) INFORMATION FOR SEQ ID NO:890:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:890:

CUAAGUGUAG ACUUAAU                17

( 2 ) INFORMATION FOR SEQ ID NO:891:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:891:

AUUAAGUCCU GAUGAGGCCG AAAGGCCGAA ACACUUAG ( 2 ) INFORMATION FOR SEQ ID NO:892:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:892:

UGUAGACUUA AUACCAU                17

( 2 ) INFORMATION FOR SEQ ID NO:893:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:893:

AUGGUAUUCU GAUGAGGCCG AAAGGCCGAA AGUCUACA        38

( 2 ) INFORMATION FOR SEQ ID NO:894:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:894:

GUAGACUUAA UACCAUG                       17

( 2 ) INFORMATION FOR SEQ ID NO:895:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:895:

CAUGGUAUCU GAUGAGGCCG AAAGGCCGAA AAGUCUAC         38

( 2 ) INFORMATION FOR SEQ ID NO:896:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:896:

GACUUAAUAC CAUGUGA                      17

( 2 ) INFORMATION FOR SEQ ID NO:897:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:897:

UCACAUGGCU GAUGAGGCCG AAAGGCCGAA AUUAAGUC         38

( 2 ) INFORMATION FOR SEQ ID NO:898:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:898:

UGUGACAUUU AAUCCAG                      17

( 2 ) INFORMATION FOR SEQ ID NO:899:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:899:

CUGGAUUACU GAUGAGGCCG AAAGGCCGAA AUGUCACA         38

( 2 ) INFORMATION FOR SEQ ID NO:900:

( i ) SEQUENCE CHARACTERISTICS:
      ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:900:

GUGACAUUUA AUCCAGA                                                                  17

(2) INFORMATION FOR SEQ ID NO:901:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:901:

UCUGGAUUCU GAUGAGGCCG AAAGGCCGAA AAUGUCAC                                            38

(2) INFORMATION FOR SEQ ID NO:902:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:902:
UGACAUUUAA UCCAGAU (2) INFORMATION FOR SEQ ID NO:903:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:903:

AUCUGGAUCU GAUGAGGCCG AAAGGCCGAA AAAUGUCA                                            38

(2) INFORMATION FOR SEQ ID NO:904:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:904:

CAUUUAAUCC AGAUUGU                                                                  17

(2) INFORMATION FOR SEQ ID NO:905:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:905:

ACAAUCUGCU GAUGAGGCCG AAAGGCCGAA AUUAAAUG                                            38

(2) INFORMATION FOR SEQ ID NO:906:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:906:

AUCCAGAUUG UAAAUGC 17

( 2 ) INFORMATION FOR SEQ ID NO:907:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:907:

GCAUUUACCU GAUGAGGCCG AAAGGCCGAA AUCUGGAU 38

( 2 ) INFORMATION FOR SEQ ID NO:908:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:908:

UAAAUGCUCA UUUAUGG 17

( 2 ) INFORMATION FOR SEQ ID NO:909:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:909:

CCAUAAAUCU GAUGAGGCCG AAAGGCCGAA AGCAUUUA 38

( 2 ) INFORMATION FOR SEQ ID NO:910:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:910:

AUGCUCAUUU AUGGUUA 17

( 2 ) INFORMATION FOR SEQ ID NO:911:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:911:

UAACCAUACU GAUGAGGCCG AAAGGCCGAA AUGAGCAU 38

( 2 ) INFORMATION FOR SEQ ID NO:912:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:912:

UGCUCAUUUA UGGUUAA 17

(2) INFORMATION FOR SEQ ID NO:913:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:913:

UUAACCAUCU GAUGAGGCCG AAAGGCCGAA AAUGAGCA (2) INFORMATION FOR SEQ ID NO:914:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:914:

GCUCAUUUAU GGUUAAU 17

(2) INFORMATION FOR SEQ ID NO:915:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:915:

AUUAACCACU GAUGAGGCCG AAAGGCCGAA AAAUGAGC 38

(2) INFORMATION FOR SEQ ID NO:916:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:916:

UUAUGGUUAA UGACAUU 17

(2) INFORMATION FOR SEQ ID NO:917:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:917:

AAUGUCAUCU GAUGAGGCCG AAAGGCCGAA AACCAUAA 38

(2) INFORMATION FOR SEQ ID NO:918:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:918:

AAUGACAUUG AAGGUAC 17

(2) INFORMATION FOR SEQ ID NO:919:

(   i   ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:919:

GUACCUUCCU GAUGAGGCCG AAAGGCGAA AUGUCAUU                                38

( 2 ) INFORMATION FOR SEQ ID NO:920:

(   i   ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:920:

AGGUACAUUU AUUGUAC                                                      17

( 2 ) INFORMATION FOR SEQ ID NO:921:

(   i   ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:921:

GUACAAUACU GAUGAGGCCG AAAGGCCGAA AUGUACCU                                38

( 2 ) INFORMATION FOR SEQ ID NO:922:

(   i   ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:922:

GGUACAUUUA UUGUACC                                                      17

( 2 ) INFORMATION FOR SEQ ID NO:923:

(   i   ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:923:

GGUACAAUCU GAUGAGGCCG AAAGGCCGAA AAUGUACC                                38

( 2 ) INFORMATION FOR SEQ ID NO:924:

(   i   ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:924:
                GUACAUUUAU UGUACCA ( 2 ) INFORMATION FOR SEQ ID NO:925:

(   i   ) SEQUENCE CHARACTERISTICS:
            ( A ) LENGTH: 38 base pairs
            ( B ) TYPE: nucleic acid ( C ) STRANDEDNESS: single
            ( D ) TOPOLOGY: linear ( x i ) SEQUENCE DESCRIPTION: SEQ ID NO:925:

UGGUACAACU GAUGAGGCCG AAAGGCCGAA AAAUGUAC    38

( 2 ) INFORMATION FOR SEQ ID NO:926:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:926:

ACAUUUAUUG UACCAAA    17

( 2 ) INFORMATION FOR SEQ ID NO:927:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:927:

UUUGGUACCU GAUGAGGCCG AAAGGCCGAA AUAAAUGU    38

( 2 ) INFORMATION FOR SEQ ID NO:928:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:928:

CAAACCAUUU UAUGAGU    17

( 2 ) INFORMATION FOR SEQ ID NO:929:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:929:

ACUCAUAACU GAUGAGGCCG AAAGGCCGAA AUGGUUUG    38

( 2 ) INFORMATION FOR SEQ ID NO:930:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:930:

AAACCAUUUU AUGAGUU    17

( 2 ) INFORMATION FOR SEQ ID NO:931:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:931:

AACUCAUACU GAUGAGGCCG AAAGGCCGAA AAUGGUUU  38

( 2 ) INFORMATION FOR SEQ ID NO:932:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:932:

AACCAUUUUA UGAGUUU  17

( 2 ) INFORMATION FOR SEQ ID NO:933:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:933:

AAACUCAUCU GAUGAGGCCG AAAGGCCGAA AAAUGGUU  38

( 2 ) INFORMATION FOR SEQ ID NO:934:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:934:

ACCAUUUUAU GAGUUUU  17

( 2 ) INFORMATION FOR SEQ ID NO:935:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:935:

AAAACUCACU GAUGAGGCCG AAAGGCCGAA AAAAUGGU ( 2 ) INFORMATION FOR SEQ ID NO:936:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:936:

UAUGAGUUUU CUGUUAG  17

( 2 ) INFORMATION FOR SEQ ID NO:937:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:937:

CUAACAGACU GAUGAGGCCG AAAGGCCGAA AACUCAUA  38

( 2 ) INFORMATION FOR SEQ ID NO:938:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:938:

AUGAGUUUUC UGUUAGC                        17

( 2 ) INFORMATION FOR SEQ ID NO:939:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:939:

GCUAACAGCU GAUGAGGCCG AAAGGCCGAA AAACUCAU          38

( 2 ) INFORMATION FOR SEQ ID NO:940:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:940:

UGAGUUUUCU GUUAGCU                        17

( 2 ) INFORMATION FOR SEQ ID NO:941:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:941:

AGCUAACACU GAUGAGGCCG AAAGGCCGAA AAACUCA           38

( 2 ) INFORMATION FOR SEQ ID NO:942:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:942:

UUUCUGUUAG CUUGCUU                        17

( 2 ) INFORMATION FOR SEQ ID NO:943:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:943:

AAGCAAGCCU GAUGAGGCCG AAAGGCCGAA AACAGAAA          38

( 2 ) INFORMATION FOR SEQ ID NO:944:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:944:

UGUUAGCUUG CUUUAAA         17

( 2 ) INFORMATION FOR SEQ ID NO:945:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:945:

UUUAAAGCCU GAUGAGGCCG AAAGGCCGAA AGCUAACA         38

( 2 ) INFORMATION FOR SEQ ID NO:946:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:946:

AGCUUGCUUU AAAAAUU ( 2 ) INFORMATION FOR SEQ ID NO:947:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:947:

AAUUUUUACU GAUGAGGCCG AAAGGCCGAA AGCAAGCU         38

( 2 ) INFORMATION FOR SEQ ID NO:948:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:948:

GCUUGCUUUA AAAAUUA         17

( 2 ) INFORMATION FOR SEQ ID NO:949:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:949:

UAAUUUUUCU GAUGAGGCCG AAAGGCCGAA AAGCAAGC         38

( 2 ) INFORMATION FOR SEQ ID NO:950:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:950:

CUUGCUUUAA AAAUUAU 17

(2) INFORMATION FOR SEQ ID NO:951:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:951:

AUAAUUUUCU GAUGAGGCCG AAAGGCCGAA AAAGCAAG 38

(2) INFORMATION FOR SEQ ID NO:952:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:952:

UUAAAAAUUA UUACUGU 17

(2) INFORMATION FOR SEQ ID NO:953:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:953:

ACAGUAAUCU GAUGAGGCCG AAAGGCCGAA AUUUUUAA 38

(2) INFORMATION FOR SEQ ID NO:954:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:954:

UAAAAAUUAU UACUGUA 17

(2) INFORMATION FOR SEQ ID NO:955:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:955:

UACAGUAACU GAUGAGGCCG AAAGGCCGAA AAUUUUUA 38

(2) INFORMATION FOR SEQ ID NO:956:

(i) SEQUENCE CHARACTERISTICS:
(A) LENGTH: 17 base pairs
(B) TYPE: nucleic acid
(C) STRANDEDNESS: single (D) TOPOLOGY: linear (x i) SEQUENCE DESCRIPTION: SEQ ID NO:956:

AAAAUUAUUA CUGUAAG    17

(2) INFORMATION FOR SEQ ID NO:957:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:957:

CUUACAGUCU GAUGAGGCCG AAAGGCCGAA AUAAUUUU (2) INFORMATION FOR SEQ ID NO:958:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:958:

AAAUUAUUAC UGUAAGA    17

(2) INFORMATION FOR SEQ ID NO:959:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:959:

UCUUACAGCU GAUGAGGCCG AAAGGCCGAA AAUAAUUU    38

(2) INFORMATION FOR SEQ ID NO:960:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:960:

UAAGAAAUAG UUUUAUA    17

(2) INFORMATION FOR SEQ ID NO:961:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:961:

UAUAAAACCU GAUGAGGCCG AAAGGCCGAA AUUUCUUA    38

(2) INFORMATION FOR SEQ ID NO:962:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:962:

```
    AAAUAGUUUU  AUAAAAA                                                              17
```

( 2 ) INFORMATION FOR SEQ ID NO:963:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:963:

```
UUUUUAUACU  GAUGAGGCCG  AAAGGCCGAA  AACUAUUU                                        38
```

( 2 ) INFORMATION FOR SEQ ID NO:964:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:964:

```
    AAUAGUUUUA  UAAAAAA                                                              17
```

( 2 ) INFORMATION FOR SEQ ID NO:965:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:965:

```
UUUUUUAUCU  GAUGAGGCCG  AAAGGCCGAA  AAACUAUU                                        38
```

( 2 ) INFORMATION FOR SEQ ID NO:966:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:966:

```
    AUAGUUUUAU  AAAAAAU                                                              17
```

( 2 ) INFORMATION FOR SEQ ID NO:967:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:967:

```
AUUUUUUACU  GAUGAGGCCG  AAAGGCCGAA  AAAACUAU                                        38
```

( 2 ) INFORMATION FOR SEQ ID NO:968:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:968:
```
              AGUUUUAUAA  AAAAUUA
```

( 2 ) INFORMATION FOR SEQ ID NO:969:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:969:

UAAUUUUUCU GAUGAGGCCG AAAGGCCGAA AUAAAACU 38

( 2 ) INFORMATION FOR SEQ ID NO:970:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:970:

UAAAAAAUUA UAUUUUU 17

( 2 ) INFORMATION FOR SEQ ID NO:971:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:971:

AAAAAUAUCU GAUGAGGCCG AAAGGCCGAA AUUUUUUA 38

( 2 ) INFORMATION FOR SEQ ID NO:972:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:972:

AAAAAAUUAU AUUUUUA 17

( 2 ) INFORMATION FOR SEQ ID NO:973:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:973:

UAAAAAUACU GAUGAGGCCG AAAGGCCGAA AAUUUUUU 38

( 2 ) INFORMATION FOR SEQ ID NO:974:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:974:

AAAAUUAUAU UUUUAUU 17

( 2 ) INFORMATION FOR SEQ ID NO:975:

( i ) SEQUENCE CHARACTERISTICS:

( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:975:

AAUAAAAACU GAUGAGGCCG AAAGGCCGAA AUAAUUUU                   38

( 2 ) INFORMATION FOR SEQ ID NO:976:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:976:

AAUUAUAUUU UUAUUCA                                          17

( 2 ) INFORMATION FOR SEQ ID NO:977:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:977:

UGAAUAAACU GAUGAGGCCG AAAGGCCGAA AUAUAAUU                   38

( 2 ) INFORMATION FOR SEQ ID NO:978:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:978:

AUUAUAUUUU UAUUCAG                                          17

( 2 ) INFORMATION FOR SEQ ID NO:979:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:979:
                    CUGAAUAACU GAUGAGGCCG AAAGGCCGAA AAUAUAAU ( 2 ) INFORMATION FOR SEQ ID NO:980:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:980:

UUAUAUUUUU AUUCAGU                                          17

( 2 ) INFORMATION FOR SEQ ID NO:981:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:981:

ACUGAAUACU GAUGAGGCCG AAAGGCCGAA AAAUAUAA  38

( 2 ) INFORMATION FOR SEQ ID NO:982:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:982:

UAUAUUUUUA UUCAGUA  17

( 2 ) INFORMATION FOR SEQ ID NO:983:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:983:

UACUGAAUCU GAUGAGGCCG AAAGGCCGAA AAAAUAUA  38

( 2 ) INFORMATION FOR SEQ ID NO:984:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:984:

AUAUUUUUAU UCAGUAA  17

( 2 ) INFORMATION FOR SEQ ID NO:985:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:985:

UUACUGAACU GAUGAGGCCG AAAGGCCGAA AAAAAUAU  38

( 2 ) INFORMATION FOR SEQ ID NO:986:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:986:

AUUUUUAUUC AGUAAUU  17

( 2 ) INFORMATION FOR SEQ ID NO:987:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:987:

```
AAUUACUGCU GAUGAGGCCG AAAGGCCGAA AUAAAAAU                              38
```

(2) INFORMATION FOR SEQ ID NO:988:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:988:

```
UUUUUAUUCA GUAAUUU                                                    17
```

(2) INFORMATION FOR SEQ ID NO:989:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:989:

```
AAAUUACUCU GAUGAGGCCG AAAGGCCGAA AAUAAAAA                              38
```

(2) INFORMATION FOR SEQ ID NO:990:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:990:

```
          UCAGUAAUUU AAUUUUG
```

(2) INFORMATION FOR SEQ ID NO:991:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:991:

```
CAAAAUUACU GAUGAGGCCG AAAGGCCGAA AUUACUGA                              38
```

(2) INFORMATION FOR SEQ ID NO:992:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:992:

```
CAGUAAUUUA AUUUUGU                                                    17
```

(2) INFORMATION FOR SEQ ID NO:993:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:993:

```
ACAAAAUUCU GAUGAGGCCG AAAGGCCGAA AAUUACUG                              38
```

( 2 ) INFORMATION FOR SEQ ID NO:994:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:994:

AGUAAUUUAA UUUUGUA 17

( 2 ) INFORMATION FOR SEQ ID NO:995:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:995:

UACAAAAUCU GAUGAGGCCG AAAGGCCGAA AAAUUACU 38

( 2 ) INFORMATION FOR SEQ ID NO:996:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:996:

AAUUUAAUUU UGUAAAU 17

( 2 ) INFORMATION FOR SEQ ID NO:997:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:997:

AUUUACAACU GAUGAGGCCG AAAGGCCGAA AUUAAAUU 38

( 2 ) INFORMATION FOR SEQ ID NO:998:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:998:

AUUUAAUUUU GUAAAUG 17

( 2 ) INFORMATION FOR SEQ ID NO:999:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:999:

CAUUUACACU GAUGAGGCCG AAAGGCCGAA AAUUAAAU 38

( 2 ) INFORMATION FOR SEQ ID NO:1000:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1000:

UUUAAUUUUG UAAAUGC                                           17

( 2 ) INFORMATION FOR SEQ ID NO:1001:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1001:
         GCAUUUACCU GAUGAGGCCG AAAGGCCGAA AAAUUAAA ( 2 ) INFORMATION FOR SEQ ID NO:1002:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1002:

AAAACGUUUU UUGCUGC                                           17

( 2 ) INFORMATION FOR SEQ ID NO:1003:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1003:

GCAGCAAACU GAUGAGGCCG AAAGGCCGAA AACGUUUU                    38

( 2 ) INFORMATION FOR SEQ ID NO:1004:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1004:

AAACGUUUUU UGCUGCU                                           17

( 2 ) INFORMATION FOR SEQ ID NO:1005:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1005:

AGCAGCAACU GAUGAGGCCG AAAGGCCGAA AAACGUUU                    38

( 2 ) INFORMATION FOR SEQ ID NO:1006:

( i ) SEQUENCE CHARACTERISTICS:
      ( A ) LENGTH: 17 base pairs
      ( B ) TYPE: nucleic acid
      ( C ) STRANDEDNESS: single (D) TOPOLOGY: linear (xi) SEQUENCE DESCRIPTION: SEQ ID NO:1006:

AACGUUUUUU GCUGCUA 17

(2) INFORMATION FOR SEQ ID NO:1007:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1007:

UAGCAGCACU GAUGAGGCCG AAAGGCCGAA AAAACGUU 38

(2) INFORMATION FOR SEQ ID NO:1008:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1008:

ACGUUUUUUG CUGCUAU 17

(2) INFORMATION FOR SEQ ID NO:1009:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1009:

AUAGCAGCCU GAUGAGGCCG AAAGGCCGAA AAAAACGU 38

(2) INFORMATION FOR SEQ ID NO:1010:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1010:

UUGCUGCUAU GGUCUUA 17

(2) INFORMATION FOR SEQ ID NO:1011:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1011:

UAAGACCACU GAUGAGGCCG AAAGGCCGAA AGCAGCAA 38

(2) INFORMATION FOR SEQ ID NO:1012:

(i) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:1012:

UAUGGUCUUA GCCUGUA ( 2 ) INFORMATION FOR SEQ ID NO:1013:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1013:

UACAGGCUCU GAUGAGGCCG AAAGGCCGAA AGACCAUA     38

( 2 ) INFORMATION FOR SEQ ID NO:1014:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1014:

AUGGUCUUAG CCUGUAG     17

( 2 ) INFORMATION FOR SEQ ID NO:1015:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1015:

CUACAGGCCU GAUGAGGCCG AAAGGCCGAA AAGACCAU     38

( 2 ) INFORMATION FOR SEQ ID NO:1016:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1016:

AUGCUGCUAG UAUCAGA     17

( 2 ) INFORMATION FOR SEQ ID NO:1017:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1017:

UCUGAUACCU GAUGAGGCCG AAAGGCCGAA AGCAGCAU     38

( 2 ) INFORMATION FOR SEQ ID NO:1018:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1018:

GCUAGUAUCA GAGGGC     17

( 2 ) INFORMATION FOR SEQ ID NO:1019:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1019:

GCCCCUCUCU GAUGAGGCCG AAAGGCCGAA AUACUAGC      38

( 2 ) INFORMATION FOR SEQ ID NO:1020:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1020:

GUAGAGCUUG GACAGAA      17

( 2 ) INFORMATION FOR SEQ ID NO:1021:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1021:

UUCUGUCCCU GAUGAGGCCG AAAGGCCGAA AGCUCUAC      38

( 2 ) INFORMATION FOR SEQ ID NO:1022:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1022:

AAGAAACUUG GUGUUAG      17

( 2 ) INFORMATION FOR SEQ ID NO:1023:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1023:
    CUAACACCCU GAUGAGGCCG AAAGGCCGAA AGUUUCUU ( 2 ) INFORMATION FOR SEQ ID NO:1024:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1024:

UUGGUGUUAG GUAAUUG      17

( 2 ) INFORMATION FOR SEQ ID NO:1025:

( i ) SEQUENCE CHARACTERISTICS:

(A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1025:

CAAUUACCCU GAUGAGGCCG AAAGGCCGAA AACACCAA                    38

(2) INFORMATION FOR SEQ ID NO:1026:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1026:

UAGGUAAUUG ACUAUGC                                           17

(2) INFORMATION FOR SEQ ID NO:1027:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1027:

GCAUAGUCCU GAUGAGGCCG AAAGGCCGAA AUUACCUA                    38

(2) INFORMATION FOR SEQ ID NO:1028:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1028:

AAUUGACUAU GCACUAG                                           17

(2) INFORMATION FOR SEQ ID NO:1029:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1029:

CUAGUGCACU GAUGAGGCCG AAAGGCCGAA AGUCAAUU                    38

(2) INFORMATION FOR SEQ ID NO:1030:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1030:

UAUGCACUAG UAUUUCA                                           17

(2) INFORMATION FOR SEQ ID NO:1031:

(i) SEQUENCE CHARACTERISTICS:
        (A) LENGTH: 38 base pairs
        (B) TYPE: nucleic acid ( C ) STRANDEDNESS: single
( D ) TOPOLOGY: linear ( x i ) SEQUENCE DESCRIPTION: SEQ ID NO:1031:

UGAAAUACCU GAUGAGGCCG AAAGGCGAA AGUGCAUA         38

( 2 ) INFORMATION FOR SEQ ID NO:1032:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1032:

ACUAGUAUUU CAGACUU         17

( 2 ) INFORMATION FOR SEQ ID NO:1033:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1033:

AAGUCUGACU GAUGAGGCCG AAAGGCCGAA AUACUAGU         38

( 2 ) INFORMATION FOR SEQ ID NO:1034:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1034:
CUAGUAUUUC AGACUUU ( 2 ) INFORMATION FOR SEQ ID NO:1035:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1035:

AAAGUCUGCU GAUGAGGCCG AAAGGCCGAA AAUACUAG         38

( 2 ) INFORMATION FOR SEQ ID NO:1036:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1036:

UAGUAUUUCA GACUUUU         17

( 2 ) INFORMATION FOR SEQ ID NO:1037:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1037:

```
         AAAAGUCUCU GAUGAGGCCG AAAGGCCGAA AAAUACUA                              38
```

( 2 ) INFORMATION FOR SEQ ID NO:1038:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1038:

```
         UUCAGACUUU UUAAUUU                                                     17
```

( 2 ) INFORMATION FOR SEQ ID NO:1039:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1039:

```
         AAAUUAAACU GAUGAGGCCG AAAGGCCGAA AGUCUGAA                              38
```

( 2 ) INFORMATION FOR SEQ ID NO:1040:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1040:

```
         UCAGACUUUU UAAUUUU                                                     17
```

( 2 ) INFORMATION FOR SEQ ID NO:1041:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1041:

```
         AAAAUUAACU GAUGAGGCCG AAAGGCCGAA AAGUCUGA                              38
```

( 2 ) INFORMATION FOR SEQ ID NO:1042:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1042:

```
         CAGACUUUUU AAUUUUA                                                     17
```

( 2 ) INFORMATION FOR SEQ ID NO:1043:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1043:

```
         UAAAAUUACU GAUGAGGCCG AAAGGCCGAA AAAGUCUG                              38
```

( 2 ) INFORMATION FOR SEQ ID NO:1044:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1044:

AGACUUUUUA AUUUUAU         17

( 2 ) INFORMATION FOR SEQ ID NO:1045:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1045:

AUAAAAUUCU GAUGAGGCCG AAAGGCCGAA AAAAGUCU ( 2 ) INFORMATION FOR SEQ ID NO:1046:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1046:

GACUUUUUAA UUUUAUA         17

( 2 ) INFORMATION FOR SEQ ID NO:1047:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1047:

UAUAAAAUCU GAUGAGGCCG AAAGGCCGAA AAAAAGUC         38

( 2 ) INFORMATION FOR SEQ ID NO:1048:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1048:

UUUUUAAUUU UAUAUAU         17

( 2 ) INFORMATION FOR SEQ ID NO:1049:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1049:

AUAUAUAACU GAUGAGGCCG AAAGGCCGAA AUUAAAAA         38

( 2 ) INFORMATION FOR SEQ ID NO:1050:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1050:

UUUUAAUUUU AUAUAUA 17

( 2 ) INFORMATION FOR SEQ ID NO:1051:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1051:

UAUAUAUACU GAUGAGGCCG AAAGGCCGAA AAUUAAAA 38

( 2 ) INFORMATION FOR SEQ ID NO:1052:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1052:

UUUAAUUUUA UAUAUAU 17

( 2 ) INFORMATION FOR SEQ ID NO:1053:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1053:

AUAUAUAUCU GAUGAGGCCG AAAGGCCGAA AAAUUAAA 38

( 2 ) INFORMATION FOR SEQ ID NO:1054:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1054:

UUAAUUUUAU AUAUAUA 17

( 2 ) INFORMATION FOR SEQ ID NO:1055:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1055:

UAUAUAUACU GAUGAGGCCG AAAGGCCGAA AAAAUUAA 38

( 2 ) INFORMATION FOR SEQ ID NO:1056:

( i ) SEQUENCE CHARACTERISTICS:
      ( A ) LENGTH: 17 base pairs

```
        ( B ) TYPE: nucleic acid
        ( C ) STRANDEDNESS: single
        ( D ) TOPOLOGY: linear ( x i ) SEQUENCE DESCRIPTION: SEQ ID NO:1056:
            AAUUUUAUAU  AUAUAUA ( 2 ) INFORMATION FOR SEQ ID NO:1057:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1057:

UAUAUAUACU  GAUGAGGCCG  AAAGGCCGAA  AUAAAAUU                                 3 8

( 2 ) INFORMATION FOR SEQ ID NO:1058:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1058:

UUUUAUAUAU  AUAUACA                                                          1 7

( 2 ) INFORMATION FOR SEQ ID NO:1059:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1059:

UGUAUAUACU  GAUGAGGCCG  AAAGGCCGAA  AUAUAAAA                                 3 8

( 2 ) INFORMATION FOR SEQ ID NO:1060:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1060:

UUAUAUAUAU  AUACAUU                                                          1 7

( 2 ) INFORMATION FOR SEQ ID NO:1061:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1061:

AAUGUAUACU  GAUGAGGCCG  AAAGGCCGAA  AUAUAUAA                                 3 8

( 2 ) INFORMATION FOR SEQ ID NO:1062:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear
```

( x i ) SEQUENCE DESCRIPTION: SEQ ID NO:1062:

AUAUAUAUAU ACAUUUU 17

( 2 ) INFORMATION FOR SEQ ID NO:1063:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1063:

AAAAUGUACU GAUGAGGCCG AAAGGCCGAA AUAUAUAU 38

( 2 ) INFORMATION FOR SEQ ID NO:1064:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1064:

AUAUAUAUAC AUUUUUU 17

( 2 ) INFORMATION FOR SEQ ID NO:1065:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1065:

AAAAAAUGCU GAUGAGGCCG AAAGGCCGAA AUAUAUAU 38

( 2 ) INFORMATION FOR SEQ ID NO:1066:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1066:

AUAUACAUUU UUUUUCC 17

( 2 ) INFORMATION FOR SEQ ID NO:1067:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1067:

GGAAAAAACU GAUGAGGCCG AAAGGCCGAA AUGUAUAU ( 2 ) INFORMATION FOR SEQ ID NO:1068:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1068:

UAUACAUUUU UUUUCCU 17

( 2 ) INFORMATION FOR SEQ ID NO:1069:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1069:

AGGAAAACU GAUGAGGCCG AAAGGCGAA AAUGUAUA        38

( 2 ) INFORMATION FOR SEQ ID NO:1070:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1070:

AUACAUUUUU UUUCCUU        17

( 2 ) INFORMATION FOR SEQ ID NO:1071:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1071:

AAGGAAAACU GAUGAGGCCG AAAGGCCGAA AAAUGUAU        38

( 2 ) INFORMATION FOR SEQ ID NO:1072:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1072:

UACAUUUUUU UUCCUUC        17

( 2 ) INFORMATION FOR SEQ ID NO:1073:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1073:

GAAGGAAACU GAUGAGGCCG AAAGGCCGAA AAAAUGUA        38

( 2 ) INFORMATION FOR SEQ ID NO:1074:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1074:

ACAUUUUUUU UCCUUCU        17

( 2 ) INFORMATION FOR SEQ ID NO:1075:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1075:

AGAAGGAACU GAUGAGGCCG AAAGGCCGAA AAAAAUGU     38

( 2 ) INFORMATION FOR SEQ ID NO:1076:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1076:

CAUUUUUUUU CCUUCUG     17

( 2 ) INFORMATION FOR SEQ ID NO:1077:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1077:

CAGAAGGACU GAUGAGGCCG AAAGGCCGAA AAAAAAUG     38

( 2 ) INFORMATION FOR SEQ ID NO:1078:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1078:
AUUUUUUUUC CUUCUGC ( 2 ) INFORMATION FOR SEQ ID NO:1079:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1079:

GCAGAAGGCU GAUGAGGCCG AAAGGCCGAA AAAAAAAU     38

( 2 ) INFORMATION FOR SEQ ID NO:1080:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1080:

UUUUUUUUCC UUCUGCA     17

( 2 ) INFORMATION FOR SEQ ID NO:1081:

( i ) SEQUENCE CHARACTERISTICS:
      ( A ) LENGTH: 38 base pairs
      ( B ) TYPE: nucleic acid (C) STRANDEDNESS: single
(D) TOPOLOGY: linear (xi) SEQUENCE DESCRIPTION: SEQ ID NO:1081:

UGCAGAAGCU GAUGAGGCCG AAAGGCCGAA AAAAAAA    38

(2) INFORMATION FOR SEQ ID NO:1082:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1082:

UUUUUCCUUC UGCAAUA    17

(2) INFORMATION FOR SEQ ID NO:1083:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1083:

UAUUGCAGCU GAUGAGGCCG AAAGGCCGAA AGGAAAA    38

(2) INFORMATION FOR SEQ ID NO:1084:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1084:

UUUCCUUCU GCAAUAC    17

(2) INFORMATION FOR SEQ ID NO:1085:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1085:

GUAUUGCACU GAUGAGGCCG AAAGGCCGAA AAGGAAAA    38

(2) INFORMATION FOR SEQ ID NO:1086:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1086:

UCUGCAAUAC AUUUGAA    17

(2) INFORMATION FOR SEQ ID NO:1087:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1087:

UUCAAAUGCU GAUGAGGCCG AAAGGCCGAA AUUGCAGA 38

( 2 ) INFORMATION FOR SEQ ID NO:1088:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1088:

CAAUACAUUU GAAAACU 17

( 2 ) INFORMATION FOR SEQ ID NO:1089:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1089:

AGUUUUCACU GAUGAGGCCG AAAGGCCGAA AUGUAUUG ( 2 ) INFORMATION FOR SEQ ID NO:1090:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1090:

AAUACAUUUG AAAACUU 17

( 2 ) INFORMATION FOR SEQ ID NO:1091:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1091:

AAGUUUUCCU GAUGAGGCCG AAAGGCCGAA AAUGUAUU 38

( 2 ) INFORMATION FOR SEQ ID NO:1092:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1092:

UGAAAACUUG UUUGGGA 17

( 2 ) INFORMATION FOR SEQ ID NO:1093:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1093:

UCCCAAACCU GAUGAGGCCG AAAGGCCGAA AGUUUUCA 38

( 2 ) INFORMATION FOR SEQ ID NO:1094:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1094:

AACUUGUUUG GGAGACU        17

( 2 ) INFORMATION FOR SEQ ID NO:1095:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1095:

AGUCUCCCU GAUGAGGCCG AAAGGCCGAA AACAAGUU        38

( 2 ) INFORMATION FOR SEQ ID NO:1096:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1096:

GGGAGACUCU GCAUUUU        17

( 2 ) INFORMATION FOR SEQ ID NO:1097:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1097:

AAAAUGCACU GAUGAGGCCG AAAGGCCGAA AGUCUCCC        38

( 2 ) INFORMATION FOR SEQ ID NO:1098:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1098:

CUCUGCAUUU UUUAUUG        17

( 2 ) INFORMATION FOR SEQ ID NO:1099:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1099:

CAAUAAAACU GAUGAGGCCG AAAGGCCGAA AUGCAGAG        38

( 2 ) INFORMATION FOR SEQ ID NO:1100:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1100:
        UCUGCAUUUU UUAUUGU ( 2 ) INFORMATION FOR SEQ ID NO:1101:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1101:

ACAAUAAACU GAUGAGGCCG AAAGGCCGAA AAUGCAGA        38

( 2 ) INFORMATION FOR SEQ ID NO:1102:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1102:

CUGCAUUUUU UAUUGUG        17

( 2 ) INFORMATION FOR SEQ ID NO:1103:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1103:

CACAAUAACU GAUGAGGCCG AAAGGCCGAA AAAUGCAG        38

( 2 ) INFORMATION FOR SEQ ID NO:1104:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1104:

UGCAUUUUUU AUUGUGG        17

( 2 ) INFORMATION FOR SEQ ID NO:1105:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1105:

CCACAAUACU GAUGAGGCCG AAAGGCCGAA AAAAUGCA        38

( 2 ) INFORMATION FOR SEQ ID NO:1106:

( i ) SEQUENCE CHARACTERISTICS:
        ( A ) LENGTH: 17 base pairs ( B ) TYPE: nucleic acid
( C ) STRANDEDNESS: single
( D ) TOPOLOGY: linear ( x i ) SEQUENCE DESCRIPTION: SEQ ID NO:1106:

GCAUUUUUUA UUGUGGU                     17

( 2 ) INFORMATION FOR SEQ ID NO:1107:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1107:

ACCACAAUCU GAUGAGGCCG AAAGGCCGAA AAAAAUGC       38

( 2 ) INFORMATION FOR SEQ ID NO:1108:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1108:

CAUUUUUAU UGUGGUU                      17

( 2 ) INFORMATION FOR SEQ ID NO:1109:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1109:

AACCACAACU GAUGAGGCCG AAAGGCCGAA AAAAAAUG       38

( 2 ) INFORMATION FOR SEQ ID NO:1110:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1110:

UUUUUUAUUG UGGUUUU                     17

( 2 ) INFORMATION FOR SEQ ID NO:1111:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1111:

AAAACCACCU GAUGAGGCCG AAAGGCCGAA AUAAAAAA       38

( 2 ) INFORMATION FOR SEQ ID NO:1112:

( i ) SEQUENCE CHARACTERISTICS:
( A ) LENGTH: 17 base pairs
( B ) TYPE: nucleic acid
( C ) STRANDEDNESS: single (D) TOPOLOGY: linear (xi) SEQUENCE DESCRIPTION: SEQ ID NO:1112:

UUGUGGUUUU UUUGUUA                                                              17

(2) INFORMATION FOR SEQ ID NO:1113:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1113:

UAACAAAACU GAUGAGGCCG AAAGGCCGAA AACCACAA                                        38

(2) INFORMATION FOR SEQ ID NO:1114:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1114:

UGUGGUUUUU UUGUUAU                                                              17

(2) INFORMATION FOR SEQ ID NO:1115:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1115:

AUAACAAACU GAUGAGGCCG AAAGGCCGAA AAACCACA                                        38

(2) INFORMATION FOR SEQ ID NO:1116:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1116:

GUGGUUUUU UGUUAUU                                                               17

(2) INFORMATION FOR SEQ ID NO:1117:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1117:

AAUAACAACU GAUGAGGCCG AAAGGCCGAA AAAACCAC                                        38

(2) INFORMATION FOR SEQ ID NO:1118:

(i) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:1118:

UGGUUUUUUU GUUAUUG 17

( 2 ) INFORMATION FOR SEQ ID NO:1119:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1119:

CAAUAACACU GAUGAGGCCG AAAGGCCGAA AAAAACCA 38

( 2 ) INFORMATION FOR SEQ ID NO:1120:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1120:

GGUUUUUUUG UUAUUGU 17

( 2 ) INFORMATION FOR SEQ ID NO:1121:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1121:

ACAAUAACCU GAUGAGGCCG AAAGGCCGAA AAAAACC 38

( 2 ) INFORMATION FOR SEQ ID NO:1122:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1122:

UUUUUUGUUA UUGUUGG 17

( 2 ) INFORMATION FOR SEQ ID NO:1123:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1123:

CCAACAAUCU GAUGAGGCCG AAAGGCCGAA ACAAAAA 38

( 2 ) INFORMATION FOR SEQ ID NO:1124:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1124:

UUUUUGUUAU UGUUGGU 17

( 2 ) INFORMATION FOR SEQ ID NO:1125:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1125:

ACCAACAACU GAUGAGGCCG AAAGGCCGAA AACAAAAA 38

( 2 ) INFORMATION FOR SEQ ID NO:1126:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1126:

UUUGUUAUUG UUGGUUU 17

( 2 ) INFORMATION FOR SEQ ID NO:1127:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1127:

AAACCAACCU GAUGAGGCCG AAAGGCCGAA AUAACAAA 38

( 2 ) INFORMATION FOR SEQ ID NO:1128:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1128:

UGUUGGUUUA UACAAGC 17

( 2 ) INFORMATION FOR SEQ ID NO:1129:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1129:

GCUUGUAUCU GAUGAGGCCG AAAGGCCGAA AACCAACA 38

( 2 ) INFORMATION FOR SEQ ID NO:1130:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1130:

GUUGGUUUAU ACAAGCA 17

( 2 ) INFORMATION FOR SEQ ID NO:1131:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1131:

UGCUUGUACU GAUGAGGCCG AAAGGCCGAA AAACCAAC     38

( 2 ) INFORMATION FOR SEQ ID NO:1132:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1132:

UGGUUUAUAC AAGCAUG     17

( 2 ) INFORMATION FOR SEQ ID NO:1133:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1133:

CAUGCUUGCU GAUGAGGCCG AAAGGCCGAA AUAAACCA ( 2 ) INFORMATION FOR SEQ ID NO:1134:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1134:

GUUGCACUUC UUUUUUG     17

( 2 ) INFORMATION FOR SEQ ID NO:1135:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1135:

CAAAAAAGCU GAUGAGGCCG AAAGGCCGAA AGUGCAAC     38

( 2 ) INFORMATION FOR SEQ ID NO:1136:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1136:

UUGCACUUCU UUUUUGG     17

( 2 ) INFORMATION FOR SEQ ID NO:1137:

( i ) SEQUENCE CHARACTERISTICS:

( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1137:

CCAAAAACU GAUGAGGCCG AAAGGCCGAA AAGUGCAA     38

( 2 ) INFORMATION FOR SEQ ID NO:1138:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1138:

GCACUUCUUU UUUGGGA     17

( 2 ) INFORMATION FOR SEQ ID NO:1139:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1139:

UCCCAAAACU GAUGAGGCCG AAAGGCCGAA AGAAGUGC     38

( 2 ) INFORMATION FOR SEQ ID NO:1140:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1140:

CACUUCUUUU UUGGGAG     17

( 2 ) INFORMATION FOR SEQ ID NO:1141:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1141:

CUCCCAAACU GAUGAGGCCG AAAGGCCGAA AAGAAGUG     38

( 2 ) INFORMATION FOR SEQ ID NO:1142:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1142:

ACUUCUUUUU UGGGAGA     17

( 2 ) INFORMATION FOR SEQ ID NO:1143:

( i ) SEQUENCE CHARACTERISTICS:
( A ) LENGTH: 38 base pairs
( B ) TYPE: nucleic acid ( C ) STRANDEDNESS: single
        ( D ) TOPOLOGY: linear ( x i ) SEQUENCE DESCRIPTION: SEQ ID NO:1143:

UCUCCAACU GAUGAGGCCG AAAGGCCGAA AAAGAAGU        38

( 2 ) INFORMATION FOR SEQ ID NO:1144:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1144:

CUUCUUUUUU GGGAGAU        17

( 2 ) INFORMATION FOR SEQ ID NO:1145:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1145:

AUCUCCCACU GAUGAGGCCG AAAGGCCGAA AAAAGAAG        38

( 2 ) INFORMATION FOR SEQ ID NO:1146:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1146:

UUCUUUUUUG GGAGAUG        17

( 2 ) INFORMATION FOR SEQ ID NO:1147:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1147:

CAUCUCCCCU GAUGAGGCCG AAAGGCCGAA AAAAAGAA        38

( 2 ) INFORMATION FOR SEQ ID NO:1148:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1148:

UUGAUGUUCU AUGUUUU        17

( 2 ) INFORMATION FOR SEQ ID NO:1149:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1149:

AAAACAUACU GAUGAGGCCG AAAGGCCGAA AACAUCAA 38

( 2 ) INFORMATION FOR SEQ ID NO:1150:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1150:

GAUGUUCUAU GUUUUGU 17

( 2 ) INFORMATION FOR SEQ ID NO:1151:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1151:

ACAAAACACU GAUGAGGCCG AAAGGCCGAA AGAACAUC 38

( 2 ) INFORMATION FOR SEQ ID NO:1152:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1152:

UCUAUGUUUU GUUUUGA 17

( 2 ) INFORMATION FOR SEQ ID NO:1153:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1153:

UCAAAACACU GAUGAGGCCG AAAGGCCGAA AACAUAGA 38

( 2 ) INFORMATION FOR SEQ ID NO:1154:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1154:

CUAUGUUUUG UUUUGAG 17

( 2 ) INFORMATION FOR SEQ ID NO:1155:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1155:

```
CUCAAAACCU GAUGAGGCCG AAAGGCCGAA AAACAUAG                    38
```

(2) INFORMATION FOR SEQ ID NO:1156:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1156:

```
GUUUUGUUUU GAGUGUA                                           17
```

(2) INFORMATION FOR SEQ ID NO:1157:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1157:

```
UACACUCACU GAUGAGGCCG AAAGGCCGAA AACAAAAC                    38
```

(2) INFORMATION FOR SEQ ID NO:1158:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1158:

```
UUUUGUUUUG AGUGUAG                                           17
```

(2) INFORMATION FOR SEQ ID NO:1159:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1159:

```
CUACACUCCU GAUGAGGCCG AAAGGCCGAA AAACAAAA                    38
```

(2) INFORMATION FOR SEQ ID NO:1160:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1160:

```
UGACUGUUUU AUAAUUU                                           17
```

(2) INFORMATION FOR SEQ ID NO:1161:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1161:

```
AAAUUAUACU GAUGAGGCCG AAAGGCCGAA AACAGUCA                    38
```

( 2 ) INFORMATION FOR SEQ ID NO:1162:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1162:

GACUGUUUUA UAAUUUG    17

( 2 ) INFORMATION FOR SEQ ID NO:1163:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1163:

CAAAUUAUCU GAUGAGGCCG AAAGGCCGAA AAACAGUC    38

( 2 ) INFORMATION FOR SEQ ID NO:1164:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1164:

ACUGUUUUAU AAUUUGG    17

( 2 ) INFORMATION FOR SEQ ID NO:1165:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1165:

CCAAAUUACU GAUGAGGCCG AAAGGCCGAA AAAACAGU    38

( 2 ) INFORMATION FOR SEQ ID NO:1166:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1166:

UGUUUUAUAA UUUGGGA    17

( 2 ) INFORMATION FOR SEQ ID NO:1167:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1167:

UCCCAAAUCU GAUGAGGCCG AAAGGCCGAA AUAAAACA    38

( 2 ) INFORMATION FOR SEQ ID NO:1168:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1168:

UUUAUAAUUU GGGAGUU     17

( 2 ) INFORMATION FOR SEQ ID NO:1169:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1169:

AACUCCCACU GAUGAGGCCG AAAGGCCGAA AUUAUAAA     38

( 2 ) INFORMATION FOR SEQ ID NO:1170:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1170:

UUAUAAUUUG GGAGUUC     17

( 2 ) INFORMATION FOR SEQ ID NO:1171:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1171:

GAACUCCCCU GAUGAGGCCG AAAGGCCGAA AAUUAUAA     38

( 2 ) INFORMATION FOR SEQ ID NO:1172:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1172:

UGGGAGUUCU GCAUUUG     17

( 2 ) INFORMATION FOR SEQ ID NO:1173:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1173:

CAAAUGCACU GAUGAGGCCG AAAGGCCGAA AACUCCCA     38

( 2 ) INFORMATION FOR SEQ ID NO:1174:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1174:

UUCUGCAUUU GAUCCGC     17

( 2 ) INFORMATION FOR SEQ ID NO:1175:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1175:

GCGGAUCACU GAUGAGGCCG AAAGGCCGAA AUGCAGAA     38

( 2 ) INFORMATION FOR SEQ ID NO:1176:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1176:

UCUGCAUUUG AUCCGCA     17

( 2 ) INFORMATION FOR SEQ ID NO:1177:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1177:

UGCGGAUCCU GAUGAGGCCG AAAGGCCGAA AAUGCAGA     38

( 2 ) INFORMATION FOR SEQ ID NO:1178:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1178:

CAUUUGAUCC GCAUCCC     17

( 2 ) INFORMATION FOR SEQ ID NO:1179:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1179:

GGGAUGCGCU GAUGAGGCCG AAAGGCCGAA AUCAAAUG     38

( 2 ) INFORMATION FOR SEQ ID NO:1180:

( i ) SEQUENCE CHARACTERISTICS:
    ( A ) LENGTH: 17 base pairs (B) TYPE: nucleic acid
        (C) STRANDEDNESS: single
        (D) TOPOLOGY: linear (xi) SEQUENCE DESCRIPTION: SEQ ID NO:1180:

AUCCGCAUCC CCUGUGG    17

(2) INFORMATION FOR SEQ ID NO:1181:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1181:

CCACAGGGCU GAUGAGGCCG AAAGGCCGAA AUGCGGAU    38

(2) INFORMATION FOR SEQ ID NO:1182:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1182:

CUGUGGUUUC UAAGUGU    17

(2) INFORMATION FOR SEQ ID NO:1183:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1183:

ACACUUAGCU GAUGAGGCCG AAAGGCCGAA AACCACAG    38

(2) INFORMATION FOR SEQ ID NO:1184:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1184:

UGUGGUUUCU AAGUGUA    17

(2) INFORMATION FOR SEQ ID NO:1185:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1185:

UACACUUACU GAUGAGGCCG AAAGGCCGAA AAACCACA    38

(2) INFORMATION FOR SEQ ID NO:1186:

(i) SEQUENCE CHARACTERISTICS:
        (A) LENGTH: 17 base pairs
        (B) TYPE: nucleic acid
        (C) STRANDEDNESS: single ( D ) TOPOLOGY: linear ( x i ) SEQUENCE DESCRIPTION: SEQ ID NO:1186:

UGGUUUCUAA GUGUAUG                                                                                          17

( 2 ) INFORMATION FOR SEQ ID NO:1187:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1187:

CAUACACUCU GAUGAGGCCG AAAGGCCGAA AGAAACCA                                                                    38

( 2 ) INFORMATION FOR SEQ ID NO:1188:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1188:
            UAUGGUCUCA GAACUGU ( 2 ) INFORMATION FOR SEQ ID NO:1189:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1189:

ACAGUUCUCU GAUGAGGCCG AAAGGCCGAA AGACCAUA                                                                    38

( 2 ) INFORMATION FOR SEQ ID NO:1190:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1190:

GCAUGGAUCC UGUGUUU                                                                                          17

( 2 ) INFORMATION FOR SEQ ID NO:1191:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1191:

AAACACAGCU GAUGAGGCCG AAAGGCCGAA AUCCAUGC                                                                    38

( 2 ) INFORMATION FOR SEQ ID NO:1192:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1192:

UCCUGUGUUU GCAACUG 17

( 2 ) INFORMATION FOR SEQ ID NO:1193:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1193:

CAGUUGCACU GAUGAGGCCG AAAGGCCGAA ACACAGGA 38

( 2 ) INFORMATION FOR SEQ ID NO:1194:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1194:

CCUGUGUUUG CAACUGG 17

( 2 ) INFORMATION FOR SEQ ID NO:1195:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1195:

CCAGUUGCCU GAUGAGGCCG AAAGGCCGAA AACACAGG 38

( 2 ) INFORMATION FOR SEQ ID NO:1196:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1196:

UGGUUGAUAG CCAGUCA 17

( 2 ) INFORMATION FOR SEQ ID NO:1197:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1197:

UGACUGGCCU GAUGAGGCCG AAAGGCCGAA AUCAACCA 38

( 2 ) INFORMATION FOR SEQ ID NO:1198:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1198:

CACUGCCUUA AGAACAU 17

( 2 ) INFORMATION FOR SEQ ID NO:1199:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1199:

AUGUUCUUCU GAUGAGGCCG AAAGGCCGAA AGGCAGUG    38

( 2 ) INFORMATION FOR SEQ ID NO:1200:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1200:

ACUGCCUUAA GAACAUU    17

( 2 ) INFORMATION FOR SEQ ID NO:1201:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1201:

AAUGUUCUCU GAUGAGGCCG AAAGGCCGAA AAGGCAGU    38

( 2 ) INFORMATION FOR SEQ ID NO:1202:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1202:

AAGAACAUUU GAUGCAA    17

( 2 ) INFORMATION FOR SEQ ID NO:1203:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1203:

UUGCAUCACU GAUGAGGCCG AAAGGCCGAA AUGUUCUU    38

( 2 ) INFORMATION FOR SEQ ID NO:1204:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1204:

AGAACAUUUG AUGCAAG    17

( 2 ) INFORMATION FOR SEQ ID NO:1205:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1205:

CUUGCAUCCU GAUGAGGCCG AAAGGCCGAA AAUGUUCU  38

( 2 ) INFORMATION FOR SEQ ID NO:1206:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1206:

ACUGAACUUU UGAGAUA  17

( 2 ) INFORMATION FOR SEQ ID NO:1207:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1207:

UAUCUCAACU GAUGAGGCCG AAAGGCCGAA AGUUCAGU  38

( 2 ) INFORMATION FOR SEQ ID NO:1208:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1208:

CUGAACUUUU GAGAUAU  17

( 2 ) INFORMATION FOR SEQ ID NO:1209:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1209:

AUAUCUCACU GAUGAGGCCG AAAGGCCGAA AAGUUCAG  38

( 2 ) INFORMATION FOR SEQ ID NO:1210:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1210:

UGAACUUUUG AGAUAUG  17

( 2 ) INFORMATION FOR SEQ ID NO:1211:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1211:

CAUAUCUCCU GAUGAGGCCG AAAGGCCGAA AAAGUUCA    38

(2) INFORMATION FOR SEQ ID NO:1212:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1212:

UUUGAGAUAU GACGGUG    17

(2) INFORMATION FOR SEQ ID NO:1213:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1213:

CACCGUCACU GAUGAGGCCG AAAGGCCGAA AUCUCAAA    38

(2) INFORMATION FOR SEQ ID NO:1214:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1214:

GGUGUACUUA CUGCCUU    17

(2) INFORMATION FOR SEQ ID NO:1215:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1215:

AAGGCAGUCU GAUGAGGCCG AAAGGCCGAA AGUACACC    38

(2) INFORMATION FOR SEQ ID NO:1216:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1216:

GUGUACUUAC UGCCUUG    17

(2) INFORMATION FOR SEQ ID NO:1217:

(i) SEQUENCE CHARACTERISTICS:
(A) LENGTH: 38 base pairs
(B) TYPE: nucleic acid

-continued (C) STRANDEDNESS: single
            (D) TOPOLOGY: linear (xi) SEQUENCE DESCRIPTION: SEQ ID NO:1217:

CAAGGCAGCU GAUGAGGCCG AAAGGCCGAA AAGUACAC                                38

(2) INFORMATION FOR SEQ ID NO:1218:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1218:

UACUGCCUUG UAGCAAA                                                      17

(2) INFORMATION FOR SEQ ID NO:1219:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:1219:

UUUGCUACCU GAUGAGGCCG AAAGGCCGAA AGGCAGUA                                38

(2) INFORMATION FOR SEQ ID NO:1220:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1220:

AGCAAAAUAA AGAUGUG                                                      17

(2) INFORMATION FOR SEQ ID NO:1221:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:1221:

CACAUCUUCU GAUGAGGCCG AAAGGCCGAA AUUUGCU                                 38

(2) INFORMATION FOR SEQ ID NO:1222:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1222:

UGUGCCCUUA UUUUACC                                                      17

(2) INFORMATION FOR SEQ ID NO:1223:

(i) SEQUENCE CHARACTERISTICS:
            (A) LENGTH: 38 base pairs
            (B) TYPE: nucleic acid
            (C) STRANDEDNESS: single
            (D) TOPOLOGY: linear ( x i ) SEQUENCE DESCRIPTION: SEQ ID NO:1223:

GGUAAAAUCU GAUGAGGCCG AAAGGCCGAA AGGGCACA    38

( 2 ) INFORMATION FOR SEQ ID NO:1224:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1224:

GUGCCCUUAU UUUACCU    17

( 2 ) INFORMATION FOR SEQ ID NO:1225:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1225:

AGGUAAAACU GAUGAGGCCG AAAGGCCGAA AAGGGCAC    38

( 2 ) INFORMATION FOR SEQ ID NO:1226:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1226:

UCCGCCAACU GAUGAGGCCG AAAGGCCGAA AGCCCGG    38

( 2 ) INFORMATION FOR SEQ ID NO:1227:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1227:

CCGGGGCUCU UGGCGGA    17

( 2 ) INFORMATION FOR SEQ ID NO:1228:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1228:

GCUCCGCCCU GAUGAGGCCG AAAGGCCGAA AGAGCCCC    38

( 2 ) INFORMATION FOR SEQ ID NO:1229:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1229:

```
GGGGCUCUUG GCGGAGC                                                                17
```

( 2 ) INFORMATION FOR SEQ ID NO:1230:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1230:

```
GCCAUGGCCU GAUGAGGCCG AAAGGCCGAA AGGCGGGC                                         38
```

( 2 ) INFORMATION FOR SEQ ID NO:1231:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1231:

```
GCCCGCCUCG CCAUGGC                                                                17
```

( 2 ) INFORMATION FOR SEQ ID NO:1232:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1232:

```
CUACUGUACU GAUGAGGCCG AAAGGCCGAA AUGCUGUG                                         38
```

( 2 ) INFORMATION FOR SEQ ID NO:1233:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1233:

```
CACAGCAUCU ACAGUAG                                                                17
```

( 2 ) INFORMATION FOR SEQ ID NO:1234:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1234:

```
CGCUACUGCU GAUGAGGCCG AAAGGCCGAA AGAUGCUG                                         38
```

( 2 ) INFORMATION FOR SEQ ID NO:1235:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1235:

```
CAGCAUCUAC AGUAGCG                                                                17
```

( 2 ) INFORMATION FOR SEQ ID NO:1236:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1236:

UUCAUCGCCU GAUGAGGCCG AAAGGCCGAA ACUGUAGA　　　　　　　　　　38

( 2 ) INFORMATION FOR SEQ ID NO:1237:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1237:

UCUACAGUAG CGAUGAA　　　　　　　　　　17

( 2 ) INFORMATION FOR SEQ ID NO:1238:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1238:

CACAUCUCCU GAUGAGGCCG AAAGGCCGAA AUGUCUUC　　　　　　　　　　38

( 2 ) INFORMATION FOR SEQ ID NO:1239:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1239:

GAAGACAUUG AGAUGUG　　　　　　　　　　17

( 2 ) INFORMATION FOR SEQ ID NO:1240:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1240:

GCCCAUCGCU GAUGAGGCCG AAAGGCCGAA AGUCAUGG　　　　　　　　　　38

( 2 ) INFORMATION FOR SEQ ID NO:1241:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1241:

CCAUGACUAC GAUGGGC　　　　　　　　　　17

( 2 ) INFORMATION FOR SEQ ID NO:1242:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1242:

GCUUCCACU GAUGAGGCCG AAAGGCCGAA AUUUGGGC        38

( 2 ) INFORMATION FOR SEQ ID NO:1243:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1243:

GCCCAAAUCU GGAAAGC ( 2 ) INFORMATION FOR SEQ ID NO:1244:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1244:

CCCCAAGUCU GAUGAGGCCG AAAGGCCGAA ACGCUUUC        38

( 2 ) INFORMATION FOR SEQ ID NO:1245:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1245:

GAAAGCGUCA CUUGGGG        17

( 2 ) INFORMATION FOR SEQ ID NO:1246:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1246:

UUUUCCCCU GAUGAGGCCG AAAGGCCGAA AGUGACGC        38

( 2 ) INFORMATION FOR SEQ ID NO:1247:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1247:

GCGUCACUUG GGGAAAA        17

( 2 ) INFORMATION FOR SEQ ID NO:1248:

( i ) SEQUENCE CHARACTERISTICS:
        ( A ) LENGTH: 38 base pairs ( B ) TYPE: nucleic acid
        ( C ) STRANDEDNESS: single
        ( D ) TOPOLOGY: linear ( x i ) SEQUENCE DESCRIPTION: SEQ ID NO:1248:

UGUCCACCCU GAUGAGGCCG AAAGGCCGAA AGUUUCC 38

( 2 ) INFORMATION FOR SEQ ID NO:1249:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1249:

GGAAAACUAG GUGGACA 17

( 2 ) INFORMATION FOR SEQ ID NO:1250:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1250:

UUGGCAAUCU GAUGAGGCCG AAAGGCCGAA ACUUUCCA 38

( 2 ) INFORMATION FOR SEQ ID NO:1251:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1251:

UGGAAAGUCA UUGCCAA 17

( 2 ) INFORMATION FOR SEQ ID NO:1252:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1252:

UAAUUGGCCU GAUGAGGCCG AAAGGCCGAA AUGACUUU 38

( 2 ) INFORMATION FOR SEQ ID NO:1253:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1253:

AAAGUCAUUG CCAAUUA 17

( 2 ) INFORMATION FOR SEQ ID NO:1254:

( i ) SEQUENCE CHARACTERISTICS:
        ( A ) LENGTH: 38 base pairs
        ( B ) TYPE: nucleic acid
        ( C ) STRANDEDNESS: single ( D ) TOPOLOGY: linear ( x i ) SEQUENCE DESCRIPTION: SEQ ID NO:1254:

GGGCAGAUCU GAUGAGGCCG AAAGGCCGAA AUUGGCAA     38

( 2 ) INFORMATION FOR SEQ ID NO:1255:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1255:

UUGCCAAUUA UCUGCCC     17

( 2 ) INFORMATION FOR SEQ ID NO:1256:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1256:

UGGGCAGACU GAUGAGGCCG AAAGGCCGAA AAUUGGCA     38

( 2 ) INFORMATION FOR SEQ ID NO:1257:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1257:

UGCCAAUUAU CUGCCCA     17

( 2 ) INFORMATION FOR SEQ ID NO:1258:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1258:

GUUGGGCACU GAUGAGGCCG AAAGGCCGAA AUAAUUGG     38

( 2 ) INFORMATION FOR SEQ ID NO:1259:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1259:

CCAAUUAUCU GCCCAAC     17

( 2 ) INFORMATION FOR SEQ ID NO:1260:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1260:

UGGCACUGCU GAUGAGGCCG AAAGGCCGAA ACAUCUGU    38

( 2 ) INFORMATION FOR SEQ ID NO:1261:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1261:

ACAGAUGUAC AGUGCCA    17

( 2 ) INFORMATION FOR SEQ ID NO:1262:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1262:

CCUUUGAUCU GAUGAGGCCG AAAGGCCGAA AGUUCAGG    38

( 2 ) INFORMATION FOR SEQ ID NO:1263:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1263:

CCUGAACUCA UCAAAGG    17

( 2 ) INFORMATION FOR SEQ ID NO:1264:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1264:

GGACCUUUCU GAUGAGGCCG AAAGGCCGAA AUGAGUUC    38

( 2 ) INFORMATION FOR SEQ ID NO:1265:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1265:

GAACUCAUCA AAGGUCC ( 2 ) INFORMATION FOR SEQ ID NO:1266:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1266:

GGUCCAGGCU GAUGAGGCCG AAAGGCCGAA ACCUUUGA    38

( 2 ) INFORMATION FOR SEQ ID NO:1267:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1267:

UCAAAGGUCC CUGGACC     17

( 2 ) INFORMATION FOR SEQ ID NO:1268:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1268:

GACUCUCUCU GAUGAGGCCG AAAGGCCGAA AUCUUCUU     38

( 2 ) INFORMATION FOR SEQ ID NO:1269:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1269:

AAGAAGAUCA GAGAGUC     17

( 2 ) INFORMATION FOR SEQ ID NO:1270:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1270:

AGCUUUAUCU GAUGAGGCCG AAAGGCCGAA ACUCUCUG     38

( 2 ) INFORMATION FOR SEQ ID NO:1271:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1271:

CAGAGAGUCA UAAAGCU     17

( 2 ) INFORMATION FOR SEQ ID NO:1272:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1272:

ACAAGCUUCU GAUGAGGCCG AAAGGCCGAA AUGACUCU     38

( 2 ) INFORMATION FOR SEQ ID NO:1273:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1273:

AGAGUCAUAA AGCUUGU 17

( 2 ) INFORMATION FOR SEQ ID NO:1274:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1274:

UUCUGGACCU GAUGAGGCCG AAAGGCCGAA AGCUUUAU 38

( 2 ) INFORMATION FOR SEQ ID NO:1275:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1275:

AUAAAGCUUG UCCAGAA 17

( 2 ) INFORMATION FOR SEQ ID NO:1276:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1276:

UAUUUCUGCU GAUGAGGCCG AAAGGCCGAA ACAAGCUU 38

( 2 ) INFORMATION FOR SEQ ID NO:1277:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1277:

AAGCUUGUCC AGAAAUA 17

( 2 ) INFORMATION FOR SEQ ID NO:1278:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1278:

UCGGACCACU GAUGAGGCCG AAAGGCCGAA AUUUCUGG 38

( 2 ) INFORMATION FOR SEQ ID NO:1279:

( i ) SEQUENCE CHARACTERISTICS:

( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1279:

CCAGAAAUAU GGUCCGA                                                                          17

( 2 ) INFORMATION FOR SEQ ID NO:1280:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1280:

ACGCUUCGCU GAUGAGGCCG AAAGGCCGAA ACCAUAUU                                                    38

( 2 ) INFORMATION FOR SEQ ID NO:1281:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1281:

AAUAUGGUCC GAAGCGU                                                                          17

( 2 ) INFORMATION FOR SEQ ID NO:1282:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1282:

AACAGACCCU GAUGAGGCCG AAAGGCCGAA ACGCUUCG                                                    38

( 2 ) INFORMATION FOR SEQ ID NO:1283:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1283:

CGAAGCGUUG GUCUGUU                                                                          17

( 2 ) INFORMATION FOR SEQ ID NO:1284:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1284:

CAAUAACACU GAUGAGGCCG AAAGGCCGAA ACCAACGC                                                    38

( 2 ) INFORMATION FOR SEQ ID NO:1285:

( i ) SEQUENCE CHARACTERISTICS:
            ( A ) LENGTH: 17 base pairs
            ( B ) TYPE: nucleic acid (C) STRANDEDNESS: single
(D) TOPOLOGY: linear (xi) SEQUENCE DESCRIPTION: SEQ ID NO:1285:

GCGUUGGUCU GUUAUUG                                                      17

(2) INFORMATION FOR SEQ ID NO:1286:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:1286:

UUGGCAAUCU GAUGAGGCCG AAAGGCCGAA ACAGACCA                                38

(2) INFORMATION FOR SEQ ID NO:1287:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:1287:
           UGGUCUGUUA UUGCCAA (2) INFORMATION FOR SEQ ID NO:1288:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:1288:

CUUGGCAACU GAUGAGGCCG AAAGGCCGAA AACAGACC                                38

(2) INFORMATION FOR SEQ ID NO:1289:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:1289:

GGUCUGUUAU UGCCAAG                                                      17

(2) INFORMATION FOR SEQ ID NO:1290:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:1290:

UGCUUGGCCU GAUGAGGCCG AAAGGCCGAA AUAACAGA                                38

(2) INFORMATION FOR SEQ ID NO:1291:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:1291:

```
        UCUGUUAUUG  CCAAGCA                                                              17
```

( 2 ) INFORMATION FOR SEQ ID NO:1292:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1292:

```
    UCCCUUUUCU  GAUGAGGCCG  AAAGGCCGAA  AGUGCUUG                                        38
```

( 2 ) INFORMATION FOR SEQ ID NO:1293:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1293:

```
    CAAGCACUUA  AAAGGGA                                                                 17
```

( 2 ) INFORMATION FOR SEQ ID NO:1294:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1294:

```
    CUCCCUUUCU  GAUGAGGCCG  AAAGGCCGAA  AAGUGCUU                                        38
```

( 2 ) INFORMATION FOR SEQ ID NO:1295:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1295:

```
    AAGCACUUAA  AAGGGAG                                                                 17
```

( 2 ) INFORMATION FOR SEQ ID NO:1296:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1296:

```
    UGCUUUCCCU  GAUGAGGCCG  AAAGGCCGAA  AUUCUCCC                                        38
```

( 2 ) INFORMATION FOR SEQ ID NO:1297:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1297:

```
    GGGAGAAUUG  GAAAGCA                                                                 17
```

( 2 ) INFORMATION FOR SEQ ID NO:1298:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1298:

CCUCUCCCCU GAUGAGGCCG AAAGGCCGAA ACACUGCU       38

( 2 ) INFORMATION FOR SEQ ID NO:1299:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1299:

AGCAGUGUCG GGAGAGG       17

( 2 ) INFORMATION FOR SEQ ID NO:1300:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1300:

UGGAUUCACU GAUGAGGCCG AAAGGCCGAA AUGGUUGU       38

( 2 ) INFORMATION FOR SEQ ID NO:1301:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1301:

ACAACCAUUU GAAUCCA       17

( 2 ) INFORMATION FOR SEQ ID NO:1302:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1302:

CUGGAUUCCU GAUGAGGCCG AAAGGCCGAA AAUGGUUG       38

( 2 ) INFORMATION FOR SEQ ID NO:1303:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1303:

CAACCAUUUG AAUCCAG       17

( 2 ) INFORMATION FOR SEQ ID NO:1304:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1304:

AACUUCUGCU GAUGAGGCCG AAAGGCCGAA AUUCAAAU    38

( 2 ) INFORMATION FOR SEQ ID NO:1305:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1305:

AUUUGAAUCC AGAAGUU    17

( 2 ) INFORMATION FOR SEQ ID NO:1306:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1306:

GUUUCUUCU GAUGAGGCCG AAAGGCCGAA ACUUCUGG    38

( 2 ) INFORMATION FOR SEQ ID NO:1307:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1307:

CCAGAAGUUA AGAAAAC    17

( 2 ) INFORMATION FOR SEQ ID NO:1308:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1308:

GGUUUUCUCU GAUGAGGCCG AAAGGCCGAA AACUUCUG    38

( 2 ) INFORMATION FOR SEQ ID NO:1309:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1309:

CAGAAGUUAA GAAAACC    17

( 2 ) INFORMATION FOR SEQ ID NO:1310:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1310:

CUGUCCAGCU GAUGAGGCCG AAAGGCCGAA AGGUUUUC 38

(2) INFORMATION FOR SEQ ID NO:1311:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1311:

GAAACCUCC UGGACAG 17

(2) INFORMATION FOR SEQ ID NO:1312:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1312:

UGGUAAAUCU GAUGAGGCCG AAAGGCCGAA AUUCUGUC 38

(2) INFORMATION FOR SEQ ID NO:1313:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1313:

GACAGAAUCA UUUACCA 17

(2) INFORMATION FOR SEQ ID NO:1314:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1314:

GCCUGGUACU GAUGAGGCCG AAAGGCCGAA AUGAUUCU 38

(2) INFORMATION FOR SEQ ID NO:1315:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1315:

AGAAUCAUUU ACCAGGC 17

(2) INFORMATION FOR SEQ ID NO:1316:

(i) SEQUENCE CHARACTERISTICS:
    (A) LENGTH: 38 base pairs (B) TYPE: nucleic acid
(C) STRANDEDNESS: single
(D) TOPOLOGY: linear (xi) SEQUENCE DESCRIPTION: SEQ ID NO:1316:

UGCCUGGUCU GAUGAGGCCG AAAGGCCGAA AAUGAUUC    38

(2) INFORMATION FOR SEQ ID NO:1317:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:1317:

GAAUCAUUUA CCAGGCA    17

(2) INFORMATION FOR SEQ ID NO:1318:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (xi) SEQUENCE DESCRIPTION: SEQ ID NO:1318:

GUGCCUGGCU GAUGAGGCCG AAAGGCCGAA AAAUGAUU    38

(2) INFORMATION FOR SEQ ID NO:1319:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:1319:

AAUCAUUUAC CAGGCAC    17

(2) INFORMATION FOR SEQ ID NO:1320:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (xi) SEQUENCE DESCRIPTION: SEQ ID NO:1320:

GUUCCCCACU GAUGAGGCCG AAAGGCCGAA ACGCUUGU    38

(2) INFORMATION FOR SEQ ID NO:1321:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:1321:

ACAAGCGUCU GGGGAAC    17

(2) INFORMATION FOR SEQ ID NO:1322:

(i) SEQUENCE CHARACTERISTICS:
  (A) LENGTH: 38 base pairs
  (B) TYPE: nucleic acid
  (C) STRANDEDNESS: single -continued ( D ) TOPOLOGY: linear ( x i ) SEQUENCE DESCRIPTION: SEQ ID NO:1322:

AGCUUUGCCU GAUGAGGCCG AAAGGCCGAA AUCUCUGC 38

( 2 ) INFORMATION FOR SEQ ID NO:1323:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1323:

GCAGAGAUCG CAAAGCU 17

( 2 ) INFORMATION FOR SEQ ID NO:1324:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1324:

GAUAGCAUCU GAUGAGGCCG AAAGGCCGAA AUCAGUCC 38

( 2 ) INFORMATION FOR SEQ ID NO:1325:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1325:

GGACUGAUAA UGCUAUC 17

( 2 ) INFORMATION FOR SEQ ID NO:1326:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1326:

GUUCUUGACU GAUGAGGCCG AAAGGCCGAA AGCAUUAU 38

( 2 ) INFORMATION FOR SEQ ID NO:1327:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1327:

AUAAUGCUAU CAAGAAC 17

( 2 ) INFORMATION FOR SEQ ID NO:1328:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1328:

UGGUUCUUCU GAUGAGGCCG AAAGGCCGAA AUAGCAUU 38

( 2 ) INFORMATION FOR SEQ ID NO:1329:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1329:

AAUGCUAUCA AGAACCA 17

( 2 ) INFORMATION FOR SEQ ID NO:1330:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1330:

CAUGGUGGCU GAUGAGGCCG AAAGGCCGAA AUUCCAGU 38

( 2 ) INFORMATION FOR SEQ ID NO:1331:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1331:

ACUGGAAUUC CACCAUG ( 2 ) INFORMATION FOR SEQ ID NO:1332:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1332:

GCAUGGUGCU GAUGAGGCCG AAAGGCCGAA AAUUCCAG 38

( 2 ) INFORMATION FOR SEQ ID NO:1333:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1333:

CUGGAAUUCC ACCAUGC 17

( 2 ) INFORMATION FOR SEQ ID NO:1334:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1334:

CACCUUGCCU GAUGAGGCCG AAAGGCCGAA ACGCAUGG 38

( 2 ) INFORMATION FOR SEQ ID NO:1335:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1335:

CCAUGCGUCG CAAGGUG                                                            17

( 2 ) INFORMATION FOR SEQ ID NO:1336:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1336:

UCUGCAGGCU GAUGAGGCCG AAAGGCCGAA AGCCUUCC                                     38

( 2 ) INFORMATION FOR SEQ ID NO:1337:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1337:

GGAAGGCUAC CUGCAGA                                                            17

( 2 ) INFORMATION FOR SEQ ID NO:1338:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1338:

GGCUUUGGCU GAUGAGGCCG AAAGGCCGAA AGGCUUCU                                     38

( 2 ) INFORMATION FOR SEQ ID NO:1339:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1339:

AGAAGCCUUC CAAAGCC                                                            17

( 2 ) INFORMATION FOR SEQ ID NO:1340:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1340:

UGGCUUUGCU GAUGAGGCCG AAAGGCCGAA AAGGCUUC                                     38

( 2 ) INFORMATION FOR SEQ ID NO:1341:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1341:

GAAGCCUUCC AAAGCCA 17

( 2 ) INFORMATION FOR SEQ ID NO:1342:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1342:

UCUUCUGGCU GAUGAGGCCG AAAGGCCGAA AGCUCGUG 38

( 2 ) INFORMATION FOR SEQ ID NO:1343:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1343:

CACGAGCUUC CAGAAGA 17

( 2 ) INFORMATION FOR SEQ ID NO:1344:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1344:

UUCUUCUGCU GAUGAGGCCG AAAGGCCGAA AAGCUCGU 38

( 2 ) INFORMATION FOR SEQ ID NO:1345:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1345:

ACGAGCUUCC AGAAGAA 17

( 2 ) INFORMATION FOR SEQ ID NO:1346:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1346:

CAUCAAAUCU GAUGAGGCCG AAAGGCCGAA AUUGUUCU 38

( 2 ) INFORMATION FOR SEQ ID NO:1347:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1347:

AGAACAAUCA UUUGAUG                                                17

(2) INFORMATION FOR SEQ ID NO:1348:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1348:

CCCCAUCACU GAUGAGGCCG AAAGGCCGAA AUGAUUGU                          38

(2) INFORMATION FOR SEQ ID NO:1349:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1349:

ACAAUCAUUU GAUGGGG                                                17

(2) INFORMATION FOR SEQ ID NO:1350:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1350:

ACCCCAUCCU GAUGAGGCCG AAAGGCCGAA AAUGAUUG                          38

(2) INFORMATION FOR SEQ ID NO:1351:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1351:

CAAUCAUUUG AUGGGGU                                                17

(2) INFORMATION FOR SEQ ID NO:1352:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1352:

CAUGCCCACU GAUGAGGCCG AAAGGCCGAA ACCCCAUC                          38

(2) INFORMATION FOR SEQ ID NO:1353:

(i) SEQUENCE CHARACTERISTICS:
        (A) LENGTH: 17 base pairs
        (B) TYPE: nucleic acid ( C ) STRANDEDNESS: single
                    ( D ) TOPOLOGY: linear ( x i ) SEQUENCE DESCRIPTION: SEQ ID NO:1353:

GAUGGGGUUU GGGCAUG                                                              17

( 2 ) INFORMATION FOR SEQ ID NO:1354:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1354:

GCAUGCCCCU GAUGAGGCCG AAAGGCGAA AACCCCAU                                        38

( 2 ) INFORMATION FOR SEQ ID NO:1355:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1355:

AUGGGGUUUG GGCAUGC                                                              17

( 2 ) INFORMATION FOR SEQ ID NO:1356:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1356:

AUGGAGGUCU GAUGAGGCCG AAAGGCCGAA AGGCAUGC                                       38

( 2 ) INFORMATION FOR SEQ ID NO:1357:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1357:

GCAUGCCUCA CCUCCAU                                                              17

( 2 ) INFORMATION FOR SEQ ID NO:1358:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1358:

CUGAGAUGCU GAUGAGGCCG AAAGGCCGAA AGGUGAGG                                       38

( 2 ) INFORMATION FOR SEQ ID NO:1359:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1359:

CCUCACCUCC AUCUCAG 17

( 2 ) INFORMATION FOR SEQ ID NO:1360:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1360:

AGAGCUGACU GAUGAGGCCG AAAGGCCGAA AUGGAGGU 38

( 2 ) INFORMATION FOR SEQ ID NO:1361:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1361:

ACCUCCAUCU CAGCUCU 17

( 2 ) INFORMATION FOR SEQ ID NO:1362:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1362:

AGAGAGCUCU GAUGAGGCCG AAAGGCCGAA AGAUGGAG 38

( 2 ) INFORMATION FOR SEQ ID NO:1363:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1363:

CUCCAUCUCA GCUCUCU 17

( 2 ) INFORMATION FOR SEQ ID NO:1364:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1364:

CUUGGAGACU GAUGAGGCCG AAAGGCCGAA AGCUGAGA 38

( 2 ) INFORMATION FOR SEQ ID NO:1365:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1365:

UCUCAGCUCU CUCCAAG                                                                                    17

( 2 ) INFORMATION FOR SEQ ID NO:1366:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1366:

CACUUGGACU GAUGAGGCCG AAAGGCCGAA AGAGCUGA                                                              38

( 2 ) INFORMATION FOR SEQ ID NO:1367:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1367:

UCAGCUCUCU CCAAGUG                                                                                    17

( 2 ) INFORMATION FOR SEQ ID NO:1368:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1368:

GCCACUUGCU GAUGAGGCCG AAAGGCCGAA AGAGAGCU                                                              38

( 2 ) INFORMATION FOR SEQ ID NO:1369:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1369:

AGCUCUCUCC AAGUGGC                                                                                    17

( 2 ) INFORMATION FOR SEQ ID NO:1370:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1370:

UGACGGAGCU GAUGAGGCCG AAAGGCCGAA ACUGGCCA                                                              38

( 2 ) INFORMATION FOR SEQ ID NO:1371:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1371:

UGGCCAGUCC UCCGUCA                                                                                    17

( 2 ) INFORMATION FOR SEQ ID NO:1372:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1372:

UGUUGACGCU GAUGAGGCCG AAAGGCCGAA AGGACUGG        38

( 2 ) INFORMATION FOR SEQ ID NO:1373:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1373:

CCAGUCCUCC GUCAACA        17

( 2 ) INFORMATION FOR SEQ ID NO:1374:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1374:

UCGCUGUUCU GAUGAGGCCG AAAGGCCGAA ACGGAGGA        38

( 2 ) INFORMATION FOR SEQ ID NO:1375:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1375:

UCCUCCGUCA ACAGCGA        17

( 2 ) INFORMATION FOR SEQ ID NO:1376:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1376:

AAUAGGGACU GAUGAGGCCG AAAGGCCGAA AUUCGCUG        38

( 2 ) INFORMATION FOR SEQ ID NO:1377:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1377:

CAGCGAAUAU CCCUAUU        17

( 2 ) INFORMATION FOR SEQ ID NO:1378:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1378:

GUAAUAGGCU GAUGAGGCCG AAAGGCCGAA AUAUUCGC        38

( 2 ) INFORMATION FOR SEQ ID NO:1379:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1379:

GCGAAUAUCC CUAUUAC        17

( 2 ) INFORMATION FOR SEQ ID NO:1380:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1380:

UGUGGUAACU GAUGAGGCCG AAAGGCCGAA AGGGAUAU        38

( 2 ) INFORMATION FOR SEQ ID NO:1381:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1381:

AUAUCCCUAU UACCACA        17

( 2 ) INFORMATION FOR SEQ ID NO:1382:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1382:

GAUGUGGUCU GAUGAGGCCG AAAGGCCGAA AUAGGGAU        38

( 2 ) INFORMATION FOR SEQ ID NO:1383:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1383:

AUCCCUAUUA CCACAUC        17

( 2 ) INFORMATION FOR SEQ ID NO:1384:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1384:

CGAUGUGGCU GAUGAGGCCG AAAGGCCGAA AAUAGGGA                    38

( 2 ) INFORMATION FOR SEQ ID NO:1385:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1385:

UCCCUAUUAC CACAUCG                                           17

( 2 ) INFORMATION FOR SEQ ID NO:1386:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1386:

GCUUCGGCCU GAUGAGGCCG AAAGGCCGAA AUGUGGUA                    38

( 2 ) INFORMATION FOR SEQ ID NO:1387:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1387:

UACCACAUCG CCGAAGC                                           17

( 2 ) INFORMATION FOR SEQ ID NO:1388:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1388:

UGACUGGACU GAUGAGGCCG AAAGGCCGAA AUGUUUUG                    38

( 2 ) INFORMATION FOR SEQ ID NO:1389:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1389:

CAAAACAUCU CCAGUCA                                           17

( 2 ) INFORMATION FOR SEQ ID NO:1390:

( i ) SEQUENCE CHARACTERISTICS:
        ( A ) LENGTH: 38 base pairs ( B ) TYPE: nucleic acid
            ( C ) STRANDEDNESS: single
            ( D ) TOPOLOGY: linear ( x i ) SEQUENCE DESCRIPTION: SEQ ID NO:1390:

CGUGACUGCU GAUGAGGCCG AAAGGCCGAA AGAUGUUU                    38

( 2 ) INFORMATION FOR SEQ ID NO:1391:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1391:

AAACAUCUCC AGUCACG                                           17

( 2 ) INFORMATION FOR SEQ ID NO:1392:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1392:

GGGAACGUCU GAUGAGGCCG AAAGGCCGAA ACUGGAGA                    38

( 2 ) INFORMATION FOR SEQ ID NO:1393:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1393:

UCUCCAGUCA CGUUCCC                                           17

( 2 ) INFORMATION FOR SEQ ID NO:1394:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1394:

GGAUAGGGCU GAUGAGGCCG AAAGGCCGAA ACGUGACU                    38

( 2 ) INFORMATION FOR SEQ ID NO:1395:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1395:

AGUCACGUUC CCUAUCC                                           17

( 2 ) INFORMATION FOR SEQ ID NO:1396:

( i ) SEQUENCE CHARACTERISTICS:
            ( A ) LENGTH: 38 base pairs
            ( B ) TYPE: nucleic acid
            ( C ) STRANDEDNESS: single

529

5,646,042

530

-continued ( D ) TOPOLOGY: linear ( x i ) SEQUENCE DESCRIPTION: SEQ ID NO:1396:

AGGAUAGGCU GAUGAGGCCG AAAGGCCGAA AACGUGAC                                      3 8

( 2 ) INFORMATION FOR SEQ ID NO:1397:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:1397:

GUCACGUUCC CUAUCCU                                                             1 7

( 2 ) INFORMATION FOR SEQ ID NO:1398:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:1398:

CGACAGGACU GAUGAGGCCG AAAGGCCGAA AGGGAACG                                      3 8

( 2 ) INFORMATION FOR SEQ ID NO:1399:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:1399:

CGUUCCCUAU CCUGUCG                                                             1 7

( 2 ) INFORMATION FOR SEQ ID NO:1400:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:1400:

UGCGACAGCU GAUGAGGCCG AAAGGCCGAA AUAGGGAA                                      3 8

( 2 ) INFORMATION FOR SEQ ID NO:1401:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:1401:

UUCCCUAUCC UGUCGCA                                                             1 7

( 2 ) INFORMATION FOR SEQ ID NO:1402:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear (xi) SEQUENCE DESCRIPTION: SEQ ID NO:1402:

UGCAAUGCCU GAUGAGGCCG AAAGGCCGAA ACAGGAUA          38

(2) INFORMATION FOR SEQ ID NO:1403:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1403:

UAUCCUGUCG CAUUGCA          17

(2) INFORMATION FOR SEQ ID NO:1404:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1404:

UAACAUGCCU GAUGAGGCCG AAAGGCCGAA AUGCGACA          38

(2) INFORMATION FOR SEQ ID NO:1405:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1405:

UGUCGCAUUG CAUGUUA          17

(2) INFORMATION FOR SEQ ID NO:1406:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1406:

ACUAUAUUCU GAUGAGGCCG AAAGGCCGAA ACAUGCAA          38

(2) INFORMATION FOR SEQ ID NO:1407:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1407:

UUGCAUGUUA AUAUAGU          17

(2) INFORMATION FOR SEQ ID NO:1408:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1408:

GACUAUAUCU GAUGAGGCCG AAAGGCCGAA AACAUGCA                                  38

( 2 ) INFORMATION FOR SEQ ID NO:1409:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1409:

UGCAUGUUAA UAUAGUC                                                         17

( 2 ) INFORMATION FOR SEQ ID NO:1410:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1410:

GUUGACUACU GAUGAGGCCG AAAGGCCGAA AUUAACAU                                  38

( 2 ) INFORMATION FOR SEQ ID NO:1411:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1411:

AUGUUAAUAU AGUCAAC                                                         17

( 2 ) INFORMATION FOR SEQ ID NO:1412:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1412:

ACGUUGACCU GAUGAGGCCG AAAGGCCGAA AUAUUAAC                                  38

( 2 ) INFORMATION FOR SEQ ID NO:1413:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1413:

GUUAAUAUAG UCAACGU                                                         17

( 2 ) INFORMATION FOR SEQ ID NO:1414:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1414:

GGGACGUUCU GAUGAGGCCG AAAGGCCGAA ACUAUAUU                                  38

( 2 ) INFORMATION FOR SEQ ID NO:1415:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1415:

AAUAUAGUCA ACGUCCC 17

( 2 ) INFORMATION FOR SEQ ID NO:1416:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1416:

GGCUGAGGCU GAUGAGGCCG AAAGGCCGAA ACGUUGAC 38

( 2 ) INFORMATION FOR SEQ ID NO:1417:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1417:

GUCAACGUCC CUCAGCC 17

( 2 ) INFORMATION FOR SEQ ID NO:1418:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1418:

AGCCGGCUCU GAUGAGGCCG AAAGGCCGAA AGGGACGU 38

( 2 ) INFORMATION FOR SEQ ID NO:1419:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1419:

ACGUCCCUCA GCCGGCU 17

( 2 ) INFORMATION FOR SEQ ID NO:1420:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1420:

UGUCUCUGCU GAUGAGGCCG AAAGGCCGAA AUGGCUGC 38

( 2 ) INFORMATION FOR SEQ ID NO:1421:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1421:

GCAGCCAUCC AGAGACA    17

( 2 ) INFORMATION FOR SEQ ID NO:1422:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1422:

CGUCGUUACU GAUGAGGCCG AAAGGCCGAA AGUGUCUC    38

( 2 ) INFORMATION FOR SEQ ID NO:1423:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1423:

GAGACACUAU AACGACG    17

( 2 ) INFORMATION FOR SEQ ID NO:1424:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1424:

UUCGUCGUCU GAUGAGGCCG AAAGGCCGAA AUAGUGUC    38

( 2 ) INFORMATION FOR SEQ ID NO:1425:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1425:

GACACUAUAA CGACGAA    17

( 2 ) INFORMATION FOR SEQ ID NO:1426:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1426:

AGCUCCUUCU GAUGAGGCCG AAAGGCCGAA AUUCGCUU    38

( 2 ) INFORMATION FOR SEQ ID NO:1427:

( i ) SEQUENCE CHARACTERISTICS:

(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1427:

AAGCGAAUAA AGGAGCU  17

(2) INFORMATION FOR SEQ ID NO:1428:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1428:

UCAGGAGCCU GAUGAGGCCG AAAGGCCGAA ACUCCAGC  38

(2) INFORMATION FOR SEQ ID NO:1429:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1429:

GCUGGAGUUG CUCCUGA  17

(2) INFORMATION FOR SEQ ID NO:1430:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1430:

GACAUCAGCU GAUGAGGCCG AAAGGCCGAA AGCAACUC  38

(2) INFORMATION FOR SEQ ID NO:1431:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1431:

GAGUUGCUCC UGAUGUC  17

(2) INFORMATION FOR SEQ ID NO:1432:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1432:

UCUCUGUUCU GAUGAGGCCG AAAGGCCGAA ACAUCAGG  38

(2) INFORMATION FOR SEQ ID NO:1433:

(i) SEQUENCE CHARACTERISTICS:
(A) LENGTH: 17 base pairs
(B) TYPE: nucleic acid (C) STRANDEDNESS: single
(D) TOPOLOGY: linear (xi) SEQUENCE DESCRIPTION: SEQ ID NO:1433:

CCUGAUGUCA ACAGAGA  17

(2) INFORMATION FOR SEQ ID NO:1434:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1434:

GUGUUGGUCU GAUGAGGCCG AAAGGCCGAA AUGCCUGC  38

(2) INFORMATION FOR SEQ ID NO:1435:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1435:

GCAGGCAUUA CCAACAC  17

(2) INFORMATION FOR SEQ ID NO:1436:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1436:

UGUGUUGGCU GAUGAGGCCG AAAGGCCGAA AAUGCCUG  38

(2) INFORMATION FOR SEQ ID NO:1437:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1437:

CAGGCAUUAC CAACACA  17

(2) INFORMATION FOR SEQ ID NO:1438:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1438:

GUAGCUGCCU GAUGAGGCCG AAAGGCCGAA AGUGUGGU  38

(2) INFORMATION FOR SEQ ID NO:1439:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:1439:

ACCACACUUG CAGCUAC 17

( 2 ) INFORMATION FOR SEQ ID NO:1440:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1440:

ACCCGGGGCU GAUGAGGCCG AAAGGCCGAA AGCUGCAA 38

( 2 ) INFORMATION FOR SEQ ID NO:1441:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1441:

UUGCAGCUAC CCCGGGU 17

( 2 ) INFORMATION FOR SEQ ID NO:1442:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1442:

CCACAAUGCU GAUGAGGCCG AAAGGCCGAA AGGUGCUG 38

( 2 ) INFORMATION FOR SEQ ID NO:1443:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1443:

CAGCACCUCC AUUGUGG 17

( 2 ) INFORMATION FOR SEQ ID NO:1444:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1444:

UGGUCCACCU GAUGAGGCCG AAAGGCCGAA AUGGAGGU 38

( 2 ) INFORMATION FOR SEQ ID NO:1445:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1445:

ACCUCCAUUG UGGACCA 17

( 2 ) INFORMATION FOR SEQ ID NO:1446:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1446:

AUCCCCAUCU GAUGAGGCCG AAAGGCCGAA AGGUCUGG 38

( 2 ) INFORMATION FOR SEQ ID NO:1447:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1447:

CCAGACCUCA UGGGGAU 17

( 2 ) INFORMATION FOR SEQ ID NO:1448:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1448:

AGGUGCACCU GAUGAGGCCG AAAGGCCGAA AUCCCCAU 38

( 2 ) INFORMATION FOR SEQ ID NO:1449:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1449:

AUGGGGAUAG UGCACCU 17

( 2 ) INFORMATION FOR SEQ ID NO:1450:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1450:

AAACAGGACU GAUGAGGCCG AAAGGCCGAA ACAGGUGC 38

( 2 ) INFORMATION FOR SEQ ID NO:1451:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1451:

GCACCUGUUU CCUGUUU 17

( 2 ) INFORMATION FOR SEQ ID NO:1452:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1452:

CAAACAGGCU GAUGAGGCCG AAAGGCCGAA AACAGGUG     38

( 2 ) INFORMATION FOR SEQ ID NO:1453:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1453:

CACCUGUUUC CUGUUUG     17

( 2 ) INFORMATION FOR SEQ ID NO:1454:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1454:

CCAAACAGCU GAUGAGGCCG AAAGGCCGAA AAACAGGU     38

( 2 ) INFORMATION FOR SEQ ID NO:1455:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1455:

ACCUGUUUCC UGUUUGG     17

( 2 ) INFORMATION FOR SEQ ID NO:1456:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1456:

UUCUCCCACU GAUGAGGCCG AAAGGCCGAA ACAGGAAA     38

( 2 ) INFORMATION FOR SEQ ID NO:1457:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1457:

UUUCCUGUUU GGGAGAA     17

(2) INFORMATION FOR SEQ ID NO:1458:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1458:

GUUCUCCCU GAUGAGGCCG AAAGGCCGAA AACAGGAA    38

(2) INFORMATION FOR SEQ ID NO:1459:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1459:

UUCCUGUUUG GGAGAAC    17

(2) INFORMATION FOR SEQ ID NO:1460:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1460:

CAGGCAGACU GAUGAGGCCG AAAGGCCGAA AUGGGGUG    38

(2) INFORMATION FOR SEQ ID NO:1461:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1461:

CACCCCAUCU CUGCCUG    17

(2) INFORMATION FOR SEQ ID NO:1462:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1462:

UGCAGGCACU GAUGAGGCCG AAAGGCCGAA AGAUGGGG    38

(2) INFORMATION FOR SEQ ID NO:1463:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1463:

CCCCAUCUCU GCCUGCA    17

(2) INFORMATION FOR SEQ ID NO:1464:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1464:

GGAGCCGGCU GAUGAGGCCG AAAGGCCGAA AUCUGCAG 38

( 2 ) INFORMATION FOR SEQ ID NO:1465:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1465:

CUGCAGAUCC CGGCUCC 17

( 2 ) INFORMATION FOR SEQ ID NO:1466:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1466:

CAGGUAGGCU GAUGAGGCCG AAAGGCCGAA AGCCGGGA 38

( 2 ) INFORMATION FOR SEQ ID NO:1467:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1467:

UCCCGGCUCC CUACCUG 17

( 2 ) INFORMATION FOR SEQ ID NO:1468:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1468:

UCUUCAGGCU GAUGAGGCCG AAAGGCCGAA AGGGAGCC 38

( 2 ) INFORMATION FOR SEQ ID NO:1469:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1469:

GGCUCCCUAC CUGAAGA 17

( 2 ) INFORMATION FOR SEQ ID NO:1470:

( i ) SEQUENCE CHARACTERISTICS:
 ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO:1470:

UUGCUGGUCU GAUGAGGCCG AAAGGCCGAA AGGCACUU     38

(2) INFORMATION FOR SEQ ID NO:1471:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1471:

AAGUGCCUCA CCAGCAA     17

(2) INFORMATION FOR SEQ ID NO:1472:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1472:

UGGUGGACCU GAUGAGGCCG AAAGGCCGAA AUCAUGCA     38

(2) INFORMATION FOR SEQ ID NO:1473:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1473:

UGCAUGAUCG UCCACCA     17

(2) INFORMATION FOR SEQ ID NO:1474:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1474:

CCCUGGUGCU GAUGAGGCCG AAAGGCCGAA ACGAUCAU     38

(2) INFORMATION FOR SEQ ID NO:1475:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1475:

AUGAUCGUCC ACCAGGG     17

(2) INFORMATION FOR SEQ ID NO:1476:

(i) SEQUENCE CHARACTERISTICS:
(A) LENGTH: 38 base pairs
(B) TYPE: nucleic acid
(C) STRANDEDNESS: single ( D ) TOPOLOGY: linear ( x i ) SEQUENCE DESCRIPTION: SEQ ID NO:1476:

UUGUCCAGCU GAUGAGGCCG AAAGGCCGAA AUGGUGCC 38

( 2 ) INFORMATION FOR SEQ ID NO:1477:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1477:

GGCACCAUUC UGGACAA 17

( 2 ) INFORMATION FOR SEQ ID NO:1478:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1478:

AUUGUCCACU GAUGAGGCCG AAAGGCCGAA AAUGGUGC 38

( 2 ) INFORMATION FOR SEQ ID NO:1479:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1479:

GCACCAUUCU GGACAAU 17

( 2 ) INFORMATION FOR SEQ ID NO:1480:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1480:

AGGUUCUUCU GAUGAGGCCG AAAGGCCGAA ACAUUGUC 38

( 2 ) INFORMATION FOR SEQ ID NO:1481:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1481:

GACAAUGUUA AGAACCU 17

( 2 ) INFORMATION FOR SEQ ID NO:1482:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1482:

GAGGUUCUCU GAUGAGGCCG AAAGGCCGAA AACAUUGU        38

( 2 ) INFORMATION FOR SEQ ID NO:1483:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1483:

ACAAUGUUAA GAACCUC        17

( 2 ) INFORMATION FOR SEQ ID NO:1484:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1484:

AAUUCUAACU GAUGAGGCCG AAAGGCCGAA AGGUUCUU        38

( 2 ) INFORMATION FOR SEQ ID NO:1485:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1485:

AAGAACCUCU UAGAAUU        17

( 2 ) INFORMATION FOR SEQ ID NO:1486:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1486:

CAAAUUCUCU GAUGAGGCCG AAAGGCCGAA AGAGGUUC        38

( 2 ) INFORMATION FOR SEQ ID NO:1487:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1487:

GAACCUCUUA GAAUUUG        17

( 2 ) INFORMATION FOR SEQ ID NO:1488:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1488:

```
GCAAAUUCCU  GAUGAGGCCG  AAAGGCCGAA  AAGAGGUU                                                    38
```

( 2 ) INFORMATION FOR SEQ ID NO:1489:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1489:

```
AACCUCUUAG  AAUUUGC                                                                             17
```

( 2 ) INFORMATION FOR SEQ ID NO:1490:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1490:

```
UUUCUGCACU  GAUGAGGCCG  AAAGGCCGAA  AUUCUAAG                                                    38
```

( 2 ) INFORMATION FOR SEQ ID NO:1491:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1491:

```
CUUAGAAUUU  GCAGAAA                                                                             17
```

( 2 ) INFORMATION FOR SEQ ID NO:1492:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1492:

```
GUUUCUGCCU  GAUGAGGCCG  AAAGGCCGAA  AAUUCUAA                                                    38
```

( 2 ) INFORMATION FOR SEQ ID NO:1493:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1493:

```
UUAGAAUUUG  CAGAAAC                                                                             17
```

( 2 ) INFORMATION FOR SEQ ID NO:1494:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1494:

```
AUAAACUGCU  GAUGAGGCCG  AAAGGCCGAA  AGUGUUUC                                                    38
```

( 2 ) INFORMATION FOR SEQ ID NO:1495:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1495:

GAAACACUCC AGUUUAU                                            17

( 2 ) INFORMATION FOR SEQ ID NO:1496:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1496:

AAUCUAUACU GAUGAGGCCG AAAGGCCGAA ACUGGAGU            38

( 2 ) INFORMATION FOR SEQ ID NO:1497:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1497:

ACUCCAGUUU AUAGAUU                                            17

( 2 ) INFORMATION FOR SEQ ID NO:1498:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1498:

GAAUCUAUCU GAUGAGGCCG AAAGGCCGAA AACUGGAG            38

( 2 ) INFORMATION FOR SEQ ID NO:1499:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1499:

CUCCAGUUUA UAGAUUC                                            17

( 2 ) INFORMATION FOR SEQ ID NO:1500:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1500:

AGAAUCUACU GAUGAGGCCG AAAGGCCGAA AAACUGGA            38

( 2 ) INFORMATION FOR SEQ ID NO:1501:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1501:

UCCAGUUUAU AGAUUCU                17

( 2 ) INFORMATION FOR SEQ ID NO:1502:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1502:

AAAGAAUCCU GAUGAGGCCG AAAGGCCGAA AUAAACUG      38

( 2 ) INFORMATION FOR SEQ ID NO:1503:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1503:

CAGUUUAUAG AUUCUUU                17

( 2 ) INFORMATION FOR SEQ ID NO:1504:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1504:

CAAGAAAGCU GAUGAGGCCG AAAGGCCGAA AUCUAUAA      38

( 2 ) INFORMATION FOR SEQ ID NO:1505:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1505:

UUAUAGAUUC UUUCUUG                17

( 2 ) INFORMATION FOR SEQ ID NO:1506:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1506:

UCAAGAAACU GAUGAGGCCG AAAGGCCGAA AAUCUAUA      38

( 2 ) INFORMATION FOR SEQ ID NO:1507:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1507:

UAUAGAUUCU UUCUUGA ( 2 ) INFORMATION FOR SEQ ID NO:1508:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1508:

GUUCAAGACU GAUGAGGCCG AAAGGCCGAA AGAAUCUA        38

( 2 ) INFORMATION FOR SEQ ID NO:1509:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1509:

UAGAUUCUUU CUUGAAC        17

( 2 ) INFORMATION FOR SEQ ID NO:1510:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1510:

UGUUCAAGCU GAUGAGGCCG AAAGGCCGAA AAGAAUCU        38

( 2 ) INFORMATION FOR SEQ ID NO:1511:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1511:

AGAUUCUUUC UUGAACA        17

( 2 ) INFORMATION FOR SEQ ID NO:1512:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1512:

GUGUUCAACU GAUGAGGCCG AAAGGCCGAA AAAGAAUC        38

( 2 ) INFORMATION FOR SEQ ID NO:1513:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1513:

GAUUCUUUCU UGAACAC     17

( 2 ) INFORMATION FOR SEQ ID NO:1514:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1514:

AAGUGUUCCU GAUGAGGCCG AAAGGCCGAA AGAAAGAA     38

( 2 ) INFORMATION FOR SEQ ID NO:1515:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1515:

UUCUUUCUUG AACACUU     17

( 2 ) INFORMATION FOR SEQ ID NO:1516:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1516:

GUUGCUGGCU GAUGAGGCCG AAAGGCCGAA AGUGUUCA     38

( 2 ) INFORMATION FOR SEQ ID NO:1517:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1517:

UGAACACUUC CAGCAAC     17

( 2 ) INFORMATION FOR SEQ ID NO:1518:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1518:

GGUUGCUGCU GAUGAGGCCG AAAGGCCGAA AAGUGUUC     38

( 2 ) INFORMATION FOR SEQ ID NO:1519:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1519:

```
       GAACACUUCC AGCAACC                                                                    17
```

( 2 ) INFORMATION FOR SEQ ID NO:1520:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1520:

```
       CUAAGCCCCU GAUGAGGCCG AAAGGCCGAA AGUUUUCA                                             38
```

( 2 ) INFORMATION FOR SEQ ID NO:1521:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1521:

```
       UGAAAACUCG GGCUUAG                                                                    17
```

( 2 ) INFORMATION FOR SEQ ID NO:1522:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1522:

```
       GUGCAUCUCU GAUGAGGCCG AAAGGCCGAA AGCCCGAG                                             38
```

( 2 ) INFORMATION FOR SEQ ID NO:1523:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1523:

```
       CUCGGGCUUA GAUGCAC                                                                    17
```

( 2 ) INFORMATION FOR SEQ ID NO:1524:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1524:

```
       GGUGCAUCCU GAUGAGGCCG AAAGGCCGAA AAGCCCGA                                             38
```

( 2 ) INFORMATION FOR SEQ ID NO:1525:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1525:

```
       UCGGGCUUAG AUGCACC                                                                    17
```

( 2 ) INFORMATION FOR SEQ ID NO:1526:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1526:

GGGUAAGGCU GAUGAGGCCG AAAGGCCGAA AGGUGCAU    38

( 2 ) INFORMATION FOR SEQ ID NO:1527:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1527:

AUGCACCUAC CUUACCC    17

( 2 ) INFORMATION FOR SEQ ID NO:1528:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1528:

UGGAGGGUCU GAUGAGGCCG AAAGGCCGAA AGGUAGGU    38

( 2 ) INFORMATION FOR SEQ ID NO:1529:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1529:

ACCUACCUUA CCCUCCA    17

( 2 ) INFORMATION FOR SEQ ID NO:1530:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1530:

GUGGAGGGCU GAUGAGGCCG AAAGGCCGAA AAGGUAGG    38

( 2 ) INFORMATION FOR SEQ ID NO:1531:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1531:

CCUACCUUAC CCUCCAC    17

( 2 ) INFORMATION FOR SEQ ID NO:1532:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1532:

GAGGAGUGCU GAUGAGGCCG AAAGGCCGAA AGGGUAAG         38

( 2 ) INFORMATION FOR SEQ ID NO:1533:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1533:

CUUACCCUCC ACUCCUC         17

( 2 ) INFORMATION FOR SEQ ID NO:1534:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1534:

AAUGAGAGCU GAUGAGGCCG AAAGGCCGAA AGUGGAGG         38

( 2 ) INFORMATION FOR SEQ ID NO:1535:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1535:

CCUCCACUCC UCUCAUU         17

( 2 ) INFORMATION FOR SEQ ID NO:1536:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1536:

ACCAAUGACU GAUGAGGCCG AAAGGCCGAA AGGAGUGG         38

( 2 ) INFORMATION FOR SEQ ID NO:1537:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1537:

CCACUCCUCU CAUUGGU         17

( 2 ) INFORMATION FOR SEQ ID NO:1538:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1538:

UGACCAAUCU GAUGAGGCCG AAAGGCCGAA AGAGGAGU                    38

( 2 ) INFORMATION FOR SEQ ID NO:1539:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1539:

ACUCCUCUCA UUGGUCA                                           17

( 2 ) INFORMATION FOR SEQ ID NO:1540:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1540:

UUGUGACCCU GAUGAGGCCG AAAGGCCGAA AUGAGAGG                    38

( 2 ) INFORMATION FOR SEQ ID NO:1541:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1541:

CCUCUCAUUG GUCACAA                                           17

( 2 ) INFORMATION FOR SEQ ID NO:1542:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1542:

CAGUUUGUCU GAUGAGGCCG AAAGGCCGAA ACCAAUGA                    38

( 2 ) INFORMATION FOR SEQ ID NO:1543:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1543:

UCAUUGGUCA CAAACUG                                           17

( 2 ) INFORMATION FOR SEQ ID NO:1544:

( i ) SEQUENCE CHARACTERISTICS:
        ( A ) LENGTH: 38 base pairs (B) TYPE: nucleic acid
            (C) STRANDEDNESS: single
            (D) TOPOLOGY: linear (xi) SEQUENCE DESCRIPTION: SEQ ID NO:1544:

CUGGUCUCCU GAUGAGGCCG AAAGGCCGAA ACAUGGUG    38

(2) INFORMATION FOR SEQ ID NO:1545:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1545:

CACCAUGUCG AGACCAG    17

(2) INFORMATION FOR SEQ ID NO:1546:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:1546:

AAAGAUGGCU GAUGAGGCCG AAAGGCCGAA AUUUCCU    38

(2) INFORMATION FOR SEQ ID NO:1547:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1547:

AGGAAAAUUC CAUCUUU    17

(2) INFORMATION FOR SEQ ID NO:1548:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:1548:

UAAAGAUGCU GAUGAGGCCG AAAGGCCGAA AAUUUUCC    38

(2) INFORMATION FOR SEQ ID NO:1549:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1549:

GGAAAAUUCC AUCUUUA    17

(2) INFORMATION FOR SEQ ID NO:1550:

(i) SEQUENCE CHARACTERISTICS:
            (A) LENGTH: 38 base pairs
            (B) TYPE: nucleic acid
            (C) STRANDEDNESS: single ( D ) TOPOLOGY: linear ( x i ) SEQUENCE DESCRIPTION: SEQ ID NO:1550:

GUUCUAAACU GAUGAGGCCG AAAGGCCGAA AUGGAAUU                                  38

( 2 ) INFORMATION FOR SEQ ID NO:1551:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1551:

AAUUCCAUCU UUAGAAC                                                         17

( 2 ) INFORMATION FOR SEQ ID NO:1552:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1552:

GAGUUCUACU GAUGAGGCCG AAAGGCCGAA AGAUGGAA                                  38

( 2 ) INFORMATION FOR SEQ ID NO:1553:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1553:

UUCCAUCUUU AGAACUC                                                         17

( 2 ) INFORMATION FOR SEQ ID NO:1554:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1554:

GGAGUUCUCU GAUGAGGCCG AAAGGCCGAA AAGAUGGA                                  38

( 2 ) INFORMATION FOR SEQ ID NO:1555:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1555:

UCCAUCUUUA GAACUCC                                                         17

( 2 ) INFORMATION FOR SEQ ID NO:1556:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1556:

UGGAGUUCCU GAUGAGGCCG AAAGGCCGAA AAAGAUGG 38

( 2 ) INFORMATION FOR SEQ ID NO:1557:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1557:

CCAUCUUUAG AACUCCA 17

( 2 ) INFORMATION FOR SEQ ID NO:1558:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1558:

GAUAGCUGCU GAUGAGGCCG AAAGGCCGAA AGUUCUAA 38

( 2 ) INFORMATION FOR SEQ ID NO:1559:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1559:

UUAGAACUCC AGCUAUC 17

( 2 ) INFORMATION FOR SEQ ID NO:1560:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1560:

CCUUUUGACU GAUGAGGCCG AAAGGCCGAA AGCUGGAG 38

( 2 ) INFORMATION FOR SEQ ID NO:1561:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1561:

CUCCAGCUAU CAAAAGG 17

( 2 ) INFORMATION FOR SEQ ID NO:1562:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1562:

GACCUUUUCU GAUGAGGCCG AAAGGCCGAA AUAGCUGG 38

( 2 ) INFORMATION FOR SEQ ID NO:1563:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1563:

CCAGCUAUCA AAAGGUC 17

( 2 ) INFORMATION FOR SEQ ID NO:1564:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1564:

CGAGGAUUCU GAUGAGGCCG AAAGGCCGAA ACCUUUG 38

( 2 ) INFORMATION FOR SEQ ID NO:1565:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1565:

CAAAAGGUCA AUCCUCG 17

( 2 ) INFORMATION FOR SEQ ID NO:1566:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1566:

CUUUCGAGCU GAUGAGGCCG AAAGGCCGAA AUUGACCU 38

( 2 ) INFORMATION FOR SEQ ID NO:1567:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1567:

AGGUCAAUCC UCGAAAG 17

( 2 ) INFORMATION FOR SEQ ID NO:1568:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1568:

GAGCUUUCCU GAUGAGGCCG AAAGGCCGAA AGGAUUGA 38

( 2 ) INFORMATION FOR SEQ ID NO:1569:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1569:

UCAAUCCUCG AAAGCUC                                         17

( 2 ) INFORMATION FOR SEQ ID NO:1570:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1570:

UUCGAGGACU GAUGAGGCCG AAAGGCCGAA AGCUUUCG           38

( 2 ) INFORMATION FOR SEQ ID NO:1571:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1571:

CGAAAGCUCU CCUCGAA                                         17

( 2 ) INFORMATION FOR SEQ ID NO:1572:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1572:

AGUUCGAGCU GAUGAGGCCG AAAGGCCGAA AGAGCUUU           38

( 2 ) INFORMATION FOR SEQ ID NO:1573:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1573:

AAAGCUCUCC UCGAACU                                         17

( 2 ) INFORMATION FOR SEQ ID NO:1574:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1574:

GGGAGUUCCU GAUGAGGCCG AAAGGCCGAA AGGAGAGC           38

( 2 ) INFORMATION FOR SEQ ID NO:1575:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1575:

GCUCCCUCG AACUCCC  17

( 2 ) INFORMATION FOR SEQ ID NO:1576:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1576:

UGGUGUGGCU GAUGAGGCCG AAAGGCCGAA AGUUCGAG  38

( 2 ) INFORMATION FOR SEQ ID NO:1577:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1577:

CUCGAACUCC CACACCA  17

( 2 ) INFORMATION FOR SEQ ID NO:1578:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1578:

CAUGUUUGCU GAUGAGGCCG AAAGGCCGAA AUGGUGUG  38

( 2 ) INFORMATION FOR SEQ ID NO:1579:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1579:

CACACCAUUC AAACAUG  17

( 2 ) INFORMATION FOR SEQ ID NO:1580:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1580:

GCAUGUUUCU GAUGAGGCCG AAAGGCCGAA AAUGGUGU  38

( 2 ) INFORMATION FOR SEQ ID NO:1581:

( i ) SEQUENCE CHARACTERISTICS:

(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1581:

ACACCAUUCA AACAUGC                                              17

(2) INFORMATION FOR SEQ ID NO:1582:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1582:

UGAGCUGCCU GAUGAGGCCG AAAGGCCGAA AGGGCAUG                       38

(2) INFORMATION FOR SEQ ID NO:1583:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1583:

CAUGCCCUUG CAGCUCA                                              17

(2) INFORMATION FOR SEQ ID NO:1584:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1584:

AAUUUCUUCU GAUGAGGCCG AAAGGCCGAA AGCUGCAA                       38

(2) INFORMATION FOR SEQ ID NO:1585:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1585:

UUGCAGCUCA AGAAAUU                                              17

(2) INFORMATION FOR SEQ ID NO:1586:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1586:

CCGUAUUUCU GAUGAGGCCG AAAGGCCGAA AUUUCUUG                       38

(2) INFORMATION FOR SEQ ID NO:1587:

(i) SEQUENCE CHARACTERISTICS:
    (A) LENGTH: 17 base pairs
    (B) TYPE: nucleic acid (C) STRANDEDNESS: single
(D) TOPOLOGY: linear (xi) SEQUENCE DESCRIPTION: SEQ ID NO:1587:

CAAGAAAUUA AAUACGG 17

(2) INFORMATION FOR SEQ ID NO:1588:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1588:

ACCGUAUUCU GAUGAGGCCG AAAGGCCGAA AAUUUCUU 38

(2) INFORMATION FOR SEQ ID NO:1589:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1589:

AAGAAAUUAA AUACGGU 17

(2) INFORMATION FOR SEQ ID NO:1590:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1590:

GGGGACCGCU GAUGAGGCCG AAAGGCCGAA AUUUAAUU 38

(2) INFORMATION FOR SEQ ID NO:1591:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1591:

AAUUAAAUAC GGUCCCC 17

(2) INFORMATION FOR SEQ ID NO:1592:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1592:

CUUCAGGGCU GAUGAGGCCG AAAGGCCGAA ACCGUAUU 38

(2) INFORMATION FOR SEQ ID NO:1593:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:1593:

AAUACGGUCC CCUGAAG    17

( 2 ) INFORMATION FOR SEQ ID NO:1594:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1594:

GUCUGAGGCU GAUGAGGCCG AAAGGCCGAA AGCAUCUU    38

( 2 ) INFORMATION FOR SEQ ID NO:1595:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1595:

AAGAUGCUAC CUCAGAC    17

( 2 ) INFORMATION FOR SEQ ID NO:1596:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1596:

GGGGGUCUCU GAUGAGGCCG AAAGGCCGAA AGGUAGCA    38

( 2 ) INFORMATION FOR SEQ ID NO:1597:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1597:

UGCUACCUCA GACCCCC    17

( 2 ) INFORMATION FOR SEQ ID NO:1598:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1598:

CUGCAUGGCU GAUGAGGCCG AAAGGCCGAA AGGGGGUC    38

( 2 ) INFORMATION FOR SEQ ID NO:1599:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1599:

GACCCCCUCC CAUGCAG 17

( 2 ) INFORMATION FOR SEQ ID NO:1600:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1600:

ACAUCUUGCU GAUGAGGCCG AAAGGCCGAA AGGUCCUC 38

( 2 ) INFORMATION FOR SEQ ID NO:1601:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1601:

GAGGACCUAC AAGAUGU 17

( 2 ) INFORMATION FOR SEQ ID NO:1602:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1602:

UCCCGCUUCU GAUGAGGCCG AAAGGCCGAA AUCACAUC 38

( 2 ) INFORMATION FOR SEQ ID NO:1603:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1603:

GAUGUGAUUA AGCGGGA 17

( 2 ) INFORMATION FOR SEQ ID NO:1604:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1604:

UUCCGCUCU GAUGAGGCCG AAAGGCCGAA AAUCACAU 38

( 2 ) INFORMATION FOR SEQ ID NO:1605:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1605:

AUGUGAUUAA GCGGGAA 17

( 2 ) INFORMATION FOR SEQ ID NO:1606:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1606:

AUUCAUCCCU GAUGAGGCCG AAAGGCCGAA AUUCCGC     38

( 2 ) INFORMATION FOR SEQ ID NO:1607:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1607:

GCGGGAAUCG GAUGAAU     17

( 2 ) INFORMATION FOR SEQ ID NO:1608:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1608:

CAAUUCCACU GAUGAGGCCG AAAGGCCGAA AUUCAUCC     38

( 2 ) INFORMATION FOR SEQ ID NO:1609:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1609:

GGAUGAAUCU GGAAUUG     17

( 2 ) INFORMATION FOR SEQ ID NO:1610:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1610:

UCAGCAACCU GAUGAGGCCG AAAGGCCGAA AUUCCAGA     38

( 2 ) INFORMATION FOR SEQ ID NO:1611:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1611:

UCUGGAAUUG UUGCUGA     17

( 2 ) INFORMATION FOR SEQ ID NO:1612:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1612:

AACUCAGCCU GAUGAGGCCG AAAGGCCGAA ACAAUUCC      38

( 2 ) INFORMATION FOR SEQ ID NO:1613:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1613:

GGAAUUGUUG CUGAGUU      17

( 2 ) INFORMATION FOR SEQ ID NO:1614:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1614:

UCUCUUGACU GAUGAGGCCG AAAGGCCGAA ACUCAGCA      38

( 2 ) INFORMATION FOR SEQ ID NO:1615:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1615:

UGCUGAGUUU CAAGAGA      17

( 2 ) INFORMATION FOR SEQ ID NO:1616:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1616:

CUCUCUUGCU GAUGAGGCCG AAAGGCCGAA AACUCAGC      38

( 2 ) INFORMATION FOR SEQ ID NO:1617:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1617:

GCUGAGUUUC AAGAGAG      17

( 2 ) INFORMATION FOR SEQ ID NO:1618:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1618:

ACUCUCUUCU GAUGAGGCCG AAAGGCCGAA AAACUCAG    38

( 2 ) INFORMATION FOR SEQ ID NO:1619:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1619:

CUGAGUUUCA AGAGAGU    17

( 2 ) INFORMATION FOR SEQ ID NO:1620:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1620:

UUUUCAGUCU GAUGAGGCCG AAAGGCCGAA ACGGUGGU    38

( 2 ) INFORMATION FOR SEQ ID NO:1621:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1621:

ACCACCGUUA CUGAAAA    17

( 2 ) INFORMATION FOR SEQ ID NO:1622:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1622:

UUUUUCAGCU GAUGAGGCCG AAAGGCCGAA AACGGUGG    38

( 2 ) INFORMATION FOR SEQ ID NO:1623:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1623:

CCACCGUUAC UGAAAAA    17

( 2 ) INFORMATION FOR SEQ ID NO:1624:

( i ) SEQUENCE CHARACTERISTICS:
 ( A ) LENGTH: 38 base pairs ( B ) TYPE: nucleic acid
            ( C ) STRANDEDNESS: single
            ( D ) TOPOLOGY: linear ( x i ) SEQUENCE DESCRIPTION: SEQ ID NO:1624:

GCCUGCUUCU GAUGAGGCCG AAAGGCCGAA AUUUUUUU    38

( 2 ) INFORMATION FOR SEQ ID NO:1625:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1625:

AAAAAAAUCA AGCAGGC    17

( 2 ) INFORMATION FOR SEQ ID NO:1626:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1626:

CAGUUGGCCU GAUGAGGCCG AAAGGCCGAA ACUCCACC    38

( 2 ) INFORMATION FOR SEQ ID NO:1627:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1627:

GGUGGAGUCG CCAACUG    17

( 2 ) INFORMATION FOR SEQ ID NO:1628:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1628:

AGUUUCCCCU GAUGAGGCCG AAAGGCCGAA AUUUCUCA    38

( 2 ) INFORMATION FOR SEQ ID NO:1629:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1629:

UGAGAAAUCG GGAAACU    17

( 2 ) INFORMATION FOR SEQ ID NO:1630:

( i ) SEQUENCE CHARACTERISTICS:
            ( A ) LENGTH: 38 base pairs
            ( B ) TYPE: nucleic acid
            ( C ) STRANDEDNESS: single ( D ) TOPOLOGY: linear ( x i ) SEQUENCE DESCRIPTION: SEQ ID NO:1630:

AGCAGAAGCU GAUGAGGCCG AAAGGCCGAA AGUUUCCC 38

( 2 ) INFORMATION FOR SEQ ID NO:1631:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1631:

GGGAAACUUC UUCUGCU 17

( 2 ) INFORMATION FOR SEQ ID NO:1632:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1632:

GAGCAGAACU GAUGAGGCCG AAAGGCCGAA AAGUUUCC 38

( 2 ) INFORMATION FOR SEQ ID NO:1633:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1633:

GGAAACUUCU UCUGCUC 17

( 2 ) INFORMATION FOR SEQ ID NO:1634:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1634:

UUGAGCAGCU GAUGAGGCCG AAAGGCCGAA AGAAGUUU 38

( 2 ) INFORMATION FOR SEQ ID NO:1635:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1635:

AAACUUCUUC UGCUCAA 17

( 2 ) INFORMATION FOR SEQ ID NO:1636:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1636:

UUUGAGCACU GAUGAGGCCG AAAGGCCGAA AAGAAGUU  38

( 2 ) INFORMATION FOR SEQ ID NO:1637:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1637:

AACUUCUUCU GCUCAAA  17

( 2 ) INFORMATION FOR SEQ ID NO:1638:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1638:

AGUGGUUUCU GAUGAGGCCG AAAGGCCGAA AGCAGAAG  38

( 2 ) INFORMATION FOR SEQ ID NO:1639:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1639:
        CUUCUGCUCA AACCACU ( 2 ) INFORMATION FOR SEQ ID NO:1640:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1640:

CCUGCGAGCU GAUGAGGCCG AAAGGCCGAA ACAGUUGG  38

( 2 ) INFORMATION FOR SEQ ID NO:1641:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1641:

CCAACUGUUC UCGCAGG  17

( 2 ) INFORMATION FOR SEQ ID NO:1642:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1642:

GCCUGCGACU GAUGAGGCCG AAAGGCCGAA AACAGUUG  38

( 2 ) INFORMATION FOR SEQ ID NO:1643:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1643:

CAACUGUUCU CGCAGGC                            17

( 2 ) INFORMATION FOR SEQ ID NO:1644:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1644:

ACGCCUGCCU GAUGAGGCCG AAAGGCCGAA AGAACAGU           38

( 2 ) INFORMATION FOR SEQ ID NO:1645:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1645:

ACUGUUCUCG CAGGCGU                           17

( 2 ) INFORMATION FOR SEQ ID NO:1646:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1646:

CCACAGGACU GAUGAGGCCG AAAGGCCGAA ACGCCUGC           38

( 2 ) INFORMATION FOR SEQ ID NO:1647:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1647:

GCAGGCGUCU CCUGUGG                           17

( 2 ) INFORMATION FOR SEQ ID NO:1648:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1648:

UGCCACAGCU GAUGAGGCCG AAAGGCCGAA AGACGCCU           38

( 2 ) INFORMATION FOR SEQ ID NO:1649:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1649:

AGGCGUCUCC UGUGGCA 17

( 2 ) INFORMATION FOR SEQ ID NO:1650:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1650:

UGUAAGAACU GAUGAGGCCG AAAGGCCGAA AUUGGGG ( 2 ) INFORMATION FOR SEQ ID NO:1651:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1651:

CCCCAAAUAU UCUUACA 17

( 2 ) INFORMATION FOR SEQ ID NO:1652:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1652:

CUUGUAAGCU GAUGAGGCCG AAAGGCCGAA AUAUUUGG 38

( 2 ) INFORMATION FOR SEQ ID NO:1653:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1653:

CCAAAUAUUC UUACAAG 17

( 2 ) INFORMATION FOR SEQ ID NO:1654:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1654:

GCUUGUAACU GAUGAGGCCG AAAGGCCGAA AAUAUUUG 38

( 2 ) INFORMATION FOR SEQ ID NO:1655:

( i ) SEQUENCE CHARACTERISTICS:
 ( A ) LENGTH: 17 base pairs
 ( B ) TYPE: nucleic acid ( C ) STRANDEDNESS: single
         ( D ) TOPOLOGY: linear ( x i ) SEQUENCE DESCRIPTION: SEQ ID NO:1655:

CAAAUAUUCU UACAAGC                                                                              17

( 2 ) INFORMATION FOR SEQ ID NO:1656:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1656:

GAGCUUGUCU GAUGAGGCCG AAAGGCCGAA AGAAUAUU                                                        38

( 2 ) INFORMATION FOR SEQ ID NO:1657:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1657:

AAUAUUCUUA CAAGCUC                                                                              17

( 2 ) INFORMATION FOR SEQ ID NO:1658:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1658:

AGAGCUUGCU GAUGAGGCCG AAAGGCCGAA AAGAAUAU                                                        38

( 2 ) INFORMATION FOR SEQ ID NO:1659:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1659:

AUAUUCUUAC AAGCUCU                                                                              17

( 2 ) INFORMATION FOR SEQ ID NO:1660:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1660:

UUAAAACACU GAUGAGGCCG AAAGGCCGAA AGCUUGUA                                                        38

( 2 ) INFORMATION FOR SEQ ID NO:1661:

( i ) SEQUENCE CHARACTERISTICS:
         ( A ) LENGTH: 17 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1661:

UACAAGCUCU GUUUUAA 17

( 2 ) INFORMATION FOR SEQ ID NO:1662:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1662:

GUCAUUAACU GAUGAGGCCG AAAGGCCGAA ACAGAGCU 38

( 2 ) INFORMATION FOR SEQ ID NO:1663:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1663:

AGCUCUGUUU UAAUGAC 17

( 2 ) INFORMATION FOR SEQ ID NO:1664:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1664:

UGUCAUUACU GAUGAGGCCG AAAGGCCGAA AACAGAGC 38

( 2 ) INFORMATION FOR SEQ ID NO:1665:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1665:

GCUCUGUUUU AAUGACA 17

( 2 ) INFORMATION FOR SEQ ID NO:1666:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1666:

GUGUCAUUCU GAUGAGGCCG AAAGGCCGAA AAACAGAG 38

( 2 ) INFORMATION FOR SEQ ID NO:1667:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1667:

CUCUGUUUUA AUGACAC 17

(2) INFORMATION FOR SEQ ID NO:1668:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1668:

GGUGUCAUCU GAUGAGGCCG AAAGGCCGAA AAAACAGA 38

(2) INFORMATION FOR SEQ ID NO:1669:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1669:

UCUGUUUUAA UGACACC 17

(2) INFORMATION FOR SEQ ID NO:1670:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1670:

UCUUCUGACU GAUGAGGCCG AAAGGCCGAA ACAGGUGU 38

(2) INFORMATION FOR SEQ ID NO:1671:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1671:

ACACCUGUAU CAGAAGA 17

(2) INFORMATION FOR SEQ ID NO:1672:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1672:

CAUCUUCUCU GAUGAGGCCG AAAGGCCGAA AUACAGGU 38

(2) INFORMATION FOR SEQ ID NO:1673:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1673:

ACCUGUAUCA GAAGAUG 17

( 2 ) INFORMATION FOR SEQ ID NO:1674:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1674:

GCUUUGAGCU GAUGAGGCCG AAAGGCCGAA ACAUUGUC    38

( 2 ) INFORMATION FOR SEQ ID NO:1675:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1675:

GACAAUGUCC UCAAAGC    17

( 2 ) INFORMATION FOR SEQ ID NO:1676:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1676:

AAGGCUUUCU GAUGAGGCCG AAAGGCCGAA AGGACAUU    38

( 2 ) INFORMATION FOR SEQ ID NO:1677:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1677:

AAUGUCCUCA AAGCCUU    17

( 2 ) INFORMATION FOR SEQ ID NO:1678:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1678:

GUACGGUACU GAUGAGGCCG AAAGGCCGAA AGGCUUUG    38

( 2 ) INFORMATION FOR SEQ ID NO:1679:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1679:

CAAAGCCUUU ACCGUAC    17

( 2 ) INFORMATION FOR SEQ ID NO:1680:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1680:

GGUACGGUCU GAUGAGGCCG AAAGGCCGAA AAGGCUUU         38

( 2 ) INFORMATION FOR SEQ ID NO:1681:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1681:

AAAGCCUUUA CCGUACC         17

( 2 ) INFORMATION FOR SEQ ID NO:1682:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1682:

AGGUACGGCU GAUGAGGCCG AAAGGCCGAA AAAGGCUU         38

( 2 ) INFORMATION FOR SEQ ID NO:1683:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1683:

AAGCCUUUAC CGUACCU         17

( 2 ) INFORMATION FOR SEQ ID NO:1684:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1684:

UUCUUAGGCU GAUGAGGCCG AAAGGCCGAA ACGGUAAA         38

( 2 ) INFORMATION FOR SEQ ID NO:1685:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1685:

UUUACCGUAC CUAAGAA         17

( 2 ) INFORMATION FOR SEQ ID NO:1686:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1686:

CCUGUUCUCU GAUGAGGCCG AAAGGCCGAA AGGUACGG 38

( 2 ) INFORMATION FOR SEQ ID NO:1687:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1687:

CCGUACCUAA GAACAGG 17

( 2 ) INFORMATION FOR SEQ ID NO:1688:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1688:

CUGCAAGGCU GAUGAGGCCG AAAGGCCGAA ACCCACCA 38

( 2 ) INFORMATION FOR SEQ ID NO:1689:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1689:

UGGUGGGUCC CUUGCAG 17

( 2 ) INFORMATION FOR SEQ ID NO:1690:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1690:

AUGGCUGCCU GAUGAGGCCG AAAGGCCGAA AGGGACCC 38

( 2 ) INFORMATION FOR SEQ ID NO:1691:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1691:

GGGUCCCUUG CAGCCAU 17

( 2 ) INFORMATION FOR SEQ ID NO:1692:

( i ) SEQUENCE CHARACTERISTICS:
    ( A ) LENGTH: 38 base pairs (B) TYPE: nucleic acid
    (C) STRANDEDNESS: single
    (D) TOPOLOGY: linear (xi) SEQUENCE DESCRIPTION: SEQ ID NO:1692:

UCCCACAGCU GAUGAGGCCG AAAGGCCGAA AUGCUGGC                                38

(2) INFORMATION FOR SEQ ID NO:1693:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1693:

GCCAGCAUCC UGUGGGA                                                      17

(2) INFORMATION FOR SEQ ID NO:1694:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1694:

CCGGACCGCU GAUGAGGCCG AAAGGCCGAA AGGCCGUC                                38

(2) INFORMATION FOR SEQ ID NO:1695:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1695:

GACGGCCUCC GGUCCGG                                                      17

(2) INFORMATION FOR SEQ ID NO:1696:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:1696:

CCGAGCCGCU GAUGAGGCCG AAAGGCCGAA ACCGGAGG                                38

(2) INFORMATION FOR SEQ ID NO:1697:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:1697:

CCUCCGGUCC GGCUCGG                                                      17

(2) INFORMATION FOR SEQ ID NO:1698:

(i) SEQUENCE CHARACTERISTICS:
    (A) LENGTH: 38 base pairs
    (B) TYPE: nucleic acid
    (C) STRANDEDNESS: single ( D ) TOPOLOGY: linear ( x i ) SEQUENCE DESCRIPTION: SEQ ID NO:1698:

GUAUUUCCCU GAUGAGGCCG AAAGGCCGAA AGCCGGAC    38

( 2 ) INFORMATION FOR SEQ ID NO:1699:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1699:

GUCCGGCUCG GAAAUAC    17

( 2 ) INFORMATION FOR SEQ ID NO:1700:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1700:

CGUUCACGCU GAUGAGGCCG AAAGGCCGAA AUUCCGA    38

( 2 ) INFORMATION FOR SEQ ID NO:1701:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1701:

UCGGAAAUAC GUGAACG    17

( 2 ) INFORMATION FOR SEQ ID NO:1702:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1702:

GAGCUGAGCU GAUGAGGCCG AAAGGCCGAA ACGCGUUC    38

( 2 ) INFORMATION FOR SEQ ID NO:1703:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1703:

GAACGCGUUC UCAGCUC    17

( 2 ) INFORMATION FOR SEQ ID NO:1704:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1704:

CGAGCUGACU GAUGAGGCCG AAAGGCCGAA AACGCGUU 38

( 2 ) INFORMATION FOR SEQ ID NO:1705:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1705:

AACGCGUUCU CAGCUCG 17

( 2 ) INFORMATION FOR SEQ ID NO:1706:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1706:

UUCGAGCUCU GAUGAGGCCG AAAGGCCGAA AGAACGCG 38

( 2 ) INFORMATION FOR SEQ ID NO:1707:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1707:

CGCGUUCUCA GCUCGAA 17

( 2 ) INFORMATION FOR SEQ ID NO:1708:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1708:

CAGAGUUCCU GAUGAGGCCG AAAGGCCGAA AGCUGAGA 38

( 2 ) INFORMATION FOR SEQ ID NO:1709:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1709:

UCUCAGCUCG AACUCUG 17

( 2 ) INFORMATION FOR SEQ ID NO:1710:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1710:

```
CAUGACCACU GAUGAGGCCG AAAGGCCGAA AGUUCGAG                              38
```

(2) INFORMATION FOR SEQ ID NO:1711:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1711:

```
CUCGAACUCU GGUCAUG                                                     17
```

(2) INFORMATION FOR SEQ ID NO:1712:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1712:

```
UCUCACAUCU GAUGAGGCCG AAAGGCCGAA ACCAGAGU                              38
```

(2) INFORMATION FOR SEQ ID NO:1713:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1713:

```
ACUCGGUCA UGUGAGA                                                      17
```

(2) INFORMATION FOR SEQ ID NO:1714:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1714:

```
UUUCUGGACU GAUGAGGCCG AAAGGCCGAA AUGUCUCA                              38
```

(2) INFORMATION FOR SEQ ID NO:1715:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1715:

```
UGAGACAUUU CCAGAAA                                                     17
```

(2) INFORMATION FOR SEQ ID NO:1716:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1716:

```
UUUUCUGGCU GAUGAGGCCG AAAGGCCGAA AAUGUCUC                              38
```

( 2 ) INFORMATION FOR SEQ ID NO:1717:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1717:

GAGACAUUUC CAGAAAA 17

( 2 ) INFORMATION FOR SEQ ID NO:1718:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1718:

CUUUCUGCU GAUGAGGCCG AAAGGCCGAA AAAUGUCU 38

( 2 ) INFORMATION FOR SEQ ID NO:1719:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1719:

AGACAUUUCC AGAAAAG 17

( 2 ) INFORMATION FOR SEQ ID NO:1720:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1720:

AAAACCAUCU GAUGAGGCCG AAAGGCCGAA AUGCUUUU 38

( 2 ) INFORMATION FOR SEQ ID NO:1721:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1721:

AAAAGCAUUA UGGUUUU 17

( 2 ) INFORMATION FOR SEQ ID NO:1722:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1722:

GAAAACCACU GAUGAGGCCG AAAGGCCGAA AAUGCUUU 38

( 2 ) INFORMATION FOR SEQ ID NO:1723:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1723:

AAAGCAUUAU GGUUUUC                                                                17

( 2 ) INFORMATION FOR SEQ ID NO:1724:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1724:

GUUCUGAACU GAUGAGGCCG AAAGGCCGAA ACCAUAAU                                          38

( 2 ) INFORMATION FOR SEQ ID NO:1725:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1725:

AUUAUGGUUU UCAGAAC                                                                 17

( 2 ) INFORMATION FOR SEQ ID NO:1726:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1726:

UGUUCUGACU GAUGAGGCCG AAAGGCCGAA AACCAUAA                                          38

( 2 ) INFORMATION FOR SEQ ID NO:1727:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1727:

UUAUGGUUUU CAGAACA                                                                 17

( 2 ) INFORMATION FOR SEQ ID NO:1728:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1728:

GUGUUCUGCU GAUGAGGCCG AAAGGCCGAA AAACCAUA                                          38

( 2 ) INFORMATION FOR SEQ ID NO:1729:

( i ) SEQUENCE CHARACTERISTICS:

(A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1729:

UAUGGUUUUC AGAACAC                                                17

(2) INFORMATION FOR SEQ ID NO:1730:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:1730:

AGUGUUCUCU GAUGAGGCCG AAAGGCCGAA AAAACCAU                          38

(2) INFORMATION FOR SEQ ID NO:1731:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1731:

AUGGUUUUCA GAACACU                                                17

(2) INFORMATION FOR SEQ ID NO:1732:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:1732:

CAACUUUUCU GAUGAGGCCG AAAGGCCGAA AGUGUUCU                          38

(2) INFORMATION FOR SEQ ID NO:1733:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:1733:

AGAACACUUA AAAGUUG                                                17

(2) INFORMATION FOR SEQ ID NO:1734:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:1734:

UCAACUUUCU GAUGAGGCCG AAAGGCCGAA AAGUGUUC                          38

(2) INFORMATION FOR SEQ ID NO:1735:

(i) SEQUENCE CHARACTERISTICS:
            (A) LENGTH: 17 base pairs
            (B) TYPE: nucleic acid (C) STRANDEDNESS: single
(D) TOPOLOGY: linear (xi) SEQUENCE DESCRIPTION: SEQ ID NO:1735:

GAACACUUAA AAGUUGA                                                17

(2) INFORMATION FOR SEQ ID NO:1736:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO:1736:

CGAAAGUCCU GAUGAGGCCG AAAGGCCGAA ACUUUUAA                          38

(2) INFORMATION FOR SEQ ID NO:1737:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:1737:

UUAAAAGUUG ACUUUCG                                                 17

(2) INFORMATION FOR SEQ ID NO:1738:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO:1738:

UGUGUCGACU GAUGAGGCCG AAAGGCCGAA AGUCAACU                          38

(2) INFORMATION FOR SEQ ID NO:1739:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:1739:

AGUUGACUUU CGACACA                                                 17

(2) INFORMATION FOR SEQ ID NO:1740:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO:1740:

AUGUGUCGCU GAUGAGGCCG AAAGGCCGAA AAGUCAAC                          38

(2) INFORMATION FOR SEQ ID NO:1741:

(i) SEQUENCE CHARACTERISTICS:
      (A) LENGTH: 17 base pairs
      (B) TYPE: nucleic acid
      (C) STRANDEDNESS: single
      (D) TOPOLOGY: linear ( x i ) SEQUENCE DESCRIPTION: SEQ ID NO:1741:

GUUGACUUUC GACACAU                                                17

( 2 ) INFORMATION FOR SEQ ID NO:1742:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1742:

CAUGUGUCCU GAUGAGGCCG AAAGGCCGAA AAAGUCAA                          38

( 2 ) INFORMATION FOR SEQ ID NO:1743:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1743:

UUGACUUUCG ACACAUG                                                17

( 2 ) INFORMATION FOR SEQ ID NO:1744:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1744:

ACGCUGAGCU GAUGAGGCCG AAAGGCCGAA AGCCAUGU                          38

( 2 ) INFORMATION FOR SEQ ID NO:1745:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1745:

ACAUGGCUCC UCAGCGU                                                17

( 2 ) INFORMATION FOR SEQ ID NO:1746:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1746:

UCCACGCUCU GAUGAGGCCG AAAGGCCGAA AGGAGCCA                          38

( 2 ) INFORMATION FOR SEQ ID NO:1747:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1747:

UGGCUCCUCA GCGUGGA 17

( 2 ) INFORMATION FOR SEQ ID NO:1748:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1748:

CAGCCAUGCU GAUGAGGCCG AAAGGCCGAA AGCGCUCC 38

( 2 ) INFORMATION FOR SEQ ID NO:1749:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1749:

GGAGCGCUCC AUGGCUG 17

( 2 ) INFORMATION FOR SEQ ID NO:1750:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1750:

CACAACAACU GAUGAGGCCG AAAGGCCGAA AUCAGGCU 38

( 2 ) INFORMATION FOR SEQ ID NO:1751:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1751:

AGCCUGAUUU UGUUGUG 17

( 2 ) INFORMATION FOR SEQ ID NO:1752:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1752:

CCACAACACU GAUGAGGCCG AAAGGCCGAA AAUCAGGC 38

( 2 ) INFORMATION FOR SEQ ID NO:1753:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1753:

GCCUGAUUUU GUUGUGG 17

( 2 ) INFORMATION FOR SEQ ID NO:1754:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1754:

ACCACAACCU GAUGAGGCCG AAAGGCCGAA AAAUCAGG 38

( 2 ) INFORMATION FOR SEQ ID NO:1755:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1755:

CCUGAUUUUG UUGUGGU 17

( 2 ) INFORMATION FOR SEQ ID NO:1756:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1756:

UGUACCACCU GAUGAGGCCG AAAGGCCGAA ACAAAAUC 38

( 2 ) INFORMATION FOR SEQ ID NO:1757:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1757:

GAUUUUGUUG UGGUACA 17

( 2 ) INFORMATION FOR SEQ ID NO:1758:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1758:

AACUGUUGCU GAUGAGGCCG AAAGGCCGAA ACCACAAC 38

( 2 ) INFORMATION FOR SEQ ID NO:1759:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1759:

GUUGUGGUAC AACAGUU 17

( 2 ) INFORMATION FOR SEQ ID NO:1760:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1760:

CUGCUCUCCU GAUGAGGCCG AAAGGCCGAA ACUGUUGU    38

( 2 ) INFORMATION FOR SEQ ID NO:1761:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1761:

ACAACAGUUG AGAGCAG    17

( 2 ) INFORMATION FOR SEQ ID NO:1762:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1762:

CAACUAAACU GAUGAGGCCG AAAGGCCGAA AUGCACUU    38

( 2 ) INFORMATION FOR SEQ ID NO:1763:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1763:

AAGUGCAUUU UUAGUUG    17

( 2 ) INFORMATION FOR SEQ ID NO:1764:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1764:

GCAACUAACU GAUGAGGCCG AAAGGCCGAA AAUGCACU    38

( 2 ) INFORMATION FOR SEQ ID NO:1765:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1765:

AGUGCAUUUU UAGUUGC    17

( 2 ) INFORMATION FOR SEQ ID NO:1766:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1766:

AGCAACUACU GAUGAGGCCG AAAGGCCGAA AAAUGCAC 38

( 2 ) INFORMATION FOR SEQ ID NO:1767:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1767:

GUGCAUUUUU AGUUGCU 17

( 2 ) INFORMATION FOR SEQ ID NO:1768:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1768:

AAGCAACUCU GAUGAGGCCG AAAGGCCGAA AAAAUGCA 38

( 2 ) INFORMATION FOR SEQ ID NO:1769:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1769:

UGCAUUUUUA GUUGCUU 17

( 2 ) INFORMATION FOR SEQ ID NO:1770:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1770:

CAAGCAACCU GAUGAGGCCG AAAGGCCGAA AAAAAUGC 38

( 2 ) INFORMATION FOR SEQ ID NO:1771:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1771:

GCAUUUUUAG UUGCUUG 17

( 2 ) INFORMATION FOR SEQ ID NO:1772:

( i ) SEQUENCE CHARACTERISTICS:
  ( A ) LENGTH: 38 base pairs ( B ) TYPE: nucleic acid
            ( C ) STRANDEDNESS: single
            ( D ) TOPOLOGY: linear ( x i ) SEQUENCE DESCRIPTION: SEQ ID NO:1772:

UCUCAAGCCU GAUGAGGCCG AAAGGCCGAA ACUAAAAA 38

( 2 ) INFORMATION FOR SEQ ID NO:1773:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1773:

UUUUUAGUUG CUUGAGA 17

( 2 ) INFORMATION FOR SEQ ID NO:1774:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1774:

GAGAUCUCCU GAUGAGGCCG AAAGGCCGAA AGCAACUA 38

( 2 ) INFORMATION FOR SEQ ID NO:1775:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1775:

UAGUUGCUUG AGAUCUC 17

( 2 ) INFORMATION FOR SEQ ID NO:1776:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1776:

UCAAGUGACU GAUGAGGCCG AAAGGCCGAA AUCUCAAG 38

( 2 ) INFORMATION FOR SEQ ID NO:1777:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1777:

CUUGAGAUCU CACUUGA 17

( 2 ) INFORMATION FOR SEQ ID NO:1778:

( i ) SEQUENCE CHARACTERISTICS:
            ( A ) LENGTH: 38 base pairs
            ( B ) TYPE: nucleic acid
            ( C ) STRANDEDNESS: single ( D ) TOPOLOGY: linear ( x i ) SEQUENCE DESCRIPTION: SEQ ID NO:1778:

AAUCAAGUCU GAUGAGGCCG AAAGGCCGAA AGAUCUCA    38

( 2 ) INFORMATION FOR SEQ ID NO:1779:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1779:

UGAGAUCUCA CUUGAUU    17

( 2 ) INFORMATION FOR SEQ ID NO:1780:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1780:

GUGAAAUCCU GAUGAGGCCG AAAGGCCGAA AGUGAGAU    38

( 2 ) INFORMATION FOR SEQ ID NO:1781:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1781:

AUCUCACUUG AUUUCAC    17

( 2 ) INFORMATION FOR SEQ ID NO:1782:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1782:

UUGUGUGACU GAUGAGGCCG AAAGGCCGAA AUCAAGUG    38

( 2 ) INFORMATION FOR SEQ ID NO:1783:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1783:

CACUUGAUUU CACACAA    17

( 2 ) INFORMATION FOR SEQ ID NO:1784:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear -continued ( x i ) SEQUENCE DESCRIPTION: SEQ ID NO:1784:

GUUGUGUGCU GAUGAGGCCG AAAGGCCGAA AAUCAAGU                    38

( 2 ) INFORMATION FOR SEQ ID NO:1785:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1785:

ACUUGAUUUC ACACAAC                                           17

( 2 ) INFORMATION FOR SEQ ID NO:1786:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1786:

AGUUGUGUCU GAUGAGGCCG AAAGGCCGAA AAAUCAAG                    38

( 2 ) INFORMATION FOR SEQ ID NO:1787:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1787:

CUUGAUUUCA CACAACU                                           17

( 2 ) INFORMATION FOR SEQ ID NO:1788:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1788:

AUCCUUUUCU GAUGAGGCCG AAAGGCCGAA AGUUGUGU                    38

( 2 ) INFORMATION FOR SEQ ID NO:1789:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1789:

ACACAACUAA AAAGGAU                                           17

( 2 ) INFORMATION FOR SEQ ID NO:1790:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1790:

AAAAAAAACU GAUGAGGCCG AAAGGCCGAA AUCCUUUU     38

( 2 ) INFORMATION FOR SEQ ID NO:1791:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1791:

AAAAGGAUUU UUUUUUU     17

( 2 ) INFORMATION FOR SEQ ID NO:1792:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1792:

UAAAAAAACU GAUGAGGCCG AAAGGCCGAA AAUCCUUU     38

( 2 ) INFORMATION FOR SEQ ID NO:1793:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1793:

AAAGGAUUUU UUUUUUA     17

( 2 ) INFORMATION FOR SEQ ID NO:1794:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1794:

UUAAAAAACU GAUGAGGCCG AAAGGCCGAA AAAUCCUU     38

( 2 ) INFORMATION FOR SEQ ID NO:1795:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1795:

AAGGAUUUUU UUUUUAA     17

( 2 ) INFORMATION FOR SEQ ID NO:1796:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1796:

UUUAAAAACU GAUGAGGCCG AAAGGCCGAA AAAAUCCU     38

( 2 ) INFORMATION FOR SEQ ID NO:1797:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1797:

AGGAUUUUUU UUUUAAA 17

( 2 ) INFORMATION FOR SEQ ID NO:1798:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1798:

UUUUAAAACU GAUGAGGCCG AAAGGCCGAA AAAAAUCC 38

( 2 ) INFORMATION FOR SEQ ID NO:1799:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1799:

GGAUUUUUUU UUUAAAA 17

( 2 ) INFORMATION FOR SEQ ID NO:1800:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1800:

UUUUUAAACU GAUGAGGCCG AAAGGCCGAA AAAAAAUC 38

( 2 ) INFORMATION FOR SEQ ID NO:1801:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1801:

GAUUUUUUUU UUAAAAA 17

( 2 ) INFORMATION FOR SEQ ID NO:1802:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1802:

AUUUUUAACU GAUGAGGCCG AAAGGCCGAA AAAAAAU 38

( 2 ) INFORMATION FOR SEQ ID NO:1803:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1803:

AUUUUUUUUU UAAAAAU  17

( 2 ) INFORMATION FOR SEQ ID NO:1804:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1804:

UAUUUUUACU GAUGAGGCCG AAAGGCCGAA AAAAAAA  38

( 2 ) INFORMATION FOR SEQ ID NO:1805:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1805:

UUUUUUUUUU AAAAAUA  17

( 2 ) INFORMATION FOR SEQ ID NO:1806:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1806:

UUAUUUUUCU GAUGAGGCCG AAAGGCCGAA AAAAAAA  38

( 2 ) INFORMATION FOR SEQ ID NO:1807:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1807:

UUUUUUUUUA AAAAUAA  17

( 2 ) INFORMATION FOR SEQ ID NO:1808:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1808:

AUUAUUUUCU GAUGAGGCCG AAAGGCCGAA AAAAAAA  38

( 2 ) INFORMATION FOR SEQ ID NO:1809:

( i ) SEQUENCE CHARACTERISTICS:

( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1809:

UUUUUUUUAA AAAUAAU  17

( 2 ) INFORMATION FOR SEQ ID NO:1810:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1810:

AUUAUUAUCU GAUGAGGCCG AAAGGCCGAA AUUUUUAA  38

( 2 ) INFORMATION FOR SEQ ID NO:1811:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1811:

UUAAAAAUAA UAAUAAU  17

( 2 ) INFORMATION FOR SEQ ID NO:1812:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1812:

UUCAUUAUCU GAUGAGGCCG AAAGGCCGAA AUUAUUUU  38

( 2 ) INFORMATION FOR SEQ ID NO:1813:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1813:

AAAAUAAUAA UAAUGAA  17

( 2 ) INFORMATION FOR SEQ ID NO:1814:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1814:

UUAUUCAUCU GAUGAGGCCG AAAGGCCGAA AUUAUUAU  38

( 2 ) INFORMATION FOR SEQ ID NO:1815:

( i ) SEQUENCE CHARACTERISTICS:
        ( A ) LENGTH: 17 base pairs
        ( B ) TYPE: nucleic acid ( C ) STRANDEDNESS: single
            ( D ) TOPOLOGY: linear ( x i ) SEQUENCE DESCRIPTION: SEQ ID NO:1815:

AUAAUAAUAA UGAAUAA                                                                                      17

( 2 ) INFORMATION FOR SEQ ID NO:1816:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1816:

AAGACUGUCU GAUGAGGCCG AAAGGCCGAA AUUCAUUA                                                                38

( 2 ) INFORMATION FOR SEQ ID NO:1817:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1817:

UAAUGAAUAA CAGUCUU                                                                                      17

( 2 ) INFORMATION FOR SEQ ID NO:1818:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1818:

UUAGGUAACU GAUGAGGCCG AAAGGCCGAA ACUGUUAU                                                                38

( 2 ) INFORMATION FOR SEQ ID NO:1819:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1819:

AUAACAGUCU UACCUAA                                                                                      17

( 2 ) INFORMATION FOR SEQ ID NO:1820:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1820:

AUUUAGGUCU GAUGAGGCCG AAAGGCCGAA AGACUGUU                                                                38

( 2 ) INFORMATION FOR SEQ ID NO:1821:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1821:

AACAGUCUUA CCUAAAU                                                                                                  17

( 2 ) INFORMATION FOR SEQ ID NO:1822:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1822:

AAUUUAGGCU GAUGAGGCCG AAAGGCCGAA AAGACUGU                                                                            38

( 2 ) INFORMATION FOR SEQ ID NO:1823:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1823:

ACAGUCUUAC CUAAAUU                                                                                                  17

( 2 ) INFORMATION FOR SEQ ID NO:1824:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1824:

UAAUAAUUCU GAUGAGGCCG AAAGGCCGAA AGGUAAGA                                                                            38

( 2 ) INFORMATION FOR SEQ ID NO:1825:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1825:

UCUUACCUAA AUUAUUA                                                                                                  17

( 2 ) INFORMATION FOR SEQ ID NO:1826:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1826:

UACCUAAUCU GAUGAGGCCG AAAGGCCGAA AUUUAGGU                                                                            38

( 2 ) INFORMATION FOR SEQ ID NO:1827:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1827:

ACCUAAAUUA UUAGGUA                                                                                       17

( 2 ) INFORMATION FOR SEQ ID NO:1828:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1828:

UUACCUAACU GAUGAGGCCG AAAGGCCGAA AAUUUAGG                                                                 38

( 2 ) INFORMATION FOR SEQ ID NO:1829:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1829:

CCUAAAUUAU UAGGUAA                                                                                       17

( 2 ) INFORMATION FOR SEQ ID NO:1830:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1830:

CAUUACCUCU GAUGAGGCCG AAAGGCCGAA AUAAUUUA                                                                 38

( 2 ) INFORMATION FOR SEQ ID NO:1831:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1831:

UAAAUUAUUA GGUAAUG                                                                                       17

( 2 ) INFORMATION FOR SEQ ID NO:1832:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1832:

UCAUUACCCU GAUGAGGCCG AAAGGCCGAA AAUAAUUU                                                                 38

( 2 ) INFORMATION FOR SEQ ID NO:1833:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1833:

AAAUUAUUAG GUAAUGA                                                                                       17

( 2 ) INFORMATION FOR SEQ ID NO:1834:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1834:

CAAUUCAUCU GAUGAGGCCG AAAGGCCGAA ACCUAAUA         38

( 2 ) INFORMATION FOR SEQ ID NO:1835:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1835:

UAUUAGGUAA UGAAUUG         17

( 2 ) INFORMATION FOR SEQ ID NO:1836:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1836:

AUGGUCACCU GAUGAGGCCG AAAGGCCGAA AUUCAUUA         38

( 2 ) INFORMATION FOR SEQ ID NO:1837:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1837:

UAAUGAAUUG UGACCAU         17

( 2 ) INFORMATION FOR SEQ ID NO:1838:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1838:

UAUUAACACU GAUGAGGCCG AAAGGCCGAA AUGGUCAC         38

( 2 ) INFORMATION FOR SEQ ID NO:1839:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1839:

GUGACCAUUU GUUAAUA         17

( 2 ) INFORMATION FOR SEQ ID NO:1840:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1840:

AUAUUAACCU GAUGAGGCCG AAAGGCCGAA AAUGGUCA       38

( 2 ) INFORMATION FOR SEQ ID NO:1841:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1841:

UGACCAUUUG UUAAUAU       17

( 2 ) INFORMATION FOR SEQ ID NO:1842:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1842:

AUGAUAUUCU GAUGAGGCCG AAAGGCCGAA ACAAAUGG       38

( 2 ) INFORMATION FOR SEQ ID NO:1843:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1843:

CCAUUUGUUA AUAUCAU       17

( 2 ) INFORMATION FOR SEQ ID NO:1844:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1844:

UAUGAUAUCU GAUGAGGCCG AAAGGCCGAA AACAAAUG       38

( 2 ) INFORMATION FOR SEQ ID NO:1845:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1845:

CAUUUGUUAA UAUCAUA       17

( 2 ) INFORMATION FOR SEQ ID NO:1846:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1846:

GAUUAUGACU GAUGAGGCCG AAAGGCCGAA AUUAACAA    38

( 2 ) INFORMATION FOR SEQ ID NO:1847:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1847:

UUGUUAAUAU CAUAAUC    17

( 2 ) INFORMATION FOR SEQ ID NO:1848:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1848:

CUGAUUAUCU GAUGAGGCCG AAAGGCCGAA AUAUUAAC    38

( 2 ) INFORMATION FOR SEQ ID NO:1849:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1849:

GUUAAUAUCA UAAUCAG    17

( 2 ) INFORMATION FOR SEQ ID NO:1850:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1850:

AAUCUGAUCU GAUGAGGCCG AAAGGCCGAA AUGAUAUU    38

( 2 ) INFORMATION FOR SEQ ID NO:1851:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1851:

AAUAUCAUAA UCAGAUU    17

( 2 ) INFORMATION FOR SEQ ID NO:1852:

( i ) SEQUENCE CHARACTERISTICS:
    ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO:1852:

AAAAAUCUCU GAUGAGGCCG AAAGGCCGAA AUUAUGAU  38

(2) INFORMATION FOR SEQ ID NO:1853:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1853:

AUCAUAAUCA GAUUUUU  17

(2) INFORMATION FOR SEQ ID NO:1854:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1854:

UUUUAAAACU GAUGAGGCCG AAAGGCCGAA AUCUGAUU  38

(2) INFORMATION FOR SEQ ID NO:1855:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1855:

AAUCAGAUUU UUUAAAA  17

(2) INFORMATION FOR SEQ ID NO:1856:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1856:

UUUUUAAACU GAUGAGGCCG AAAGGCCGAA AAUCUGAU  38

(2) INFORMATION FOR SEQ ID NO:1857:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1857:

AUCAGAUUUU UUAAAAA  17

(2) INFORMATION FOR SEQ ID NO:1858:

(i) SEQUENCE CHARACTERISTICS:
(A) LENGTH: 38 base pairs
(B) TYPE: nucleic acid
(C) STRANDEDNESS: single (D) TOPOLOGY: linear (xi) SEQUENCE DESCRIPTION: SEQ ID NO:1858:

UUUUUUAACU GAUGAGGCCG AAAGGCCGAA AAAUCUGA    38

(2) INFORMATION FOR SEQ ID NO:1859:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1859:

UCAGAUUUUU UAAAAAA    17

(2) INFORMATION FOR SEQ ID NO:1860:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1860:

UUUUUUUACU GAUGAGGCCG AAAGGCCGAA AAAAUCUG    38

(2) INFORMATION FOR SEQ ID NO:1861:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1861:

CAGAUUUUUU AAAAAAA    17

(2) INFORMATION FOR SEQ ID NO:1862:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1862:

UUUUUUUUCU GAUGAGGCCG AAAGGCCGAA AAAAAUCU    38

(2) INFORMATION FOR SEQ ID NO:1863:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1863:

AGAUUUUUUA AAAAAAA    17

(2) INFORMATION FOR SEQ ID NO:1864:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1864:

AUUUUUUUCU GAUGAGGCCG AAAGGCCGAA AAAAAAUC                38

( 2 ) INFORMATION FOR SEQ ID NO:1865:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1865:

GAUUUUUUAA AAAAAAU                17

( 2 ) INFORMATION FOR SEQ ID NO:1866:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1866:

AAUCAUUUCU GAUGAGGCCG AAAGGCCGAA AUUUUUUU                38

( 2 ) INFORMATION FOR SEQ ID NO:1867:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1867:

AAAAAAAUAA AAUGAUU                17

( 2 ) INFORMATION FOR SEQ ID NO:1868:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1868:

UACAAAUACU GAUGAGGCCG AAAGGCCGAA AUCAUUUU                38

( 2 ) INFORMATION FOR SEQ ID NO:1869:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1869:

AAAAUGAUUU AUUUGUA                17

( 2 ) INFORMATION FOR SEQ ID NO:1870:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1870:

```
AUACAAAUCU GAUGAGGCCG AAAGGCCGAA AAUCAUUU                    38
```

( 2 ) INFORMATION FOR SEQ ID NO:1871:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1871:

```
AAAUGAUUUA UUUGUAU                                           17
```

( 2 ) INFORMATION FOR SEQ ID NO:1872:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1872:

```
AAUACAAACU GAUGAGGCCG AAAGGCCGAA AAAUCAUU                    38
```

( 2 ) INFORMATION FOR SEQ ID NO:1873:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1873:

```
AAUGAUUUAU UUGUAUU                                           17
```

( 2 ) INFORMATION FOR SEQ ID NO:1874:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1874:

```
AAAAUACACU GAUGAGGCCG AAAGGCCGAA AUAAAUCA                    38
```

( 2 ) INFORMATION FOR SEQ ID NO:1875:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1875:

```
UGAUUUAUUU GUAUUUU                                           17
```

( 2 ) INFORMATION FOR SEQ ID NO:1876:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1876:

```
UAAAUACCU GAUGAGGCCG AAAGGCCGAA AAUAAAUC                     38
```

( 2 ) INFORMATION FOR SEQ ID NO:1877:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1877:

GAUUUAUUUG UAUUUA 17

( 2 ) INFORMATION FOR SEQ ID NO:1878:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1878:

CUCUAAAACU GAUGAGGCCG AAAGGCCGAA ACAAAUAA 38

( 2 ) INFORMATION FOR SEQ ID NO:1879:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1879:

UUAUUUGUAU UUUAGAG 17

( 2 ) INFORMATION FOR SEQ ID NO:1880:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1880:

UUCUCUAACU GAUGAGGCCG AAAGGCCGAA AUACAAAU 38

( 2 ) INFORMATION FOR SEQ ID NO:1881:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1881:

AUUUGUAUUU UAGAGAA 17

( 2 ) INFORMATION FOR SEQ ID NO:1882:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:1882:

AUUCUCUACU GAUGAGGCCG AAAGGCCGAA AAUACAAA 38

( 2 ) INFORMATION FOR SEQ ID NO:1883:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1883:

UUUGUAUUUU AGAGAAU          17

( 2 ) INFORMATION FOR SEQ ID NO:1884:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1884:

UAUUCUCUCU GAUGAGGCCG AAAGGCCGAA AAAUACAA          38

( 2 ) INFORMATION FOR SEQ ID NO:1885:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1885:

UUGUAUUUUA GAGAAUA          17

( 2 ) INFORMATION FOR SEQ ID NO:1886:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1886:

GUAUUCUCCU GAUGAGGCCG AAAGGCCGAA AAAAUACA          38

( 2 ) INFORMATION FOR SEQ ID NO:1887:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1887:

UGUAUUUUAG AGAAUAC          17

( 2 ) INFORMATION FOR SEQ ID NO:1888:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1888:

AUCUGUUGCU GAUGAGGCCG AAAGGCCGAA AUUCUCUA          38

( 2 ) INFORMATION FOR SEQ ID NO:1889:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1889:

UAGAGAAUAC AACAGAU                                                                              17

(2) INFORMATION FOR SEQ ID NO:1890:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1890:

AAAAUACUCU GAUGAGGCCG AAAGGCCAA AUCUGUUG                                                         38

(2) INFORMATION FOR SEQ ID NO:1891:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1891:

CAACAGAUCA GUAUUUU                                                                              17

(2) INFORMATION FOR SEQ ID NO:1892:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1892:

GUCAAAAACU GAUGAGGCCG AAAGGCCGAA ACUGAUCU                                                         38

(2) INFORMATION FOR SEQ ID NO:1893:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1893:

AGAUCAGUAU UUUUGAC                                                                              17

(2) INFORMATION FOR SEQ ID NO:1894:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1894:

CAGUCAAACU GAUGAGGCCG AAAGGCCGAA AUACUGAU                                                         38

(2) INFORMATION FOR SEQ ID NO:1895:

(i) SEQUENCE CHARACTERISTICS:
        (A) LENGTH: 17 base pairs
        (B) TYPE: nucleic acid (C) STRANDEDNESS: single
(D) TOPOLOGY: linear (xi) SEQUENCE DESCRIPTION: SEQ ID NO:1895:

AUCAGUAUUU UUGACUG 17

(2) INFORMATION FOR SEQ ID NO:1896:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1896:

ACAGUCAACU GAUGAGGCCG AAAGGCCGAA AAUACUGA 38

(2) INFORMATION FOR SEQ ID NO:1897:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1897:

UCAGUAUUUU UGACUGU 17

(2) INFORMATION FOR SEQ ID NO:1898:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1898:

CACAGUCACU GAUGAGGCCG AAAGGCCGAA AAAUACUG 38

(2) INFORMATION FOR SEQ ID NO:1899:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1899:

CAGUAUUUUU GACUGUG 17

(2) INFORMATION FOR SEQ ID NO:1900:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1900:

CCACAGUCCU GAUGAGGCCG AAAGGCCGAA AAAAUACU 38

(2) INFORMATION FOR SEQ ID NO:1901:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:1901:

AGUAUUUUUG ACUGUGG　　　　　　　　　　　　　　　　　　　　　　　　　　17

(2) INFORMATION FOR SEQ ID NO:1902:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:1902:

UUUUUUUACU GAUGAGGCCG AAAGGCCGAA AUUCACCA　　　　　　　　　　38

(2) INFORMATION FOR SEQ ID NO:1903:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:1903:

UGGUGAAUUU AAAAAAA　　　　　　　　　　　　　　　　　　　　　　　　17

(2) INFORMATION FOR SEQ ID NO:1904:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:1904:

UUUUUUUUCU GAUGAGGCCG AAAGGCCGAA AAUUCACC　　　　　　　　　　38

(2) INFORMATION FOR SEQ ID NO:1905:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:1905:

GGUGAAUUUA AAAAAAA　　　　　　　　　　　　　　　　　　　　　　　　17

(2) INFORMATION FOR SEQ ID NO:1906:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (x i) SEQUENCE DESCRIPTION: SEQ ID NO:1906:

UUUUUUUUCU GAUGAGGCCG AAAGGCCGAA AAAUUCAC　　　　　　　　　　38

(2) INFORMATION FOR SEQ ID NO:1907:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:1907:

```
GUGAAUUUAA AAAAAAA                                                                                    17
```

( 2 ) INFORMATION FOR SEQ ID NO:1908:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1908:

```
UUUGUGUACU GAUGAGGCCG AAAGGCCGAA AUUUUUUU                                                              38
```

( 2 ) INFORMATION FOR SEQ ID NO:1909:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1909:

```
AAAAAAAUUU ACACAAA                                                                                    17
```

( 2 ) INFORMATION FOR SEQ ID NO:1910:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1910:

```
CUUUGUGUCU GAUGAGGCCG AAAGGCCGAA AAUUUUUU                                                              38
```

( 2 ) INFORMATION FOR SEQ ID NO:1911:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1911:

```
AAAAAAUUUA CACAAAG                                                                                    17
```

( 2 ) INFORMATION FOR SEQ ID NO:1912:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1912:

```
UCUUUGUGCU GAUGAGGCCG AAAGGCCGAA AAAUUUUU                                                              38
```

( 2 ) INFORMATION FOR SEQ ID NO:1913:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1913:

```
AAAAAUUUAC ACAAAGA                                                                                    17
```

( 2 ) INFORMATION FOR SEQ ID NO:1914:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1914:

UACUGGGACU GAUGAGGCCG AAAGGCCGAA AUUUCUUU 38

( 2 ) INFORMATION FOR SEQ ID NO:1915:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1915:

AAAGAAAUAU CCCAGUA 17

( 2 ) INFORMATION FOR SEQ ID NO:1916:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1916:

AAUACUGGCU GAUGAGGCCG AAAGGCCGAA AUAUUUCU 38

( 2 ) INFORMATION FOR SEQ ID NO:1917:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1917:

AGAAAUAUCC CAGUAUU 17

( 2 ) INFORMATION FOR SEQ ID NO:1918:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1918:

ACAUGGAACU GAUGAGGCCG AAAGGCCGAA ACUGGGAU 38

( 2 ) INFORMATION FOR SEQ ID NO:1919:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1919:

AUCCCAGUAU UCCAUGU 17

( 2 ) INFORMATION FOR SEQ ID NO:1920:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1920:

AUACAUGGCU GAUGAGGCCG AAAGGCCGAA AUACUGGG     38

( 2 ) INFORMATION FOR SEQ ID NO:1921:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1921:

CCCAGUAUUC CAUGUAU     17

( 2 ) INFORMATION FOR SEQ ID NO:1922:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1922:

GAUACAUGCU GAUGAGGCCG AAAGGCCGAA AAUACUGG     38

( 2 ) INFORMATION FOR SEQ ID NO:1923:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1923:

CCAGUAUUCC AUGUAUC     17

( 2 ) INFORMATION FOR SEQ ID NO:1924:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1924:

GACUGAGACU GAUGAGGCCG AAAGGCCGAA ACAUGGAA     38

( 2 ) INFORMATION FOR SEQ ID NO:1925:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1925:

UUCCAUGUAU CUCAGUC     17

( 2 ) INFORMATION FOR SEQ ID NO:1926:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1926:

GUGACUGACU GAUGAGGCCG AAAGGCCGAA AUACAUGG  38

( 2 ) INFORMATION FOR SEQ ID NO:1927:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1927:

CCAUGUAUCU CAGUCAC  17

( 2 ) INFORMATION FOR SEQ ID NO:1928:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1928:

UAGUGACUCU GAUGAGGCCG AAAGGCCGAA AGAUACAU  38

( 2 ) INFORMATION FOR SEQ ID NO:1929:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1929:

AUGUAUCUCA GUCACUA  17

( 2 ) INFORMATION FOR SEQ ID NO:1930:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1930:

UGUUUAGUCU GAUGAGGCCG AAAGGCCGAA ACUGAGAU  38

( 2 ) INFORMATION FOR SEQ ID NO:1931:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1931:

AUCUCAGUCA CUAAACA  17

( 2 ) INFORMATION FOR SEQ ID NO:1932:

( i ) SEQUENCE CHARACTERISTICS:
  ( A ) LENGTH: 38 base pairs ( B ) TYPE: nucleic acid
            ( C ) STRANDEDNESS: single
            ( D ) TOPOLOGY: linear ( x i ) SEQUENCE DESCRIPTION: SEQ ID NO:1932:

UGUAUGUUCU GAUGAGGCCG AAAGGCCGAA AGUGACUG 38

( 2 ) INFORMATION FOR SEQ ID NO:1933:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1933:

CAGUCACUAA ACAUACA 17

( 2 ) INFORMATION FOR SEQ ID NO:1934:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1934:

UCUCUGUGCU GAUGAGGCCG AAAGGCCGAA AUGUUUAG 38

( 2 ) INFORMATION FOR SEQ ID NO:1935:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1935:

CUAAACAUAC ACAGAGA 17

( 2 ) INFORMATION FOR SEQ ID NO:1936:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1936:

UUUUUAAACU GAUGAGGCCG AAAGGCCGAA AUCUCUCU 38

( 2 ) INFORMATION FOR SEQ ID NO:1937:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1937:

AGAGAGAUUU UUAAAAA 17

( 2 ) INFORMATION FOR SEQ ID NO:1938:

( i ) SEQUENCE CHARACTERISTICS:
            ( A ) LENGTH: 38 base pairs
            ( B ) TYPE: nucleic acid
            ( C ) STRANDEDNESS: single (D) TOPOLOGY: linear (xi) SEQUENCE DESCRIPTION: SEQ ID NO:1938:

GUUUUUAACU GAUGAGGCCG AAAGGCCGAA AAUCUCUC 38

(2) INFORMATION FOR SEQ ID NO:1939:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1939:

GAGAGAUUUU UAAAAAC 17

(2) INFORMATION FOR SEQ ID NO:1940:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1940:

GGUUUUUACU GAUGAGGCCG AAAGGCCGAA AAAUCUCU 38

(2) INFORMATION FOR SEQ ID NO:1941:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1941:

AGAGAUUUUU AAAAACC 17

(2) INFORMATION FOR SEQ ID NO:1942:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1942:

UGGUUUUUCU GAUGAGGCCG AAAGGCCGAA AAAAUCUC 38

(2) INFORMATION FOR SEQ ID NO:1943:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1943:

GAGAUUUUUA AAACCA 17

(2) INFORMATION FOR SEQ ID NO:1944:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1944:

CUGGUUUUCU GAUGAGGCCG AAAGGCCGAA AAAAAUCU                    3 8

( 2 ) INFORMATION FOR SEQ ID NO:1945:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1945:

AGAUUUUUAA AAACCAG                                           1 7

( 2 ) INFORMATION FOR SEQ ID NO:1946:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1946:

UUCAAAAUCU GAUGAGGCCG AAAGGCCGAA AUGCUUCU                    3 8

( 2 ) INFORMATION FOR SEQ ID NO:1947:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1947:

AGAAGCAUUA UUUUGAA                                           1 7

( 2 ) INFORMATION FOR SEQ ID NO:1948:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1948:

AUUCAAAACU GAUGAGGCCG AAAGGCCGAA AAUGCUUC                    3 8

( 2 ) INFORMATION FOR SEQ ID NO:1949:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1949:

GAAGCAUUAU UUUGAAU                                           1 7

( 2 ) INFORMATION FOR SEQ ID NO:1950:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1950:

ACAUUCAACU GAUGAGGCCG AAAGGCCGAA AUAAUGCU          38

( 2 ) INFORMATION FOR SEQ ID NO:1951:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1951:

AGCAUUAUUU UGAAUGU          17

( 2 ) INFORMATION FOR SEQ ID NO:1952:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1952:

AACAUUCACU GAUGAGGCCG AAAGGCCGAA AAUAAUGC          38

( 2 ) INFORMATION FOR SEQ ID NO:1953:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1953:

GCAUUAUUUU GAAUGUU          17

( 2 ) INFORMATION FOR SEQ ID NO:1954:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1954:

UAACAUUCCU GAUGAGGCCG AAAGGCCGAA AAAUAAUG          38

( 2 ) INFORMATION FOR SEQ ID NO:1955:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1955:

CAUUAUUUUG AAUGUUA          17

( 2 ) INFORMATION FOR SEQ ID NO:1956:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1956:

AUUUAGCUCU GAUGAGGCCG AAAGGCCGAA ACAUUCAA          38

( 2 ) INFORMATION FOR SEQ ID NO:1957:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1957:

UUGAAUGUUA GCUAAAU         17

( 2 ) INFORMATION FOR SEQ ID NO:1958:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1958:

GAUUUAGCCU GAUGAGGCCG AAAGGCCGAA AACAUUCA         38

( 2 ) INFORMATION FOR SEQ ID NO:1959:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1959:

UGAAUGUUAG CUAAAUC         17

( 2 ) INFORMATION FOR SEQ ID NO:1960:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1960:

UUGGGAUUCU GAUGAGGCCG AAAGGCCGAA AGCUAACA         38

( 2 ) INFORMATION FOR SEQ ID NO:1961:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1961:

UGUUAGCUAA AUCCCAA         17

( 2 ) INFORMATION FOR SEQ ID NO:1962:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1962:

UUACUUGGCU GAUGAGGCCG AAAGGCCGAA AUUUAGCU         38

( 2 ) INFORMATION FOR SEQ ID NO:1963:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1963:

AGCUAAAUCC CAAGUAA     17

( 2 ) INFORMATION FOR SEQ ID NO:1964:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1964:

UUAAGUAUCU GAUGAGGCCG AAAGGCCGAA ACUUGGGA     38

( 2 ) INFORMATION FOR SEQ ID NO:1965:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1965:

UCCCAAGUAA UACUUAA     17

( 2 ) INFORMATION FOR SEQ ID NO:1966:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1966:

GCAUUAAGCU GAUGAGGCCG AAAGGCCGAA AUUACUUG     38

( 2 ) INFORMATION FOR SEQ ID NO:1967:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1967:

CAAGUAAUAC UUAAUGC     17

( 2 ) INFORMATION FOR SEQ ID NO:1968:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1968:

GUUGCAUUCU GAUGAGGCCG AAAGGCCGAA AGUAUUAC     38

( 2 ) INFORMATION FOR SEQ ID NO:1969:

( i ) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1969:

GUAAUACUUA AUGCAAC                                                                                17

(2) INFORMATION FOR SEQ ID NO:1970:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1970:

GGUUGCAUCU GAUGAGGCCG AAAGGCCGAA AAGUAUUA                                                          38

(2) INFORMATION FOR SEQ ID NO:1971:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1971:

UAAUACUUAA UGCAACC                                                                                17

(2) INFORMATION FOR SEQ ID NO:1972:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1972:

AGCUCCUACU GAUGAGGCCG AAAGGCCGAA AGGGUUGC                                                          38

(2) INFORMATION FOR SEQ ID NO:1973:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:1973:

GCAACCCUCU AGGAGCU                                                                                17

(2) INFORMATION FOR SEQ ID NO:1974:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:1974:

UGAGCUCCCU GAUGAGGCCG AAAGGCCGAA AGAGGGUU                                                          38

(2) INFORMATION FOR SEQ ID NO:1975:

(i) SEQUENCE CHARACTERISTICS:
        (A) LENGTH: 17 base pairs
        (B) TYPE: nucleic acid (C) STRANDEDNESS: single
(D) TOPOLOGY: linear (xi) SEQUENCE DESCRIPTION: SEQ ID NO:1975:

AACCCUCUAG GAGCUCA 17

(2) INFORMATION FOR SEQ ID NO:1976:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1976:

CCACAAAUCU GAUGAGGCCG AAAGGCCGAA AGCUCCUA 38

(2) INFORMATION FOR SEQ ID NO:1977:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1977:

UAGGAGCUCA UUUGUGG 17

(2) INFORMATION FOR SEQ ID NO:1978:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1978:

UAGCCACACU GAUGAGGCCG AAAGGCCGAA AUGAGCUC 38

(2) INFORMATION FOR SEQ ID NO:1979:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:1979:

GAGCUCAUUU GUGGCUA 17

(2) INFORMATION FOR SEQ ID NO:1980:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:1980:

UUAGCCACCU GAUGAGGCCG AAAGGCCGAA AAUGAGCU 38

(2) INFORMATION FOR SEQ ID NO:1981:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:1981:

AGCUCAUUUG UGGCUAA 17

( 2 ) INFORMATION FOR SEQ ID NO:1982:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1982:

AAGAUUAUCU GAUGAGGCCG AAAGGCGAA AGCCACAA 38

( 2 ) INFORMATION FOR SEQ ID NO:1983:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1983:

UUGUGGCUAA UAAUCUU 17

( 2 ) INFORMATION FOR SEQ ID NO:1984:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1984:

UCCAAGAUCU GAUGAGGCCG AAAGGCCGAA AUUAGCCA 38

( 2 ) INFORMATION FOR SEQ ID NO:1985:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1985:

UGGCUAAUAA UCUUGGA 17

( 2 ) INFORMATION FOR SEQ ID NO:1986:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1986:

AUUUCCAACU GAUGAGGCCG AAAGGCCGAA AUUAUUAG 38

( 2 ) INFORMATION FOR SEQ ID NO:1987:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1987:

CUAAUAAUCU UGGAAAU 17

( 2 ) INFORMATION FOR SEQ ID NO:1988:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1988:

AUAUUCCCU GAUGAGGCCG AAAGGCCGAA AGAUUAUU 38

( 2 ) INFORMATION FOR SEQ ID NO:1989:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1989:

AAUAAUCUUG GAAAUAU 17

( 2 ) INFORMATION FOR SEQ ID NO:1990:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1990:

AAUAAAGACU GAUGAGGCCG AAAGGCCGAA AUUUCCAA 38

( 2 ) INFORMATION FOR SEQ ID NO:1991:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1991:

UUGGAAAUAU CUUUAUU 17

( 2 ) INFORMATION FOR SEQ ID NO:1992:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1992:

AUAAUAAACU GAUGAGGCCG AAAGGCCGAA AUAUUUCC 38

( 2 ) INFORMATION FOR SEQ ID NO:1993:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1993:

GGAAAUAUCU UUAUUAU 17

( 2 ) INFORMATION FOR SEQ ID NO:1994:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1994:

AUAUAAUACU GAUGAGGCCG AAAGGCCGAA AGAUAUUU    38

( 2 ) INFORMATION FOR SEQ ID NO:1995:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1995:

AAAUAUCUUU AUUAUAU    17

( 2 ) INFORMATION FOR SEQ ID NO:1996:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1996:

UAUAUAAUCU GAUGAGGCCG AAAGGCCGAA AAGAUAUU    38

( 2 ) INFORMATION FOR SEQ ID NO:1997:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1997:

AAUAUCUUUA UUAUAUA    17

( 2 ) INFORMATION FOR SEQ ID NO:1998:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1998:

CUAUAUAACU GAUGAGGCCG AAAGGCCGAA AAAGAUAU    38

( 2 ) INFORMATION FOR SEQ ID NO:1999:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1999:

AUAUCUUUAU UAUAUAG    17

( 2 ) INFORMATION FOR SEQ ID NO:2000:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2000:

UGCUAUAUCU GAUGAGGCCG AAAGGCCGAA AUAAAGAU       38

( 2 ) INFORMATION FOR SEQ ID NO:2001:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2001:

AUCUUUAUUA UAUAGCA       17

( 2 ) INFORMATION FOR SEQ ID NO:2002:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2002:

AUGCUAUACU GAUGAGGCCG AAAGGCCGAA AAUAAAGA       38

( 2 ) INFORMATION FOR SEQ ID NO:2003:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2003:

UCUUUAUUAU AUAGCAU       17

( 2 ) INFORMATION FOR SEQ ID NO:2004:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2004:

AAAUGCUACU GAUGAGGCCG AAAGGCCGAA AUAAUAAA       38

( 2 ) INFORMATION FOR SEQ ID NO:2005:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2005:

UUUAUUAUAU AGCAUUU       17

( 2 ) INFORMATION FOR SEQ ID NO:2006:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:2006:

AUAAAUGCCU GAUGAGGCCG AAAGGCCGAA AUAUAAUA    38

( 2 ) INFORMATION FOR SEQ ID NO:2007:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2007:

UAUUAUAUAG CAUUUAU    17

( 2 ) INFORMATION FOR SEQ ID NO:2008:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2008:

UCCUCAUACU GAUGAGGCCG AAAGGCCGAA AUGCUAUA    38

( 2 ) INFORMATION FOR SEQ ID NO:2009:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2009:

UAUAGCAUUU AUGAGGA    17

( 2 ) INFORMATION FOR SEQ ID NO:2010:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2010:

CUCCUCAUCU GAUGAGGCCG AAAGGCCGAA AAUGCUAU    38

( 2 ) INFORMATION FOR SEQ ID NO:2011:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2011:

AUAGCAUUUA UGAGGAG    17

( 2 ) INFORMATION FOR SEQ ID NO:2012:

( i ) SEQUENCE CHARACTERISTICS:
      ( A ) LENGTH: 38 base pairs (B) TYPE: nucleic acid
                (C) STRANDEDNESS: single
                (D) TOPOLOGY: linear (xi) SEQUENCE DESCRIPTION: SEQ ID NO:2012:

UCUCCUCACU GAUGAGGCCG AAAGGCCGAA AAAUGCUA                38

(2) INFORMATION FOR SEQ ID NO:2013:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:2013:

UAGCAUUUAU GAGGAGA                17

(2) INFORMATION FOR SEQ ID NO:2014:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:2014:

GACAACAACU GAUGAGGCCG AAAGGCCGAA AUCUCCUC                38

(2) INFORMATION FOR SEQ ID NO:2015:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:2015:

GAGGAGAUUU UGUUGUC                17

(2) INFORMATION FOR SEQ ID NO:2016:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:2016:

UGACAACACU GAUGAGGCCG AAAGGCCGAA AAUCUCCU                38

(2) INFORMATION FOR SEQ ID NO:2017:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:2017:

AGGAGAUUUU GUUGUCA                17

(2) INFORMATION FOR SEQ ID NO:2018:

(i) SEQUENCE CHARACTERISTICS:
                (A) LENGTH: 38 base pairs
                (B) TYPE: nucleic acid
                (C) STRANDEDNESS: single ( D ) TOPOLOGY: linear ( x i ) SEQUENCE DESCRIPTION: SEQ ID NO:2018:

CUGACAACCU GAUGAGGCCG AAAGGCCGAA AAAUCUCC 38

( 2 ) INFORMATION FOR SEQ ID NO:2019:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2019:

GGAGAUUUUG UUGUCAG 17

( 2 ) INFORMATION FOR SEQ ID NO:2020:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2020:

AAGCUGACCU GAUGAGGCCG AAAGGCCGAA ACAAAAUC 38

( 2 ) INFORMATION FOR SEQ ID NO:2021:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2021:

GAUUUUGUUG UCAGCUU 17

( 2 ) INFORMATION FOR SEQ ID NO:2022:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2022:

AGCAAGCUCU GAUGAGGCCG AAAGGCCGAA ACAACAAA 38

( 2 ) INFORMATION FOR SEQ ID NO:2023:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2023:

UUUGUUGUCA GCUUGCU 17

( 2 ) INFORMATION FOR SEQ ID NO:2024:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2024:

UUUCAAGCCU GAUGAGGCCG AAAGGCCGAA AGCUGACA                                    38

( 2 ) INFORMATION FOR SEQ ID NO:2025:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2025:

UGUCAGCUUG CUUGAAA                                                            17

( 2 ) INFORMATION FOR SEQ ID NO:2026:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2026:

UAACUUUCCU GAUGAGGCCG AAAGGCCGAA AGCAAGCU                                    38

( 2 ) INFORMATION FOR SEQ ID NO:2027:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2027:

AGCUUGCUUG AAAGUUA                                                            17

( 2 ) INFORMATION FOR SEQ ID NO:2028:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2028:

UACAUAAUCU GAUGAGGCCG AAAGGCCGAA ACUUCAA                                     38

( 2 ) INFORMATION FOR SEQ ID NO:2029:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2029:

UUGAAAGUUA UUAUGUA                                                            17

( 2 ) INFORMATION FOR SEQ ID NO:2030:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2030:

AUACAUAACU GAUGAGGCCG AAAGGCCGAA AACUUUCA   38

( 2 ) INFORMATION FOR SEQ ID NO:2031:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2031:

UGAAAGUUAU UAUGUAU   17

( 2 ) INFORMATION FOR SEQ ID NO:2032:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2032:

UCAUACAUCU GAUGAGGCCG AAAGGCCGAA AUAACUUU   38

( 2 ) INFORMATION FOR SEQ ID NO:2033:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2033:

AAAGUUAUUA UGUAUGA   17

( 2 ) INFORMATION FOR SEQ ID NO:2034:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2034:

UUCAUACACU GAUGAGGCCG AAAGGCCGAA AAUAACUU   38

( 2 ) INFORMATION FOR SEQ ID NO:2035:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2035:

AAGUUAUUAU GUAUGAA   17

( 2 ) INFORMATION FOR SEQ ID NO:2036:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2036:

ACUAUUCACU GAUGAGGCCG AAAGGCCGAA ACAUAAUA   38

( 2 ) INFORMATION FOR SEQ ID NO:2037:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2037:

UAUUAUGUAU GAAUAGU                       17

( 2 ) INFORMATION FOR SEQ ID NO:2038:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2038:

AAUAAAACCU GAUGAGGCCG AAAGGCCGAA AUUCAUAC      38

( 2 ) INFORMATION FOR SEQ ID NO:2039:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2039:

GUAUGAAUAG UUUUAUU                       17

( 2 ) INFORMATION FOR SEQ ID NO:2040:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2040:

UUCAAUAACU GAUGAGGCCG AAAGGCCGAA ACUAUUCA      38

( 2 ) INFORMATION FOR SEQ ID NO:2041:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2041:

UGAAUAGUUU UAUUGAA                       17

( 2 ) INFORMATION FOR SEQ ID NO:2042:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2042:

UUUCAAUACU GAUGAGGCCG AAAGGCCGAA AACUAUUC      38

( 2 ) INFORMATION FOR SEQ ID NO:2043:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2043:

GAAUAGUUUU AUUGAAA                                             17

( 2 ) INFORMATION FOR SEQ ID NO:2044:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2044:

UUUUCAAUCU GAUGAGGCCG AAAGGCCGAA AAACUAUU                    38

( 2 ) INFORMATION FOR SEQ ID NO:2045:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2045:

AAUAGUUUUA UUGAAAA                                             17

( 2 ) INFORMATION FOR SEQ ID NO:2046:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2046:

UUUUUCAACU GAUGAGGCCG AAAGGCCGAA AAACUAU                     38

( 2 ) INFORMATION FOR SEQ ID NO:2047:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2047:

AUAGUUUUAU UGAAAAA                                             17

( 2 ) INFORMATION FOR SEQ ID NO:2048:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2048:

AUUUUUUCCU GAUGAGGCCG AAAGGCCGAA AUAAAACU                    38

( 2 ) INFORMATION FOR SEQ ID NO:2049:

( i ) SEQUENCE CHARACTERISTICS:

( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2049:

AGUUUUAUUG AAAAAAU                    17

( 2 ) INFORMATION FOR SEQ ID NO:2050:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2050:

AAAAAUAUCU GAUGAGGCCG AAAGGCCGAA AUUUUUUC                    38

( 2 ) INFORMATION FOR SEQ ID NO:2051:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2051:

GAAAAAAUUA UAUUUUU                    17

( 2 ) INFORMATION FOR SEQ ID NO:2052:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2052:

UAAAAAUACU GAUGAGGCCG AAAGGCCGAA AAUUUUUU                    38

( 2 ) INFORMATION FOR SEQ ID NO:2053:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2053:

AAAAAAUUAU AUUUUUA                    17

( 2 ) INFORMATION FOR SEQ ID NO:2054:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2054:

AAUAAAAACU GAUGAGGCCG AAAGGCCGAA AUAAUUUU                    38

( 2 ) INFORMATION FOR SEQ ID NO:2055:

( i ) SEQUENCE CHARACTERISTICS:
        ( A ) LENGTH: 17 base pairs
        ( B ) TYPE: nucleic acid ( C ) STRANDEDNESS: single
( D ) TOPOLOGY: linear ( x i ) SEQUENCE DESCRIPTION: SEQ ID NO:2055:

AAAAUUAUAU UUUUAUU                                                                17

( 2 ) INFORMATION FOR SEQ ID NO:2056:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2056:

UGAAUAAACU GAUGAGGCCG AAAGGCCGAA AUAUAAUU                                          38

( 2 ) INFORMATION FOR SEQ ID NO:2057:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2057:

AAUUAUAUUU UUAUUCA                                                                17

( 2 ) INFORMATION FOR SEQ ID NO:2058:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2058:

CUGAAUAACU GAUGAGGCCG AAAGGCCGAA AAUAUAAU                                          38

( 2 ) INFORMATION FOR SEQ ID NO:2059:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2059:

AUUAUAUUUU UAUUCAG                                                                17

( 2 ) INFORMATION FOR SEQ ID NO:2060:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2060:

ACUGAAUACU GAUGAGGCCG AAAGGCCGAA AAAUAUAA                                          38

( 2 ) INFORMATION FOR SEQ ID NO:2061:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2061:

UUAUAUUUUU AUUCAGU 17

( 2 ) INFORMATION FOR SEQ ID NO:2062:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2062:

UACUGAAUCU GAUGAGGCCG AAAGGCCGAA AAAAUAUA 38

( 2 ) INFORMATION FOR SEQ ID NO:2063:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2063:

UAUAUUUUUA UUCAGUA 17

( 2 ) INFORMATION FOR SEQ ID NO:2064:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2064:

UUACUGAACU GAUGAGGCCG AAAGGCCGAA AAAAAUAU 38

( 2 ) INFORMATION FOR SEQ ID NO:2065:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2065:

AUAUUUUUAU UCAGUAA 17

( 2 ) INFORMATION FOR SEQ ID NO:2066:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2066:

AAUUACUGCU GAUGAGGCCG AAAGGCCGAA AUAAAAAU 38

( 2 ) INFORMATION FOR SEQ ID NO:2067:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2067:

AUUUUUAUUC AGUAAUU        17

( 2 ) INFORMATION FOR SEQ ID NO:2068:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2068:

AAAUUACUCU GAUGAGGCCG AAAGGCCGAA AAUAAAAA        38

( 2 ) INFORMATION FOR SEQ ID NO:2069:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2069:

UUUUUAUUCA GUAAUUU        17

( 2 ) INFORMATION FOR SEQ ID NO:2070:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2070:

AAUUAAAUCU GAUGAGGCCG AAAGGCCGAA ACUGAAUA        38

( 2 ) INFORMATION FOR SEQ ID NO:2071:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2071:

UAUUCAGUAA UUUAAUU        17

( 2 ) INFORMATION FOR SEQ ID NO:2072:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2072:

CAAAAUUACU GAUGAGGCCG AAAGGCCGAA AUUACUGA        38

( 2 ) INFORMATION FOR SEQ ID NO:2073:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2073:

UCAGUAAUUU AAUUUUG        17

( 2 ) INFORMATION FOR SEQ ID NO:2074:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2074:

ACAAAAUUCU GAUGAGGCCG AAAGGCCGAA AAUUACUG    38

( 2 ) INFORMATION FOR SEQ ID NO:2075:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2075:

CAGUAAUUUA AUUUUGU    17

( 2 ) INFORMATION FOR SEQ ID NO:2076:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2076:

UACAAAAUCU GAUGAGGCCG AAAGGCCGAA AAAUUACU    38

( 2 ) INFORMATION FOR SEQ ID NO:2077:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2077:

AGUAAUUUAA UUUUGUA    17

( 2 ) INFORMATION FOR SEQ ID NO:2078:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2078:

AUUUACAACU GAUGAGGCCG AAAGGCCGAA AUUAAAUU    38

( 2 ) INFORMATION FOR SEQ ID NO:2079:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2079:

AAUUUAAUUU UGUAAAU    17

( 2 ) INFORMATION FOR SEQ ID NO:2080:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2080:

CAUUUACACU GAUGAGGCCG AAAGGCCGAA AAUUAAAU    38

( 2 ) INFORMATION FOR SEQ ID NO:2081:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2081:

AUUUAAUUUU GUAAAUG    17

( 2 ) INFORMATION FOR SEQ ID NO:2082:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2082:

GCAUUUACCU GAUGAGGCCG AAAGGCCGAA AAAUUAAA    38

( 2 ) INFORMATION FOR SEQ ID NO:2083:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2083:

UUUAAUUUUG UAAAUGC    17

( 2 ) INFORMATION FOR SEQ ID NO:2084:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2084:

UUGGCAUUCU GAUGAGGCCG AAAGGCCGAA ACAAAAUU    38

( 2 ) INFORMATION FOR SEQ ID NO:2085:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2085:

AAUUUUGUAA AUGCCAA    17

( 2 ) INFORMATION FOR SEQ ID NO:2086:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2086:

UAGCAGCGCU GAUGAGGCCG AAAGGCCGAA ACACAUUU  38

( 2 ) INFORMATION FOR SEQ ID NO:2087:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2087:

AAAUGUGUUC GCUGCUA  17

( 2 ) INFORMATION FOR SEQ ID NO:2088:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2088:

AUAGCAGCCU GAUGAGGCCG AAAGGCCGAA AACACAUU  38

( 2 ) INFORMATION FOR SEQ ID NO:2089:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2089:

AAUGUGUUCG CUGCUAU  17

( 2 ) INFORMATION FOR SEQ ID NO:2090:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2090:

UAAAACCACU GAUGAGGCCG AAAGGCCGAA AGCAGCGA  38

( 2 ) INFORMATION FOR SEQ ID NO:2091:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2091:

UCGCUGCUAU GGUUUUA  17

( 2 ) INFORMATION FOR SEQ ID NO:2092:

( i ) SEQUENCE CHARACTERISTICS:
  ( A ) LENGTH: 38 base pairs ( B ) TYPE: nucleic acid
            ( C ) STRANDEDNESS: single
            ( D ) TOPOLOGY: linear ( x i ) SEQUENCE DESCRIPTION: SEQ ID NO:2092:

UAGGCUAACU GAUGAGGCCG AAAGGCCGAA ACCAUAGC            38

( 2 ) INFORMATION FOR SEQ ID NO:2093:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2093:

GCUAUGGUUU UAGCCUA            17

( 2 ) INFORMATION FOR SEQ ID NO:2094:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2094:

AUAGGCUACU GAUGAGGCCG AAAGGCCGAA AACCAUAG            38

( 2 ) INFORMATION FOR SEQ ID NO:2095:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2095:

CUAUGGUUUU AGCCUAU            17

( 2 ) INFORMATION FOR SEQ ID NO:2096:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2096:

UAUAGGCUCU GAUGAGGCCG AAAGGCCGAA AAACCAUA            38

( 2 ) INFORMATION FOR SEQ ID NO:2097:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2097:

UAUGGUUUUA GCCUAUA            17

( 2 ) INFORMATION FOR SEQ ID NO:2098:

( i ) SEQUENCE CHARACTERISTICS:
            ( A ) LENGTH: 38 base pairs
            ( B ) TYPE: nucleic acid
            ( C ) STRANDEDNESS: single ( D ) TOPOLOGY: linear ( x i ) SEQUENCE DESCRIPTION: SEQ ID NO:2098:

CUAUAGGCCU GAUGAGGCCG AAAGGCCGAA AAAACCAU    38

( 2 ) INFORMATION FOR SEQ ID NO:2099:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2099:

AUGGUUUUAG CCUAUAG    17

( 2 ) INFORMATION FOR SEQ ID NO:2100:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2100:

CAUGACUACU GAUGAGGCCG AAAGGCCGAA AGGCUAAA    38

( 2 ) INFORMATION FOR SEQ ID NO:2101:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2101:

UUUAGCCUAU AGUCAUG    17

( 2 ) INFORMATION FOR SEQ ID NO:2102:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2102:

AGCAUGACCU GAUGAGGCCG AAAGGCCGAA AUAGGCUA    38

( 2 ) INFORMATION FOR SEQ ID NO:2103:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2103:

UAGCCUAUAG UCAUGCU    17

( 2 ) INFORMATION FOR SEQ ID NO:2104:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2104:

AGCAGCAUCU GAUGAGGCCG AAAGGCCGAA ACUAUAGG    38

( 2 ) INFORMATION FOR SEQ ID NO:2105:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2105:

CCUAUAGUCA UGCUGCU    17

( 2 ) INFORMATION FOR SEQ ID NO:2106:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2106:

ACACUAGCCU GAUGAGGCCG AAAGGCCGAA AGCAGCAU    38

( 2 ) INFORMATION FOR SEQ ID NO:2107:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2107:

AUGCUGCUAG CUAGUGU    17

( 2 ) INFORMATION FOR SEQ ID NO:2108:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2108:

CCUGACACCU GAUGAGGCCG AAAGGCCGAA AGCUAGCA    38

( 2 ) INFORMATION FOR SEQ ID NO:2109:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2109:

UGCUAGCUAG UGUCAGG    17

( 2 ) INFORMATION FOR SEQ ID NO:2110:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2110:

```
UGCCCCUCU  GAUGAGGCCG  AAAGGCCGAA  ACACUAGC                                    3 8
```

( 2 ) INFORMATION FOR SEQ ID NO:2111:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2111:

```
GCUAGUGUCA  GGGGGCA                                                            1 7
```

( 2 ) INFORMATION FOR SEQ ID NO:2112:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2112:

```
CUAAGCUCCU  GAUGAGGCCG  AAAGGCCGAA  AUUGCCCC                                   3 8
```

( 2 ) INFORMATION FOR SEQ ID NO:2113:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2113:

```
GGGGCAAUAG  AGCUUAG                                                            1 7
```

( 2 ) INFORMATION FOR SEQ ID NO:2114:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2114:

```
UUCCAUCUCU  GAUGAGGCCG  AAAGGCCGAA  AGCUCUAU                                   3 8
```

( 2 ) INFORMATION FOR SEQ ID NO:2115:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2115:

```
AUAGAGCUUA  GAUGGAA                                                            1 7
```

( 2 ) INFORMATION FOR SEQ ID NO:2116:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2116:

```
UUUCCAUCCU  GAUGAGGCCG  AAAGGCCGAA  AAGCUCUA                                   3 8
```

( 2 ) INFORMATION FOR SEQ ID NO:2117:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2117:

UAGAGCUUAG AUGGAAA                                  17

( 2 ) INFORMATION FOR SEQ ID NO:2118:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2118:

CUAACACCCU GAUGAGGCCG AAAGGCCGAA AGUCUCUU        38

( 2 ) INFORMATION FOR SEQ ID NO:2119:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2119:

AAGAGACUCG GUGUUAG                                  17

( 2 ) INFORMATION FOR SEQ ID NO:2120:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2120:

CGUUAUCUCU GAUGAGGCCG AAAGGCCGAA ACACCGAG        38

( 2 ) INFORMATION FOR SEQ ID NO:2121:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2121:

CUCGGUGUUA GAUAACG                                  17

( 2 ) INFORMATION FOR SEQ ID NO:2122:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2122:

CCGUUAUCCU GAUGAGGCCG AAAGGCCGAA AACACCGA        38

( 2 ) INFORMATION FOR SEQ ID NO:2123:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2123:

UCGGUGUUAG AUAACGG       17

( 2 ) INFORMATION FOR SEQ ID NO:2124:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2124:

UAGUCCGUCU GAUGAGGCCG AAAGGCCGAA AUCUAACA       38

( 2 ) INFORMATION FOR SEQ ID NO:2125:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2125:

UGUUAGAUAA CGGACUA       17

( 2 ) INFORMATION FOR SEQ ID NO:2126:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2126:

CUAGUGCACU GAUGAGGCCG AAAGGCCGAA AGUCCGUU       38

( 2 ) INFORMATION FOR SEQ ID NO:2127:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2127:

AACGGACUAU GCACUAG       17

( 2 ) INFORMATION FOR SEQ ID NO:2128:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2128:

UGGAAUACCU GAUGAGGCCG AAAGGCCGAA AGUGCAUA       38

( 2 ) INFORMATION FOR SEQ ID NO:2129:

( i ) SEQUENCE CHARACTERISTICS:

(A) LENGTH: 17 base pairs
    (B) TYPE: nucleic acid
    (C) STRANDEDNESS: single
    (D) TOPOLOGY: linear ( x i ) SEQUENCE DESCRIPTION: SEQ ID NO:2129:

UAUGCACUAG UAUUCCA                                                17

( 2 ) INFORMATION FOR SEQ ID NO:2130:

( i ) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:2130:

GUCUGGAACU GAUGAGGCCG AAAGGCCGAA ACUAGUGC                          38

( 2 ) INFORMATION FOR SEQ ID NO:2131:

( i ) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:2131:

GCACUAGUAU UCCAGAC                                                 17

( 2 ) INFORMATION FOR SEQ ID NO:2132:

( i ) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:2132:

AAGUCUGGCU GAUGAGGCCG AAAGGCCGAA AUACUAGU                          38

( 2 ) INFORMATION FOR SEQ ID NO:2133:

( i ) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:2133:

ACUAGUAUUC CAGACUU                                                 17

( 2 ) INFORMATION FOR SEQ ID NO:2134:

( i ) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:2134:

AAAGUCUGCU GAUGAGGCCG AAAGGCCGAA AAUACUAG                          38

( 2 ) INFORMATION FOR SEQ ID NO:2135:

( i ) SEQUENCE CHARACTERISTICS:
        (A) LENGTH: 17 base pairs
        (B) TYPE: nucleic acid ( C ) STRANDEDNESS: single
            ( D ) TOPOLOGY: linear ( x i ) SEQUENCE DESCRIPTION: SEQ ID NO:2135:

CUAGUAUUCC AGACUUU                                                                          17

( 2 ) INFORMATION FOR SEQ ID NO:2136:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2136:

AAAUAAAACU GAUGAGGCCG AAAGGCCGAA AGUCUGGA                                                    38

( 2 ) INFORMATION FOR SEQ ID NO:2137:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2137:

UCCAGACUUU UUUAUUU                                                                          17

( 2 ) INFORMATION FOR SEQ ID NO:2138:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2138:

AAAAUAAACU GAUGAGGCCG AAAGGCCGAA AAGUCUGG                                                    38

( 2 ) INFORMATION FOR SEQ ID NO:2139:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2139:

CCAGACUUUU UUAUUUU                                                                          17

( 2 ) INFORMATION FOR SEQ ID NO:2140:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2140:

AAAAAUAACU GAUGAGGCCG AAAGGCCGAA AAAGUCUG                                                    38

( 2 ) INFORMATION FOR SEQ ID NO:2141:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2141:

CAGACUUUUU UAUUUUU                                                                                              17

( 2 ) INFORMATION FOR SEQ ID NO:2142:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2142:

AAAAAAUACU GAUGAGGCCG AAAGGCCGAA AAAAGUCU                                                                        38

( 2 ) INFORMATION FOR SEQ ID NO:2143:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2143:

AGACUUUUUU AUUUUUU                                                                                              17

( 2 ) INFORMATION FOR SEQ ID NO:2144:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2144:

UAAAAAUCU GAUGAGGCCG AAAGGCCGAA AAAAGUC                                                                          38

( 2 ) INFORMATION FOR SEQ ID NO:2145:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2145:

GACUUUUUUA UUUUUUA                                                                                              17

( 2 ) INFORMATION FOR SEQ ID NO:2146:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2146:

AUAAAAAACU GAUGAGGCCG AAAGGCCGAA AAAAAGU                                                                         38

( 2 ) INFORMATION FOR SEQ ID NO:2147:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2147:

ACUUUUUUAU UUUUUAU 17

( 2 ) INFORMATION FOR SEQ ID NO:2148:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2148:

AUAUAAAACU GAUGAGGCCG AAAGGCCGAA AUAAAAAA 38

( 2 ) INFORMATION FOR SEQ ID NO:2149:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2149:

UUUUUUAUUU UUUAUAU 17

( 2 ) INFORMATION FOR SEQ ID NO:2150:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2150:

UAUAUAAACU GAUGAGGCCG AAAGGCCGAA AAUAAAAA 38

( 2 ) INFORMATION FOR SEQ ID NO:2151:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2151:

UUUUUAUUUU UUAUAUA 17

( 2 ) INFORMATION FOR SEQ ID NO:2152:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2152:

AUAUAUAACU GAUGAGGCCG AAAGGCCGAA AAAUAAAA 38

( 2 ) INFORMATION FOR SEQ ID NO:2153:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2153:

UUUUAUUUUU UAUAUAU 17

( 2 ) INFORMATION FOR SEQ ID NO:2154:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2154:

UAUAUAUACU GAUGAGGCCG AAAGGCCGAA AAAAUAAA         38

( 2 ) INFORMATION FOR SEQ ID NO:2155:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2155:

UUUAUUUUUU AUAUAUA         17

( 2 ) INFORMATION FOR SEQ ID NO:2156:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2156:

AUAUAUAUCU GAUGAGGCCG AAAGGCCGAA AAAAAUAA         38

( 2 ) INFORMATION FOR SEQ ID NO:2157:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2157:

UUAUUUUUA UAUAUAU         17

( 2 ) INFORMATION FOR SEQ ID NO:2158:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2158:

CAUAUAUACU GAUGAGGCCG AAAGGCCGAA AAAAAAUA         38

( 2 ) INFORMATION FOR SEQ ID NO:2159:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2159:

UAUUUUUUAU AUAUAUG         17

( 2 ) INFORMATION FOR SEQ ID NO:2160:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2160:

UACAUAUACU GAUGAGGCCG AAAGGCCGAA AUAAAAAA       38

( 2 ) INFORMATION FOR SEQ ID NO:2161:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2161:

UUUUUUAUAU AUAUGUA       17

( 2 ) INFORMATION FOR SEQ ID NO:2162:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2162:

GGUACAUACU GAUGAGGCCG AAAGGCCGAA AUAUAAAA       38

( 2 ) INFORMATION FOR SEQ ID NO:2163:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2163:

UUUUAUAUAU AUGUACC       17

( 2 ) INFORMATION FOR SEQ ID NO:2164:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2164:

AAGGUACACU GAUGAGGCCG AAAGGCCGAA AUAUAUAA       38

( 2 ) INFORMATION FOR SEQ ID NO:2165:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2165:

UUAUAUAUAU GUACCUU       17

( 2 ) INFORMATION FOR SEQ ID NO:2166:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2166:

GGAAAAGGCU GAUGAGGCCG AAAGGCCGAA ACAUAUAU 38

( 2 ) INFORMATION FOR SEQ ID NO:2167:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2167:

AUAUAUGUAC CUUUUCC 17

( 2 ) INFORMATION FOR SEQ ID NO:2168:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2168:

AAAAGGAACU GAUGAGGCCG AAAGGCCGAA AGGUACAU 38

( 2 ) INFORMATION FOR SEQ ID NO:2169:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2169:

AUGUACCUUU UCCUUUU 17

( 2 ) INFORMATION FOR SEQ ID NO:2170:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2170:

CAAAAGGACU GAUGAGGCCG AAAGGCCGAA AAGGUACA 38

( 2 ) INFORMATION FOR SEQ ID NO:2171:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2171:

UGUACCUUUU CCUUUUG 17

( 2 ) INFORMATION FOR SEQ ID NO:2172:

( i ) SEQUENCE CHARACTERISTICS:
    ( A ) LENGTH: 38 base pairs ( B ) TYPE: nucleic acid
            ( C ) STRANDEDNESS: single
            ( D ) TOPOLOGY: linear ( x i ) SEQUENCE DESCRIPTION: SEQ ID NO:2172:

ACAAAAGGCU GAUGAGGCCG AAAGGCCGAA AAAGGUAC                                    38

( 2 ) INFORMATION FOR SEQ ID NO:2173:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2173:

GUACCUUUUC CUUUUGU                                                          17

( 2 ) INFORMATION FOR SEQ ID NO:2174:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2174:

GACAAAAGCU GAUGAGGCCG AAAGGCCGAA AAAAGGUA                                    38

( 2 ) INFORMATION FOR SEQ ID NO:2175:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2175:

UACCUUUUCC UUUUGUC                                                          17

( 2 ) INFORMATION FOR SEQ ID NO:2176:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2176:

AUUGACAACU GAUGAGGCCG AAAGGCCGAA AGGAAAAG                                    38

( 2 ) INFORMATION FOR SEQ ID NO:2177:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2177:

CUUUUCCUUU UGUCAAU                                                          17

( 2 ) INFORMATION FOR SEQ ID NO:2178:

( i ) SEQUENCE CHARACTERISTICS:
            ( A ) LENGTH: 38 base pairs
            ( B ) TYPE: nucleic acid
            ( C ) STRANDEDNESS: single ( D ) TOPOLOGY: linear ( x i ) SEQUENCE DESCRIPTION: SEQ ID NO:2178:

AAUUGACACU GAUGAGGCCG AAAGGCCGAA AAGGAAAA 38

( 2 ) INFORMATION FOR SEQ ID NO:2179:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2179:

UUUUCCUUUU GUCAAUU 17

( 2 ) INFORMATION FOR SEQ ID NO:2180:

( i ) SEQUENCE CHARACTERISTICS:
       ( A ) LENGTH: 38 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2180:

CAAUUGACCU GAUGAGGCCG AAAGGCCGAA AAAGGAAA 38

( 2 ) INFORMATION FOR SEQ ID NO:2181:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2181:

UUUCCUUUUG UCAAUUG 17

( 2 ) INFORMATION FOR SEQ ID NO:2182:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2182:

GCGAGGCGAG AAGGGCUAC CAGAGAAACA CACGUUGUGG UACAUUACCU GGUA 54

( 2 ) INFORMATION FOR SEQ ID NO:2183:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2183:

AGCCCCGGCC CGCCUCGC 18

( 2 ) INFORMATION FOR SEQ ID NO:2184:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2184:

CAUGGCGAAG AAGGCCGGAC CAGAGAAACA CACGUUGUGG UACAUUACCU GGUA    54

( 2 ) INFORMATION FOR SEQ ID NO:2185:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2185:

CCGGCCCGCC UCGCCAUG    18

( 2 ) INFORMATION FOR SEQ ID NO:2186:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2186:

AUUUGGGCAG AAGCCCAUAC CAGAGAAACA CACGUUGUGG UACAUUACCU GGUA    54

( 2 ) INFORMATION FOR SEQ ID NO:2187:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2187:

AUGGGCUGCU GCCCAAAU    18

( 2 ) INFORMATION FOR SEQ ID NO:2188:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2188:

CAGAUUUGAG AAGCAGCCAC CAGAGAAACA CACGUUGUGG UACAUUACCU GGUA    54

( 2 ) INFORMATION FOR SEQ ID NO:2189:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2189:

GGCUGCUGCC CAAAUCUG    18

( 2 ) INFORMATION FOR SEQ ID NO:2190:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2190:

UUCCAGUCAG AAGUUCCGAC CAGAGAAACA CACGUUGUGG UACAUUACCU GGUA    54

( 2 ) INFORMATION FOR SEQ ID NO:2191:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2191:

CGGAACAGAC GACUGGAA    18

( 2 ) INFORMATION FOR SEQ ID NO:2192:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2192:

UCCGGUUGAG AAGAUAAUAC CAGAGAAACA CACGUUGUGG UACAUUACCU GGUA    54

( 2 ) INFORMATION FOR SEQ ID NO:2193:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2193:

AUUAUCUGCC CAACCGGA    18

( 2 ) INFORMATION FOR SEQ ID NO:2194:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2194:

CACUGUACAG AAGUCCGGAC CAGAGAAACA CACGUUGUGG UACAUUACCU GGUA    54

( 2 ) INFORMATION FOR SEQ ID NO:2195:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2195:

CCGGACAGAU GUACAGUG    18

( 2 ) INFORMATION FOR SEQ ID NO:2196:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2196:

CUCUGCCCAG AAGUUCCCAC CAGAGAAACA CACGUUGUGG UACAUUACCU GGUA    54

( 2 ) INFORMATION FOR SEQ ID NO:2197:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2197:

GGGAACAGAU GGGCAGAG 18

( 2 ) INFORMATION FOR SEQ ID NO:2198:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2198:

GUCCGGGCAG AAGCUUGAC CAGAGAAACA CACGUUGUGG UACAUUACCU GGUA 54

( 2 ) INFORMATION FOR SEQ ID NO:2199:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2199:

CAAAGCUGCU GCCCGGAC 18

( 2 ) INFORMATION FOR SEQ ID NO:2200:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2200:

UCCGUCCGAG AAGCAGCUAC CAGAGAAACA CACGUUGUGG UACAUUACCU GGUA 54

( 2 ) INFORMATION FOR SEQ ID NO:2201:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2201:

AGCUGCUGCC CGGACGGA 18

( 2 ) INFORMATION FOR SEQ ID NO:2202:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2202:

AUCAGUCCAG AAGGGCAGAC CAGAGAAACA CACGUUGUGG UACAUUACCU GGUA 54

( 2 ) INFORMATION FOR SEQ ID NO:2203:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2203:

CUGCCCGGAC GGACUGAU 18

( 2 ) INFORMATION FOR SEQ ID NO:2204:

( i ) SEQUENCE CHARACTERISTICS:
 ( A ) LENGTH: 54 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2204:

CAUUAUCAAG AAGUCCGGAC CAGAGAAACA CACGUUGUGG UACAUUACCU GGUA 54

( 2 ) INFORMATION FOR SEQ ID NO:2205:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2205:

CCGGACGGAC UGAUAAUG 18

( 2 ) INFORMATION FOR SEQ ID NO:2206:

( i ) SEQUENCE CHARACTERISTICS:
 ( A ) LENGTH: 54 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2206:

CCACUGGCAG AAGGCUGGAC CAGAGAAACA CACGUUGUGG UACAUUACCU GGUA 54

( 2 ) INFORMATION FOR SEQ ID NO:2207:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2207:

CCAGCCAGAC GCCAGUGG 18

( 2 ) INFORMATION FOR SEQ ID NO:2208:

( i ) SEQUENCE CHARACTERISTICS:
 ( A ) LENGTH: 54 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2208:

UUGGAGAGAG AAGAGAUGAC CAGAGAAACA CACGUUGUGG UACAUUACCU GGUA 54

( 2 ) INFORMATION FOR SEQ ID NO:2209:

( i ) SEQUENCE CHARACTERISTICS:

( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2209:

CAUCUCAGCU CUCUCCAA                                                                 18

( 2 ) INFORMATION FOR SEQ ID NO:2210:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2210:

UGACGGAGAG AAGGCCACAC CAGAGAAACA CACGUUGUGG UACAUUACCU GGUA         54

( 2 ) INFORMATION FOR SEQ ID NO:2211:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2211:

GUGGCCAGUC CUCCGUCA                                                                 18

( 2 ) INFORMATION FOR SEQ ID NO:2212:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2212:

UGCAAUGCAG AAGGAUAGAC CAGAGAAACA CACGUUGUGG UACAUUACCU GGUA         54

( 2 ) INFORMATION FOR SEQ ID NO:2213:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2213:

CUAUCCUGUC GCAUUGCA                                                                 18

( 2 ) INFORMATION FOR SEQ ID NO:2214:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2214:

CCGCAGCCAG AAGAGGGAAC CAGAGAAACA CACGUUGUGG UACAUUACCU GGUA         54

( 2 ) INFORMATION FOR SEQ ID NO:2215:

( i ) SEQUENCE CHARACTERISTICS:
( A ) LENGTH: 18 base pairs
( B ) TYPE: nucleic acid ( C ) STRANDEDNESS: single
( D ) TOPOLOGY: linear ( x i ) SEQUENCE DESCRIPTION: SEQ ID NO:2215:

UCCCUCAGCC GGCUGCGG 18

( 2 ) INFORMATION FOR SEQ ID NO:2216:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2216:

GCUGCCGCAG AAGGCUGAAC CAGAGAAACA CACGUUGUGG UACAUUACCU GGUA 54

( 2 ) INFORMATION FOR SEQ ID NO:2217:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2217:

UCAGCCGGCU GCGGCAGC 18

( 2 ) INFORMATION FOR SEQ ID NO:2218:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2218:

CUGUUGACAG AAGGAGCAAC CAGAGAAACA CACGUUGUGG UACAUUACCU GGUA 54

( 2 ) INFORMATION FOR SEQ ID NO:2219:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2219:

UGCUCCUGAU GUCAACAG 18

( 2 ) INFORMATION FOR SEQ ID NO:2220:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2220:

GAGGUCUGAG AAGGUCCAAC CAGAGAAACA CACGUUGUGG UACAUUACCU GGUA 54

( 2 ) INFORMATION FOR SEQ ID NO:2221:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2221:

UGGACCAGAC CAGACCUC                                                                18

( 2 ) INFORMATION FOR SEQ ID NO:2222:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2222:

CCCAUGAGAG AAGGUCUGAC CAGAGAAACA CACGUUGUGG UACAUUACCU GGUA                        54

( 2 ) INFORMATION FOR SEQ ID NO:2223:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2223:

CAGACCAGAC CUCAUGGG                                                                18

( 2 ) INFORMATION FOR SEQ ID NO:2224:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2224:

AAACAGGAAG AAGGUGCAAC CAGAGAAACA CACGUUGUGG UACAUUACCU GGUA                        54

( 2 ) INFORMATION FOR SEQ ID NO:2225:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2225:

UGCACCUGUU UCCUGUUU                                                                18

( 2 ) INFORMATION FOR SEQ ID NO:2226:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2226:

UUCUCCCAAG AAGGAAACAC CAGAGAAACA CACGUUGUGG UACAUUACCU GGUA                        54

( 2 ) INFORMATION FOR SEQ ID NO:2227:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2227:

```
GUUCCUGUU  UGGGAGAA                                                                    18
```

( 2 ) INFORMATION FOR SEQ ID NO:2228:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2228:

```
GAUCUGCAAG  AAGAGAUGAC  CAGAGAAACA  CACGUUGUGG  UACAUUACCU  GGUA         54
```

( 2 ) INFORMATION FOR SEQ ID NO:2229:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2229:

```
CAUCUCUGCC  UGCAGAUC                                                                   18
```

( 2 ) INFORMATION FOR SEQ ID NO:2230:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2230:

```
GAGCCGGGAG  AAGCAGGCAC  CAGAGAAACA  CACGUUGUGG  UACAUUACCU  GGUA         54
```

( 2 ) INFORMATION FOR SEQ ID NO:2231:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2231:

```
GCCUGCAGAU  CCCGGCUC                                                                   18
```

( 2 ) INFORMATION FOR SEQ ID NO:2232:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2232:

```
AGGUAGGGAG  AAGGAUCAC   CAGAGAAACA  CACGUUGUGG  UACAUUACCU  GGUA         54
```

( 2 ) INFORMATION FOR SEQ ID NO:2233:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2233:

```
GAUCCCGGCU  CCCUACCU                                                                   18
```

( 2 ) INFORMATION FOR SEQ ID NO:2234:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2234:

AAUCUAUAAG AAGGAGUGAC CAGAGAAACA CACGUUGUGG UACAUUACCU GGUA    54

( 2 ) INFORMATION FOR SEQ ID NO:2235:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2235:

CACUCCAGUU UAUAGAUU    18

( 2 ) INFORMATION FOR SEQ ID NO:2236:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2236:

UUUUCACAAG AAGGUCUCAC CAGAGAAACA CACGUUGUGG UACAUUACCU GGUA    54

( 2 ) INFORMATION FOR SEQ ID NO:2237:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2237:

GAGACCAGAC UGUGAAAA    18

( 2 ) INFORMATION FOR SEQ ID NO:2238:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2238:

AUUUCUUGAG AAGCAAGGAC CAGAGAAACA CACGUUGUGG UACAUUACCU GGUA    54

( 2 ) INFORMATION FOR SEQ ID NO:2239:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2239:

CCUUGCAGCU CAAGAAAU    18

( 2 ) INFORMATION FOR SEQ ID NO:2240:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2240:

CUUCAGGGAG AAGUAUUUAC CAGAGAAACA CACGUUGUGG UACAUUACCU GGUA    54

( 2 ) INFORMATION FOR SEQ ID NO:2241:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2241:

AAAUACGGUC CCCUGAAG    18

( 2 ) INFORMATION FOR SEQ ID NO:2242:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2242:

GGGAGGGGAG AAGAGGUAAC CAGAGAAACA CACGUUGUGG UACAUUACCU GGUA    54

( 2 ) INFORMATION FOR SEQ ID NO:2243:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2243:

UACCUCAGAC CCCCUCCC    18

( 2 ) INFORMATION FOR SEQ ID NO:2244:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2244:

CCAGAUUCAG AAGAUCCAC CAGAGAAACA CACGUUGUGG UACAUUACCU GGUA    54

( 2 ) INFORMATION FOR SEQ ID NO:2245:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2245:

GGAAUCGGAU GAAUCUGG    18

( 2 ) INFORMATION FOR SEQ ID NO:2246:

(  i  ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2246:

GUGGUUUGAG AAGAAGAAAC CAGAGAAACA CACGUUGUGG UACAUUACCU GGUA          54

( 2 ) INFORMATION FOR SEQ ID NO:2247:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2247:

UUCUUCUGCU CAAACCAC          18

( 2 ) INFORMATION FOR SEQ ID NO:2248:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2248:

GGUGCUCAAG AAGUUCUCAC CAGAGAAACA CACGUUGUGG UACAUUACCU GGUA          54

( 2 ) INFORMATION FOR SEQ ID NO:2249:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2249:

GAGAACAGCC UGAGCACC          18

( 2 ) INFORMATION FOR SEQ ID NO:2250:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2250:

CCUGCGAGAG AAGUUGGGAC CAGAGAAACA CACGUUGUGG UACAUUACCU GGUA          54

( 2 ) INFORMATION FOR SEQ ID NO:2251:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2251:

CCCAACUGUU CUCGCAGG          18

( 2 ) INFORMATION FOR SEQ ID NO:2252:

( i ) SEQUENCE CHARACTERISTICS:
        ( A ) LENGTH: 54 base pairs (B) TYPE: nucleic acid
        (C) STRANDEDNESS: single
        (D) TOPOLOGY: linear (xi) SEQUENCE DESCRIPTION: SEQ ID NO:2252:

UUUGGGCAG AAGCCACAAC CAGAGAAACA CACGUUGUGG UACAUUACCU GGUA   54

(2) INFORMATION FOR SEQ ID NO:2253:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2253:

UGUGGCAGAU GCCCCAAA   18

(2) INFORMATION FOR SEQ ID NO:2254:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2254:

GUCAUUAAAG AAGAGCUUAC CAGAGAAACA CACGUUGUGG UACAUUACCU GGUA   54

(2) INFORMATION FOR SEQ ID NO:2255:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2255:

AAGCUCUGUU UUAAUGAC   18

(2) INFORMATION FOR SEQ ID NO:2256:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2256:

AGGCCGUCAG AAGGUCCUAC CAGAGAAACA CACGUUGUGG UACAUUACCU GGUA   54

(2) INFORMATION FOR SEQ ID NO:2257:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2257:

AGGACCAGAU GACGGCCU   18

(2) INFORMATION FOR SEQ ID NO:2258:

(i) SEQUENCE CHARACTERISTICS:
        (A) LENGTH: 54 base pairs
        (B) TYPE: nucleic acid
        (C) STRANDEDNESS: single (D) TOPOLOGY: linear (xi) SEQUENCE DESCRIPTION: SEQ ID NO:2258:

GGACCGGAAG AAGUCAUCAC CAGAGAAACA CACGUUGUGG UACAUUACCU GGUA          54

(2) INFORMATION FOR SEQ ID NO:2259:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2259:

GAUGACGGCC UCCGGUCC          18

(2) INFORMATION FOR SEQ ID NO:2260:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2260:

CCGAGCCGAG AAGGAGGCAC CAGAGAAACA CACGUUGUGG UACAUUACCU GGUA          54

(2) INFORMATION FOR SEQ ID NO:2261:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2261:

GCCUCCGGUC CGGCUCGG          18

(2) INFORMATION FOR SEQ ID NO:2262:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2262:

UAUUUCCGAG AAGGACCGAC CAGAGAAACA CACGUUGUGG UACAUUACCU GGUA          54

(2) INFORMATION FOR SEQ ID NO:2263:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2263:

CGGUCCGGCU CGGAAAUA          18

(2) INFORMATION FOR SEQ ID NO:2264:

(i) SEQUENCE CHARACTERISTICS:
        (A) LENGTH: 54 base pairs
        (B) TYPE: nucleic acid
        (C) STRANDEDNESS: single
        (D) TOPOLOGY: linear ( x i ) SEQUENCE DESCRIPTION: SEQ ID NO:2264:

AGAGUUCGAG AAGAGAACAC CAGAGAAACA CACGUUGUGG UACAUUACCU GGUA 54

( 2 ) INFORMATION FOR SEQ ID NO:2265:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2265:

GUUCUCAGCU CGAACUCU 18

( 2 ) INFORMATION FOR SEQ ID NO:2266:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2266:

ACAACAAAAG AAGGCUCUAC CAGAGAAACA CACGUUGUGG UACAUUACCU GGUA 54

( 2 ) INFORMATION FOR SEQ ID NO:2267:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2267:

AGAGCCUGAU UUUGUUGU 18

( 2 ) INFORMATION FOR SEQ ID NO:2268:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2268:

CUGCUCUCAG AAGUUGUAAC CAGAGAAACA CACGUUGUGG UACAUUACCU GGUA 54

( 2 ) INFORMATION FOR SEQ ID NO:2269:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2269:

UACAACAGUU GAGAGCAG 18

( 2 ) INFORMATION FOR SEQ ID NO:2270:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2270:

UUAGGUAAAG AAGUUAUUAC CAGAGAAACA CACGUUGUGG UACAUUACCU GGUA 54

( 2 ) INFORMATION FOR SEQ ID NO:2271:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2271:

AAUAACAGUC UUACCUAA 18

( 2 ) INFORMATION FOR SEQ ID NO:2272:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2272:

UUUAAAAAG AAGAUUAUAC CAGAGAAACA CACGUUGUGG UACAUUACCU GGUA 54

( 2 ) INFORMATION FOR SEQ ID NO:2273:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2273:

AUAAUCAGAU UUUUUAAA 18

( 2 ) INFORMATION FOR SEQ ID NO:2274:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2274:

AAAUACUGAG AAGUUGUAAC CAGAGAAACA CACGUUGUGG UACAUUACCU GGUA 54

( 2 ) INFORMATION FOR SEQ ID NO:2275:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2275:

UACAACAGAU CAGUAUUU 18

( 2 ) INFORMATION FOR SEQ ID NO:2276:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2276:

UUCAAGCAAG AAGACAACAC CAGAGAAACA CACGUUGUGG UACAUUACCU GGUA 54

( 2 ) INFORMATION FOR SEQ ID NO:2277:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2277:

GUUGUCAGCU UGCUUGAA      18

( 2 ) INFORMATION FOR SEQ ID NO:2278:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2278:

AGUGCAUAAG AAGUUAUCAC CAGAGAAACA CACGUUGUGG UACAUUACCU GGUA    54

( 2 ) INFORMATION FOR SEQ ID NO:2279:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2279:

GAUAACGGAC UAUGCACU      18

( 2 ) INFORMATION FOR SEQ ID NO:2280:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2280:

AUAAAAAAG AAGGAAUAAC CAGAGAAACA CACGUUGUGG UACAUUACCU GGUA    54

( 2 ) INFORMATION FOR SEQ ID NO:2281:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2281:

UAUUCCAGAC UUUUUUAU      18

( 2 ) INFORMATION FOR SEQ ID NO:2282:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2282:

CCCUUGAUCU GAUGAGGCCG AAAGGCCGAA AGAUNAGG    38

( 2 ) INFORMATION FOR SEQ ID NO:2283:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2283:

CCUNAUCUCA UCAAGGG                                      17

( 2 ) INFORMATION FOR SEQ ID NO:2284:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2284:

GGACCCUUCU GAUGAGGCCG AAAGGCCGAA AUGAGAUN              38

( 2 ) INFORMATION FOR SEQ ID NO:2285:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2285:

NAUCUCAUCA AGGGUCC                                      17

( 2 ) INFORMATION FOR SEQ ID NO:2286:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2286:

GGUCCAAGCU GAUGAGGCCG AAAGGCCGAA ACCCUUGA              38

( 2 ) INFORMATION FOR SEQ ID NO:2287:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2287:

UCAAGGGUCC UUGGACC                                      17

( 2 ) INFORMATION FOR SEQ ID NO:2288:

( i ) SEQUENCE CHARACTERISTICS:
        ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO:2288:

UUUGGUCCCU GAUGAGGCCG AAAGGCCGAA AGGACCCU    38

(2) INFORMATION FOR SEQ ID NO:2289:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2289:

AGGGUCCUUG GACCAAA    17

(2) INFORMATION FOR SEQ ID NO:2290:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2290:

CACUCUCUCU GAUGAGGCCG AAAGGCCGAA AUCUUCUU    38

(2) INFORMATION FOR SEQ ID NO:2291:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2291:

AAGAAGAUCA GAGAGUG    17

(2) INFORMATION FOR SEQ ID NO:2292:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2292:

ACAAGCUCCU GAUGAGGCCG AAAGGCCGAA AUCACUCU    38

(2) INFORMATION FOR SEQ ID NO:2293:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2293:

AGAGUGAUAG AGCUUGU    17

(2) INFORMATION FOR SEQ ID NO:2294:

(i) SEQUENCE CHARACTERISTICS:
        (A) LENGTH: 38 base pairs
        (B) TYPE: nucleic acid
        (C) STRANDEDNESS: single ( D ) TOPOLOGY: linear ( x i ) SEQUENCE DESCRIPTION: SEQ ID NO:2294:

UUCUGUACCU GAUGAGGCCG AAAGGCCGAA AGCUCUAU 38

( 2 ) INFORMATION FOR SEQ ID NO:2295:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2295:

AUAGAGCUUG UACAGAA 17

( 2 ) INFORMATION FOR SEQ ID NO:2296:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2296:

UAUUUCUGCU GAUGAGGCCG AAAGGCCGAA ACAAGCUC 38

( 2 ) INFORMATION FOR SEQ ID NO:2297:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2297:

GAGCUUGUAC AGAAAUA 17

( 2 ) INFORMATION FOR SEQ ID NO:2298:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2298:

UCGGACCGCU GAUGAGGCCG AAAGGCCGAA AUUUCUGU 38

( 2 ) INFORMATION FOR SEQ ID NO:2299:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2299:

ACAGAAAUAC GGUCCGA 17

( 2 ) INFORMATION FOR SEQ ID NO:2300:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2300:

ACGUUUCGCU GAUGAGGCCG AAAGGCCGAA ACCGUAUU 38

( 2 ) INFORMATION FOR SEQ ID NO:2301:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2301:

AAUACGGUCC GAAACGU 17

( 2 ) INFORMATION FOR SEQ ID NO:2302:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2302:

AACAGACCCU GAUGAGGCCG AAAGGCCGAA ACGUUUCG 38

( 2 ) INFORMATION FOR SEQ ID NO:2303:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2303:

CGAAACGUUG GUCUGUU 17

( 2 ) INFORMATION FOR SEQ ID NO:2304:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2304:

CAAUAACACU GAUGAGGCCG AAAGGCCGAA ACCAACGU 38

( 2 ) INFORMATION FOR SEQ ID NO:2305:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2305:

ACGUUGGUCU GUUAUUG 17

( 2 ) INFORMATION FOR SEQ ID NO:2306:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2306:

UUGGCAAUCU GAUGAGGCCG AAAGGCCGAA ACAGACCA                    38

( 2 ) INFORMATION FOR SEQ ID NO:2307:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2307:

UGGUCUGUUA UUGCCAA                                           17

( 2 ) INFORMATION FOR SEQ ID NO:2308:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2308:

CUUGGCAACU GAUGAGGCCG AAAGGCCGAA AACAGACC                    38

( 2 ) INFORMATION FOR SEQ ID NO:2309:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2309:

GGUCUGUUAU UGCCAAG                                           17

( 2 ) INFORMATION FOR SEQ ID NO:2310:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2310:

UGCUUGGCCU GAUGAGGCCG AAAGGCCGAA AUAACAGA                    38

( 2 ) INFORMATION FOR SEQ ID NO:2311:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2311:

UCUGUUAUUG CCAAGCA                                           17

( 2 ) INFORMATION FOR SEQ ID NO:2312:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2312:

UCCCCUUUCU GAUGAGGCCG AAAGGCCGAA AGUGCUUG                    38

( 2 ) INFORMATION FOR SEQ ID NO:2313:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2313:

CAAGCACUUA AAGGGGA 17

( 2 ) INFORMATION FOR SEQ ID NO:2314:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2314:

CUCCCUUCU GAUGAGGCCG AAAGGCCGAA AAGUGCUU 38

( 2 ) INFORMATION FOR SEQ ID NO:2315:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2315:

AAGCACUUAA AGGGGAG 17

( 2 ) INFORMATION FOR SEQ ID NO:2316:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2316:

UGUUUUCCCU GAUGAGGCCG AAAGGCCGAA AUUCUCCC 38

( 2 ) INFORMATION FOR SEQ ID NO:2317:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2317:

GGGAGAAUUG GAAAACA 17

( 2 ) INFORMATION FOR SEQ ID NO:2318:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2318:

CCUCUCCCCU GAUGAGGCCG AAAGGCCGAA ACAUUGUU 38

( 2 ) INFORMATION FOR SEQ ID NO:2319:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2319:

AACAAUGUAG GGAGAGG                                              17

( 2 ) INFORMATION FOR SEQ ID NO:2320:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2320:

CAAGUGGUCU GAUGAGGCCG AAAGGCCGAA AUGCCACC                       38

( 2 ) INFORMATION FOR SEQ ID NO:2321:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2321:

GGUGGCAUAA CCACUUG                                              17

( 2 ) INFORMATION FOR SEQ ID NO:2322:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2322:

CUGGAUUCCU GAUGAGGCCG AAAGGCCGAA AGUGGUUA                       38

( 2 ) INFORMATION FOR SEQ ID NO:2323:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2323:

UAACCACUUG AAUCCAG                                              17

( 2 ) INFORMATION FOR SEQ ID NO:2324:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2324:

AACUUCUGCU GAUGAGGCCG AAAGGCCGAA AUUCAAGU                       38

( 2 ) INFORMATION FOR SEQ ID NO:2325:

( i ) SEQUENCE CHARACTERISTICS:

( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2325:

ACUUGAAUCC AGAAGUU                                                                              17

( 2 ) INFORMATION FOR SEQ ID NO:2326:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2326:

GUUUCUUCU GAUGAGGCCG AAAGGCCGAA ACUUCUGG                                                         38

( 2 ) INFORMATION FOR SEQ ID NO:2327:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2327:

CCAGAAGUUA AGAAAAC                                                                              17

( 2 ) INFORMATION FOR SEQ ID NO:2328:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2328:

GGUUUUCUCU GAUGAGGCCG AAAGGCCGAA AACUUCUG                                                        38

( 2 ) INFORMATION FOR SEQ ID NO:2329:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2329:

CAGAAGUUAA GAAAACC                                                                              17

( 2 ) INFORMATION FOR SEQ ID NO:2330:

( i ) SEQUENCE CHARACTERISTICS:
                    ( A ) LENGTH: 38 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2330:

CUGUCCAGCU GAUGAGGCCG AAAGGCCGAA AGGUUUUC                                                        38

( 2 ) INFORMATION FOR SEQ ID NO:2331:

( i ) SEQUENCE CHARACTERISTICS:
                    ( A ) LENGTH: 17 base pairs
                    ( B ) TYPE: nucleic acid (C) STRANDEDNESS: single
        (D) TOPOLOGY: linear (xi) SEQUENCE DESCRIPTION: SEQ ID NO:2331:

GAAAACCUCC UGGACAG                                                                17

(2) INFORMATION FOR SEQ ID NO:2332:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2332:

UGGUAAAUCU GAUGAGGCCG AAAGGCCGAA AUUCUGUC                                         38

(2) INFORMATION FOR SEQ ID NO:2333:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2333:

GACAGAAUUA UUUACCA                                                                17

(2) INFORMATION FOR SEQ ID NO:2334:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2334:

CUGGUAAACU GAUGAGGCCG AAAGGCCGAA AAUUCUGU                                         38

(2) INFORMATION FOR SEQ ID NO:2335:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2335:

ACAGAAUUAU UUACCAG                                                                17

(2) INFORMATION FOR SEQ ID NO:2336:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2336:

GCCUGGUACU GAUGAGGCCG AAAGGCCGAA AUAAUUCU                                         38

(2) INFORMATION FOR SEQ ID NO:2337:

(i) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:2337:

AGAAUUAUUU ACCAGGC                        17

( 2 ) INFORMATION FOR SEQ ID NO:2338:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2338:

UGCCUGGUCU GAUGAGGCCG AAAGGCCGAA AAUAAUUC                        38

( 2 ) INFORMATION FOR SEQ ID NO:2339:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2339:

GAAUUAUUUA CCAGGCA                        17

( 2 ) INFORMATION FOR SEQ ID NO:2340:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2340:

GUGCCUGGCU GAUGAGGCCG AAAGGCCGAA AAAUAAUU                        38

( 2 ) INFORMATION FOR SEQ ID NO:2341:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2341:

AAUUAUUUAC CAGGCAC                        17

( 2 ) INFORMATION FOR SEQ ID NO:2342:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2342:

AGCUUUGCCU GAUGAGGCCG AAAGGCCGAA AUUCCGC                        38

( 2 ) INFORMATION FOR SEQ ID NO:2343:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2343:

GCGGAAAUCG CAAAGCU         17

( 2 ) INFORMATION FOR SEQ ID NO:2344:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2344:

CCAGGCAGCU GAUGAGGCCG AAAGGCCGAA AGCUUUGC         38

( 2 ) INFORMATION FOR SEQ ID NO:2345:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2345:

GCAAAGCUAC UGCCUGG         17

( 2 ) INFORMATION FOR SEQ ID NO:2346:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2346:

GUGUUUAACU GAUGAGGCCG AAAGGCCGAA AAAGAAUC         38

( 2 ) INFORMATION FOR SEQ ID NO:2347:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2347:

GAUUCUUUCU UAAACAC         17

( 2 ) INFORMATION FOR SEQ ID NO:2348:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2348:

AAGUGUUUCU GAUGAGGCCG AAAGGCCGAA AGAAAGAA         38

( 2 ) INFORMATION FOR SEQ ID NO:2349:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2349:

UUCUUUCUUA AACACUU         17

( 2 ) INFORMATION FOR SEQ ID NO:2350:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2350:

GAAGUGUUCU GAUGAGGCCG AAAGGCCGAA AAGAAAGA     38

( 2 ) INFORMATION FOR SEQ ID NO:2351:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2351:

UCUUUCUUAA ACACUUC     17

( 2 ) INFORMATION FOR SEQ ID NO:2352:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2352:

GUUAUUGGCU GAUGAGGCCG AAAGGCCGAA AGUGUUUA     38

( 2 ) INFORMATION FOR SEQ ID NO:2353:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2353:

UAAACACUUC CAAUAAC     17

( 2 ) INFORMATION FOR SEQ ID NO:2354:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2354:

GGUUAUUGCU GAUGAGGCCG AAAGGCCGAA AAGUGUUU     38

( 2 ) INFORMATION FOR SEQ ID NO:2355:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2355:

AAACACUUCC AAUAACC     17

( 2 ) INFORMATION FOR SEQ ID NO:2356:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2356:

UUCAUGGUCU GAUGAGGCCG AAAGGCCGAA AUUGGAAG        38

( 2 ) INFORMATION FOR SEQ ID NO:2357:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2357:

CUUCCAAUAA CCAUGAA        17

( 2 ) INFORMATION FOR SEQ ID NO:2358:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2358:

CCAAGUCUCU GAUGAGGCCG AAAGGCCGAA AGUUUUCA        38

( 2 ) INFORMATION FOR SEQ ID NO:2359:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2359:

UGAAAACUUA GACUUGG        17

( 2 ) INFORMATION FOR SEQ ID NO:2360:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2360:

UCCAAGUCCU GAUGAGGCCG AAAGGCCGAA AAGUUUUC        38

( 2 ) INFORMATION FOR SEQ ID NO:2361:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2361:

GAAAACUUAG ACUUGGA        17

( 2 ) INFORMATION FOR SEQ ID NO:2362:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2362:

GCAUUCCCU GAUGAGGCCG AAAGGCCGAA AGUCUAAG　　　　　　　　　　　　　　38

( 2 ) INFORMATION FOR SEQ ID NO:2363:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2363:

CUUAGACUUG GAAAUGC　　　　　　　　　　　　　　　　　　　　　　　　　17

( 2 ) INFORMATION FOR SEQ ID NO:2364:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2364:

CGUUAAAGCU GAUGAGGCCG AAAGGCCGAA AGGCAUUU　　　　　　　　　　　　　　38

( 2 ) INFORMATION FOR SEQ ID NO:2365:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2365:

AAAUGCCUUC UUUAACG　　　　　　　　　　　　　　　　　　　　　　　　　17

( 2 ) INFORMATION FOR SEQ ID NO:2366:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2366:

ACGUUAAACU GAUGAGGCCG AAAGGCCGAA AAGGCAUU　　　　　　　　　　　　　　38

( 2 ) INFORMATION FOR SEQ ID NO:2367:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2367:

AAUGCCUUCU UUAACGU　　　　　　　　　　　　　　　　　　　　　　　　　17

( 2 ) INFORMATION FOR SEQ ID NO:2368:

( i ) SEQUENCE CHARACTERISTICS:
        ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO:2368:

GGACGUUACU GAUGAGGCCG AAAGGCCGAA AGAAGGCA                                38

(2) INFORMATION FOR SEQ ID NO:2369:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2369:

UGCCUUCUUU AACGUCC                                                      17

(2) INFORMATION FOR SEQ ID NO:2370:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2370:

UGGACGUUCU GAUGAGGCCG AAAGGCCGAA AAGAAGGC                                38

(2) INFORMATION FOR SEQ ID NO:2371:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2371:

GCCUUCUUUA ACGUCCA                                                      17

(2) INFORMATION FOR SEQ ID NO:2372:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2372:

GUGGACGUCU GAUGAGGCCG AAAGGCCGAA AAAGAAGG                                38

(2) INFORMATION FOR SEQ ID NO:2373:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2373:

CCUUCUUUAA CGUCCAC                                                      17

(2) INFORMATION FOR SEQ ID NO:2374:

(i) SEQUENCE CHARACTERISTICS:
(A) LENGTH: 38 base pairs
(B) TYPE: nucleic acid
(C) STRANDEDNESS: single ( D ) TOPOLOGY: linear ( x i ) SEQUENCE DESCRIPTION: SEQ ID NO:2374:

GAGGCGUGCU GAUGAGGCCG AAAGGCCGAA ACGUUAAA                    38

( 2 ) INFORMATION FOR SEQ ID NO:2375:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2375:

UUUAACGUCC ACGCCUC                                          17

( 2 ) INFORMATION FOR SEQ ID NO:2376:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2376:

ACCACUGACU GAUGAGGCCG AAAGGCCGAA AGGCGUGG                    38

( 2 ) INFORMATION FOR SEQ ID NO:2377:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2377:

CCACGCCUCU CAGUGGU                                          17

( 2 ) INFORMATION FOR SEQ ID NO:2378:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2378:

UGACCACUCU GAUGAGGCCG AAAGGCCGAA AGAGGCGU                    38

( 2 ) INFORMATION FOR SEQ ID NO:2379:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2379:

ACGCCUCUCA GUGGUCA                                          17

( 2 ) INFORMATION FOR SEQ ID NO:2380:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2380:

CAAUUUGUCU GAUGAGGCCG AAAGGCCGAA ACCACUGA 38

( 2 ) INFORMATION FOR SEQ ID NO:2381:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2381:

UCAGUGGUCA CAAAUUG 17

( 2 ) INFORMATION FOR SEQ ID NO:2382:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2382:

UAACAGUCCU GAUGAGGCCG AAAGGCCGAA AUUUGUGA 38

( 2 ) INFORMATION FOR SEQ ID NO:2383:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2383:

UCACAAAUUG ACUGUUA 17

( 2 ) INFORMATION FOR SEQ ID NO:2384:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2384:

GGUGUUGUCU GAUGAGGCCG AAAGGCCGAA ACAGUCAA 38

( 2 ) INFORMATION FOR SEQ ID NO:2385:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2385:

UUGACUGUUA CAACACC 17

( 2 ) INFORMATION FOR SEQ ID NO:2386:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2386:

```
UGGUGUUGCU  GAUGAGGCCG  AAAGGCCGAA  AACAGUCA                              38
```

( 2 ) INFORMATION FOR SEQ ID NO:2387:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2387:

```
UGACUGUUAC  AACACCA                                                       17
```

( 2 ) INFORMATION FOR SEQ ID NO:2388:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2388:

```
CUCUAUGACU  GAUGAGGCCG  AAAGGCCGAA  AUGGUGUU                              38
```

( 2 ) INFORMATION FOR SEQ ID NO:2389:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2389:

```
AACACCAUUU  CAUAGAG                                                       17
```

( 2 ) INFORMATION FOR SEQ ID NO:2390:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2390:

```
UCUCUAUGCU  GAUGAGGCCG  AAAGGCCGAA  AAUGGUGU                              38
```

( 2 ) INFORMATION FOR SEQ ID NO:2391:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2391:

```
ACACCAUUUC  AUAGAGA                                                       17
```

( 2 ) INFORMATION FOR SEQ ID NO:2392:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2392:

```
GUCUCUAUCU  GAUGAGGCCG  AAAGGCCGAA  AAAUGGUG                              38
```

(2) INFORMATION FOR SEQ ID NO:2393:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:2393:

CACCAUUUCA UAGAGAC                                                            17

(2) INFORMATION FOR SEQ ID NO:2394:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:2394:

CUGGUCUCCU GAUGAGGCCG AAAGGCCGAA AUGAAAUG                                     38

(2) INFORMATION FOR SEQ ID NO:2395:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:2395:

CAUUUCAUAG AGACCAG                                                            17

(2) INFORMATION FOR SEQ ID NO:2396:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:2396:

AAAAUAUGCU GAUGAGGCCG AAAGGCCGAA AUUUUCCU                                     38

(2) INFORMATION FOR SEQ ID NO:2397:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:2397:

AGGAAAAUAC AUAUUUU                                                            17

(2) INFORMATION FOR SEQ ID NO:2398:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO:2398:

UUCAAAAACU GAUGAGGCCG AAAGGCCGAA AUGUAUUU                                     38

(2) INFORMATION FOR SEQ ID NO:2399:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2399:

AAAUACAUAU UUUUGAA     17

( 2 ) INFORMATION FOR SEQ ID NO:2400:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2400:

AGUUCAAACU GAUGAGGCCG AAAGGCCGAA AUAUGUAU     38

( 2 ) INFORMATION FOR SEQ ID NO:2401:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2401:

AUACAUAUUU UUGAACU     17

( 2 ) INFORMATION FOR SEQ ID NO:2402:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2402:

GAGUUCAACU GAUGAGGCCG AAAGGCCGAA AAUAUGUA     38

( 2 ) INFORMATION FOR SEQ ID NO:2403:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2403:

UACAUAUUUU UGAACUC     17

( 2 ) INFORMATION FOR SEQ ID NO:2404:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2404:

GGAGUUCACU GAUGAGGCCG AAAGGCCGAA AAAUAUGU     38

( 2 ) INFORMATION FOR SEQ ID NO:2405:

( i ) SEQUENCE CHARACTERISTICS:

( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2405:

ACAUAUUUUU GAACUCC                                                              17

( 2 ) INFORMATION FOR SEQ ID NO:2406:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2406:

CGGAGUUCCU GAUGAGGCCG AAAGGCCGAA AAAAUAUG                                       38

( 2 ) INFORMATION FOR SEQ ID NO:2407:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2407:

CAUAUUUUUG AACUCCG                                                              17

( 2 ) INFORMATION FOR SEQ ID NO:2408:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2408:

GAUAGCCGCU GAUGAGGCCG AAAGGCCGAA AGUUCAAA                                       38

( 2 ) INFORMATION FOR SEQ ID NO:2409:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2409:

UUUGAACUCC GGCUAUC                                                              17

( 2 ) INFORMATION FOR SEQ ID NO:2410:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2410:

CCUUUUGACU GAUGAGGCCG AAAGGCCGAA AGCCGGAG                                       38

( 2 ) INFORMATION FOR SEQ ID NO:2411:

( i ) SEQUENCE CHARACTERISTICS:
        ( A ) LENGTH: 17 base pairs
        ( B ) TYPE: nucleic acid ( C ) STRANDEDNESS: single
( D ) TOPOLOGY: linear ( x i ) SEQUENCE DESCRIPTION: SEQ ID NO:2411:

CUCCGGCUAU CAAAAGG 17

( 2 ) INFORMATION FOR SEQ ID NO:2412:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2412:

GACCUUUUCU GAUGAGGCCG AAAGGCCGAA AUAGCCGG 38

( 2 ) INFORMATION FOR SEQ ID NO:2413:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2413:

CCGGCUAUCA AAAGGUC 17

( 2 ) INFORMATION FOR SEQ ID NO:2414:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2414:

CCAGGAUUCU GAUGAGGCCG AAAGGCCGAA ACCUUUUG 38

( 2 ) INFORMATION FOR SEQ ID NO:2415:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2415:

CAAAAGGUCA AUCCUGG 17

( 2 ) INFORMATION FOR SEQ ID NO:2416:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2416:

CUUUCCAGCU GAUGAGGCCG AAAGGCCGAA AUUGACCU 38

( 2 ) INFORMATION FOR SEQ ID NO:2417:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear (xi) SEQUENCE DESCRIPTION: SEQ ID NO:2417:

AGGUCAAUCC UGGAAAG                                                17

(2) INFORMATION FOR SEQ ID NO:2418:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2418:

UUCUUGGACU GAUGAGGCCG AAAGGCCGAA AGCUUUCC                          38

(2) INFORMATION FOR SEQ ID NO:2419:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2419:

GGAAAGCUCU CCAAGAA                                                17

(2) INFORMATION FOR SEQ ID NO:2420:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2420:

AGUUCUUGCU GAUGAGGCCG AAAGGCCGAA AGAGCUUU                          38

(2) INFORMATION FOR SEQ ID NO:2421:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2421:

AAAGCUCUCC AAGAACU                                                17

(2) INFORMATION FOR SEQ ID NO:2422:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2422:

CGGUGUAGCU GAUGAGGCCG AAAGGCCGAA AGUUCUUG                          38

(2) INFORMATION FOR SEQ ID NO:2423:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2423:

CAAGAACUCC UACACCG                                                                              17

( 2 ) INFORMATION FOR SEQ ID NO:2424:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2424:

GAACGGUGCU GAUGAGGCCG AAAGGCCGAA AGGAGUUC                                                        38

( 2 ) INFORMATION FOR SEQ ID NO:2425:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2425:

GAACUCCUAC ACCGUUC                                                                              17

( 2 ) INFORMATION FOR SEQ ID NO:2426:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2426:

CAUGUUUGCU GAUGAGGCCG AAAGGCCGAA ACGGUGUA                                                        38

( 2 ) INFORMATION FOR SEQ ID NO:2427:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2427:

UACACCGUUC AAACAUG                                                                              17

( 2 ) INFORMATION FOR SEQ ID NO:2428:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2428:

GCAUGUUUCU GAUGAGGCCG AAAGGCCGAA AACGGUGU                                                        38

( 2 ) INFORMATION FOR SEQ ID NO:2429:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2429:

ACACCGUUCA AACAUGC                                                                              17

( 2 ) INFORMATION FOR SEQ ID NO:2430:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2430:

UGAGCUGCCU GAUGAGGCCG AAAGGCCGAA AGUGCAUG     38

( 2 ) INFORMATION FOR SEQ ID NO:2431:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2431:

CAUGCACUCG CAGCUCA     17

( 2 ) INFORMATION FOR SEQ ID NO:2432:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2432:

AAUUUCUUCU GAUGAGGCCG AAAGGCCGAA AGCUGCGA     38

( 2 ) INFORMATION FOR SEQ ID NO:2433:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2433:

UCGCAGCUCA AGAAAUU     17

( 2 ) INFORMATION FOR SEQ ID NO:2434:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2434:

CCAUAUUUCU GAUGAGGCCG AAAGGCCGAA AUUUCUUG     38

( 2 ) INFORMATION FOR SEQ ID NO:2435:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2435:

CAAGAAAUUA AAUAUGG     17

( 2 ) INFORMATION FOR SEQ ID NO:2436:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2436:

ACCAUAUUCU GAUGAGGCCG AAAGGCCGAA AAUUUCUU 38

( 2 ) INFORMATION FOR SEQ ID NO:2437:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2437:

AAGAAAUUAA AUAUGGU 17

( 2 ) INFORMATION FOR SEQ ID NO:2438:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2438:

GGGGACCACU GAUGAGGCCG AAAGGCCGAA AUUUAAUU 38

( 2 ) INFORMATION FOR SEQ ID NO:2439:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2439:

AAUUAAAUAU GGUCCCC 17

( 2 ) INFORMATION FOR SEQ ID NO:2440:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2440:

CUUCAGGGCU GAUGAGGCCG AAAGGCCGAA ACCAUAUU 38

( 2 ) INFORMATION FOR SEQ ID NO:2441:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2441:

AAUAUGGUCC CCUGAAG 17

( 2 ) INFORMATION FOR SEQ ID NO:2442:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:2442:

GUCUGAGGCU GAUGAGGCCG AAAGGCCGAA AGCAUCUU    38

( 2 ) INFORMATION FOR SEQ ID NO:2443:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2443:

AAGAUGCUAC CUCAGAC    17

( 2 ) INFORMATION FOR SEQ ID NO:2444:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2444:

UGGUGUCUCU GAUGAGGCCG AAAGGCCGAA AGGUAGCA    38

( 2 ) INFORMATION FOR SEQ ID NO:2445:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2445:

UGCUACCUCA GACACCA    17

( 2 ) INFORMATION FOR SEQ ID NO:2446:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2446:

CUAAAUGACU GAUGAGGCCG AAAGGCCGAA AUGGUGUC    38

( 2 ) INFORMATION FOR SEQ ID NO:2447:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2447:

GACACCAUCU CAUUUAG    17

( 2 ) INFORMATION FOR SEQ ID NO:2448:

( i ) SEQUENCE CHARACTERISTICS:
      ( A ) LENGTH: 38 base pairs (B) TYPE: nucleic acid
        (C) STRANDEDNESS: single
        (D) TOPOLOGY: linear (xi) SEQUENCE DESCRIPTION: SEQ ID NO:2448:

UACUAAAUCU GAUGAGGCCG AAAGGCCGAA AGAUGGUG                        38

(2) INFORMATION FOR SEQ ID NO:2449:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2449:

CACCAUCUCA UUUAGUA                                               17

(2) INFORMATION FOR SEQ ID NO:2450:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2450:

UUCUACUACU GAUGAGGCCG AAAGGCCGAA AUGAGAUG                        38

(2) INFORMATION FOR SEQ ID NO:2451:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2451:

CAUCUCAUUU AGUAGAA                                               17

(2) INFORMATION FOR SEQ ID NO:2452:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2452:

CUUCUACUCU GAUGAGGCCG AAAGGCCGAA AAUGAGAU                        38

(2) INFORMATION FOR SEQ ID NO:2453:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2453:

AUCUCAUUUA GUAGAAG                                               17

(2) INFORMATION FOR SEQ ID NO:2454:

(i) SEQUENCE CHARACTERISTICS:
        (A) LENGTH: 38 base pairs
        (B) TYPE: nucleic acid
        (C) STRANDEDNESS: single ( D ) TOPOLOGY: linear ( x i ) SEQUENCE DESCRIPTION: SEQ ID NO:2454:

UCUUCUACCU GAUGAGGCCG AAAGGCCGAA AAAUGAGA                         38

( 2 ) INFORMATION FOR SEQ ID NO:2455:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2455:

UCUCAUUUAG UAGAAGA                                                17

( 2 ) INFORMATION FOR SEQ ID NO:2456:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2456:

AGGUCUUCCU GAUGAGGCCG AAAGGCCGAA ACUAAAUG                          38

( 2 ) INFORMATION FOR SEQ ID NO:2457:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2457:

CAUUUAGUAG AAGACCU                                                17

( 2 ) INFORMATION FOR SEQ ID NO:2458:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2458:

UUUUCACAAG AAGGUCUCAC CAGAGAAACA CACGUUGUGG UACAUUACCU GGUA         54

( 2 ) INFORMATION FOR SEQ ID NO:2459:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2459:

GAGACCAGAC UGUGAAAA                                               18

( 2 ) INFORMATION FOR SEQ ID NO:2460:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2460:

CAUGUUUGAG AAGUGUAGAC CAGAGAAACA CACGUUGUGG UACAUUACCU GGUA    54

( 2 ) INFORMATION FOR SEQ ID NO:2461:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2461:

CUACACCGUU CAAACAUG    18

( 2 ) INFORMATION FOR SEQ ID NO:2462:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2462:

AUUUCUUGAG AAGCGAGUAC CAGAGAAACA CACGUUGUGG UACAUUACCU GGUA    54

( 2 ) INFORMATION FOR SEQ ID NO:2463:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2463:

ACUCGCAGCU CAAGAAAU    18

( 2 ) INFORMATION FOR SEQ ID NO:2464:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2464:

ACGUUUCGAG AAGUAUUUAC CAGAGAAACA CACGUUGUGG UACAUUACCU GGUA    54

( 2 ) INFORMATION FOR SEQ ID NO:2465:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2465:

AAAUACGGUC CGAAACGU    18

( 2 ) INFORMATION FOR SEQ ID NO:2466:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2466:

UUCCGCCCAG AAGUUCCCAC CAGAGAAACA CACGUUGUGG UACAUUACCU GGUA    54

( 2 ) INFORMATION FOR SEQ ID NO:2467:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2467:

GGGAACAGAU GGGCGGAA    18

( 2 ) INFORMATION FOR SEQ ID NO:2468:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2468:

CCUUUGAUCU GAUGAGGCCG AAAGGCCGAA AGCUCAGG    38

( 2 ) INFORMATION FOR SEQ ID NO:2469:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2469:

CCUGAGCUCA UCAAAGG    17

( 2 ) INFORMATION FOR SEQ ID NO:2470:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2470:

GGACCUUUCU GAUGAGGCCG AAAGGCCGAA AUGAGCUC    38

( 2 ) INFORMATION FOR SEQ ID NO:2471:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2471:

GAGCUCAUCA AAGGUCC    17

( 2 ) INFORMATION FOR SEQ ID NO:2472:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2472:

GGUCCAGGCU GAUGAGGCCG AAAGGCCGAA ACCUUGA    38

( 2 ) INFORMATION FOR SEQ ID NO:2473:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2473:

UCAAAGGUCC CUGGACC                               17

( 2 ) INFORMATION FOR SEQ ID NO:2474:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2474:

CACUCUUUCU GAUGAGGCCG AAAGGCCGAA AUCUUCUU           38

( 2 ) INFORMATION FOR SEQ ID NO:2475:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2475:

AAGAAGAUCA AAGAGUG                                17

( 2 ) INFORMATION FOR SEQ ID NO:2476:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2476:

ACAAGCUCCU GAUGAGGCCG AAAGGCCGAA AUCACUCU           38

( 2 ) INFORMATION FOR SEQ ID NO:2477:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2477:

AGAGUGAUAG AGCUUGU                                17

( 2 ) INFORMATION FOR SEQ ID NO:2478:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2478:

UUCUGGACCU GAUGAGGCCG AAAGGCCGAA AGCUCUAU           38

( 2 ) INFORMATION FOR SEQ ID NO:2479:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:2479:

AUAGAGCUUG UCCAGAA 17

( 2 ) INFORMATION FOR SEQ ID NO:2480:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2480:

UAUUCUGCU GAUGAGGCCG AAAGGCCGAA ACAAGCUC 38

( 2 ) INFORMATION FOR SEQ ID NO:2481:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2481:

GAGCUUGUCC AGAAAUA 17

( 2 ) INFORMATION FOR SEQ ID NO:2482:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2482:

UCGGACCGCU GAUGAGGCCG AAAGGCCGAA AUUUCUGG 38

( 2 ) INFORMATION FOR SEQ ID NO:2483:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2483:

CCAGAAAUAC GGUCCGA 17

( 2 ) INFORMATION FOR SEQ ID NO:2484:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2484:

GCGCUUCGCU GAUGAGGCCG AAAGGCCGAA ACCGUAUU 38

( 2 ) INFORMATION FOR SEQ ID NO:2485:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2485:

AAUACGGUCC GAAGCGC 17

( 2 ) INFORMATION FOR SEQ ID NO:2486:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2486:

CAAUAACACU GAUGAGGCCG AAAGGCCGAA ACCAGCGC 38

( 2 ) INFORMATION FOR SEQ ID NO:2487:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2487:

GCGCUGGUCU GUUAUUG 17

( 2 ) INFORMATION FOR SEQ ID NO:2488:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2488:

UUGGCAAUCU GAUGAGGCCG AAAGGCCGAA ACAGACCA 38

( 2 ) INFORMATION FOR SEQ ID NO:2489:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2489:

UGGUCUGUUA UUGCCAA 17

( 2 ) INFORMATION FOR SEQ ID NO:2490:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2490:

CUUGGCAACU GAUGAGGCCG AAAGGCCGAA AACAGACC 38

( 2 ) INFORMATION FOR SEQ ID NO:2491:

( i ) SEQUENCE CHARACTERISTICS:
( A ) LENGTH: 17 base pairs
( B ) TYPE: nucleic acid ( C ) STRANDEDNESS: single
( D ) TOPOLOGY: linear ( x i ) SEQUENCE DESCRIPTION: SEQ ID NO:2491:

GGUCUGUUAU UGCCAAG     17

( 2 ) INFORMATION FOR SEQ ID NO:2492:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2492:

UGCUUGGCCU GAUGAGGCCG AAAGGCCGAA AUAACAGA     38

( 2 ) INFORMATION FOR SEQ ID NO:2493:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2493:

UCUGUUAUUG CCAAGCA     17

( 2 ) INFORMATION FOR SEQ ID NO:2494:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2494:

UCCCUUUUCU GAUGAGGCCG AAAGGCCGAA AGUGCUUG     38

( 2 ) INFORMATION FOR SEQ ID NO:2495:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2495:

CAAGCACUUA AAAGGGA     17

( 2 ) INFORMATION FOR SEQ ID NO:2496:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2496:

CUCCCUUUCU GAUGAGGCCG AAAGGCCGAA AAGUGCUU     38

( 2 ) INFORMATION FOR SEQ ID NO:2497:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear (x i) SEQUENCE DESCRIPTION: SEQ ID NO:2497:

AAGCACUUAA AAGGGAG (2) INFORMATION FOR SEQ ID NO:2498:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:2498:

UGUUUCCCU GAUGAGGCCG AAAGGCCGAA AUUCUCCC 38

(2) INFORMATION FOR SEQ ID NO:2499:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:2499:

GGGAGAAUUG GAAAACA 17

(2) INFORMATION FOR SEQ ID NO:2500:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:2500:

CCUCUCCCCU GAUGAGGCCG AAAGGCCGAA ACAUUGUU 38

(2) INFORMATION FOR SEQ ID NO:2501:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:2501:

AACAAUGUCG GGAGAGG 17

(2) INFORMATION FOR SEQ ID NO:2502:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (x i) SEQUENCE DESCRIPTION: SEQ ID NO:2502:

UGGAUUCACU GAUGAGGCCG AAAGGCCGAA AUGGUUGU 38

(2) INFORMATION FOR SEQ ID NO:2503:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO:2503:

ACAACCAUUU GAAUCCA 17

( 2 ) INFORMATION FOR SEQ ID NO:2504:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2504:

CUGGAUUCCU GAUGAGGCCG AAAGGCCGAA AAUGGUUG        38

( 2 ) INFORMATION FOR SEQ ID NO:2505:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2505:

CAACCAUUUG AAUCCAG        17

( 2 ) INFORMATION FOR SEQ ID NO:2506:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2506:

AACUUCUGCU GAUGAGGCCG AAAGGCCGAA AUUCAAAU        38

( 2 ) INFORMATION FOR SEQ ID NO:2507:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2507:

AUUUGAAUCC AGAAGUU        17

( 2 ) INFORMATION FOR SEQ ID NO:2508:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2508:

GUUUCUUCU GAUGAGGCCG AAAGGCCGAA ACUUCUGG        38

( 2 ) INFORMATION FOR SEQ ID NO:2509:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2509:

CCAGAAGUUA AGAAAAC        17

(2) INFORMATION FOR SEQ ID NO:2510:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2510:

GGUUUCUCU GAUGAGGCCG AAAGGCCGAA AACUUCUG 38

(2) INFORMATION FOR SEQ ID NO:2511:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2511:

CAGAAGUUAA GAAAACC 17

(2) INFORMATION FOR SEQ ID NO:2512:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2512:

CUGUCCAUCU GAUGAGGCCG AAAGGCCGAA AGGUUUUC 38

(2) INFORMATION FOR SEQ ID NO:2513:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2513:

GAAAACCUCA UGGACAG 17

(2) INFORMATION FOR SEQ ID NO:2514:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:2514:

UGAUAAAUCU GAUGAGGCCG AAAGGCCGAA AUUCUGUC 38

(2) INFORMATION FOR SEQ ID NO:2515:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:2515:

GACAGAAUCA UUUAUCA 17

(2) INFORMATION FOR SEQ ID NO:2516:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2516:

GCCUGAUACU GAUGAGGCCG AAAGGCCGAA AUGAUUCU      38

( 2 ) INFORMATION FOR SEQ ID NO:2517:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2517:

AGAAUCAUUU AUCAGGC      17

( 2 ) INFORMATION FOR SEQ ID NO:2518:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2518:

UGCCUGAUCU GAUGAGGCCG AAAGGCCGAA AAUGAUUC      38

( 2 ) INFORMATION FOR SEQ ID NO:2519:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2519:

GAAUCAUUUA UCAGGCA      17

( 2 ) INFORMATION FOR SEQ ID NO:2520:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2520:

GUGCCUGACU GAUGAGGCCG AAAGGCCGAA AAAUGAUU      38

( 2 ) INFORMATION FOR SEQ ID NO:2521:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2521:

AAUCAUUUAU CAGGCAC      17

( 2 ) INFORMATION FOR SEQ ID NO:2522:

( i ) SEQUENCE CHARACTERISTICS:
        ( A ) LENGTH: 38 base pairs ( B ) TYPE: nucleic acid
                ( C ) STRANDEDNESS: single
                ( D ) TOPOLOGY: linear ( x i ) SEQUENCE DESCRIPTION: SEQ ID NO:2522:

GUGUGCCUCU GAUGAGGCCG AAAGGCCGAA AUAAAUGA                                                38

( 2 ) INFORMATION FOR SEQ ID NO:2523:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2523:

UCAUUUAUCA GGCACAC                                                                        17

( 2 ) INFORMATION FOR SEQ ID NO:2524:

( i ) SEQUENCE CHARACTERISTICS:
                ( A ) LENGTH: 38 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2524:

GCGUAUCUCU GAUGAGGCCG AAAGGCCGAA AGCCCGAG                                                38

( 2 ) INFORMATION FOR SEQ ID NO:2525:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2525:

CUCGGGCUUA GAUACGC                                                                        17

( 2 ) INFORMATION FOR SEQ ID NO:2526:

( i ) SEQUENCE CHARACTERISTICS:
                ( A ) LENGTH: 38 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2526:

GGCGUAUCCU GAUGAGGCCG AAAGGCCGAA AAGCCCGA                                                38

( 2 ) INFORMATION FOR SEQ ID NO:2527:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2527:

UCGGGCUUAG AUACGCC                                                                        17

( 2 ) INFORMATION FOR SEQ ID NO:2528:

( i ) SEQUENCE CHARACTERISTICS:
                ( A ) LENGTH: 38 base pairs
                ( B ) TYPE: nucleic acid
                ( C ) STRANDEDNESS: single ( D ) TOPOLOGY: linear ( x i ) SEQUENCE DESCRIPTION: SEQ ID NO:2528:

AGUAGGCGCU GAUGAGGCCG AAAGGCCGAA AUCUAAGC  38

( 2 ) INFORMATION FOR SEQ ID NO:2529:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2529:

GCUUAGAUAC GCCUACU  17

( 2 ) INFORMATION FOR SEQ ID NO:2530:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2530:

GGGUAAAGCU GAUGAGGCCG AAAGGCCGAA AGGCGUAU  38

( 2 ) INFORMATION FOR SEQ ID NO:2531:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2531:

AUACGCCUAC UUUACCC  17

( 2 ) INFORMATION FOR SEQ ID NO:2532:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2532:

GGAGGGUACU GAUGAGGCCG AAAGGCCGAA AGUAGGCG  38

( 2 ) INFORMATION FOR SEQ ID NO:2533:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2533:

CGCCUACUUU ACCCUCC  17

( 2 ) INFORMATION FOR SEQ ID NO:2534:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear (x i) SEQUENCE DESCRIPTION: SEQ ID NO:2534:

UGGAGGGUCU GAUGAGGCCG AAAGGCCGAA AAGUAGGC     38

(2) INFORMATION FOR SEQ ID NO:2535:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2535:

GCCUACUUUA CCCUCCA     17

(2) INFORMATION FOR SEQ ID NO:2536:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2536:

GUGGAGGGCU GAUGAGGCCG AAAGGCCGAA AAAGUAGG     38

(2) INFORMATION FOR SEQ ID NO:2537:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2537:

CCUACUUUAC CCUCCAC     17

(2) INFORMATION FOR SEQ ID NO:2538:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2538:

GAGGCGUGCU GAUGAGGCCG AAAGGCCGAA AGGGUAAA     38

(2) INFORMATION FOR SEQ ID NO:2539:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO:2539:

UUUACCCUCC ACGCCUC     17

(2) INFORMATION FOR SEQ ID NO:2540:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:2540:

ACCAAUGACU GAUGAGGCCG AAAGGCCGAA AGGCGUGG 38

( 2 ) INFORMATION FOR SEQ ID NO:2541:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2541:

CCACGCCUCU CAUUGGU 17

( 2 ) INFORMATION FOR SEQ ID NO:2542:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2542:

UGACCAAUCU GAUGAGGCCG AAAGGCCGAA AGAGGCGU 38

( 2 ) INFORMATION FOR SEQ ID NO:2543:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2543:

ACGCCUCUCA UUGGUCA 17

( 2 ) INFORMATION FOR SEQ ID NO:2544:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2544:

UUGUGACCCU GAUGAGGCCG AAAGGCCGAA AUGAGAGG 38

( 2 ) INFORMATION FOR SEQ ID NO:2545:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2545:

CCUCUCAUUG GUCACAA 17

( 2 ) INFORMATION FOR SEQ ID NO:2546:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2546:

CAGUUUGUCU GAUGAGGCCG AAAGGCCGAA ACCAAUGA 38

( 2 ) INFORMATION FOR SEQ ID NO:2547:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2547:

UCAUUGGUCA CAAACUG        17

( 2 ) INFORMATION FOR SEQ ID NO:2548:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2548:

GUCUCGGUCU GAUGAGGCCG AAAGGCCGAA ACACGGUG        38

( 2 ) INFORMATION FOR SEQ ID NO:2549:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2549:

CACCGUGUCA CCGAGAC        17

( 2 ) INFORMATION FOR SEQ ID NO:2550:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2550:

UUCCUUUUCU GAUGAGGCCG AAAGGCCGAA AGUUUUCA        38

( 2 ) INFORMATION FOR SEQ ID NO:2551:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2551:

UGAAAACUNA AAAGGAA        17

( 2 ) INFORMATION FOR SEQ ID NO:2552:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2552:

UAAAGAUNCU GAUGAGGCCG AAAGGCCGAA AGUUUCC    38

( 2 ) INFORMATION FOR SEQ ID NO:2553:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2553:

GGAAAACUCN AUCUUUA    17

( 2 ) INFORMATION FOR SEQ ID NO:2554:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2554:

GUUCUAAACU GAUGAGGCCG AAAGGCCGAA AUNGAGUU    38

( 2 ) INFORMATION FOR SEQ ID NO:2555:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2555:

AACUCNAUCU UUAGAAC    17

( 2 ) INFORMATION FOR SEQ ID NO:2556:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2556:

GAGUUCUACU GAUGAGGCCG AAAGGCCGAA AGAUNGAG    38

( 2 ) INFORMATION FOR SEQ ID NO:2557:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2557:

CUCNAUCUUU AGAACUC 17

( 2 ) INFORMATION FOR SEQ ID NO:2558:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2558:

GGAGUUCUCU GAUGAGGCCG AAAGGCCGAA AAGAUNGA 38

( 2 ) INFORMATION FOR SEQ ID NO:2559:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2559:

UCNAUCUUUA GAACUCC 17

( 2 ) INFORMATION FOR SEQ ID NO:2560:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2560:

UGGAGUUCCU GAUGAGGCCG AAAGGCCGAA AAAGAUNG 38

( 2 ) INFORMATION FOR SEQ ID NO:2561:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2561:

CNAUCUUUAG AACUCCA 17

( 2 ) INFORMATION FOR SEQ ID NO:2562:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2562:

GAUAGCUGCU GAUGAGGCCG AAAGGCCGAA AGUUCUAA 38

( 2 ) INFORMATION FOR SEQ ID NO:2563:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2563:
        UUAGAACUCC AGCUAUC ( 2 ) INFORMATION FOR SEQ ID NO:2564:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2564:

CCUUUUGACU GAUGAGGCCG AAAGGCCGAA AGCUGGAG     38

( 2 ) INFORMATION FOR SEQ ID NO:2565:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2565:

CUCCAGCUAU CAAAAGG     17

( 2 ) INFORMATION FOR SEQ ID NO:2566:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2566:

NACCUUUUCU GAUGAGGCCG AAAGGCCGAA AUAGCUGG     38

( 2 ) INFORMATION FOR SEQ ID NO:2567:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2567:

CCAGCUAUCA AAAGGUN     17

( 2 ) INFORMATION FOR SEQ ID NO:2568:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2568:

CGAGGAUUCU GAUGAGGCCG AAAGGCCGAA ACCUUUUG                     38

( 2 ) INFORMATION FOR SEQ ID NO:2569:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2569:

CAAAAGGUNA AUCCUCG                                           17

( 2 ) INFORMATION FOR SEQ ID NO:2570:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2570:

CUUUCGAGCU GAUGAGGCCG AAAGGCCGAA AUUNACCU                     38

( 2 ) INFORMATION FOR SEQ ID NO:2571:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2571:

AGGUNAAUCC UCGAAAG                                           17

( 2 ) INFORMATION FOR SEQ ID NO:2572:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2572:

GAGCUUUCCU GAUGAGGCCG AAAGGCCGAA AGGAUUNA                     38

( 2 ) INFORMATION FOR SEQ ID NO:2573:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2573:

UNAAUCCUCG AAAGCUC                                                          17

(2) INFORMATION FOR SEQ ID NO:2574:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2574:

UUCUGGGACU GAUGAGGCCG AAAGGCCGAA AGCUUUCG                                    38

(2) INFORMATION FOR SEQ ID NO:2575:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2575:

CGAAAGCUCU CCCAGAA                                                          17

(2) INFORMATION FOR SEQ ID NO:2576:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2576:

AGUUCUGGCU GAUGAGGCCG AAAGGCCGAA AGAGCUUU                                    38

(2) INFORMATION FOR SEQ ID NO:2577:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2577:

AAAGCUCUCC CAGAACU                                                          17

(2) INFORMATION FOR SEQ ID NO:2578:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:2578:

UGGUGUGGCU GAUGAGGCCG AAAGGCCGAA AGUUCUGG                                    38

(2) INFORMATION FOR SEQ ID NO:2579:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2579:

CCAGAACUCC CACACCA                                                          17

( 2 ) INFORMATION FOR SEQ ID NO:2580:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2580:

CAUGUUUGCU GAUGAGGCCG AAAGGCCGAA AUGGUGUG                    38

( 2 ) INFORMATION FOR SEQ ID NO:2581:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2581:

CACACCAUUC AAACAUG                    17

( 2 ) INFORMATION FOR SEQ ID NO:2582:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2582:

GCAUGUUUCU GAUGAGGCCG AAAGGCCGAA AAUGGUGU                    38

( 2 ) INFORMATION FOR SEQ ID NO:2583:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2583:

ACACCAUUCA AACAUGC                    17

( 2 ) INFORMATION FOR SEQ ID NO:2584:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:2584:

AAUUUCUUCU GAUGAGGCCG AAAGGCCGAA AGCUGCCA                    38

( 2 ) INFORMATION FOR SEQ ID NO:2585:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2585:

UGGCAGCUCA AGAAAUU                    17

( 2 ) INFORMATION FOR SEQ ID NO:2586:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2586:

CCGUAUUUCU GAUGAGGCCG AAAGGCCGAA AUUUCUUG 38

( 2 ) INFORMATION FOR SEQ ID NO:2587:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2587:

CAAGAAAUUA AAUACGG 17

( 2 ) INFORMATION FOR SEQ ID NO:2588:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2588:

ACCGUAUUCU GAUGAGGCCG AAAGGCCGAA AAUUUCUU 38

( 2 ) INFORMATION FOR SEQ ID NO:2589:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2589:

AAGAAAUUAA AUACGGU 17

( 2 ) INFORMATION FOR SEQ ID NO:2590:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2590:

GGGGACCGCU GAUGAGGCCG AAAGGCCGAA AUUUAAUU 38

( 2 ) INFORMATION FOR SEQ ID NO:2591:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2591:

AAUUAAAUAC GGUCCCC 17

( 2 ) INFORMATION FOR SEQ ID NO:2592:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2592:

CUUCAGGGCU GAUGAGGCCG AAAGGCCGAA ACCGUAUU    38

( 2 ) INFORMATION FOR SEQ ID NO:2593:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2593:

AAUACGGUCC CCUGAAG    17

( 2 ) INFORMATION FOR SEQ ID NO:2594:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for any base.

( x i ) SEQUENCE DESCRIPTION: SEQ ID NO:2594:

GUCUNAGGCU GAUGAGGCCG AAAGGCCGAA AGCAUCUU    38

( 2 ) INFORMATION FOR SEQ ID NO:2595:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for any base.

( x i ) SEQUENCE DESCRIPTION: SEQ ID NO:2595:

AAGAUGCUAC CUNAGAC    17

( 2 ) INFORMATION FOR SEQ ID NO:2596:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for any base.

( x i ) SEQUENCE DESCRIPTION: SEQ ID NO:2596:

GGGGGUCUCU GAUGAGGCCG AAAGGCCGAA AGGUAGCA    38

( 2 ) INFORMATION FOR SEQ ID NO:2597:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear 5,646,042

( i x ) FEATURE:
    ( D ) OTHER INFORMATION: The letter "N" stands for any base.

( x i ) SEQUENCE DESCRIPTION: SEQ ID NO:2597:

UGCUACCUNA GACCCCC     17

( 2 ) INFORMATION FOR SEQ ID NO:2598:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2598:

CUACAUNACU GAUGAGGCCG AAAGGCCGAA AGGGGGUC     38

( 2 ) INFORMATION FOR SEQ ID NO:2599:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2599:

GACCCCUNU NAUGUAG     17

( 2 ) INFORMATION FOR SEQ ID NO:2600:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2600:

NACUACAUCU GAUGAGGCCG AAAGGCCGAA ANAGGGGG     38

( 2 ) INFORMATION FOR SEQ ID NO:2601:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2601:

CCCCCUNUNA UGUAGUN     17

( 2 ) INFORMATION FOR SEQ ID NO:2602:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
    ( D ) OTHER INFORMATION: The letter "N" stands for any base.

( x i ) SEQUENCE DESCRIPTION: SEQ ID NO:2602:

UNUNNNACCU GAUGAGGCCG AAAGGCCGAA ACAUNANA    38

( 2 ) INFORMATION FOR SEQ ID NO:2603:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2603:

UNUNAUGUAG UNNNANA    17

( 2 ) INFORMATION FOR SEQ ID NO:2604:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2604:

AGGUNUNNCU GAUGAGGCCG AAAGGCCGAA ACUACAUN    38

( 2 ) INFORMATION FOR SEQ ID NO:2605:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2605:

NAUGUAGUNN NANACCU    17

( 2 ) INFORMATION FOR SEQ ID NO:2606:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO:2606:

ACAUCNUGCU GAUGAGGCCG AAAGGCCGAA AGGUNUNN    38

( 2 ) INFORMATION FOR SEQ ID NO:2607:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear

```
     ( i x ) FEATURE:
              ( D ) OTHER INFORMATION: The letter "N" stands for any base.

( x i ) SEQUENCE DESCRIPTION: SEQ ID NO:2607:

NNANACCUNC ANGAUGU                                                                              17

( 2 ) INFORMATION FOR SEQ ID NO:2608:

( i ) SEQUENCE CHARACTERISTICS:
              ( A ) LENGTH: 54 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:2608:

GCGCUUCGAG AAGUAUUUAC CAGAGAAACA CACGUUGUGG UACAUUACCU GGUA                                      54

( 2 ) INFORMATION FOR SEQ ID NO:2609:

( i ) SEQUENCE CHARACTERISTICS:
              ( A ) LENGTH: 18 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:2609:

AAAUACGGUC CGAAGCGC                                                                             18

( 2 ) INFORMATION FOR SEQ ID NO:2610:

( i ) SEQUENCE CHARACTERISTICS:
              ( A ) LENGTH: 54 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:2610:

UUCUGCCCAG AAGUUCCAC CAGAGAAACA CACGUUGUGG UACAUUACCU GGUA                                       54

( 2 ) INFORMATION FOR SEQ ID NO:2611:

( i ) SEQUENCE CHARACTERISTICS:
              ( A ) LENGTH: 18 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:2611:

GGAAACAGAU GGGCAGAA                                                                             18

( 2 ) INFORMATION FOR SEQ ID NO:2612:

( i ) SEQUENCE CHARACTERISTICS:
              ( A ) LENGTH: 54 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:2612:

UUUUCACAAG AAGGUCUCAC CAGAGAAACA CACGUUGUGG UACAUUACCU GGUA                                      54

( 2 ) INFORMATION FOR SEQ ID NO:2613:

( i ) SEQUENCE CHARACTERISTICS:
              ( A ) LENGTH: 18 base pairs
              ( B ) TYPE: nucleic acid
              ( C ) STRANDEDNESS: single
              ( D ) TOPOLOGY: linear
```

(x i) SEQUENCE DESCRIPTION: SEQ ID NO:2613:

GAGACCAGAC UGUGAAAA                                                                 18

(2) INFORMATION FOR SEQ ID NO:2614:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (x i) SEQUENCE DESCRIPTION: SEQ ID NO:2614:

AUUCUUGAG AAGCCAGGAC CAGAGAAACA CACGUUGUGG UACAUUACCU GGUA           54

(2) INFORMATION FOR SEQ ID NO:2615:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2615:

CCUGGCAGCU CAAGAAAU                                                                 18

(2) INFORMATION FOR SEQ ID NO:2616:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (x i) SEQUENCE DESCRIPTION: SEQ ID NO:2616:

CUUCAGGGAG AAGUAUUUAC CAGAGAAACA CACGUUGUGG UACAUUACCU GGUA          54

(2) INFORMATION FOR SEQ ID NO:2617:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2617:

AAAUACGGUC CCCUGAAG                                                                 18

(2) INFORMATION FOR SEQ ID NO:2618:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i x) FEATURE:
        (D) OTHER INFORMATION: The letter "N" stands for any
            base. The letter "H" stands for
            A, U, or C.

(x i) SEQUENCE DESCRIPTION: SEQ ID NO:2618:

NNNNUHNNNN N                                                                        11

(2) INFORMATION FOR SEQ ID NO:2619:

(i) SEQUENCE CHARACTERISTICS:
        (A) LENGTH: 28 base pairs (B) TYPE: nucleic acid
(C) STRANDEDNESS: single
(D) TOPOLOGY: linear (ix) FEATURE:
(D) OTHER INFORMATION: The letter "N"stands for any base.

(xi) SEQUENCE DESCRIPTION: SEQ ID NO:2619:

NNNNNCUGAN GAGNNNNNNC GAAANNNN                                          28

(2) INFORMATION FOR SEQ ID NO:2620:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(D) OTHER INFORMATION: The letter "N"stands for any
base. The letter "Y"stands for
U or C. The letter "H"stands
for A, U, or C.

(xi) SEQUENCE DESCRIPTION: SEQ ID NO:2620:

NNNNNNN YNG HYNNN                                                        15

(2) INFORMATION FOR SEQ ID NO:2621:

(i) SEQUENCE CHARACTERISTICS:
(A) LENGTH: 47 base pairs
(B) TYPE: nucleic acid
(C) STRANDEDNESS: single
(D) TOPOLOGY: linear (ix) FEATURE:
(D) OTHER INFORMATION: The letter "N"stands for any
base. The letter "H"stands for
A, U, or C.

(xi) SEQUENCE DESCRIPTION: SEQ ID NO:2621:

NNNNGAAGNN NNNNNNNNA AAHANNNNNN NACAUUACNN NNNNNNN                       47

(2) INFORMATION FOR SEQ ID NO:2622:

(i) SEQUENCE CHARACTERISTICS:
(A) LENGTH: 85 base pairs
(B) TYPE: nucleic acid
(C) STRANDEDNESS: single
(D) TOPOLOGY: linear (xi) SEQUENCE DESCRIPTION: SEQ ID NO:2622:

UGGCCGGCAU GGUCCCAGCC UCCUCGCUGG CGCCGGCUGG GCAACAUUCC GAGGGGACCG        60

UCCCCUCGGU AAUGGCGAAU GGGAC                                              85

(2) INFORMATION FOR SEQ ID NO:2623:

(i) SEQUENCE CHARACTERISTICS:
(A) LENGTH: 176 base pairs
(B) TYPE: nucleic acid
(C) STRANDEDNESS: single
(D) TOPOLOGY: linear (xi) SEQUENCE DESCRIPTION: SEQ ID NO:2623:

GGGAAAGCUU GCGAAGGGCG UCGUCGCCCC GAGCGGUAGU AAGCAGGGAA CUCACCUCCA        60

AUUUCAGUAC UGAAAUUGUC GUAGCAGUUG ACUACUGUUA UGUGAUGGU AGAGGCUAAG        120

UGACGGUAUU GGCGUAAGUC AGUAUUGCAG CACAGCACAA GCCCGCUUGC GAGAAU          176

( 2 ) INFORMATION FOR SEQ ID NO:2624:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2624:

GGAGAAUUGG AAAAC         15

( 2 ) INFORMATION FOR SEQ ID NO:2625:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2625:

GUUUUCCCUG AUGAGGCCGA AAGGCCGAAA AUCUCC         36

( 2 ) INFORMATION FOR SEQ ID NO:2626:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2626:

GGAGAAUUGG AAAAC         15

( 2 ) INFORMATION FOR SEQ ID NO:2627:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "H"stands for A, U or C.

( x i ) SEQUENCE DESCRIPTION: SEQ ID NO:2627:

GUUUUCCCUG AUGAGGCCGA AAGGCCGAAA UUCUCCH         37

C-MYB TARGETED RIBOZYMES

This application is a continuation-in-part of Draper, "Method and Reagent for Treatment of a Stenotic Condition", filed Dec. 7, 1992, U.S. Ser. No. 07/987,132, now abandoned; Thompson et al., "Method and Reagent for Treatment of diseases caused by expression of the c-myc gene," U.S. Ser. No. 08/192,943, filed Feb. 7, 1994, pending, which is a continuation of U.S. Ser. No. 07/936,422, filed Aug. 26, 1992, now abandoned, and Stinchcomb et al., "Methods and compositions for the treatment of restenosis and cancer using ribozymes," U.S. Ser. No. 08/245,466, filed May 18, 1994, now abandoned.

BACKGROUND OF THE INVENTION

The present invention concerns therapeutic compositions and methods for the treatment of restenosis and cancer.

The following is a brief description of the physiology, cellular pathology and treatment of restenosis. The discussion is not meant to be complete and is provided only for understanding of the invention that follows. This summary is not an admission that any of the work described below is prior art to the claimed invention.

Coronary angioplasty is one of the major surgical treatments for heart disease. Its use has been accelerating rapidly; over 450,000 procedures are performed in the U.S. annually. The short term success rate of angioplasty is 80 to 90%. However, in spite of a number of technical improvements in the procedure, post-operative occlusions of the arteries, or restenosis, still occur. Thirty-five to forty-five percent of patients who have undergone a single vessel angioplasty develop clinically significant restenosis within 6 months of the procedure. The rate of restenosis is even higher (50 to 60%) in patients who have undergone multivessel angioplasty (Califf, R. M., et al., 1990, in *Textbook of Interventional Cardiology.*, E. J. Topol, ed., W. B. Saunders, Philadelphia, pp 363–394.).

Histopathological studies have shown that restenosis after angioplasty is characterized by migration of medial smooth muscle cells to the intima and a striking hyper-proliferative response of these neointimal cells (Garratt, K. N., et al., 1991, *J. Am. Coll. Cardio.*, 17, 442–428; Austin, G. E., et al., 1985, *J. Am. Coll. Cardiol.*, 6, 369–375). Smooth muscle cell proliferation could be an overly robust response to injury. Alternatively, the intimal smooth muscle cells within atherosclerotic lesions are already in an activated or "synthetic" state (Sjolund, M., et al., 1988, *J. Cell. Biol.*, 106, 403–413 and thus may be poised to proliferate. One recent study demonstrated a positive correlation between the presence of activated smooth muscle cells in coronary lesions and the extent of subsequent luminal narrowing after atherectomy (Simons, M., et al., 1993, *New Engl. J. Med.*, 328, 608–613). In any case, slowing smooth muscle cell proliferation after angioplasty could prevent intimal thickening and restenosis.

The presently preferred therapeutic treatment for restenosis is the use of streptokinase, urokinase or other thrombolytic compounds, such as fish oil, anticoagulants, ACE (angiotensin converting enzyme) inhibitors, aspirin and cholesterol lowering compounds. Alternative treatment includes the surgical incorporation of endoluminal stents. The occurrence of pharmacologic side-effects (particularly bleeding disorders associated with anti-coagulants and platelet inhibitors) is an issue with current therapies. Popoma, J. J., et al., report that the current therapies have not significantly impacted the rates of restenosis occurrence. (*Circulation*, 84, 1426–1436, 1991).

Recently, the results of a clinical trial of the efficacy of an anti-platelet therapy have been reported. Patients undergoing coronary angioplasty were given a single bolus injection followed by a 12 hour infusion of an antibody directed against the platelet adhesion molecule, gpIIb/gpIIIa. After six months, patients with the treatment showed a 23% reduction in the occurrence of restenosis than patients receiving placebo (27 vs. 35%; p=0.001).

A number of growth factors have been shown to induce smooth muscle cell proliferation. In vitro, platelet-derived growth factor (PDGF) is a potent smooth muscle cell mitogen (Ross, R., et al., 1974, *Proc. Natl. Acad. Sci. USA*, 71, 1207–1210) and a smooth muscle cell chemoattractant (Grotendorst, G., et al., 1982, *Proc. Natl. Acad. Sci. USA*, 71, 3669–3672.). In vivo, when PDGF is expressed ectopically in porcine arteries, it induces intimal hyperplasia (Nabel, E. B., et al., 1993, *J. Clin. Invest.*, 91, 1822–1829). Furthermore, antibodies to PDGF have been shown to reduce intimal thickening after arterial injury (Ferns, G. A. A., et al., 1991, *Science*, 253, 1129–1132). Analysis of $^3$H-thymidine incorporation in the lesions indicates that the anti-PDGF antibodies primarily inhibit smooth muscle cell migration.

Basic fibroblast growth factor (bFGF) is another smooth muscle cell mitogen in vitro (Klagsbrun, M. and Edelman, E. R., 1989, *Arteriosclerosis*, 9, 269–278). In a rat model, anti-bFGF antibodies inhibit the proliferation of medial smooth muscle cells 24 to 48 hours after balloon catheter injury (Lidner, V. and Reidy, M. A., 1991, *Proc. Natl. Acad. Sci. USA*, 88, 3739–3743). In addition to bFGF, heparin binding epidermal growth factor (HB-EGF) (Higashiyama, S., et al., 1991, *Science*, 251, 936–939.), insulin-like growth factor I (IGF-I) (Banskota, N. K., et al., 1989, *Molec. Endocrinol.*, 3, 1183–1190) and endothelin (Komuro, I., et al., 1988, *FEBS Letters*, 238, 249–252) have been shown to induce smooth muscle cell proliferation. A number of other factors (such as interleukin-1 and tumor necrosis factor-$\alpha$) may indirectly affect smooth muscle cell proliferation by inducing the expression of PDGF (Hajjar, K. A., et al., 1987, *J. Exp. Med.*, 166, 235–245; Raines, E. W., et al., 1989, *Science*, 243, 393–396).

When whole serum is added to serum-starved smooth muscle cells in vitro, the oncogenes, c-myc, c-fos, and c-myb, are induced (Kindy, M. S. and Sonenshein, G. E., 1986, *J. Biol. Chem.*, 261, 12865–12868; Brown, K. E., et al., 1992, *J. Biol. Chem.*, 267, 4625–4630) and cell proliferation ensues. Blocking c-myb with an antisense oligonucleotide prevents cells from entering S phase (Brown, K. E., et al., 1992, *J. Biol. Chem.*, 267, 4625–4630.). Thus, c-myb is required for the $G_1$ to S transition after stimulation by the multitude of growth factors present in serum. In vivo, a c-myb antisense oligonucleotide inhibits restenosis when applied to rat arteries after balloon angioplasty (Simons, M., et al., 1992, *Nature*, 359, 67–70). Similarly, an antisense oligonucleotide directed against mRNA of the oncogene c-myc was shown to inhibit human smooth muscle cell proliferation (Shi, Y., et al., 1993, *Circulation*, 88, 1190–5) and migration (Biro, S., et al., 1993, *Proc. Natl. Acad. Sci. U S A*, 90, 654–8).

Ohno et al., 1994 *Science* 265, 781, have shown that a combination of viral thymidine kinase enzyme expression (gene therapy) and treatment with anti-viral drug ganciclovir inhibits smooth muscle cell proliferation in pigs, following baloon angioplasty.

Epstein et al., "Inhibition of non-transformed cell proliferation using antisense oligonucleotides," NTIS publication 1992 discusses use of antisense oligonucleotides to c-myc, PCNA or cyclin B. Fung et al., PCT WO91/15580, describes gene therapy for cell proliferative disease and mentions administration of a ribozyme construct against a PGR element. Mention is made of inactivation of c-myb. Rosenberg et al., WO93/08845, Calabretta et al., WO92/20348 and Gewirtz WO93/09789 concern c-myb antisense oligonucleotides for treatment of melanoma or colorectal cancer, and administration locally. Sytkowski, PCT WO 93/02654, describe the uses of antisense oligonucleotides to inhibit c-myb gene expression in red blood cells to stimulate hemoglobin synthesis.

Nabel and Nabel, U.S. Pat. No. 5,328,470, describe a method for the treatment of diseases by delivering therapeutic reagents directly to the sites of disease. They state that—

" . . . Method is based on the delivery of proteins by catheterization to discrete blood vessel segments using genetically modified or normal cells or other vector systems . . . In addition,, catalytic RNAs, called ribozymes, can specifically degrade RNA sequences. . . . The requirements for a successful RNA cleavage include a hammerhead structure with conserved RNA sequence at the region flanking this structure . . . any GUG sequence within the RNA transcript can serve as a target for degradation by the ribozyme . . . gene transfer using vectors expressing such proteins as tPA for the treatment of thrombosis and restenosis, anglogenesis or growth factors for the purpose of revascularization . . . "

SUMMARY OF THE INVENTION

This invention relates to ribozymes, or enzymatic RNA molecules, directed to cleave mRNA species that are required for cellular growth responses. In particular, applicant describes the selection and function of ribozymes capable of cleaving RNA encoded by the oncogene, c-myb. Such ribozymes may be used to inhibit the hyperproliferation of smooth muscle cells in restenosis and of tumor cells in numerous cancers. To block restenosis, a target molecule required for the induction of smooth muscle cell proliferation by a number of different growth factors is preferred. To this end c-myc, c-fos, and c-myb are useful targets in this invention.

Other transcription factors involved in the response to growth and proliferation signals include NF-κB, oct-1 and SRF. NF-κB protein activates cellular transcription and induces increases in cellular synthetic pathways. In a resting cell, this protein is found in the cytoplasm, complexed with its inhibitor, I-κB. Upon phosphorylation of the I-κB molecule, the complex dissociates and NF-κB is released for transport to the nucleus, where it binds DNA and induces transcriptional activity in (NF-κB)-responsive genes. One of the (NF-κB)-responsive genes is the NF-κB gene itself. Thus, release of the NF-κB protein from the inhibitory complex results in a cascade of gene expression which is auto-induced. Early inhibition of NF-κB can reduce expression of a number of genes required for growth and proliferation, such as c-myb.

Two other transcription factors, oct-1 and serum response factor (SRF) have been shown to be expressed selectively in dividing cells. Both oct-1 and SRF are expressed ubiquitously in cultured cells, including smooth muscle cells. However, R. Majack and his colleagues have recently shown that these transcription factors are not expressed by the smooth muscle cells in intact vessels. Both oct-1 and SRF are rapidly expressed upon dispersal of tissue into single cell suspensions. Thus, these transcription factors are thought to be regulated by their interactions with the extracellular matrix (Weiser, M. C. M., et al., 1994. *J. Cell. Biochem.*, S18A, 282; Belknap, J. K., et al., 1994. *J. Cell. Biochem.*, S18A, 277). Upon injury during angioplasty, the expression of oct-1 and SRF may be enhanced, leading to increased smooth muscle cell proliferation. Treatment with ribozymes that block the expression of these transcription factors can alleviate the smooth muscle cell proliferation associated with restenosis.

While some of the above mentioned studies demonstrated that antisense oligonucleotides can efficiently reduce the expression of factors required for smooth muscle cell proliferation, enzymatic RNAs, or ribozymes have yet to be demonstrated to inhibit smooth muscle cell proliferation. Such ribozymes, with their catalytic activity and increased site specificity (as described below), represent more potent and safe therapeutic molecules than antisense oligonucleotides. In the present invention, ribozymes that cleave c-myb mRNA are described. Moreover, applicant shows that these ribozymes are able to inhibit smooth muscle cell proliferation and that the catalytic activity of the ribozymes is required for their inhibitory effect. From those of ordinary skill in the art, it is clear from the examples described, that other ribozymes that cleave target mRNAs required for smooth muscle cell proliferation may be readily designed and are within the invention.

By "inhibit" is meant that the activity of c-myb or level of mRNAs encoded by c-myb is reduced below that observed in the absence of the nucleic acid, particularly, inhibition with ribozymes and preferably is below that level observed in the presence of an inactive RNA molecule able to bind to the same site on the mRNA, but unable to cleave that RNA.

By "enzymatic nucleic acid molecule" it is meant a nucleic acid molecule which has complementarity in a substrate binding region to a specified gene target, and also has an enzymatic activity which is active to specifically cleave RNA in that target. That is, the enzymatic nucleic acid molecule is able to intermolecularly cleave RNA and thereby inactivate a target RNA molecule. This complementarity functions to allow sufficient hybridization of the enzymatic nucleic acid molecule to the target RNA to allow the cleavage to occur. One hundred percent complementarity is preferred, but complementarity as low as 50–75% may also be useful in this invention. By "equivalent" RNA to c-myb is meant to include those naturally occurring RNA molecules associated with restenosis and cancer in various animals, including human, rat and pig. Such a molecule will generally contain some ribonucleotides, but the other nucleotides may be substituted at the 2'-hydroxyl position and in other locations with other moeities as discussed below.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. USA*, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target mRNAs encoding c-myb proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res.*, 20, 4581–9; Sarver et al., 1990 *Science* 247, 1222–1225). Those skilled in the art realize that any ribozyme can be expressed in eukaryotic cells from the appropriate DNA/RNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25656).

Thus, in a first aspect, the invention features ribozymes that inhibit cell proliferation. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target mRNAs, preventing translation and protein accumulation. In the absence of the expression of the target gene, cell proliferation is inhibited.

In a preferred embodiment, the enzymatic RNA molecules cleave c-myb mRNA and inhibit smooth muscle cell proliferation. Such ribozymes are useful for the prevention of restenosis after coronary angioplasty. Ribozymes are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. The ribozymes, similarly delivered, also are useful for inhibiting proliferation of certain cancers associated with elevated levels of the c-myb oncogene, particularly leukemias, neuroblastomas, and lung, colon, and breast carcinomas. Using the methods described herein, other enzymatic RNA molecules that cleave c-myb, c-myc, oct-1, SRF, NF-κB, PDGF receptor, bFGF receptor, angiotensin II, and endothelium-derived relaxing factor and thereby inhibit smooth muscle cell proliferation and/or tumor cell proliferation may be derived and used as described above. Specific examples are provided below in the Tables.

Such ribozymes are useful for the prevention of the diseases and conditions discussed above, and any other diseases or conditions that are related to the level of c-myb activity in a cell or tissue. By "related" is meant that the inhibition of c-myb mRNAs and thus reduction in the level of protein activity will relieve to some extent the symptoms of the disease or condition.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers.

In another aspect of the invention, ribozymes that cleave target molecules and inhibit c-myb activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

In preferred embodiments, the ribozymes have binding arms which are complementary to the sequences in the tables, shown as Seq. I.D. Nos. 1–100. Examples of such ribozymes are shown as Seq. I.D. Nos. 101–129. Those in the art will recognize that while such examples are designed to mouse RNA, similar ribozymes can be made complementary to human RNA. By complementary is thus meant that the binding arms are able to cause cleavage of a human or mouse mRNA target. Examples of such ribozymes consist essentially of sequences defined as Seq. I.D. Nos. 101–129 below. By "consists essentially of" is meant that the active ribozyme contains an enzymatic center equivalent to those in the examples, and binding arms able to bind human mRNA such that cleavage at the target site occurs. Other sequences may be present which do not interfere with such cleavage.

In another aspect of the invention, ribozymes that cleave target molecules and inhibit cell proliferation are expressed from transcription units inserted into DNA, RNA, or vital vectors. Preferably, the recombinant vectors capable of expressing the ribozymes are locally delivered as described above, and transiently persist in smooth muscle cells. Once expressed, the ribozymes cleave their target mRNAs and prevent proliferation of their host cells. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.
Drawings:

FIG. 1 is a diagrammatic representation of the hammerhead ribozyme domain known in the art. Stem II can be $\geq 2$ base-pair long.

FIG. 2a is a diagrammatic representation of the hammerhead ribozyme domain known in the art; FIG. 2b is a diagrammatic representation of the hammerhead ribozyme as divided by Uhlenbeck (1987, Nature, 327, 596–600) into a substrate and enzyme portion; FIG. 2c is a similar diagram showing the hammerhead divided by Haseloff and Gerlach (1988, Nature, 334, 585–591) into two portions; and FIG. 2d is a similar diagram showing the hammerhead divided by Jeffries and Symons (1989, Nucl. Acids. Res., 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H refers to bases A, U, or C. Y refers to pyrimidine bases. "—" refers to a covalent bond.

Figure 6B:
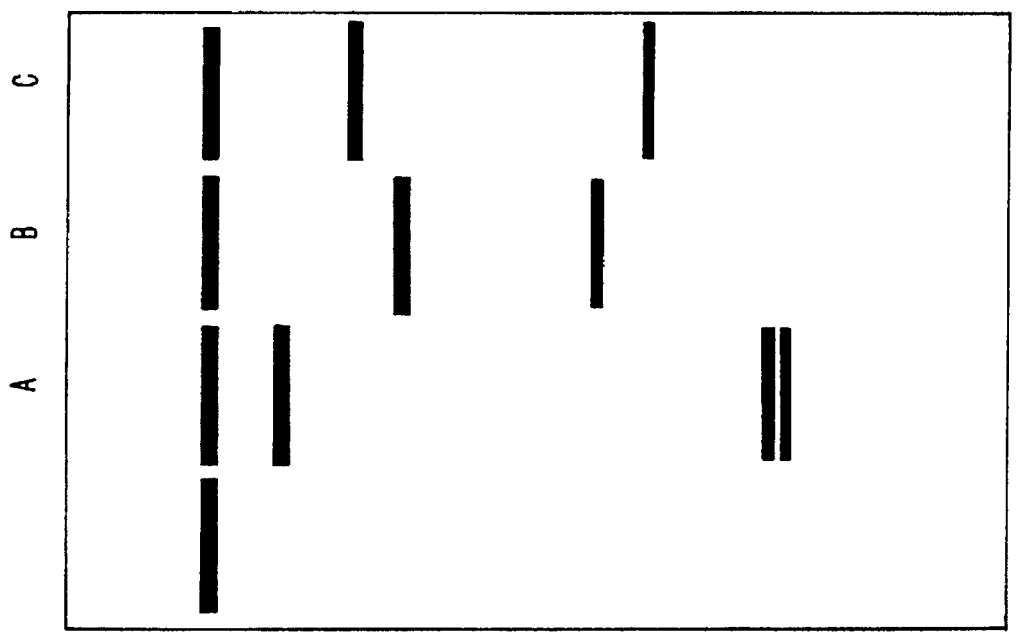
Figure 6A:
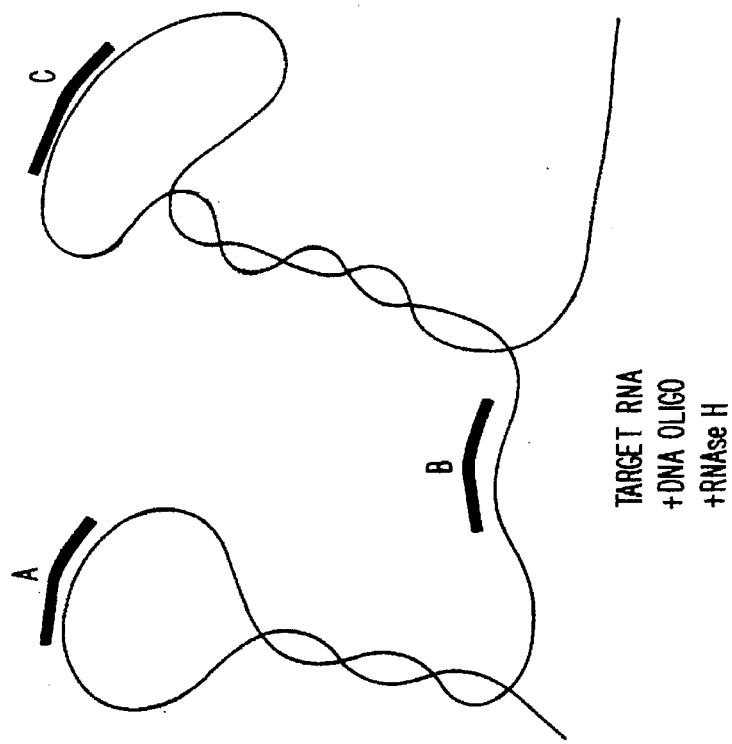

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figure 7:
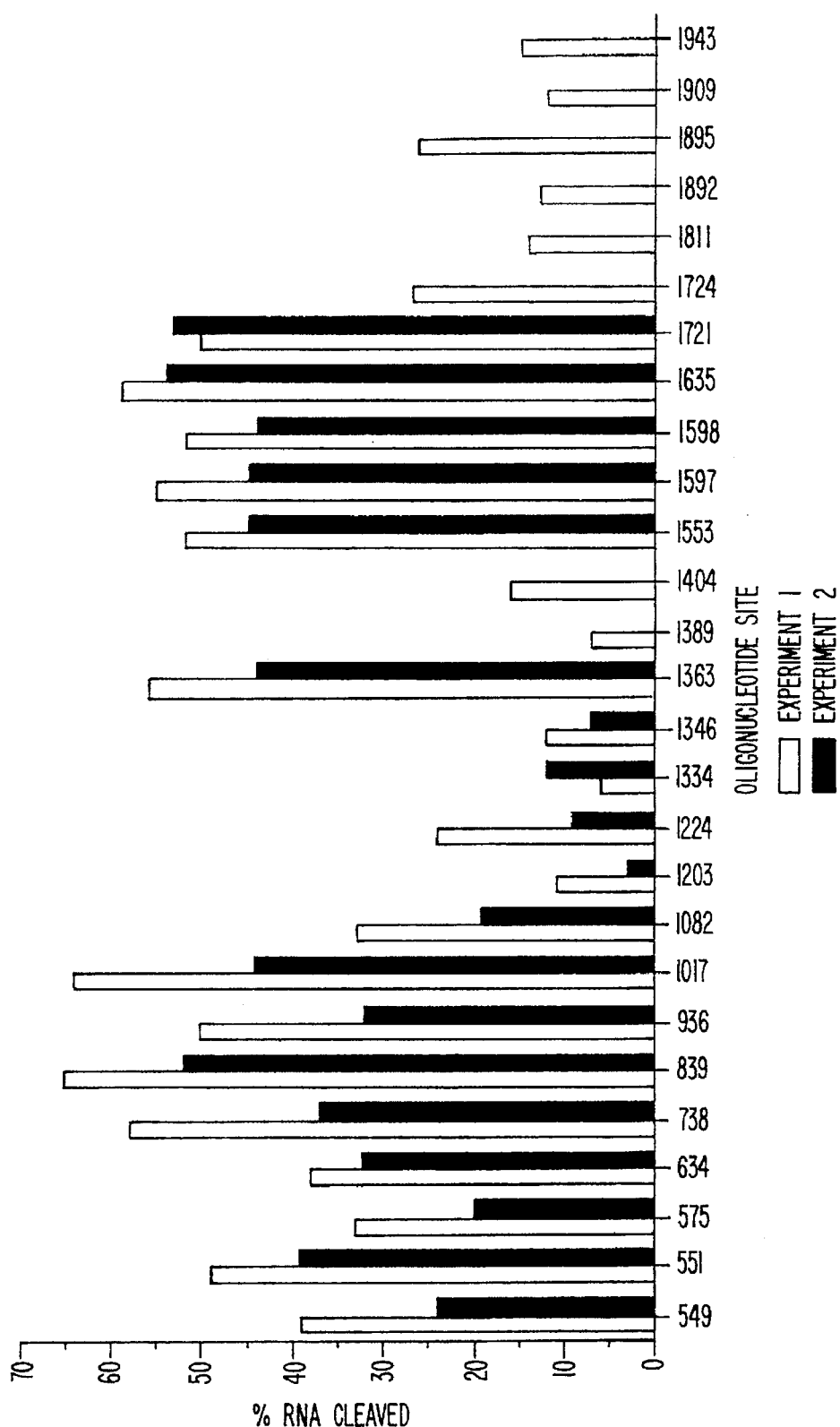

FIG. 7 is a graph of the results of an RNAseH accessibility assay of murine c-myb RNA. On the abscissa is the sequence number of the DNA oligonucleotide that is homologous to the ribozyme target site. The ordinate represents the percentage of the intact transcript that was cleaved by RNAse H.

Figure 8:
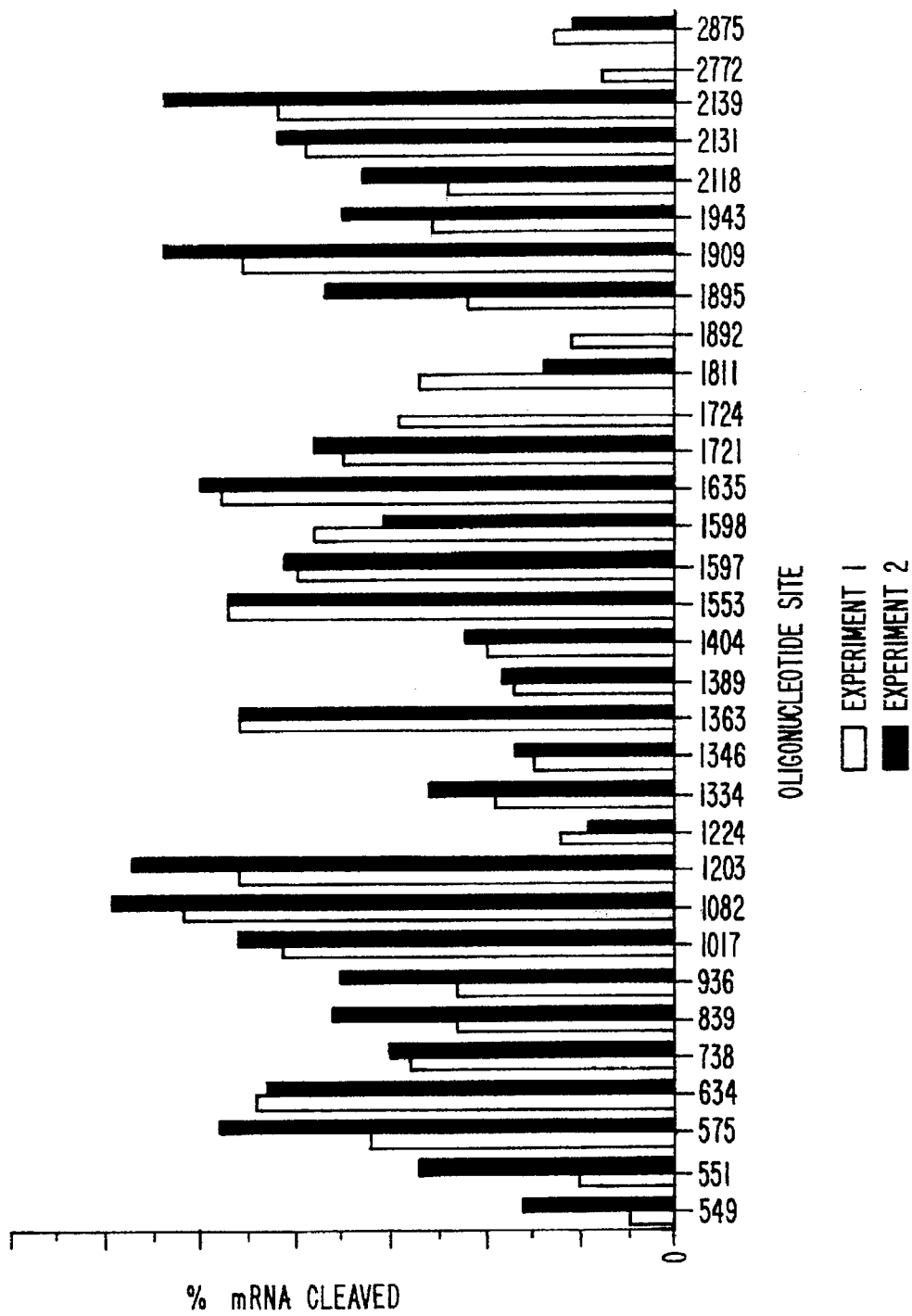
Figures 1, 9A:
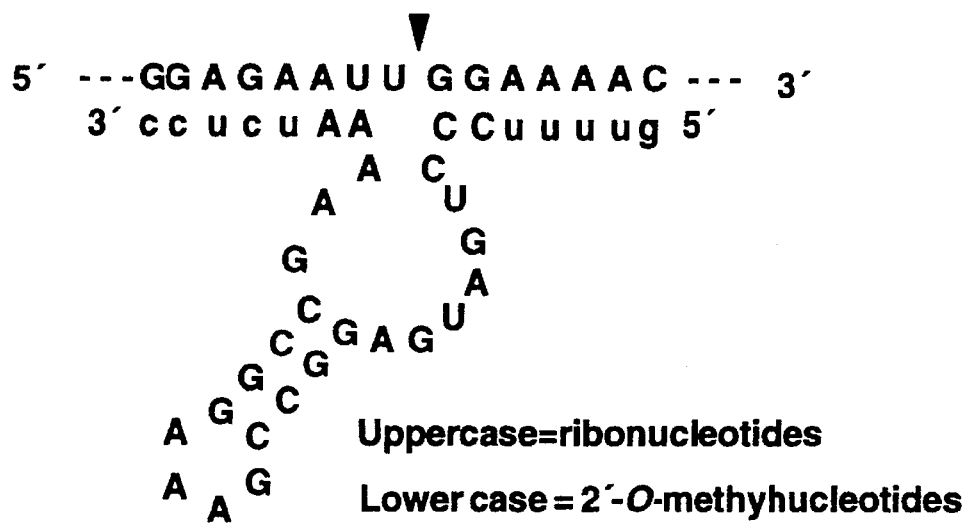
Figures 2, 9A:
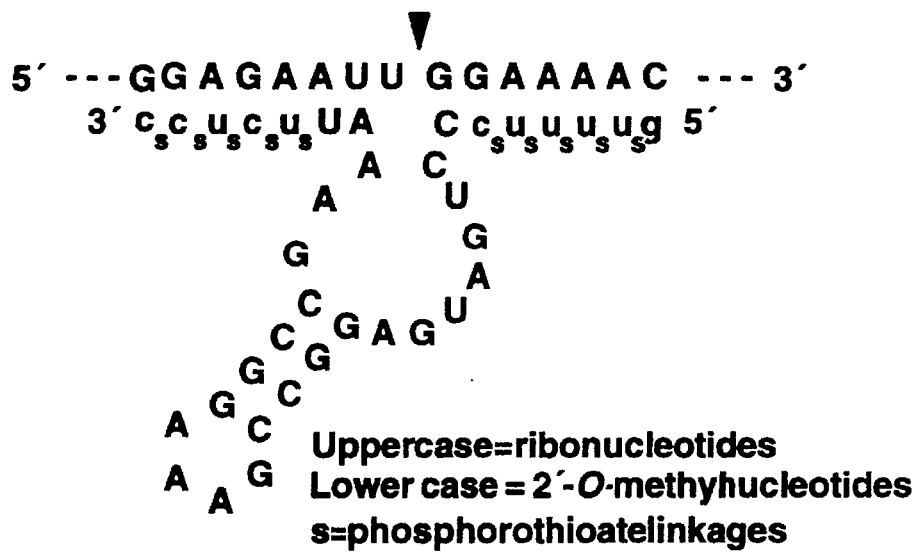
Figures 3, 9A:
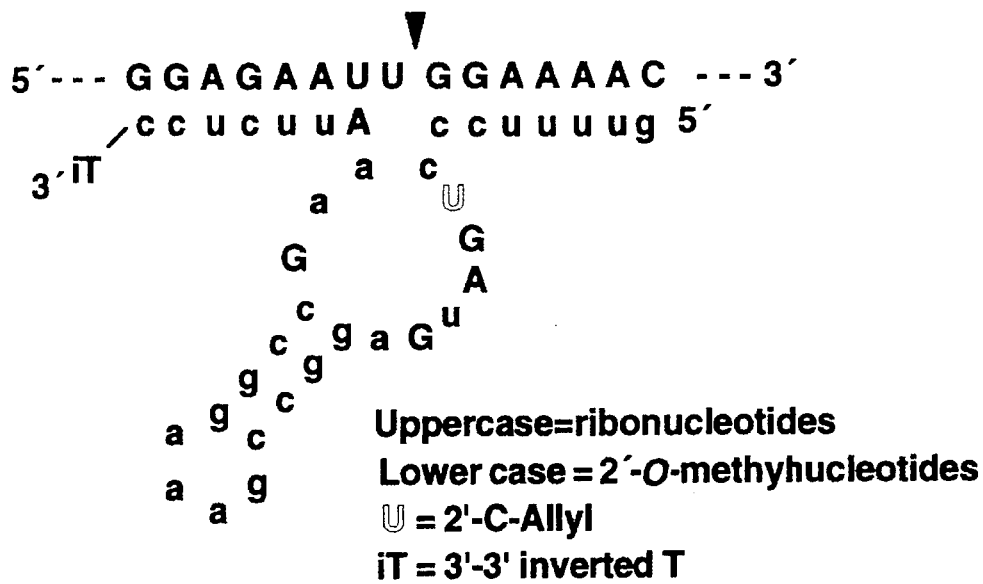
Figures 4, 9A:
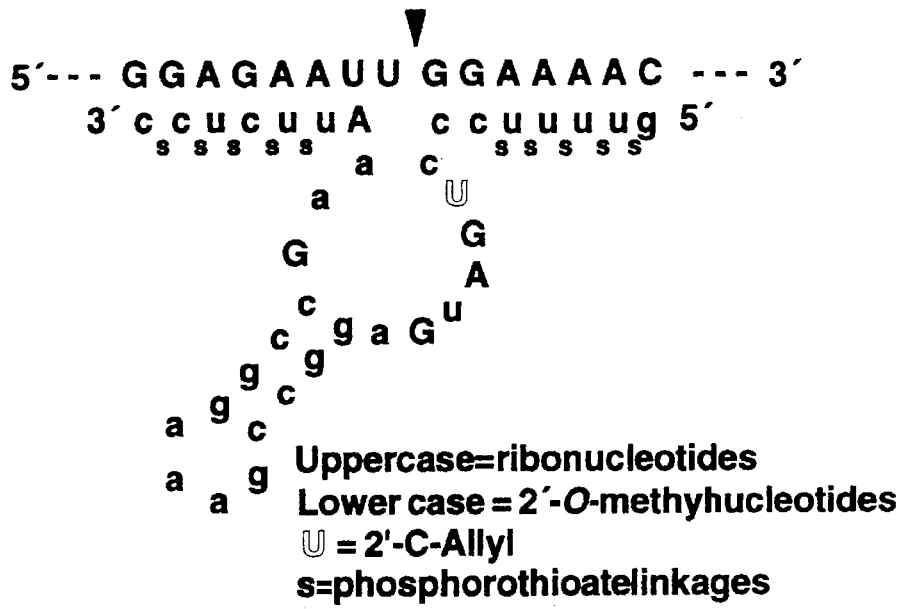

FIG. 8 is a graph of the outcome of an RNAseH accessibility assay of human c-myb mRNA. The graphs are labeled as in FIG. 7.

FIG. 9 shows the effect of chemical modifications on the catalytic activity of hammerhead ribozyme targeted to c-myb site 575. A) diagrammatic representation of 575 hammerhead ribozyme•substrate complex. 2'-O-methyl ribozyme represents a hammerhead (HH) ribozyme containing 2'-O-methyl substitutions at five nucleotides in the 5' and 3' termini. 2'-O-methyl P=S ribozyme represents a hammerhead (HH) ribozyme containing 2'-O-methyl and phosphorothioate substitutions at five nucleotides in the 5' and 3' termini. 2'-C-allyl iT ribozyme represents a hammerhead containing ribose residues at five positions. The remaining 31 nucleotide positions contain 2'-hydroxyl group substitutions, wherein 30 nucleotides contain 2'-O-methyl substitutions and one nucleotide ($U_4$) contains 2'-C-allyl substitution. Additionally, 3' end of this ribozyme contains a 3'-3' linked inverted T. 2'-C-allyl P=S ribozyme is similar to 2'-C-allyl iT ribozyme with the following changes: five nucleotides at the 5' and 3' termini contain phosphorothioate substitutions and the ribozyme lacks the 3'-end inverted T modification. B) shows the ability of ribozymes described in FIG. 9A to inhibit smooth muscle cell proliferation.

Figure 10:
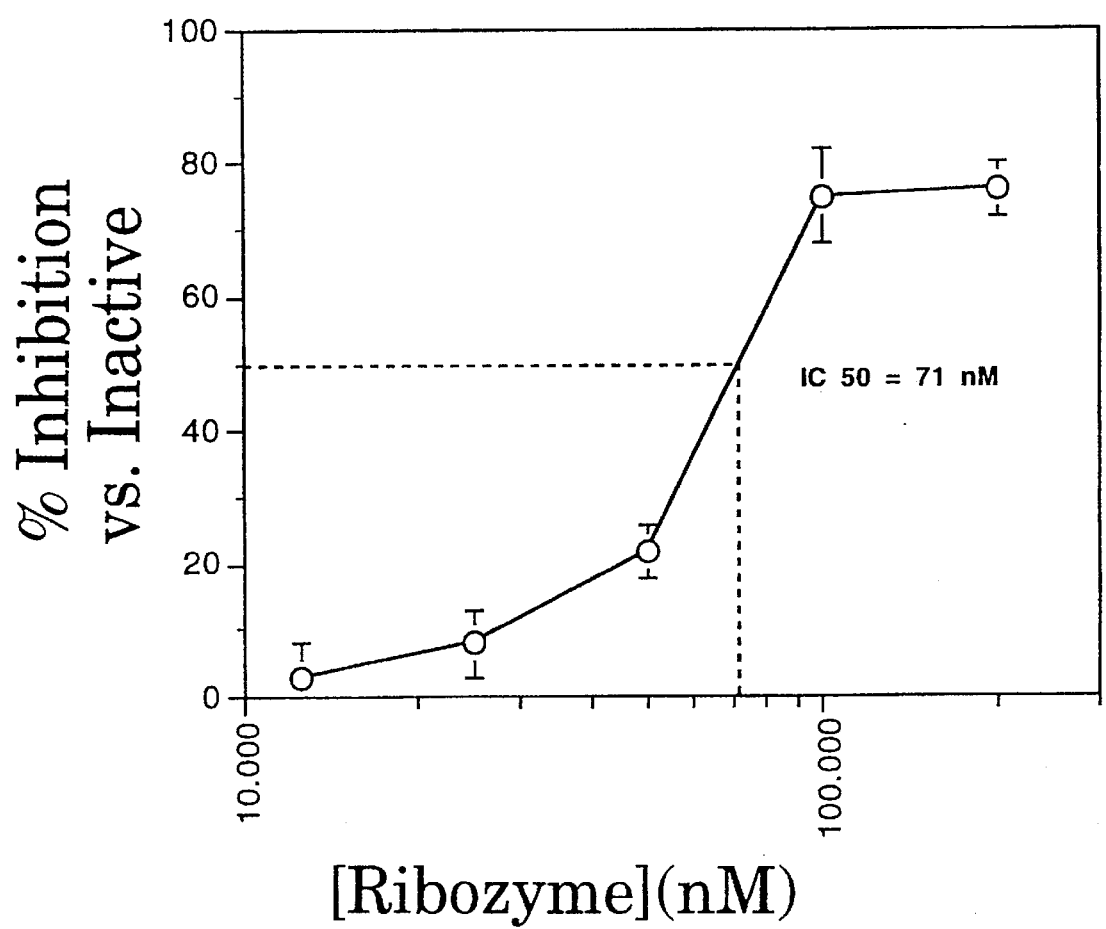

FIG. 10 shows the effect of 2'-C-allyl P=S 575 HH ribozyme concentration on smooth muscle cell proliferation. A plot of percent inhibition of smooth muscle cell proliferation (normalized to the effect of a catalytically inactive ribozyme) as a function of ribozyme concentration is shown.

Figure 11:
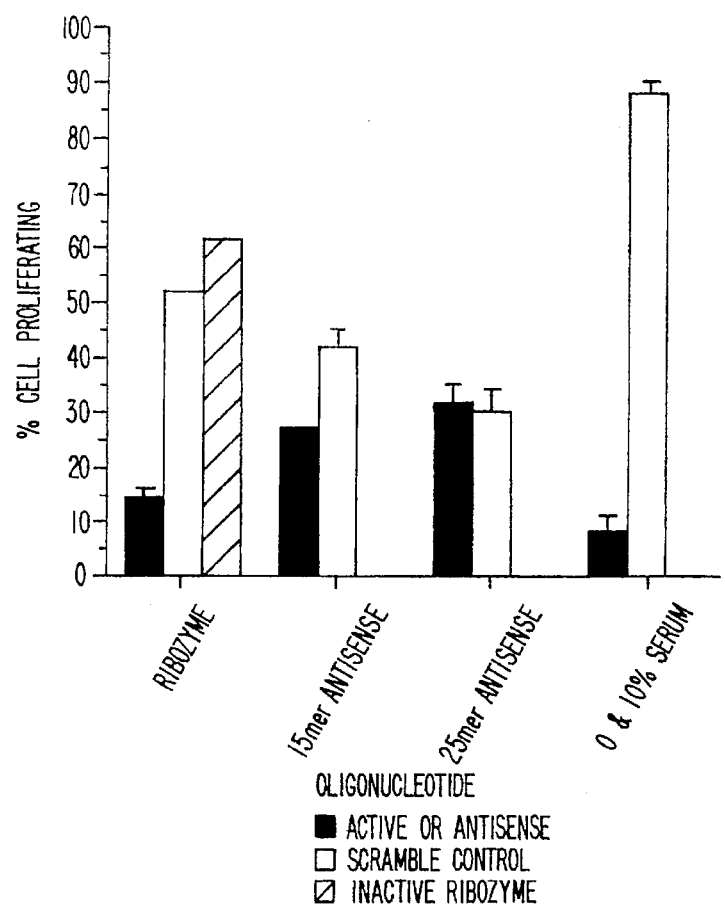

FIG. 11 shows a comparison of the effects of 2'-C-allyl P=S 575 HH ribozyme and phosphorothioate antisense DNA on the proliferation of smooth muscle cells.

Figure 12:
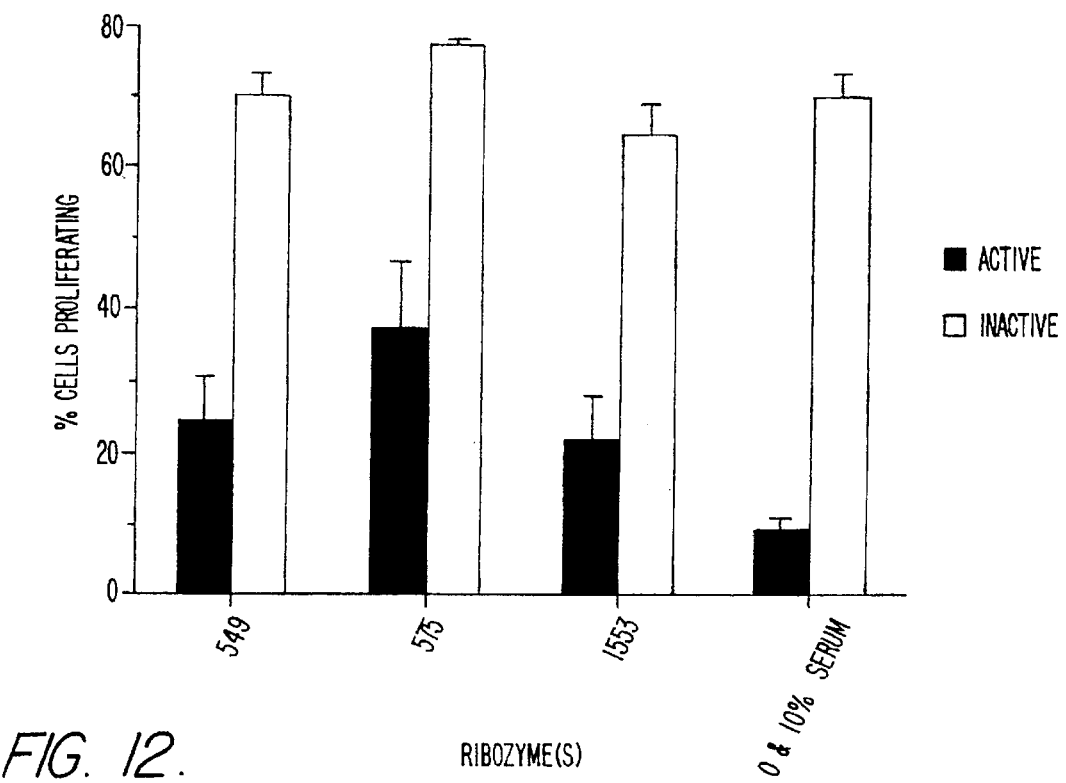

FIG. 12 shows the inhibition of smooth muscle cell proliferation catalyzed by 2'-C-allyl P=S HH ribozymes targeted to sites 549, 575, and 1533 within c-myb mRNA.

FIG. 13 shows the effect of phosphorthioate substitutions on the catalytic activity of 2'-C-allyl 575 HH ribozyme. A) diagrammatic representation of 575 hammerhead ribozyme•substrate complex. 10 P=S 5' and 3' ribozyme is identical to the 2'-C-allyl P=S ribozyme described in FIG. 9. 5 P=S 3' ribozyme is same as 10 P=S 5' and 3' ribozyme, with the exception that only five nucleotides at the 3' termini contain phosphorothioate substitutions. 5 P=S Loop ribozyme is similar to 2'-C-allyl iT described in FIG. 9, with the exception that five nucleotides within loop II of this ribozyme contain phosphorothioate substitutions. 5 P=S 5' ribozyme is same as 10 P=S 5' and 3' ribozyme, with the exception that only five nucleotides at the 5' termini contain phosphorothioate substitutions. Additionally, this ribozyme contains a 3'-3' linked inverted T at its 3' end. B) shows the ability of ribozymes described in FIG. 13A to inhibit smooth muscle cell proliferation.

FIG. 14 shows the minimum number of phosphorothioate substitutions required at the 5' termini of 575 HH ribozyme to achieve efficient inhibition of smooth muscle cell proliferation.

Figure 15:
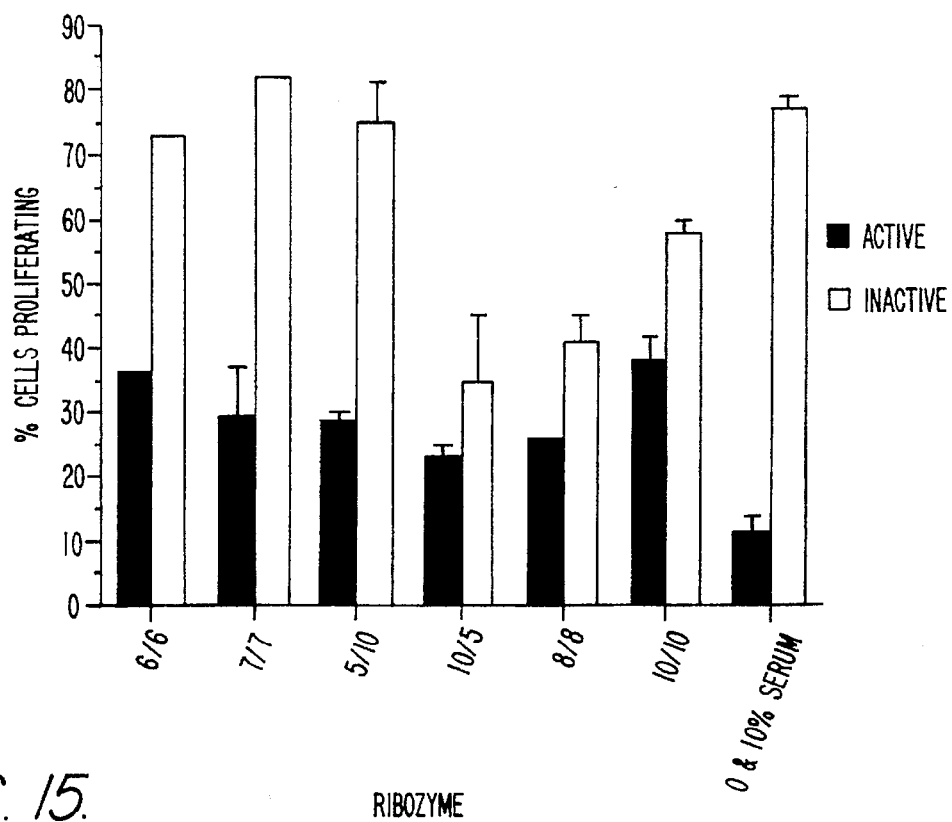

FIG. 15 shows the effect of varying the length of substrate binding arm of 575 HH ribozyme on the inhibition of smooth muscle cell proliferation.

Figure 16:
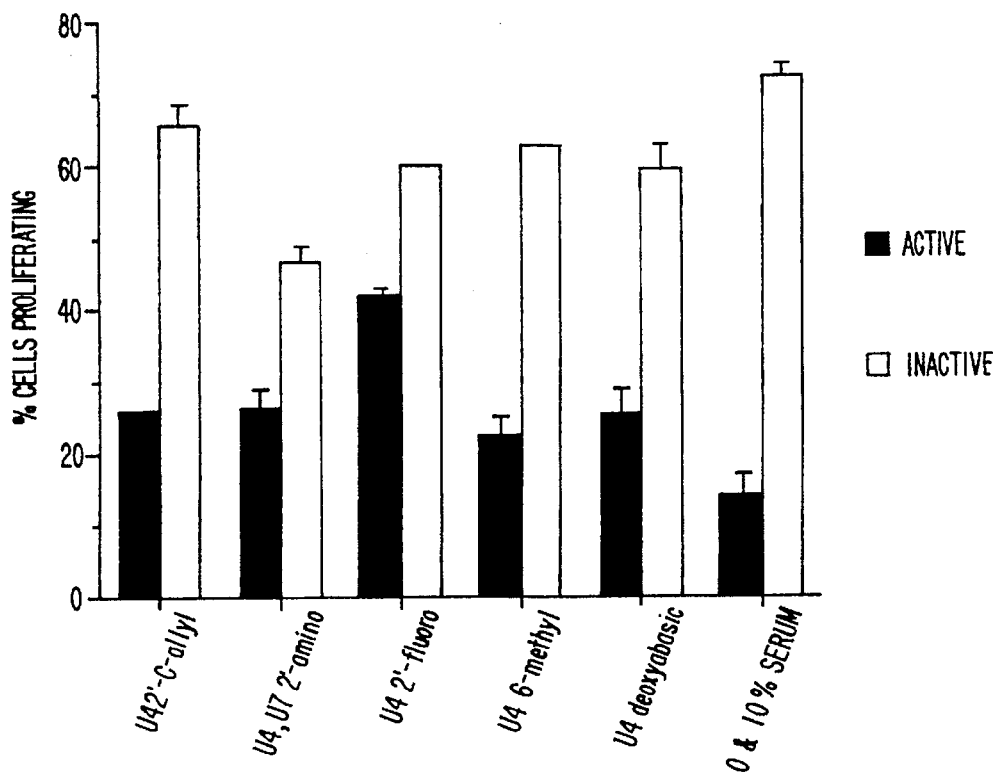

FIG. 16 shows the effect of various chemical modifications, at $U_4$ and/or $U_7$ positions within 575 HH ribozyme core, on the ability of the ribozyme to inhibit smooth muscle cell proliferation.

Figure 17:
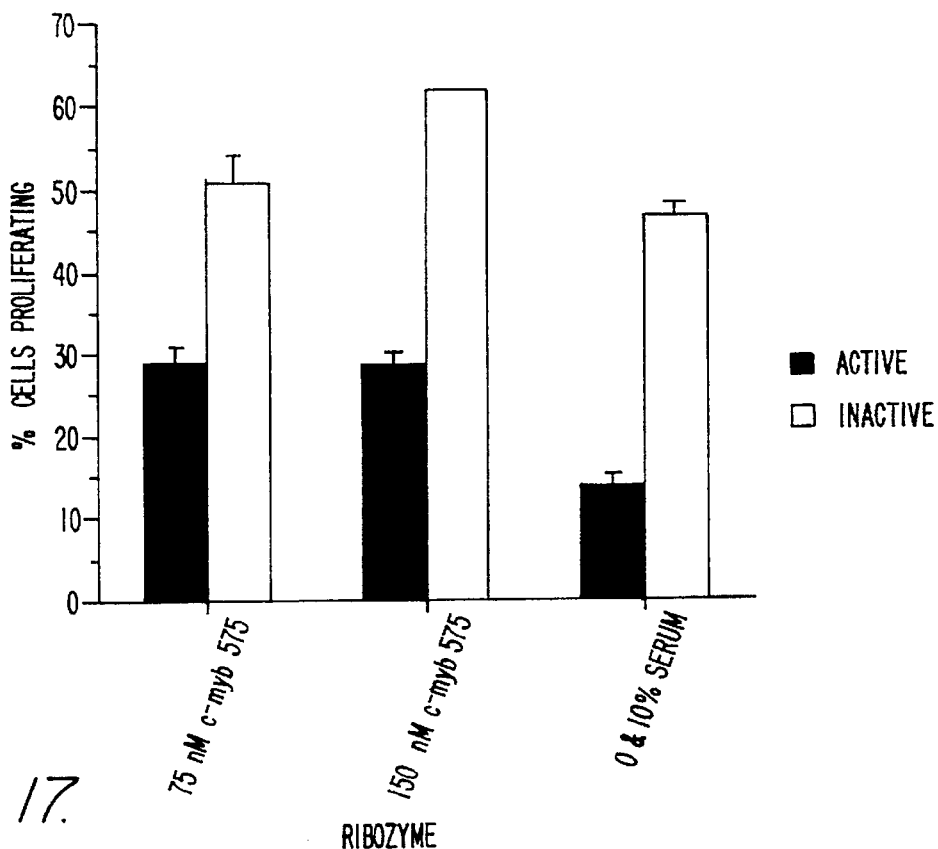

FIG. 17 shows the inhibition of pig smooth muscle cell proliferation by active c-myb 575 HH ribozyme.

Figure 18:
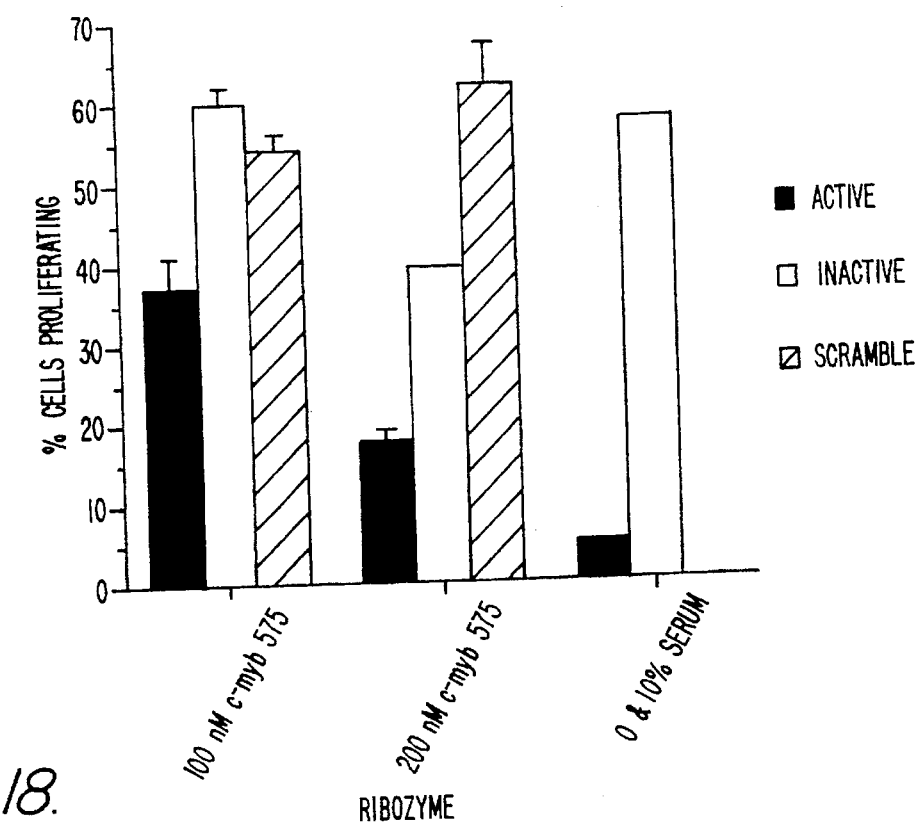

FIG. 18 shows the inhibition of human smooth muscle cell proliferation by active c-myb 575 HH ribozyme.

Figure 19:
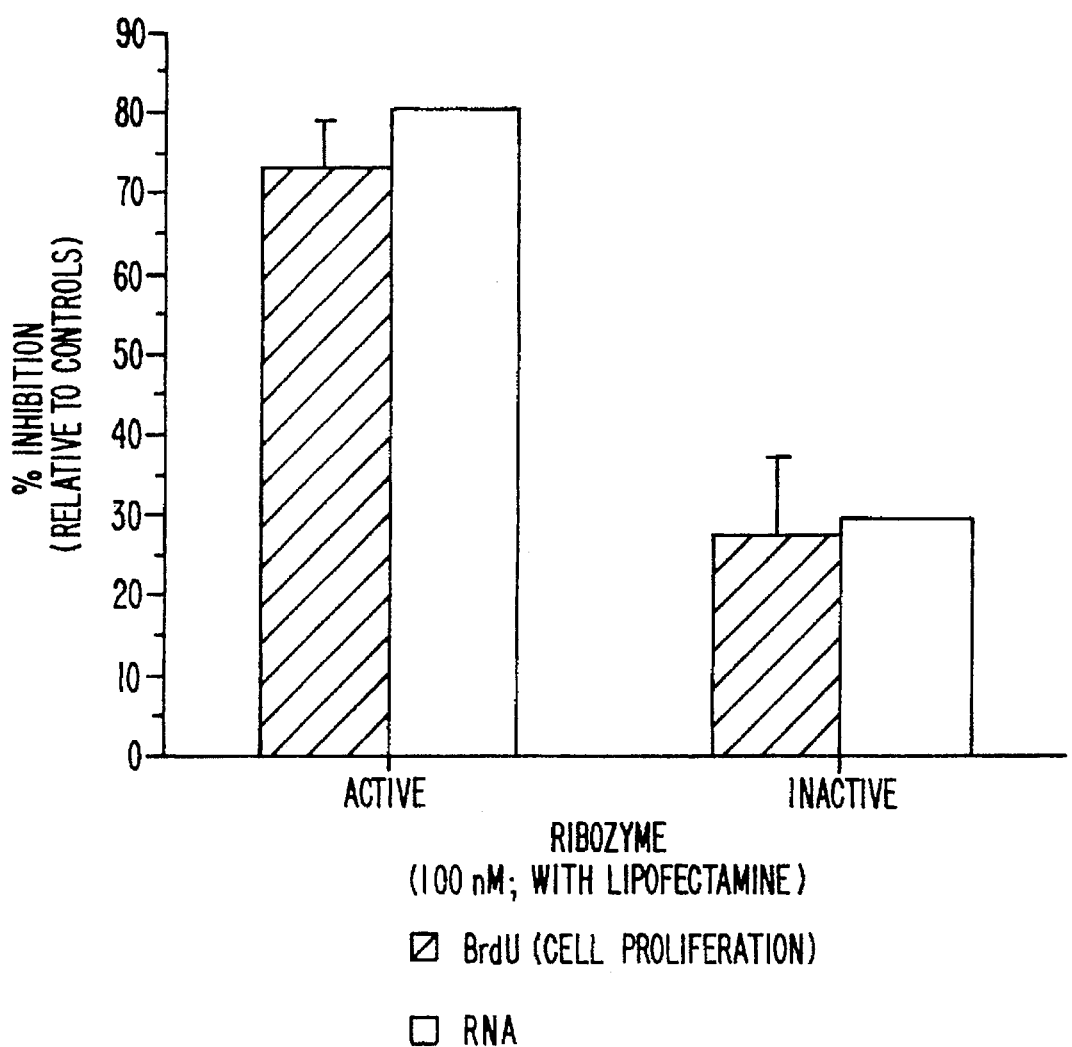

FIG. 19 shows ribozyme-mediated inhibition of c-myb expression and smooth muscle cell proliferation.

Figure 20:
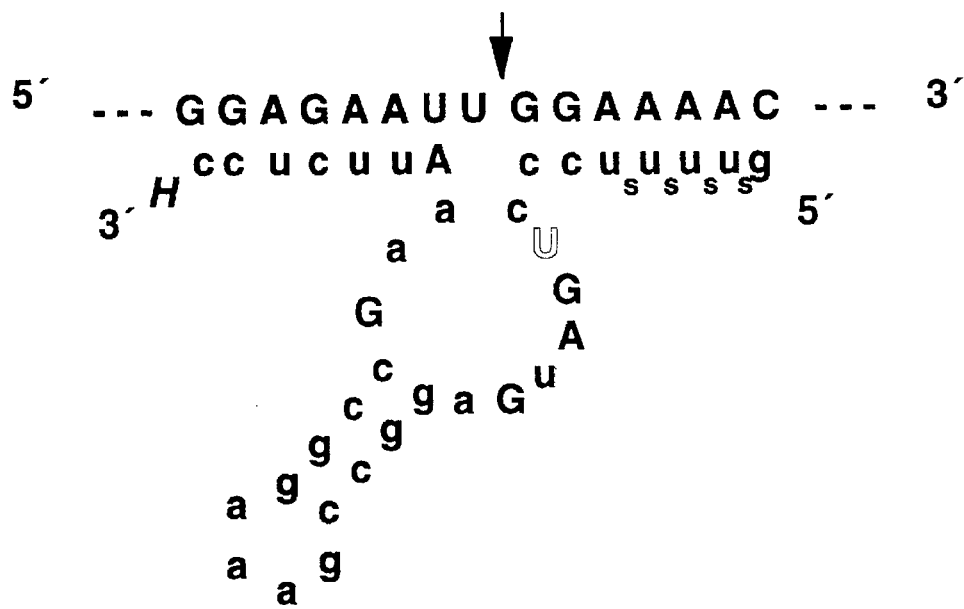

FIG. 20 is digrammatic representation of an optimal c-myb HH ribozyme that can be used to treat diseases like restenosis.

Figure 21:
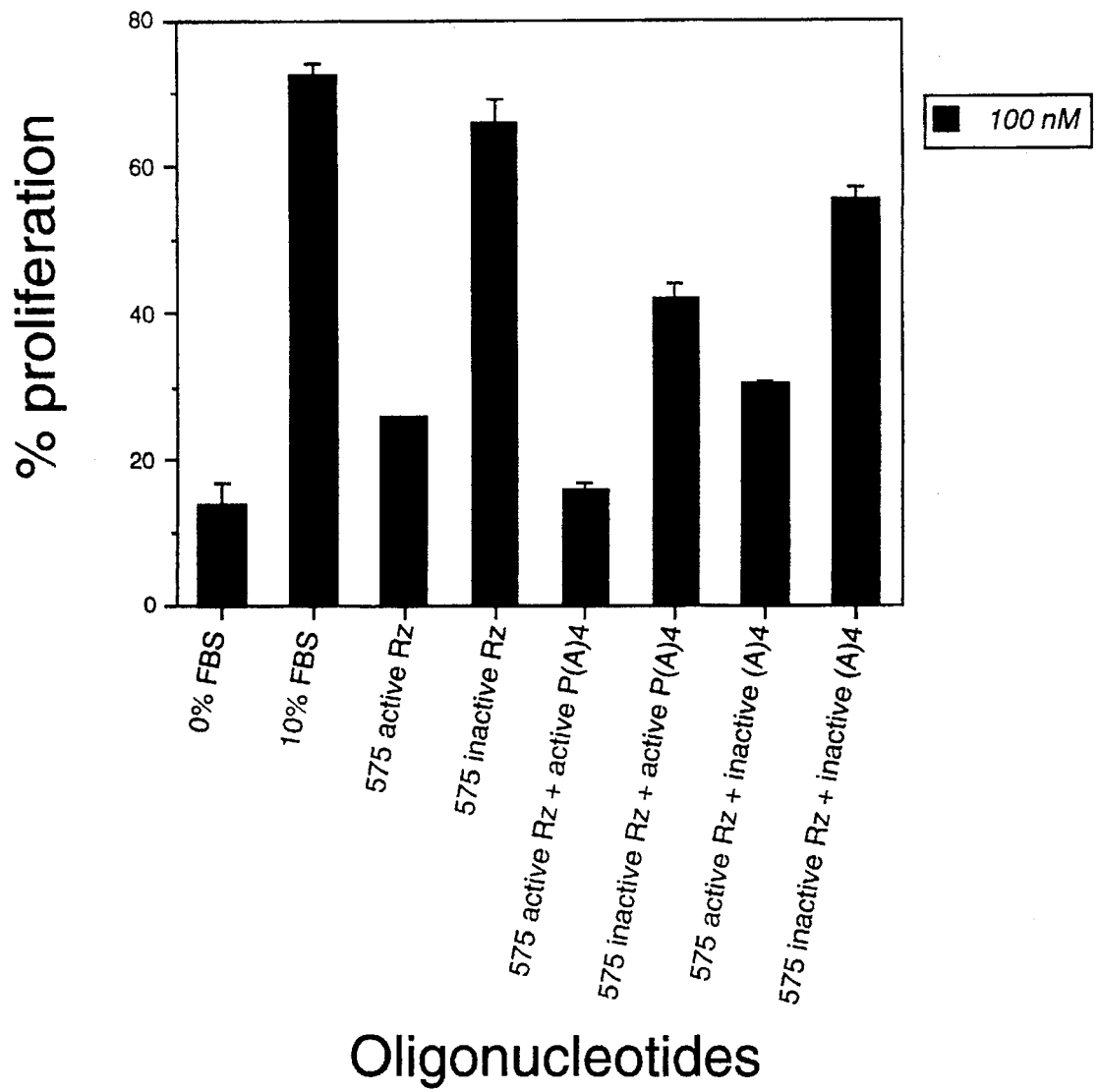

FIG. 21 shows the inhibition of Rat smooth muscle cells by 2-5A containing nucleic acids.

Target sites

Targets for useful ribozymes can be determined as disclosed in Draper et al supra, Sullivan et al., supra, as well as by Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to mouse RNA are provided, those in the art will recognize that equivalent human RNA targets can be used as described below. Thus, the same target may be used, but binding arms suitable for targetting human RNA sequences are present in the ribozyme. Such targets may also be selected as described below.

The sequence of human, pig and murine c-myb mRNAs were screened for optimal ribozyme target sites using a computer folding algorithm. Hammerhead or hairpin ribozyme cleavage sites were identified. These sites are shown in Tables II and IV (All sequences are 5' to 3' in the tables) The nucleotide base position is noted in the Tables as that site to be cleaved by the designated type of ribozyme. While murine, pig and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, murine and pig targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

The sequences of the ribozymes that are chemically synthesized, useful in this study, are shown in Table III. Those in the art will recognize that these sequences are representative only of many more such sequences where the enzymatic portion of the ribozyme (all but the binding arms) is altered to affect activity. For example, stem-loop II sequence of hammerhead ribozymes listed in Table III (5'-GGCCGAAAGGCC-3') can be altered (substitution, deletion, and/or insertion) to contain any sequences provided a minimum of two base-paired stem structure can form. Similarly, stem-loop IV sequence of hairpin ribozymes listed in Table III (5'-CACGUUGUG-3') can be altered (substitution, deletion, and/or insertion) to contain any sequence, provided a minimum of two base-paired stem structure can form. The sequences listed in Table III may be formed of ribonucleotides or other nucleotides or non-nucleotides. Such ribozymes are equivalent to the ribozymes described specifically in the Tables.

Optimizing Ribozyme Activity

Ribozyme activity can be optimized as described in this application. These include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application Ser. No. 07/829,729, and Sproat, European Patent Application 92110298.4 which describe various chemical modifications that can be made to the sugar moieties of enzymatic RNA molecules, modifications which enhance their efficacy in cells, and removal of stem II bases to shorten RNA synthesis times and reduce chemical requirements. (All these publications are hereby incorporated by reference herein.).

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. U S A*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. U S A*, 89, 10802–6; Chen et al., 1992 *Nucleic Acids Res.*, 20, 4581–9; Yu et al., 1993 *Proc. Natl. Acad. Sci. U S A*, 90, 6340–4; L'Huillier et al., 1992 *EMBO J.* 11, 4411–8; Lisziewicz et al, 1993 *Proc. Natl. Acad. Sci. U. S. A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves mRNAs encoded by c-myb is inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo.

In another preferred embodiment, the ribozyme is administered to the site of c-myb expression (e.g., smooth muscle cells) in an appropriate liposomal vesicle.

EXAMPLES

Ability of Exogenously-Delivered Ribozymes Directed Against c-myb to Inhibit Vascular Smooth Muscle Cell Proliferation The following examples demonstrate the selection of ribozymes that cleave c-myb mRNA. The methods described herein represent a scheme by which ribozymes may be derived that cleave other mRNA targets required for cell division. Also provided is a description of how such ribozymes may be delivered to smooth muscle cells. The examples demonstrate that upon delivery, the ribozymes inhibit cell proliferation in culture. Moreover, no inhibition is observed if mutated ribozymes that are catalytically inactive are applied to the cells. Thus, inhibition requires the catalytic activity of the ribozymes. The cell division assay used represents a model system for smooth muscle cell hyperproliferation in restenotic lesions.

Example 1

Identification of Potential Ribozyme Cleavage Sites in Human c-myb mRNA

The sequence of human c-myb mRNA was screened for accessible sites using a computer folding algorithm. Regions of the mRNA that did not form secondary folding structures and contained potential hammerhead ribozyme cleavage sites were identified. These sites are shown in Table II and are identical to Table I of Draper, "Method and Reagent for Treatment of a Stenotic Condition", U.S. Ser. No. 07/987, 132. (All sequences are 5' to 3' in the tables.) In the original, the sites were identified using nucleotide numbers from (Majello, B., et al., 1986, *Proc. Natl. Acad. Sci. USA*, 83, 9636–9640) (GenBank Accession No. M15024). Here, we report sites using the sequence numbers from (Westin, E. H., et al., 1990, *Oncogene*, 5, 1117–1124) (GenBank Accession No. X52125); the latter sequence is derived from a longer c-myb cDNA isolate and thus is more representative of the full-length RNA.

Example 2

Selection of Ribozyme Cleavage Sites in Murine and Human c-myb mRNA

To test whether the sites predicted by the computer-based RNA folding algorithm corresponded to accessible sites in c-myb RNA, 41 hammerhead sites were selected for analysis. Ribozyme target sites were chosen by comparing cDNA sequences of mouse and human c-myb (GenBank Accession No. X02774 and GenBank Accession No. X52125, repsectively) and prioritizing the sites on the basis of overall nucleotide sequence homology. Hammerhead ribozymes were designed that could bind each target (see FIG. 2C) and were individually analyzed by computer folding (Jaeger, J. A., et al., 1989, *Proc. Natl. Acad. Sci USA*, 86, 7706–7710) to assess whether the ribozyme sequences fold into the appropriate secondary structure. Those ribozymes with unfavorable intramolecular interactions between the binding arms and the catalytic core were eliminated from consideration. As noted below, varying binding arm lengths can be chosen to optimize activity. Generally, at least 5 bases on each arm are able to bind to, or otherwise interact with, the target RNA.

Example 3

Screening Ribozyme Cleavage Sites by RNaseH Protection

Murine and human mRNA was screened for accessible cleavage sites by the method described generally in McSwiggen, U.S. patent application No. 07/883,849 filed May 1, 1992, entitled "Assay for ribozyme target site," hereby incorporated by reference herein. Briefly, DNA oligonucleotides representing 41 potential hammerhead ribozyme cleavage sites were synthesized. A polymerase chain reaction was used to generate a substrate for T7 RNA polymerase transcription from human or murine c-myb cDNA clones. Labeled RNA transcripts were synthesized in vitro from the two templates. The oligonucleotides and the labeled transcripts were annealed, RNAseH was added and the mixtures were incubated for the designated times at 37° C. Reactions were stopped and RNA separated on sequencing polyacrylamide gels. The percentage of the substrate cleaved was determined by autoradiographic quantitation using a phosphor imaging system. The results are shown in FIGS. 7 and 8. From these data, 20 hammerhead ribozyme sites were chosen as the most accessible (see Table III). Eighteen of the twenty sites chosen overlap sequences shown in Table II; thus, the RNA folding is predictive of accessible regions in the RNA.

Example 4

Chemical Synthesis and Purification of Ribozymes for Efficient Cleavage of c-myb RNA Ribozymes of the hammerhead or hairpin motif were designed to anneal to various sites in the mRNA message. The binding arms are complementary to the target site sequences described above. The ribozymes were chemically synthesized. The method of synthesis used followed the procedure for normal RNA synthesis as described in Usman et al., 1987 *J. Am. Chem. Soc.*, 109, 7845 and in Scaringe et al., 1990 *Nucleic Acids Res.*, 18, 5433 and made use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.*, 20, 3252). Hairpin ribozymes were synthesized in two parts and annealed to reconstruct the active ribozyme (Chowrira and Burke, 1992 *Nucleic Acids Res.*, 20, 2835–2840). Ribozymes were also synthesized from DNA templates using bacteriophage T7 RNA polymerase (Milligan and Uhlenbeok, 1989, *Methods Enzymol.* 180, 51). All ribozymes were modified extensively to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34). Ribozymes were purified by gel electrophoresis using general methods or were purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and were resuspended in water. The sequences of the chemically synthesized ribozymes used in this study are shown below in Table III.

Example 5

Ribozyme Cleavage of Long Substrate RNA Corresponding to c-myb mRNA Target

Hammerhead-type ribozymes which were targeted to the murine c-myb mRNA were designed and synthesized to test the cleavage activity at the 20 most accessible sites in in vitro transcripts of both mouse and human c-myb RNAs. The target sequences and the nucleotide location within the c-myb mRNA are given in Table IV. All hammerhead ribozymes were synthesized with binding arm (Stems I and III; see FIG. 2C) lengths of seven nucleotides. Two hairpin ribozymes were synthesized to sites 1632 and 2231. The relative abilities of these ribozymes to cleave both murine and human RNAs is summarized in Table IV. Ribozymes (1 µM) were incubated with $^{32}$P-labeled substrate RNA (prepared as described in Example 3, approximately 20 nM) for 60 minutes at 37° C. using buffers described previously. Intact RNA and cleavage products were separated by electrophoresis through polyacrylamide gels. The percentage of cleavage was determined by Phosphor Imager® quantitation of bands representing the intact substrate and the cleavage products.

Five hammerhead ribozymes (directed against sites 549, 575, 1553, 1597, and 1635) and one hairpin ribozyme (directed against site 1632) were very active; they cleaved >70% of both murine and human c-myb RNA in 60 minutes. Nine of the hammerhead ribozymes (directed against sites 551, 634, 936, 1082, 1597, 1721, 1724, 1895, and 1943) were intermediate in activity, cleaving >50% of both murine and human c-myb RNA in 60 minutes. All of the sites cleaved by these active ribozymes were predicted to be accessible to ribozyme cleavage in Table 2. Six hammerhead ribozymes and one hairpin ribozyme showed low activity on at least one of the substrates. The observed differences in accessibility between the two species of c-myb RNA demonstrate the sensitivity of ribozyme action to RNA structure and suggest that even when homologous target sequences exist, ribozymes may be excluded from cleaving that RNA by structural constraints. This level of specificity minimizes non-specific toxicity of ribozymes within cells.

Example 6

Ability of Hammerhead Ribozymes to Inhibit Smooth Muscle Cell Proliferation

The ribozymes that cleaved c-myb RNA described above were assayed for their effect on smooth muscle cell proliferation. Rat vascular smooth muscle cells were isolated and cultured as follows. Aortas from adult Sprague-Dawley rats were dissected, connective tissue was removed under a dissecting microscope, and 1 mm² pieces of the vessel were placed, intimal side up, in a Petri dish in Modified Eagle's Medium (MEM) with the following additives: 10% FBS, 2% tryptose phosphate broth, 1% penicillin/streptomycin and 2 mM L-Glutamine. The smooth muscle cells were allowed to migrate and grow to confluence over a 3–4 week period. These primary cells were frozen and subsequent passages were grown at 37° C. in 5% $CO_2$ in Dulbecco's modified Eagle's medium (DMEM), 10% fetal bovine serum (FBS), and the following additives: 2 mM L-Glutamine, 1% penicillin/streptomycin, 1 mM sodium pyruvate, non-essential amino acids (0.1 mM of each amino acid), and 20 mM Hepes pH 7.4. Cells passed four to six times were used in proliferation assays. For the cell proliferation assays, 24-well tissue culture plates were prepared by coating the wells with 0.2% gelatin and washing once with phosphate-buffered saline (PBS). RASMC were inoculated at $1 \times 10^4$ cells per well in 1 ml of DMEM plus 10% FBS and additives and incubated for 24 hours. The cells were subconfluent when plated at this density. The cells were serum-starved by removing the medium, washing once with PBS, and incubating 48–72 hours in DMEM containing 0.5% FBS plus additives.

In several other systems, cationic lipids have been shown to enhance the bioavailability of oligonucleotides to cells in culture (Bennet, C. F., et al., 1992, *Mol. Pharmacology*, 41, 1023–1033). In many of the following experiments, ribozymes were complexed with cationic lipids. The cationic lipid, Lipofectamine (a 3:1 (w/w) formulation of DOSPA (2,3-dioleyloxy-N-[2(sperminecarboxamido)ethyl]-N,N-dimethyl-1-propanaminium trifluoroacetate) and dioleoyl phosphatidylethanolamine (DOPE)), was purchased from Life Technologies, Inc. DMRIE (N-[1-(2,3-ditetradecyloxy)propyl]-N,N-dimethyl-N-hydroxyethylammonium bromide) was obtained from VICAL. DMRIE was resuspended in $CHCl_3$ and mixed at a 1:1 molar ratio with dioleoyl phosphatidylethanolamine (DOPE). The $CHCl_3$ was evaporated, the lipid was resuspended in water, vortexed for 1 minute and bath sonicated for 5 minutes. Ribozyme and cationic lipid mixtures were prepared in serum-free DMEM immediately prior to addition to the cells. DMEM plus additives was warmed to room temperature (about 20°–25° C.), cationic lipid was added to the final desired concentration and the solution was vortexed briefly. RNA oligonucleotides were added to the final desired concentration and the solution was again vortexed briefly and incubated for 10 minutes at room temperature. In dose response experiments, the RNA/lipid complex was serially diluted into DMEM following the 10 minute incubation.

Serum-starved smooth muscle cells were washed twice with PBS, and the RNA/lipid complex was added. The plates were incubated for 4 hours at 37° C. The medium was then removed and DMEM containing 10% FBS, additives and 10 µM bromodeoxyuridine (BrdU) was added. In some wells, FBS was omitted to determine the baseline of unstimulated proliferation. The plates were incubated at 37° C. for 20–24 hours, fixed with 0.3% $H_2O_2$ in 100% methanol, and stained for BrdU incorporation by standard methods. In this procedure, cells that have proliferated and incorporated BrdU stain brown; non-proliferating cells are counterstained a light purple. Both BrdU positive and BrdU negative cells were counted under the microscope. 300–600 total cells per well were counted. In the following experiments, the percentage of the total cells that have incorporated BrdU (% cell proliferation) is presented. Errors represent the range of duplicate wells. Percent inhibition then is calculated from the % cell proliferation values as follows: % inhibition= 100–100((Ribozyme–0% serum)/(Control–0% serum)).

Six hammerhead ribozymes, including the best five ribozymes from the in vitro RNA cleavage test (directed against sites 549, 575, 1553, 1598, and 1635) and one with intermediate cleavage levels (directed against site 1597) and their catalytically inactive controls were synthesized and purified as described above. The ribozymes were delivered at a concentration of 0.3 µM, complexed with DMRIE/DOPE such that the cationic lipid charges and the anionic RNA charges were at 1:1 molar ratio. The results, shown in Table V, demonstrate a considerable range in the efficacy of ribozymes directed against different sites. Five of the six hammerhead ribozymes (directed against sites 549, 575, 1553, 1597, and 1598) significantly inhibit smooth muscle cell proliferation. The control, inactive ribozymes that cannot cleave c-myb RNA due to alterations in their catalytic core sequence fail to inhibit rat smooth muscle cell proliferation. Thus, inhibition of cell proliferation by these five hammerhead sequences is due to their ability to cleave c-myb RNA, and not because of any antisense activity. The sixth ribozyme (directed against site 1635) fails to function in smooth muscle cells. This ribozyme cleaved c-myb RNA very efficiently in vitro. In this experiment, 10% FBS (no ribozyme added) induced 64±1% proliferation; 0% FBS produced a background of 9±1% proliferation.

Example 7

Ability of Exogenously Delivered Hairpin Ribozyme Against c-myb to Inhibit Vascular Smooth Muscle Cell Proliferation In addition to the hammerhead ribozymes tested above, a bipartite hairpin ribozyme (Chowrira, B. M., supra, 1992, *Nucleic Acids Res.*, 20, 2835–2840) was identified that also cleaves c-myb RNA. The effect of this ribozyme on smooth muscle cell proliferation was tested. Ribozymes were delivered at the indicated doses with Lipofectamine at a 1:1 charge ratio. In this experiment, 10% FBS (no ribozyme) induced 87±1% proliferation; 0% FBS produced 5±1% proliferation. The results of a dose-response experiment are shown in Table VI. In this example, the control was an irrelevant hammerhead ribozyme. The irrelevant ribozyme control contains the same catalytic core sequences, but has binding arms that are directed to a cellular RNA that is not required for smooth muscle cell proliferation. This control failed to significantly inhibit cell proliferation, demonstrating the sequence specificity of these ribozymes. Another control that could be run is an irrelevant catalytically active ribozyme having the same GC content as the test ribozyme.

Example 8

Ribozymes Inhibit Proliferation of Rat Smooth Muscle Cells in a Dose-dependent Fashion If the inhibition of proliferation observed in Example 6 is caused by the ribozymes, the level of inhibition should be proportional to the dose of RNA added. Rat aortic smooth muscle cells were assayed for proliferation in the presence of differing doses of two hammerhead ribozymes. The results shown in Table VII indicate that two hammerhead ribozymes that cleave c-myb RNA at sites 575 and 549 inhibit SMC proliferation in a dose-dependent fashion. Ribozymes were delivered with the cationic lipid, Lipofectamine at a 1:1 charge ratio. In this experiment, 10% FBS (no ribozyme) gave 92±1% proliferation; 0% FBS gave 6±1% proliferation. The control is an active ribozyme directed against an irrelevant mRNA target and shows no inhibition over the dose range tested. The control ribozyme contains the same catalytic core sequences as the active ribozymes but differs in its binding arm sequences (stems I and III in FIG. 2c). Thus, ribozyme inhibition of smooth muscle cell proliferation requires sequence-specific binding by the hammerhead arms to c-myb mRNA.

Example 9

Delivery of a c-myb Ribozyme With Different Cationic Lipids

The experiment in Table VIII shows the response of rat smooth muscle cells to a hammerhead ribozyme that cleaves c-myb RNA at site 575 delivered with two different cationic lipids, DMRIE and Lipofectamine. Similar efficacy is observed with either lipid. 10% FBS (no ribozyme) induced 78±2% proliferation; 0% FBS produced a background of 6±1% proliferation.

Example 10

Effect of Varying Arm-lengths on Ribozyme Activity

Figure 2B:
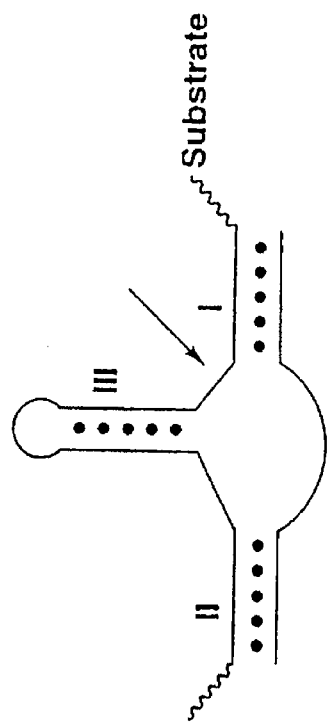
Figure 2D:
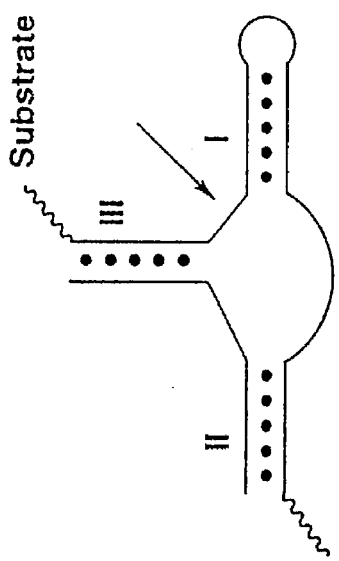
Figure 2A:
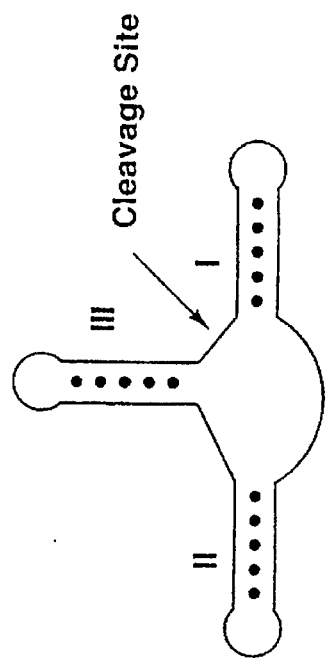
Figure 2C:
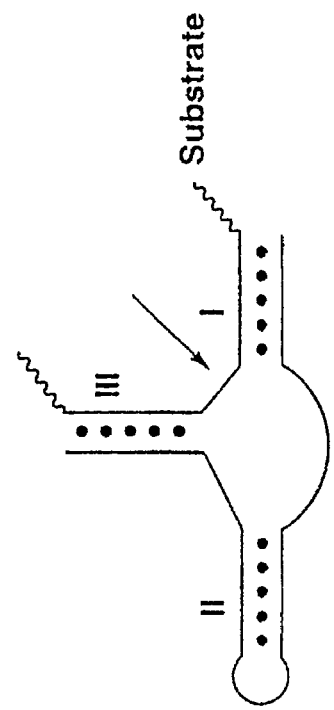

The exact configuration of each ribozyme can be optimized by altering the length of the binding arms (stems I and III, see FIG. 2C). The length of the binding arms may have an effect on both the binding and the catalytic cleavage step (Herschlag, D., 1991, Proc. Natl. Acad. Sci. U S A, 88, 6921–5). For example, Table IX shows the ability of arm length variants of c-myb hammerhead 575 to inhibit SMC proliferation. Note that the dose used in this experiment (0.1 µM) is 3-fold lower than in previous experiments. At this concentration, the 7/7 arm variant gives relatively little inhibition. In this case, the degree of inhibition increases with concomitant increases in arm length.

The optimum arm length may be site-specific and should be determined empirically for each ribozyme. Towards this end, hammerhead ribozymes target with 7 nucleotide binding arms (7/7) and ribozymes with 12 nucleotide binding arms (12/12) targeted to three different cleavage sites were compared.

Ribozymes were delivered at 0.2 µM with the cationic lipid DMRIE at a 1:1 charge ratio of oligonucleotide to cationic lipid as described in Example 6. The data are shown below in Table X. As can be seen, all three ribozymes demonstrated enhanced inhibition of smooth muscle cell proliferation with twelve nucleotide binding arms. Each ribozyme showed greater inhibition than its catalytically inactive control, again demonstrating that the ribozymes function via their ability to cleave c-myb RNA. In this experiment, 10% stimulation resulted in 54±2% cell proliferation; unstimulated cells showed 8±0.5% cell proliferation.

Example 11

Effect of Chloroquine on Ribozyme Activity

A number of substances that effect the trafficking of macromolecules through the endosome have been shown to enhance the efficacy of DNA delivery to cells. These include, but are not limited to, ammonium chloride, carbonyl cyanide p-trifluoromethoxy phenyl hydrazone (FCCP), chloroquine, monensin, colchicine, and viral particles (Cotten, M. et al., 1990, Proc. Natl. Acad. Sci. USA, 87, 4033–4037; Cotten, M. et al., 1993, J. Virol., 67, 3777–3785; Cotten, M. et al., 1992, Proc. Natl. Acad. Sci USA, 89, 6094–6098; Cristiano, R. J. et al., 1993, Proc. Natl. Acad. Sci. U S A, 90, 2122–6; Cudel, D. T. et al., 1991, Proc. Nat. Acad. Sci., USA, 88, 8850–8854; Ege, T. et al., 1984, Exp. Cell Res., 155, 9–16; Harris, C. E. et al., 1993, Am. J. Respir. Cell Mol. Biol., 9, 441–7; Seth, P. et al., 1994, J. Virol., 68, 933–40; Zenke, M. et al., 1990, Proc. Natl. Acad. Sci. USA, 87, 3655–3659). It is thought that DNA is taken up by cells by endocytosis, resulting in DNA accumulation in endosomes (Akhtar, S. and Juliano, R. L., 1992, Trends Cell Biol., 2, 139–144). Thus, the above agents may enhance DNA expression by promoting DNA release from endosomes. To determine whether such agents may augment the functional delivery of RNA and ribozymes to smooth muscle cells, the effects of chloroquine on ribozyme inhibition of smooth muscle cell proliferation were assessed. A ribozyme with twelve nucleotide binding arms that cleaves c-ruby RNA was delivered to rat smooth muscle cells as described in Example 6 (0.2 µM ribozyme complexed with DMRIE/ DOPE at a 1:1 charge ratio). In some cases, 10 µM chloroquine was added upon stimulation of the cells. The addition of chloroquine had no effect on untreated cells (stimulation with 10% serum in the presence or absence of chloroquine resulted in 80.5±1.5% and 83±2% cell proliferation, respectively; unstimulated cells with and without chloroquine showed 7±0.5% and 7±1% cell proliferation, respectively). As shown in Table XI below, addition of chloroquine augments ribozyme inhibition of smooth muscle cell proliferation two- to three-fold.

Example 12

Effect of a Hammerhead Ribozyme on Human Smooth Muscle Cell Proliferation

The hammerhead ribozyme that cleaves human c-myb RNA at site 549 was tested for its ability to inhibit human aortic smooth muscle cell proliferation. The binding site for this ribozyme is completely conserved between the mouse and human cDNA sequences. Human aortic smooth muscle cells (AOSMC) were obtained from Clonetics and were grown in SmGM (Clonetics®). Cells from passage five or six were used for assays. Conditions for the proliferation assay were the same as for the rat cells (see Example 6), except that the cells were plated in SmGM and starved in SmBM plus 0.5% FBS. The ribozyme that cleaves site 549 was delivered at varying doses complexed with the cationic lipid DMRIE at a 1:1 charge ratio. In this experiment, 10% FBS (no ribozyme) induced 57±7% proliferation; the uninduced background was 6±1% proliferation. The results in Table XII show that inhibition is observed over a similar concentration range as was seen with rat smooth muscle cells.

Example 13

Inhibition by Direct Addition of a Modified, Stabilized Ribozyme

A hammerhead ribozyme that cleaves site 575 was chemically synthesized with 12 nucleotide binding arms (sequence ID NO. 127, in Table III). Chemically modified nucleotides were incorporated into this ribozyme that have been shown to enhance ribozyme stability in serum without greatly impacting catalytic activity. (See Eckstein et al., International Publication No. WO 92/07065, Perrault et al., 1990, Nature, 344, 565–568, Pieken, W. et al. 1991, Science, 253, 314–317, Usman, N.; Cedergren, R. J., 1992, Trends in Biochem. Sci., 17, 334–339, Usman, N. et al. U.S. patent application Ser. No. 07/829,729, and Sproat, B. European Patent Application 92110298.4 describe various chemical modifications that can be made to the sugar moieties of enzymatic RNA molecules. All these publications are hereby incorporated by reference herein.) The modifications used were as follows. All the nucleotides of the ribozyme contained 2'-O-methyl groups with the following exceptions: $U_4$ and $U_7$ contained 2'-amino substitutions; $G_5$, $A_6$, $G_8$, $G_{12}$, and A$_{15.1}$ were 2'-OH ribonucleotides (numbering as in FIG. 1). An inactive ribozyme was chemically synthesized in which G$_5$ and A$_{14}$ were substituted with 2'-O-methyl U. Ribozymes were added to rat smooth muscle cells at the indicated concentrations as per Example 6 except that cationic lipids were omitted. Proliferation was assessed by BrdU incorporation and staining. Table XIII shows that the modified ribozyme is capable of inhibiting rat smooth muscle cell proliferation without addition of cationic lipids. In this experiment, 10% serum induced 45±2% proliferation while uninduced cells showed a background of 2.3±0.1% proliferation.

Optimizing Ribozyme Activity

As demonstrated in the above examples, ribozymes that cleave c-myb RNA are capable of inhibiting 50% of the smooth muscle cells from proliferating in response to serum. This level of inhibition does not represent the maximal effect obtainable with the ribozymes; in each dose response experiment, the highest dose produced the greatest extent of inhibition. Thus, optimizing activity of the ribozyme within the cells and/or optimizing the delivery of the ribozyme to the cells is expected to increase the extent of inhibition.

Tables IX and X demonstrate one means of optimizing ribozyme activity. By altering the length of the ribozyme binding arms (stems I and III, see FIG. 2c), the ability of the ribozyme to inhibit smooth muscle cell proliferation is greatly enhanced. Ribozymes with increasing arm lengths will be synthesized either chemically in one or two pads (see above and see Mamone, U.S. Ser. No. 07/882,689, filed May 11, 1992, hereby incorporated by reference herein) or by in vitro transcription (see Cech et al., U.S. Pat. No. 4,987,071). Ribozymes are chemically synthesized with modifications that prevent their degradation by serum ribonucleases (as described in Example 13, above). When synthesized in two parts, the fragments are ligated or otherwise juxtaposed as described (see original application and Mamone, supra). The effects of the ribozymes on smooth muscle cell proliferation are assessed as in Examples 6 and 12, above. As the length of stems I and III can affect both hybridization to the target and the catalytic rate, the arm length of each ribozyme will be optimized for maximal inhibitory effect in cells. Similarly, the precise sequence of modified nucleotides in the stabilized ribozyme will affect the activity in cells. The nature of the stabilizing modifications will be optimized for maximal inhibitory effect in cells. In each case, activity of the ribozyme that cleaves c-myb RNA will be compared to the activity of its catalytically inactive control (substitution of 2'-O- methyl U for G$_5$ and a 2'-O-methyl U for A$_{14}$) and to a ribozyme targeted to an irrelevant RNA (same catalytic core, with appropriate modifications, but different binding arm sequences).

Sullivan, et al., supra, describes the general methods for delivery of enzymatic RNA molecules. The data presented in Example 9 indicate that different cationic lipids can deliver active ribozymes to rat smooth muscle cells. In this example, 0.6 µM ribozyme delivered with Lipofectamine produced the same inhibitory effect as 0.3 µM ribozyme delivered with DMRIE. Thus, DMRIE is twice as efficacious as Lipofectamine at delivering active ribozymes to smooth muscle cells. There are a number of other cationic lipids known to those skilled in the art that can be used to deliver nucleic acid to cells, including but not limited to dioctadecylamidoglycylspermine (DOGS), dioleoxltrimetylammonium propane (DOTAP), N-[1-(2,3-dioleoyloxy)-propyl]-n,n,n-trimethylammoniumchloride (DOTMA), N-[1-(2,3-dioleoyloxy)-propyl]-N,N-dimethyl-N-hydroxyethylammonium bromide (DORIE), and N-[1-(2,3-dioleoyloxy)propyl]-N,N-dimethyl-N-hydroxypropylammonium bromide (DORIE-HP). Experiments similar to those performed in Example 9 are used to determine which lipids give optimal delivery of ribozymes to smooth muscle cells. Other such delivery methods are known in the art and can be utilized in this invention.

The data described in Example 11 show that ribozyme delivery and efficacy may be augmented by agents that disrupt or alter cellular endosome metabolism. Chloroquine was shown to increase the ability of a ribozyme to inhibit smooth muscle cell proliferation by 2- to 3-fold. Experiments similar to those described in Example 11 can be performed to determine the optimal concentration of chloroquine to be used to augment delivery of ribozymes alone (as in Example 13), or delivery in the presence different cationic lipids (as in Example 9 and described above) or with other delivery agents (as described below). Other agents that disrupt or alter endosomes known to those familiar with the art can be used to similarly augment ribozyme effects. These agents may include, but are not limited to, ammonium chloride, carbonyl cyanide p-trifluoromethoxy phenyl hydrazone (FCCP), chloroquine, monensin, colchicine, amphipathic peptides, viral proteins, and viral particles. Such compounds may be used in conjunction with ribozymes as described above, may be chemically conjugated directly to ribozymes may be chemically conjugated to liposomes, or may be incorporated with ribozymes in liposome particles (see Sullivan, et al., supra, incorporated by reference herein).

The data presented in Example 13 indicate that the proliferation of smooth muscle cells can be inhibited by the direct addition of chemically stabilized ribozymes. Presumably, uptake is mediated by passive diffusion of the anionic nucleic acid across the cell membrane. In this case, efficacy could be greatly enhanced by directly coupling a ligand to the ribozyme. The ribozymes are then delivered to the cells by receptor-mediated uptake. Using such conjugated adducts, cellular uptake can be increased by several orders of magnitude without having to alter the phosphodiester linkages necessary for ribozyme cleavage activity.

Alternatively, ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/ vehicle combination is locally delivered by direct injection or by use of a catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Example 14

Phosphorothioate Linkages Enhance the Ability of Ribozymes to Inhibit Smooth Muscle Cell Proliferation As the applicant had shown in Example 13, the hammerhead (HH) ribozyme that cleaves c-myb RNA at site 575 can be modified to confer resistance to nucleases while maintaining catalytic activity (see also Usman et al., supra). To identify ribozymes with optimal activity in cells, several different chemically-modified ribozymes were directly compared for inhibition of rat smooth muscle cell proliferation. Chemically-modified ribozymes used are diagrammed in FIG. 9A. One ribozyme (designated "2'-O-methyl") contains ribonucleotide residues at all positions except the 5 terminal nucleotides of each target binding arm (Stems I and III). The ribozyme designated "2'-O-methyl P=S" in addition contains five phosphorothioate linkages between the terminal nucleotides in each target binding arm. The ribozyme termed "2'-C-allyl iT" contains thirty 2'-O-methyl nucleotides as specified in Example 13. The ribozyme also contains 2'-C-allyl U (Usman et al., 1994 Nucleic Acids Symp. Ser. 31, 163) at the U4 position and 2'-O-methyl U at the U7 position and a 3'-3'-linked inverted thymidine (Ortigao et al., 1992 Antisense Res. & Development 2, 129; Seliger et al., Canadian Patent Application No. 2,106,819) at the 3' end of the molecule (referred to as 2'-C-allyl iT). The fourth ribozyme contains the same 2'-O-methyl and 2'-C-allyl residues described above with the addition of 5 phosphorothioate linkages between the terminal nucleotides in each target binding arm (referred to as "2'-C-allyl P=S").

Ribozymes were delivered to smooth muscle cells as cationic lipid complexes (Sullivan et al., supra). In this example, the cationic lipid, Lipofectamine (GIBCO-BRL), was used at a charged lipid concentration of 3.6 µM (see Examples 6 and 9). Active versus inactive forms of each ribozyme were compared to determined whether inhibition is mediated specifically by ribozyme cleavage. As shown in FIG. 9B, the ribozyme synthesized with the 2'-C-allyl modification and the phosphorothioate linkages demonstrated enhanced inhibition of smooth muscle cell proliferation. The catalytically inactive form of the ribozyme had little effect on cell proliferation; thus, the inhibition observed requires the catalytic activity of the ribozyme. In contrast, ribozymes without the stable 2'-O-methyl- and 2'-C-allyl-modified catalytic core (2'-O-methyl and 2'-O-methyl P=S) at best showed only modest inhibition of smooth muscle cell proliferation. The stable core chemistry alone was not sufficient to greatly enhance ribozyme-mediated inhibition; without terminal P=S linkages, the 2'-C-allyl-modified ribozyme showed very little specific inhibition when compared to its inactive ribozyme control. These results demonstrate that certain chemical modifications greatly enhance the ability of exogenously-delivered ribozymes to cleave c-myb RNA and impact cell proliferation.

Example 15

Dose Response of the Chemically Modified Ribozyme

Varying doses of the 2'-C-allyl P=S-modified ribozyme were delivered to rat aortic smooth muscle cells as described above. As in previous examples, percent inhibition was calculated by comparing the effects of the active ribozyme to the effects of the inactive ribozyme. As shown in FIG. 10, the ribozyme concentration at which cell proliferation is inhibited by 50% ($IC_{50}$) is approximately 70 nM. From day to day, the $IC_{50}$ varies between 25 and 100 nM.

Example 16

Direct Comparison of the Effects of Ribozymes and Antisense DNA

Ribozymes are thought to be more specific reagents for the inhibition of gene expression than antisense oligonucleotides due to their catalytic activity and strict sequence requirements around the site of cleavage (Castanotto et al., 1994 Adv. in Pharmacol. 25, 289). To test this hypothesis, ribozyme activity was directly compared to the activity of phosphorothioate DNA oligonucleotides that target the same site in the c-myb mRNA. The ribozyme used was the 2'-C-allyl P=S-modified ribozyme described in Example 14, above. This ribozyme binds to a 15 nucleotide long region of the c-myb mRNA. Thus, a 15 nucleotide antisense phosphorothioate DNA molecule was prepared. A phosphorothioate DNA oligonucleotide with a randomly scrambled sequence of the same 15 nucleotides and a 2'-C-allyl P=S-modified ribozyme with randomly scrambled target binding arm sequences were synthesized as controls (by comparison to the murine c-myb cDNA sequence, the scrambled controls would not be expected to bind any region of the c-myb mRNA). Since longer phosphorothioate DNA oligonucleotides are often utilized as antisense inhibitors (for a review see Wagner, 1994 Science 372, 333), a symmetrically placed, 25 nucleotide phosphorothioate DNA antisense oligonucleotide and its scrambled sequence control were also synthesized. The ribozymes and the antisense oligonucleotides were delivered to rat smooth muscle cells as complexes with the cationic lipid, Lipofectamine, and serum-stimulated smooth muscle cell proliferation was measured subsequently.

As shown in FIG. 11, the 2'-C-allyl P=S-modified ribozyme demonstrated greater inhibition of smooth muscle cell proliferation than either of the antisense oligonucleotides. Furthermore, the scrambled arm ribozyme and inactive ribozyme controls demonstrated less non-specific inhibition than either of the scrambled sequence antisense control oligonucleotides. In fact, the non-specific inhibition demonstrated by the 25 nucleotide phosphorothioate molecule completely masked any specific effect of the antisense molecule. Similar results have been obtained with phosphorothioate DNA targeting other sites in the c-myb mRNA. Thus, a ribozyme that cleaves c-myb RNA is a more potent and more specific inhibitor of smooth muscle cell proliferation than phosphorothioate antisense DNA molecules.

Example 17

Chemically-modified Ribozymes Targeting Different Sites in the c-myb mRNA Specifically Inhibit Smooth Muscle Cell Proliferation If the observed inhibition of smooth muscle cell proliferation is mediated by ribozyme cleavage of c-myb mRNA, then other ribozymes that target the same mRNA should have the same effect. Two other ribozymes targeting two disparate sites in the c-myb mRNA (sites 549 and 1553, ribozyme Seq. ID Nos. 102 and 112) were synthesized with the 2'-C-allyl P=S modifications as described in Example 14. Inactive ribozyme controls also were synthesized corresponding to each new target sequence. Chemically-modified ribozymes targeting sites 549, 575, and 1553 were delivered to rat smooth muscle cells and their ability to inhibit serum-stimulated cell proliferation was assessed. Equivalent levels of inhibition are obtained with active ribozymes targeting sites 549, 575 and 1553 (see FIG. 12). None of the inactive ribozymes inhibited cell proliferation. Active ribozymes targeting other mRNA sequences not present in c-myb or ribozymes with scrambled arm sequences also fail to inhibit smooth muscle cell proliferation (see FIG. 12). Thus, inhibition of cell proliferation requires a catalytically active ribozyme that can bind to accessible c-myb mRNA sequences and is likely due to the reduction of c-myb mRNA levels by ribozyme cleavage.

Examples 18 and 19 describe experiments designed to determine the position and minimum number of phosphorothioate residues required for efficacy.

Example 18

Effect of Position of Phosphorothioate Linkages on Ribozyme Inhibition

Ribozymes targeting c-myb site 575 were synthesized with the 2'-C-allyl modification and with phosphorothioate linkages between various nucleotides in the ribozyme. One ribozyme contained a total of 10 phosphorothioate linkages, 5 in Stem I and 5 in Stem III, identical to the ribozyme described in Examples 14 through 17 above (referred to as 10 P=S 5' and 3' in FIG. 13A). One ribozyme contained only 5 phosphorothioate linkages in Stem III (5 P=S 3' in FIG. 13A). Another ribozyme contained 5 phosphorothioate linkages between the 6 nucleotides comprising the last base pair of stem II and the GAAA loop (5 P=S loop in FIG. 13A). The fourth ribozyme contained 5 phosphorothioate linkages in stem I (5 P=S 5' in FIG. 13A). The latter two ribozymes also were synthesized with the 3'-3' thymidine at the 3' end to help protect the ribozyme from 3' exonucleases (Ortigao et al., 1992 *Antisense Res. & Development* 2, 129; Seliger et al., Canadian Patent Application No. 2,106,819). The structure of these four different ribozymes is diagrammed in FIG. 13A. Inactive ribozyme controls were synthesized for each individual ribozyme. The active and inactive ribozymes were applied to rat smooth muscle cells as RNA/Lipofectamine complexes and their effects on cell proliferation were measured.

Referring to FIG. 13B, the ribozyme containing 5 phosphorothioate linkages in Stem I and the 3' inverted thymidine inhibited smooth muscle cell proliferation as well as the parent ribozyme with 10 total phosphorothioate linkages. None of the other ribozymes demonstrated significant differences between active and inactive controls. Therefore, the 3' inverted T can effectively substitute for the 5 phosphorothioate linkages in Stem III. Phosphorothioate linkages in the loop position lead to non-specific inhibition of smooth muscle cell proliferation, while phosphorothioate linkages in Stem I are necessary for enhanced efficacy in cells. Additionally, these results suggest that 3'-end modifications, such as iT, is desirable to minimize the amount of phosphorothioate contained in the ribozymes in order to minimize toxicity and facilitate chemical synthesis, while maintaining protection from endogenous 3'-exonuclease digestion.

Example 19

Minimizing Phosphorothioate Linkages in Stem I

Fewer phosphorothioate linkages in the ribozyme will reduce the complexity and cost of chemical synthesis. Furthermore, phosphorothioate DNA molecules are known to have some undesirable and non-specific effects on cellular functions (for a review see Wagner, supra); reducing the phosphorothioate linkages in these RNA molecules is expected to enhance their specificity. A series of ribozymes targeting c-myb were synthesized to determine how many phosphorothioate linkages in Stem I are required for optimal ribozyme activity. The ribozymes contained 5, 4, 3, 2, or 1 phosphorothioate linkage(s) in Stem I, beginning with the phosphodiester bond between the first and second nucleotides and proceeding 3'. Each ribozyme contained the 2'-O-methyl modifications, the $U_4$ 2'-C-allyl nucleotide, and the inverted T nucleotide at the 3' end as described above. Activity of each of these ribozymes was compared to the activity of the ribozyme with 10 phosphorothioate linkages, 5 each in Stems I and III (referred to as 10 P=S in FIG. 14). Active and inactive ribozymes were applied to rat smooth muscle cells as complexes with Lipofectamine and their effects on smooth muscle cell proliferation were measured in two separate experiments. The results are diagrammed in FIG. 14. Ribozymes with 10, 5, and 4 phosphorothioate linkages showed equivalent efficacy. Ribozymes with fewer than four phosphorothioate linkages also showed efficacy, but the level of inhibition of smooth muscle cell proliferation was modestly reduced.

Example 20

Varying the Length of Stems I and III

Ribozymes that cleave c-myb RNA at position 575 were synthesized with varying arm lengths. Each ribozyme contained 4 phosphorothioate linkages at the 5' end, 2'-O-methyl and 2'-C-allyl modifications and an inverted thymidine nucleotide at the 3' end as described above. FIG. 15 shows the effects of these ribozymes upon rat smooth muscle cell proliferation. Ribozymes were delivered at 100 nM with cationic lipid. Ribozymes with 6/6, 7/7 and 5/10 arms (where x/y denotes the nucleotides in Stem I/nucleotides in Stem III; see FIG. 2) all showed comparable efficacy. As shown in FIG. 15, ribozymes with longer arm lengths tended to demonstrate more non-specific inhibition (the inactive ribozyme controls with longer binding arms inhibited smooth muscle cell proliferation) when compared to ribozymes with shorter binding arms. From these data, it appears that ribozymes with 6/6, 7/7, 5/10, 10/5, 8/8 and 10/10 nucleotide arms all specifically inhibit smooth muscle cell proliferation, optimal inhibition, however, is observed with 6/6, 7/7 and 5/10 nucleotide arms.

Example 21

Ribozymes with Different Modified Nucleotides Inhibit Smooth Muscle Cell Proliferation Ribozymes containing seven nucleotides in both Stems I and III, four phosphorothioate residues at the 5' end and a 3'-3' inverted thymidine at the 3' end, were synthesized with various modified nucleotides at the $U_4$ and $U_7$ positions within the core of a HH ribozyme. All of the modified catalytic core chemistries retained ribozyme activity and demonstrated enhanced stability to serum nucleases (Usman et al., 1994 supra). The ribozyme termed U4 2'-C-allyl contains a 2'-C-allyl uridine at the $U_4$ position and a 2'-O-methyl nucleotide at the $U_7$ position. The ribozyme termed U4,U7 2'-amino contains a 2'-amino nucleotide at both U4 and U7. The ribozyme termed U4 2'-fluoro contains a 2'-fluoro-modified nucleotide at U4 and 2'-O-methyl at U7. The ribozyme termed U4 6-methyl contains a 6-methyl uridine nucleotide at U4 and 2'-O-methyl at U7. The ribozyme termed U4 deoxyabasic contains a deoxyribose moeity and lacks a base at U4 (Beigelman et al., 1994 *Bioorganic & Med. Chem. Letters* 4, 1715) and 2'-O-methyl at U7. Active and inactive versions of each of the chemically-modified ribozymes were applied to rat smooth muscle cells using Lipofectamine as described above. As diagrammed in FIG. 16, all of the nuclease-stable, chemically-modified ribozymes demonstrated significant inhibition of rat smooth muscle cell proliferation. Thus, the requirements for ribozyme activity in smooth muscle cells appear to be a catalytically core that is modified to minimize endonucleolytic degradation and modifications at the 5' and 3' ends which may prevent exonucleolytic degradation.

Chemical modifications described in this invention are meant to be non-limiting examples, and those skilled in the art will recognize that other modifications (base, sugar and phosphate modifications) to enhance nuclease stability of a ribozyme can be readily generated using standard techniques and are hence within the scope of this invention.

Example 22

Ribozyme Inhibition of Pig Smooth Muscle Cell Proliferation

Of the commonly used animal models of intimal hyperplasia after balloon angioplasty, the pig model is believed to be most predictive of human disease (Steele et al., 1985 Circ. Res. 57, 105; Ohno et al., 1994 Science 265, 781; Baringa, 1994 Science 265, 738). Therefore, we wished to assess the ability of c-myb ribozymes to inhibit pig smooth muscle cell proliferation. Yucatan pig smooth muscle cells (YSM) were obtained from Dr. Elizabeth Nabel (University of Michigan Medical Center) and were grown in Dulbecco's modified Eagle's medium as described (see Example 6). The YSM cells were starved for 72 hours in DMEM with 0.1% FBS. Active and inactive ribozymes (four phosphorothioate linkages at the 5' end, 2'-C-allyl-modified core and 3'-3' inverted thymidine at the 3' end) were applied as RNA/Lipofectamine® complexes as described in the above examples. Proliferation was stimulated with serum and assessed by BrdU incorporation. FIG. 17 shows that a ribozyme dose of as low as 75 nM can inhibit pig smooth muscle cell proliferation by as much as 60%. The same chemical modifications of the ribozymes (2'-modified, stable core, 5' phosphorothioate linkages and 3' inverted thymidine) are required to obtain significant and reproducible inhibition of pig smooth muscle cell proliferation as were shown to be required for inhibition of rat cells in the above Examples.

Example 23

Ribozyme Inhibition of Human Smooth Muscle Cell Proliferation

In Example 12, we demonstrated that a minimally modified ribozyme directed against c-myb site 549 could significantly inhibit human smooth muscle cell proliferation. The 2'-C-allyl and phosphorothioate-modified ribozyme targeting c-myb site 575 characterized above was applied to human smooth muscle cells as RNA/Lipofectamine® complexes. Inactive ribozyme and inactive, scrambled arm ribozymes were applied as controls. At 200 nM, the active ribozyme inhibits human smooth muscle proliferation by greater than 75% while the inactive ribozyme inhibits proliferation by only 38%. The ribozyme with scrambled binding arm sequences fails to inhibit. At 100 nM, the active ribozyme still demonstrates significant inhibition while neither the inactive or scramble controls inhibit cell proliferation (see FIG. 18). Thus, the active ribozyme identified in these studies mediates significant inhibition of human smooth muscle cell proliferation and represents a novel therapeutic for restenosis and/or vascular disease.

Example 24

Delivery of c-myb Ribozymes to Vessels in vivo

The ribozyme that cleaves c-myb RNA at site 575 was synthesized in two parts (Mamone, supra), the internal 5' end was labeled with $^{33}P$ using polynucleotide kinase and the two fragments were ligated with RNA ligase. The resulting RNA was an intact ribozyme with an internal $^{33}P$ label. This internally-labeled ribozyme was delivered to balloon injured rat carotid arteries as described (Simons et al., 1992 Nature 359, 67). Rats were anesthetized and the carotid artery was surgically exposed. The external carotid was dissected and a 2F Fogarty balloon catheter was inserted and directed into the carotid artery. Injury was caused by repeated (3 times) inflation and retraction of the balloon. The injured region was isolated by ligatures and a cannula was inserted in the external carotid. Ribozymes alone (two rat vessels) or ribozyme/Lipofectamine® complexes (two rat vessels) were applied to the injured vessel through the cannula and were left in the vessel for twenty minutes. After application, blood flow was restored by removal of the ligatures for five minutes and the vessels were harvested and processed as described below.

Half of the vessel was frozen in liquid nitrogen, crushed into a fine powder, and RNA was extracted using standard protocols. The extracted RNA was applied to a denaturing polyacrylamide gels and subjected to electrophoresis. Autoradiography of the gel permitted detection of the $^{33}P$ label; the amount of radioactivity in each band was quantitated using a Phosphor-imaging system. The amount of extracted and intact ribozyme was calculated by direct comparison to labeled ribozyme controls run on the same gel. The percentage of the ribozyme delivered intact could be estimated by quantifying the percentage of label that co-migrates with the intact ribozyme controls. After delivery of ribozymes in phosphate-buffered saline (PBS), 3% of the $^{33}P$ label was recovered from the rat vessels and >90% of the label was present in the form of intact ribozyme. After delivery of ribozyme in RNA/Lipofectamine complexes, 10 to 11% of the $^{33}P$ label was recovered from the rat vessels and 20 to 90% of the label was present in the form of intact ribozyme. The significant uptake of the intact ribozyme demonstrates that local delivery of modified ribozymes to arterial walls is feasible.

The other half of each vessel was fixed in PBS-buffered 2% glutaraldehyde, sectioned onto slides and coated with emulsion. After autoradiography for four days, the emulsion was developed and the sections were stained with hematoxylin and eosin by standard techniques (Simons et al., 1992 supra). Inspection of the sections showed a majority of the grains present over the medial smooth muscle cells after application of the ribozyme. Some 33p label could be detected in the underlying adventilia as well. Similar density and distribution of grains was observed when the ribozyme was delivered with or without Lipofectamine. These data demonstrate that ribozyme can penetrate the injured vessel wall and is in close apposition or within the underlying medial smooth muscle cells. Thus, therapeutic ribozymes can be locally delivered to vessels for the treatment of vascular disease.

Similar experiments were performed in pig iliofemoral vessels. After balloon injury, a ribozyme, internally labeled with $^{33}P$ as described above, was delivered with a double balloon catheter device (Nabel and Nabel, supra; Ohno et al., 1994 supra). After 20 minutes, blood flow was restored by deflating the balloons. The vessels were harvested after an additional hour or the surgical injuries were sutured and the vessels harvested one day later. Harvested vessels were sectioned, subjected to autoradiography and stained. One hour after delivery, the majority of the $^{33}P$ label could be detected in the media, overlying or within smooth muscle cells. Some label was also detected at the luminal surface of the vessel and in the adventitial tissue. One day after delivery, grains could be still be detected associated with remaining medial smooth muscle cells. No major differences in density or distribution was observed between ribozymes delivered with or without Lipofectamine®. These data demonstrate that ribozymes can be locally delivered to smooth muscle cells of injured vessels in a large animal model that is clinically relevant to human vascular disease.

Example 25

Ribozyme-mediated Decrease in the Level of c-myb RNA in Rat Smooth Muscle Cells To determine whether a ribozyme catalyzes the cleavage of c-myb RNA in a mammalian cell, applicant has used a sensitive quantitative competitive polymerase chain reaction (QCPCR) to assay the level of c-myb RNA in rat smooth muscle cells treated with either catalytically active or inactive ribozyme.

Rat smooth muscle cells (RASMC) were treated with ribozymes as described above. Following the ribozyme treatment for 4 h, cells were stimulated with 10% serum (in the presence or absence of BrdU). After 24 h, cells were harvested for further analysis. Cells, that were treated with BrdU, were assayed for proliferation as described above. Cells, that were not treated with BrdU, were used for the QCPCR assay.

The following is a brief description of the QCPCR technique used to quantitate levels of c-myb mRNA from RASMC, normalizing to the housekeeping gene, GAPDH. This method was adapted from Thompson et al, *Blood* 79: 1692, 1992. Briefly, total RNA was isolated from RASMC using the Guanidinium isothiocyanate technique of Chomczynski and Sacchi (*Analytical Biochemistry*, 162: 156, 1987). In order to construct a deletion competitor and control wild-type RNA, a cDNA clone of the rat c-myb message, referred to as pc8myb, was used. The competitor RNA comprises a deletion of 50 bases, making it smaller than the wild-type cellular RNA, and spansfrom nucleotide 428 to nucleotide 753.

A house-keeping gene, GAPDH, that is constitutively expressed by the RASMC, was used as an internal control for QCPCR assay. A deletion competitor and wild-type controls for GAPDH were made the same way as for c-myb. GAPDH-containing plasmid (pTri-GAPDH) was purchased from Ambion. The GAPDH competitor is also a deletion mutant, lacking 50 bases. The GAPDH competitor was used to quantitate the amount of this housekeeping gene in each sample, thus allowing for a confirmation of cellular RNA's integrity and for the efficiency of RNA isolation. All quantitations for the level of c-myb expression were normalized to the level of GAPDH expression in the same sample of cells.

Referring to FIG. 19, RASMC that were treated with a stabilized catalytically active 575 HH ribozyme did not proliferate well. There was greater than 70% inhibition of RASMC proliferation when compared with approximately 25% inhibition of cell proliferation by a catalytically inactive version of the 575 HH ribozyme. The level of inhibition of RASMC proliferation correlates very well with the greater than 70% decrease in the level of c-myb RNA. This shows that the inhibition of smooth muscle cell proliferation is directly mediated by the cleavage of c-myb RNA by a ribozyme in RASMC.

FIG. 20 shows what Applicant presently believes is an optimal ribozyme configuration.

Example 26

Inhibition of Smooth Muscle Cell Proliferation by 2-5A Antisense Chimera

By "2-5A antisense chimera" is meant, an antisense oligonucleotide containing a 5' phosphorylated 2'-5'-linked adenylate residues. These chimeras bind to target RNA in a sequence-specific manner and activate a cellular 2-5A-dependent ribonuclease which in turn cleaves the target RNA (Torrence et al., 1993 *Proc. Natl. Acad. Sci. USA* 90, 1300). RNAs containing 2'-5' Adenosine with a terminal 5' phosphate has been shown to activate RNAse L (Torrence et al., 1993 *Proc. Natl. Acad. Sci. USA* 90, 1300). The terminal phosphate is required for efficient activation of RNAse L. Ribozymes targeting c-myb site 575 were synthesized with 2-5A moieties on the 5' end, with and without the terminal 5' phosphate. The ribozyme-2-5A chimera was complexed with LipofectAMINE and assayed on rat aortic smooth muscle cells (RASMC) as described above.

As shown in FIG. 21, when no terminal phosphate is present, the active ribozyme [575 inactive Rz+ inactive (A)4] functions similarly to a normal active ribozyme lacking a 2-5A modification (575 active Rz). An inactive ribozyme core with 5' phosphate-2-5A [575 inactive Rz+active P(A)4] shows significant inhibition relative to the controls, but has significantly lower activity when compared with an active ribozyme. A molecule that contains both an active ribozyme core and 5' phosphate-continig 2-5A [575 active Rz+active P (A)4] shows even greater inhibition than that obtained by either mechanism individually, inhibiting the smooth muscle cell proliferation to baseline levels (0% FBS). Thus the ribozyme and 2-5A anitisense chimera together show an additive effect in inhibiting RASMC proliferation.

Use of Ribozymes That Cleave c-myb RNA to Treat Restenosis.

The above discussion demonstrates, by way of example, how ribozymes that inhibit smooth muscle cell proliferation are delivered directly, or through the use of expression vectors, to vessels. Preferably, ribozymes cleaving c-myb RNA are delivered to vessels at the time of coronary angioplasty. Local delivery during intervention can be achieved through the use of double balloon catheters, porous balloon catheters, balloon catheters coated with polymers (Riessen, R., et al., 1993, *Human Gene Therapy*, 4, 749–758), or biopolymer stents (Slepian and Schindler, U.S. Pat. No. 5,213,580). In the above examples, ribozymes were identified that could inhibit roughly half of the smooth muscle cells in culture from proliferating in response to the growth factors present in serum. A corresponding 50% (or even lower) reduction in intimal thickening will significantly improve the outcome of patients undergoing coronary angioplasty.

Use of Ribozymes Targeting c-myb to Treat Cancer

Overexpression of the c-myb oncogene has been reported in a number of cancers, including leukemias, neuroblastomas, and lung, colon, and breast carcinomas (Torelli, G., et al., 1987, *Cancer Res.*, 47, 5266–5269; Slamon, D. J., et al., 1986, *Science*, 233, 203–206; Slamon, D. J., et al., 1984, *Science*, 224, 256–262; Thiele, C. J., et al., 1988, *Mol. Cell. Biol.*, 8, 1677–1683; Griffin, C. A. and Baylin, S. B., 1985, *Cancer Res.*, 45, 272–275; Alitalo, K., et al., 1984, *Proc. Natl. Acad. Sci. USA*, 81, 4534–4538). Thus, inhibition of c-myb expression can reduce cell proliferation of a number of cancers. Indeed, in tissue culture, treatment of colon adenocarcinoma, neurectodermal, and myeloid leukemia cell lines with antisense c-myb oligonucleotides inhibits their proliferation (Melani, C., et al., 1991, *Cancer Res.*, 51, 2897–2901; Raschella, F., et al., 1992, *Cancer Res.*, 52, 4221–4226; Anfossi, G., et al., 1989, *Proc. Natl. Acad. Sci. USA*, 86, 3379–3383). Furthermore, myeloid cells from patients with chronic myelogenous leukemia and acute myelogenous leukemia are differentially sensitive to c-myb antisense oligonucleotides (Calabretta, B., et al., 1991, *Proc. Natl. Acad. Sci. USA*, 88, 2351–2355). Ratajczak, et al. (1992, *Proc. Natl. Acad. Sci. USA*, 89, 11823–11827) treated mice bearing human leukemia cells with c-myb antisense oligonucleotides and significantly prolonged their survival and reduced their tumor burden. Thus, reduction of c-myb expression in leukemic cells in tissue culture and in vivo can reduce their proliferative potential.

While the above studies demonstrated that antisense oligonucleotides can efficiently reduce the expression of c-myb in cancer cells and reduce their ability to proliferate and spread, this invention describes the first enzymatic RNAs, or ribozymes, shown to cleave c-myb RNA. Such ribozymes, with their catalytic activity and increased site specificity (see above), are likely to represent more potent and safe therapeutic molecules than antisense oligonucleotides for the treatment of cancer as well as restenosis. In the present invention, ribozymes are shown to inhibit smooth muscle cell proliferation. From those practiced in the art, it is clear from the examples described, that the same ribozymes may be delivered in a similar fashion to cancer cells to block their proliferation.

In a preferred embodiment, autologous bone marrow from patients suffering with acute myelogenous leukemia or chronic myelogenous leukemia are treated with ribozymes that cleave c-myb RNA. Ribozymes will be delivered to the autologous bone marrow cells ex vivo at 0.1 to 50 μM with or without forming complexes of the ribozymes with cationic lipids, encapsulating in liposomes or alternative delivery agents. After several days, the proliferative capacity of the leukemic cells in the patients bone marrow will be reduced. The patient's endogenous bone marrow cells will be depleted by chemical or radiation treatments and their bone marrow reconstituted with the ex vivo treated cells. In such autologous bone marrow reconstitution treatments of leukemic patients, recurrence of the disease can be caused by proliferation of leukemic cells present in the transplanted bone marrow. Significantly reducing the proliferative potential of the leukemic cells by treating with ribozymes that cleave c-myb RNA will reduce the risk of recurrent leukemia.

Diagnostic uses

Ribozymes of this invention may be used as diagnostic tools to examine genetic drift and mutations within diseased cells or to detect the presence of c-myb RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with c-myb related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., c-myb) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucletides at 5' side of cleavage site.
Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Figure 1:
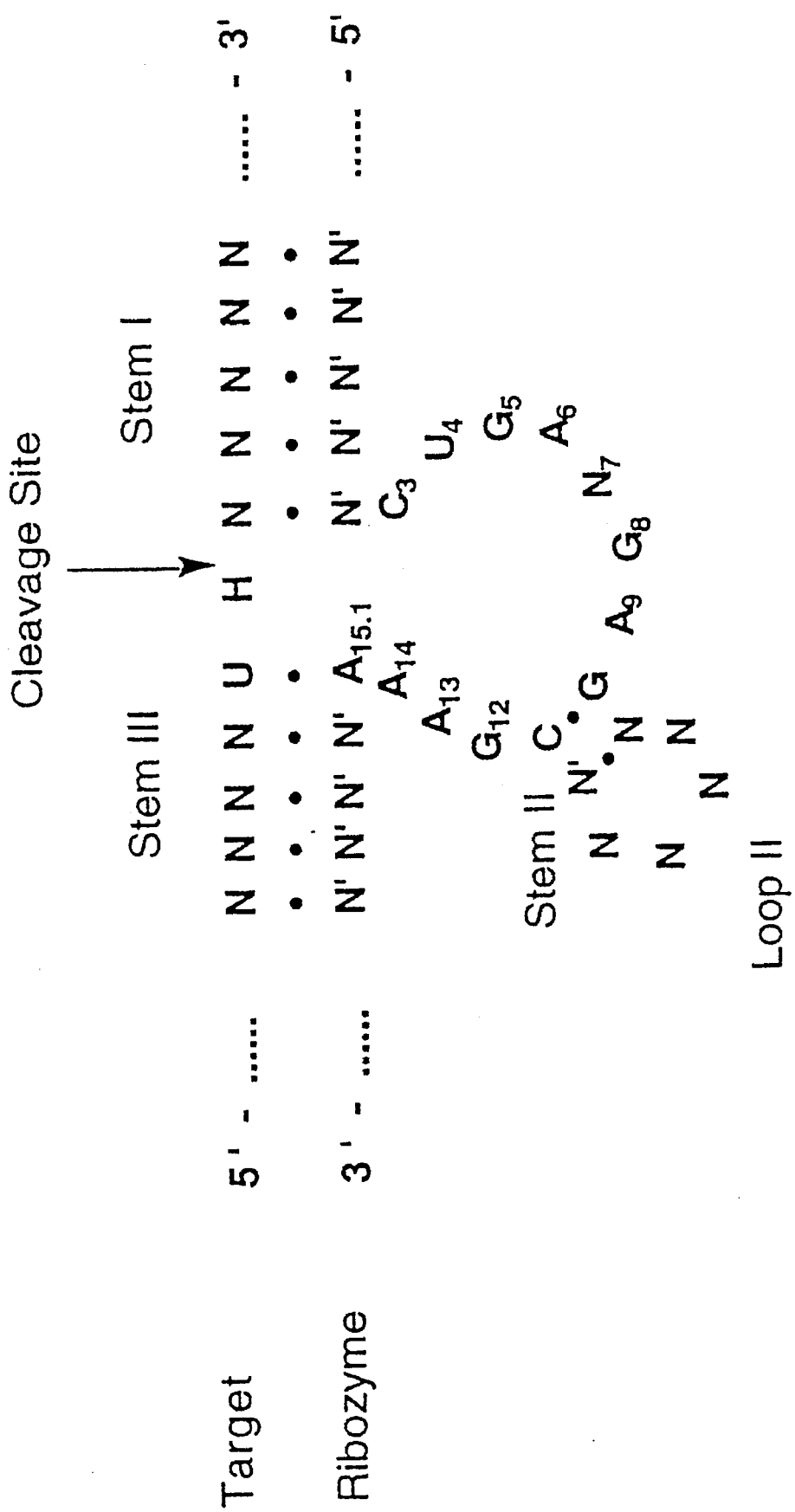

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)

Hairpin Ribozyme

Figure 3:
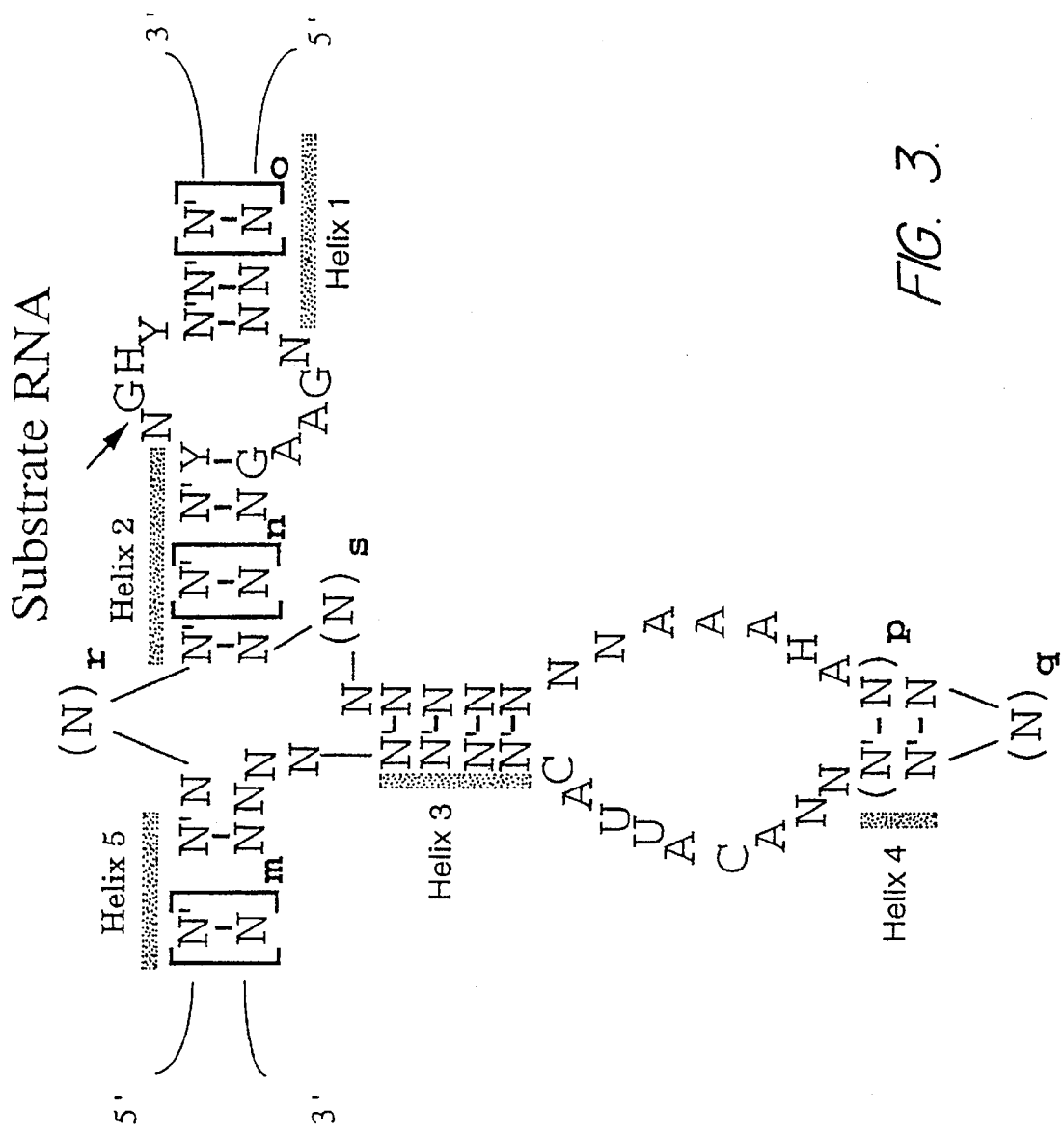

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosiac virus and chicory yellow mottle virus) which uses RNA as the infectious agent (FIG. 3).

Hepatitis Delta Virus (HDV) Ribozyme

Figure 4:
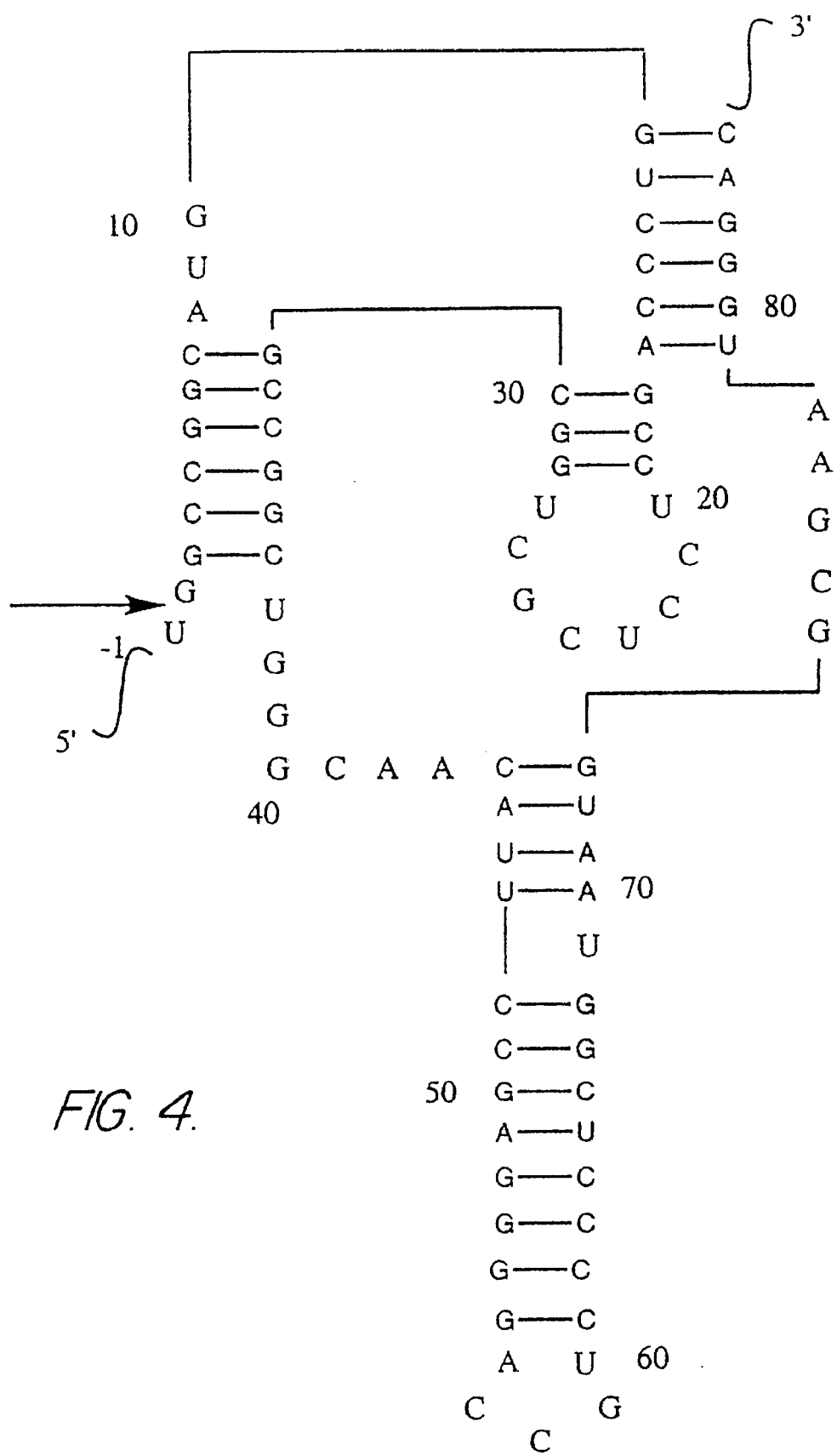
FIG. 4 is a representation of the general structure of the hepatitis delta virus ribozyme domain known in the art.

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Figure 5:
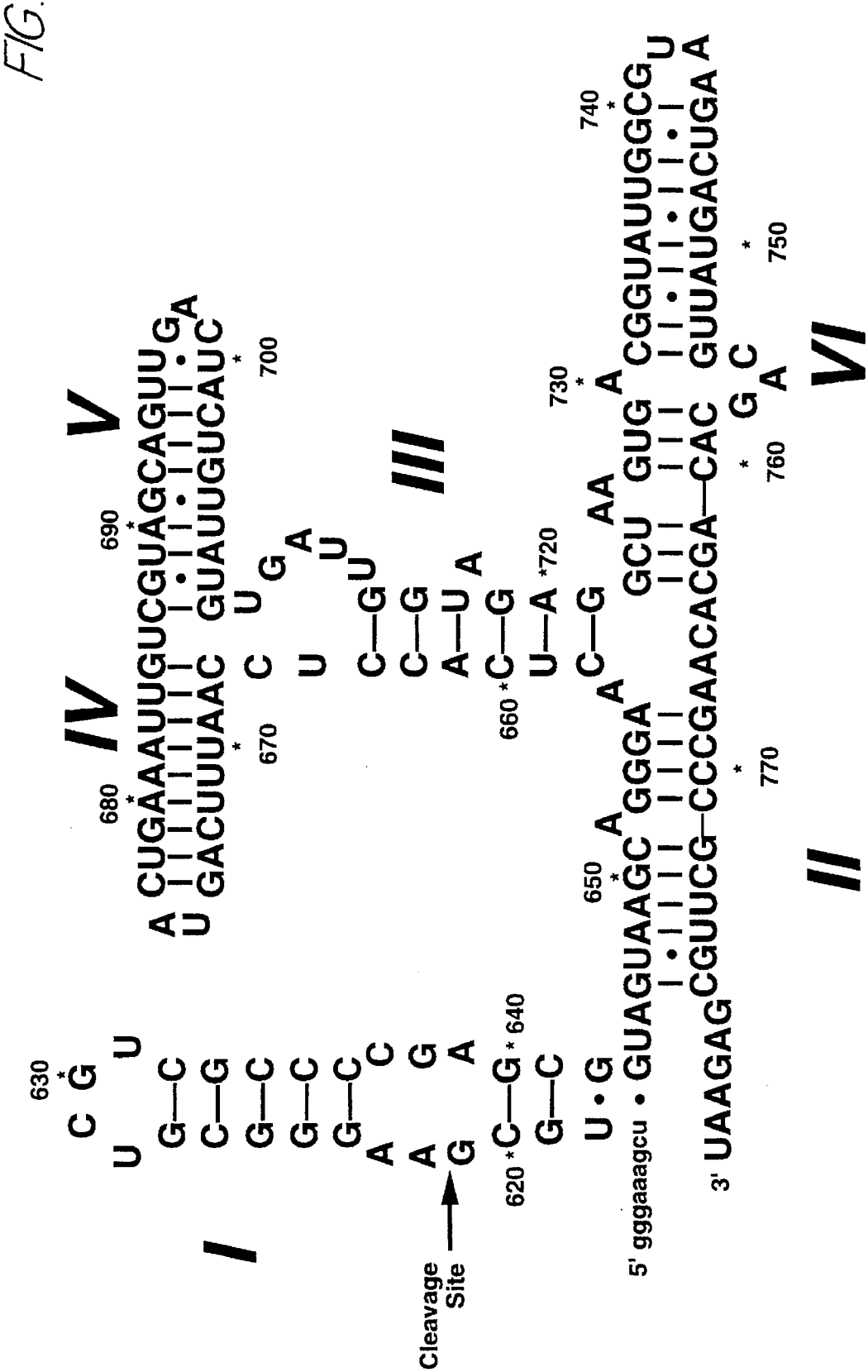
FIG. 5 is a representation of the general structure of the self-cleaving VS RNA ribozyme domain.

Size: ~144 nucleotides (at present)
Cleavage of target RNAs recently demonstrated.
Sequence requirements not fully determined.
Binding sites and structural requirements not fully determined.
Only 1 known member of this class.
Found in Neurospora VS RNA (FIG. 5).

TABLE II

Human c-myb Target Sequence

| Site | Target Sequence | Sequence I.D. No. |
|---|---|---|
| 86 | GGCGGCAGCGCCCUGCCGACGCCGGGG | ID. NO. 01 |
| 162 | CCGCGGCUCUCGGC | ID. NO. 02 |
| 195 | GCCAUGGCCCGAA | ID. NO. 03 |
| 213 | CGGCACAGCAUAUAUAGCAGUGACGAGGA | ID. NO. 04 |
| 249 | GACUUUGAGAUGUGUGACCAUGACUAUGAUGGG | ID. NO. 05 |
| 295 | CUGGAAAGCGUC | ID. NO. 06 |
| 332 | GGAAGAGGAUGAAAAACUGAAGAAG | ID. NO. 07 |
| 350 | GAAGAACUGGUGGAACAGAAUGGAAC | ID. NO. 08 |
| 383 | CUGGAAAGUUAUUGCCAA | ID. NO. 09 |
| 407 | CCCGAAUCGAACAGAUGUGCAG | ID. NO. 10 |
| 446 | GAAAGUACUAAACCCUGAG | ID. NO. 11 |
| 478 | CUUGGACCAAAGAAGAAGAUCAGAGAGUGAUA | ID. NO. 12 |
| 518 | ACAGAAAUACGGUCCGAAACGUUGGUCUG | ID. NO. 13 |
| 547 | UUAUUGCCAAGCACUUAAAGGGGAGAAUUGGAA | ID. NO. 14 |
| 611 | GAAUCCAGAAGUUAAGAA | ID. NO. 15 |
| 647 | GGAAGACAGAAUUAUUUACCAGGCACA | ID. NO. 16 |
| 674 | CAAGAGACUGGGGAACAGAU | ID. NO. 17 |
| 700 | AAAUCGCAAAGCUA | ID. NO. 18 |
| 720 | GGACGAACUGAUAAUGCUAUCAAGAACC | ID. NO. 19 |
| 748 | ACUGGAAUUCUACAAUGCGUCGGAAGGUCGAACA | ID. NO. 20 |
| 816 | CAGCCAGCAGUGGCCACAA | ID. NO. 21 |
| 852 | CAUUUGAUGGGUUUUGCUCAGGCUCCGCCUACA | ID. NO. 22 |
| 885 | GCUCAACUCCCUGCCACUGGCCAGCCC | ID. NO. 23 |
| 918 | AACAACGACUAUUCCUAUUACCACA | ID. NO. 24 |
| 954 | CAAAAUGUCUCCAGUCAUGUUCCAUACCCU | ID. NO. 25 |
| 998 | AAAUAUAGUCAAUGUCCCUCAGCCAGCUGCCGCA | ID. NO. 26 |
| 1039 | AGAGACACUAUAAUGAUGAAGACCCUGAGAAGGA | ID. NO. 27 |
| 1073 | AAAGCGAAUAAAGGAAUUAGAAUUG | ID. NO. 28 |
| 1098 | CUCCUAAUGUCAACCGA | ID. NO. 29 |
| 1120 | AGCUAAAAGGACAGCAGGUGCUACCAACACAGAA | ID. NO. 30 |
| 1161 | CCCGGGUGGCACAGCACCACCAUUGCCGACCACA | ID. NO. 31 |
| 1237 | AACACCACUCCACUCCAUCUCUGCCAGCGGAUCC | ID. NO. 32 |
| 1279 | UACCUGAAGAAA | ID. NO. 33 |
| 1311 | AUGAUCGUCCACCAGGGCACCAUU | ID. NO. 34 |
| 1366 | CAGAAACACUCCAAUUUA | ID. NO. 35 |
| 1418 | AAACUCAGACU | ID. NO. 36 |
| 1434 | AUGCCUUCUUUAAC | ID. NO. 37 |
| 1480 | UUACAACACCA | ID. NO. 38 |
| 1515 | ACUCAAAAGGAAAAUACUGUUUUUAGAACCC | ID. NO. 39 |
| 1546 | CAGCUAUCAAAAGGUCAAUCUUAGAAAGCU | ID. NO. 40 |
| 1576 | CUCCAAGAACUCCUACACCAUUCAA | ID. NO. 41 |
| 1601 | ACAUGCACUUGCAGCUCAAGAA | ID. NO. 42 |
| 1630 | UACGGUCCCUGAAGAUGCUACCUCAGA | ID. NO. 43 |
| 1657 | CACCCUCUCAUCUAGUAGAAGAUCUGCAGGA | ID. NO. 44 |
| 1693 | UCAAACAGGAAUCUGAUGAAUCUGGA | ID. NO. 45 |
| 1735 | AAGAAAAUGGA | ID. NO. 46 |
| 1751 | CUUACUGAAGAAAAUCAAACAAGA | ID. NO. 47 |
| 1780 | AAUCUCCAACUGAUAAAUCAG | ID. NO. 48 |
| 1813 | GCUCACACCACUGGGA | ID. NO. 49 |
| 1864 | CCUCGCCUGUGCGAGAUGCACCGAAUAUUC | ID. NO. 50 |
| 1913 | GGCACCAGCAUCAGAAGAUGAAGAC | ID. NO. 51 |
| 1951 | CAUUUACAGUACC | ID. NO. 52 |
| 1975 | CCCUGGCGAGCCCCUUGCA | ID. NO. 53 |
| 1994 | GCCUUGUAGCAGUACCUGGGA | ID. NO. 54 |
| 2059 | GUCAAGCUCGUAAAUACGUGAA | ID. NO. 55 |
| 2142 | GAACAGUUCAA | ID. NO. 56 |
| 2181 | AUGAAACUUUUCAU | ID. NO. 57 |
| 2304 | AAAAUAAAUAACAGUC | ID. NO. 58 |
| 2340 | UGAAUUGUAGCC | ID. NO. 59 |
| 2357 | UUAAUAUCUUAAU | ID. NO. 60 |
| 2399 | AUUUAUCUGGUAUUUAAAGGAUCCAACAGAUC | ID. NO. 6,1 |
| 2483 | CCAGUAUUUCA | ID. NO. 62 |
| 2499 | CUCGAUCACUAAACAUAUG | ID. NO. 63 |
| 2518 | CAUAUAUUUUUAAAAAUC | ID. NO. 64 |
| 2767 | UGCUAUGGUCUUAGCCU | ID. NO. 65 |
| 2799 | AGUAUCAGAGG | ID. NO. 66 |
| 2849 | UAGGUAAUUGACUAU | ID. NO. 67 |
| 2871 | UAUUUCAGACUUUUAAUUUUAUAUAUAUAUACA | ID. NO. 68 |
| 2920 | CAAUACAUUUGAAAACUUGUUUGGGAGACUCUGC | ID. NO. 69 |
| 2964 | GUGGUUUUUUUGUUAUUGUUGGUUU | ID. NO. 70 |
| 3008 | UUCUUUUUUGGGAGAU | ID. NO. 71 |
| 3040 | CUAUGUUUUGUUUUG | ID. NO. 72 |
| 3060 | AGCCUGACUGUUUUAUA | ID. NO. 73 |
| 3089 | UCGAUUUGAUC | ID. NO. 74 |
| 3145 | UGGAUCCUGUGUU | ID. NO. 75 |

TABLE II-continued

Human c-myb Target Sequence

| Site | Target Sequence | Sequence I.D. No. |
|---|---|---|
| 3184 | UUGAUAGCCAGUCACUGCCUUAAGA | ID. NO. 76 |
| 3209 | ACAUUUGAUGCAAGAUGGCCAGCACU | ID. NO. 77 |
| 3252 | CGGUGUACUUACUGCC | ID. NO. 78 |

TABLE III

Sequences of ribozymes used in these studies.

| Target Site | Sequence ID No. | Ribozyme Sequence |
|---|---|---|
| | | Hammerhead ribozymes with 7 nucleotide binding arms |
| 310 | 101 | UUUCCCCCUGAUGAGGCCGAAAGGCCGAAAGUGACG |
| 549 | 102 | UUGGCAACUGAUGAGGCCGAAAGGCCGAAAACAGAC |
| 551 | 103 | GCUUGGCCUGAUGAGGCCGAAAGGCCGAAAUAACAG |
| 575 | 104 | GCUUUCCUGAUGAGGCCGAAAGGCCGAAAUUCUCC |
| 634 | 105 | UGUCCAGCUGAUGAGGCCGAAAGGCCGAAAGGUUUU |
| 738 | 106 | UUCUUGACUGAUGAGGCCGAAAGGCCGAAAGCAUUA |
| 839 | 107 | UCUUCUGCUGAUGAGGCCGAAAGGCCGAAAAGCUCG |
| 936 | 108 | AUGUGGUCUGAUGAGGCCGAAAGGCCGAAAUAGGAA |
| 1017 | 109 | GCCGGCUCUGAUGAGCGCGAAAGCGCGAAAGGGACG |
| 1082 | 110 | GCUCCUUCUGAUGAGGCCGAAAGGCCGAAAUUCGCU |
| 1363 | 111 | UUCUGCACUGAUGAGGCCGAAAGGCCGAAAUUCUAA |
| 1553 | 112 | ACCUUUUCUGAUGAGGCCGAAAGGCCGAAAUAGCUG |
| 1597 | 113 | AUGUUUGCUGAUGAGGCCGAAAGGCCGAAAUGGUGU |
| 1598 | 114 | CAUGUUUCUGAUGAGGCCGAAAGGCCGAAAAUGGUG |
| 1635 | 115 | UUCAGGGCUGAUGAGGCCGAAAGGCCGAAACCGUAU |
| 1721 | 116 | CAGCAACCUGAUGAGGCCGAAAGGCCGAAAUUCCAG |
| 1724 | 117 | ACUCAGCCUGAUGAGGCCGAAAGGCCGAAACAAUUC |
| 1895 | 118 | AGCUUGUCUGAUGAGGCCGAAAGGCCGAAAGAAUAU |
| 1909 | 119 | UGUCAUUCUGAUGAGGCCGAAAGGCCGAAAAACAGA |
| 1943 | 120 | CUUUGAGCUGAUGAGGCCGAAAGGCCGAAACAUUGU |
| | | Bimolecular Hairpin Ribozymes |
| 1632[a] | 121 | 5' Fragment: UCAGGGAGAAGUAUACCAGAGAAACACACGCG |
| | | 3' Fragment: CGCGUGGUACAUUACCUGGUA |
| 2231[a] | 122 | 5' Fragment: GCUCUCAGAAGUUGACCAGAGAAACACACGCG |
| | | 3' Fragment: CGCGUGGUACAUUACCUGGUA |
| | | Hammerhead riboyzmes with 6, 8, 9, 10, and 12 nucleotide binding arms |
| 575 6/6[b] | 123 | CUUUCCCUGAUGAGGCCGAAAGGCCGAA AUUCUC |
| 575 8/8 | 124 | UGUUUCCCUGAUGAGGCCGAAAGGCCGAA AUUCUCCC |
| 575 9/9 | 125 | CUGCUUUCCCUGAUGAGGCCGAAAGGCCGAA AUUCUCCCU |
| 575 10/10 | 126 | ACUGCUUUCCCUGAUGAGGCCGAAAGGCCGAA AUUCUCCCUU |
| 575 12/12 | 127 | ACACUGCUUUCCCUGAUGAGGCCGAAAGGCCGAA AUUCUCCCUUUU |
| 549 12/12 | 128 | AGUGCUUGGCAACUGAUGAGGCCGAAAGGCCGAA AACAGACCAACG |
| 1553 12/12 | 129 | GAUUGACCUUUUCUGAUGAGGCCGAAAGGCCGAA AUAGCUGGAGUU |

[a]The hairpin ribozymes were synthesized in two pieces as indicated. The two oligonucleotides were annealed and tested for activity against the c-myb RNA as described above. See Mamone, Ribozyme synthesis, filed May 11, 1992, U.S.S.N. 07/882,689, hereby incorporated by reference herein.
[b]Designation of the ribozymes with different arm lengths is a/b where (a) represents the nucleotides in stem I and (b) represents the nucleotides in stem III (see FIG. 1).

TABLE IV

Ribozyme catalyzed cleavage of c-myb RNA

| Cleavage Site | Sequence ID No. | Target sequence | % Cleavage Mouse c-myb RNA | % Cleavage Human c-myb RNA |
|---|---|---|---|---|
| Hammerhead Sites | | | | |
| 310 | 79 | CGUCACU U GGGGAAA | 28.5 | 0.1 |
| 549 | 80 | GUCUGUU A UUGCCAA | 87.4 | 91.6 |
| 551 | 81 | CUGUUAU U GCCAAGC | 56.8 | 82.4 |
| 575 | 82 | GGAGAAU U GGAAAAC | 93.9 | 91.3 |
| 634 | 83 | AAAACCU C CUGGACA | 68.4 | 87.1 |
| 738 | 84 | UAAUGCU A UCAAGAA | 78.1 | 0.01 |
| 839 | 85 | CAAGCUU C CAGAAGA | 27.2 | 0.01 |
| 936 | 86 | UUCCUAU U ACCACAU | 61.8 | 60.6 |
| 1017 | 97 | UGUCCCU C AGCCAGC | 40.3 | 0.1 |
| 1082 | 88 | AGCGAAU A AAGGAAU | 55.2 | 89.2 |
| 1363 | 89 | UUAGAAU U UGCAGAA | 11.6 | 0.1 |
| 1553 | 90 | CAGCUAU C AAAAGGU | 87.1 | 92.5 |
| 1597 | 91 | ACACCAU U CAAACAU | 71.2 | 62.7 |
| 1598 | 92 | CACCAUU C AAACAUG | 79.6 | 85.5 |
| 1635 | 93 | AUACGGU C CCCUGAA | 84.4 | 82.3 |
| 1721 | 94 | CUGGAAU U GUUGCUG | 62.1 | 79.3 |
| 1724 | 95 | GAAUUGU U GCUGAGU | 65.6 | 86 |
| 1895 | 96 | AUAUUCU U ACAAGCU | 79.1 | 66.2 |
| 1909 | 97 | UCCGUUU U AAUGGCA | 31.1 | 0.1 |
| 1943 | 98 | ACAAUGU U CUCAAAG | 66.1 | 80 |
| Hairpin Ribozymes | | | | |
| 1632 | 99 | ACG GUCC CCUGAAG | 92.8 | 84.6 |
| 2231 | 100 | ACA GUUG AGAGCAG | 0.1 | 0.1 |

*The nucleotide numbers given correspond to the nucleotide just 5' of the ribozyme cleavage site in the human c-myb sequence taken from Westin, et al., supra (GenBank Accession No. X52125). All but two of the sequences (310; I.D. No. 79 and 2231; I.D. No. 100) overlap sequences in Table I.

TABLE V

Comparison of the effects six hammerhead ribozymes, that cleave c-myb RNA, on smooth muscle cell proliferation.

| Ribozyme Site | Inactive Ribozyme % Cell Proliferation | Active Ribozyme % Cell Proliferation | % Inhibition (Active vs. Inactive) |
|---|---|---|---|
| 549 | 68 ± 1 | 59.5 ± 1.5 | 14 ± 4 |
| 575 | 66.5 ± 0.5 | 54.5 ± 1.5 | 21 ± 3 |
| 1553 | 68.5 ± 0.5 | 52 ± 1 | 28 ± 1 |
| 1597 | 66 ± 1 | 57 ± 3 | 16 ± 7 |
| 1598 | 67 ± 1 | 58.5 ± 0.5 | 1.5 ± 1 |
| 1635 | 62.5 ± 2.5 | 64 ± 1 | 0 |

TABLE VI

Dose Response of c-myb Hairpin Ribozyme 1632

| Ribozyme Dose (μM) | Control Ribozyme % Proliferation | Ribozyme 1632 % Proliferation | % Inhibition (vs. control) |
|---|---|---|---|
| 0.05 | 86.5 ± 1.5 | 88 ± 5 | 0 |
| 0.15 | 89.5 ± 1.5 | 78.5 ± 2.5 | 10 ± 5 |
| 0.45 | 87.5 ± 1 | 66.5 ± 1.5 | 25 ± 4 |

TABLE VII

Dose Response of c-myb Hammerhead Ribozymes 575 and 549

| Ribozyme Dose (μM) | Control Ribozyme % cells in S phase | Ribozyme 575 % cells in S phase | Ribozyme 575 % Inhibition (vs. control) | Ribozyme 549 % cells in S phase | Ribozyme 549 % Inhibition (vs. control) |
|---|---|---|---|---|---|
| 0.05 | 89 ± 5 | 77.5 ± 1.5 | 14 ± 8 | 92 ± 1 | 0 |
| 0.15 | 90 ± 1 | 68.5 ± 1.5 | 26 ± 2 | 84 ± 2 | 9 ± 4 |
| 0.45 | 91.5 ± 0.5 | 59 ± 5 | 38 ± 7 | 76.5 ± 2.5 | 18 ± 5 |

TABLE VIII

| Ribozyme Dose (μM) | Inactive Ribozyme 575 % cells in S phase | Active Ribozyme 575 % cells in S phase | % Inhibition (vs. inactive) |
|---|---|---|---|
| Delivery with DMRIE/DOPE | | | |
| 0.075 | 79 ± 6 | 74.5 ± 1.5 | 6 ± 6 |
| 0.15 | 79.5 ± 0.5 | 67 ± 1 | 17 ± 4 |
| 0.30 | 77 ± 1 | 57 ± 2 | 28 ± 5 |
| Delivery with Lipofectamine | | | |
| 0.075 | 81 ± 1 | 83 ± 1 | 0 |
| 0.15 | 79 ± 3 | 71 ± 1 | 11 ± 4 |
| 0.30 | 82 ± 1 | 68.5 ± 1.5 | 18 ± 4 |
| 0.60 | 75 ± 1 | 59.5 ± 3.5 | 22 ± 7 |

TABLE IX

Arm Length Variations of c-myb Hammerhead Ribozyme 575

| Arm Length (base-pairs) | % cells in S phase | % Inhibition (vs. Inactive 7/7) |
|---|---|---|
| 6/6 | 62 ± 1 | 4 ± 4 |
| 7/7 | 60 ± 1 | 7 ± 3 |
| 8/8 | 60.5 ± 0.5 | 6 ± 2 |
| 9/9 | 53.5 ± 0.5 | 18 ± 2 |
| 10/10 | 55 ± 1 | 16 ± 4 |
| 12/12 | 48 ± 1 | 28 ± 3 |

TABLE X

Hammerhead ribozymes with 7 vs. 12-nucleotide binding arms targeting three different sites.

| Ribozyme Target Site | Length of Binding Arms | Inactive Ribozyme (% Cell Proliferation) | Active Ribozyme (% Cell Proliferation) | % Inhibition (Active vs. Inactive) |
|---|---|---|---|---|
| 575 | 7/7 | 51.5 ± 0.5 | 43 ± 0.5 | 24 ± 5 |
| 575 | 12/12 | 50.5 ± 3.5 | 37 ± 0.5 | 37 ± 4 |
| 549 | 7/7 | 49.5 ± 1.5 | 44.5 ± 1.5 | 21 ± 7 |
| 659 | 12/12 | 48.5 ± 1.5 | 35 ± 2 | 41 ± 7 |
| 1553 | 7/7 | 49.5 ± 0.5 | 43.5 ± 2.5 | 23 ± 9 |
| 1553 | 12/12 | 49 ± 1 | 33.5 ± 1.5 | 45 ± 6 |

TABLE XI

Effect of chloroquine on ribozyme inhibition of smooth muscle cell proliferation.

| Ribozyme | Chloroquine (μM) | Inactive Ribozyme (% Cell Proliferation) | Active Ribozyme (% Cell Proliferation) | % Inhibition (Active vs. Inactive) |
|---|---|---|---|---|
| 575, 12/12 | 0 | 81.8 ± 0.5 | 74 ± 1 | 10 ± 2 |
| 575, 12/12 | 10 | 83 ± 4 | 62.5 ± 0.5 | 28 ± 6 |

TABLE XII

Inhibition of Human Aortic Smooth Muscle Cells by c-myb Ribozyme 549

| Ribozyme Dose (μM) | Inactive Ribozyme % Proliferation | Active Ribozyme % Proliferation | % Inhibition (active vs. inactive) |
|---|---|---|---|
| 0.075 | 55 ± 2 | 40.5 ± 4.5 | 30 ± 13 |
| 0.15 | 53 ± 10 | 42 ± 1 | 23 ± 23 |
| 0.30 | 53 ± 7 | 32.5 ± 4.5 | 44 ± 22 |

TABLE XIII

Inhibition of Rat Smooth Muscle Cell Proliferation by Direct Addition of a Chemically-Modified c-myb Ribozyme 575

| Ribozyme Dose (μM) | Inactive Ribozyme % Proliferation | Active Ribozyme % Proliferation | % Inhibition (active vs. inactive) |
|---|---|---|---|
| 0.22 | 42 ± 3 | 36 ± 0.5 | 15 ± 8 |
| 0.67 | 48 ± 3 | 35 ± 2 | 28 ± 9 |
| 2.0 | 52 ± 5 | 25 ± 1 | 54 ± 7 |

TABLE XIV

Human c-myb Hairpin Ribozyme and Target Sequences

| Position | Ribozyme Sequenc | | | | Target | | |
|---|---|---|---|---|---|---|---|
| 104 | CCCUCCCC | AGAA | GCGC | ACCAGAGAAACACACGUUGUGGUACAUUACCUGGUA | GCGCA | GCC | GGGGAGGG |
| 148 | ACCGACCG | AGAA | GCCG | ACCAGAGAAACACACGUUGUGGUACAUUACCUGGUA | CGGCA | GCC | CGGUCGGU |
| 185 | GCGCGGCG | AGAA | GCGG | ACCAGAGAAACACACGUUGUGGUACAUUACCUGGUA | CCGCC | GCC | CGCCGCGC |
| 528 | ACGUUUCG | AGAA | GUAU | ACCAGAGAAACACACGUUGUGGUACAUUACCUGGUA | AUACG | GUC | CGAAACGU |
| 715 | UUCGUCCA | AGAA | GUAG | ACCAGAGAAACACACGUUGUGGUACAUUACCUGGUA | CUACU | GCC | UGGACGAA |
| 1025 | AUGGCUGC | AGAA | GCUG | ACCAGAGAAACACACGUUGUGGUACAUUACCUGGUA | CAGCU | GCC | GCAGCCAU |
| 1187 | CUGGUGUG | AGAA | GCAA | ACCAGAGAAACACACGUUGUGGUACAUUACCUGGUA | UUGCC | GAC | CACACCAG |
| 1532 | GUUCUAAA | AGAA | GUAU | ACCAGAGAAACACACGUUGUGGUACAUUACCUGGUA | AUACU | GUU | UUUAGAAC |
| 1632 | CUUCAGGG | AGAA | GUAU | ACCAGAGAAACACACGUUGUGGUACAUUACCUGGUA | AUACG | GUC | CCCUGAAG |
| 1836 | GGUAUUCA | AGAA | GUCC | ACCAGAGAAACACACGUUGUGGUACAUUACCUGGUA | GGACA | GUC | UGAAUACC |
| 1852 | UCUGCGUG | AGAA | GUUG | ACCAGAGAAACACACGUUGUGGUACAUUACCUGGUA | CAACU | GUU | CACGCAGA |
| 1861 | CAGGCGAG | AGAA | GCGU | ACCAGAGAAACACACGUUGUGGUACAUUACCUGGUA | ACGCA | GAC | CUCGCCUG |
| 1993 | UGCUACAA | AGAA | GCAA | ACCAGAGAAACACACGUUGUGGUACAUUACCUGGUA | UUGCA | GCC | UUGUAGCA |
| 2231 | CUGCUCUC | AGAA | GUUG | ACCAGAGAAACACACGUUGUGGUACAUUACCUGGUA | CAACA | GUU | GAGAGCAG |
| 2316 | UUAGGUAA | AGAA | GUUA | ACCAGAGAAACACACGUUGUGGUACAUUACCUGGUA | UAACA | GUC | UUACCUAA |
| 3068 | AAUUAUAA | AGAA | GUCA | ACCAGAGAAACACACGUUGUGGUACAUUACCUGGUA | UGACU | GUU | UUAUAAUU |
| 3138 | AUCCAUGC | AGAA | GUUC | ACCAGAGAAACACACGUUGUGGUACAUUACCUGGUA | GAACU | GUU | GCAUGGAU |
| 3199 | GUUCUUAA | AGAA | GUGA | ACCAGAGAAACACACGUUGUGGUACAUUACCUGGUA | UCACU | GCC | UUAAGAAC |
| 3264 | UGCUACAA | AGAA | GUAA | ACCAGAGAAACACACGUUGUGGUACAUUACCUGGUA | UUACU | GCC | UUGUAGCA |

TABLE XV

Human c-myb Hammerhead Ribozyme and Target Sequences
(REVISED)

| nt. | Target Seqence | Seq. ID No. | HH Ribozyme Seqence | Seq. ID No. |
|---|---|---|---|---|
| 15 | AACCUGUU U CCUCCUCC | 170 | GGAGGAGG CUGAUGAGGCCGAAAGGCCGAA AACAGGUU | 171 |
| 16 | ACCUGUUU C CUCCUCCU | 172 | AGGAGGAG CUGAUGAGGCCGAAAGGCCGAA AAACAGGU | 173 |
| 19 | UGUUUCCU C CUCCUCCU | 174 | AGGAGGAG CUGAUGAGGCCGAAAGGCCGAA AGGAAACA | 175 |
| 22 | UUCCUCCU C CUCCUUCU | 176 | AGAAGGAG CUGAUGAGGCCGAAAGGCCGAA AGGAGGAA | 177 |
| 25 | CUCCUCCU C CUUCCUCU | 178 | AGAGAGGAG CUGAUGAGGCCGAAAGGCCGAA AGGAGGAG | 179 |
| 28 | CUCCUCCU U CUCCUCCU | 180 | AGGAGGAG CUGAUGAGGCCGAAAGGCCGAA AGGAGGAG | 181 |
| 29 | UCCUCCUU C UCCUCCUC | 182 | GAGGAGGA CUGAUGAGGCCGAAAGGCCGAA AAGGAGGA | 183 |
| 31 | CUCCUUCU C CUCCUCCU | 184 | AGGAGGAG CUGAUGAGGCCGAAAGGCCGAA AGAAGGAG | 185 |
| 34 | CUUCUCCU C CUCCUCCG | 186 | CGGAGGAG CUGAUGAGGCCGAAAGGCCGAA AGGAGAAG | 187 |
| 37 | CUCCUCCU C CUCCGUCA | 188 | UCACGGAG CUGAUGAGGCCGAAAGGCCGAA AGGAGGAG | 189 |
| 40 | CUCCUCCU C CGUCACCU | 190 | AGGUCACG CUGAUGAGGCCGAAAGGCCGAA AGGAGGAG | 191 |
| 49 | CGUGACCU C CUCCUCCU | 192 | AGGAGGAG CUGAUGAGGCCGAAAGGCCGAA AGGUCACG | 193 |
| 52 | GACCUCCU C CUCCUCUU | 194 | AAGAGGAG CUGAUGAGGCCGAAAGGCCGAA AGGAGGUC | 195 |
| 55 | CUCCUCCU C CUCUUUCU | 196 | AGAAAGAG CUGAUGAGGCCGAAAGGCCGAA AGGAGGAG | 197 |
| 58 | CUCCUCCU C UUUCUCCU | 198 | AGGAGAAA CUGAUGAGGCCGAAAGGCCGAA AGGAGGAG | 199 |
| 60 | CCUCCUCU U UCUCCUGA | 200 | UCAGGAGA CUGAUGAGGCCGAAAGGCCGAA AGAGGAGG | 201 |
| 61 | CUCCUCUU U CUCCUGAG | 202 | CUCAGGAG CUGAUGAGGCCGAAAGGCCGAA AAGAGGAG | 203 |
| 62 | UCCUCUUU C UCCUGAGA | 204 | UCUCAGGA CUGAUGAGGCCGAAAGGCCGAA AAAGAGGA | 205 |
| 64 | CUCUUUCU C CUGAGAAA | 206 | UUUCUCAG CUGAUGAGGCCGAAAGGCCGAA AGAAAGAG | 207 |
| 75 | GAGAAACU U CGCCCCAG | 208 | CUGGGGCG CUGAUGAGGCCGAAAGGCCGAA AGUUUCUC | 209 |
| 76 | AGAAACUU C GCCCCAGC | 210 | GCUGGGGC CUGAUGAGGCCGAAAGGCCGAA AAGUUUCU | 211 |
| 170 | CCGCGGCU C UCGCGGAG | 212 | CUCCGCGA CUGAUGAGGCCGAAAGGCCGAA AGCCGCGG | 213 |
| 172 | GCGGCUCU C GCGGAGCC | 214 | GGCUCCGC CUGAUGAGGCCGAAAGGCCGAA AGAGCCGC | 215 |
| 224 | CACAGCAU A UAUAGCAG | 216 | CUGCUAUA CUGAUGAGGCCGAAAGGCCGAA AUGCUGUG | 217 |
| 226 | CAGCAUAU A UAGCAGUG | 218 | CACUGCUA CUGAUGAGGCCGAAAGGCCGAA AUAUGCUG | 219 |
| 228 | GCAUAUAU A GCAGUGAC | 220 | GUCACUGC CUGAUGAGGCCGAAAGGCCGAA AUAUAUGC | 221 |
| 253 | UGAGGACU U UGAGAUGU | 222 | ACAUCUCA CUGAUGAGGCCGAAAGGCCGAA AGUCCUCA | 223 |
| 254 | GAGGACUU U GAGAUGUG | 224 | CACAUCUC CUGAUGAGGCCGAAAGGCCGAA AAGUCCUC | 225 |
| 274 | CCAUGACU A UGAUGGGC | 226 | GCCCAUCA CUGAUGAGGCCGAAAGGCCGAA AGUCAUGG | 227 |
| 287 | GGGCUGCU U CCCAAGUC | 228 | GACUUGGG CUGAUGAGGCCGAAAGGCCGAA AGCAGCCC | 229 |
| 288 | GGCUGCUU C CCAAGUCU | 230 | AGACUUGG CUGAUGAGGCCGAAAGGCCGAA AAGCAGCC | 231 |
| 310 | GCGUCAUC U GGGGAAAA | 232 | UUUUCCCC CUGAUGAGGCCGAAAGGCCGAA AGUGACGC | 233 |
| 393 | GGAAAGUU A UUGCCAAU | 234 | AUUGGCAA CUGAUGAGGCCGAAAGGCCGAA AACUUUCC | 235 |
| 395 | AAAGUUAU U GCCAAUUA | 236 | UAAUUGGC CUGAUGAGGCCGAAAGGCCGAA AUAACUUU | 237 |
| 402 | UUGCCAAU U AUCUCCCG | 238 | CGGGAGAU CUGAUGAGGCCGAAAGGCCGAA AUUGGCAA | 239 |
| 403 | UGCCAAUU A UCCUCCGA | 240 | UCGGGAGA CUGAUGAGGCCGAAAGGCCGAA AAUUGGCA | 241 |
| 405 | CCAAUUAU C UCCCGAAU | 242 | AUUCGGGA CUGAUGAGGCCGAAAGGCCGAA AUAAUUGG | 243 |
| 497 | AAUUAUCU C CCGAAUCG | 244 | CGAUUCGG CUGAUGAGGCCGAAAGGCCGAA AGAUAAUU | 245 |
| 414 | UCCCGAAU C GAACAGAU | 246 | AUCUGUUC CUGAUGAGGCCGAAAGGCCGAA AUUCGGGA | 247 |
| 455 | AAAGUACU A AACCCUGA | 248 | UCAGGGUU CUGAUGAGGCCGAAAGGCCGAA AGUACUUU | 249 |
| 467 | CCUGAGCU C AUCAAGGG | 250 | CCCUUGAU CUGAUGAGGCCGAAAGGCCGAA AGCUCAGG | 251 |
| 470 | GAGCUCAU C AAGGGUCC | 252 | GGACCCUU CUGAUGAGGCCGAAAGGCCGAA AUGAGCUC | 253 |
| 480 | AGGGUCCU U GGACCAAA | 254 | UUUGGUCC CUGAUGAGGCCGAAAGGCCGAA AGGACCCU | 255 |
| 498 | AAGAAGAU C AGAGAGUG | 256 | CACUCUCU CUGAUGAGGCCGAAAGGCCGAA AUCUUCUU | 257 |
| 509 | AGAGUGAU A GAGCUUGU | 258 | ACAAGCUC CUGAUGAGGCCGAAAGGCCGAA AUCACUCU | 259 |
| 515 | AUAGAGCU U GUACAGAA | 260 | UUCUGUAC CUGAUGAGGCCGAAAGGCCGAA AGCUCUAU | 261 |
| 526 | ACAGAAAU A CGGUCCGA | 262 | UCGGACCG CUGAUGAGGCCGAAAGGCCGAA AUUUCUGU | 263 |
| 549 | GGUCUGUU A UUGCCAAG | 264 | CUUGGCAA CUGAUGAGGCCGAAAGGCCGAA AACAGACC | 265 |
| 551 | UCUGUUAU U GCCAAGCA | 266 | UGCUUGGC CUGAUGAGGCCGAAAGGCCGAA AUAACAGA | 267 |
| 562 | CAAGCACU U AAAGGGGA | 268 | UCCCCUUU CUGAUGAGGCCGAAAGGCCGAA AGUGCUUG | 269 |
| 563 | AAGCACUU A AAGGGGAG | 270 | CUCCCCUU CUGAUGAGGCCGAAAGGCCGAA AAGUGCUU | 271 |
| 575 | GGGAGAAU U GGAAAACA | 272 | UGUUUUCC CUGAUGAGGCCGAAAGGCCGAA AUUAUCCC | 273 |
| 603 | GGUGGCAU A ACCACUUG | 274 | CAAGUGGU CUGAUGAGGCCGAAAGGCCGAA AUGCCACC | 275 |
| 610 | UAACCACU U GAAUCCAG | 276 | CUGGAUUC CUGAUGAGGCCGAAAGGCCGAA AGUGGUUA | 277 |
| 615 | ACUUGAAU C CAGAAGUU | 278 | AACUUCUG CUGAUGAGGCCGAAAGGCCGAA AUUCAAGU | 279 |
| 624 | CAGAAGUU A AGAAACC | 280 | GGUUUUCU CUGAUGAGGCCGAAAGGCCGAA AACUUCUG | 281 |
| 634 | GAAAACCU C CUGGACAG | 282 | CUGUCCAG CUGAUGAGGCCGAAAGGCCGAA AGGUUUUC | 283 |
| 659 | GACAGAAU U AUUUACCA | 284 | UGGUAAAU CUGAUGAGGCCGAAAGGCCGAA AUUCUGUC | 285 |
| 660 | ACAGAAUU A UUUACCAG | 286 | CUGGUAAA CUGAUGAGGCCGAAAGGCCGAA AAUUCUGU | 287 |
| 662 | AGAAUUAU U UACCAGGC | 288 | GCCUGGUA CUGAUGAGGCCGAAAGGCCGAA AAUAAUUCU | 289 |
| 663 | GAAUUAUU U ACCAGGCA | 290 | UGCCUGGU CUGAUGAGGCCGAAAGGCCGAA AAUAAUUC | 291 |
| 664 | AAUUAUUU A CCAGGCAC | 292 | GUGCCUGG CUGAUGAGGCCGAAAGGCCGAA AAAUAAUU | 293 |
| 704 | GCAGAAAU C GCAAAGCU | 294 | AGCUUUGC CUGAUGAGGCCGAAAGGCCGAA AUUUCUGC | 295 |
| 713 | GCAAAGCU A CUGCCUGG | 296 | CCAGGCAG CUGAUGAGGCCGAAAGGCCGAA AAGCUUUGC | 297 |
| 732 | GAACUGAU A AUGCUAUC | 298 | GAUAGCAU CUGAUGAGGCCGAAAGGCCGAA AUCAGUUC | 299 |
| 738 | AUAAUGCU A UCAAGAAC | 300 | GUUCUUGA CUGAUGAGGCCGAAAGGCCGAA AGCAUUAU | 301 |
| 740 | AAUGCUAU C AAGAACCA | 302 | UGGUUCUU CUGAUGAGGCCGAAAGGCCGAA AUAGCAUU | 303 |
| 756 | ACUGGAAU U CUACAAUG | 304 | CAUUGUAG CUGAUGAGGCCGAAAGGCCGAA AUUCCAGU | 305 |
| 757 | CUGGAAUU C UACAAUGC | 306 | GCAUUGUA CUGAUGAGGCCGAAAGGCCGAA AAUUCCAG | 307 |
| 759 | GGAAUUCU A CAAUGCGU | 308 | ACGCAUUG CUGAUGAGGCCGAAAGGCCGAA AGAAUUCC | 309 |
| 790 | GGAAGGUU A UCUGCAGG | 310 | CCUGCAGA CUGAUGAGGCCGAAAGGCCGAA AACCUUCC | 311 |
| 792 | AAGGUUAU C UGCAGGAG | 312 | CUCCUGCA CUGAUGAGGCCGAAAGGCCGAA AUAACCUU | 313 |
| 804 | AGGAGUCU U CAAAAGCC | 314 | GGCUUUUG CUGAUGAGGCCGAAAGGCCGAA AGACUCCU | 315 |

TABLE XV-continued

Human c-myb Hammerhead Ribozyme and Target Sequences
(REVISED)

| nt. | Target Seqence | Seq. ID No. | HH Ribozyme Sequence | Seq. ID No. |
|---|---|---|---|---|
| 805 | GGAGUCUU C AAAAGCCA | 316 | UGGCUUUU CUGAUGAGGCCGAAAGGCCGAA AAGACUCC | 317 |
| 838 | CACAAGCU U CCAGAAGA | 318 | UCUUCUGG CUGAUGAGGCCGAAAGGCCGAA AGCUUGUG | 319 |
| 839 | ACAAGCUU C CAGAAGAA | 320 | UUCUUCUG CUGAUGAGGCCGAAAGGCCGAA AAGCUUGU | 321 |
| 855 | ACAGUCAU U UGAUGGGU | 322 | ACCCAUCA CUGAUGAGGCCGAAAGGCCGAA AUGACUGU | 323 |
| 856 | CAGUCAUU U GAUGGGUU | 324 | AACCCAUC CUGAUGAGGCCGAAAGGCCGAA AAUGACUG | 325 |
| 865 | GAUGGGUU U UGCUCAGG | 326 | CCUGAGCA CUGAUGAGGCCGAAAGGCCGAA AACCCAUC | 327 |
| 866 | AUGGGUUU U GCUCAGGC | 328 | GCCUGAGC CUGAUGAGGCCGAAAGGCCGAA AAACCCAU | 329 |
| 870 | GUUUUGCU C AGGCUCCG | 330 | CGGAGCCU CUGAUGAGGCCGAAAGGCCGAA AGCAAAAC | 331 |
| 876 | CUCAGGCU C CGCCUACA | 332 | UGUAGGCG CUGAUGAGGCCGAAAGGCCGAA AGCCUGAG | 333 |
| 882 | CUCCGCCU A CAGCUCAA | 334 | UUGAGCUG CUGAUGAGGCCGAAAGGCCGAA AGGCGGAG | 335 |
| 888 | CUACAGCU C AACUCCCU | 336 | AGGGAGUU CUGAUGAGGCCGAAAGGCCGAA AGCUGUAG | 337 |
| 893 | GCUCAACU C CCUGCCAC | 338 | GUGGCAGG CUGAUGAGGCCGAAAGGCCGAA AGUUGAGC | 339 |
| 918 | CCACUGUU A ACAACGAC | 340 | GUCGUUGU CUGAUGAGGCCGAAAGGCCGAA AACAGUGG | 341 |
| 928 | CAACGACU A UUCCUAUU | 342 | AAUAGGAA CUGAUGAGGCCGAAAGGCCGAA AGUCGUUG | 343 |
| 930 | ACGACUAU U CCUAUUAC | 344 | GUAAUAGG CUGAUGAGGCCGAAAGGCCGAA AUAGUCGU | 345 |
| 931 | CGACUAUU C CUAUUACC | 346 | GGUAAUAG CUGAUGAGGCCGAAAGGCCGAA AAUAGUCG | 347 |
| 934 | CUAUUCCU A UUACCACA | 348 | UGUGGUAA CUGAUGAGGCCGAAAGGCCGAA AGGAAUAG | 349 |
| 936 | AUUCCUAU U ACCACAUU | 350 | AAUGUGGU CUGAUGAGGCCGAAAGGCCGAA AUAGGAAU | 351 |
| 937 | UUCCUAUU A CCACAUUU | 352 | AAAUGUGG CUGAUGAGGCCGAAAGGCCGAA AAUAGGAA | 353 |
| 944 | UACCACAU U UCUGAAGC | 354 | GCUUCAGA CUGAUGAGGCCGAAAGGCCGAA AUGUGGUA | 355 |
| 945 | ACCACAUU U CUGAAGCA | 356 | UGCUUCAG CUGAUGAGGCCGAAAGGCCGAA AAUGUGGU | 357 |
| 946 | CCACAUUU C UGAAGCAC | 358 | GUGCUUCA CUGAUGAGGCCGAAAGGCCGAA AAAUGUGG | 359 |
| 964 | AAAUGUUC C CAGUCAUG | 360 | CAUGACUG CUGAUGAGGCCGAAAGGCCGAA AGACAUUU | 361 |
| 975 | GUCAUGUU C CAUACCCU | 362 | AGGGUAUG CUGAUGAGGCCGAAAGGCCGAA AACAUGAC | 363 |
| 979 | UGUUCCAU A CCCUGUAG | 364 | CUACAGGG CUGAUGAGGCCGAAAGGCCGAA AUGGAACA | 365 |
| 992 | GUAGCGUU A CAUGUAAA | 366 | UUUACAUG CUGAUGAGGCCGAAAGGCCGAA AACGCUAC | 367 |
| 998 | UUACAUGU A AAUAUAGU | 368 | ACUAUAUU CUGAUGAGGCCGAAAGGCCGAA ACAUGUAA | 369 |
| 1002 | GUAAAUAU A GUCAAUGU | 370 | AUUGACUA CUGAUGAGGCCGAAAGGCCGAA AUUUACAU | 371 |
| 1004 | GUAAAUAU A GUCAAUGU | 372 | ACAUUGAC CUGAUGAGGCCGAAAGGCCGAA AUAUUUAC | 373 |
| 1017 | AUGUCCCU C AGCCAGCU | 374 | AGCUGGCU CUGAUGAGGCCGAAAGGCCGAA AGGGACAU | 375 |
| 1037 | GCAGCCAU U CAGAGACA | 376 | UGUCUCUG CUGAUGAGGCCGAAAGGCCGAA AUGGCUGC | 377 |
| 1038 | CAGCCAUU C AGAGACAC | 378 | GUGUCUCU CUGAUGAGGCCGAAAGGCCGAA AAUGGCUG | 379 |
| 1048 | GAGACACU A UAAUGAUG | 380 | CAUCAUUA CUGAUGAGGCCGAAAGGCCGAA AGUGUCUC | 381 |
| 1050 | GACACUAU A AUGAUGAA | 382 | UUCAUCAU CUGAUGAGGCCGAAAGGCCGAA AUAGUGUC | 383 |
| 1082 | AAGCGAAU A AAGGAAUU | 384 | AAUUCCUU CUGAUGAGGCCGAAAGGCCGAA AUUCGCUU | 385 |
| 1090 | AAAGGAAU U AGAAUUGC | 386 | GCAAUUCU CUGAUGAGGCCGAAAGGCCGAA AUUCCUUU | 387 |
| 1091 | AAGGAAUU A GAAUUGCU | 388 | AGCAAUUC CUGAUGAGGCCGAAAGGCCGAA AAUUCCUU | 389 |
| 1096 | AUUAGAAU U GCUCCUAA | 390 | UUAGGAGC CUGAUGAGGCCGAAAGGCCGAA AUUCUAAU | 391 |
| 1100 | GAAUUGCU C CUAAUGUC | 392 | GACAUUAG CUGAUGAGGCCGAAAGGCCGAA AGCAAUUC | 393 |
| 1103 | UUGCUCCU A AUGUCAAC | 394 | GUUGACAU CUGAUGAGGCCGAAAGGCCGAA AGGAGCAA | 395 |
| 1124 | AAUGAGCU A AAAGGACA | 396 | UGUCCUUU CUGAUGAGGCCGAAAGGCCGAA AGCUCAUU | 397 |
| 1159 | AUGCAGCU A CCCCGGGU | 398 | ACCCGGGG CUGAUGAGGCCGAAAGGCCGAA AGCUGCAU | 399 |
| 1184 | ACCACCAU U GCCGACCA | 400 | UGGUCGGC CUGAUGAGGCCGAAAGGCCGAA AUGGUGGU | 401 |
| 1203 | CCAGACCU C AUGGAGAC | 402 | GUCUCCAU CUGAUGAGGCCGAAAGGCCGAA AGGUCUGG | 403 |
| 1224 | CACCUGUU U CUGUUUGG | 404 | CAAACAGG CUGAUGAGGCCGAAAGGCCGAA AACAGGUG | 405 |
| 1225 | ACCUGUUU C UGUUUGGG | 406 | CCAAACAG CUGAUGAGGCCGAAAGGCCGAA AAACAGGU | 407 |
| 1231 | UUCCUGUU U GGGAGAAC | 408 | GUUCUCCC CUGAUGAGGCCGAAAGGCCGAA AACAGGAA | 409 |
| 1246 | ACACCACU C CACUCCAU | 410 | AUGGAGUG CUGAUGAGGCCGAAAGGCCGAA AGUGGUGU | 411 |
| 1251 | ACUCCACU C CAUCUCUG | 412 | CAGAGAUG CUGAUGAGGCCGAAAGGCCGAA AGUGGAGU | 413 |
| 1255 | CACUCCAU C UCUGCCAG | 414 | CUGGCAGA CUGAUGAGGCCGAAAGGCCGAA AUGGAGUG | 415 |
| 1257 | CUCCAUCU C UGCCAGUG | 416 | CGCUGGCA CUGAUGAGGCCGAAAGGCCGAA AGAUGGAG | 417 |
| 1269 | CAGCGGAU C CUGGCUCC | 418 | GGAGCCAG CUGAUGAGGCCGAAAGGCCGAA AUCCGCUG | 419 |
| 1276 | UCCUGGCU C CUACCUG | 420 | CAGGUAGG CUGAUGAGGCCGAAAGGCCGAA AGCCAGGA | 421 |
| 1280 | GGCUCCCU A CCUGAAGA | 422 | UCUUCAGG CUGAUGAGGCCGAAAGGCCGAA AGGGAGCC | 423 |
| 1297 | AAGCGCCU C GCCAGCAA | 424 | UUGCUGGC CUGAUGAGGCCGAAAGGCCGAA AGGCGCUU | 425 |
| 1316 | UGCAUGAU C GUCCACCA | 426 | UGGUGGAC CUGAUGAGGCCGAAAGGCCGAA AUCAUGCA | 427 |
| 1334 | GGCACCAU U CUGGAUAA | 428 | UUAUCCAG CUGAUGAGGCCGAAAGGCCGAA AUGGUGCC | 429 |
| 1335 | GCACCAUU C UGGAUAAU | 430 | AUUAUCCA CUGAUGAGGCCGAAAGGCCGAA AAUGGUGC | 431 |
| 1341 | UUCUGGAU A AUGUUAAG | 432 | CUUAACAU CUGAUGAGGCCGAAAGGCCGAA AUCCAGAA | 433 |
| 1347 | AUAAUGUU A AGAACCUC | 434 | GAGGUUCU CUGAUGAGGCCGAAAGGCCGAA AACAUUAU | 435 |
| 1355 | AAGAACCU C UUAGAAUU | 436 | AAUUCUAA CUGAUGAGGCCGAAAGGCCGAA AGGUUCUU | 437 |
| 1357 | GAACCUCU U AGAAUUUG | 438 | CAAAUUCU CUGAUGAGGCCGAAAGGCCGAA AGAGGUUC | 439 |
| 1358 | AACCUCUU A GAAUUUGC | 440 | GCAAAUUC CUGAUGAGGCCGAAAGGCCGAA AAGAGGUU | 441 |
| 1363 | CUUAGAAU U UGCAGAAA | 442 | UUUCUGCA CUGAUGAGGCCGAAAGGCCGAA AUUCUAAG | 443 |
| 1364 | UUAGAAUU U GCAGAAAC | 444 | GUUUCUGC CUGAUGAGGCCGAAAGGCCGAA AAUUCUAA | 445 |
| 1376 | GAAACACU C CAAUUUAU | 446 | AUAAAUUG CUGAUGAGGCCGAAAGGCCGAA AGUGUUUC | 447 |
| 1381 | ACUCCAAU U UAUAGAUU | 448 | AAUCUAUA CUGAUGAGGCCGAAAGGCCGAA AUUGGAGU | 449 |
| 1382 | CUCCAAUU U AUAGAUUC | 450 | GAAUCUAU CUGAUGAGGCCGAAAGGCCGAA AAUUGGAG | 451 |
| 1383 | UCCAAUUU A UAGAUUCU | 452 | AGAAUCUA CUGAUGAGGCCGAAAGGCCGAA AAAUUGGA | 453 |
| 1385 | CAAUUUAU A GAUUCUUU | 454 | AAAGAACU CUGAUGAGGCCGAAAGGCCGAA AUAAAUUG | 455 |
| 1389 | UUAUAGAU U CUUCUUA | 456 | UAAGAAAG CUGAUGAGGCCGAAAGGCCGAA AUCUAUAA | 457 |
| 1390 | UAUAGAUU C UUUCUUAA | 458 | UUAAGAAA CUGAUGAGGCCGAAAGGCCGAA AAUCUAUA | 459 |
| 1392 | UAGAUUCU U UCUUAAAC | 460 | GUUUAAGA CUGAUGAGGCCGAAAGGCCGAA AGAAUCUA | 461 |

TABLE XV-continued

Human c-myb Hammerhead Ribozyme and Target Sequences
(REVISED)

| nt. | Target Seqence | Seq. ID No. | HH Ribozyme Sequence | Seq. ID No. |
|---|---|---|---|---|
| 1393 | AGAUUCUU U CUUAAACA | 462 | UGUUUAAG CUGAUGAGGCCGAAAGGCCGAA AAGAAUCU | 463 |
| 1394 | GAUUCUUU C UUAAACAC | 464 | GUGUUUAA CUGAUGAGGCCGAAAGGCCGAA AAAGAAUC | 465 |
| 1396 | UUCUUUCU U AAACACUU | 466 | AAGUGUUU CUGAUGAGGCCGAAAGGCCGAA AGAAAGAA | 467 |
| 1397 | UCUUUCUU A AACACUUC | 468 | GAAGUGUU CUGAUGAGGCCGAAAGGCCGAA AAGAAAGA | 469 |
| 1404 | UAAACACU U CCAGUAAC | 470 | GUUACUGG CUGAUGAGGCCGAAAGGCCGAA AGUGUUUA | 471 |
| 1404 | AAACACUU C CAGUAACC | 472 | GGUUACUG CUGAUGAGGCCGAAAGGCCGAA AAGUGUUU | 473 |
| 1423 | UGAAAACU C AGACUUGG | 474 | CCAAGUCU CUGAUGAGGCCGAAAGGCCGAA AGUUUUCA | 475 |
| 1429 | CUCAGACU U GGAAAUGC | 476 | GCAUUUCC CUGAUGAGGCCGAAAGGCCGAA AGUCUGAG | 477 |
| 1440 | AAAUGCCU U CUUUAACU | 478 | AGUUAAAG CUGAUGAGGCCGAAAGGCCGAA AGGCAUUU | 479 |
| 1441 | AAUGCCUU C UUUAACUU | 480 | AAGUUAAA CUGAUGAGGCCGAAAGGCCGAA AAGGCAUU | 481 |
| 1443 | UGCCUUCU U UAACUUCC | 482 | GGAAGUUA CUGAUGAGGCCGAAAGGCCGAA AGAAGGCA | 483 |
| 1444 | GCCUUCUU U AACUUCCA | 484 | UGGAAGUU CUGAUGAGGCCGAAAGGCCGAA AAGAAGGC | 485 |
| 1445 | CCUUCUUU A ACUUCCAC | 486 | GUGGAAGU CUGAUGAGGCCGAAAGGCCGAA AAAGAAGG | 487 |
| 1449 | CUUUAACU U CCACCCCC | 488 | GGGGGUGG CUGAUGAGGCCGAAAGGCCGAA AGUUAAAG | 489 |
| 1450 | UUUAACUU C CACCCCCC | 490 | GGGGGGUG CUGAUGAGGCCGAAAGGCCGAA AAGUUAAA | 491 |
| 1460 | ACCCCCCU C AUUGGUCA | 492 | UGACCAAU CUGAUGAGGCCGAAAGGCCGAA AGGGGGGU | 493 |
| 1463 | CCCCUCAU U GGUCACAA | 494 | UUGUGACC CUGAUGAGGCCGAAAGGCCGAA AUGAGGGG | 495 |
| 1474 | UCACAAAU U GACUGUUA | 496 | UAACAGUC CUGAUGAGGCCGAAAGGCCGAA AUUUGUGA | 497 |
| 1482 | UGACUGUU A CAACACCA | 498 | UGGUGUUG CUGAUGAGGCCGAAAGGCCGAA AACAGUCA | 499 |
| 1492 | AACACCAU U CAUAGAG | 500 | CUCUAUGA CUGAUGAGGCCGAAAGGCCGAA AUGGUGUU | 501 |
| 1493 | ACACCAUU U CAUAGAGA | 502 | UCUCUAUG CUGAUGAGGCCGAAAGGCCGAA AAUGGUGU | 503 |
| 1494 | CACCAUUU C AUAGAGAC | 504 | GUCUCUAU CUGAUGAGGCCGAAAGGCCGAA AAAUGGUG | 505 |
| 1497 | CAUUUCAU A GAGACCAG | 506 | CUGGUCUC CUGAUGAGGCCGAAAGGCCGAA AUGAAAUG | 507 |
| 1518 | UGAAAACU C AAAAGGAA | 508 | UUCCUUUU CUGAUGAGGCCGAAAGGCCGAA AGUUUUCA | 509 |
| 1530 | AGGAAAAU A CUGUUUUU | 510 | AAAAACAG CUGAUGAGGCCGAAAGGCCGAA AUUUUCCU | 511 |
| 1536 | AUACUGUU U UUAGAACC | 512 | GGUUCUAA CUGAUGAGGCCGAAAGGCCGAA AACAGUAU | 513 |
| 1537 | UACUGUUU U UAGAACCC | 514 | GGGUUCUA CUGAUGAGGCCGAAAGGCCGAA AAACAGUA | 515 |
| 1538 | ACUGUUUU U AGAACCCC | 516 | GGGGUUCU CUGAUGAGGCCGAAAGGCCGAA AAAACAGU | 517 |
| 1539 | CUGUUUUU A GAACCCCA | 518 | UGGGGUUC CUGAUGAGGCCGAAAGGCCGAA AAAAACAG | 519 |
| 1551 | CCCCAGCU A UCAAAGG | 520 | CCUUUUGA CUGAUGAGGCCGAAAGGCCGAA AGCUGGGG | 521 |
| 1553 | CCAGCUAU C AAAGGUC | 522 | GACCUUUU CUGAUGAGGCCGAAAGGCCGAA AUAGCUGG | 523 |
| 1565 | AGGUCAAU C UUAGAAAG | 524 | CUUUCUAA CUGAUGAGGCCGAAAGGCCGAA AUUGACCU | 525 |
| 1567 | GUCAAUCU U AGAAAGCA | 526 | AGCUUUCU CUGAUGAGGCCGAAAGGCCGAA AGAUUGAC | 527 |
| 1568 | UCAAUCUU A GAAAGCUC | 528 | GAGCUUUC CUGAUGAGGCCGAAAGGCCGAA AAGAUUGA | 529 |
| 1576 | AGAAAGCU U UCCAAGAA | 530 | UUCUUGGA CUGAUGAGGCCGAAAGGCCGAA AGCUUUCU | 531 |
| 1578 | AAAGCUCU C CAAGAACU | 532 | AGUUCUUG CUGAUGAGGCCGAAAGGCCGAA AGAGCUUU | 533 |
| 1587 | CAAGAACU C CUACACCA | 534 | UGGUGUAG CUGAUGAGGCCGAAAGGCCGAA AGUUCUUG | 535 |
| 1590 | GAACUCCU A CACCAUUC | 536 | GAAUGGUG CUGAUGAGGCCGAAAGGCCGAA AGGAGUUC | 537 |
| 1597 | UACACCAU U CAAACAUG | 538 | CAUGUUUG CUGAUGAGGCCGAAAGGCCGAA AUGGUGUA | 539 |
| 1598 | ACACCAUU C AAACAUGC | 540 | GCAUGUUU CUGAUGAGGCCGAAAGGCCGAA AAUGGUGU | 541 |
| 1610 | CAUGCACU U GCAGCUCU | 542 | UGAGCUGC CUGAUGAGGCCGAAAGGCCGAA AGUGCAUG | 543 |
| 1617 | UUGCAGCU C AGGAAAUU | 544 | AAUUUCUU CUGAUGAGGCCGAAAGGCCGAA AGCUGCAA | 545 |
| 1625 | CAAGAAAU U AAAUACGG | 546 | CCGUAUUU CUGAUGAGGCCGAAAGGCCGAA AUUUCUUG | 547 |
| 1626 | AAGAAAUU A AAUACGGU | 548 | ACCGUAUU CUGAUGAGGCCGAAAGGCCGAA AAUUUCUU | 549 |
| 1630 | AAUUAAAU A CGGUCCCC | 550 | GGGGACCG CUGAUGAGGCCGAAAGGCCGAA AUUUAAUU | 551 |
| 1649 | AAGAUGCU A CCUCAGAC | 552 | GUCUGAGG CUGAUGAGGCCGAAAGGCCGAA AGCAUCUU | 553 |
| 1653 | UGCUACCU C AGACACCC | 554 | GGGUGUCU CUGAUGAGGCCGAAAGGCCGAA AGGUAGCA | 555 |
| 1663 | GACACCCU C UCAUCUAG | 556 | CUAGAUGA CUGAUGAGGCCGAAAGGCCGAA AGGGUGUC | 557 |
| 1665 | CACCCUCU C AUCUAGUA | 558 | UACUAGAU CUGAUGAGGCCGAAAGGCCGAA AGAGGGUG | 559 |
| 1668 | CCUCUCAU C UAGUAGAA | 560 | UUCUACUA CUGAUGAGGCCGAAAGGCCGAA AUGAGAGG | 561 |
| 1670 | UCUCAUCU A GUAGAAGA | 562 | UCUUCUAC CUGAUGAGGCCGAAAGGCCGAA AGAUGAGA | 563 |
| 1680 | UAGAAGAU C UGCAGGAU | 564 | AUCCUGCA CUGAUGAGGCCGAAAGGCCGAA AUCUUCUA | 565 |
| 1694 | GAUGUGAU C AAACAGGA | 566 | UCCUGUUU CUGAUGAGGCCGAAAGGCCGAA AUCACAUC | 567 |
| 1705 | ACAGGAAU C UGAUGAAU | 568 | AUUCAUCA CUGAUGAGGCCGAAAGGCCGAA AUUCCUGU | 569 |
| 1714 | UGAUGAAU C UGGAAUUG | 570 | CAAUUCCA CUGAUGAGGCCGAAAGGCCGAA AUUCAUCA | 571 |
| 1721 | UCUGGAAU U GUUGCUGA | 572 | UCAGCAAC CUGAUGAGGCCGAAAGGCCGAA AUUCCAGA | 573 |
| 1733 | GCUGAGUU U CAAGAAAA | 574 | UUUUCUUG CUGAUGAGGCCGAAAGGCCGAA AACUCAGC | 575 |
| 1734 | CUGAGUUU C AAGAAAAU | 576 | AUUUUCUU CUGAUGAGGCCGAAAGGCCGAA AAACUCAG | 577 |
| 1753 | ACCACCCU U ACUGAAGA | 578 | UCUUCAGU CUGAUGAGGCCGAAAGGCCGAA AGGGUGGU | 579 |
| 1754 | CCACCCUU A CUGAAGAA | 580 | UUCUUCAG CUGAUGAGGCCGAAAGGCCGAA AAGGGUGG | 581 |
| 1766 | AAGAAAAU C AAACAAGA | 582 | UCUUGUUU CUGAUGAGGCCGAAAGGCCGAA AUUUUCUU | 583 |
| 1783 | GGUGGAAU C UCCAACUG | 584 | CAGUUGGA CUGAUGAGGCCGAAAGGCCGAA AUUCCACC | 585 |
| 1785 | UGGAAUCU C CAACUGAU | 586 | AUCAGUUG CUGAUGAGGCCGAAAGGCCGAA AGAUUCCA | 587 |
| 1794 | CAACUGAU A AAUCAGGA | 588 | UCCUGAUU CUGAUGAGGCCGAAAGGCCGAA AUCAGUUG | 589 |
| 1798 | UGAUAAAU C AGGAAACU | 590 | AGUUUCCU CUGAUGAGGCCGAAAGGCCGAA AUUUAUCA | 591 |
| 1807 | AGGAAACU U CUUCUGCU | 592 | AGCAGAAG CUGAUGAGGCCGAAAGGCCGAA AGUUUCCU | 593 |
| 1808 | GGAAACUU C UUCUGCUC | 594 | GAGCAGAA CUGAUGAGGCCGAAAGGCCGAA AAGUUUCC | 595 |
| 1810 | AAACUUCU U CUGCUCAC | 596 | GUGAGCAG CUGAUGAGGCCGAAAGGCCGAA AGAAGUUU | 597 |
| 1811 | AACUUCUU C UGCUCACA | 598 | UGUGAGCA CUGAUGAGGCCGAAAGGCCGAA AAGAAGUU | 599 |
| 1816 | CUUCUGCU C ACCACU | 600 | AGUGGUGU CUGAUGAGGCCGAAAGGCCGAA AGCAGAAG | 601 |
| 1845 | GUCUGAAU A CCCAACUG | 602 | CAGUUGGG CUGAUGAGGCCGAAAGGCCGAA AUUCAGAC | 603 |
| 1856 | CAACUGUU C ACGCAGAC | 604 | GUCUGCGU CUGAUGAGGCCGAAAGGCCGAA AACAGUUG | 605 |
| 1867 | GCAGACCU C GCCUGUGG | 606 | CCACAGGC CUGAUGAGGCCGAAAGGCCGAA AGGUCUGC | 607 |

TABLE XV-continued

Human c-myb Hammerhead Ribozyme and Target Sequences
(REVISED)

| nt. | Target Seqence | Seq. ID No. | HH Ribozyme Sequence | Seq. ID No. |
|---|---|---|---|---|
| 1890 | CACCGAAU A UUCUUACA | 608 | UGUAAGAA CUGAUGAGGCCGAAAGGCCGAA AUUCGGUG | 609 |
| 1892 | CCGAAUAU U CUUACAAG | 610 | CUUGUAAC CUGAUGAGGCCGAAAGGCCGAA AUAUUCGG | 611 |
| 1893 | CGAAUAUU C UUACAAGC | 612 | GCUUGUAA CUGAUGAGGCCGAAAGGCCGAA AAUAUUCG | 613 |
| 1895 | AAUAUUCU U ACAAGCUC | 614 | GAGCUUGU CUGAUGAGGCCGAAAGGCCGAA AGAAUAUU | 615 |
| 1896 | AUAUUCUU A CAAGCUCC | 616 | GGAGCUUG CUGAUGAGGCCGAAAGGCCGAA AAGAAUAU | 617 |
| 1903 | UACAAGCU C CGUUUUAA | 618 | UUAAAACG CUGAUGAGGCCGAAAGGCCGAA AGCUUGUA | 619 |
| 1908 | GCUCCGUU U UAAUGGCA | 620 | UGCCAUUA CUGAUGAGGCCGAAAGGCCGAA AACGGACG | 621 |
| 1909 | CUCCGUUU U AAUGGCAC | 622 | GUGCCAUU CUGAUGAGGCCGAAAGGCCGAA AAACGGAG | 623 |
| 1910 | UCCGUUUU A AUGGCACC | 624 | GGUGCCAU CUGAUGAGGCCGAAAGGCCGAA AAAACGGA | 625 |
| 1924 | ACCAGCAU C AGAAGAUG | 626 | CAUCUUCU CUGAUGAGGCCGAAAGGCCGAA AUGCUGGU | 627 |
| 1944 | ACAAUGUU C UCAAAGCA | 628 | UGCUUUGA CUGAUGAGGCCGAAAGGCCGAA AACAUUGU | 629 |
| 1946 | AAUGUUCU C AAAGCAUU | 630 | AAUGCUUU CUGAUGAGGCCGAAAGGCCGAA AGAACAUU | 631 |
| 1954 | CAAAGCAU U UACAGUAC | 632 | GUACUGUA CUGAUGAGGCCGAAAGGCCGAA AUGCUUUG | 633 |
| 1955 | AAAGCAUU U ACAGUACC | 634 | GGUACUGU CUGAUGAGGCCGAAAGGCCGAA AAUGCUUU | 635 |
| 1956 | AAGCAUUU A CAGUACCU | 636 | AGGUACUG CUGAUGAGGCCGAAAGGCCGAA AAAUGCUU | 637 |
| 1965 | CAGUACCU A AAAACAGG | 638 | CCUGUUUU CUGAUGAGGCCGAAAGGCCGAA AGGUACUG | 639 |
| 1990 | GAGCCCCU U GCAGCCUU | 640 | AAGGCUGC CUGAUGAGGCCGAAAGGCCGAA AGGGGCUC | 641 |
| 1998 | UGCAGCCU U GUAGCAGU | 642 | ACUGCUAC CUGAUGAGGCCGAAAGGCCGAA AGGCUGCA | 643 |
| 2023 | ACCUGCAU C CUGUGGAA | 644 | UUCCACAG CUGAUGAGGCCGAAAGGCCGAA AUGCAGGU | 645 |
| 2053 | GAUGACAU C UUCCAGUC | 646 | GACUGGAA CUGAUGAGGCCGAAAGGCCGAA AUGUCAUC | 647 |
| 2055 | UGACAUCU U CCAGUCAA | 648 | UUGACUGG CUGAUGAGGCCGAAAGGCCGAA AGAUGUCA | 649 |
| 2056 | GACAUCUU C CAGUCAAG | 650 | CUUGACUG CUGAUGAGGCCGAAAGGCCGAA AAGAUGUC | 651 |
| 2061 | CUUCCAGU C AAGCUCGU | 652 | ACGAGCUU CUGAUGAGGCCGAAAGGCCGAA ACUGGAAG | 653 |
| 2067 | GUCAAGCU C GUAAAUAC | 654 | GUAUUUAC CUGAUGAGGCCGAAAGGCCGAA AGCUUGAC | 655 |
| 2074 | UCGUAAAU A CGUGAAUG | 656 | CAUUCACG CUGAUGAGGCCGAAAGGCCGAA AUUUACGA | 657 |
| 2086 | GAAUGCAU U CUCAGCCC | 658 | GGGCUGAG CUGAUGAGGCCGAAAGGCCGAA AUGCAUUC | 659 |
| 2087 | AAUGCAUU C UCAGCCCG | 660 | CGGGCUGA CUGAUGAGGCCGAAAGGCCGAA AAUGCAUU | 661 |
| 2089 | UGCAUUCU C AGCCCGGA | 662 | UCCGGGCU CUGAUGAGGCCGAAAGGCCGAA AGAAUGCA | 663 |
| 2117 | UGAGACAU U UCCAGAAA | 664 | UUUCUGGA CUGAUGAGGCCGAAAGGCCGAA AUGUCUCA | 665 |
| 2188 | GAGACAUU U CCAGAAAA | 666 | UUUUCUGG CUGAUGAGGCCGAAAGGCCGAA AAUGUCUC | 667 |
| 2119 | AGACAUUU C CAGAAAAG | 668 | CUUUUCUG CUGAUGAGGCCGAAAGGCCGAA AAAUGUCU | 669 |
| 2131 | AAAAGCAU U AUGGUUUU | 670 | AAAACCAU CUGAUGAGGCCGAAAGGCCGAA AUGCUUUU | 671 |
| 2132 | AAAGCAUU A UGGUUUUC | 672 | GAAAACCA CUGAUGAGGCCGAAAGGCCGAA AAUGCUUU | 673 |
| 2138 | UUAUGGUU U UCAGAACA | 674 | UGUUCUGA CUGAUGAGGCCGAAAGGCCGAA AACCAUAA | 675 |
| 2139 | UAUGGUUU U CAGAACAC | 676 | GUGUUCUG CUGAUGAGGCCGAAAGGCCGAA AAACCAUA | 677 |
| 2140 | AUGGUUUU C AGAACACU | 678 | AGUGUUCU CUGAUGAGGCCGAAAGGCCGAA AAAACCAU | 679 |
| 2149 | AGAACACU U CAAGUUGA | 680 | UCAACUUG CUGAUGAGGCCGAAAGGCCGAA AGUGUUCU | 681 |
| 2150 | GAACACUU C AAGUUGAC | 682 | GUCAACUU CUGAUGAGGCCGAAAGGCCGAA AAGUGUUC | 683 |
| 2155 | CUUCAAGU U GACUUGGG | 684 | CCCAAGUC CUGAUGAGGCCGAAAGGCCGAA ACUUGAAG | 685 |
| 2160 | AGUUGACU U GGGAUAUA | 686 | UAUAUCCC CUGAUGAGGCCGAAAGGCCGAA AGUCAACU | 687 |
| 2166 | CUUGGGAU A UAUCAUUC | 688 | GAAUGAUA CUGAUGAGGCCGAAAGGCCGAA AUCCCAAG | 689 |
| 2168 | UGGGAUAU A UCAUUCCU | 690 | AGGAAUGA CUGAUGAGGCCGAAAGGCCGAA AUAUCCCA | 691 |
| 2170 | GGAUAUAU C AUUCCUCA | 692 | UGAGGAAU CUGAUGAGGCCGAAAGGCCGAA AUAUAUCC | 693 |
| 2173 | UAUAUCAU U CCUCAACA | 694 | UGUUGAGG CUGAUGAGGCCGAAAGGCCGAA AUGAUAUA | 695 |
| 2174 | AUAUCAUU C CUCAACAU | 696 | AUGUUGAG CUGAUGAGGCCGAAAGGCCGAA AAUGAUAU | 697 |
| 2177 | UCAUUCCU C AACAUGAA | 698 | UUCAUGUU CUGAUGAGGCCGAAAGGCCGAA AGGAAUGA | 699 |
| 2189 | AUGAAACU U UUCAUGAA | 700 | UUCAUGAA CUGAUGAGGCCGAAAGGCCGAA AGUUUCAU | 701 |
| 2190 | UGAAACUU U UCAUGAAU | 702 | AUUCAUGA CUGAUGAGGCCGAAAGGCCGAA AAGUUUCA | 703 |
| 2191 | GAAACUUU U CAUGAAUG | 704 | CAUUCAUG CUGAUGAGGCCGAAAGGCCGAA AAAGUUUC | 705 |
| 2192 | AAACUUUU C AUGAAUGG | 706 | CCAUUCAU CUGAUGAGGCCGAAAGGCCGAA AAAAGUUU | 707 |
| 2212 | AAGAACCU A UUUGUUGU | 708 | AACAAAAA CUGAUGAGGCCGAAAGGCCGAA AGGUUCUU | 709 |
| 2214 | GAACCUAU U UUUGUUGU | 710 | ACAACAAA CUGAUGAGGCCGAAAGGCCGAA AUAGGUUC | 711 |
| 2215 | AACCUAUU U UUGUUGUG | 712 | CACAACAA CUGAUGAGGCCGAAAGGCCGAA AAUAGGUU | 713 |
| 2216 | ACCUAUUU U UGUUGUGG | 714 | CCACAACA CUGAUGAGGCCGAAAGGCCGAA AAAUAGGU | 715 |
| 2217 | CCUAUUUU U GUUGUGGU | 716 | ACCACAAC CUGAUGAGGCCGAAAGGCCGAA AAAAUAGG | 717 |
| 2255 | AAGUGCAU U UAGUUGAA | 718 | UUCAACUA CUGAUGAGGCCGAAAGGCCGAA AUGCACUU | 719 |
| 2256 | AGUGCAUU U AGUUGAAU | 720 | AUUCAACU CUGAUGAGGCCGAAAGGCCGAA AAUGCACU | 721 |
| 2257 | GUGCAUUU A GUUGAAUG | 722 | CAUUCAAC CUGAUGAGGCCGAAAGGCCGAA AAAUGCAC | 723 |
| 2272 | UGAAGUCU U CUUGGAUU | 724 | AAUCCAAG CUGAUGAGGCCGAAAGGCCGAA AGACUUCA | 725 |
| 2273 | GAAGUCUU C UUGGAUUU | 726 | AAAUCCAA CUGAUGAGGCCGAAAGGCCGAA AAGACUUC | 727 |
| 2275 | AGUCUUCU U GGAUUUCA | 728 | UGAAAUCC CUGAUGAGGCCGAAAGGCCGAA AGAAGACU | 729 |
| 2280 | UCUUGGAU U UCACCCAA | 730 | UUGGGUGA CUGAUGAGGCCGAAAGGCCGAA AUCCAAGA | 731 |
| 2281 | CUUGGAUU U CACCAAC | 732 | GUUGGGUG CUGAUGAGGCCGAAAGGCCGAA AAUCCAAG | 733 |
| 2282 | UUGGAUUU C ACCCAACU | 734 | AGUUGGGU CUGAUGAGGCCGAAAGGCCGAA AAAUCCAA | 735 |
| 2291 | ACCCAACU A AAAGGAUU | 736 | AAUCCUUU CUGAUGAGGCCGAAAGGCCGAA AGUUGGGU | 737 |
| 2299 | AAAAGGAU U UUUAAAAA | 738 | UUUUUAAA CUGAUGAGGCCGAAAGGCCGAA AUCCUUUU | 739 |
| 2300 | AAAGGAUU U UUAAAAAU | 740 | AUUUUUAA CUGAUGAGGCCGAAAGGCCGAA AAUCCUUU | 741 |
| 2301 | AAGGAUUU U UAAAAAUA | 742 | UAUUUUUA CUGAUGAGGCCGAAAGGCCGAA AAAUCCUU | 743 |
| 2302 | AGGAUUUU U AAAAAUAA | 744 | UUAUUUUU CUGAUGAGGCCGAAAGGCCGAA AAAAUCCU | 745 |
| 2303 | GGAUUUUU A AAAAUAAA | 746 | UUUAUUUU CUGAUGAGGCCGAAAGGCCGAA AAAAAUCC | 747 |
| 2309 | UUAAAAAU A AAUAACAG | 748 | CUGUUAUU CUGAUGAGGCCGAAAGGCCGAA AUUUUUAA | 749 |
| 2313 | AAAAUAAU A ACAGUCUU | 750 | AAGACUGU CUGAUGAGGCCGAAAGGCCGAA AUUUAUUU | 751 |
| 2321 | AACAGUCU U ACCUAAAU | 752 | AUUUAGGU CUGAUGAGGCCGAAAGGCCGAA AGACUGUU | 753 |

TABLE XV-continued

Human c-myb Hammerhead Ribozyme and Target Sequences
(REVISED)

| nt. | Target Seqence | Seq. ID No. | HH Ribozyme Seqence | Seq. ID No. |
|---|---|---|---|---|
| 2322 | ACAGUCUU A CCUAAAUU | 754 | AAUUUAGG CUGAUGAGGCCGAAAGGCCGAA AAGACUGU | 755 |
| 2326 | UCUUACCU A AAUUAUUA | 756 | UAAUAAUU CUGAUGAGGCCGAAAGGCCGAA AGGUAAGA | 757 |
| 2330 | ACCUAAAU U AUUAGGUA | 758 | UACCUAAU CUGAUGAGGCCGAAAGGCCGAA AUUUAGGU | 759 |
| 2331 | CCUAAAUU A UUAGGUAA | 760 | UUACCUAA CUGAUGAGGCCGAAAGGCCGAA AAUUUAGG | 761 |
| 2333 | UAAAUUAU U AGGUAAUG | 762 | CAUUACCU CUGAUGAGGCCGAAAGGCCGAA AUAAUUUA | 763 |
| 2334 | AAAUUAUU A GGUAAUGA | 764 | UCAUUACC CUGAUGAGGCCGAAAGGCCGAA AAUAAUUU | 765 |
| 2345 | UAAUGAAU U GUAGCCAG | 766 | CUGGCUAC CUGAUGAGGCCGAAAGGCCGAA AUUCAUUA | 767 |
| 2359 | CAGUUGUU A AUAUCUUA | 768 | UAAGAUAU CUGAUGAGGCCGAAAGGCCGAA AACAACUG | 769 |
| 2362 | UUGUUAAU A UCUUAAUG | 770 | CAUUAAGA CUGAUGAGGCCGAAAGGCCGAA AUUAACAA | 771 |
| 2364 | GUUAAUAU C UUAAUGCA | 772 | UGCAUUAA CUGAUGAGGCCGAAAGGCCGAA AUAUUAAC | 773 |
| 2366 | UAAUAUCU U AAUGCAGA | 774 | UCUGCAUU CUGAUGAGGCCGAAAGGCCGAA AGAUAUUA | 775 |
| 2367 | AAUAUCUU A AUGCAGAU | 776 | AUCUGCAU CUGAUGAGGCCGAAAGGCCGAA AAGAUAUU | 777 |
| 2376 | AUGCAGAU U UUUUUAAA | 778 | UUUAAAAA CUGAUGAGGCCGAAAGGCCGAA AUCUGCAU | 779 |
| 2377 | UGCAGAUU U UUUUAAAA | 780 | UUUUAAAA CUGAUGAGGCCGAAAGGCCGAA AAUCUGCA | 781 |
| 2378 | GCAGAUUU U UUUAAAAA | 782 | UUUUUAAA CUGAUGAGGCCGAAAGGCCGAA AAAUCUGC | 783 |
| 2379 | CAGAUUUU U UUAAAAAA | 784 | UUUUUUAA CUGAUGAGGCCGAAAGGCCGAA AAAAUCUG | 785 |
| 2380 | AGAUUUUU U UAAAAAAA | 786 | UUUUUUUA CUGAUGAGGCCGAAAGGCCGAA AAAAAUCU | 787 |
| 2381 | GAUUUUUU U AAAAAAAA | 788 | UUUUUUUU CUGAUGAGGCCGAAAGGCCGAA AAAAAAUC | 789 |
| 2382 | AUUUUUUU A AAAAAAAC | 790 | GUUUUUUU CUGAUGAGGCCGAAAGGCCGAA AAAAAAAU | 791 |
| 2393 | AAAAACAU A AAAUGAUU | 792 | AAUCAUUU CUGAUGAGGCCGAAAGGCCGAA AUGUUUUU | 793 |
| 2401 | AAAAUGAU U UAUCUGAU | 794 | UACAGAUA CUGAUGAGGCCGAAAGGCCGAA AUCAUUUU | 795 |
| 2402 | AAAUGAUU U AUCUGUAU | 796 | AUACAGAU CUGAUGAGGCCGAAAGGCCGAA AAUCAUUU | 797 |
| 2403 | AAUGAUUU A UCUGUAUU | 798 | AAUACAGA CUGAUGAGGCCGAAAGGCCGAA AAAUCAUU | 799 |
| 2405 | UGAUUUAU C UGUAUUUU | 800 | AAAAUACA CUGAUGAGGCCGAAAGGCCGAA AUAAAUCA | 801 |
| 2411 | AUCUGUAU U UUAAAGGA | 802 | UCCUUUAA CUGAUGAGGCCGAAAGGCCGAA AUACAGAU | 803 |
| 2412 | UCUGUAUU U UAAAGGAU | 804 | AUCCUUUA CUGAUGAGGCCGAAAGGCCGAA AAUACAGA | 805 |
| 2413 | CUGUAUUU U AAAGGAUC | 806 | CAUCCUUU CUGAUGAGGCCGAAAGGCCGAA AAAUACAG | 807 |
| 2414 | UGUAUUUU A AAGGAUCC | 808 | GGAUCCUU CUGAUGAGGCCGAAAGGCCGAA AAAAUACA | 809 |
| 2421 | UAAAGGAU C CAACAGAU | 810 | AUCUGUUG CUGAUGAGGCCGAAAGGCCGAA AUCCUUUA | 811 |
| 2430 | CAACAGAU C AGUAUUUU | 812 | AAAAUACU CUGAUGAGGCCGAAAGGCCGAA AUCUGUUG | 813 |
| 2436 | AUCAGUAU U UUUUCCUG | 814 | CAGGAAAA CUGAUGAGGCCGAAAGGCCGAA AUACUGAU | 815 |
| 2437 | UCAGUAUU U UUUCCUGU | 816 | ACAGGAAA CUGAUGAGGCCGAAAGGCCGAA AAUACUGA | 817 |
| 2438 | CAGUAUUU U UUCCUGUG | 818 | CACAGGAA CUGAUGAGGCCGAAAGGCCGAA AAAUACUG | 819 |
| 2439 | AGUAUUUU U UCCUGUGA | 820 | UCACAGGA CUGAUGAGGCCGAAAGGCCGAA AAAAUACU | 821 |
| 2440 | GUAUUUUU U CCUGUGAU | 822 | AUCACAGG CUGAUGAGGCCGAAAGGCCGAA AAAAAUAC | 823 |
| 2441 | UAUUUUUU C CUGUGAUG | 824 | CAUCACAG CUGAUGAGGCCGAAAGGCCGAA AAAAAAUA | 825 |
| 2454 | GAUGGGUU U UUUGAAAU | 826 | AUUUCAAA CUGAUGAGGCCGAAAGGCCGAA AACCCAUC | 827 |
| 2455 | AUGGGUUU U UUGAAAUU | 828 | AAUUUCAA CUGAUGAGGCCGAAAGGCCGAA AAACCCAU | 829 |
| 2456 | UGGGUUUU U UGAAAUUU | 830 | AAAUUUCA CUGAUGAGGCCGAAAGGCCGAA AAAACCCA | 831 |
| 2457 | GGGUUUUU U GAAAUUUG | 832 | CAAAUUUC CUGAUGAGGCCGAAAGGCCGAA AAAAACCC | 833 |
| 2463 | UUUCAAAU U UGACACAU | 834 | AUGUGUCA CUGAUGAGGCCGAAAGGCCGAA AUUUCAAA | 835 |
| 2464 | UUGAAAUU U GACACAUU | 836 | AAUGUGUC CUGAUGAGGCCGAAAGGCCGAA AAUUUCAA | 837 |
| 2472 | UGACACAU U AAAAGGAU | 838 | UACCUUUU CUGAUGAGGCCGAAAGGCCGAA AUGUGUCA | 839 |
| 2473 | GACACAUU A AAAGGUAC | 840 | GUACCUUU CUGAUGAGGCCGAAAGGCCGAA AAUGUGUC | 841 |
| 2483 | AAGGUACU C CAGUAUUU | 842 | AAAUACUG CUGAUGAGGCCGAAAGGCCGAA AGUACCUU | 843 |
| 2490 | UCCAGUAU U UCACUUUU | 844 | AAAAGUGA CUGAUGAGGCCGAAAGGCCGAA AUACUGGA | 845 |
| 2491 | CCAGUAUU U CACUUUUC | 846 | GAAAAGUG CUGAUGAGGCCGAAAGGCCGAA AAUACUGG | 847 |
| 2492 | CAGUAUUU C ACUUUUCU | 848 | AGAAAAGU CUGAUGAGGCCGAAAGGCCGAA AAAUACUG | 849 |
| 2496 | AUUUCACU U UUCUCGAU | 850 | AUCGAGAA CUGAUGAGGCCGAAAGGCCGAA AGUGAAAU | 851 |
| 2497 | UUUCACUU U UCUCGAUC | 852 | GAUCGAGA CUGAUGAGGCCGAAAGGCCGAA AAGUGAAA | 853 |
| 2498 | UUCACUUU U CUCGAUCA | 854 | UGAUCGAG CUGAUGAGGCCGAAAGGCCGAA AAAGUGAA | 855 |
| 2499 | UCACUUUU C UCGAUCAC | 856 | GUGAUCGA CUGAUGAGGCCGAAAGGCCGAA AAAAGUGA | 857 |
| 2501 | UUCUCGAU C ACUAAACA | 860 | UAGUGAUC CUGAUGAGGCCGAAAGGCCGAA AGAAAAGU | 859 |
| 2505 | UUCUCGAU C ACUAAACA | 860 | UGUUUAGU CUGAUGAGGCCGAAAGGCCGAA AUCGAGAA | 861 |
| 2509 | CGAUCACU A AACAUAUG | 862 | CAUAUGUU CUGAUGAGGCCGAAAGGCCGAA AGUGAUCG | 863 |
| 2515 | CUAAACAU A UGCAUAUA | 864 | UAUAUGCA CUGAUGAGGCCGAAAGGCCGAA AUGUUUAG | 865 |
| 2521 | AUAUGCAU A UAUUUUUA | 866 | UAAAAAUA CUGAUGAGGCCGAAAGGCCGAA AUGCAUAU | 867 |
| 2523 | AUGCAUAU A UUUUUAAA | 868 | UUUAAAAA CUGAUGAGGCCGAAAGGCCGAA AUAUGCAU | 869 |
| 2525 | GCAUAUAU U UUUAAAAA | 870 | UUUUUAAA CUGAUGAGGCCGAAAGGCCGAA AUAUAUGC | 871 |
| 2526 | CAUAUAUU U UUAAAAAU | 872 | AUUUUAAA CUGAUGAGGCCGAAAGGCCGAA AAUAUAUG | 873 |
| 2527 | AUAUAUUU U UAAAAAUC | 874 | GAUUUUUA CUGAUGAGGCCGAAAGGCCGAA AAAUAUAU | 875 |
| 2528 | UAUAUUUU U AAAAAUCA | 876 | UGAUUUUU CUGAUGAGGCCGAAAGGCCGAA AAAAUAUA | 877 |
| 2529 | AUAUUUUU A UUUUCAG | 878 | CUGAUUUU CUGAUGAGGCCGAAAGGCCGAA AAAAAUAU | 879 |
| 2535 | UUAAAAAU C AGUAAAAG | 880 | CUUUUACU CUGAUGAGGCCGAAAGGCCGAA AUUUUUAA | 881 |
| 2547 | AAAAGCAU U ACUCUAAG | 882 | CUUAGAGU CUGAUGAGGCCGAAAGGCCGAA AUGCUUUU | 883 |
| 2548 | AAAGCAUU A CUCUAAGU | 884 | ACUUAGAG CUGAUGAGGCCGAAAGGCCGAA AAUGCUUU | 885 |
| 2551 | GCAUUACU C UAAGUGUA | 886 | UACACUUA CUGAUGAGGCCGAAAGGCCGAA AGUAAUGC | 887 |
| 2553 | AUUACUCU A AGUGUAGA | 888 | UCUACACU CUGAUGAGGCCGAAAGGCCGAA AGAGUAAU | 889 |
| 2559 | CUAAGUGU A GACUUAAU | 890 | AUUAAGUC CUGAUGAGGCCGAAAGGCCGAA ACACUUAG | 891 |
| 2564 | UGUAGACU U AAUACCAU | 892 | AUGGUAUU CUGAUGAGGCCGAAAGGCCGAA AGUCUACA | 893 |
| 2565 | GUAGACUU A AUACCAUG | 894 | CAUGGUAU CUGAUGAGGCCGAAAGGCCGAA AAGUCUAC | 895 |
| 2568 | GACUUAAU A CCAUGUGA | 896 | UCACAUGG CUGAUGAGGCCGAAAGGCCGAA AUUAAGUC | 897 |
| 2580 | UGUGACAU U UAAUCCAG | 898 | CUGGAUUA CUGAUGAGGCCGAAAGGCCGAA AUGUCACA | 899 |

TABLE XV-continued

Human c-myb Hammerhead Ribozyme and Target Sequences
(REVISED)

| nt. | Target Seqence | Seq. ID No. | HH Ribozyme Sequence | Seq. ID No. |
|---|---|---|---|---|
| 2581 | GUGACAUU U AAUCCAGA | 900 | UCUGGAUU CUGAUGAGGCCGAAAGGCCGAA AAUGUCAC | 901 |
| 2582 | UGACAUUU A AUCCAGAU | 902 | AUCUGGAU CUGAUGAGGCCGAAAGGCCGAA AAAUGUCA | 903 |
| 2585 | CAUUUAAU C CAGAUUGU | 904 | ACAAUCUG CUGAUGAGGCCGAAAGGCCGAA AUUAAAUG | 905 |
| 2591 | AUCCAGAU U GUAAAUGC | 906 | GCAUUUAC CUGAUGAGGCCGAAAGGCCGAA AUCUGGAU | 907 |
| 2601 | UAAAUGCU C AUUUAUGG | 908 | CCAUAAAU CUGAUGAGGCCGAAAGGCCGAA AGCAUUUA | 909 |
| 2604 | AUGCUCAU U UAUGGUUA | 910 | UAACCAUA CUGAUGAGGCCGAAAGGCCGAA AUGAGCAU | 911 |
| 2605 | UGCUCAUU U AUGGUUAA | 912 | UUAACCAU CUGAUGAGGCCGAAAGGCCGAA AAUGAGCA | 913 |
| 2606 | GCUGAUUU A UGGUUAAU | 914 | AUUAACCA CUGAUGAGGCCGAAAGGCCGAA AAAUGAGC | 915 |
| 2612 | UUAUGGUU A AUGACAUU | 916 | AAUGUCAU CUGAUGAGGCCGAAAGGCCGAA AACCAUAA | 917 |
| 2620 | AAUGACAU U GAAGGUAC | 918 | GUACCUUC CUGAUGAGGCCGAAAGGCCGAA AUGUCAUU | 919 |
| 2631 | AGGUACAU U UAUUGUAC | 920 | GUACAAUA CUGAUGAGGCCGAAAGGCCGAA AUGUACCU | 921 |
| 2632 | GGUACAUU U AUUGUACC | 922 | GGUACAAU CUGAUGAGGCCGAAAGGCCGAA AAUGUACC | 923 |
| 2633 | GUACAUUU A UUGUACCA | 924 | UGGUACAA CUGAUGAGGCCGAAAGGCCGAA AAAUGUAC | 925 |
| 2635 | ACAUUUAU U GUACCAAA | 926 | UUUGGUAC CUGAUGAGGCCGAAAGGCCGAA AUAAAUGU | 927 |
| 2648 | CAAACCAU U UUAUGAGU | 928 | ACUCAUAA CUGAUGAGGCCGAAAGGCCGAA AUGGUUUG | 929 |
| 2649 | AAACCAUU U UAUGAGUU | 930 | AACUCAUA CUGAUGAGGCCGAAAGGCCGAA AAUGGUUU | 931 |
| 2650 | AACCAUUU U AUGAGUUU | 932 | AAACUCAU CUGAUGAGGCCGAAAGGCCGAA AAAUGGUU | 933 |
| 2651 | ACCAUUUU A UGAGUUUU | 934 | AAAACUCA CUGAUGAGGCCGAAAGGCCGAA AAAAUGGU | 935 |
| 2658 | UAUGAGUU U UCUGUUAG | 936 | CUAACAGA CUGAUGAGGCCGAAAGGCCGAA AACUCAUA | 937 |
| 2659 | AUGAGUUU U CUGUUAGC | 938 | GCUAACAG CUGAUGAGGCCGAAAGGCCGAA AAACUCAU | 939 |
| 2660 | UGAGUUUU C UGUUAGCU | 940 | AGCUAACA CUGAUGAGGCCGAAAGGCCGAA AAAACUCA | 941 |
| 2665 | UUUCUGUU A GCUUGCUU | 942 | AAGCAAGC CUGAUGAGGCCGAAAGGCCGAA AACAGAAA | 943 |
| 2669 | UGUUAGCU U GCUUUAAA | 944 | UUUAAAGC CUGAUGAGGCCGAAAGGCCGAA AGCUAACA | 945 |
| 2673 | AGCUUGCU U UAAAAAUU | 946 | AAUUUUUA CUGAUGAGGCCGAAAGGCCGAA AGCAAGCU | 947 |
| 2674 | GCUUGCUU U AAAAAUUA | 948 | UAAUUUUU CUGAUGAGGCCGAAAGGCCGAA AAGCAAGC | 949 |
| 2675 | CUUGCUUU A AAAAUUAU | 950 | AUAAUUUU CUGAUGAGGCCGAAAGGCCGAA AAAGCAAG | 951 |
| 2681 | UUAAAAAU U AUUACUGU | 952 | ACAGUAAU CUGAUGAGGCCGAAAGGCCGAA AUUUUUAA | 953 |
| 2682 | UAAAAAUU A UUACUGUA | 954 | UACAGUAA CUGAUGAGGCCGAAAGGCCGAA AAUUUUUA | 955 |
| 2684 | AAAAUUAU U ACUGUAAG | 956 | CUUACAGU CUGAUGAGGCCGAAAGGCCGAA AUAAUUUU | 957 |
| 2685 | AAAUUAUU A CUGUAAGA | 958 | UCUUACAG CUGAUGAGGCCGAAAGGCCGAA AAUAAUUU | 959 |
| 2697 | UAAGAAAU A GUUUAUA | 960 | UAUAAAAC CUGAUGAGGCCGAAAGGCCGAA AUUUCUUA | 961 |
| 2701 | AAAUAGUU U UAUAAAAA | 962 | UUUUUAUA CUGAUGAGGCCGAAAGGCCGAA AACUAUUU | 963 |
| 2702 | AAUAGUUU U AUAAAAAA | 964 | UUUUUUAU CUGAUGAGGCCGAAAGGCCGAA AAACUAUU | 965 |
| 2703 | AUAGUUUU A UAAAAAAU | 966 | AUUUUUUA CUGAUGAGGCCGAAAGGCCGAA UUUUCUAU | 967 |
| 2705 | AGUUUUAU A AAAAAUUA | 968 | UAAUUUUU CUGAUGAGGCCGAAAGGCCGAA AUAAAACU | 969 |
| 2712 | UAAAAAAU U AUAUUUUU | 970 | AAAAAUAU CUGAUGAGGCCGAAAGGCCGAA AUUUUUUA | 971 |
| 2713 | AAAAAAUU A UAUUUUUA | 972 | UAAAAAUA CUGAUGAGGCCGAAAGGCCGAA AAUUUUUU | 973 |
| 2715 | AAAAUUAU A UUUUUAUU | 974 | AAUAAAAA CUGAUGAGGCCGAAAGGCCGAA AUAAUUUU | 975 |
| 2717 | AAUUAUAU U UUUAUUCA | 976 | UGAAUAAA CUGAUGAGGCCGAAAGGCCGAA AUAUAAUU | 977 |
| 2718 | AUUAUAUU U UUAUUCAG | 978 | CUGAAUAA CUGAUGAGGCCGAAAGGCCGAA AAUAUAAU | 979 |
| 2719 | UUAUAUUU U UAUUCAGU | 980 | ACUGAAUA CUGAUGAGGCCGAAAGGCCGAA AAAUAUAA | 981 |
| 2720 | UAUAUUUU U AUUCAGUA | 982 | UACUGAAU CUGAUGAGGCCGAAAGGCCGAA AAAAUAUA | 983 |
| 2721 | AUAUUUUU A UUCAGUAA | 984 | UUACUGAA CUGAUGAGGCCGAAAGGCCGAA AAAAAUAU | 985 |
| 2723 | AUUUUUAU U CAGUAAUU | 986 | AAUUACUG CUGAUGAGGCCGAAAGGCCGAA AUAAAAAU | 987 |
| 2724 | UUUUUAUU C AGUAAUUU | 988 | AAAUUACU CUGAUGAGGCCGAAAGGCCGAA AAUAAAAA | 989 |
| 2731 | UCAGUAAU U UAAUUUUG | 990 | CAAAAUUA CUGAUGAGGCCGAAAGGCCGAA AUUACUGA | 991 |
| 2732 | CAGUAAUU U AAUUUUGU | 992 | ACAAAAUU CUGAUGAGGCCGAAAGGCCGAA AAUUACUG | 993 |
| 2733 | AGUAAUUU A AUUUUGUA | 994 | UACAAAAU CUGAUGAGGCCGAAAGGCCGAA AAAUUACU | 995 |
| 2736 | AAUUUAAU U UUGUAAAU | 996 | AUUUACAA CUGAUGAGGCCGAAAGGCCGAA AUUAAAUU | 997 |
| 2737 | AUUUAAUU U UGUAAAUG | 998 | CAUUUACA CUGAUGAGGCCGAAAGGCCGAA AAUUAAAU | 999 |
| 2738 | UUUAAUUU U GUAAAUGC | 1000 | GCAUUUAC CUGAUGAGGCCGAAAGGCCGAA AAAUUAAA | 1001 |
| 2762 | AAAACGUU U UUGCUGC | 1002 | GCAGCAAA CUGAUGAGGCCGAAAGGCCGAA AACGUUUU | 1003 |
| 2763 | AAACGUUU U UGCUGCU | 1004 | AGCAGCAA CUGAUGAGGCCGAAAGGCCGAA AAACGUUU | 1005 |
| 2764 | AACGUUUU U UGCUGCUA | 1006 | UAGCAGCA CUGAUGAGGCCGAAAGGCCGAA AAAACGUU | 1007 |
| 2765 | ACGUUUUU U GCUGCUAU | 1008 | AUAGCAGC CUGAUGAGGCCGAAAGGCCGAA AAAAACGU | 1009 |
| 2772 | UUGCUGCU A UGGUCUUA | 1010 | UAAGACCA CUGAUGAGGCCGAAAGGCCGAA AGCAGCAA | 1011 |
| 2779 | UAUGGUCU U AGCCUGUA | 1012 | UACAGGCU CUGAUGAGGCCGAAAGGCCGAA AGACCAUA | 1013 |
| 2780 | AUGGUCUU A GCCUGUAG | 1014 | CUACAGGC CUGAUGAGGCCGAAAGGCCGAA AAGACCAU | 1015 |
| 2799 | AUGCUGCU A GUAUCAGA | 1016 | UCUGAUAC CUGAUGAGGCCGAAAGGCCGAA AGCAGCAU | 1017 |
| 2804 | GCUAGUAU C AGAGGGGC | 1018 | GCCCCUCU CUGAUGAGGCCGAAAGGCCGAA AUACUAGC | 1019 |
| 2822 | GUAGAGCU U GGACAGAA | 1020 | UUCUGUCC CUGAUGAGGCCGAAAGGCCGAA AGCUCUAC | 1021 |
| 2843 | AAGAAACU U GGUGUUAG | 1022 | CUAACACC CUGAUGAGGCCGAAAGGCCGAA AGUUUCUU | 1023 |
| 2850 | UUGGUGUU A GGUAAUUG | 1024 | CAAUUACC CUGAUGAGGCCGAAAGGCCGAA AACACCAA | 1025 |
| 2857 | UAGGUAAU U GACUAUGC | 1026 | GCAUAGUC CUGAUGAGGCCGAAAGGCCGAA AUUACCUA | 1027 |
| 2862 | AAUUGACU A UGCACUAG | 1028 | CUAGUGCA CUGAUGAGGCCGAAAGGCCGAA AGUCAAUU | 1029 |
| 2869 | UAUGCACU A GUAUUUCA | 1030 | UGAAAUAC CUGAUGAGGCCGAAAGGCCGAA AGUGCAUA | 1031 |
| 2874 | ACUAGUAU U UCAGACUU | 1032 | AAGUCUGA CUGAUGAGGCCGAAAGGCCGAA AUACUAGU | 1033 |
| 2875 | CUAGUAUU U CAGACUUU | 1034 | AAAGUCUG CUGAUGAGGCCGAAAGGCCGAA AAUACUAG | 1035 |
| 2876 | UAGUAUUU C AGACUUUU | 1036 | AAAAGUCU CUGAUGAGGCCGAAAGGCCGAA AAAUACUA | 1037 |
| 2882 | UUCAGACU U UUUAAUUU | 1038 | AAAUUAAA CUGAUGAGGCCGAAAGGCCGAA AGUCUGAA | 1039 |
| 2883 | UCAGACUU U UUAAUUUU | 1040 | AAAAUUAA CUGAUGAGGCCGAAAGGCCGAA AAGUCUGA | 1041 |
| 2884 | CAGACUUU U UAAUUUUA | 1042 | UAAAAUUA CUGAUGAGGCCGAAAGGCCGAA AAAGUCUG | 1043 |
| 2885 | AGACUUUU U AAUUUUAU | 1044 | AUAAAAUU CUGAUGAGGCCGAAAGGCCGAA AAAAGUCU | 1045 |

TABLE XV-continued

Human c-myb Hammerhead Ribozyme and Target Sequences
(REVISED)

| nt. | Target Seqence | Seq. ID No. | HH Ribozyme Sequence | Seq. ID No. |
|---|---|---|---|---|
| 2886 | GACUUUUU A AUUUUAUA | 1046 | UAUAAAAU CUGAUGAGGCCGAAAGGCCGAA AAAAAGUC | 1047 |
| 2889 | UUUUUAAU U UUAUAUAU | 1048 | AUAUAUAA CUGAUGAGGCCGAAAGGCCGAA AUUAAAAA | 1049 |
| 2890 | UUUUAAUU U UAUAUAUA | 1050 | UAUAUAUA CUGAUGAGGCCGAAAGGCCGAA AAUUAAAA | 1051 |
| 2891 | UUUAAUUU U AUAUAUAU | 1052 | AUAUAUAU CUGAUGAGGCCGAAAGGCCGAA AAAUUAAA | 1053 |
| 2892 | UUAAUUUU A UAUAUAUA | 1054 | UAUAUAUA CUGAUGAGGCCGAAAGGCCGAA AAAAUUAA | 1055 |
| 2894 | AAUUUUAU A UAUAUAUA | 1056 | UAUAUAUA CUGAUGAGGCCGAAAGGCCGAA AUAAAAUU | 1057 |
| 2896 | UUUUUAUA A UAUAUACA | 1058 | UGUAUAUA CUGAUGAGGCCGAAAGGCCGAA AUAUAAAA | 1059 |
| 2898 | UUAUAUAU A UAUACAUU | 1060 | AAUGUAUA CUGAUGAGGCCGAAAGGCCGAA AUAUAUAA | 1061 |
| 2900 | AUAUAUAU A UACAUUUU | 1062 | AAAAUGUA CUGAUGAGGCCGAAAGGCCGAA AUAUAUAU | 1063 |
| 2902 | AUAUAUAU A UCAUUUUU | 1064 | AAAAAAUG CUGAUGAGGCCGAAAGGCCGAA AUAUAUAU | 1065 |
| 2906 | AUAUACAU U UUUUUUCC | 1066 | GGAAAAAA CUGAUGAGGCCGAAAGGCCGAA AUGUAUAU | 1067 |
| 2907 | UAUACAUU U UUUUUCCU | 1068 | AGGAAAAA CUGAUGAGGCCGAAAGGCCGAA AAUGUAUA | 1069 |
| 2908 | AUACAUUU U UUUUCCUU | 1070 | AAGGAAAA CUGAUGAGGCCGAAAGGCCGAA AAAUGUAU | 1071 |
| 2909 | UACAUUUU U UUUCCUUC | 1072 | GAAGGAAA CUGAUGAGGCCGAAAGGCCGAA AAAAUGUA | 1073 |
| 2910 | ACAUUUUU U UUCCUUCU | 1074 | AGAAGGAA CUGAUGAGGCCGAAAGGCCGAA AAAAAUGU | 1075 |
| 2911 | CAUUUUUU U UCCUUCUG | 1076 | CAGAAGGA CUGAUGAGGCCGAAAGGCCGAA AAAAAAUG | 1077 |
| 2912 | AUUUUUUU U CCUUCUGC | 1078 | GCAGAAGG CUGAUGAGGCCGAAAGGCCGAA AAAAAAAU | 1079 |
| 2913 | UUUUUUUU C UUCUGCA | 1080 | UGCAGAAG CUGAUGAGGCCGAAAGGCCGAA AAAAAAAA | 1081 |
| 2916 | UUUUUCCU U CUGCAAUA | 1082 | UAUUGCAG CUGAUGAGGCCGAAAGGCCGAA AGGAAAAA | 1083 |
| 2917 | UUUUCCUU C UGCAAUAC | 1084 | GUAUUGCA CUGAUGAGGCCGAAAGGCCGAA AAGGAAAA | 1085 |
| 2924 | UCUGCAAU A CAUUUGAA | 1086 | UUCAAAUG CUGAUGAGGCCGAAAGGCCGAA AUUGCAGA | 1987 |
| 2928 | CAAUACAU U UGAAAACU | 1088 | AGUUUUCA CUGAUGAGGCCGAAAGGCCGAA AUGUAUUG | 1089 |
| 2929 | AAUACAUU U GAAAACUU | 1090 | AAGUUUUC CUGAUGAGGCCGAAAGGCCGAA AAUGUAUU | 1091 |
| 2937 | UGAAAACU U GUUUGGGA | 1092 | UCCCAAAC CUGAUGAGGCCGAAAGGCCGAA AGUUUUCA | 1093 |
| 2941 | AACUUGUU U GGGAGACU | 1094 | AGUCUCCC CUGAUGAGGCCGAAAGGCCGAA AACAAGUU | 1095 |
| 2950 | GGGAGACU C UGCAUUUU | 1096 | AAAAUGCA CUGAUGAGGCCGAAAGGCCGAA AGUCUCCC | 1097 |
| 2956 | CUCUGCAU U UUAUUGA | 1098 | CAAUAAA CUGAUGAGGCCGAAAGGCCGAA AUGCAGAG | 1099 |
| 2957 | UCUGCAUU U UUAUUGU | 1100 | ACAAUAAA CUGAUGAGGCCGAAAGGCCGAA AAUGCAGA | 1101 |
| 2958 | CUGCAUUU U UUAUUGUA | 1102 | CACAAUAA CUGAUGAGGCCGAAAGGCCGAA AAAUGCAG | 1103 |
| 2959 | UGCAUUUU U UAUUGUGG | 1104 | CCACAAUA CUGAUGAGGCCGAAAGGCCGAA AAAAUGCA | 1105 |
| 2960 | GCAUUUUU U AUUGUGGU | 1106 | ACCACAAU CUGAUGAGGCCGAAAGGCCGAA AAAAAUGC | 1107 |
| 2961 | CAUUUUUU A UUGUGGUU | 1108 | AACCACAA CUGAUGAGGCCGAAAGGCCGAA AAAAAAUG | 1109 |
| 2963 | UUUUUUAU U GUGGUUUU | 1110 | AAAACCAC CUGAUGAGGCCGAAAGGCCGAA AUAAAAAA | 1111 |
| 2970 | UUGUGGUU U UUUUGUUA | 1112 | UAACAAAA CUGAUGAGGCCGAAAGGCCGAA AACCACAA | 1113 |
| 2971 | UGUGGUUU U UUUGUUAU | 1114 | AUAACAAA CUGAUGAGGCCGAAAGGCCGAA AAACCACA | 1115 |
| 2972 | GUGGUUUU U UUGUUAUU | 1116 | AAUAACAA CUGAUGAGGCCGAAAGGCCGAA AAAACCAC | 1117 |
| 2973 | UGGUUUUU U UGUUAUUG | 1118 | CAAUAACA CUGAUGAGGCCGAAAGGCCGAA AAAAACCA | 1119 |
| 2974 | GGUUUUUU U GUUAUUGU | 1120 | ACAAUAAC CUGAUGAGGCCGAAAGGCCGAA AAAAAACC | 1121 |
| 2977 | UUUUUUGU U AUUGUUGG | 1122 | CCAACAAU CUGAUGAGGCCGAAAGGCCGAA ACAAAAAA | 1123 |
| 2978 | UUUUUGUU A UUGUUGGU | 1124 | ACCAACAA CUGAUGAGGCCGAAAGGCCGAA ACAAAAAA | 1125 |
| 2980 | UUUGUUAU U GUUGGUUU | 1126 | AAACCAAC CUGAUGAGGCCGAAAGGCCGAA AUAACAAA | 1127 |
| 2988 | UGUUGGUU U AUACAAGC | 1128 | GCUUGUAU CUGAUGAGGCCGAAAGGCCGAA AACCAACA | 1129 |
| 2989 | GUUGGUUU A UACAAGCA | 1130 | UGCUUGUA CUGAUGAGGCCGAAAGGCCGAA AAACCAAC | 1131 |
| 2991 | UGGUUUAU A CAAGCAUG | 1132 | CAUGCUUG CUGAUGAGGCCGAAAGGCCGAA AUAAACCA | 1133 |
| 3009 | GUUGCACU U CUUUUUUG | 1134 | CAAAAAAG CUGAUGAGGCCGAAAGGCCGAA AGUGCAAC | 1135 |
| 3010 | UUGCACUU C UUUUUUGG | 1136 | CCAAAAAA CUGAUGAGGCCGAAAGGCCGAA AAGUGCAA | 1137 |
| 3012 | GCACUUCU U UUUUGGGA | 1138 | UCCCAAAA CUGAUGAGGCCGAAAGGCCGAA AGAAGUGC | 1139 |
| 3013 | CACUUCUU U UUUGGGAG | 1140 | CUCCCAAA CUGAUGAGGCCGAAAGGCCGAA AAGAAGUG | 1141 |
| 3014 | ACUUCUUU U UUGGGAGA | 1142 | UCUCCCAA CUGAUGAGGCCGAAAGGCCGAA AAAGAAGU | 1143 |
| 3015 | CUUCUUUU U UGGGAGAU | 1144 | AUCUCCCA CUGAUGAGGCCGAAAGGCCGAA AAAAGAAG | 1145 |
| 3016 | UUCUUUUU U GGGAGAUG | 1146 | CAUCUCCC CUGAUGAGGCCGAAAGGCCGAA AAAAAGAA | 1147 |
| 3040 | AUGAUGUU C UAUGUUUU | 1148 | AAAACAUA CUGAUGAGGCCGAAAGGCCGAA AACAUCAU | 1149 |
| 3042 | GAUGUUCU A UGUUUUGU | 1150 | ACAAAACA CUGAUGAGGCCGAAAGGCCGAA AGAACAUC | 1151 |
| 3047 | UCUAUGUU U UGUUUUGA | 1152 | UCAAAACA CUGAUGAGGCCGAAAGGCCGAA AACAUAGA | 1153 |
| 3048 | CUAUGUUU U GUUUUGAG | 1154 | CUCAAAAC CUGAUGAGGCCGAAAGGCCGAA AAACAUAG | 1155 |
| 3052 | GUUUUGUU U UGAGUGUA | 1156 | UACACUCA CUGAUGAGGCCGAAAGGCCGAA AACAAAAC | 1157 |
| 2053 | UUUUGUUU U GAGUGUAG | 1158 | CUACACUC CUGAUGAGGCCGAAAGGCCGAA AACAAAA | 1159 |
| 3072 | UGACUGUU U UAUAAUUU | 1160 | AAAUUAUA CUGAUGAGGCCGAAAGGCCGAA AACAGUCA | 1161 |
| 3073 | GACUGUUU U AUAAUUUG | 1162 | CAAAUUAU CUGAUGAGGCCGAAAGGCCGAA AAACAGUC | 1163 |
| 3074 | ACUGUUUU A UAAUUUGG | 1164 | CCAAAUUA CUGAUGAGGCCGAAAGGCCGAA AAAACAGU | 1165 |
| 3076 | UGUUUUAU A AUUUGGGA | 1166 | UCCCAAAU CUGAUGAGGCCGAAAGGCCGAA AUAAAACA | 1167 |
| 3079 | UUUAUAAU U UGGGAGUU | 1168 | AACUCCCA CUGAUGAGGCCGAAAGGCCGAA AUUAUAAA | 1169 |
| 3080 | UUAUAAUU U GGGAGUUC | 1170 | GAACUCCC CUGAUGAGGCCGAAAGGCCGAA AAUUAUAA | 1171 |
| 3088 | UGGGAGUU C UGCAUUUG | 1172 | CAAAUGCA CUGAUGAGGCCGAAAGGCCGAA AACUCCCA | 1173 |
| 3094 | UUCUGCAU U UGAUCCGA | 1174 | GCGGAUCA CUGAUGAGGCCGAAAGGCCGAA AUGCAGAA | 1175 |
| 3095 | UCUGCAUU U GAUCCGCA | 1176 | UGCGGAUC CUGAUGAGGCCGAAAGGCCGAA AAUGCAGA | 1177 |
| 3099 | CAUUUGAU C CGCAUCCC | 1178 | GGGAUGCG CUGAUGAGGCCGAAAGGCCGAA AUCAAAUG | 1179 |
| 3105 | AUCCGCAU C CCUGUGG | 1180 | CCACAGGG CUGAUGAGGCCGAAAGGCCGAA AUGCGGAU | 1181 |
| 3116 | CUGUGGUU U CUAAGUGU | 1182 | ACACUUAG CUGAUGAGGCCGAAAGGCCGAA AACCACAG | 1183 |
| 3117 | UGUGGUUU C UAAGUGUA | 1184 | UACACUUA CUGAUGAGGCCGAAAGGCCGAA AAACCACA | 1185 |
| 3119 | UGGUUUCU A AGUGUAUG | 1186 | CAUACACU CUGAUGAGGCCGAAAGGCCGAA AGAAACCA | 1187 |
| 3132 | UAUGGUCU C AGAACUGU | 1188 | ACAGUUCU CUGAUGAGGCCGAAAGGCCGAA AGACCAUA | 1189 |
| 3150 | GCAUGGAU C CUGUGUUU | 1190 | AAACACAG CUGAUGAGGCCGAAAGGCCGAA AUCCAUGC | 1191 |

TABLE XV-continued

Human c-myb Hammerhead Ribozyme and Target Sequences
(REVISED)

| nt. | Target Seqence | Seq. ID No. | HH Ribozyme Sequence | Seq. ID No. |
|---|---|---|---|---|
| 3157 | UCCUGUGU U UGCAACUA | 1192 | CAGUUGCA CUGAUGAGGCCGAAAGGCCGAA ACACAGGA | 1193 |
| 3158 | CCUGUGUU U GCAACUGG | 1194 | CCAGUUGC CUGAUGAGGCCGAAAGGCCGAA AACACAGG | 1195 |
| 3189 | UGGUUGAU A GCCAGUCA | 1196 | UGACUGGC CUGAUGAGGCCGAAAGGCCGAA AUCAACCA | 1197 |
| 3204 | CACUGCCU U AAGAACAU | 1198 | AUGUUCUU CUGAUGAGGCCGAAAGGCCGAA AGGCAGUG | 1199 |
| 3205 | ACUGCCUU A AGAACAUU | 1200 | AAUGUUCU CUGAUGAGGCCGAAAGGCCGAA AAGGCAGU | 1201 |
| 3213 | AAGAACAU U UGAUGCAA | 1202 | UUGCAUCA CUGAUGAGGCCGAAAGGCCGAA AUGUUCUU | 1203 |
| 3214 | AGAACAUU U GAUGCAAG | 1204 | CUUGCAUC CUGAUGAGGCCGAAAGGCCGAA AAUGUUCU | 1205 |
| 3240 | ACUGAACU U UUGAGAUA | 1206 | UAUCUCAA CUGAUGAGGCCGAAAGGCCGAA AGUUCAGU | 1207 |
| 3241 | CUGAACUU U UGAGAUAU | 1208 | AUAUCUCA CUGAUGAGGCCGAAAGGCCGAA AAGUUCAG | 1209 |
| 3242 | UGAACUUU U GAGAUAUG | 1210 | CAUAUCUC CUGAUGAGGCCGAAAGGCCGAA AAAGUUCA | 1211 |
| 3248 | UUUGAGAU A UGACGGUG | 1212 | CACCGUCA CUGAUGAGGCCGAAAGGCCGAA AUCUCAAA | 1213 |
| 3261 | GGUGUACU U ACUGCCUU | 1214 | AAGGCAGU CUGAUGAGGCCGAAAGGCCGAA AGUACCC | 1215 |
| 3262 | GUGUACUU A CUGCCUUG | 1216 | CAAGGCAG CUGAUGAGGCCGAAAGGCCGAA AAGUACAC | 1217 |
| 3269 | UACUGCCU U GUAGCAAA | 1218 | UUUGCUAC CUGAUGAGGCCGAAAGGCCGAA AGGCAGUA | 1219 |
| 3280 | AGCAAAAU A AAGAUGUG | 1220 | CACAUCUU CUGAUGAGGCCGAAAGGCCGAA AUUUUGCU | 1221 |
| 3293 | UGUGCCCU U AUUUUACC | 1222 | GGUAAAAU CUGAUGAGGCCGAAAGGCCGAA AGGGCACA | 1223 |
| 3294 | GUGCCCUU A UUUUACCU | 1224 | AGGUAAAA CUGAUGAGGCCGAAAGGCCGAA AAGGGCAC | 1225 |

TABLE XVI

Mouse c-myb Hammerhead Ribozyme and Target Sequences
(REVISED)

| nt. | HH Ribozyme Sequence | Seq. ID No. | Target | Seq. ID No. |
|---|---|---|---|---|
| 10 | UCCGCCAA CUGAUGAGGCCGAAAGGCCGAA AGCCCCGG | 1226 | CCGGGGCUC UUGGCGGA | 1227 |
| 12 | GCUCCGCC CUGAUGAGGCCGAAAGGCCGAA AGAGCCCC | 1228 | GGGGCUCUU GGCGGAGC | 1229 |
| 33 | GCCAUGGC CUGAUGAGGCCGAAAGGCCGAA AGGCGGGC | 1230 | GCCCGCCUC GCCAUGGC | 1231 |
| 63 | CUACUGUA CUGAUGAGGCCGAAAGGCCGAA AUGCUGUA | 1232 | CACAGCAUC UACAGUAG | 1233 |
| 65 | CGCUACUG CUGAUGAGGCCGAAAGGCCGAA AGAUGCUG | 1234 | CAGCAUCUA CAGUAGCG | 1235 |
| 70 | UUCAUCGC CUGAUGAGGCCGAAAGGCCGAA ACUGUAGA | 1236 | UCUACAGUA GCGAUGAA | 1237 |
| 93 | CACAUCUC CUGAUGAGGCCGAAAGGCCGAA AUGUCUUC | 1238 | GAAGACAUU GAGAUGUG | 1239 |
| 113 | GCCCAUCG CUGAUGAGGCCGAAAGGCCGAA AGUCAUGG | 1240 | CCAUGACUA CGAUGGGC | 1241 |
| 134 | GCUUUCCA CUGAUGAGGCCGAAAGGCCGAA AUUUGGGC | 1242 | GCCCAAAUC UGGAAAGC | 1243 |
| 145 | CCCCAAGU CUGAUGAGGCCGAAAGGCCGAA ACGCUUUC | 1244 | GAAAGCGUC ACUUGGGG | 1245 |
| 149 | UUUUCCCC CUGAUGAGGCCGAAAGGCCGAA AGUGACGC | 1246 | GCGUCACUU GGGGAAAA | 1247 |
| 160 | UGUCCACC CUGAUGAGGCCGAAAGGCCGAA AGUUUCC | 1248 | GGAAAACUA GGUGGACA | 1249 |
| 231 | UUGGCAAU CUGAUGAGGCCGAAAGGCCGAA ACUUUCCA | 1250 | UGGAAAGUC AUUGCCAA | 1251 |
| 234 | UAAUUGGC CUGAUGAGGCCGAAAGGCCGAA AUGACUUU | 1252 | AAAGUCAUU GCCAAUUA | 1253 |
| 241 | GGGCAGAU CUGAUGAGGCCGAAAGGCCGAA AUUGGCAA | 1254 | UUGCCAAUU AUCUGCCC | 1255 |
| 242 | UGGGCAGA CUGAUGAGGCCGAAAGGCCGAA AAUUGGCA | 1256 | UGCCAAUUA UCUGCCCA | 1257 |
| 244 | GUUGGGCA CUGAUGAGGCCGAAAGGCCGAA AUAAUUGG | 1258 | CCAAUUAUC UGCCCAAC | 1259 |
| 264 | UGCACUG CUGAUGAGGCCGAAAGGCCGAA ACAUCUGU | 1260 | ACAGAUGUA CAGUGCCA | 1261 |
| 306 | CCUUUGAU CUGAUGAGGCCGAAAGGCCGAA AGUUCAGG | 1262 | CCUGAACAC AUCAAAGG | 1263 |
| 309 | GGACCUUU CUGAUGAGGCCGAAAGGCCGAA AUGAGUUC | 1264 | GAACUCAUC AAAGGUCC | 1265 |
| 316 | GGUCCAGG CUGAUGAGGCCGAAAGGCCGAA ACCUUUGA | 1266 | UCAAAGGUC CCUGGACC | 1267 |
| 337 | GACUCUCU CUGAUGAGGCCGAAAGGCCGAA AUCUUCUU | 1268 | AAGAAGAUC AGAGAGUC | 1269 |
| 345 | AGCUUUAU CUGAUGAGGCCGAAAGGCCGAA ACUCUCUG | 1270 | CAGAGAGUC AUAAAGCU | 1271 |
| 348 | ACAAGCUU CUGAUGAGGCCGAAAGGCCGAA AUGACUCU | 1272 | AGAGUCAUA AAGCUUGU | 1273 |
| 354 | UUCUGGAC CUGAUGAGGCCGAAAGGCCGAA AGCUUUAU | 1274 | AUAAAGCUU GUCCAGAA | 1275 |
| 357 | UAUUUCUG CUGAUGAGGCCGAAAGGCCGAA ACAAGCUU | 1276 | AAGCUUGUC CAGAAAUA | 1277 |
| 365 | UCGGACCA CUGAUGAGGCCGAAAGGCCGAA AUUUCUGG | 1278 | CCAGAAAUA UGGUCCGA | 1279 |
| 370 | ACGCUUCG CUGAUGAGGCCGAAAGGCCGAA ACCAUAUU | 1280 | AAUAUGGUC CGAAGCGU | 1281 |
| 379 | AACAGACC CUGAUGAGGCCGAAAGGCCGAA ACGCUUCG | 1282 | CGAAGCGUU GGUCUGUU | 1283 |
| 383 | CAAUAACA CUGAUGAGGCCGAAAGGCCGAA ACCAACGC | 1284 | GCGUUGGUC UGUUAUUG | 1285 |
| 387 | UUGGCAAU CUGAUGAGGCCGAAAGGCCGAA ACAGACCA | 1286 | UGGUCUGUU AUUGCCAA | 1287 |
| 388 | CUUGGCAA CUGAUGAGGCCGAAAGGCCGAA AACAGACC | 1288 | GGUCUGUUA UUGCCAAG | 1289 |
| 390 | UGCUUGGC CUGAUGAGGCCGAAAGGCCGAA AUAACAGA | 1290 | UCUGUUAUU GCCAAGCA | 1291 |
| 401 | UCCCUUUU CUGAUGAGGCCGAAAGGCCGAA AGUGCUUG | 1292 | CAAGCACUU AAAAGGGA | 1293 |
| 402 | CUCCCUUU CUGAUGAGGCCGAAAGGCCGAA AAGUGCUU | 1294 | AAGCACUUA AAAGGGAG | 1295 |
| 414 | UGCUUUCC CUGAUGAGGCCGAAAGGCCGAA AUUCUCCC | 1296 | GGGAGAAUU GGAAAGCA | 1297 |
| 427 | CCUCUCCC CUGAUGAGGCCGAAAGGCCGAA ACACUGCU | 1298 | AGCAGUGUC GGGAGAGG | 1299 |
| 448 | UGGAUUCA CUGAUGAGGCCGAAAGGCCGAA AUGGUUGA | 1300 | ACAACCAUU UGAAUCCA | 1301 |
| 449 | CUGGAUUC CUGAUGAGGCCGAAAGGCCGAA AAUGGUUG | 1302 | CAACCAUUU GAAUCCAG | 1303 |
| 454 | AACUUCUG CUGAUGAGGCCGAAAGGCCGAA AUUCAAAU | 1304 | AUUUGAAUC CAGAAGUU | 1305 |
| 462 | GUUUUCUU CUGAUGAGGCCGAAAGGCCGAA ACUUCUGG | 1306 | CCAGAAGUU AAGAAAAC | 1307 |
| 463 | GGUUUUCU CUGAUGAGGCCGAAAGGCCGAA AACUUCUG | 1308 | CAGAAGUUA AGAAAACC | 1309 |
| 473 | CUGUCCAG CUGAUGAGGCCGAAAGGCCGAA AGGUUUUC | 1310 | GAAACCUC CUGGACAG | 1311 |
| 498 | UGGUAAAU CUGAUGAGGCCGAAAGGCCGAA AUUCUGUC | 1312 | GACAGAAUC AUUUACCA | 1313 |

TABLE XVI-continued

Mouse c-myb Hammerhead Ribozyme and Target Sequences
(REVISED)

| nt. | HH Ribozyme Sequence | Seq. ID No. | Target | Seq. ID No. |
|---|---|---|---|---|
| 501 | GCCUGGUA CUGAUGAGGCCGAAAGGCCGAA AUGAUUCU | 1314 | AGAAUCAUU UACCAGGC | 1315 |
| 502 | UGCCUGGU CUGAUGAGGCCGAAAGGCCGAA AAUGAUUC | 1316 | GAAUCAUUU ACCAGGCA | 1317 |
| 503 | GUGCCUGG CUGAUGAGGCCGAAAGGCCGAA AAAUGAUU | 1318 | AAUCAUUUA CCAGGCAC | 1319 |
| 520 | GUUCCCCA CUGAUGAGGCCGAAAGGCCGAA ACGCUUGU | 1320 | ACAAGCGUC UGGGGAAC | 1321 |
| 543 | AGCUUUGC CUGAUGAGGCCGAAAGGCCGAA AUCUCUGC | 1322 | GCAGAGAUC GCAAAGCU | 1323 |
| 571 | GAUAGCAU CUGAUGAGGCCGAAAGGCCGAA AUCAGUCC | 1324 | GGACUGAUA AUGCUAUC | 1325 |
| 577 | GUUCUUGA CUGAUGAGGCCGAAAGGCCGAA AGCAUUAU | 1326 | AUAAUGCUA UCAAGAAC | 1327 |
| 579 | UGGUUCUU CUGAUGAGGCCGAAAGGCCGAA AUAGCAUU | 1328 | AAUGCUAUC AAGAACCA | 1329 |
| 595 | CAUGGUGG CUGAUGAGGCCGAAAGGCCGAA AUUCCAGU | 1330 | ACUGGAAUU CCACCAUG | 1331 |
| 596 | GCAUGGUG CUGAUGAGGCCGAAAGGCCGAA AAUUCCAG | 1332 | CUGGAAUUC CACCAUGC | 1333 |
| 607 | CACCUUGC CUGAUGAGGCCGAAAGGCCGAA ACGCAUGG | 1334 | CCAUGCGUC GCAAGGUG | 1335 |
| 629 | UCUGCAGG CUGAUGAGGCCGAAAGGCCGAA AGCCUUCC | 1336 | GGAAGGCUA CCUGCAGA | 1337 |
| 643 | GGCUUUGG CUGAUGAGGCCGAAAGGCCGAA AGGCUUCU | 1338 | AGAAGCCUU CCAAAGCC | 1339 |
| 644 | UGGCUUUG CUGAUGAGGCCGAAAGGCCGAA AAGGCUUC | 1340 | GAAGCCUUC CAAAGCCA | 1341 |
| 677 | UCUUCUGG CUGAUGAGGCCGAAAGGCCGAA AGCUCGUG | 1342 | CACGAGCUU CCAGAAGA | 1343 |
| 678 | UUCUUCUG CUGAUGAGGCCGAAAGGCCGAA AAGCUCGU | 1344 | ACGAGCUUC CAGAAGAA | 1345 |
| 691 | CAUCAAAU CUGAUGAGGCCGAAAGGCCGAA AUUGUUCU | 1346 | AGAACAAUC AUUUGAUG | 1347 |
| 694 | CCCCAUCA CUGAUGAGGCCGAAAGGCCGAA AUGAUUGU | 1348 | ACAAUCAUU UGAUGGGG | 1349 |
| 695 | ACCCCAUC CUGAUGAGGCCGAAAGGCCGAA AAUGAUUG | 1350 | CAAUCAUUU GAUGGGGU | 1351 |
| 704 | CAUGCCCA CUGAUGAGGCCGAAAGGCCGAA ACCCCAUC | 1352 | GAUGGGGUU GGGCAUG | 1353 |
| 705 | GCAUGCCC CUGAUGAGGCCGAAAGGCCGAA AACCCCAU | 1354 | AUGGGGUUU GGCAUGC | 1355 |
| 716 | AUGGAGGU CUGAUGAGGCCGAAAGGCCGAA AGGCAUGC | 1356 | GCAUGCCUC ACCUCCAU | 1357 |
| 721 | CUGAGAUG CUGAUGAGGCCGAAAGGCCGAA AGGUGAGG | 1358 | CCUCACCUC CAUCUCAG | 1359 |
| 725 | AGAGCUGA CUGAUGAGGCCGAAAGGCCGAA AUGGAGGU | 1360 | ACCUCCAUC UCAGCUCU | 1361 |
| 727 | AGAGAGCU CUGAUGAGGCCGAAAGGCCGAA AGAUGGAG | 1362 | CUCCAUCUC AGCUCUCU | 1363 |
| 732 | CUUGGAGA CUGAUGAGGCCGAAAGGCCGAA AGCUGAGA | 1364 | UCUCAGCUC UCUCCAAG | 1365 |
| 734 | CACUUGGA CUGAUGAGGCCGAAAGGCCGAA AGCUGAGA | 1366 | UCAGCUCUC UCCAAGUG | 1367 |
| 736 | GCCACUUG CUGAUGAGGCCGAAAGGCCGAA AGAGAGCU | 1368 | AGCUCUCUC CAAGUGGC | 1369 |
| 749 | UGACGGAG CUGAUGAGGCCGAAAGGCCGAA ACUGGCCA | 1370 | UGGCCAGUC UCCGUCA | 1371 |
| 752 | UGUUGACG CUGAUGAGGCCGAAAGGCCGAA AGGACUGG | 1372 | CCAGUCCUC CGUCAACA | 1373 |
| 756 | UCGCUGUU CUGAUGAGGCCGAAAGGCCGAA ACGAGGA | 1374 | UCCUCCGUC AACAGCGA | 1375 |
| 767 | AAUAGGGA CUGAUGAGGCCGAAAGGCCGAA AUUCGCUG | 1376 | CAGCGAAUA UCCCUAUU | 1377 |
| 769 | GUAAUAGG CUGAUGAGGCCGAAAGGCCGAA AUAUUCGC | 1378 | GCGAAUAUC CUAUUAC | 1379 |
| 773 | UGUGGUAA CUGAUGAGGCCGAAAGGCCGAA AGGGAUAU | 1380 | AUAUCCCUA UUACCACA | 1381 |
| 775 | GAUGUGGU CUGAUGAGGCCGAAAGGCCGAA AUAGGGAU | 1382 | AUCCCUAUU ACCACAUC | 1383 |
| 776 | CGAUGUGG CUGAUGAGGCCGAAAGGCCGAA AAUAGGGA | 1384 | UCCCUAUUA CCACAUCG | 1385 |
| 783 | GCUUCGGC CUGAUGAGGCCGAAAGGCCGAA AUGUGGUA | 1386 | UACCACAUC GCCGAAGC | 1387 |
| 801 | UGACUGGA CUGAUGAGGCCGAAAGGCCGAA AUGUUUUG | 1388 | CAAAACAUC UCCAGUCA | 1389 |
| 803 | CGUGACUG CUGAUGAGGCCGAAAGGCCGAA AGAUGUUU | 1390 | AAACAUCUC CAGUCACG | 1391 |
| 808 | GGGAACGU CUGAUGAGGCCGAAAGGCCGAA ACUGGAGA | 1392 | UCUCCAGUC ACGUUCCC | 1393 |
| 813 | GGAUAGGG CUGAUGAGGCCGAAAGGCCGAA ACGUGACU | 1394 | AGUCACGUU CCCUAUCC | 1395 |
| 814 | AGGAUAGG CUGAUGAGGCCGAAAGGCCGAA AACGUGAC | 1396 | GUCACGUUC CCUAUCCU | 1397 |
| 818 | CGACAGGA CUGAUGAGGCCGAAAGGCCGAA AGGGAACG | 1398 | CGUUCCCUA UCCUGUCG | 1399 |
| 820 | UGCGACAG CUGAUGAGGCCGAAAGGCCGAA AUAGGGAA | 1400 | UUCCCUAUC CUGUGCA | 1401 |
| 825 | UGCAAUGC CUGAUGAGGCCGAAAGGCCGAA ACAGGAUA | 1402 | UAUCCUGUC GCAUUGCA | 1403 |
| 830 | UAACAUGC CUGAUGAGGCCGAAAGGCCGAA AUGCGACA | 1404 | UGUCGCAUU GCAUGUUA | 1405 |
| 837 | ACUAUAUU CUGAUGAGGCCGAAAGGCCGAA ACAUGCAA | 1406 | UUGCAUGUU AAUAUAGU | 1407 |
| 838 | GACUAUAU CUGAUGAGGCCGAAAGGCCGAA AACAUGCA | 1408 | UGCAUGUUA AUAUAGUC | 1409 |
| 841 | GUUGACUA CUGAUGAGGCCGAAAGGCCGAA AUUAACAU | 1410 | AUGUUAAUA UAGUCAAC | 1411 |
| 843 | ACGUUGAC CUGAUGAGGCCGAAAGGCCGAA AUAUUAAC | 1412 | GUUAAUAUA GUCAACGU | 1413 |
| 846 | GGGACGUU CUGAUGAGGCCGAAAGGCCGAA ACUAUAUU | 1414 | AAUAUAGUC AACGUCCC | 1415 |
| 852 | GGCUGAGG CUGAUGAGGCCGAAAGGCCGAA ACGUUGAC | 1416 | GUCAACGUC CCUCAGCC | 1417 |
| 856 | AGCCGGCU CUGAUGAGGCCGAAAGGCCGAA AGGGACGU | 1418 | ACGUCCCUC AGCCGGCU | 1419 |
| 876 | UGUCUCUG CUGAUGAGGCCGAAAGGCCGAA AUGGCUGC | 1420 | GCAGCCAUC CAGAGACA | 1421 |
| 887 | CGUCGUUA CUGAUGAGGCCGAAAGGCCGAA AGUGUCUC | 1422 | GAGACACUA UAACGACG | 1423 |
| 889 | UUCGUCGU CUGAUGAGGCCGAAAGGCCGAA AUAGUGUC | 1424 | GACACUAUA ACGACGAA | 1425 |
| 921 | AGCUCCUU CUGAUGAGGCCGAAAGGCCGAA AUUCGCUU | 1426 | AAGCGAAUA AAGGAGCU | 1427 |
| 935 | UCAGGACG CUGAUGAGGCCGAAAGGCCGAA ACUCCAGC | 1428 | GCUGGAGUU GCUCCUGA | 1429 |
| 939 | GACAUCAG CUGAUGAGGCCGAAAGGCCGAA AGCAACUC | 1430 | GAGUUGCUC CUGAUGUC | 1431 |
| 947 | UCUCUGUU CUGAUGAGGCCGAAAGGCCGAA ACAUCAGG | 1432 | CCUGAUGUC AACAGAGA | 1433 |
| 980 | GUGUUGGU CUGAUGAGGCCGAAAGGCCGAA AUGCCUGC | 1434 | GCAGGCAUU ACCAACAC | 1435 |
| 981 | UGUGUUGG CUGAUGAGGCCGAAAGGCCGAA AAUGCCUG | 1436 | CAGGCAUUA CCAACACA | 1437 |
| 1000 | GUAGCUGC CUGAUGAGGCCGAAAGGCCGAA AGUGUGGU | 1438 | ACCACACUU GCAGCUAC | 1439 |
| 1007 | ACCCGGGG CUGAUGAGGCCGAAAGGCCGAA AGCUGCAA | 1440 | UUGCAGCUA CCCCGGGU | 1441 |
| 1028 | CCACAAUG CUGAUGAGGCCGAAAGGCCGAA AGGCCUG | 1442 | CAGCACCUC CAUUGUGG | 1443 |
| 1032 | UGGUCCAC CUGAUGAGGCCGAAAGGCCGAA AUGGAGGU | 1444 | ACCUCCAUU GGGACCA | 1445 |
| 1051 | AUCCCCAU CUGAUGAGGCCGAAAGGCCGAA AGGUCUGG | 1446 | CCAGACCUC AUGGGGAU | 1447 |
| 1060 | AGGUGCAC CUGAUGAGGCCGAAAGGCCGAA AUCCCCAU | 1448 | AUGGGGAUA GUGCACCU | 1449 |
| 1071 | AAACAGGU CUGAUGAGGCCGAAAGGCCGAA ACACAGGG | 1450 | GCACCUGUU UCCUGUUU | 1451 |
| 1072 | CAAACAGG CUGAUGAGGCCGAAAGGCCGAA AACAGGUG | 1452 | CACCUGUUU CCUGUUUG | 1453 |
| 1073 | CCAAACAG CUGAUGAGGCCGAAAGGCCGAA AAACAGGU | 1454 | ACCUGUUUC CUGUUUGG | 1455 |
| 1078 | UUCUCCCA CUGAUGAGGCCGAAAGGCCGAA ACAGGAAA | 1456 | UUUCCUGUU UGGGAGAA | 1457 |
| 1079 | GUUCUCCC CUGAUGAGGCCGAAAGGCCGAA AACAGGAA | 1458 | UUCCUGUUU GGGAGAAC | 1459 |

TABLE XVI-continued

Mouse c-myb Hammerhead Ribozyme and Target Sequences
(REVISED)

| nt. | HH Ribozyme Sequence | Seq. ID No. | Target | Seq. ID No. |
|---|---|---|---|---|
| 1103 | CAGGCAGA CUGAUGAGGCCGAAAGGCCGAA AUGGGGUG | 1460 | CACCCCAUC UCUGCCUG | 1461 |
| 1105 | UGCAGGCA CUGAUGAGGCCGAAAGGCCGAA AGAUGGGG | 1462 | CCCCAUCUC UGCCUGCA | 1463 |
| 1117 | GGAGCCGG CUGAUGAGGCCGAAAGGCCGAA AUCUGCAG | 1464 | CAGCAGAUC CCGGCUCC | 1465 |
| 1124 | CAGGUAGG CUGAUGAGGCCGAAAGGCCGAA AGCCGGGA | 1466 | UCCCGGCUC CCUACCUG | 1467 |
| 1128 | UCUUCAGG CUGAUGAGGCCGAAAGGCCGAA AGGGAGCC | 1468 | GGCUCCCUA CCUGAAGA | 1469 |
| 1145 | UUGCUGGU CUGAUGAGGCCGAAAGGCCGAA AGGCACUU | 1470 | AAGUGCCUC ACCAGCAA | 1471 |
| 1164 | UGGUGGAC CUGAUGAGGCCGAAAGGCCGAA AUCAUGCA | 1472 | UGCAUGAUC GUCCACCA | 1473 |
| 1167 | CCCUGGUG CUGAUGAGGCCGAAAGGCCGAA ACGAUCAU | 1474 | AUGAUCGUC CACCAGGG | 1475 |
| 1182 | UUGUCCAG CUGAUGAGGCCGAAAGGCCGAA AUGGUGCC | 1476 | GGCACCAUU CUGGACAA | 1477 |
| 1183 | AUUGUCCA CUGAUGAGGCCGAAAGGCCGAA AAUGGUGC | 1478 | GCACCAUUC UGGACAAU | 1479 |
| 1194 | AGGUUCUU CUGAUGAGGCCGAAAGGCCGAA ACAUUGU | 1480 | GACAAUGU AAGAACCU | 1481 |
| 1195 | GAGGUUCU CUGAUGAGGCCGAAAGGCCGAA AACAUUGU | 1482 | ACAAUGUUA GAACCUC | 1483 |
| 1203 | AAUUCUAA CUGAUGAGGCCGAAAGGCCGAA AGGUUCUU | 1484 | AAGAACCUC UUAGAAUU | 1485 |
| 1205 | CAAAUUCU CUGAUGAGGCCGAAAGGCCGAA AGAGGUUC | 1486 | GAACCUCUU AGAAUUUG | 1487 |
| 1206 | GCAAAUUC CUGAUGAGGCCGAAAGGCCGAA AAGAGGUU | 1488 | AACCUCUUA GAAUUUGC | 1489 |
| 1211 | UUUCUGCA CUGAUGAGGCCGAAAGGCCGAA AUUCUAAG | 1490 | CUUAGAAUU UGCAGAAA | 1491 |
| 1212 | GUUUCUGC CUGAUGAGGCCGAAAGGCCGAA AAUUCUAA | 1492 | UUAGAAUUU GCAGAAAC | 1493 |
| 1224 | AUAAACUG CUGAUGAGGCCGAAAGGCCGAA AGUGUUUC | 1494 | GAAACACUC CAGUUUAU | 1495 |
| 1229 | AAUCUAUA CUGAUGAGGCCGAAAGGCCGAA ACUGGAGU | 1496 | ACUCCAGUU UAUAGAUU | 1497 |
| 1230 | GAAUCUAU CUGAUGAGGCCGAAAGGCCGAA AACUGGAG | 1498 | CACCAGUUU AUAGAUUC | 1499 |
| 1231 | AGAAUCUA CUGAUGAGGCCGAAAGGCCGAA AAACUGGA | 1500 | UCCAGUUUA UAGAUUCU | 1501 |
| 1233 | AAAGAAUC CUGAUGAGGCCGAAAGGCCGAA AUAAACUG | 1502 | CAGUUUAUA GAUUCUUU | 1503 |
| 1237 | CAAGAAAG CUGAUGAGGCCGAAAGGCCGAA AUCUAUAA | 1504 | UUAUAGAUU CUUUCUUG | 1505 |
| 1238 | UCAAGAAA CUGAUGAGGCCGAAAGGCCGAA AAUCUAUA | 1506 | UAUAGAUUC UUUCUUGA | 1507 |
| 1240 | GUUCAAGA CUGAUGAGGCCGAAAGGCCGAA AGAAUCUA | 1508 | UAGAUUCUU UCUUGAAC | 1509 |
| 1241 | UGUUCAAG CUGAUGAGGCCGAAAGGCCGAA AAGAAUCU | 1510 | AGAUUCUUU CUUGAACA | 1511 |
| 1242 | GUGUUCAA CUGAUGAGGCCGAAAGGCCGAA AAAGAAUC | 1512 | GAUUCUUUC UUGAACAC | 1513 |
| 1244 | AAGUGUUC CUGAUGAGGCCGAAAGGCCGAA AGAACACU | 1514 | UUCUUUCUU GAACACUU | 1515 |
| 1252 | GUUGCUGG CUGAUGAGGCCGAAAGGCCGAA AGUGUUCA | 1516 | UGAACACUU CCAGCAAC | 1517 |
| 1253 | GGUUGCUG CUGAUGAGGCCGAAAGGCCGAA AAGUGUUC | 1518 | GAACACUUC CAGCAACC | 1519 |
| 1271 | CUAAGCCC CUGAUGAGGCCGAAAGGCCGAA AGUUUUCA | 1520 | UGAAAACUC GGGCUUAG | 1521 |
| 1277 | GUGCAUCU CUGAUGAGGCCGAAAGGCCGAA AGCCCGAG | 1522 | CUCGGGCUC AGAUGCAG | 1523 |
| 1278 | GGUGCAUC CUGAUGAGGCCGAAAGGCCGAA AAGCCCGA | 1524 | UCGGGCUUA GAUGCACC | 1525 |
| 1288 | GGGUAAGG CUGAUGAGGCCGAAAGGCCGAA AGGUGCAU | 1526 | AUGCACCUA CCUUACCC | 1527 |
| 1292 | UGGAGGGU CUGAUGAGGCCGAAAGGCCGAA AGGUAGGU | 1528 | ACCUACCUU ACCCUCCA | 1529 |
| 1293 | GUGGAGGG CUGAUGAGGCCGAAAGGCCGAA AACCUAGG | 1530 | CCUACCUUA CCCUCCAC | 1531 |
| 1298 | GAGGAGUG CUGAUGAGGCCGAAAGGCCGAA AGGGUAAG | 1532 | CUUACCCUC CACUCCUC | 1533 |
| 1303 | AAUGAGAG CUGAUGAGGCCGAAAGGCCGAA AGUGGAGG | 1534 | CCUCCACUC UCUCAUU | 1535 |
| 1306 | ACCAAUGA CUGAUGAGGCCGAAAGGCCGAA AGGAGUGG | 1536 | CCACUCCUC UCAUUGGU | 1537 |
| 1308 | UGACCAZU CUGAUGAGGCCGAAAGGCCGAA AGAGGAGU | 1538 | ACUCCUCUC AUUGGUCA | 1539 |
| 1311 | UUGUGACC CUGAUGAGGCCGAAAGGCCGAA AUGAGAGG | 1540 | CCUCUCAUU GGUCACAA | 1541 |
| 1315 | CAGUUUGU CUGAUGAGGCCGAAAGGCCGAA ACCAAUGA | 1542 | UCAUUGGUC ACAAACUG | 1543 |
| 1333 | CUGGUCUC CUGAUGAGGCCGAAAGGCCGAA ACAUGGUG | 1544 | CACCAUGUC GAGACCAG | 1545 |
| 1366 | AAAGAUGG CUGAUGAGGCCGAAAGGCCGAA AUUUUCCU | 1546 | AGGAAAAUU CCAUCUUU | 1547 |
| 1367 | UAAAGAUG CUGAUGAGGCCGAAAGGCCGAA AAUUUUCC | 1548 | GGAAAAUUC CAUCUUUA | 1549 |
| 1371 | GUUCUAAA CUGAUGAGGCCGAAAGGCCGAA AUGGAAUU | 1550 | AAUUCCAUC UUUAGAAC | 1551 |
| 1373 | GAGUUCUA CUGAUGAGGCCGAAAGGCCGAA AGAUGGAA | 1552 | UUCCAUCUU UAGAACUC | 1553 |
| 1374 | GGAGUUCU CUGAUGAGGCCGAAAGGCCGAA AAGAUGGA | 1554 | UCCAUCUUU AGAACUCC | 1555 |
| 1375 | UGGAGUUC CUGAUGAGGCCGAAAGGCCGAA AAAGAUGG | 1556 | CCAUCUUUA GAACUCCA | 1557 |
| 1381 | GAUAGCUG CUGAUGAGGCCGAAAGGCCGAA AGUUCUAA | 1558 | UUAGAACUC CAGCUAUC | 1559 |
| 1387 | CCUUUUGA CUGAUGAGGCCGAAAGGCCGAA AGCUGGAG | 1560 | CUCCAGCUA UCAAAAGG | 1561 |
| 1389 | GACCUUUU CUGAUGAGGCCGAAAGGCCGAA AUAGCUGG | 1562 | CCAGCUAUC AAAAGGUC | 1563 |
| 1397 | CGAGGAUU CUGAUGAGGCCGAAAGGCCGAA ACCUUUUG | 1564 | CAAAAGGUC AAUCCUCG | 1565 |
| 1401 | CUUUCGAG CUGAUGAGGCCGAAAGGCCGAA AUUGACCU | 1566 | AGGUCAAUC CUCGAAAG | 1567 |
| 1404 | GAGCUUUC CUGAUGAGGCCGAAAGGCCGAA AGGAUUGA | 1568 | UCAAUCCUC GAAAGCUC | 1569 |
| 1412 | UUCGAGGA CUGAUGAGGCCGAAAGGCCGAA AGCUUUCG | 1570 | CGAAAGCUC UCCUCGAA | 1571 |
| 1414 | AGUUCGAG CUGAUGAGGCCGAAAGGCCGAA AGAGCUUU | 1572 | AAAGCUCUC CUCGAACU | 1573 |
| 1417 | GGGAGUUC CUGAUGAGGCCGAAAGGCCGAA AGGAGAGC | 1574 | GCUCUCCUC GAACUCCC | 1575 |
| 1423 | UGGUGUGG CUGAUGAGGCCGAAAGGCCGAA AGUUCGAG | 1576 | CUCGAACUC CCACACCA | 1577 |
| 1433 | CAUGUUUG CUGAUGAGGCCGAAAGGCCGAA AUGGUGUG | 1578 | CACACCAUU CAAACAUG | 1579 |
| 1434 | GCAUGUUU CUGAUGAGGCCGAAAGGCCGAA AAUGGUGU | 1580 | ACACCAUUC AAACAUGC | 1581 |
| 1446 | UGAGCUGA CUGAUGAGGCCGAAAGGCCGAA AGGGCAUG | 1582 | CAUGCCCUU GCAGCUCA | 1583 |
| 1453 | AAUUUCUU CUGAUGAGGCCGAAAGGCCGAA AGCUGCAA | 1584 | UUGCAGCUC AAGAAAUU | 1585 |
| 1461 | CCGUAUUU CUGAUGAGGCCGAAAGGCCGAA AUUUCUUG | 1586 | CAAGAAAUU AAAUACGG | 1587 |
| 1462 | ACCGUAUU CUGAUGAGGCCGAAAGGCCGAA AAUUUCUU | 1588 | AAGAAAUUA AAUACGGU | 1589 |
| 1466 | GGGGACCG CUGAUGAGGCCGAAAGGCCGAA AUUUAAUU | 1590 | AAUUAAAUA CGGUCCCC | 1591 |
| 1471 | CUUCAGGG CUGAUGAGGCCGAAAGGCCGAA ACCGUAUU | 1592 | AAUACGGUC CCCUGAAG | 1593 |
| 1485 | GUCUGAGG CUGAUGAGGCCGAAAGGCCGAA AGCAUCUU | 1594 | AAGAUGCUA CCUCAGAC | 1595 |
| 1489 | GGGGGUCU CUGAUGAGGCCGAAAGGCCGAA AGGUAGCA | 1596 | UGCUACCUC AGACCCCC | 1597 |
| 1599 | CUGCAUGG CUGAUGAGGCCGAAAGGCCGAA AGGGGGUC | 1598 | GACCCCCUC CAUGCAG | 1599 |
| 1518 | ACACUUG CUGAUGAGGCCGAAAGGCCGAA ACCUCCUC | 1600 | GAGGACCUA CAAGAUGU | 1601 |
| 1530 | UCCCGCUU CUGAUGAGGCCGAAAGGCCGAA AUCACAUC | 1602 | GAUGUGAUU AAGCGGGA | 1603 |
| 1531 | UUCCCGCU CUGAUGAGGCCGAAAGGCCGAA AAUCACAU | 1604 | AUGUGAUUA AGCGGGAA | 1605 |

TABLE XVI-continued

Mouse c-myb Hammerhead Ribozyme and Target Sequences
(REVISED)

| nt. | HH Ribozyme Sequence | Seq. ID No. | Target | Seq. ID No. |
|---|---|---|---|---|
| 1541 | AUUCAUCC CUGAUGAGGCCGAAAGGCCGAA AUUCCCGC | 1606 | GCGGGAAUC GGAUGAAU | 1607 |
| 1550 | CAAUUCCA CUGAUGAGGCCGAAAGGCCGAA AUUCAUCC | 1608 | GGAUGAAUC UGGAAUUG | 1609 |
| 1557 | UCAGCAAC CUGAUGAGGCCGAAAGGCCGAA AUUCCAGA | 1610 | UCUGGAAUU GUUGCUGA | 1611 |
| 1560 | AACUCAGC CUGAUGAGGCCGAAAGGCCGAA ACAAUUCC | 1612 | GGAAUUGUU GCUGAGUU | 1613 |
| 1568 | UCUCUUGA CUGAUGAGGCCGAAAGGCCGAA ACUCAGCA | 1514 | UGCUGAGUU UCAAGAGA | 1615 |
| 1569 | CUCUCUUG CUGAUGAGGCCGAAAGGCCGAA AACUCAGC | 1616 | GCUGAGUUU CAAGAGAG | 1617 |
| 1570 | ACUCUCUU CUGAUGAGGCCGAAAGGCCGAA AAACUCGA | 1618 | CUGAGUUUC AAGAGAGU | 1619 |
| 1589 | UUUUCAGU CUGAUGAGGCCGAAAGGCCGAA ACGGUGGU | 1620 | ACCACCGUU ACUGAAAA | 1621 |
| 1590 | UUUUUCAG CUGAUGAGGCCGAAAGGCCGAA AACGGUGG | 1622 | CCACCGUUA CUGAAAAA | 1623 |
| 1602 | GCCUGCUU CUGAUGAGGCCGAAAGGCCGAA AUUUUUUU | 1624 | AAAAAAAUC AAGCAGGC | 1625 |
| 1619 | CAGUUGGC CUGAUGAGGCCGAAAGGCCGAA ACUCCACC | 1626 | GGUGGAGUC GCCAACUG | 1627 |
| 1634 | AGUUUCCC CUGAUGAGGCCGAAAGGCCGAA AUUUCUCA | 1628 | UGAGAAAUC GGGAAACU | 1629 |
| 1643 | AGCAGAAA CUGAUGAGGCCGAAAGGCCGAA AGUUUCCC | 1630 | GGGAAACUU CUUCUGCU | 1631 |
| 1644 | GAGCAGAA CUGAUGAGGCCGAAAGGCCGAA AAGUUUCC | 1632 | GGAAACUUC UUCUGCUC | 1633 |
| 1646 | UUGAGCAG CUGAUGAGGCCGAAAGGCCGAA AGAAGUUU | 1634 | AAACUUCUU CUGCUCAA | 1635 |
| 1647 | UUUGAGCA CUGAUGAGGCCGAAAGGCCGAA AAGAAGUU | 1636 | AACUUCUUC UGCUCAAA | 1637 |
| 1652 | AGUGGUUU CUGAUGAGGCCGAAAGGCCGAA AAACCACU | 1638 | CUUCUGCUC AAACCACU | 1639 |
| 1691 | CCUGCGAG CUGAUGAGGCCGAAAGGCCGAA ACAGUUGG | 1640 | CCAACUGUU CUCGCAGG | 1641 |
| 1692 | GCCUGCGA CUGAUGAGGCCGAAAGGCCGAA AACAGUUG | 1642 | CAACUGUUC UCGCAGGC | 1643 |
| 1694 | ACGCCUGC CUGAUGAGGCCGAAAGGCCGAA AGAACAGU | 1644 | ACUGUUCUC GCAGGCGU | 1645 |
| 1703 | CCACAGGA CUGAUGAGGCCGAAAGGCCGAA ACGCCUGC | 1646 | GCAGGCGUC UCCUGUGG | 1647 |
| 1705 | UGCCACAG CUGAUGAGGCCGAAAGGCCGAA AGACGCCU | 1648 | AGGCGUCUC CUGUGGCA | 1649 |
| 1726 | UGUAAGAA CUGAUGAGGCCGAAAGGCCGAA AUUUGGGG | 1650 | CCCCAAAUA UUCUUACA | 1651 |
| 1728 | CUUGUAAG CUGAUGAGGCCGAAAGGCCGAA AUAUUUGG | 1652 | CCAAAUAUU CUUACAAG | 1653 |
| 1729 | GCUUGUAA CUGAUGAGGCCGAAAGGCCGAA AAUAUUUG | 1654 | CAAAUAUUC UUACAAGC | 1655 |
| 1731 | GAGCUUGU CUGAUGAGGCCGAAAGGCCGAA AGAAUAUU | 1656 | AAUAUUCUU ACAAGCUC | 1657 |
| 1732 | AGAGCUUG CUGAUGAGGCCGAAAGGCCGAA AAGAAUAU | 1658 | AUAUUCUUA CAAGCUCU | 1659 |
| 1739 | UUAAAACA CUGAUGAGGCCGAAAGGCCGAA AGCUUGUA | 1660 | UACAAGCUC UGUUUUAA | 1661 |
| 1743 | GUCAUUAA CUGAUGAGGCCGAAAGGCCGAA ACAGAGCU | 1662 | AGCUCUGUU UUAAUGAC | 1663 |
| 1744 | UGUCAUUA CUGAUGAGGCCGAAAGGCCGAA AACAGAGC | 1664 | GCUCUGUUU UAAUGACA | 1665 |
| 1745 | GUGUGAUU CUGAUGAGGCCGAAAGGCCGAA AAACAGAG | 1666 | CUCUGUUUU AAUGACAC | 1667 |
| 1746 | GGUGUCAU CUGAUGAGGCCGAAAGGCCGAA AAAACAGA | 1668 | UCUGUUUUA AUGACACC | 1669 |
| 1758 | UCUUCUGA CUGAUGAGGCCGAAAGGCCGAA ACAGGUGU | 1670 | ACACCUGUA UCAGAAGA | 1671 |
| 1760 | CAUCUUCU CUGAUGAGGCCGAAAGGCCGAA AUACAGGU | 1672 | ACCUGUAUC AGAAGAUG | 1673 |
| 1779 | GCUUUGAG CUGAUGAGGCCGAAAGGCCGAA ACAUUGUC | 1674 | GACAAUGUC UCAAAGC | 1675 |
| 1782 | AAGGCUUU CUGAUGAGGCCGAAAGGCCGAA AGGACAUU | 1676 | AAUGUCCUC AAAGCCUU | 1677 |
| 1790 | GUACGGUA CUGAUGAGGCCGAAAGGCCGAA AGGCUUUG | 1678 | CAAAGCCUU UACCGUAC | 1679 |
| 1791 | GGUACGGU CUGAUGAGGCCGAAAGGCCGAA AAGGCUUU | 1680 | AAAGCCUUU ACCGUACC | 1681 |
| 1792 | AGGUACGG CUGAUGAGGCCGAAAGGCCGAA AAAGGCUU | 1682 | AAGCCUUUA CCGUACCU | 1683 |
| 1797 | UUCUUAGG CUGAUGAGGCCGAAAGGCCGAA ACGGUAAA | 1684 | UUUACCGUA CCUAAGAA | 1685 |
| 1801 | CCUGUUCU CUGAUGAGGCCGAAAGGCCGAA AGGUACGG | 1686 | CCGUACCUA GAACAGG | 1687 |
| 1822 | CUGCAAGG CUGAUGAGGCCGAAAGGCCGAA ACCCACCA | 1688 | UGGUGGGUC CUUGCAG | 1689 |
| 1826 | AUGGCUGC CUGAUGAGGCCGAAAGGCCGAA AGGGACCC | 1690 | GGGUCCCUU GCAGCCUA | 1691 |
| 1859 | UCCCACAG CUGAUGAGGCCGAAAGGCCGAA AUGCUGGC | 1692 | GCCAGCAUC UGUGGGA | 1693 |
| 1892 | CCGGACCG CUGAUGAGGCCGAAAGGCCGAA AGGCCGUC | 1694 | GACGGCCUC CGGUCCGG | 1695 |
| 1897 | CCGAGCCG CUGAUGAGGCCGAAAGGCCGAA ACCGGAGG | 1696 | CCUCCGGUC CGGCUCGG | 1697 |
| 1903 | GUAUUUCC CUGAUGAGGCCGAAAGGCCGAA AGCCGGAC | 1698 | GUCCGGCUC GGAAAUAC | 1699 |
| 1910 | CGUUCACG CUGAUGAGGCCGAAAGGCCGAA AUUUCCGA | 1700 | UCGGAAAUA CGUGAACG | 1701 |
| 1922 | GAGCUGAG CUGAUGAGGCCGAAAGGCCGAA ACGCGUUC | 1702 | GAACGCGUU CUCAGCUC | 1703 |
| 1923 | CGAGCUGA CUGAUGAGGCCGAAAGGCCGAA AACGCGUU | 1704 | AACGCGUUC UCAGCUCG | 1705 |
| 1925 | UUCGACUC CUGAUGAGGCCGAAAGGCCGAA AGAACGCG | 1706 | CGCGUUCUC AGCUCGAA | 1707 |
| 1930 | CAGAGUUC CUGAUGAGGCCGAAAGGCCGAA AGCUGAGA | 1708 | UCUCAGCUC GAACUCUG | 1709 |
| 1936 | CAUGACCA CUGAUGAGGCCGAAAGGCCGAA AGUUCGAG | 1710 | CUCGAACUC UGGUCAUG | 1711 |
| 1941 | UCUCACAU CUGAUGAGGCCGAAAGGCCGAA ACCAGAGU | 1712 | ACUCUGGUC AUGUGAGA | 1713 |
| 1953 | UUUCUGGA CUGAUGAGGCCGAAAGGCCGAA AUGUCUCA | 1714 | UGAGACAUU UCCAGAAA | 1715 |
| 1954 | UUUUCUGG CUGAUGAGGCCGAAAGGCCGAA AAUGUCUC | 1716 | GAGACAUUU CCAGAAAA | 1717 |
| 1955 | CUUUUCUG CUGAUGAGGCCGAAAGGCCGAA AAAUGUCU | 1718 | AGACAUUUC CAGAAAAG | 1719 |
| 1967 | AAAACCAU CUGAUGAGGCCGAAAGGCCGAA AUGCUUUU | 1720 | AAAAGCAUU AUGGUUUU | 1721 |
| 1968 | GAAAACCA CUGAUGAGGCCGAAAGGCCGAA AAUGCUUU | 1722 | AAAGCAUUA UGGUUUUC | 1723 |
| 1973 | GUUCUGAA CUGAUGAGGCCGAAAGGCCGAA ACCAUAAU | 1724 | AUUAUGGUU UUCGAAC | 1725 |
| 1974 | UGUUCUGA CUGAUGAGGCCGAAAGGCCGAA AACCAUAA | 1726 | UUAUGGUUU UCAGAACA | 1727 |
| 1975 | GUGUUCUG CUGAUGAGGCCGAAAGGCCGAA AAACCAUA | 1728 | UAUGGUUUU CAGAACAC | 1729 |
| 1976 | AGUGUUCU CUGAUGAGGCCGAAAGGCCGAA AAAACCAU | 1730 | AUGGUUUUC AGAACACU | 1731 |
| 1985 | CAACUUUU CUGAUGAGGCCGAAAGGCCGAA AGUGUUCU | 1732 | AGAACACUU AAAGUUGA | 1733 |
| 1986 | UCAACUUU CUGAUGAGGCCGAAAGGCCGAA AAGUGUUC | 1734 | GAACACUUA AAGUUGAC | 1735 |
| 1992 | CGAAAGUC CUGAUGAGGCCGAAAGGCCGAA ACUUUUAA | 1736 | UUAAAAGUU GACUUUCG | 1737 |
| 1997 | UGUGUCGA CUGAUGAGGCCGAAAGGCCGAA AGUCAACU | 1738 | AGUUGACUU UCGACACA | 1739 |
| 1998 | AUGUGUCG CUGAUGAGGCCGAAAGGCCGAA AAGUCAAC | 1740 | GUUGACUUU CGACACAU | 1741 |
| 1999 | CAUGUGUC CUGAUGAGGCCGAAAGGCCGAA AAAGUCAA | 1742 | UUGACUUUC GACACAUG | 1743 |
| 2911 | ACGCUGAG CUGAUGAGGCCGAAAGGCCGAA AGCCAUGU | 1744 | ACAUGGCUC CUCAGCGU | 1745 |
| 2014 | UCCACGCU CUGAUGAGGCCGAAAGGCCGAA AGGAGCCA | 1746 | UGGCUCCUC AGCGUGGA | 1747 |
| 2028 | CAGCCAUG CUGAUGAGGCCGAAAGGCCGAA AGCGCUCC | 1748 | GGAGCGCUC CAUGGCUG | 1749 |
| 2052 | CACAACAA CUGAUGAGGCCGAAAGGCCGAA AUCAGGCU | 1750 | AGCCUGAUU UUGUUGUG | 1751 |

TABLE XVI-continued

Mouse c-myb Hammerhead Ribozyme and Target Sequences
(REVISED)

| nt. | HH Ribozyme Sequence | Seq. ID No. | Target | Seq. ID No. |
|---|---|---|---|---|
| 2053 | CCACAACA CUGAUGAGGCCGAAAGGCCGAA AAUCAAAC | 1752 | GCCUGAUUU UGUUGUGG | 1753 |
| 2054 | ACCACAAC CUGAUGAGGCCGAAAGGCCGAA AAAUCAGG | 1754 | CCUGAUUUU GUUGUGGU | 1755 |
| 2057 | UGUACCAC CUGAUGAGGCCGAAAGGCCGAA ACAAAAUC | 1756 | GAUUUUGUU GUGGUACA | 1757 |
| 2063 | AACUGUUG CUGAUGAGGCCGAAAGGCCGAA ACCACAAC | 1758 | GUUGUGGUA CAACAGUU | 1759 |
| 2071 | CUGCUCUC CUGAUGAGGCCGAAAGGCCGAA ACUGUUGU | 1760 | ACAACAGUU GAGAGCAG | 1761 |
| 2092 | CAACUAAA CUGAUGAGGCCGAAAGGCCGAA AUGCACUU | 1762 | AAGUGCAUU UUUAGUUG | 1763 |
| 2093 | GCAACUAA CUGAUGAGGCCGAAAGGCCGAA AAUGCACU | 1764 | AGUGCAUUU UUAGUUGC | 1765 |
| 2094 | AGCAACUA CUGAUGAGGCCGAAAGGCCGAA AAAUGCAC | 1766 | GUGCAUUUU UAGUUGCU | 1767 |
| 2095 | AAGCAACU CUGAUGAGGCCGAAAGGCCGAA AAAAUGCA | 1768 | UGCAUUUUU AGUUGCUU | 1769 |
| 2096 | CAAGCAAC CUGAUGAGGCCGAAAGGCCGAA AAAAAUGC | 1770 | GCAUUUUUA GUUGCUUG | 1771 |
| 2099 | UCUCAAGC CUGAUGAGGCCGAAAGGCCGAA ACUAAAAA | 1772 | UUUUUAGUU GCUUGAGA | 1773 |
| 2103 | GAGAUCUC CUGAUGAGGCCGAAAGGCCGAA AGCAACUA | 1774 | UAGUUGCUU GAGAUCUC | 1775 |
| 2109 | UCAAGUGA CUGAUGAGGCCGAAAGGCCGAA AUCUCAAG | 1776 | CUUGAGAUC UCACUUGA | 1777 |
| 2111 | AAUCAAGU CUGAUGAGGCCGAAAGGCCGAA AGAUCUCA | 1778 | UGAGAUCUC ACUUGAUU | 1779 |
| 2115 | GUGAAAUC CUGAUGAGGCCGAAAGGCCGAA AGUGAGAU | 1780 | AUCUCACUU GAUUUCAC | 1781 |
| 2119 | UUGUGUGA CUGAUGAGGCCGAAAGGCCGAA AUCAAGAG | 1782 | CACUUGAUU UCACACAA | 1783 |
| 2120 | GUUGUGUG CUGAUGAGGCCGAAAGGCCGAA AAUCAAGU | 1784 | ACUUGAUUU CACACAAC | 1785 |
| 2121 | AGUUGUGU CUGAUGAGGCCGAAAGGCCGAA AAAUCAAG | 1786 | CUUGAUUUC ACACAACU | 1787 |
| 2130 | AUCCUUUU CUGAUGAGGCCGAAAGGCCGAA AGUUGUGU | 1788 | ACACAACUA AAAGGAU | 1789 |
| 2139 | AAAAAAAA CUGAUGAGGCCGAAAGGCCGAA AUCCUUUU | 1790 | AAAAGGAUU UUUUUUU | 1791 |
| 2140 | UAAAAAAA CUGAUGAGGCCGAAAGGCCGAA AAUCCUUU | 1792 | AAAGGAUUU UUUUUUA | 1793 |
| 2141 | UUAAAAAA CUGAUGAGGCCGAAAGGCCGAA AAAUCCUU | 1794 | AAGGAUUUU UUUUUAA | 1795 |
| 2142 | UUUAAAAA CUGAUGAGGCCGAAAGGCCGAA AAAAUCCU | 1796 | AGGAUUUUU UUUUAAA | 1797 |
| 2143 | UUUUAAAA CUGAUGAGGCCGAAAGGCCGAA AAAAAUCC | 1798 | GGAUUUUUU UUUAAAA | 1799 |
| 2144 | UUUUUAAA CUGAUGAGGCCGAAAGGCCGAA AAAAAAUC | 1800 | GAUUUUUUU UUAAAAA | 1801 |
| 2145 | AUUUUUAA CUGAUGAGGCCGAAAGGCCGAA AAAAAAAU | 1802 | AUUUUUUUU UUAAAAAU | 1803 |
| 2146 | UAUUUUUA CUGAUGAGGCCGAAAGGCCGAA AAAAAAAA | 1804 | UUUUUUUUU UAAAAAUA | 1805 |
| 2147 | UUAUUUUU CUGAUGAGGCCGAAAGGCCGAA AAAAAAAA | 1806 | UUUUUUUUU AAAAAUAA | 1807 |
| 2148 | AUUAUUUU CUGAUGAGGCCGAAAGGCCGAA AAAAAAAA | 1808 | UUUUUUUA AAAAUAAU | 1809 |
| 2154 | AUUAUUAU CUGAUGAGGCCGAAAGGCCGAA AUUUUUAA | 1810 | UUAAAAAUA AUAAUAAU | 1811 |
| 2157 | UUCAUUAU CUGAUGAGGCCGAAAGGCCGAA AUUAUUUU | 1812 | AAAAUAAUA AUAAUGAA | 1813 |
| 2160 | UUAUUCAU CUGAUGAGGCCGAAAGGCCGAA AUUAUUAU | 1814 | AUAAUAAUA AUGAAUAA | 1815 |
| 2167 | AAGACUGU CUGAUGAGGCCGAAAGGCCGAA AUUCAUUA | 1816 | UAAUGAAUA ACAGUCUU | 1817 |
| 2173 | UUAGGUAA CUGAUGAGGCCGAAAGGCCGAA ACUGUUAU | 1818 | AUAACAGUC UUACCUAA | 1819 |
| 2175 | AUUUAGGU CUGAUGAGGCCGAAAGGCCGAA AGACUGUU | 1820 | AACAGUCUU ACCUAAAU | 1821 |
| 2176 | AAUUUAGG CUGAUGAGGCCGAAAGGCCGAA AAGACUGU | 1822 | ACAGUCUUA CCUAAAUU | 1823 |
| 2180 | UAAUAAUU CUGAUGAGGCCGAAAGGCCGAA AGGUAAGA | 1824 | UCUUACCUA AAUUAUUA | 1825 |
| 2184 | UACCUAAU CUGAUGAGGCCGAAAGGCCGAA AAUUUAGG | 1826 | ACCUAAAUU AUUAGGUA | 1827 |
| 2185 | UUACCUAA CUGAUGAGGCCGAAAGGCCGAA AAUUUAGG | 1828 | CCUAAAUUA UUAGGUAA | 1829 |
| 2187 | CAUUACCU CUGAUGAGGCCGAAAGGCCGAA AUAAUUUA | 1830 | UAAAUUAUU AGGUAAUG | 1831 |
| 2188 | UCAUUACC CUGAUGAGGCCGAAAGGCCGAA AAUAAUUU | 1832 | AAAUUAUUA GGUAAUGA | 1833 |
| 2192 | CAAUACGU CUGAUGAGGCCGAAAGGCCGAA ACCUAAUA | 1834 | UAUUAGGUA AUGAAUUG | 1835 |
| 2199 | AUGGUCAC CUGAUGAGGCCGAAAGGCCGAA AUUCAUUA | 1836 | UAAUGAAUU GUGACCAU | 1837 |
| 2208 | UAUUAACA CUGAUGAGGCCGAAAGGCCGAA AUGGUCAC | 1838 | GUGACCAUU UGUUAAUA | 1839 |
| 2209 | AUAUUAAC CUGAUGAGGCCGAAAGGCCGAA AAUGGUCA | 1840 | UGACCAUUU GUUAAUAU | 1841 |
| 2212 | AUGAUAUU CUGAUGAGGCCGAAAGGCCGAA ACAAAUGG | 1842 | CCAUUUGUU AAUAUCAU | 1843 |
| 2213 | UAUGAUAU CUGAUGAGGCCGAAAGGCCGAA AACAAAUG | 1844 | CAUUUGUUA AUAUCAUA | 1845 |
| 2216 | GAUUAUGA CUGAUGAGGCCGAAAGGCCGAA AUUAACAA | 1846 | UUGUUAAUA UCAUAAUC | 1847 |
| 2218 | CUGAUUAU CUGAUGAGGCCGAAAGGCCGAA AUAUUAAC | 1848 | GUUAAUAUC AUAAUCAG | 1849 |
| 2221 | AAUCUGAU CUGAUGAGGCCGAAAGGCCGAA AUGAUAUU | 1850 | AAUAUCAUA AUCAGAUU | 1851 |
| 2224 | AAAAAUCU CUGAUGAGGCCGAAAGGCCGAA AUUAUGAU | 1852 | AUCAUAAUC AGAUUUUU | 1853 |
| 2229 | UUUUAAAA CUGAUGAGGCCGAAAGGCCGAA AUCUGAUU | 1854 | AAUCAGAUU UUUUAAAA | 1855 |
| 2230 | UUUUUAAA CUGAUGAGGCCGAAAGGCCGAA AAUCUGAU | 1856 | AUCAGAUUU UUUAAAAA | 1857 |
| 2231 | UUUUUUAA CUGAUGAGGCCGAAAGGCCGAA AAAUCUGA | 1858 | UCAGAUUUU UUAAAAAA | 1859 |
| 2232 | UUUUUUUA CUGAUGAGGCCGAAAGGCCGAA AAAAUCUG | 1860 | CAGAUUUUU UAAAAAAA | 1861 |
| 2233 | UUUUUUUU CUGAUGAGGCCGAAAGGCCGAA AAAAAUCU | 1862 | AGAUUUUUU AAAAAAAA | 1863 |
| 2234 | AUUUUUUU CUGAUGAGGCCGAAAGGCCGAA AAAAAAUC | 1864 | GAUUUUUUA AAAAAAAU | 1865 |
| 2243 | AAUCAUUU CUGAUGAGGCCGAAAGGCCGAA AUUUUUUU | 1866 | AAAAAAAUA AAAUGAUU | 1867 |
| 2251 | UACAAAUA CUGAUGAGGCCGAAAGGCCGAA AUCAUUUU | 1868 | AAAAUGAUU UAUUUGUA | 1869 |
| 2252 | AUACAAAU CUGAUGAGGCCGAAAGGCCGAA AAUCAUUU | 1870 | AAAUGAUUU AUUUGUAU | 1871 |
| 2253 | AAUACAAA CUGAUGAGGCCGAAAGGCCGAA AAAUCAUU | 1872 | AAUGAUUUA UUUGUAUU | 1873 |
| 2255 | AAAAUACA CUGAUGAGGCCGAAAGGCCGAA AUAAAUCA | 1874 | UGAUUUAUU UGAUUUUU | 1875 |
| 2256 | UAAAAAUAC CUGAUGAGGCCGAAAGGCCGAA AAAUAAUC | 1876 | GAUUUAUUU GUAUUUUA | 1877 |
| 2259 | CUCUAAAA CUGAUGAGGCCGAAAGGCCGAA ACAAAUAA | 1878 | UUAUUUGUA UUUUAGAG | 1879 |
| 2261 | UUCUCUAA CUGAUGAGGCCGAAAGGCCGAA AUACAAAU | 1880 | AUUUGUAUU UUAGAGAA | 1881 |
| 2262 | AUUCUCUA CUGAUGAGGCCGAAAGGCCGAA AAUACAAA | 1882 | UUUGUAUUU UAGAGAAU | 1883 |
| 2263 | UAUUCUCU CUGAUGAGGCCGAAAGGCCGAA AAAUACAA | 1884 | UUGUAUUUU AGAGAAUA | 1885 |
| 2264 | GUAUUCUC CUGAUGAGGCCGAAAGGCCGAA AAAAUACA | 1886 | UGUAUUUUA GAGAAUAC | 1887 |
| 2271 | AUCUGUUG CUGAUGAGGCCGAAAGGCCGAA AUUCUCUA | 1888 | UAGAGAAUA CAACAGAU | 1889 |
| 2280 | AAAAUACU CUGAUGAGGCCGAAAGGCCGAA AUCUGUUG | 1890 | CAACAGAUC AGUAUUUU | 1891 |
| 2284 | GUCAAAAA CUGAUGAGGCCGAAAGGCCGAA ACUGAUCU | 1892 | AGAUCAGUA UUUUUGAC | 1893 |
| 2286 | CAGUCAAA CUGAUGAGGCCGAAAGGCCGAA AUACUGAU | 1894 | AUCAGUAUU UUGACUG | 1895 |
| 2287 | ACAGUCAA CUGAUGAGGCCGAAAGGCCGAA AAUACUGA | 1896 | UCAGUAUUU UGACUGU | 1897 |

TABLE XVI-continued

Mouse c-myb Hammerhead Ribozyme and Target Sequences
(REVISED)

| nt. | HH Ribozyme Sequence | Seq. ID No. | Target | Seq. ID No. |
|---|---|---|---|---|
| 2288 | CACAGUCA CUGAUGAGGCCGAAAGGCCGAA AAAUACUG | 1898 | CAGUAUUUU UGACUGUG | 1899 |
| 2289 | CCACAGUC CUGAUGAGGCCGAAAGGCCGAA AAAAUACU | 1900 | AGUAUUUUU GACUGUGG | 1901 |
| 2303 | UUUUUUUA CUGAUGAGGCCGAAAGGCCGAA AUUCACCA | 1902 | UGUGGAAUU UAAAAAAA | 1903 |
| 2304 | UUUUUUUU CUGAUGAGGCCGAAAGGCCGAA AAUUCACC | 1904 | GGUGAAUUU AAAAAAAA | 1905 |
| 2305 | UUUUUUU CUGAUGAGGCCGAAAGGCCGAA AAAUUCAC | 1906 | GUGAAUUUU AAAAAAAA | 1907 |
| 2316 | UUUGUGUA CUGAUGAGGCCGAAAGGCCGAA AUUUUUUU | 1908 | AAAAAAAUU UACACAAA | 1909 |
| 2317 | CUUUGUGU CUGAUGAGGCCGAAAGGCCGAA AAUUUUUU | 1910 | AAAAAAUUU ACACAAAG | 1911 |
| 2318 | UCUUUGUG CUGAUGAGGCCGAAAGGCCGAA AAAUUUUU | 1912 | AAAAAUUUA CACAAAGA | 1913 |
| 2330 | UACUGGGA CUGAUGAGGCCGAAAGGCCGAA AUUUCUUU | 1914 | AAAGAAAUA UCCCAGUA | 1915 |
| 2332 | AAUACUGG CUGAUGAGGCCGAAAGGCCGAA AUAUUUCU | 1916 | AGAAAUAUC CCAGUAUU | 1917 |
| 2338 | ACAUGGAA CUGAUGAGGCCGAAAGGCCGAA ACUGGGAU | 1918 | AUCCCAGUA UUCCAUGU | 1919 |
| 2340 | AUACAUGG CUGAUGAGGCCGAAAGGCCGAA AUACUGGG | 1920 | CCCAGUAUU CCAUGUAU | 1921 |
| 2341 | GAUACAUG CUGAUGAGGCCGAAAGGCCGAA AAUACUGG | 1922 | CCAGUAUUC CAUGUAUC | 1923 |
| 2347 | GACUGAGA CUGAUGAGGCCGAAAGGCCGAA ACAUGGAA | 1924 | UUCCAUGUA UCUCAGUC | 1925 |
| 2349 | GUGACUGA CUGAUGAGGCCGAAAGGCCGAA AUACAUGG | 1926 | CCAUGUAUC UCAGUCAC | 1927 |
| 2351 | UAGUGACU CUGAUGAGGCCGAAAGGCCGAA AGAUACAU | 1928 | AUGUAUCUC AGUCACUA | 1929 |
| 2355 | UGUUUAGU CUGAUGAGGCCGAAAGGCCGAA ACUGAGAU | 1930 | AUCUCAGUC ACUAAACA | 1031 |
| 2359 | AGUAUGU CUGAUGAGGCCGAAAGGCCGAA AGUGACUG | 1932 | CAGUCACUA AACAUACA | 1033 |
| 2365 | UCUCUGUG CUGAUGAGGCCGAAAGGCCGAA AUGUUUAG | 1934 | CUAAACAUA CACAGAGA | 1935 |
| 2377 | UUUUUAAA CUGAUGAGGCCGAAAGGCCGAA AUCUCUCU | 1936 | AGAGAGAUU UUUAAAAA | 1937 |
| 2378 | GUUUUUAA CUGAUGAGGCCGAAAGGCCGAA AAUCUCUC | 1938 | GAGAGAUUU UUAAAAAC | 1939 |
| 2379 | GGUUUUUA CUGAUGAGGCCGAAAGGCCGAA AAAUCUCU | 1940 | AGAGAUUUU UAAAAACC | 1941 |
| 2380 | UGGUUUUU CUGAUGAGGCCGAAAGGCCGAA AAAAUCUC | 1942 | GAGAUUUUU AAAAACCA | 1943 |
| 2381 | CUGGUUUU CUGAUGAGGCCGAAAGGCCGAA AAAAAUCU | 1944 | AGAUUUUUA AAAACCAG | 1945 |
| 2399 | UUCAAAAU CUGAUGAGGCCGAAAGGCCGAA AUGCUUCU | 1946 | AGAAGCAUU AUUUUGAA | 1947 |
| 2400 | AUUCAAAA CUGAUGAGGCCGAAAGGCCGAA AAUGCUUC | 1948 | GAAGCAUUA UUUUGAAU | 1948 |
| 2402 | ACAUUCAA CUGAUGAGGCCGAAAGGCCGAA AUAAUGCU | 1950 | AGCAUUAUU UUGAAUGU | 1951 |
| 2403 | AACAUUCA CUGAUGAGGCCGAAAGGCCGAA AAUAAUGC | 1952 | GCAUUAUUU UGAAUGUU | 1953 |
| 2404 | UAACAUUC CUGAUGAGGCCGAAAGGCCGAA AAAUAAUG | 1954 | CAUUAUUUU GAAUGUUA | 1955 |
| 2411 | AUUUAGCU CUGAUGAGGCCGAAAGGCCGAA ACAUUCAA | 1956 | UUGAAUGUU AGCUAAAU | 1957 |
| 2412 | GAUUUAGC CUGAUGAGGCCGAAAGGCCGAA UACAUUCA | 1958 | UGAAUGUUA GCUAAAUC | 1959 |
| 2416 | UUGGGAUU CUGAUGAGGCCGAAAGGCCGAA AGCUAACA | 1960 | UGUUAGCUA AAUCCCAA | 1961 |
| 2420 | UUACUUGG CUGAUGAGGCCGAAAGGCCGAA AUUUAGCU | 1962 | AGCUAAAUC CAAGUAA | 1963 |
| 2427 | UUAAGUAU CUGAUGAGGCCGAAAGGCCGAA ACUUGGGA | 1964 | UCCCAAGUA AUACUUAA | 1965 |
| 2430 | GCAUUAAGA CUGAUGAGGCCGAAAGGCCGAA AUUACUUG | 1966 | CAAGUAACA CUUAAUGC | 1967 |
| 2433 | GUUGCAUU CUGAUGAGGCCGAAAGGCCGAA AGUAUUAC | 1968 | GUAAUACUU AAUGCAAC | 1969 |
| 2434 | GGUUGCAU CUGAUGAGGCCGAAAGGCCGAA AAGUAUUA | 1970 | UAAUACUUA AUGCAACC | 1971 |
| 2445 | AGCUCCUA CUGAUGAGGCCGAAAGGCCGAA AGGGUUGC | 1972 | GCAACCCUC UAGGAGCU | 1973 |
| 2447 | UGAGCUCC CUGAUGAGGCCGAAAGGCCGAA AGAGGGUU | 1974 | AACCCUCUA GGAGCUCA | 1975 |
| 2454 | CCACAAAU CUGAUGAGGCCGAAAGGCCGAA AGCUCCUA | 1976 | UAGGAGCUC AUUUGUGG | 1977 |
| 2457 | UAGCCACA CUGAUGAGGCCGAAAGGCCGAA AUGAGCUC | 1978 | GAGCUCAUU UGUGGCUA | 1979 |
| 2458 | UUAGCCAC CUGAUGAGGCCGAAAGGCCGAA AAUGAGCU | 1980 | AGCUCAUUU GUGGCUAA | 1981 |
| 2465 | AAGAUUAU CUGAUGAGGCCGAAAGGCCGAA AGCCACAA | 1982 | UUGUGGCUA AUAAUCUU | 1983 |
| 2468 | UCCAAGAU CUGAUGAGGCCGAAAGGCCGAA AUAUUAGGCA | 1984 | UGGCUAAUA AUCUUGGA | 1985 |
| 2471 | AUUUCCAA CUGAUGAGGCCGAAAGGCCGAA AUUAUUAG | 1986 | CUAAUAAUC UUGGAAAU | 1987 |
| 2473 | AUAUUUCC CUGAUGAGGCCGAAAGGCCGAA AGAUUAUU | 1988 | AAUAAUCUU GGAAAUAU | 1989 |
| 2480 | AAUAAAGA CUGAUGAGGCCGAAAGGCCGAA AUUUCCAA | 1990 | UUGGAAAUA UCUUUAUU | 1991 |
| 2482 | AUAAAUAA CUGAUGAGGCCGAAAGGCCGAA AUAUUUCC | 1992 | GGAAAUAUC UUUAUUCC | 1993 |
| 2484 | AUAUAAUA CUGAUGAGGCCGAAAGGCCGAA AGAUAUUU | 1994 | AAAUAUCUU UAUUAUAU | 1995 |
| 2485 | UAUAUAAU CUGAUGAGGCCGAAAGGCCGAA AAGAUAUU | 1996 | AAUAUCUUU AUUAUAUA | 1997 |
| 2486 | CUAUAUAA CUGAUGAGGCCGAAAGGCCGAA AAAGAUAU | 1998 | AUAUCUUUA UUAUAUAG | 1999 |
| 2488 | UGCUAUAU CUGAUGAGGCCGAAAGGCCGAA AUAUAGCA | 2000 | AUCUUUAUU AUAUAGCA | 2001 |
| 2489 | AUGCUAUA CUGAUGAGGCCGAAAGGCCGAA AAUAAAGA | 2002 | UCUUUAUUA UAUAGCAU | 2003 |
| 2491 | AAAUGCUA CUGAUGAGGCCGAAAGGCCGAA AUAAUAAA | 2004 | UUUAUUAUA UAGCAUUU | 2005 |
| 2493 | AUAAAUGC CUGAUGAGGCCGAAAGGCCGAA AUAUAAUA | 2006 | UAUUAUAUA GCAUUUAU | 2007 |
| 2498 | UCCUCAUA CUGAUGAGGCCGAAAGGCCGAA AUGCUAUA | 2008 | UAUAGCAUU UAUGAGGA | 2009 |
| 2499 | CUCCUCAU CUGAUGAGGCCGAAAGGCCGAA AAUGCUAU | 2010 | AUAGCAUUU AUGAGGAG | 2011 |
| 2500 | UCUCCUCA CUGAUGAGGCCGAAAGGCCGAA AAAUGCUA | 2012 | UAGCAUUUA UGAGGAGA | 2013 |
| 2510 | GACAACAA CUGAUGAGGCCGAAAGGCCGAA AUCUCCUC | 2014 | GAGGAGAUU UGUUGUC | 2015 |
| 2511 | UGACAACA CUGAUGAGGCCGAAAGGCCGAA AAUCUCCU | 2016 | AGGAGAUUU GUUGUCA | 2017 |
| 2512 | CUGACAAC CUGAUGAGGCCGAAAGGCCGAA AAAUCUCC | 2018 | GGAGAUUUU GUUGUCAG | 2019 |
| 2515 | AAGCUGAC CUGAUGAGGCCGAAAGGCCGAA ACAAAAUC | 2020 | GAUUUUGUU GUCAGCUU | 2021 |
| 2518 | AGCAAGCU CUGAUGAGGCCGAAAGGCCGAA ACAACAAA | 2022 | UUUGUUGUC AGCUUGCU | 2023 |
| 2523 | UUUCAAGC CUGAUGAGGCCGAAAGGCCGAA AGCUGACA | 2024 | UGUCAGCUU GCUUGAAA | 2025 |
| 2527 | UAACUUUC CUGAUGAGGCCGAAAGGCCGAA AGCAAGCU | 2026 | AGCUUGCUU GAAAGUUA | 2027 |
| 2534 | UACAUAAU CUGAUGAGGCCGAAAGGCCGAA ACUUUCAA | 2028 | UUGAAAGUU AUUAAGUA | 2029 |
| 2535 | AUACAUAA CUGAUGAGGCCGAAAGGCCGAA AACUUUCA | 2030 | UGAAAGUUA UUAAGUAU | 2031 |
| 2537 | UCAUACAU CUGAUGAGGCCGAAAGGCCGAA AUAACUUU | 2032 | AAAGUUAUU AAGUAUGA | 2033 |
| 2538 | UUCAUACA CUGAUGAGGCCGAAAGGCCGAA AAUAACUU | 2034 | AAGUUAUUA AGUAUGAA | 2035 |
| 2542 | ACUAUUCA CUGAUGAGGCCGAAAGGCCGAA ACAUAAUA | 2036 | UAUUAUGUA UGAAUAGU | 2037 |
| 2548 | AAUAAAAC CUGAUGAGGCCGAAAGGCCGAA AUUCAUAC | 2038 | GUAUGAAUA GUUUUAUU | 2039 |
| 2551 | UUCAAUAA CUGAUGAGGCCGAAAGGCCGAA ACUAUUCA | 2040 | UGAAUAGUU UUAUUGAA | 2041 |
| 2552 | UUUCAAUA CUGAUGAGGCCGAAAGGCCGAA AACUAUUC | 2042 | GAAUAGUUU UAUUGAAA | 2043 |

TABLE XVI-continued

Mouse c-myb Hammerhead Ribozyme and Target Sequences
(REVISED)

| nt. | HH Ribozyme Sequence | Seq. ID No. | Target | Seq. ID No. |
|---|---|---|---|---|
| 2553 | UUUUCAAU CUGAUGAGGCCGAAAGGCCGAA AAACUAUU | 2044 | AAUAGUUUU AUUGAAAA | 2045 |
| 2554 | UUUUUCAA CUGAUGAGGCCGAAAGGCCGAA AAAACUAU | 2046 | AUAGUUUUA UUGAAAAA | 2047 |
| 2556 | AUUUUUUA CUGAUGAGGCCGAAAGGCCGAA AUAAAACU | 2048 | AGUUUUAUU GAAAAAAU | 2049 |
| 2565 | AAAAAUAU CUGAUGAGGCCGAAAGGCCGAA AUUUUUUC | 2050 | GAAAAAAUU AUAUUUUU | 2051 |
| 2566 | UAAAAAUA CUGAUGAGGCCGAAAGGCCGAA AAUUUUUU | 2052 | AAAAAAUUA UAUUUUUA | 2053 |
| 2568 | AAUAAAAA CUGAUGAGGCCGAAAGGCCGAA AUAAUUUU | 2054 | AAAAUUAUA UUUUUAUU | 2055 |
| 2570 | UGAAUAAA CUGAUGAGGCCGAAAGGCCGAA AUAUAAUU | 2056 | AAUUAUAUU UUUAUUCA | 2057 |
| 2571 | CUGAAUAA CUGAUGAGGCCGAAAGGCCGAA AAUAUAAU | 2058 | AUUAUAUUU UUAUUCAG | 2059 |
| 2572 | ACUGAAUA CUGAUGAGGCCGAAAGGCCGAA AAAUAUAA | 2060 | UUAUAUUUU UAUUCAGU | 2061 |
| 2573 | UACUGAAU CUGAUGAGGCCGAAAGGCCGAA AAAAUAUA | 2062 | UAUAUUUUU AUUCAGUA | 2063 |
| 2574 | UUACUGAA CUGAUGAGGCCGAAAGGCCGAA AAAAAUAU | 2064 | AUAUUUUUA UUCAGUAA | 2065 |
| 2576 | AAUUACUA CUGAUGAGGCCGAAAGGCCGAA AUAAAAAU | 2066 | AUUUUUAUU CAGUAAUU | 2067 |
| 2577 | AAAUUACU CUGAUGAGGCCGAAAGGCCGAA AAUAAAAA | 2068 | UUUUUAUUC AGUAAUUU | 2069 |
| 2581 | AAUUAAAU CUGAUGAGGCCGAAAGGCCGAA ACUGAAUA | 2070 | UAUUCAGUA AUUUAAUU | 2071 |
| 2584 | CAAAAUUA CUGAUGAGGCCGAAAGGCCGAA AUUACUGA | 2072 | UCAGUAAUU UAAUUUUG | 2073 |
| 2585 | ACAAAAUU CUGAUGAGGCCGAAAGGCCGAA AAUUUUCGU | 2074 | CAGUAAUUU AAUUUUGU | 2075 |
| 2586 | UACAAAAU CUGAUGAGGCCGAAAGGCCGAA AAAUUACU | 2076 | AGUAAUUUA AUUUUGUA | 2077 |
| 2589 | AUUUACAA CUGAUGAGGCCGAAAGGCCGAA AUUAAAUU | 2078 | AAUUUAAUU UUGUAAAU | 2079 |
| 2590 | CAUUUACA CUGAUGAGGCCGAAAGGCCGAA AAUUAAAU | 2080 | AUUUAAUUU UGUAAAUG | 2081 |
| 2591 | GCAUUUAC CUGAUGAGGCCGAAAGGCCGAA AAAUUAAA | 2082 | UUUAAUUUU GUAAAUGC | 2083 |
| 2594 | UUGGCAUU CUGAUGAGGCCGAAAGGCCGAA ACAAAAUU | 2084 | AAUUUUGUA AAUGCCAA | 2085 |
| 2617 | UAGCAGCG CUGAUGAGGCCGAAAGGCCGAA ACACAUUU | 2086 | AAAUGUGUU CGCUGCUA | 2087 |
| 2618 | AUAGCAGC CUGAUGAGGCCGAAAGGCCGAA AACACAUU | 2088 | AAUGUGUUC GCUGCUAU | 2089 |
| 2625 | UAAAACCA CUGAUGAGGCCGAAAGGCCGAA AGCAGCGA | 2090 | UCGCUGCUA UGGUUUUA | 2091 |
| 2630 | UAAGCUAA CUGAUGAGGCCGAAAGGCCGAA ACCAUAGC | 2092 | GCUAUGGUU UUAGCCUA | 2093 |
| 2631 | AUAGGCUA CUGAUGAGGCCGAAAGGCCGAA AACCAUAG | 2094 | CUAUGGUUU UAGCCUAU | 2095 |
| 2632 | UAUAGGCU CUGAUGAGGCCGAAAGGCCGAA AAACCAUA | 2096 | UAUGGUUUU AGCCUAUA | 2097 |
| 2633 | CUAUAGGC CUGAUGAGGCCGAAAGGCCGAA AAAACCAU | 2098 | AUGGUUUUA GCCUAUAG | 2099 |
| 2638 | CAUGACUA CUGAUGAGGCCGAAAGGCCGAA AGGCUAAA | 2100 | UUUAGCCUA UAGUCAUG | 2101 |
| 2640 | AGCAUGAC CUGAUGAGGCCGAAAGGCCGAA AUAGGCUA | 2102 | UAGCCUAUA GUCAUGCU | 2103 |
| 2643 | AGCAGCAU CUGAUGAGGCCGAAAGGCCGAA ACUAUAGG | 2104 | CCUAUAGUC AUGCUGCU | 2105 |
| 2652 | ACACUAGC CUGAUGAGGCCGAAAGGCCGAA AGCAGCAU | 2106 | AUGCUGCUA GCUAGUGU | 2107 |
| 2656 | CCUGACAC CUGAUGAGGCCGAAAGGCCGAA AGCUAGCA | 2108 | UGCUAGCUA GUGUCAGG | 2109 |
| 2661 | UGCCCCCU CUGAUGAGGCCGAAAGGCCGAA ACACUAGC | 2110 | GCUAGUGUC AGGGGGCA | 2111 |
| 2672 | CUAAGCUC CUGAUGAGGCCGAAAGGCCGAA AUUGCCCC | 2112 | GGGGCAAUA GAGCUUAG | 2113 |
| 2678 | UUCCAUCU CUGAUGAGGCCGAAAGGCCGAA AGCUCUAU | 2114 | AUAGAGCUU AGAUGGAA | 2115 |
| 2679 | UUUCCAUC CUGAUGAGGCCGAAAGGCCGAA AAGCUCUA | 2116 | UACAGCUUA GAUGGAAA | 2117 |
| 2703 | CUAACACC CUGAUGAGGCCGAAAGGCCGAA AGUCUCUU | 2118 | AAGAGACUC GGUGUUAG | 2119 |
| 2709 | CGUUAUCU CUGAUGAGGCCGAAAGGCCGAA ACACCGAG | 2120 | CUCGGUGUU AGAUAACG | 2121 |
| 2710 | CCGUUAUC CUGAUGAGGCCGAAAGGCCGAA AACACCGA | 2122 | UCGGUGUUA GAUAACGG | 2123 |
| 2714 | UAGUCCGU CUGAUGAGGCCGAAAGGCCGAA AUCUAACA | 2124 | UGUUAGAUA ACGGACUA | 2125 |
| 2722 | CUACGCCA CUGAUGAGGCCGAAAGGCCGAA AGUCCGUU | 2126 | AACGGACUA UGCACUAG | 2127 |
| 2729 | UGGAAUAC CUGAUGAGGCCGAAAGGCCGAA AGUGCAUA | 2128 | UAUGCACUA GUAUUCCA | 2129 |
| 2732 | GUCUGGAA CUGAUGAGGCCGAAAGGCCGAA ACUAGUGC | 2130 | UCACUAGUA UUCCAGAC | 2131 |
| 2734 | AAGUCUGG CUGAUGAGGCCGAAAGGCCGAA AUACUAGU | 2132 | ACUAGUAUU CCAGACUU | 2133 |
| 2735 | AAAGUCUG CUGAUGAGGCCGAAAGGCCGAA AAUACUAG | 2134 | CUAGUAUUC CAGACUUU | 2135 |
| 2742 | AAAUAAAA CUGAUGAGGCCGAAAGGCCGAA AGUCUGGA | 2136 | UCCAGACUU UUUUAUUU | 2137 |
| 2743 | AAAAUAAA CUGAUGAGGCCGAAAGGCCGAA AAGUCUGG | 2138 | CCAGACUUU UUUAUUUU | 2139 |
| 2744 | AAAAAUAA CUGAUGAGGCCGAAAGGCCGAA AAAGUCUG | 2140 | CAGACUUUU UUAUUUUU | 2141 |
| 2745 | AAAAAAUA CUGAUGAGGCCGAAAGGCCGAA AAAGUCU | 2142 | AGACUUUUU UAUUUUUU | 2143 |
| 2746 | UAAAAAAU CUGAUGAGGCCGAAAGGCCGAA AAAAAGUC | 2144 | GACUUUUUU AUUUUUUA | 2145 |
| 2747 | AUAAAAAA CUGAUGAGGCCGAAAGGCCGAA AAAAAAGU | 2146 | ACUUUUUUA UUUUUUAU | 2147 |
| 2749 | AUAUAAAA CUGAUGAGGCCGAAAGGCCGAA AUAAAAAA | 2148 | UUUUUAUUU UUUAUAUU | 2149 |
| 2750 | UAUAUAAA CUGAUGAGGCCGAAAGGCCGAA AAUAAAAA | 2150 | UUUUUAUUU UUUAUAUA | 2151 |
| 2751 | AUAUAUAA CUGAUGAGGCCGAAAGGCCGAA AAAUAAAA | 2152 | UUUUAUUUU UAUAUAU | 2153 |
| 2752 | UAUAUAUA CUGAUGAGGCCGAAAGGCCGAA AAAAUAAA | 2154 | UUUAUUUUU UAUAUAUA | 2155 |
| 2753 | AUAUAUAU CUGAUGAGGCCGAAAGGCCGAA AAAAAUAA | 2156 | UUAUUUUUU AUAUAUAU | 2157 |
| 2754 | CAUAUAUA CUGAUGAGGCCGAAAGGCCGAA AAAAAAUA | 2158 | UAUUUUUUA UAUAUAUG | 2159 |
| 2756 | UACAUAUA CUGAUGAGGCCGAAAGGCCGAA AUAAAAAA | 2160 | UUUUUUAUA UAUAUGUA | 2161 |
| 2758 | GGUACAUA CUGAUGAGGCCGAAAGGCCGAA AUAUAAAA | 2162 | UUUUAUAUA UAUGUACC | 2163 |
| 2760 | AAGGUACA CUGAUGAGGCCGAAAGGCCGAA AUAUAUAA | 2164 | UUAUAUAUA UGUACCUU | 2165 |
| 2764 | GGAAAAGG CUGAUGAGGCCGAAAGGCCGAA ACAUAUAU | 2166 | AUAUAUGUA CCUUUUCC | 2167 |
| 2768 | AAAAGGAA CUGAUGAGGCCGAAAGGCCGAA AGGUACAU | 2168 | AUGUACCUU UUCCUUUU | 2169 |
| 2769 | CAAAAGGA CUGAUGAGGCCGAAAGGCCGAA AAGGUACA | 2170 | UGUACCUUU UCCUUUUG | 2171 |
| 2770 | ACAAAAGG CUGAUGAGGCCGAAAGGCCGAA AAAGGUAC | 2172 | GUACCUUUU CCUUUUGU | 2173 |
| 2771 | GACAAAAG CUGAUGAGGCCGAAAGGCCGAA AAAAGGUA | 2174 | UACCUUUUC CUUUUGUC | 2175 |
| 2774 | AUUGACAA CUGAUGAGGCCGAAAGGCCGAA AGGAAAAG | 2176 | CUUUUCCUU UUGUCAAU | 2177 |
| 2775 | AAUUGACA CUGAUGAGGCCGAAAGGCCGAA AAGGAAAA | 2178 | UUUUCCUUU UGUCAAUU | 2179 |
| 2276 | CAAUUGAC CUGAUGAGGCCGAAAGGCCGAA AAAGGAAA | 2180 | UUUCCUUUU GUCAAUUG | 2181 |

TABLE XVII

Mouse c-myb Hairpin ribozyme and target sequences (REVISED)

| Position | Ribozyme | Seq. ID No. | Substrate | Seq. ID No. |
|---|---|---|---|---|
| 24 | GCGAGGCG AGAA GGGGCU ACCAGAGAAACACGUUGUGUGGUACAUUACCUGGUA | 2182 | CGCCUCGC GCC AGCCCCG | 2183 |
| 28 | CAUGCGGA AGAA GGCCGG ACCAGAGAAACACGUUGUGUGGUACAUUACCUGGUA | 2184 | UCGCCAUG GCC CCGGCCC | 2185 |
| 122 | AUUGGGC AGAA GCCCAU ACCAGAGAAACACGUUGUGUGGUACAUUACCUGGUA | 2186 | GCCCAAAU GCU AUGGGCU | 2187 |
| 125 | CAGAUUUG AGAA GCAGCC ACCAGAGAAACACGUUGUGUGGUACAUUACCUGGUA | 2188 | GGCUGCU GCC CAAAUCUG | 2189 |
| 216 | UUCCAGUC AGAA GUUCGG ACCAGAGAAACACGUUGUGUGGUACAUUACCUGGUA | 2190 | CGGAACA GAC GACUGGAA | 2191 |
| 245 | UCCCGUUG AGAA GAUAAU ACCAGAGAAACACGUUGUGUGGUACAUUACCUGGUA | 2192 | AUUAUCU GCC CAACGGGA | 2193 |
| 258 | CACUGUAC AGAA GUCCGG ACCAGAGAAACACGUUGUGUGGUACAUUACCUGGUA | 2194 | CCGGACA GAU GUACAGUG | 2195 |
| 529 | CUCUCGCC AGAA GUUCCC ACCAGAGAAACACGUUGUGUGGUACAUUACCUGGUA | 2196 | GGGAACA GAU GGCGAGAG | 2197 |
| 551 | GUCCGGGC AGAA GCUUUG ACCAGAGAAACACGUUGUGUGGUACAUUACCUGGUA | 2198 | CAAAGCU GCU GCCCGGAC | 2199 |
| 554 | UCCUCCG AGAA GCAGCU ACCAGAGAAACACGUUGUGUGGUACAUUACCUGGUA | 2200 | AGCUGCU GCC CGGACGGA | 2201 |
| 559 | AUCAGUCC AGAA GGGCAG ACCAGAGAAACACGUUGUGUGGUACAUUACCUGGUA | 2202 | CUGCCCG GAC GGACUGAU | 2203 |
| 563 | CAUUAUCA AGAA GUCCGG ACCAGAGAAACACGUUGUGUGGUACAUUACCUGGUA | 2204 | CCGGACG GAC UGAUAAUG | 2205 |
| 656 | CCACUGAG AGAA GGCUGG ACCAGAGAAACACGUUGUGUGGUACAUUACCUGGUA | 2206 | CCAGCCA GAC GCCAGUGG | 2207 |
| 728 | UUGGAGAG AGAA GAGAUG ACCAGAGAAACACGUUGUGUGGUACAUUACCUGGUA | 2208 | CAUCUCA GCU CUCUCCAA | 2209 |
| 746 | UGACGGAG AGAA GGCCAC ACCAGAGAAACACGUUGUGUGGUACAUUACCUGGUA | 2210 | GUGGCCA GUC CUCCGUCA | 2211 |
| 822 | UGCAAUGC AGAA GGAUAG ACCAGAGAAACACGUUGUGUGGUACAUUACCUGGUA | 2212 | CUAUCCU GAU GCAUUGCA | 2213 |
| 857 | CCCGAGCC AGAA GAGGGA ACCAGAGAAACACGUUGUGUGGUACAUUACCUGGUA | 2214 | UCCCUCA GCC GGCUCGGG | 2215 |
| 861 | GCUGCCGC AGAA GGCUGA ACCAGAGAAACACGUUGUGUGGUACAUUACCUGGUA | 2216 | UCAGCCG GCU GCGGCAGC | 2217 |
| 941 | CUGUUGAC AGAA GGAGCA ACCAGAGAAACACGUUGUGUGGUACAUUACCUGGUA | 2218 | UGCUCCU GAU GUCAACAG | 2218 |
| 1040 | GAGGUCUG AGAA GGUCCA ACCAGAGAAACACGUUGUGUGGUACAUUACCUGGUA | 2220 | UGGACCA GAC CAGACCUC | 2221 |
| 1045 | CCCAUGAG AGAA GGUCUG ACCAGAGAAACACGUUGUGUGGUACAUUACCUGGUA | 2222 | CAGACCA GAC CUCAUGGG | 2223 |
| 1068 | AAACAGGA AGAA GGUGCA ACCAGAGAAACACGUUGUGUGGUACAUUACCUGGUA | 2224 | UGCACCU GUU UCCUGUUU | 2225 |
| 1075 | UUCUCCCA AGAA GGAAAC ACCAGAGAAACACGUUGUGUGGUACAUUACCUGGUA | 2226 | GUUUCCU GUU UGGGAGAA | 2227 |
| 1106 | GAUCUGCA AGAA GAGAUG ACCAGAGAAACACGUUGUGUGGUACAUUACCUGGUA | 2228 | CAUCUCU GCC GCAUUGCA | 2229 |
| 1113 | AGCCGCC AGAA GCAGGG ACCAGAGAAACACGUUGUGUGGUACAUUACCUGGUA | 2230 | CCCUGCA GAU CCCGGCU | 2231 |
| 1120 | AGGUAGGG AGAA GGGAUC ACCAGAGAAACACGUUGUGUGGUACAUUACCUGGUA | 2232 | GAUCCCG GCU CCCUACCU | 2233 |
| 1226 | AAUCUAUA AGAA GGAGUG ACCAGAGAAACACGUUGUGUGGUACAUUACCUGGUA | 2234 | CACUCCA GUU UAUAGAUU | 2235 |
| 1340 | UUUUCACA AGAA GGUCUC ACCAGAGAAACACGUUGUGUGGUACAUUACCUGGUA | 2236 | GAGACCA GAC UGUGAAAA | 2237 |
| 1449 | AUUUCUUG AGAA GCAAGG ACCAGAGAAACACGUUGUGUGGUACAUUACCUGGUA | 2238 | CCUUGCA GCU CAAGAAAU | 2239 |
| 1468 | CUUCAGGG AGAA GUAUUU ACCAGAGAAACACGUUGUGUGGUACAUUACCUGGUA | 2240 | AAAUACG GUC CCCUGAAG | 2241 |
| 1490 | GGGAGGGG AGAA GAGGUA ACCAGAGAAACACGUUGUGUGGUACAUUACCUGGUA | 2242 | UACCUCA GAC CCCUCCC | 2243 |
| 1542 | CCAGAUUC AGAA GAUUCC ACCAGAGAAACACGUUGUGUGGUACAUUACCUGGUA | 2244 | GGAAUCG GAU GAAUCUGG | 2245 |
| 1648 | GUGGUUUG AGAA GAAGAA ACCAGAGAAACACGUUGUGUGGUACAUUACCUGGUA | 2246 | UUCUUCU GCU CAAACCAC | 2247 |
| 1672 | GGUGCUCA AGAA GUUCUC ACCAGAGAAACACGUUGUGUGGUACAUUACCUGGUA | 2248 | GAGAACA GCC UGAGCACC | 2249 |
| 1688 | CCUGCGAG AGAA GUUGGG ACCAGAGAAACACGUUGUGUGGUACAUUACCUGGUA | 2250 | CCCAACU GUU CUCGCAGG | 2251 |
| 1713 | UUUUGGGC AGAA GCCACA ACCAGAGAAACACGUUGUGUGGUACAUUACCUGGUA | 2252 | UGUGGCA GAU GCCCAAAA | 2253 |
| 1740 | GUCAUUAA AGAA GAGCUU ACCAGAGAAACACGUUGUGUGGUACAUUACCUGGUA | 2254 | AAGCUCU GUU UUAAUGAC | 2255 |
| 1880 | AGGCCGUC AGAA GGUCCU ACCAGAGAAACACGUUGUGUGGUACAUUACCUGGUA | 2256 | AGGACCA GAU GACGGCCU | 2257 |
| 1887 | GGACCGGA AGAA GUCAUC ACCAGAGAAACACGUUGUGUGGUACAUUACCUGGUA | 2258 | GAUGACG GCC UCCGGUCC | 2259 |
| 1894 | CCGAGCCG AGAA GGAGGC ACCAGAGAAACACGUUGUGUGGUACAUUACCUGGUA | 2260 | GCCUCCG GUC CGGCUCGG | 2261 |
| 1899 | UAUUUCCG AGAA GGAGCC ACCAGAGAAACACGUUGUGUGGUACAUUACCUGGUA | 2262 | CGGCUCC GCU CGGAAAUA | 2263 |
| 1926 | AGAGUUCG AGAA GAGAAC ACCAGAGAAACACGUUGUGUGGUACAUUACCUGGUA | 2264 | GUUCUCA GCU CGAACUCU | 2265 |

TABLE XVII-continued

Mouse c-myb Hairpin ribozyme and target sequences (REVISED)

| Position | | | Ribozyme | Seq. ID No. | Substrate | | Seq. ID No. |
|---|---|---|---|---|---|---|---|
| 2048 | ACAACAAA | AGAA | GGCUCU | ACCAGAGAAACACGUUGUGUACAUUACCUGGUA | 2266 | AGAGCCU | GAU UUUGUUGU | 2267 |
| 2068 | CUGCUCUC | AGAA | GUUGUA | ACCAGAGAAACACGUUGUGUACAUUACCUGGUA | 2268 | UACAACA | GUU GAGAGCAG | 2269 |
| 2170 | UUAGGUAA | AGAA | GUUAUU | ACCAGAGAAACACGUUGUGUACAUUACCUGGUA | 2270 | AAUAACA | GUC UUACCUAA | 2271 |
| 2225 | UUUAAAAA | AGAA | GAUUAU | ACCAGAGAAACACGUUGUGUACAUUACCUGGUA | 2272 | AUAAUCA | GAU UUUUUAAA | 2273 |
| 2276 | AAAUACUG | AGAA | GUUGUA | ACCAGAGAAACACGUUGUGUACAUUACCUGGUA | 2274 | UACAACA | GAU CAGUAUUU | 2275 |
| 2519 | UUCAAGCA | AGAA | GACAAC | ACCAGAGAAACACGUUGUGUACAUUACCUGGUA | 2276 | GUUGUCA | GCU UGCUUGAA | 2277 |
| 2717 | AGUGCAUA | AGAA | GUUAUC | ACCAGAGAAACACGUUGUGUACAUUACCUGGUA | 2278 | GAUAACG | GAC UAUGCACU | 2279 |
| 2737 | AUAAAAAA | AGAA | GGAAUA | ACCAGAGAAACACGUUGUGUACAUUACCUGGUA | 2280 | UAUUCCA | GAC UUUUUAU | 2281 |

TABLE XVIII

Porcine c-myb (region A) Hammerhead Ribozyme and Target
Sequence (266 bp; nt. 458 start; Human numbering system) (REVISED)

| Position | HH Ribozyme | Seq. ID No. | Substrate | Seq. ID No. |
|---|---|---|---|---|
| 467 | CCCUUGAU CUGAUGAGGCCGAAAGGCCGAA AGAUNAGG | 2282 | CCUNAUCUC AUCAAGGG | 2283 |
| 470 | GGACCCUU CUGAUGAGGCCGAAAGGCCGAA AUGAGAUN | 2284 | NAUCUCAUC AAGGGUCC | 2285 |
| 477 | GGUCCAAG CUGAUGAGGCCGAAAGGCCGAA ACCCUUGA | 2286 | UCAAGGGUC CUUGGACC | 2287 |
| 480 | UUUGGUCC CUGAUGAGGCCGAAAGGCCGAA AGGACCCU | 2288 | AGGGUCCUU GGACCAAA | 2289 |
| 498 | CACUCUCU CUGAUGAGGCCGAAAGGCCGAA AUCUUCUU | 2290 | AAGAAGAUC AGAGAGUG | 2291 |
| 509 | ACAAGCUC CUGAUGAGGCCGAAAGGCCGAA AUCACUCU | 2292 | AGAGUGAUA GAGCUUGU | 2293 |
| 515 | UUCUGUAC CUGAUGAGGCCGAAAGGCCGAA AGCUCUAU | 2294 | AUAGAGCUU GUACAGAA | 2295 |
| 518 | UAUUUCUG CUGAUGAGGCCGAAAGGCCGAA ACAAGCUC | 2296 | GAGCUUGUA CAGAAAUA | 2297 |
| 526 | UCGGACCG CUGAUGAGGCCGAAAGGCCGAA AUUUCUGU | 2298 | ACAGAAAUA CGGUCCGA | 2299 |
| 531 | ACGUUUCG CUGAUGAGGCCGAAAGGCCGAA ACCGUAUU | 2300 | AAUACGGUC CGAAACGU | 2301 |
| 540 | AACAGACC CUGAUGAGGCCGAAAGGCCGAA ACGUUUCG | 2302 | CGAAACGUU GGUCUGUU | 2303 |
| 544 | CAAUAACA CUGAUGAGGCCGAAAGGCCGAA ACCAACGU | 2304 | ACGUUGGUC UGUUAUUG | 2305 |
| 548 | UUGGCAAU CUGAUGAGGCCGAAAGGCCGAA ACAGACCA | 2306 | UGGUCUGUU AUUGCCAA | 2307 |
| 549 | CUUGGCAA CUGAUGAGGCCGAAAGGCCGAA AACAGACC | 2308 | GGUCUGUUA UUGCCAAG | 2309 |
| 551 | UGCUUGGC CUGAUGAGGCCGAAAGGCCGAA AUAACAGA | 2310 | UCUGUUAUU GCCAAGCA | 2311 |
| 562 | UCCCCUUU CUGAUGAGGCCGAAAGGCCGAA AGUGCUUG | 2312 | CAAGCACUU AAAGGGGA | 2313 |
| 563 | CUCCCCUU CUGAUGAGGCCGAAAGGCCGAA AAGUGCUU | 2314 | AAGCACUUA AAGGGGAG | 2315 |
| 575 | UGUUUUCC CUGAUGAGGCCGAAAGGCCGAA AUUCUCCC | 2316 | GGGAGAAUU GGAAAACA | 2317 |
| 588 | CCUCUCCC CUGAUGAGGCCGAAAGGCCGAA ACAUUGUU | 2318 | AACAAUGUA GGGAGAGG | 2319 |
| 603 | CAAGUGGU CUGAUGAGGCCGAAAGGCCGAA AUGCCACC | 2320 | GGUGGCAUA ACCACUUG | 2321 |
| 610 | CUGGAUUC CUGAUGAGGCCGAAAGGCCGAA AGUGGUUA | 2322 | UAACCACUU GAAUCCAG | 2323 |
| 615 | AACUUCUG CUGAUGAGGCCGAAAGGCCGAA AUUCAAGU | 2324 | ACUUGAAUC AGAAGUU | 2325 |
| 623 | GUUUUCUU CUGAUGAGGCCGAAAGGCCGAA ACUUCUGG | 2326 | CCAGAAGUU AAGAAAAC | 2327 |
| 624 | GGUUUUCU CUGAUGAGGCCGAAAGGCCGAA AACUUCUG | 2328 | CAGAAGUUA AGAAAACC | 2329 |
| 634 | CUGUCCAG CUGAUGAGGCCGAAAGGCCGAA AGGUUUUC | 2330 | GAAAACCUC CUGGACAG | 2331 |
| 659 | UGGUAAAU CUGAUGAGGCCGAAAGGCCGAA AUUCUGUC | 2332 | GACAGAAUU AUUUACCA | 2333 |
| 660 | CUGGUAAA CUGAUGAGGCCGAAAGGCCGAA AAUUCUGU | 2334 | ACAGAAUUA UUUACCAG | 2335 |
| 662 | GCCUGGUA CUGAUGAGGCCGAAAGGCCGAA AUAAUUCU | 2336 | AGAAUUAUU UACCAGGC | 2337 |
| 663 | UGCCUGGU CUGAUGAGGCCGAAAGGCCGAA AAUAAUUC | 2338 | GAAUUAUUU ACCAGGCA | 2339 |
| 664 | GUGCCUGG CUGAUGAGGCCGAAAGGCCGAA AAAUAAUU | 2340 | AAUUAUUUA CCAGGCAC | 2341 |
| 704 | AGCUUUGC CUGAUGAGGCCGAAAGGCCGAA AUUUCCGC | 2342 | GCGGAAAUC GCAAAGCU | 2343 |
| 713 | CCAGGCAG CUGAUGAGGCCGAAAGGCCGAA AGCUUUGC | 2344 | GCAAAGCUA CUGCCUGG | 2345 |

TABLE XIX

Porcine c-myb (region B) Hammerhead Ribozyme and Target
Sequence (30 bp; nt. 1386 start; Human numbering system) (REVISED)

| Position | Ribozyme | Seq. ID No. | Substrate | Seq. ID No. |
|---|---|---|---|---|
| 1394 | GUGUUUAA CUGAUGAGGCCGAAAGGCCGAA AAAGAAUC | 2346 | GAUUCUUUC UUAAACAC | 2347 |
| 1396 | AAGUGUUU CUGAUGAGGCCGAAAGGCCGAA AGAAAGAA | 2348 | UUCUUUCUU AAACACUU | 2349 |
| 1397 | GAAGUGUU CUGAUGAGGCCGAAAGGCCGAA AAGAAAGA | 2350 | UCUUUCUUA AACACUUC | 2351 |
| 1404 | GUUAUUGG CUGAUGAGGCCGAAAGGCCGAA AGUGUUUA | 2352 | UAAACACUU CCAAUAAC | 2353 |
| 1405 | UGUUAUUG CUGAUGAGGCCGAAAGGCCGAA AAGUGUUU | 2354 | AAACACUUC CAAUAACC | 2355 |
| 1410 | UUCAUGGU CUGAUGAGGCCGAAAGGCCGAA AUUGGAAG | 2356 | CUUCCAAUA ACCAUGAA | 2357 |
| 1423 | CCAAGUCU CUGAUGAGGCCGAAAGGCCGAA AGUUUCA | 2358 | UGAAAACUU AGACUUGG | 2359 |
| 1424 | UCCAAGUC CUGAUGAGGCCGAAAGGCCGAA AAGUUUUC | 2360 | GAAAACUUA GACUUGGA | 2361 |
| 1429 | GCAUUUCC CUGAUGAGGCCGAAAGGCCGAA AGUCUAAG | 2362 | CUUAGACUU GGAAAUGC | 2363 |
| 1440 | CGUUAAAG CUGAUGAGGCCGAAAGGCCGAA AGGCAUUU | 2364 | AAAUGCCUU CUUUAACG | 2365 |
| 1441 | ACGUUAAA CUGAUGAGGCCGAAAGGCCGAA AAGGCAUU | 2366 | AAUGCCUUC UUUAACGU | 2367 |
| 1443 | GGACGUUA CUGAUGAGGCCGAAAGGCCGAA AGAAGGCA | 2368 | UGCCUUCUU UAACGUCC | 2369 |
| 1444 | UGGACGUU CUGAUGAGGCCGAAAGGCCGAA AAGAAGGCA | 2370 | GCCUUCUUU AACGUCCA | 2371 |
| 1445 | GUGGACGU CUGAUGAGGCCGAAAGGCCGAA AAAGAAGG | 2372 | CCUUCUUUA ACGUCCAC | 2373 |
| 1450 | GAGGCGUG CUGAUGAGGCCGAAAGGCCGAA ACGUAAAA | 2374 | UUUUAACGUC CACGCCUC | 2375 |
| 1458 | ACCACUGA CUGAUGAGGCCGAAAGGCCGAA AGGCGUGG | 2376 | CCACGCCUC UCAGUGGU | 2377 |
| 1460 | UGACCACU CUGAUGAGGCCGAAAGGCCGAA AGAGGCGU | 2378 | ACGCCUCUC AGUGGUCA | 2379 |
| 1467 | CAAUUUGU CUGAUGAGGCCGAAAGGCCGAA ACCACUGA | 2380 | UCAGUGGUC ACAAAUUG | 2381 |
| 1474 | UAACAGUC CUGAUGAGGCCGAAAGGCCGAA AUUUGUGA | 2382 | UCACAAAUU GACUGUUA | 2383 |
| 1481 | GGUGUUGU CUGAUGAGGCCGAAAGGCCGAA ACAGUCAA | 2384 | UUGACUGUU ACAACACC | 2385 |
| 1482 | UGGUGUUG CUGAUGAGGCCGAAAGGCCGAA AACAGUCA | 2386 | UGACUGUUA CAACACCA | 2387 |
| 1492 | CUCUAUGA CUGAUGAGGCCGAAAGGCCGAA AUGGUGUU | 2388 | AACACCAUU UCAUAGAG | 2389 |
| 1493 | UCUCUAUG CUGAUGAGGCCGAAAGGCCGAA AAUGGUGU | 2390 | ACACCAUUU CAUAGAGA | 2391 |
| 1494 | GUCUCUAU CUGAUGAGGCCGAAAGGCCGAA AAAUGGUG | 2392 | CACCAUUUC AUAGAGAC | 2393 |
| 1497 | CUGGUCUC CUGAUGAGGCCGAAAGGCCGAA AUGAAAUG | 2394 | CAUUUCAUA GAGACCAG | 2395 |
| 1530 | AAAAUUCU CUGAUGAGGCCGAAAGGCCGAA AUUUUCU | 2396 | AGGAAAAUA CAUAUUUU | 2397 |
| 1534 | UUCAAAAA CUGAUGAGGCCGAAAGGCCGAA AUGUAUUU | 2398 | AAAUACAUA UUUUUGAA | 2399 |
| 1536 | AGUUCAAA CUGAUGAGGCCGAAAGGCCGAA AUAUGUAU | 2400 | AUACAUAUU UUUGAACU | 2401 |
| 1537 | GAGUUCAA CUGAUGAGGCCGAAAGGCCGAA AAUAUGUA | 2402 | UACAUAUUU UUGAACUC | 2403 |
| 1538 | GGAGUUCA CUGAUGAGGCCGAAAGGCCGAA AAAUAUGU | 2404 | ACAUAUUUU UGAACUCC | 2405 |

TABLE XIX-continued

Porcine c-myb (region B) Hammerhead Ribozyme and Target
Sequence (30 bp; nt. 1386 start; Human numbering system) (REVISED)

| Position | Ribozyme | | Seq. ID No. | Substrate | | Seq. ID No. |
|---|---|---|---|---|---|---|
| 1539 | CGGAGUUC | CUGAUGAGGCCGAAAGGCCGAA | AAAAUAUG | 2406 | CAUAUUUUU | GAACUCCG | 2407 |
| 1545 | GAUAGCCG | CUGAUGAGGCCGAAAGGCCGAA | AGUUCAAA | 2408 | UUUGAACUC | CGGCUAUC | 2409 |
| 1551 | CCUUUUGA | CUGAUGAGGCCGAAAGGCCGAA | AGCCGGAG | 2410 | CUCCGGCUA | UCAAAAGG | 2411 |
| 1553 | GACCUUUU | CUGAUGAGGCCGAAAGGCCGAA | AUAGCCGG | 2412 | CCGGCUAUC | AAAAGGUC | 2413 |
| 1561 | CCAGGAUU | CUGAUGAGGCCGAAAGGCCGAA | ACCUUUUG | 2414 | CAAAAGGUC | AAUCCUGG | 2415 |
| 1565 | CUUUCCAG | CUGAUGAGGCCGAAAGGCCGAA | AUUGACCU | 2416 | AGGUCAAUC | CUGGAAAG | 2417 |
| 1576 | UUCUUGGA | CUGAUGAGGCCGAAAGGCCGAA | AGCUUUCC | 2418 | GGAAAGCUC | UCCAAGAA | 2419 |
| 1578 | AGUUCUUG | CUGAUGAGGCCGAAAGGCCGAA | AGAGCUUU | 2420 | AAAGCUCUC | CAAGAACU | 2421 |
| 1587 | CGGUGUAG | CUGAUGAGGCCGAAAGGCCGAA | AGUUCUUG | 2422 | CAAGAACUC | CUACACCG | 2423 |
| 1590 | GAACGGUG | CUGAUGAGGCCGAAAGGCCGAA | AGGAGUUC | 2424 | GAACUCCUA | CACCGUUC | 2425 |
| 1597 | CAUGUUUG | CUGAUGAGGCCGAAAGGCCGAA | ACGUGUA | 2426 | UACACCGUU | CAAACAUG | 2427 |
| 1598 | GCAUGUUU | CUGAUGAGGCCGAAAGGCCGAA | AACGGUGU | 2428 | ACACCGUUC | AAACAUGC | 2429 |
| 1610 | UGAGCUGC | CUGAUGAGGCCGAAAGGCCGAA | AGUGCAUG | 2430 | CAUGCACUC | GCAGCUCA | 2431 |
| 1617 | AAUUUCUU | CUGAUGAGGCCGAAAGGCCGAA | AGCUGCGA | 2432 | UCGCAGCUC | AAGAAAUU | 2433 |
| 1625 | CCAUAUUU | CUGAUGAGGCCGAAAGGCCGAA | AUUUCUUG | 2434 | CAAGAAAUU | AAAUAUGG | 2435 |
| 1626 | ACCAUAUU | CUGAUGAGGCCGAAAGGCCGAA | AAUUUCUU | 2436 | AAGAAAUUA | AAUAUGGU | 2437 |
| 1630 | GGGGACCA | CUGAUGAGGCCGAAAGGCCGAA | AUUUAAUU | 2438 | AAUUAAAUA | UGGUCCCC | 2439 |
| 1635 | CUUCAGGG | CUGAUGAGGCCGAAAGGCCGAA | ACCAUAUU | 2440 | AAUAUGGUC | CCCUGAAG | 2441 |
| 1649 | GUCUGAGG | CUGAUGAGGCCGAAAGGCCGAA | AGCAUCUU | 2442 | AAGAUGCUA | CCUCAGAC | 2443 |
| 1653 | UGGUGUCU | CUGAUGAGGCCGAAAGGCCGAA | AGGUAGCA | 2444 | UGCUACCUC | AGACACCA | 2445 |
| 1663 | CUAAAUGA | CUGAUGAGGCCGAAAGGCCGAA | AUGGUGUC | 2446 | GACACCAUC | UCAUUUAG | 2447 |
| 1665 | UACUAAAU | CUGAUGAGGCCGAAAGGCCGAA | AGAUGGUG | 2448 | CACCAUCUC | AUUUAGUA | 2449 |
| 1668 | UUCUACUA | CUGAUGAGGCCGAAAGGCCGAA | AUGAGAUG | 2450 | CAUCUCAUU | UAGUAGAA | 2451 |
| 1669 | CUUCUACU | CUGAUGAGGCCGAAAGGCCGAA | AAUGAGAU | 2452 | AUCUCAUUU | AGUAGAAG | 2453 |
| 1670 | UCUUCUAC | CUGAUGAGGCCGAAAGGCCGAA | AAAUGAGA | 2454 | UCUCAUUUA | GUAGAAGA | 2455 |
| 1673 | AGGUCUUC | CUGAUGAGGCCGAAAGGCCGAA | ACUAAAUG | 2456 | CAUUUAGUA | GAAGACCU | 2457 |

TABLE XX

Porcine c-myb (region B) Hairpin Ribozyme and Target Sequence (308 bp; nt. 1386 start; Human numbering system) (REVISED)

| Position | Hairpin Ribozyme | Seq. ID No. | Substrate | Seq. ID No. |
|---|---|---|---|---|
| 1504 | UUUUCACA AGAA GGUCUC ACCAGAGAAACACACGUUGUGGUACAUUACCUGGUA | 2458 | GAGACCA GAC UGUGAAAA | 2459 |
| 1594 | CAUGUUUG AGAA GUGUAG ACCAGAGAAACACACGUUGUGGUACAUUACCUGGUA | 2460 | CUACACC GUU CAAACAUG | 2461 |
| 1613 | AUUUCUUG AGAA GCGAGU ACCAGAGAAACACACGUUGUGGUACAUUACCUGGUA | 2462 | ACUCGCA GCU CAAGAAAU | 2463 |

TABLE XXI

Porcine c-myb (region A) Hairpin Ribozyme and Target Sequence (266 bp; nt. 458 start; Human numbering system) (REVISED)

| Position | RZ | Seq. ID No. | Substrate | Seq. ID No. |
|---|---|---|---|---|
| 528 | ACGUUUCG AGAA GUAUUU ACCAGAGAAACACACGUUGUGGUACAUUACCUGGUA | 2464 | AAAUACG GUC CGAAACGU | 2465 |
| 690 | UUCCGCCC AGAA GUUCCC ACCAGAGAAACACACGUUGUGGUACAUUACCUGGUA | 2466 | GGGAACA GAU GGGCGGAA | 2467 |

TABLE XXII

Rat c-myb (Region A) Hammerhead Ribozyme and Target
Sequence (282 bp; nt. 428 start; Human numbering system) (REVISED)

| Position | HH Ribozyme | Seq. ID No. | Substrate | Seq. ID No. |
|---|---|---|---|---|
| 467 | CCUUUGAU CUGAUGAGGCCGAAAGGCCGAA AGCUCAGG | 2468 | CCUGAGCUC AUCAAAGG | 2469 |
| 470 | GGACCUUU CUGAUGAGGCCGAAAGGCCGAA AUGAGCUC | 2470 | GAGCUCAUC AAAGGUCC | 2471 |
| 477 | GGUCCAGG CUGAUGAGGCCGAAAGGCCGAA ACCUUUGA | 2472 | UCAAAGGUC CUGGACC | 2473 |

TABLE XXII-continued

Rat c-myb (Region A) Hammerhead Ribozyme and Target
Sequence (282 bp; nt. 428 start; Human numbering system) (REVISED)

| Position | HH Ribozyme | Seq. ID No. | Substrate | Seq. ID No. |
|---|---|---|---|---|
| 498 | CACUCUUU CUGAUGAGGCCGAAAGGCCGAA AUCUUCUU | 2474 | AAGAAGAUC AAAGAGUG | 2475 |
| 509 | ACAAGCUC CUGAUGAGGCCGAAAGGCCGAA AUCACUCU | 2476 | AGAGUGAUA GAGCUUGU | 2477 |
| 515 | UUCGGAC CUGAUGAGGCCGAAAGGCCGAA AGCUCUAU | 2478 | AUAGAGCUU GUCCAGAA | 2479 |
| 518 | UAUUUCUG CUGAUGAGGCCGAAAGGCCGAA ACAAGCUC | 2480 | GAGCUUGUC CAGAAAUA | 2481 |
| 526 | UCGGACCG CUGAUGAGGCCGAAAGGCCGAA AUUUCUGG | 2482 | CCAGAAAUA CGGUCCGA | 2483 |
| 531 | GCGCUUCG CUGAUGAGGCCGAAAGGCCGAA ACCGUAUU | 2484 | AAUACGGUC CGAAGCGC | 2485 |
| 544 | CAAUAACA CUGAUGAGGCCGAAAGGCCGAA ACCAGCGC | 2486 | GCGCUGGUC UGUUAUUG | 2487 |
| 548 | UUGGCAAU CUGAUGAGGCCGAAAGGCCGAA ACAGACCA | 2488 | UGGUCUGUU AUUGCCAA | 2489 |
| 549 | CUUGGCAA CUGAUGAGGCCGAAAGGCCGAA AACAGACC | 2490 | GGUCUGUUA UUGCCAAG | 2491 |
| 551 | UGCUUGGC CUGAUGAGGCCGAAAGGCCGAA AUAACAGA | 2492 | UCUGUUAUU GCCAAGCA | 2493 |
| 562 | UCCCUUUU CUGAUGAGGCCGAAAGGCCGAA AGUGCUUG | 2494 | CAAGCACUU AAAAGGGA | 2495 |
| 563 | CUCCCUUU CUGAUGAGGCCGAAAGGCCGAA AAGUGCUU | 2496 | AAGCACUUA AAAGGGAC | 2497 |
| 575 | UGUUUUCC CUGAUGAGGCCGAAAGGCCGAA AUUCUCCC | 2498 | GGGAGAAUU GGAAAACA | 2499 |
| 588 | CCUCUCCC CUGAUGAGGCCGAAAGGCCGAA ACAUUGUU | 2500 | AACAAUGUC GGGAGAGG | 2501 |
| 609 | UGGAUUCA CUGAUGAGGCCGAAAGGCCGAA AUGGUUGU | 2502 | ACAACCAUU UGAAUCCA | 2503 |
| 610 | CUGGAUUC CUGAUGAGGCCGAAAGGCCGAA AAUGGUUG | 2504 | CAACCAUU GAAUCCAG | 2505 |
| 615 | AACUUCUG CUGAUGAGGCCGAAAGGCCGAA AUUCAAAU | 2506 | AUUUGAAUC CAGAAGUU | 2507 |
| 623 | GUUUUCUU CUGAUGAGGCCGAAAGGCCGAA ACUUCUGG | 2508 | CCAGAAGUU AAGAAAAC | 2509 |
| 624 | GGUUUUCU CUGAUGAGGCCGAAAGGCCGAA AACUUCUG | 2510 | CAGAAGUUA AGAAAACC | 2511 |
| 634 | CUGUCCAU CUGAUGAGGCCGAAAGGCCGAA AGGUUUUC | 2512 | GAAAACCUC AUGGACAG | 2513 |
| 659 | UGAUAAAU CUGAUGAGGCCGAAAGGCCGAA AUUCUGUC | 2514 | GACAGAAUC AUUUAUCA | 2515 |
| 662 | GCCUGAUA CUGAUGAGGCCGAAAGGCCGAA AUGAUUCU | 2516 | AGAAUCAUU UAUCAGGC | 2517 |
| 663 | UGCCUGAU CUGAUGAGGCCGAAAGGCCGAA AAUGAUUC | 2518 | GAAUCAUUU AUCAGGCA | 2519 |
| 664 | GUGCCUGA CUGAUGAGGCCGAAAGGCCGAA AAAUGAUU | 2520 | AAUCAUUUA UCAGGCAC | 2521 |
| 666 | GUGUGCCU CUGAUGAGGCCGAAAGGCCGAA AUAAAUGA | 2522 | UCAUUUAUC AGGCACAC | 2523 |

TABLE XXIII

Rat c-myb (Region B) Hammerhead Ribozyme and Target
Sequences (262 bp; nt. 1421 start; human numbering system) (REVISED)

| Position | Ribozyme | Seq. ID No. | Substrate | Seq. ID No. |
|---|---|---|---|---|
| 1429 | GCGUAUCU CUGAUGAGGCCGAAAGGCCGAA AGCCCGAG | 2524 | CUCGGGCUU AGAUACGC | 2525 |
| 1430 | GGCGUAUC CUGAUGAGGCCGAAAGGCCGAA AAGCCCGA | 2526 | UCGGGCUUA GAUACGCC | 2527 |
| 1434 | AGUAGGCG CUGAUGAGGCCGAAAGGCCGAA AUCUAAGC | 2528 | GCUUAGAUA CGCCUACU | 2529 |
| 1440 | GGGUAAAG CUGAUGAGGCCGAAAGGCCGAA AUAGGCGU | 2530 | AUACGCCUA CUUUACCC | 2531 |
| 1443 | GGAGGGUA CUGAUGAGGCCGAAAGGCCGAA AGUAGGCG | 2532 | CGCCUACUU UACCCUCC | 2533 |
| 1444 | UGGAGGGU CUGAUGAGGCCGAAAGGCCGAA AAGUAGGC | 2534 | GCCUACUUU ACCCUCCA | 2535 |
| 1445 | GUGGAGGG CUGAUGAGGCCGAAAGGCCGAA AAAGUAGG | 2536 | CCUACUUUA CCCUCCAC | 2537 |
| 1450 | GAGGCGUG CUGAUGAGGCCGAAAGGCCGAA AGGUAAA | 2538 | UUUACCCUC CACGCCUC | 2539 |
| 1458 | ACCAAUGA CUGAUGAGGCCGAAAGGCCGAA AGGCGUGG | 2540 | CCACGCCUC UCAUUGGU | 2541 |
| 1460 | UGACCAAU CUGAUGAGGCCGAAAGGCCGAA AGAGGCGU | 2542 | ACGCCUCUC AUUGGUCA | 2543 |
| 1463 | UUGUGACC CUGAUGAGGCCGAAAGGCCGAA AUGAGAGG | 2544 | CCUCUCAUU GGUCACAA | 2545 |
| 1467 | CAGUUUGU CUGAUGAGGCCGAAAGGCCGAA ACCAAUGA | 2546 | UCAUUGGUC ACAAACUG | 2547 |
| 1485 | GUCUCGGU CUGAUGAGGCCGAAAGGCCGAA ACACGGUG | 2548 | CACCGUGUC ACCGAGAC | 2549 |
| 1509 | UUCCUUUU CUGAUGAGGCCGAAAGGCCGAA AGUUUUCA | 2550 | UGAAAACUN AAAAGGAA | 2551 |
| 1522 | UAAAGAUN CUGAUGAGGCCGAAAGGCCGAA AGUUUUCC | 2552 | GGAAAACUC NAUCUUUA | 2553 |
| 1526 | GUUCUAAA CUGAUGAGGCCGAAAGGCCGAA AUNGAGUU | 2554 | AACUCNAUC UUUAGAAC | 2555 |
| 1528 | GAGUUCUA CUGAUGAGGCCGAAAGGCCGAA AGAUNGAG | 2556 | CUCNAUCUU UAGAACUC | 2557 |
| 1529 | GGAGUUCU CUGAUGAGGCCGAAAGGCCGAA AAGAUNGA | 2558 | UCNAUCUUU AGAACUCC | 2559 |
| 1530 | UGGAGUUC CUGAUGAGGCCGAAAGGCCGAA AAAGAUNG | 2560 | CNAUCUUUA GAACUCCA | 2561 |
| 1536 | GAUAGCUG CUGAUGAGGCCGAAAGGCCGAA AGUUCUAA | 2562 | UUAGAACUC CAGCUAUC | 2563 |
| 1542 | CCUUUUGA CUGAUGAGGCCGAAAGGCCGAA AGCUGGAG | 2564 | CUCCAGCUA UCAAAAGG | 2565 |
| 1544 | NACCUUUU CUGAUGAGGCCGAAAGGCCGAA AUAGCUGG | 2566 | CCAGCUAUC AAAAGGUN | 2567 |
| 1552 | CGAGGAUU CUGAUGAGGCCGAAAGGCCGAA ACCUUUUG | 2568 | CAAAAGGUN AAUCCUCG | 2569 |
| 1556 | CUUUCGAG CUGAUGAGGCCGAAAGGCCGAA AUUNACCU | 2570 | AGGUNAAUC CUCGAAAG | 2571 |
| 1559 | GAGCUUUC CUGAUGAGGCCGAAAGGCCGAA AGGAUUNA | 2572 | UNAAUCCUC GAAAGCUC | 2573 |
| 1567 | UUCUGGGA CUGAUGAGGCCGAAAGGCCGAA AGCUUUCG | 2574 | CGAAAGCUC UCCCAGAA | 2575 |
| 1569 | AGUUCUGG CUGAUGAGGCCGAAAGGCCGAA AGAGCUUU | 2576 | AAAGCUCUC CAGAACU | 2577 |
| 1578 | UGGUGUGG CUGAUGAGGCCGAAAGGCCGAA AGUUCUGG | 2578 | CCAGAACUC CACACCA | 2579 |
| 1588 | CAUGUUUG CUGAUGAGGCCGAAAGGCCGAA AUGGUGUG | 2580 | CACACCAUU CAAACAUG | 2581 |
| 1589 | GCAUGUUU CUGAUGAGGCCGAAAGGCCGAA AAUGGUGU | 2582 | ACACCAUUC AAACAUGC | 2583 |
| 1608 | AAUUUCUU CUGAUGAGGCCGAAAGGCCGAA AGCUGCCA | 2584 | UGGCAGCUC AAGAAAUU | 2585 |
| 1616 | CCGUAUUU CUGAUGAGGCCGAAAGGCCGAA AUUUCUUG | 2586 | CAAGAAAUU AAAUACGG | 2587 |
| 1617 | ACCGUAUU CUGAUGAGGCCGAAAGGCCGAA AAAUUCUU | 2588 | AAGAAAUUA AAUACGGU | 2589 |
| 1621 | GGGGACCG CUGAUGAGGCCGAAAGGCCGAA AUUUAAUU | 2590 | AAUUAAAUA CGGUCCCC | 2591 |
| 1626 | CUUCAGGG CUGAUGAGGCCGAAAGGCCGAA ACCGUAUU | 2592 | AAUACGGUC CCUGAAG | 2593 |
| 1640 | GUCUNAGG CUGAUGAGGCCGAAAGGCCGAA AGCAUCUU | 2594 | AAGAUGCUA CCUNAGAC | 2595 |
| 1644 | GGGGUCU CUGAUGAGGCCGAAAGGCCGAA AGGUAGCA | 2596 | UGCUACCUN AGACCCCC | 2597 |
| 1654 | CUACAUNA CUGAUGAGGCCGAAAGGCCGAA AGGGGGUC | 2598 | GACCCCUN UNAUGUAG | 2599 |

TABLE XXIII-continued

Rat c-myb (Region B) Hammerhead Ribozyme and Target Sequences (262 bp; nt. 1421 start; human numbering system) (REVISED)

| Position | Ribozyme | Seq. ID No. | Substrate | Seq. ID No. |
|---|---|---|---|---|
| 1656 | NACUACAU CUGAUGAGGCCGAAAGGCCGAA ANAGGGGG | 2600 | CCCCCUNUN AUGUAGUN | 2601 |
| 1661 | UNUNNNAC CUGAUGAGGCCGAAAGGCCGAA ACAUNANA | 2602 | UNUNAUGUA GUNNNANA | 2603 |
| 1664 | AGGUNUNN CUGAUGAGGCCGAAAGGCCGAA ACUACAUN | 2604 | NAUGUAGUN NNANACCU | 2605 |
| 1673 | ACAUCNUG CUGAUGAGGCCGAAAGGCCGAA AGGUNUNN | 2606 | NNANACCUN CANGAUGU | 2607 |

TABLE XXIV

Rat c-mby (Region A) Hairpin Ribozyme and Target Sequences (282 bp; nt. 428 start; human numbering system)(REVISED)

| Position RZ | | Seq. ID No. | Substrate | Seq. ID No. |
|---|---|---|---|---|
| 528 | GCGCUUCG AGAA GUAUUU ACCAGAGAAACACACGUUGUGGUACAUUACCUGGUA | 2608 | AAAUACG GUC CGAAGCGC | 2609 |
| 690 | UUCUGCCC AGAA GUUUCC ACCAGAGAAACACACGUUGUGGUACAUUACCUGGUA | 2610 | GGAAACA GAU GGGCAGAA | 2611 |

TABLE XXV

Rat c-mby (Region B) Hairpin Ribozyme and Target Sequences (262 bp; nt. 1421 start; human numbering system)(REVISED)

| Position RZ | | Seq. ID No. | Substrate | Seq. ID No. |
|---|---|---|---|---|
| 1495 | UUUUCACA AGAA GGUCUC ACCAGAGAAACACACGUUGUGGUACAUUACCUGGUA | 2612 | GAGACCA GAC UGUGAAAA | 2613 |
| 1604 | AUUUCUUG AGAA GCCAGG ACCAGAGAAACACACGUUGUGGUACAUUACCUGGUA | 2614 | CCUGGCA GCU CAAGAAAU | 2615 |
| 1623 | CUUCAGGG AGAA GUAUUU ACCAGAGAAACACACGUUGUGGUACAUUACCUGGUA | 2616 | AAAUACG GUC CCCUGAAG | 2617 |

We claim:

1. An enzymatic RNA molecule which specifically cleaves c-myb RNA.

2. An enzymatic RNA molecule of claim 1, wherein said enzymatic RNA molecule specifically cleaves any of the RNA sequences defined as SEQ. ID. NOS. 1–78, wherein said enzymatic RNA molecule is in a hepatitis delta virus motif.

3. The enzymatic RNA molecule of claim 1, wherein said enzymatic RNA molecule specifically cleaves any of the RNA sequences defined as SEQ. ID. NOS. 2, 4–6, 9–16, 18–20, 22–45, 47–98, wherein said enzymatic RNA molecule is in a hammerhead motif.

4. The enzymatic RNA molecule of claim 1, wherein said enzymatic RNA molecule is in a hammerhead motif.

5. The enzymatic RNA molecule of claim 1, wherein said enzymatic RNA molecule is in a hairpin, hepatitis delta virus, VS nucleic acid, group I intron, or RNAseP nucleic acid motif.

6. The enzymatic RNA molecule of claim 5, wherein said enzymatic RNA molecule specifically cleaves any of the RNA sequences defined as SEQ. ID. NOS. 99, 100 or 130–148, wherein said enzymatic RNA molecule is in a hairpin motif.

7. The enzymatic RNA molecule of claim 5 consisting of any sequence selected from the group of SEQ. ID NOS. 121, 122, 149–167.

8. The enzymatic RNA molecule of any of claims 1, 2, 3, 4, 5, 6 or 7, wherein said enzymatic RNA molecule comprises between 12 and 100 bases complementary to said mRNA.

9. The enzymatic RNA molecule of any of claims 1, 2, 3, 4, 5, 6 or 7, wherein said enzymatic RNA molecule comprises between 14 and 24 bases complementary to said mRNA.

10. An enzymatic RNA molecule consisting of any sequence selected from the group of SEQ. ID NOS. 101–120, 123–129, 149–167, and odd numbers from 171–1225.

11. The enzymatic RNA molecule of any of claims 3 or 4 or 10, wherein said enzymatic RNA molecule comprises at least five ribose residues, and wherein said enzymatic RNA molecule comprises phosphorothioate linkages at at least three 5' terminal nucleotides, and wherein said enzymatic RNA molecule comprises a 2'-C-allyl modification at position No. 4 of said enzymatic RNA molecule, and wherein said enzymatic RNA molecule comprises at least ten 2'-O-methyl modifications.

12. The enzymatic RNA molecule of any of claims 3 or 4 or 10, wherein said enzymatic RNA molecule comprises at least five ribose residues, and wherein said enzymatic RNA molecule comprises phosphorothioate linkages at at least three 5' terminal nucleotides, and wherein said enzymatic RNA molecule comprises a 2'-amino modification at position No. 4 and/or at position No. 7 of said nucleic acid, wherein said enzymatic RNA molecule comprises at least ten 2'-O-methyl modifications.

13. The enzymatic RNA molecule of any of claims 3 or 4 or 10, wherein said enzymatic RNA molecule comprises at least five ribose residues, and wherein said enzymatic RNA molecule comprises phosphorothioate linkages at at least three 5' terminal nucleotides, and wherein said enzymatic RNA molecule comprises abasic substitution at position No. 4 and/or at position No. 7 of said enzymatic RNA molecule, wherein said enzymatic RNA molecule comprises at least ten 2'-O-methyl modifications.

14. The enzymatic RNA molecule of any of claims 3 or 4 or 10, wherein said enzymatic RNA molecule comprises at least five ribose residues, and wherein said enzymatic RNA molecule comprises phosphorothioate linkages at at least three 5' terminal nucleotides, and wherein said enzymatic RNA molecule comprises 6-methyl uridine substitutions at position No. 4 and/or at position No. 7 of the said nucleic acid molecule, wherein said enzymatic RNA molecule comprises at least ten 2'-O-methyl modifications.

15. The enzymatic RNA molecule of any of claims 3, 4 or 10, wherein said nucleic acid molecule comprises a stem II region of length greater than or equal to two base-pairs.

16. The enzymatic RNA molecule in a hairpin motif of any of claims 5, 6 or 7, wherein said enzymatic RNA molecule comprises a stem IV region of length greater than or equal to two base-pairs.

17. The enzymatic RNA molecule of any of claims 5, 6 or 7, wherein said enzymatic RNA molecule comprises a stem II region of length between three and seven base-pairs.

18. The enzymatic nucleic acid of any one of claims 1, 2, 3, 4, 5, 6 or 7, wherein said nucleic acid comprises a 3'-3' linked inverted ribose moeity at the 3' end of said nucleic acid molecule.

19. The enzymatic RNA molecule of any one of claims 1, 2, 3, 4, 5, 6 or 7, wherein said enzymatic RNA molecule comprises a 3'-3' linked inverted thymidine moeity at the 3' end of said nucleic acid molecule.

20. The enzymatic RNA molecule of any one of claims 1, 2, 3, 4, 5, 6 or 7, wherein said enzymatic RNA molecule comprises a 2'-3' linked inverted ribose or thymidine moeity at the 3' end of said enzymatic RNA molecule.

21. The enzymatic RNA molecule of any one of claims 1, 2, 3, 4, 5, 6 or 7, wherein said enzymatic RNA molecule comprises a 5'-end modification.

22. The enzymatic RNA molecule of claim 11, wherein said enzymatic RNA molecule further comprises a 3'-3' linked inverted ribose moeity at the 3' end of said enzymatic RNA molecule.

23. The enzymatic RNA molecule of any one of claim 11, wherein said enzymatic RNA molecule further comprises a 3'-3' linked inverted thymidine moeity at the 3' end of said molecule.

24. The enzymatic RNA molecule of claim 11, wherein said enzymatic RNA molecule further comprises a 2'-3' linked inverted ribose or thymidine moeity at the 3' end of said enzymatic RNA molecule.

25. The enzymatic RNA molecule of claim 11, wherein said enzymatic RNA molecule further comprises a 5'-end modification.

26. The enzymatic RNA molecule of claim 12, wherein said enzymatic RNA molecule further comprises a 3'-3' linked inverted ribose moeity at the 3' end of said enzymatic RNA molecule.

27. The enzymatic RNA molecule of claim 12, wherein said enzymatic RNA molecule further comprises a 3'-3' linked inverted thymidine moeity at the 3' end of said enzymatic RNA molecule.

28. The enzymatic RNA molecule of claim 12, wherein said enzymatic RNA molecule further comprises a 2'-3' linked inverted ribose or thymidine moeity at the 3' end of said enzymatic RNA molecule.

29. The enzymatic RNA molecule of claim 12, wherein said enzymatic RNA molecule further comprises a 5'-end modification.

30. The enzymatic RNA molecule of claim 13, wherein said enzymatic RNA molecule further comprises a 3'-3' linked inverted ribose moeity at the 3' end of said enzymatic RNA molecule.

31. The enzymatic RNA molecule of any one of claim 13, wherein said enzymatic RNA molecule further comprises a 3'-3' linked inverted thymidine moeity at the 3' end of said enzymatic RNA molecule.

32. The enzymatic RNA molecule of claim 13, wherein said enzymatic RNA molecule further comprises a 2'-3' linked inverted ribose or thymidine moeity at the 3' end of said enzymatic RNA molecule.

33. The enzymatic RNA molecule of claim 13, wherein said enzymatic RNA molecule further comprises a 5'-end modification.

34. The enzymatic RNA molecule of claim 14, wherein said enzymatic RNA molecule further comprises a 3'-3' linked inverted ribose moeity at the 3' end of said enzymatic RNA molecule.

35. The enzymatic RNA molecule of any one of claim 14, wherein said enzymatic RNA molecule further comprises a 3'-3' linked inverted thymidine moeity at the 3' end of said enzymatic RNA molecule.

36. The enzymatic RNA molecule of claim 14, wherein said enzymatic RNA molecule further comprises a 2'-3' linked inverted ribose or thymidine moeity at the 3' end of said enzymatic RNA molecule.

37. The enzymatic RNA molecule of claim 14, wherein said enzymatic RNA molecule further comprises a 5'-end modification.

38. The enzymatic RNA molecule of claim 4, wherein the enzymatic RNA molecule molecule specifically cleaves the RNA sequence defined as SEQ ID NO. 232.

39. The enzymatic RNA molecule of claim 4, wherein said enzymatic RNA molecule specifically cleaves the RNA sequence defined as SEQ ID NO. 264.

40. The enzymatic RNA molecule of claim 4, wherein said enzymatic RNA molecule specifically cleaves the RNA sequence defined as SEQ ID NO. 266.

41. The enzymatic RNA molecule of claim 4, wherein said enzymatic RNA molecule specifically cleaves the RNA sequence defined as SEQ ID NO. 272.

42. The enzymatic RNA molecule of claim 4, wherein said enzymatic RNA molecule specifically cleaves the RNA sequence defined as SEQ ID NO. 282.

43. The enzymatic RNA molecule of claim 4, wherein said enzymatic RNA molecule specifically cleaves the RNA sequence defined as SEQ ID NO. 300.

44. The enzymatic RNA molecule of claim 4, wherein said enzymatic RNA molecule specifically cleaves the RNA sequence defined as SEQ ID NO. 320.

45. The enzymatic RNA molecule of claim 4, wherein said enzymatic RNA molecule specifically cleaves the RNA sequence defined as SEQ ID NO. 350.

46. The enzymatic RNA molecule of claim 4, wherein said enzymatic RNA molecule specifically cleaves the RNA sequence defined as SEQ ID NO. 374.

47. The enzymatic RNA molecule of claim 4, wherein said enzymatic RNA molecule specifically cleaves the RNA sequence defined as SEQ ID NO. 384.

48. The enzymatic RNA molecule of claim 4, wherein said enzymatic RNA molecule specifically cleaves the RNA sequence defined as SEQ ID NO. 442.

49. The enzymatic RNA molecule of claim 4, wherein said enzymatic RNA molecule specifically cleaves the RNA sequence defined as SEQ ID NO. 522.

50. The enzymatic RNA molecule of claim 4, wherein said enzymatic RNA molecule specifically cleaves the RNA sequence defined as SEQ ID NO. 538.

51. The enzymatic RNA molecule of claim 4, wherein said enzymatic RNA molecule specifically cleaves the RNA sequence defined as SEQ ID NO. 540.

52. The enzymatic RNA molecule of claim 4, wherein said enzymatic RNA molecule specifically cleaves the RNA sequence defined as SEQ ID NO. 93.

53. The enzymatic RNA molecule of claim 4, wherein said enzymatic RNA molecule specifically cleaves the RNA sequence defined as SEQ ID NO. 572.

54. The enzymatic RNA molecule of claim 4, wherein said enzymatic RNA molecule specifically cleaves the RNA sequence defined as SEQ ID NO. 95.

55. The enzymatic RNA molecule of claim 4, wherein said enzymatic RNA molecule specifically cleaves the RNA sequence defined as SEQ ID NO. 614.

56. The enzymatic RNA molecule of claim 4, wherein said enzymatic RNA molecule specifically cleaves the RNA sequence defined as SEQ ID NO. 622.

57. The enzymatic RNA molecule of claim 4, wherein said enzymatic RNA molecule specifically cleaves the RNA sequence defined as SEQ ID NO. 98.

58. The enzymatic RNA molecule of claim 4, wherein said enzymatic RNA molecule specifically cleaves any of the RNA sequences defined as SEQ ID NOS. 2 or 4.

59. The enzymatic RNA molecule of claim 4, wherein said enzymatic RNA molecule specifically cleaves any of the RNA sequences defined as SEQ ID NOS. 5 or 6.

60. The enzymatic RNA molecule of claim 4, wherein said enzymatic RNA molecule specifically cleaves any of the RNA sequences defined as SEQ ID NOS. 9–11.

61. The enzymatic RNA molecule of claim 4, wherein said enzymatic RNA molecule specifically cleaves any of the RNA sequences defined as SEQ ID NOS. 13–16.

62. The enzymatic RNA molecule of claim 4, wherein said enzymatic RNA molecule specifically cleaves any of the RNA sequences defined as SEQ ID NOS. 18–20.

63. The enzymatic RNA molecule of claim 4, wherein said enzymatic RNA molecule specifically cleaves any of the RNA sequences defined as SEQ ID NOS. 22–25.

64. The enzymatic RNA molecule of claim 4, wherein said enzymatic RNA molecule specifically cleaves any of the RNA sequences defined as SEQ ID NOS. 26–29.

65. The enzymatic RNA molecule of claim 4, wherein said enzymatic RNA molecule specifically cleaves any of the RNA sequences defined as SEQ ID NOS. 30–33.

66. The enzymatic RNA molecule of claim 4, wherein said enzymatic RNA molecule specifically cleaves any of the RNA sequences defined as SEQ ID NOS. 34–37.

67. The enzymatic RNA molecule of claim 4, wherein said enzymatic RNA molecule specifically cleaves any of the RNA sequences defined as SEQ ID NOS. 38–41.

68. The enzymatic RNA molecule of claim 4, wherein said enzymatic RNA molecule specifically cleaves any of the RNA sequences defined as SEQ ID NOS. 42–45.

69. The enzymatic RNA molecule of claim 4, wherein said enzymatic RNA molecule specifically cleaves any of the RNA sequences defined as SEQ ID NOS. 47–50.

70. The enzymatic RNA molecule of claim 4, wherein said enzymatic RNA molecule specifically cleaves any of the RNA sequences defined as SEQ ID NOS. 51–54.

71. The enzymatic RNA molecule of claim 4, wherein said enzymatic RNA molecule specifically cleaves any of the RNA sequences defined as SEQ ID NOS. 55–58.

72. The enzymatic RNA molecule of claim 4, wherein said enzymatic RNA molecule specifically cleaves any of the RNA sequences defined as SEQ ID NOS. 59–62.

73. The enzymatic RNA molecule of claim 4, wherein said enzymatic RNA molecule specifically cleaves any of the RNA sequences defined as SEQ ID NOS. 63–66.

74. The enzymatic RNA molecule of claim 4, wherein said enzymatic RNA molecule specifically cleaves any of the RNA sequences defined as SEQ ID NOS. 67–70.

75. The enzymatic RNA molecule of claim 4, wherein said enzymatic RNA molecule specifically cleaves any of the RNA sequences defined as SEQ ID NOS. 71–74.

76. The enzymatic RNA molecule of claim 4, wherein said enzymatic RNA molecule specifically cleaves any of the RNA sequences defined as SEQ ID NOS. 75–78.

77. The enzymatic RNA molecule of claim 6, wherein said enzymatic RNA molecule specifically cleaves the RNA sequence defined as SEQ ID NO. 99.

78. The enzymatic RNA molecule of claim 6, wherein said enzymatic RNA molecule specifically cleaves the RNA sequence defined as SEQ ID NOS. 100.

79. The enzymatic RNA molecule of claim 6, wherein said enzymatic RNA molecule specifically cleaves any of the RNA sequences defined as SEQ ID NOS. 130–133.

80. The enzymatic RNA molecule of claim 6, wherein said enzymatic RNA molecule specifically cleaves any of the RNA sequences defined as SEQ ID NOS. 134–137.

81. The enzymatic RNA molecule of claim 6, wherein said enzymatic RNA molecule specifically cleaves the RNA sequence defined as SEQ ID NO. 138.

82. The enzymatic RNA molecule of claim 6, wherein said enzymatic RNA molecule specifically cleaves any of the RNA sequences defined as SEQ ID NOS. 139–141.

83. The enzymatic RNA molecule of claim 6, wherein said enzymatic RNA molecule specifically cleaves any of the RNA sequences defined as SEQ ID NOS. 142–145.

84. The enzymatic RNA molecule of claim 6, wherein said enzymatic RNA molecule specifically cleaves any of the RNA sequences defined as SEQ ID NOS. 146–148.

85. The enzymatic RNA molecule of claim 4, wherein said enzymatic RNA molecule specifically cleaves any of the RNA sequences defined as SEQ ID NOS. 170, 172, 174, or 176.

86. The enzymatic RNA molecule of claim 4, wherein said enzymatic RNA molecule specifically cleaves any of the RNA sequences defined as SEQ ID NOS. 178, 180, 182, or 184.

87. The enzymatic RNA molecule of claim 4, wherein said enzymatic RNA molecule specifically cleaves any of the RNA sequences defined as SEQ ID NOS. 186, 188, 190, or 192.

88. The enzymatic RNA molecule of claim 4, wherein said enzymatic RNA molecule specifically cleaves any of the RNA sequences defined as SEQ ID NOS. 194, 196, 198, or 200.

89. The enzymatic RNA molecule of claim 4, wherein said enzymatic RNA molecule specifically cleaves any of the RNA sequences defined as SEQ ID NOS. 202, 204, 206, or 208.

90. The enzymatic RNA molecule of claim 4, wherein said enzymatic RNA molecule specifically cleaves any of the RNA sequences defined as SEQ ID NOS. 210, 212, 214, or 216.

91. The enzymatic RNA molecule of claim 4, wherein said enzymatic RNA molecule specifically cleaves any of the RNA sequences defined as SEQ ID NOS. 218, 220, 222, or 224.

92. The enzymatic RNA molecule of claim 4, wherein said enzymatic RNA molecule specifically cleaves any of the RNA sequences defined as SEQ ID NOS. 226, 228, or 230.

93. The enzymatic RNA molecule of claim 4, wherein said enzymatic RNA molecule specifically cleaves any of the RNA sequences defined as SEQ ID NOS. 234, 236, 238, or 240.

94. The enzymatic RNA molecule of claim 4, wherein said enzymatic RNA molecule specifically cleaves any of the RNA sequences defined as SEQ ID NO. 242, 244, 246, or 248.

95. The enzymatic RNA molecule of claim 4, wherein said enzymatic RNA molecule specifically cleaves any of the RNA sequences defined as SEQ ID NOS. 250, 252, 254, or 256.

96. The enzymatic RNA molecule of claim 4, wherein said enzymatic RNA molecule specifically cleaves any of the RNA sequences defined as SEQ ID NOS. 258, 260, or 262.

97. The enzymatic RNA molecule of claim 4, wherein said enzymatic RNA molecule specifically cleaves any of the RNA sequences defined as SEQ ID NOS. 268 or 270.

98. The enzymatic RNA molecule of claim 4, wherein said enzymatic RNA molecule specifically cleaves any of the RNA sequences defined as SEQ ID NOS. 274, 276, 278, or 280.

99. The enzymatic RNA molecule of claim 4, wherein said enzymatic RNA molecule specifically cleaves any of the RNA sequences defined as SEQ ID NOS. 284, 286, or 288.

100. The enzymatic RNA molecule of claim 4, wherein said enzymatic RNA molecule specifically cleaves any of the RNA sequences defined as SEQ ID NOS. 290, 292, 294, or 296.

101. The enzymatic RNA molecule of claim 4, wherein said enzymatic RNA molecule specifically cleaves any of the RNA sequences defined as SEQ ID NOS. 298, 302, or 304.

102. The enzymatic RNA molecule of claim 4, wherein said enzymatic RNA molecule specifically cleaves any of the RNA sequences defined as SEQ ID NOS. 306, 308, 310, or 312.

103. The enzymatic RNA molecule of claim 4, wherein said enzymatic RNA molecule specifically cleaves any of the RNA sequences defined as SEQ ID NOS. 314, 316, or 318.

104. The enzymatic RNA molecule of claim 4, wherein said enzymatic RNA molecule specifically cleaves any of the RNA sequences defined as SEQ ID NOS. 322, 324, 326, or 328.

105. The enzymatic RNA molecule of claim 4, wherein said enzymatic RNA molecule specifically cleaves any of the RNA sequences defined as SEQ ID NOS. 330, 332, 334, or 336.

106. The enzymatic RNA molecule of claim 4, wherein said enzymatic RNA molecule specifically cleaves any of the RNA sequences defined as SEQ ID NOS. 338, 340, 342, or 344.

107. The enzymatic RNA molecule of claim 4, wherein said enzymatic RNA molecule specifically cleaves any of the RNA sequences defined as SEQ ID NOS. 346, 348, or 352.

108. The enzymatic RNA molecule of claim 4, wherein said enzymatic RNA molecule specifically cleaves any of the RNA sequences defined as SEQ ID NOS. 354, 356, 358, or 360.

109. The enzymatic RNA molecule of claim 4, wherein said enzymatic RNA molecule specifically cleaves any of the RNA sequences defined as SEQ ID NOS. 362, 364, 366, or 368.

110. The enzymatic RNA molecule of claim 4, wherein said enzymatic RNA molecule specifically cleaves any of the RNA sequences defined as SEQ ID NOS. 370, 372, or 376.

111. The enzymatic RNA molecule of claim 4, wherein said enzymatic RNA molecule specifically cleaves any of the RNA sequences defined as SEQ ID NOS. 378, 380, or 382.

112. The enzymatic RNA molecule of claim 4, wherein said enzymatic RNA molecule specifically cleaves any of the RNA sequences defined as SEQ ID NOS. 386, 388, 390, or 392.

113. The enzymatic RNA molecule of claim 4, wherein said enzymatic RNA molecule specifically cleaves any of the RNA sequences defined as SEQ ID NOS. 394, 396, 398, or 400.

114. The enzymatic RNA molecule of claim 4, wherein said enzymatic RNA molecule specifically cleaves any of the RNA sequences defined as SEQ ID NOS. 402, 404, 406, or 408.

115. The enzymatic RNA molecule of claim 4, wherein said enzymatic RNA molecule specifically cleaves any of the RNA sequences defined as SEQ ID NOS. 410, 412, 414, or 416.

116. The enzymatic RNA molecule of claim 4, wherein said enzymatic RNA molecule specifically cleaves any of the RNA sequences defined as SEQ ID NOS. 418, 420, 422, or 424.

117. The enzymatic RNA molecule of claim 4, wherein said enzymatic RNA molecule specifically cleaves any of the RNA sequences defined as SEQ ID NOS. 426, 428, 430, or 432.

118. The enzymatic RNA molecule of claim 4, wherein said enzymatic RNA molecule specifically cleaves any of the RNA sequences defined as SEQ ID NOS. 434, 436, 438, or 440.

119. The enzymatic RNA molecule of claim 4, wherein said enzymatic RNA molecule specifically cleaves any of the RNA sequences defined as SEQ ID NOS. 444, 446, or 448.

120. The enzymatic RNA molecule of claim 4, wherein said enzymatic RNA molecule specifically cleaves any of the RNA sequences defined as SEQ ID NOS. 450, 452, 454, or 456.

121. The enzymatic RNA molecule of claim 4, wherein said enzymatic RNA molecule specifically cleaves any of the RNA sequences defined as SEQ ID NOS. 458, 460, 462, or 464.

122. The enzymatic RNA molecule of claim 4, wherein said enzymatic RNA molecule specifically cleaves any of the RNA sequences defined as SEQ ID NOS. 466, 468, 470, or 472.

123. The enzymatic RNA molecule of claim 4, wherein said enzymatic RNA molecule specifically cleaves any of the RNA sequences defined as SEQ ID NOS. 474, 476, 478, or 480.

124. The enzymatic RNA molecule of claim 4, wherein said enzymatic RNA molecule specifically cleaves any of the RNA sequences defined as SEQ ID NOS. 482, 484, 486, or 488.

125. The enzymatic RNA molecule of claim 4, wherein said enzymatic RNA molecule specifically cleaves any of the RNA sequences defined as SEQ ID NOS. 490, 492, 494, or 496.

126. The enzymatic RNA molecule of claim 4, wherein said enzymatic RNA molecule specifically cleaves any of the RNA sequences defined as SEQ ID NOS. 498, 500, 502, or 504.

127. The enzymatic RNA molecule of claim 4, wherein said enzymatic RNA molecule specifically cleaves any of the RNA sequences defined as SEQ ID NOS. 506, 508, 510, or 512.

128. The enzymatic RNA molecule of claim 4, wherein said enzymatic RNA molecule specifically cleaves any of the RNA sequences defined as SEQ ID NOS. 514, 516, 518, or 520.

129. The enzymatic RNA molecule of claim 4, wherein said enzymatic RNA molecule specifically cleaves any of the RNA sequences defined as SEQ ID NOS. 524, 526, or 528.

130. The enzymatic RNA molecule of claim 4, wherein said enzymatic RNA molecule specifically cleaves any of the RNA sequences defined as SEQ ID NOS. 530, 532, 534, or 536.

131. The enzymatic RNA molecule of claim 4, wherein said enzymatic RNA molecule specifically cleaves any of the RNA sequences defined as SEQ ID NOS. 540, 542, or 544.

132. The enzymatic RNA molecule of claim 4, wherein said enzymatic RNA molecule specifically cleaves any of the RNA sequences defined as SEQ ID NOS. 546, 548, 550, or 552.

133. The enzymatic RNA molecule of claim 4, wherein said enzymatic RNA molecule specifically cleaves any of the RNA sequences defined as SEQ ID NOS. 554, 556, 558, or 560.

134. The enzymatic RNA molecule of claim 4, wherein said enzymatic RNA molecule specifically cleaves any of the RNA sequences defined as SEQ ID NOS. 562, 564, 566, or 568.

135. The enzymatic RNA molecule of claim 4, wherein said enzymatic RNA molecule specifically cleaves any of the RNA sequences defined as SEQ ID NOS. 570, 574, or 576.

136. The enzymatic RNA molecule of claim 4, wherein said enzymatic RNA molecule specifically cleaves any of the RNA sequences defined as SEQ ID NOS. 578, 580, 582, or 584.

137. The enzymatic RNA molecule of claim 4, wherein said enzymatic RNA molecule specifically cleaves any of the RNA sequences defined as SEQ ID NOS. 586, 588, 590, or 592.

138. The enzymatic RNA molecule of claim 4, wherein said enzymatic RNA molecule specifically cleaves any of the RNA sequences defined as SEQ ID NOS. 594, 596, 598, or 600.

139. The enzymatic RNA molecule of claim 4, wherein said enzymatic RNA molecule specifically cleaves any of the RNA sequences defined as SEQ ID NOS. 602, 604, 606, or 608.

140. The enzymatic RNA molecule of claim 4, wherein said enzymatic RNA molecule specifically cleaves any of the RNA sequences defined as SEQ ID NOS. 610, 612, or 616.

141. The enzymatic RNA molecule of claim 4, wherein said enzymatic RNA molecule specifically cleaves any of the RNA sequences defined as SEQ ID NOS. 618, 620, or 624.

142. The enzymatic RNA molecule of claim 4, wherein said enzymatic RNA molecule specifically cleaves any of the RNA sequences defined as SEQ ID NOS. 626, 628, 630, or 632.

143. The enzymatic RNA molecule of claim 4, wherein said enzymatic RNA molecule specifically cleaves any of the RNA sequences defined as SEQ ID NOS. 634, 638, 640, or 642.

144. The enzymatic RNA molecule of claim 4, wherein said enzymatic RNA molecule specifically cleaves any of the RNA sequences defined as SEQ ID NOS. 644, 646, 648, or 670.

145. The enzymatic RNA molecule of claim 4, wherein said enzymatic RNA molecule specifically cleaves any of the RNA sequences defined as SEQ ID NOS. 672, 674, 676, or 678.

146. The enzymatic RNA molecule of claim 4, wherein said enzymatic RNA molecule specifically cleaves any of the RNA sequences defined as SEQ ID NOS. 680, 682, 684, or 686.

147. The enzymatic RNA molecule of claim 4, wherein said enzymatic RNA molecule specifically cleaves any of the RNA sequences defined as SEQ ID NOS. 688, 690, 692, or 694.

148. The enzymatic RNA molecule of claim 4, wherein said enzymatic RNA molecule specifically cleaves any of the RNA sequences defined as SEQ ID NOS. 696, 698, 700, or 702.

149. The enzymatic RNA molecule of claim 4, wherein said enzymatic RNA molecule specifically cleaves any of the RNA sequences defined as SEQ ID NOS. 704, 706, 708, or 710.

150. The enzymatic RNA molecule of claim 4, wherein said enzymatic RNA molecule specifically cleaves any of the RNA sequences defined as SEQ ID NOS. 712, 714, 716, or 718.

151. The enzymatic RNA molecule of claim 4, wherein said enzymatic RNA molecule specifically cleaves any of the RNA sequences defined as SEQ ID NOS. 720, 722, 724, or 726.

152. The enzymatic RNA molecule of claim 4, wherein said enzymatic RNA molecule specifically cleaves any of the RNA sequences defined as SEQ ID NOS. 728, 730, 732, or 734.

153. The enzymatic RNA molecule of claim 4, wherein said enzymatic RNA molecule specifically cleaves any of the RNA sequences defined as SEQ ID NOS. 736, 738, 740, or 742.

154. The enzymatic RNA molecule of claim 4, wherein said enzymatic RNA molecule specifically cleaves any of the RNA sequences defined as SEQ ID NOS. 744, 746, 748, or 750.

155. The enzymatic RNA molecule of claim 4, wherein said enzymatic RNA molecule specifically cleaves any of the RNA sequences defined as SEQ ID NOS. 752, 754, 756, or 758.

156. The enzymatic RNA molecule of claim 4, wherein said enzymatic RNA molecule specifically cleaves any of the RNA sequences defined as SEQ ID NOS. 760, 762, 764, or 766.

157. The enzymatic RNA molecule of claim 4, wherein said enzymatic RNA molecule specifically cleaves any of the RNA sequences defined as SEQ ID NOS. 778, 780, 782, or 784.

158. The enzymatic RNA molecule of claim 4, wherein said enzymatic RNA molecule specifically cleaves any of the RNA sequences defined as SEQ ID NOS. 786, 788, 790, or 792.

159. The enzymatic RNA molecule of claim 4, wherein said enzymatic RNA molecule specifically cleaves any of the RNA sequences defined as SEQ ID NOS. 794, 796, 798, or 800.

160. The enzymatic RNA molecule of claim 4, wherein said enzymatic RNA molecule specifically cleaves any of the RNA sequences defined as SEQ ID NOS. 802, 804, 806, or 808.

161. The enzymatic RNA molecule of claim 4, wherein said enzymatic RNA molecule specifically cleaves any of the RNA sequences defined as SEQ ID NOS. 810, 812, 814, or 816.

162. The enzymatic RNA molecule of claim 4, wherein said enzymatic RNA molecule specifically cleaves any of the RNA sequences defined as SEQ ID NOS. 818, 820, 822, or 824.

163. The enzymatic RNA molecule of claim 4, wherein said enzymatic RNA molecule specifically cleaves any of the RNA sequences defined as SEQ ID NOS. 826, 828, 830, or 832.

164. The enzymatic RNA molecule of claim 4, wherein said enzymatic RNA molecule specifically cleaves any of the RNA sequences defined as SEQ ID NOS. 834, 836, 838, or 840.

165. The enzymatic RNA molecule of claim 4, wherein said enzymatic RNA molecule specifically cleaves any of the RNA sequences defined as SEQ ID NOS. 842, 844, 846, or 848.

166. The enzymatic RNA molecule of claim 4, wherein said enzymatic RNA molecule specifically cleaves any of the RNA sequences defined as SEQ ID NOS. 850, 852, 854, or 856.

167. The enzymatic RNA molecule of claim 4, wherein said enzymatic RNA molecule specifically cleaves any of the RNA sequences defined as SEQ ID NOS. 858, 860, 862, or 864.

168. The enzymatic RNA molecule of claim 4, wherein said enzymatic RNA molecule specifically cleaves any of the RNA sequences defined as SEQ ID NOS. 866, 868, 870, or 872.

169. The enzymatic RNA molecule of claim 4, wherein said enzymatic RNA molecule specifically cleaves any of the RNA sequences defined as SEQ ID NOS. 874, 876, 878, or 880.

170. The enzymatic RNA molecule of claim 4, wherein said enzymatic RNA molecule specifically cleaves any of the RNA sequences defined as SEQ ID NOS. 882, 884, 886, or 888.

171. The enzymatic RNA molecule of claim 4, wherein said enzymatic RNA molecule specifically cleaves any of the RNA sequences defined as SEQ ID NOS. 890, 892, 894, or 896.

172. The enzymatic RNA molecule of claim 4, wherein said enzymatic RNA molecule specifically cleaves any of the RNA sequences defined as SEQ ID NOS. 898, 900, 902, or 904.

173. The enzymatic RNA molecule of claim 4, wherein said enzymatic RNA molecule specifically cleaves any of the RNA sequences defined as SEQ ID NOS. 906, 908, 910, or 912.

174. The enzymatic RNA molecule of claim 4, wherein said enzymatic RNA molecule specifically cleaves any of the RNA sequences defined as SEQ ID NOS. 914, 916, 918, or 920.

175. The enzymatic RNA molecule of claim 4, wherein said enzymatic RNA molecule specifically cleaves any of the RNA sequences defined as SEQ ID NOS. 922, 924, 926, or 928.

176. The enzymatic RNA molecule of claim 4, wherein said enzymatic RNA molecule specifically cleaves any of the RNA sequences defined as SEQ ID NOS. 930, 932, 934, or 936.

177. The enzymatic RNA molecule of claim 4, wherein said enzymatic RNA molecule specifically cleaves any of the RNA sequences defined as SEQ ID NOS. 938, 940, 942, or 944.

178. The enzymatic RNA molecule of claim 4, wherein said enzymatic RNA molecule specifically cleaves any of the RNA sequences defined as SEQ ID NOS. 946, 948, 950, or 952.

179. The enzymatic RNA molecule of claim 4, wherein said enzymatic RNA molecule specifically cleaves any of the RNA sequences defined as SEQ ID NOS. 954, 956, 958, or 960.

180. The enzymatic RNA molecule of claim 4, wherein said enzymatic RNA molecule specifically cleaves any of the RNA sequences defined as SEQ ID NOS. 962, 964, 966, or 968.

181. The enzymatic RNA molecule of claim 4, wherein said enzymatic RNA molecule specifically cleaves any of the RNA sequences defined as SEQ ID NOS. 970, 972, 974, or 976.

182. The enzymatic RNA molecule of claim 4, wherein said enzymatic RNA molecule specifically cleaves any of the RNA sequences defined as SEQ ID NOS. 978, 980, 982, or 984.

183. The enzymatic RNA molecule of claim 4, wherein said enzymatic RNA molecule specifically cleaves any of the RNA sequences defined as SEQ ID NOS. 986, 988, 990, or 992.

184. The enzymatic RNA molecule of claim 4, wherein said enzymatic RNA molecule specifically cleaves any of the RNA sequences defined as SEQ ID NOS. 994, 996, 998, or 1000.

185. The enzymatic RNA molecule of claim 4, wherein said enzymatic RNA molecule specifically cleaves any of the RNA sequences defined as SEQ ID NOS. 1002, 1004, 1006, 1008, or 1010.

186. The enzymatic RNA molecule of claim 4, wherein said enzymatic RNA molecule specifically cleaves any of the RNA sequences defined as SEQ ID NOS. 1012, 1014, 1016, or 1018.

187. The enzymatic RNA molecule of claim 4, wherein said enzymatic RNA molecule specifically cleaves any of the RNA sequences defined as SEQ ID NOS. 1020, 1022, 1024, or 1026.

188. The enzymatic RNA molecule of claim 4, wherein said enzymatic RNA molecule specifically cleaves any of the RNA sequences defined as SEQ ID NOS. 1028, 1030, 1032, or 1034.

189. The enzymatic RNA molecule of claim 4, wherein said enzymatic RNA molecule specifically cleaves any of the RNA sequences defined as SEQ ID NOS. 1036, 1038, 1040, or 1042.

190. The enzymatic RNA molecule of claim 4, wherein said enzymatic RNA molecule specifically cleaves any of the RNA sequences defined as SEQ ID NOS. 1042, 1044, 1046, or 1048.

191. The enzymatic RNA molecule of claim 4, wherein said enzymatic RNA molecule specifically cleaves any of the RNA sequences defined as SEQ ID NOS. 1050, 1052, 1054, or 1056.

192. The enzymatic RNA molecule of claim 4, wherein said enzymatic RNA molecule specifically cleaves any of the RNA sequences defined as SEQ ID NOS. 1058, 1060, 1062, or 1064.

193. The enzymatic RNA molecule of claim 4, wherein said enzymatic RNA molecule specifically cleaves any of the RNA sequences defined as SEQ ID NOS. 1066, 1068, 1070, or 1072.

194. The enzymatic RNA molecule of claim 4, wherein said enzymatic RNA molecule specifically cleaves any of the RNA sequences defined as SEQ ID NOS. 1074, 1076, 1078, or 1080.

195. The enzymatic RNA molecule of claim 4, wherein said enzymatic RNA molecule specifically cleaves any of the RNA sequences defined as SEQ ID NOS. 1082, 1084, 1086, or 1088.

196. The enzymatic RNA molecule of claim 4, wherein said enzymatic RNA molecule specifically cleaves any of the RNA sequences defined as SEQ ID NOS. 1090, 1092, 1094, or 1096.

197. The enzymatic RNA molecule of claim 4, wherein said enzymatic RNA molecule specifically cleaves any of the RNA sequences defined as SEQ ID NOS. 1098, 1100, 1102, or 1104.

198. The enzymatic RNA molecule of claim 4, wherein said enzymatic RNA molecule specifically cleaves any of the RNA sequences defined as SEQ ID NOS. 1106, 1108, 1110, or 1112.

199. The enzymatic RNA molecule of claim 4, wherein said enzymatic RNA molecule specifically cleaves any of the RNA sequences defined as SEQ ID NOS. 1114, 1116, 1118, or 1120.

200. The enzymatic RNA molecule of claim 4, wherein said enzymatic RNA molecule specifically cleaves any of the RNA sequences defined as SEQ ID NOS. 1122, 1124, 1126, or 1128.

201. The enzymatic RNA molecule of claim 4, wherein said enzymatic RNA molecule specifically cleaves any of the RNA sequences defined as SEQ ID NOS. 1130, 1132, 1134, or 1136.

202. The enzymatic RNA molecule of claim 4, wherein said enzymatic RNA molecule specifically cleaves any of the RNA sequences defined as SEQ ID NOS. 1138, 1140, 1142, or 1144.

203. The enzymatic RNA molecule of claim 4, wherein said enzymatic RNA molecule specifically cleaves any of the RNA sequences defined as SEQ ID NOS. 1146, 1148, 1150, or 1152.

204. The enzymatic RNA molecule of claim 4, wherein said enzymatic RNA molecule specifically cleaves any of the RNA sequences defined as SEQ ID NOS. 1154, 1156, 1158, or 1160.

205. The enzymatic RNA molecule of claim 4, wherein said enzymatic RNA molecule specifically cleaves any of the RNA sequences defined as SEQ ID NOS. 1162, 1164, 1166, or 1168.

206. The enzymatic RNA molecule of claim 4, wherein said enzymatic RNA molecule specifically cleaves any of the RNA sequences defined as SEQ ID NOS. 1170, 1172, 1174, or 1176.

207. The enzymatic RNA molecule of claim 4, wherein said enzymatic RNA molecule specifically cleaves any of the RNA sequences defined as SEQ ID NOS. 1178, 1180, 1182, or 1184.

208. The enzymatic RNA molecule of claim 4, wherein said enzymatic RNA molecule specifically cleaves any of the RNA sequences defined as SEQ ID NOS. 1186, 1188, 1190, or 1192.

209. The enzymatic RNA molecule of claim 4, wherein said enzymatic RNA molecule specifically cleaves any of the RNA sequences defined as SEQ ID NOS. 1194, 1196, 1198, or 1200.

210. The enzymatic RNA molecule of claim 4, wherein said enzymatic RNA molecule specifically cleaves any of the RNA sequences defined as SEQ ID NOS. 1202, 1204, 1206, or 1208.

211. The enzymatic RNA molecule of claim 4, wherein said enzymatic RNA molecule specifically cleaves any of the RNA sequences defined as SEQ ID NOS. 1210, 1212, 1214, or 1216.

212. The enzymatic RNA molecule of claim 4, wherein said enzymatic RNA molecule specifically cleaves any of the RNA sequences defined as SEQ ID NOS. 1218, 1220, 1222, or 1224.

213. The enzymatic RNA molecule of claim 1, wherein the binding arms of said enzymatic RNA molecule contain sequences perfectly complementary to any of the RNA sequences defined as SEQ. ID. NOS. 1–98, 101–120, or 123–129, wherein said enzymatic RNA molecule is in a hammerhead motif.

214. The enzymatic RNA molecule of claim 1, wherein the the binding arms of said enzymatic RNA molecule contain sequences perfectly complementary to any of the RNA sequences defined as SEQ. ID. NOS. 1–8, wherein said enzymatic RNA molecule is in a hepatitis delta virus motif.

215. The enzymatic RNA molecule of claim 5, wherein the binding arms of said enzymatic RNA molecule contain sequences perfectly complementary to any of the RNA sequences defined as SEQ. ID. NOS. 99, 100, or 130–148, wherein said enzymatic RNA molecule is in a hairpin motif.

216. A mammalian cell including an enzymatic RNA molecule of any one of claims 1, 2, 3, 4, 5, 10, 6 or 7 in vitro.

217. The cell of claim 216, wherein said cell is a human cell.

218. An expression vector including a nucleic acid encoding an enzymatic RNA molecule or multiple enzymatic RNA molecules of claims 1, 2, 3, 4, 5, 10, 6 or 7 in a manner which allows expression of that enzymatic RNA molecule(s) within a mammalian cell.

219. A mammalian cell including an expression vector of claim 218 in vitro.

220. The cell of claim 219, wherein said cell is a human cell.

* * * * *

UNITED STATES PATENT AND TRADEMARK OFFICE
CERTIFICATE OF CORRECTION

PATENT NO. : 5,646,042

DATED : July 8, 1997

INVENTOR(S) : DAN T. STINCHCOMB, KENNETH DRAPER, JAMES MCSWIGGEN, THALE JARVIS

It is certified that error appears in the above-identified patent and that said Letters Patent is hereby corrected as shown below:

Column 7, Line 42: Delete "vital" and insert --viral--

Column 15, Line 25: Delete "trifiuoracetate" and insert --trifluoroacetate--

Column 18, Line 9: Delete "c-ruby" and insert --c-mby--

Column 26, Line 41: Delete "adventilia" and insert --adventitia--

Column 35, Table IV, Under the Heading "Sequence ID No.", 9th entry down: Delete "97" and insert --87--

Column 36, after "Table VIII" insert --Delivery of c-myb Ribozyme 575 by Two Different Cationic Lipids--

Column 36, Table X, Under the Heading "Ribozyme Target Site", 4th entry down: Delete "659" and insert --549--

Column 43, Table XV, Under the heading "nt.", 6th entry down: Delete "1404" and insert --1405--

Column 47, Table XV, Under the Heading "Seq ID No.", 53rd entry down: Delete "860" and insert --858--

UNITED STATES PATENT AND TRADEMARK OFFICE
CERTIFICATE OF CORRECTION

PATENT NO. : 5,646,042

DATED : July 8, 1997

INVENTOR(S) : DAN T. STINCHCOMB, KENNETH DRAPER, JAMES MCSWIGGEN, THALE JARVIS

It is certified that error appears in the above-identified patent and that said Letters Patent is hereby corrected as shown below:

Column 57, Table XVI, Under the Heading "nt.", 70th entry down: Delete "1599" and insert --1499--

Column 59, Table XVI, Under the Heading "nt.", 70th entry down: Delete "2911" and insert --2011--

Column 64, Table XIV, Under the Second Column entitled "Seq ID No.", 26th entry down: Delete "1948" and insert --1949--

Column 67-68, Table XVII, Under the Second Column entitled "Seq ID No.", 19th entry down: Delete "2218" and insert --2219--

Column 77, Table XXIV, in the Title, Delete "c-mby" and insert --c-myb--

Column 77, Table XXV, in the Title, Delete "c-mby" and insert --c-myb--

Column 931, Line 51, Claim 2: Delete "An" and insert --The--

Signed and Sealed this

Nineteenth Day of January, 1999

Attest:

*Attesting Officer*

*Acting Commissioner of Patents and Trademarks*